(12) United States Patent
Noronha et al.

(10) Patent No.: US 7,825,246 B2
(45) Date of Patent: *Nov. 2, 2010

(54) BI-ARYL META-PYRIMIDINE INHIBITORS OF KINASES

(75) Inventors: Glenn Noronha, Oceanside, CA (US); Chi Ching Mak, San Diego, CA (US); Jianguo Cao, San Diego, CA (US); Joel Renick, San Diego, CA (US); Andrew McPherson, San Diego, CA (US); Binqi Zeng, San Diego, CA (US); Ved P. Pathak, San Diego, CA (US); Daniel L. Lohse, San Diego, CA (US); John D. Hood, San Diego, CA (US); Richard M. Soll, San Diego, CA (US)

(73) Assignee: TargeGen, Inc., San Diego, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 11/796,717

(22) Filed: Apr. 26, 2007

(65) Prior Publication Data

US 2007/0259904 A1    Nov. 8, 2007

Related U.S. Application Data

(63) Continuation-in-part of application No. 11/588,638, filed on Oct. 26, 2006, now Pat. No. 7,528,143.

(60) Provisional application No. 60/732,629, filed on Nov. 1, 2005, provisional application No. 60/838,003, filed on Aug. 15, 2006.

(51) Int. Cl.
C07D 239/02 (2006.01)
(52) U.S. Cl. .................................................... 544/323
(58) Field of Classification Search ........................ None
See application file for complete search history.

(56) References Cited

U.S. PATENT DOCUMENTS

| | | | |
|---|---|---|---|
| 2,001,051 A | 5/1935 | Bruno | |
| 2,002,165 A | 5/1935 | Winslow | |
| 2,003,060 A | 5/1935 | Thomas | |
| 2,003,065 A | 5/1935 | Boyce | |
| 2,003,149 A | 5/1935 | Johnson | |
| 2,003,166 A | 5/1935 | Zancan | |
| 2,003,187 A | 5/1935 | Good | |
| 2,003,199 A | 5/1935 | Johnson et al. | |
| 2,004,092 A | 6/1935 | Chaney | |
| 2,004,102 A | 6/1935 | Dickey | |
| 2,004,138 A | 6/1935 | Story et al. | |
| 2,667,486 A | 1/1954 | Cain | |
| 4,160,833 A | 7/1979 | Diel et al. | |
| 4,309,211 A | 1/1982 | Serban et al. | |
| 5,214,059 A | 5/1993 | Tegeler et al. | |
| 5,231,097 A | 7/1993 | Klausener et al. | |
| 5,332,745 A | 7/1994 | Carter et al. | |
| 5,527,763 A | 6/1996 | Miyazaki et al. | |
| 5,530,000 A | 6/1996 | Sanfilippo et al. | |
| 5,597,826 A | 1/1997 | Howard et al. | |
| 5,597,901 A | 1/1997 | Stern | |
| 5,665,724 A | 9/1997 | Sanfilippo et al. | |
| 5,776,502 A | 7/1998 | Foulkes et al. | |
| 5,830,880 A | 11/1998 | Sedlacek et al. | |
| 5,849,738 A | 12/1998 | Lee et al. | |
| 5,935,383 A | 8/1999 | Sun et al. | |
| 5,958,935 A | 9/1999 | Davis et al. | |
| 5,965,761 A | 10/1999 | Buchecker et al. | |
| 5,972,580 A | 10/1999 | Fukui et al. | |
| 6,048,675 A | 4/2000 | Hirano et al. | |
| 6,070,126 A | 5/2000 | Kokolus et al. | |
| 6,093,838 A | 7/2000 | Vasudevan et al. | |
| 6,121,434 A | 9/2000 | Peyman et al. | |
| 6,127,382 A | 10/2000 | Beard et al. | |
| 6,136,779 A | 10/2000 | Foulkes et al. | |
| 6,136,971 A | 10/2000 | Harrington et al. | |
| 6,153,752 A | 11/2000 | Bauer et al. | |
| 6,194,191 B1 | 2/2001 | Zhang et al. | |
| 6,197,779 B1 | 3/2001 | Andries et al. | |
| 6,204,260 B1 | 3/2001 | Bruns, Jr. et al. | |
| 6,235,746 B1 | 5/2001 | Davis et al. | |

(Continued)

FOREIGN PATENT DOCUMENTS

| | | |
|---|---|---|
| AU | A-38554/93 | 11/1993 |
| CA | 2375982 | 2/2001 |
| DE | 3205638 | 8/1983 |
| DE | 10024622 | 11/2001 |
| EP | 444769 | 9/1991 |

(Continued)

OTHER PUBLICATIONS

Wolff et. al., "Burger's Medicinal Chemistry and Drug Discovery," 5th Ed. Part 1, pp. 975-977 (1995).*

(Continued)

*Primary Examiner*—James O Wilson
*Assistant Examiner*—Jeffrey H Murray
(74) *Attorney, Agent, or Firm*—Morrison & Foerster LLP

(57) ABSTRACT

The invention provides biaryl meta-pyrimidine compounds having the general structure (A). The pyrimidine compounds of the invention are capable of inhibiting kinases, such as members of the Jak kinase family, and various other specific receptor and non-receptor kinases.

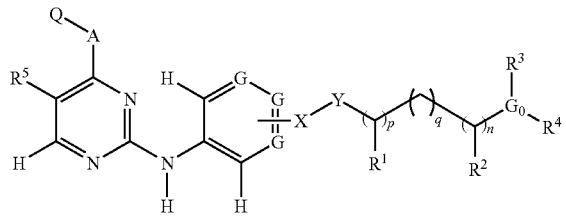

9 Claims, 39 Drawing Sheets

U.S. PATENT DOCUMENTS

| | | |
|---|---|---|
| 6,277,502 B1 | 8/2001 | Buchecker et al. |
| 6,288,082 B1 | 9/2001 | Wissner et al. |
| 6,297,258 B1 | 10/2001 | Wissner et al. |
| 6,326,487 B1 | 12/2001 | Peyman et al. |
| 6,348,312 B1 | 2/2002 | Peyman et al. |
| 6,378,526 B1 | 4/2002 | Bowman et al. |
| 6,432,963 B1 | 8/2002 | Hisamichi et al. |
| 6,471,968 B1 | 10/2002 | Baker, Jr. et al. |
| 6,489,328 B2 | 12/2002 | Snow et al. |
| 6,506,769 B2 | 1/2003 | Snow et al. |
| 6,605,615 B2 | 8/2003 | Medina et al. |
| 6,613,773 B2 | 9/2003 | Clough et al. |
| 6,635,626 B1 | 10/2003 | Barrish et al. |
| 6,649,608 B2 | 11/2003 | Pease et al. |
| 6,685,938 B1 | 2/2004 | Cheresh et al. |
| 6,689,778 B2 | 2/2004 | Bemis et al. |
| 6,777,412 B2 | 8/2004 | Clough et al. |
| 6,794,378 B2 | 9/2004 | Lino et al. |
| 6,838,464 B2 | 1/2005 | Pease et al. |
| 7,067,522 B2 | 6/2006 | Pease et al. |
| 7,208,493 B2 | 4/2007 | Wrasidlo et al. |
| 7,282,504 B2 | 10/2007 | Armistead et al. |
| 2001/0051620 A1 | 12/2001 | Berger et al. |
| 2002/0052386 A1 | 5/2002 | Armistead et al. |
| 2002/0165244 A1 | 11/2002 | Zhou et al. |
| 2003/0060626 A1 | 3/2003 | Clough et al. |
| 2003/0065180 A1 | 4/2003 | Tsou et al. |
| 2003/0134838 A1 | 7/2003 | Bornemann et al. |
| 2003/0149061 A1 | 8/2003 | Nishihara et al. |
| 2003/0149064 A1 | 8/2003 | Pease et al. |
| 2003/0166932 A1 | 9/2003 | Beard et al. |
| 2003/0199511 A1 | 10/2003 | Li et al. |
| 2004/0029902 A1 | 2/2004 | Singh et al. |
| 2004/0092746 A1 | 5/2004 | Clough et al. |
| 2004/0102630 A1 | 5/2004 | Brumby et al. |
| 2004/0106615 A1 | 6/2004 | Cochran et al. |
| 2004/0138257 A1 | 7/2004 | Bouchard et al. |
| 2005/0234049 A1 | 10/2005 | Singh et al. |
| 2005/0234083 A1 | 10/2005 | Chamberlain et al. |
| 2005/0239852 A1 | 10/2005 | Ciufolini et al. |
| 2005/0245524 A1 | 11/2005 | Noronha et al. |
| 2005/0282814 A1 | 12/2005 | Wrasidlo et al. |
| 2006/0079526 A1 | 4/2006 | Wrasidlo et al. |
| 2006/0100227 A1 | 5/2006 | Baenteli et al. |
| 2006/0131835 A1 | 6/2006 | Simpson |
| 2006/0247250 A1 | 11/2006 | Cao et al. |
| 2006/0292203 A1 | 12/2006 | Dellamary et al. |
| 2006/0293311 A1 | 12/2006 | Li et al. |
| 2007/0032493 A1 | 2/2007 | Foley et al. |
| 2007/0060603 A1 | 3/2007 | Singh et al. |
| 2007/0072682 A1 | 3/2007 | Crawford et al. |
| 2007/0149508 A1 | 6/2007 | Noronha et al. |
| 2007/0161645 A1 | 7/2007 | Noronha et al. |
| 2007/0191405 A1* | 8/2007 | Noronha et al. ............ 514/275 |
| 2007/0203162 A1 | 8/2007 | Li et al. |
| 2007/0208019 A1 | 9/2007 | Wrasidlo et al. |
| 2007/0259876 A1 | 11/2007 | Doukas et al. |
| 2007/0259904 A1 | 11/2007 | Noronha et al. |
| 2007/0299095 A1 | 12/2007 | Singh et al. |
| 2008/0027070 A1 | 1/2008 | Noronha et al. |
| 2008/0039622 A1 | 2/2008 | Singh et al. |

FOREIGN PATENT DOCUMENTS

| | | |
|---|---|---|
| EP | 1170353 | 1/2002 |
| EP | 1562938 | 8/2005 |
| JP | 02064553 | 3/1990 |
| JP | 03127790 | 5/1991 |
| JP | 03240066 | 10/1991 |
| JP | 07041461 | 2/1995 |
| JP | 07082183 | 3/1995 |
| JP | 09274290 | 10/1997 |
| JP | 10153838 | 6/1998 |
| JP | 10207019 | 8/1998 |
| JP | 10213820 | 8/1998 |
| JP | 10260512 | 9/1998 |
| JP | 10310583 | 11/1998 |
| JP | 2001089412 | 4/2001 |
| JP | 2001247411 | 9/2001 |
| JP | 2002221770 | 8/2002 |
| WO | WO-91/18887 | 12/1991 |
| WO | WO-92/01675 | 2/1992 |
| WO | WO-94/15622 | 7/1994 |
| WO | WO-97/09315 | 3/1997 |
| WO | WO-97/24122 | 7/1997 |
| WO | WO-98/24974 | 6/1998 |
| WO | WO-98/28282 | 7/1998 |
| WO | WO-99/09016 | 2/1999 |
| WO | WO-99/24404 | 5/1999 |
| WO | WO-99/31073 | 6/1999 |
| WO | WO-99/32454 | 7/1999 |
| WO | WO-99/41253 | 8/1999 |
| WO | WO-99/50250 | 10/1999 |
| WO | WO-00/18740 | 4/2000 |
| WO | WO-00/18761 | 4/2000 |
| WO | WO-00/39101 | 7/2000 |
| WO | WO-00/39108 | 7/2000 |
| WO | WO-00/46203 | 8/2000 |
| WO | WO-00/62778 | 10/2000 |
| WO | WO-00/66583 | 11/2000 |
| WO | WO-00/71536 | 11/2000 |
| WO | WO-01/07027 | 2/2001 |
| WO | WO-01/07401 | 2/2001 |
| WO | WO-01/12227 | 2/2001 |
| WO | WO-01/17995 | 3/2001 |
| WO | WO-01/21597 | 3/2001 |
| WO | WO-01/27105 | 4/2001 |
| WO | WO-01/32628 | 5/2001 |
| WO | WO-01/44194 | 6/2001 |
| WO | WO-01/47892 | 7/2001 |
| WO | WO-01/55116 | 8/2001 |
| WO | WO-01/62233 | 8/2001 |
| WO | WO-01/64646 | 9/2001 |
| WO | WO-01/64655 | 9/2001 |
| WO | WO-01/64674 | 9/2001 |
| WO | WO-01/68186 | 9/2001 |
| WO | WO-01/70668 | 9/2001 |
| WO | WO-01/72758 | 10/2001 |
| WO | WO-01/76582 | 10/2001 |
| WO | WO-02/22608 | 3/2002 |
| WO | WO-02/30358 | 4/2002 |
| WO | WO-02/36570 | 5/2002 |
| WO | WO-02/42272 | 5/2002 |
| WO | WO-02/44166 | 6/2002 |
| WO | WO-02/053101 | 7/2002 |
| WO | WO-02/053160 | 7/2002 |
| WO | WO-02/064096 | 8/2002 |
| WO | WO-02/068409 | 9/2002 |
| WO | WO-02/076438 | 10/2002 |
| WO | WO-02/090347 | 11/2002 |
| WO | WO-02/092087 | 11/2002 |
| WO | WO-02/094766 | 11/2002 |
| WO | WO-02/097116 | 12/2002 |
| WO | WO-03/004018 | 1/2003 |
| WO | WO-03/016306 | 2/2003 |
| WO | WO-03/024448 | 3/2003 |
| WO | WO-03/030909 | 4/2003 |
| WO | WO-03/032994 | 4/2003 |
| WO | WO-03/033503 | 4/2003 |
| WO | WO-03/033504 | 4/2003 |
| WO | WO-03/033505 | 4/2003 |
| WO | WO-03/037869 | 5/2003 |
| WO | WO-03/037891 | 5/2003 |
| WO | WO-03/045921 | 6/2003 |

| | | |
|---|---|---|
| WO | WO-03/050090 | 6/2003 |
| WO | WO-03/051366 | 6/2003 |
| WO | WO-03/057165 | 7/2003 |
| WO | WO-03/066575 | 8/2003 |
| WO | WO-03/078404 | 9/2003 |
| WO | WO-03/099771 | 12/2003 |
| WO | WO-04/000833 | 12/2003 |
| WO | WO-2004/005283 | 1/2004 |
| WO | WO-2004/018433 | 3/2004 |
| WO | WO-2004/024663 | 3/2004 |
| WO | WO-2004/032709 | 4/2004 |
| WO | WO-2004/037176 | 5/2004 |
| WO | WO-2004/037814 | 5/2004 |
| WO | WO-2004/039780 | 5/2004 |
| WO | WO 2004/046118 | 6/2004 |
| WO | WO-2004/052373 | 6/2004 |
| WO | WO-2004/054186 | 6/2004 |
| WO | WO-2004/056786 | 7/2004 |
| WO | WO-2004/058254 | 7/2004 |
| WO | WO-2004/058782 | 7/2004 |
| WO | WO-2004/060305 | 7/2004 |
| WO | WO-2004/060376 | 7/2004 |
| WO | WO-2004/069812 | 8/2004 |
| WO | WO-2004/071426 | 8/2004 |
| WO | WO-2004/074261 | 9/2004 |
| WO | WO-2004/074262 | 9/2004 |
| WO | WO-2004/074266 | 9/2004 |
| WO | WO-2004/080980 | 9/2004 |
| WO | WO 2004/080980 | 9/2004 |
| WO | WO-2004/097504 | 11/2004 |
| WO | WO-2005/016894 | 2/2005 |
| WO | WO-2005/026130 | 3/2005 |
| WO | WO-2005/026158 | 3/2005 |
| WO | WO2005026130 * | 3/2005 |
| WO | WO2006074057 * | 7/2006 |
| WO | WO-2006/128129 | 11/2006 |
| WO | WO-2006/131835 | 12/2006 |
| WO | WO-2007/008541 | 1/2007 |
| WO | WO2007008541 * | 1/2007 |
| WO | WO-2007/022380 | 2/2007 |
| WO | WO-2008/009458 | 1/2008 |

OTHER PUBLICATIONS

Banker, et. al., Modern Pharmaceuticals, (1996) p. 596.*
Dorwald F. A. Side Reactions in Organic Synthesis, 2005, Wiley: VCH, Weinheim p. IX of Preface.*
Bolen et al., "Expression and Interaction of the SRC family of Tyrosine Protein Kinases in T Lymphocytes", Adv. Cancer Res., vol. 57., 103-149, PMID 1950702, 1991.
Chawla et al., "Challenges in Polymorphism of Pharmaceuticals", CRIPS vol. 5, not, Jan.-Mar. 2004 ( "4 Pages").
Frohlich et al., "Inhibition of Neuronal Nitric Oxide Synthase by 4-Amino Pteridine Derivatives: Structures-Activity Relationship of Antagonists of (6R)-5,6,7,8- Tetrahydrobiopterin Cofactor", J. Med. Chem., vol. 42, 4108-4121, 1999.
Ghosh, et. al., Journal of Medicinal Chemistry, (1967), 10(5), 974-5.
Granelli-Piperno, "SRC-related proto-oncongenes and transcription factors in primary human T cells; modulation by cyclosporine A and FK506", J. Autoimmun., vol. 5, Suppl. A, 145-148, PMID.
Jacobson et al., Am J. Physiol Lung Cell Mol Physiol, 288, 1026-1032.
Kobayashi et al., "Functional coupling of the src-family protein tyrosine kinases p59fyn and p53/61yn with the interleukin 2 receptor: implications for redundancy and pleiotropism in cytokine signal transduction", Proc. Natl. Acad. Sci., USA vol. 1:90, No. 9, 4201-4205, Abstract PMID 8483935, May 1993.
Newman et al., "Solid-state analysis of the active pharmaceutical ingredient in drug products", DDT vol. 8, No. 19, Oct. 2003, p. 898-905.
O'Shea et al., "Expression of v-src in a Murine T-cell Hybridoma Results in Constitutive T-cell Receptor Phosphorylation and Interleukin 2 Production", Proc. Natl. Acad. Sci., 88:1741-1745 (1991).
Taghavi-Moghadam et al., "A New, General and Regioselective Method for the Synthesis of 2,6-Disubstituted 4-Aminopteridines", Elsevier Science Ltd., Pergamon, 6835-6836, 1997.
Tanaka et al., "novel human tyrosine kinase gene inducible in T cells by interleukin 2", *FEBS* Lett., vol. 7:324, No. 1, 1-5, PMID 9504851, Jun. 1993.
Torigoe et al., "Regulation of SRC-family protein tyrosine kinases by interleukin, IL-2, and IL-3", Leukemia, vol. 6, Supplemental 3, 94S-97S, PMID 1602836, 1992.
Vippagunta et. al. Advanced Drug Delivery Reviews 48 (2001) 3-26.
Weber, Molecular Approaches to Study Cellular Roadblocks to Transfection and Transduction (Non-Viral Vectors and AAV-Based Vectors for Gene Therapy), <http://www.mssm.edu/genetherapy/weber.htm>, 1-8, Nov. 11, 2002.
Wills et al., The New England Journal of Medicine, 2005, 353, 9, 877-889.
Yamamoto et al., "Role of src-like protooncogenes in lymphocotye proliferation", Princess Takamastu Symp., vol. 22, 293-305 Review, PMID 1668889, 1991.
http://en.wikipedia.org/wiki/Acute_respiratory_distress_syndrome (Last visited Dec. 10, 2007).
http://www.emedicinehealth.com/acute_respiratory_distress_syndrome/page2_em.htm (Dec. 10, 2007).
http://www.mayoclinic.com/health/stroke/DS00150/DSECTION=7 (Last visited Dec. 10, 2007).
http://www.medscape.com/viewarticle/544205_print (Last visited Dec. 10, 2007).
New Mexico Department of Health, INTERLEUKIN-2, http://www.aidsinfonet.org. *A Project of the New Mexico Aids Education and Training Center*, Fact Sheet No. 622, Apr. 30, 2002.

* cited by examiner

| Compound | Primary Target | Selectivity Profile |
|---|---|---|
| | JAK2 IC$_{50}$ | JAK2 vs. JAK3 (X-fold selectivity) |
| LVII | 12.5 | 83 |

| kinase | % inhibition | kinase | % inhibition |
|---|---|---|---|
| ACVR1B (ALK4) | -7 | RPS6KA3 (RSK2) | 14 |
| AKT1 (PKB alpha) | 1 | SRC | 60 |
| BRAF | -2 | STK24 (MST3) | 5 |
| CHEK1 (CHK1) | 19 | SYK | 43 |
| CSK | 20 | TYRO3 (RSE) | 46 |
| CSNK1G2 (CK1 gamma 2) | 11 | YES1 | 54 |
| CSNK2A1 (CK2 alpha 1) | 4 | ZAP70 | -9 |
| DYRK3 | -9 | ABL1 | 77 |
| EPHA2 | 16 | BMX | 36 |
| ERBB2 (HER2) | -5 | BTK | 31 |
| FES (FPS) | 60 | CDK1/cyclin B | 5 |
| FGFR1 | 56 | CSNK1A1 (CK1 alpha 1) | -2 |
| FGR | 67 | EGFR (ErbB1) | 17 |
| FLT4 (VEGFR3) | 66 | EPHA1 | 57 |
| HCK | 36 | FGFR2 | 64 |
| IGF1R | 33 | FLT1 (VEGFR1) | 9 |
| IRAK4 | 13 | FLT3 | |
| KIT | 16 | GSK3B (GSK3 beta) | 6 |
| KIT T670I | 4 | INSR | 21 |
| LYN A | 57 | MAP2K1 (MEK1) | 0 |
| MAP4K4 (HGK) | 3 | MAPK14 (p38 alpha) | 1 |
| MAPK3 (ERK1) | -2 | MET (cMet) | 11 |
| MAPKAPK2 | -10 | MYLK2 (skMLCK) | 7 |
| NEK2 | 3 | PDGFRB (PDGFR beta) | 32 |
| NTRK1 (TRKA) | 78 | PRKCB1 (PKC beta I) | 12 |
| PHKG2 | 2 | PTK2 (FAK) | 66 |
| PIM1 | 3 | RPS6KB1 (p70S6K) | 20 |
| PRKACA (PKA) | 10 | STK6 (Aurora A) | 34 |
| RET | | TEK (Tie2) | 11 |
| ROCK1 | -6 | | |

FIG. 17

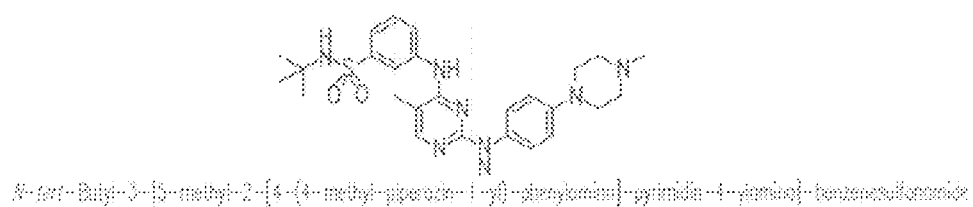
N-tert-Butyl-3-[5-methyl-2-[4-(4-methyl-piperazin-1-yl)-phenylamino]-pyrimidin-4-ylamino]-benzenesulfonamide
FIG.31A
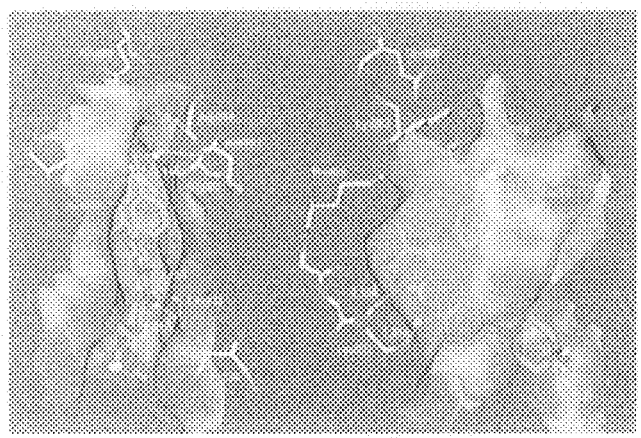
FIG.31B
| | JAK2 | JAK3 | KDR | Flt3 |
|---|---|---|---|---|
| IC50 (nM) | 6 | 160 | 150 | 25 |
FIG.31C

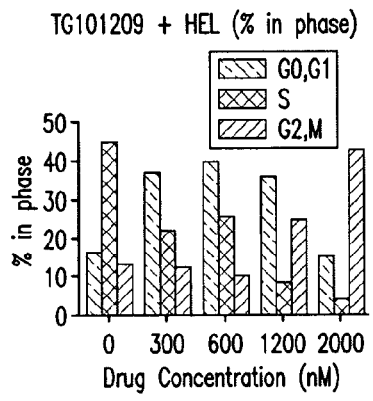
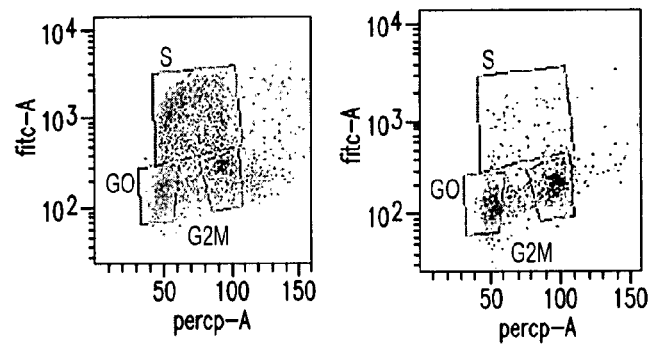
FIG.34A  FIG.34B
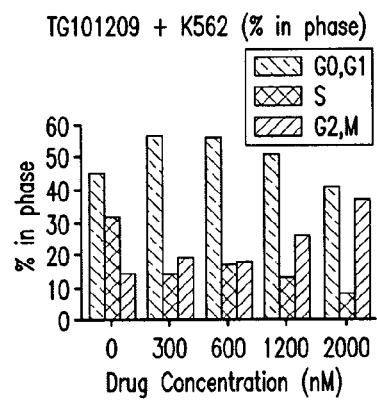
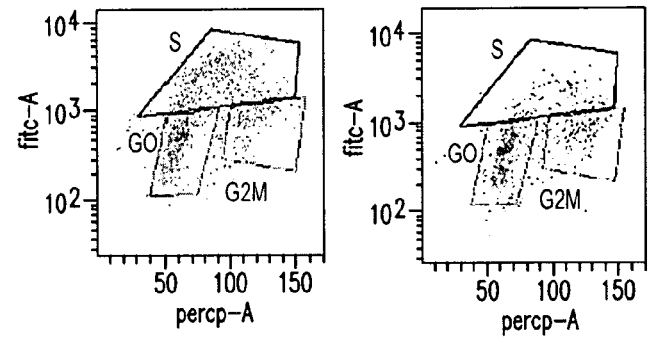
FIG.34C  FIG.34D

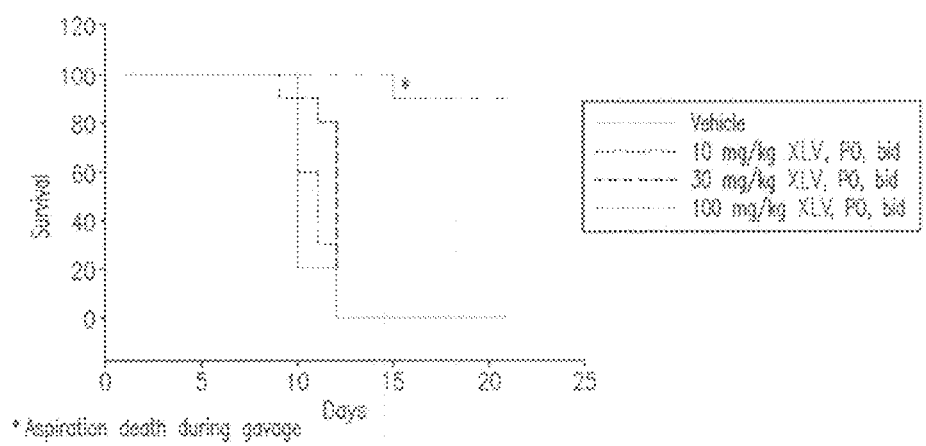
FIG.36A
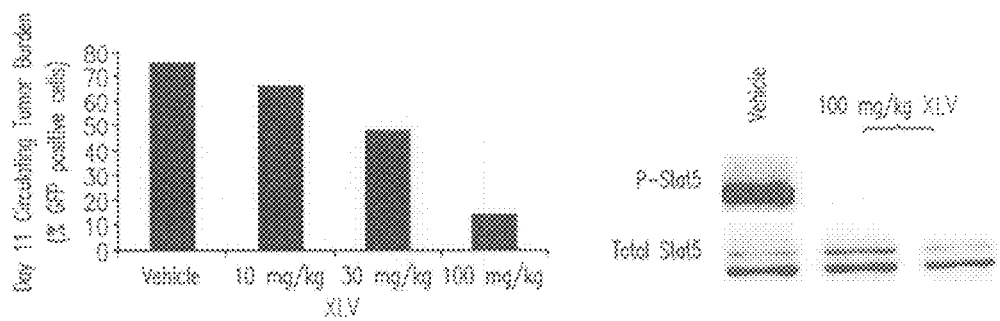
FIG.36B
FIG.36C

XLV in vivo study data using a circulating tumor model

———— Vehicle
………… 10 mg/kg XLV, PO, bid
— — — — 30 mg/kg XLV, PO, bid
— · — · — 100 mg/kg, XLV, PO, bid
*Death due to aspiration of trachea during oral gavage Drug given orally bid beginning on day 3 after tumor injection

BI-ARYL META-PYRIMIDINE INHIBITORS OF KINASES

CROSS REFERENCE TO RELATED APPLICATIONS

This application is a continuation-in-part application of U.S. patent application Ser. No. 11/588,638 filed Oct. 26, 2006 now U.S. Pat. No. 7,528,143, which claims the benefit of priority under 35 U.S.C. §119(e) of U.S. Patent Applications Ser. Nos. 60/732,629 filed Nov. 1, 2005, and 60/838,003 filed Aug. 15, 2006, the entire content of which is incorporated herein by reference.

FIELD OF INVENTION

The present invention relates to the field of inhibitors of protein tyrosine kinases, their pharmaceutically acceptable compositions comprising the compounds of the invention and the methods of using the compositions in the treatment of various disorders. In particular, the present invention relates to inhibitors of the JAK family of protein tyrosine kinases.

BACKGROUND OF INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited too cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Protein kinases have emerged as an important class of enzymes as targets for therapeutic intervention. In particular, the JAK family of cellular protein tyrosine kinases (Jak1, Jak2, Jak3, and Tyk2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-αs/β/ω/Limitin, IFN-γ, IL-10, IL-19, IL-20, IL-22), the gp130 family (IL-6, IL-11, OSM, LIF, CNTF, NNT-1/BSF-3, G-CSF, CT-1, Leptin, IL-12, IL-23), γC family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

Until recently, the therapeutic potential of JAK inhibitors has focused on diseases affecting various pathologies of the immune system. These include, but are not limited to atopy (allergic asthma, atopic dermatitis, allergic rhinitis), cell mediated hypersensitivity (allergic contact dermatitis, hypersensitivity pneumonitis), rheumatic diseases (systemic lupus erythematosus (SLE), rheumatoid arthritis, juvenile arthritis, Sjogren's Syndrome, scleroderma, polymyositis, ankylosing spondylitis, psoriatic arthritis), transplantation (transplant rejection, graft vs host disease), viral diseases (Epstein Barr Virus, Hepatitis B, Hepatitis C, HIV, HTLV1, Vaicella-Zoster Virus, Human Papilloma Virus), cancer (leukemia, lymphoma), cardiovascular disease (cardiac hypertrophy, atherosclerosis and arteriosclerosis), neurodegenerative diseases (motor neuron disease), food allergy, inflammatory bowel disease, Crohn's disease, cutaneous inflammation, and immune suppression induced by solid tumors. Most efforts to date have targeted JAK3 inhibition for immunosuppression, for example organ transplantation and allograft acceptance (for a review, see Borie et al. Current Opinion in Investigational Drugs, 2003, 4(11), 1297).

Most recently, two significant findings of the role of the EPO-JAK2 signaling pathway in myeloproliferative disorders and proliferative diabetic retinopathy were found. First, a gain-of-function, somatic (acquired) mutation of the JAK2 kinase (V617F) was reported to be a causative factor in a number of "typical" myeloproliferative disorders, including polycethemia vera, essential thrombocythemia and melofibrosis with myeloid metaplasia, and the mutation has been found in patients with either "atypical" myeloproliferative disorders and myelodysplastic syndrome (for reviews see Tefferi and Gilliland, Cell Cycle 2005, 4(8), e61; Pesu et. al. Molecular Interventions 2005, 5(4), 211). Additionally it was found that (a) the V617F JAK2 mutation was associated with constitutive phosphorylation of JAK2 and its downstream effectors as well as induction of erythropoietin hypersensitivity in cell based experiments, (b) V617F JAK2-indcued cell proliferation signals were inhibited by small molecule inhibitors of JAK2, and (c) murine bone marrow transduced with a retrovirus containing V617F JAK2 incuded erythrocytosis in the transplanted mice.

Furthermore, recently it has been found that mutations in EPO-R also keep the JAK pathway constitutively activated leading to myleoproliferative disorders.

Second, EPO was found to be a potent angiogenic factor in proliferative diabetic retinopathy, a major cause of vision loss affecting diabetic, working-age persons (see for example Aiello, New England Journal of Medicine, 2005, 353 (8), 839; Watanabe et al. New England Journal of Medicine 2005 353 (8), 782).

Further, findings from the Watanabe research showed (a) intraocular EPO levels and VEGF (another well-known angiogenic factor in proliferative diabetic retinopathy) were significantly higher among those with proliferative diabetic retinopathy than those with quiescent disease or non-diabetic control, (b) EPO and VEGF levels were not closely correlated, (c) EPO levels were more strongly correlated with the presence of proliferative diabetic retinopathy than VEGF, (d) EPO stimulated growth and intracellular signaling in retinal endothelial cells, and (e) inhibitors of either EPO or VEGF reduced hypoxia-induced retinal neovascularization in rodent models.

Recently it has been shown that mutations in the EPO receptor may also affect the signaling related to the JAK pathway and this may have implications in terms of disease states where JAK signaling is important in the cell cycle.

There is another feature regarding inhibitors of the JAK pathway. It has been demonstrated that the JAK pathway may be recruited in cell survival and proliferation. For example, in the case of the cells that are Philadelphia chromosome positive that result in chronic myelogenous leukemia (CML), there is evidence that the Jak pathway is recruited in constitutive activation. Accordingly, using a JAK inhibitor may have use in CML in which the Philadephia chromosome has been shown to produce the hybrid Bcr-Abl, thus keeping cells constitutively active.

More telling is that in cases of resistance mutations that arise on account of specific inhibitors to BCR-ABL, as in the case of the T315I gatekeeper mutation, or any other mutation, it may be possible to use a JAK inhibitor on account of the pathway used by the BCR-ABL mutant (as in the case of BCR-ABL(T315I) mutation) utilizing the Jak pathway. Thus Jak inhibitors may be used in the treatment of patients with resistance to known therapies where BCR-ABL is directly targeted and drug resistance has now been shown as the dominant (50-90%) of all resistance in patients where existing therapies fail.

The use of JAK inhibitors may also find utility in other myeloid disease states, both blood disorders and other disease states with myeloid implications, and other disease states in which the JAK pathway is implicated directly or indirectly.

Accordingly, there is a need to develop compounds useful as inhibitors of kinases, particularly, JAK kinase, given the inadequate treatments available for the aforementioned diseases where the JAK signaling pathway is dysregulated, or recruited directly or indirectly.

SUMMARY

According to one embodiment, a compound having the structure (A) is provided:

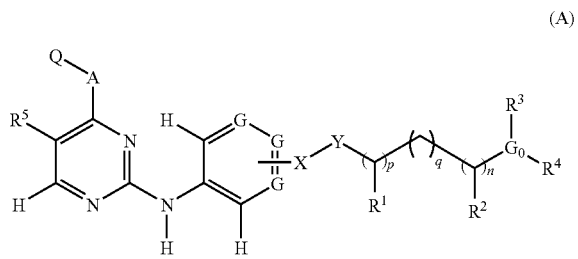

(A)

According to another embodiment, a method is provided for treating an angiogenic-associated disorder, the method including administering to a subject in need thereof a therapeutically effective amount of at least one compound having the structure (A), or pharmaceutically acceptable salts, hydrates, solvates, polymorphs, crystal forms, N-oxides, and individual enatiomers and diastereomers thereof, to a subject in need of such treatment.

According to other embodiments, pharmaceutical compositions and articles of manufacture are provided, including at least one compound having the structure (A), or pharmaceutically acceptable salts, hydrates, solvates, crystal forms and individual diastereomers thereof.

BRIEF DESCRIPTION OF THE FIGURES

FIG. 17 provides an illustration of high selectiveness of a compound of the present invention as an inhibitor for variety of kinases.

FIG. 31 shows a compound of the present invention and its selectiveness as a JAK2 inhibitor in vitro.

FIG. 34 shows selectively inducement of cell cycle arrest of JAK2V617F-expressing cells by a compound of the present invention.

FIG. 36 shows treatment OF JAK2V617F-induced hematopoietic malignancy in mice by a compound of the present invention.

DETAILED DESCRIPTION

A. Terms and Definitions

Figure 1:
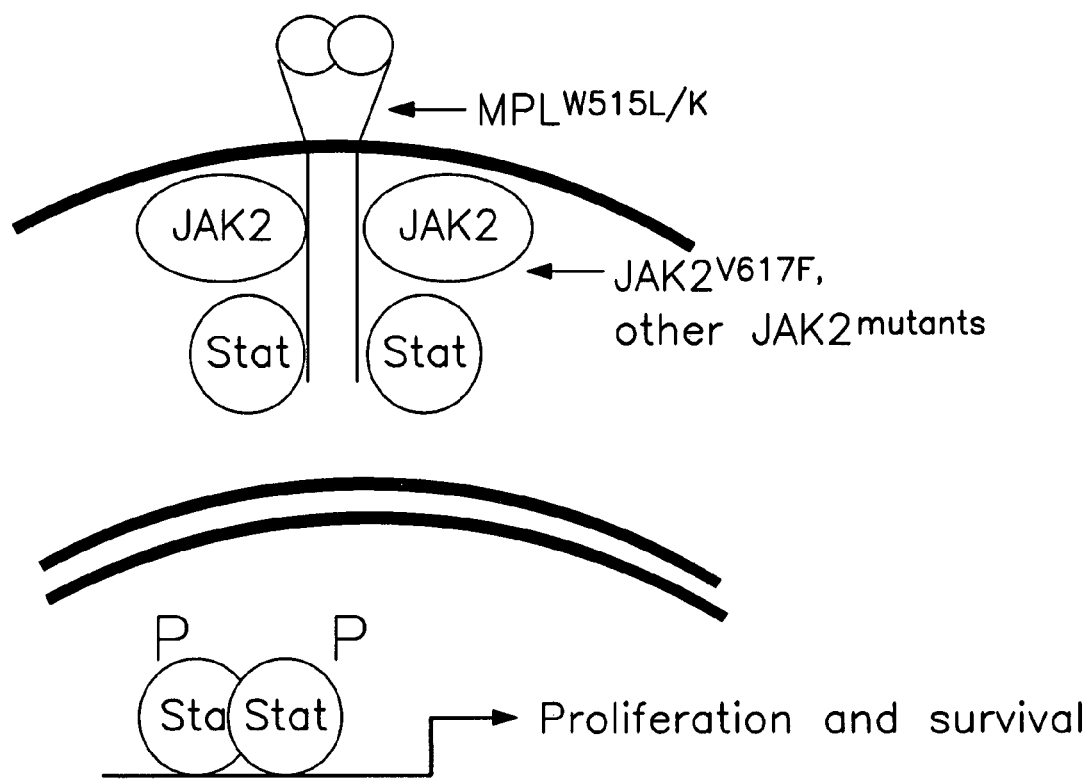
FIG. 1 is a schematic illustration of JAK2 signaling pathway.

The following terminology and definitions apply as used in the present application, generally in conformity with the terminology recommended by the International Union of Pure and Applied Chemistry (IUPAC):

The term "heteroatom" refers to any atom other than carbon, for example, N, O, or S.

The term "aromatic" refers to a cyclically conjugated molecular entity with a stability, due to delocalization, significantly greater than that of a hypothetical localized structure, such as the Kekulé structure.

The term "heterocyclic," when used to describe an aromatic ring, refers to the aromatic rings containing at least one heteroatom, as defined above.

The term "heterocyclic," when not used to describe an aromatic ring, refers to cyclic (i.e., ring-containing) groups other than aromatic groups, the cyclic group being formed by between 3 and about 14 carbon atoms and at least one heteroatom described above.

The term "substituted heterocyclic" refers, for both aromatic and non-aromatic structures, to heterocyclic groups further bearing one or more substituents described below.

The term "alkyl" refers to a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The term "lower alkyl" refers to alkyl groups having from 1 to about 6 carbon atoms.

The term "substituted alkyl" refers to alkyl groups further bearing one or more substituents such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substituents described above.

The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substituents described above.

The term "aryl" refers to aromatic groups having between about 5 and about 14 carbon atoms and the term "substituted aryl" refers to aryl groups further bearing one or more substituents described above.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substituents described above.

The term "alkoxy" refers to the moiety —O-alkyl, wherein alkyl is as defined above, and the term "substituted alkoxy" refers to alkoxy groups further bearing one or more substituents described above.

The term "cycloalkyl" refers to alkyl groups having between 3 and about 8 carbon atoms arranged as a ring, and the term "substituted cycloalkyl" refers to cycloalkyl groups further bearing one or more substituents described above.

The term "alkylaryl" refers to alkyl-substituted aryl groups and the term "substituted alkylaryl" refers to alkylaryl groups further bearing one or more substituents described above.

The term "arylalkyl" refers to aryl-substituted alkyl groups and the term "substituted arylalkyl" refers to arylalkyl groups further bearing one or more substituents described above.

The term "arylalkenyl" refers to aryl-substituted alkenyl groups and the term "substituted arylalkenyl" refers to arylalkenyl groups further bearing one or more substituents described above.

The term "arylalkynyl" refers to aryl-substituted alkynyl groups and the term "substituted arylalkynyl" refers to arylalkynyl groups further bearing one or more substituents described above.

The term "arylene" refers to divalent aromatic groups having between 5 and about 14 carbon atoms and the term "substituted arylene" refers to arylene groups further bearing one or more substituents described above.

The term "chemically connected" is defined as forming a chemical entity in which two moieties form a direct chemical bond between them.

The term "kinase" refers to any enzyme that catalyzes the addition of phosphate groups to a protein residue; for example, serine and threonine kinases catalyze the addition of phosphate groups to serine and threonine residues.

The term "JAK kinase" refers to an enzyme found in cells in the immune system that participates in the cell signaling process resulting in the development of white blood cells.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "antibody" refers to intact molecules of polyclonal or monoclonal antibodies, as well as fragments thereof, such as Fab and F(ab')$_2$, Fv and SCA fragments which are capable of binding an epitopic determinant.

The term "vasculostasis" refers to the maintenance of the homeostatic vascular functioning leading to the normal physiologic functioning.

The term "vasculostatic agents" refers to agents that seek to address conditions in which vasculostasis is compromised by preventing the loss of or restoring or maintaining vasculostasis.

B. Embodiments of the Invention

According to an embodiment of the invention, compounds having the structure (A) are provided for treatment of various diseases, disorders, and pathologies:

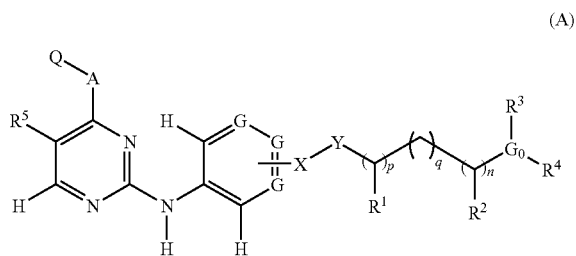

(A)

In the structure (A), X can be any of a bond, O, C=O, SO$_2$, or CH$_2$ and Y can be a bond or NR$^9$; or X and Y taken together can be a bond. Further, in the structure (A) each of R$^1$ and R$^2$ can be any of H, C$_1$-C$_6$ substituted or unsubstituted alkyl, substituted or unsubstituted cycloalkyl, substituted or unsubstituted heterocycle, substituted or unsubstituted aryl, or substituted or unsubstituted heteroaryl; or R$^1$ and R$^2$ taken together can be a bond; or R$^1$ and R$^2$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$, wherein each of p, q, r, n, m is independently an integer having the value between 0 and 6.

Further, in the structure (A) R$^9$ can be one of H, C$_1$-C$_6$ alkyl, C$_1$-C$_6$ cycloalkyl, C$_1$-C$_6$ branched alkyl, C$_1$-C$_6$ substituted alkyl, C$_1$-C$_6$ aminoalkyl, or C$_1$-C$_6$ hydroxyalkyl; G$_0$ can be one of N, O, H, of CH, with the proviso that if G$_0$ is N, then each of R$^3$ and R$^4$ can be one of H, C$_1$-C$_6$ alkyl, C$_1$-C$_6$ substituted or unsubstituted hydroxyalkyl or aminoalkyl, C$_1$-C$_6$ substituted or unsubstituted branched alkyl, substituted or unsubstituted aryl, or substituted or unsubstituted heteroaryl, or R$^3$ and R$^4$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$.

There are some additional provisos further directed to G$_0$ in the structure (A). More specifically, if G$_0$ is N, then R$^1$ and R$^9$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)m; or R$^1$ and R$^4$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)m; or R$^9$ and R$^4$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$; or R$^3$ and R$^4$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^6$—(CH$_2$)$_m$, or (CH$_2$)$_r$—O—(CH$_2$)$_m$.

If in the structure (A) G$_0$ is O, then R$^3$ can be one of H, C$_1$-C$_6$ alkyl and C$_1$-C$_6$ substituted or unsubstituted hydroxyalkyl or aminoalkyl, substituted or unsubstituted branched alkyl, substituted or unsubstituted cycloalkyl, substituted heterocyclic connected through carbon or nitrogen, substituted or unsubstituted aryl, or substituted or unsubstituted heteroaryl connected through carbon or nitrogen, with no group R$^4$; R$^1$ and R$^9$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$; or R$^1$ and R$^3$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$; or R$^9$ and R$^3$ taken together can form a moiety such as one of (CH$_2$)$_m$, (CH$_2$)$_r$—S—(CH$_2$)$_m$, (CH$_2$)$_r$—SO—(CH$_2$)$_m$, (CH$_2$)$_r$—SO$_2$—(CH$_2$)$_m$, (CH$_2$)$_r$—NR$^9$—(CH$_2$)$_m$, or (CH$_2$)$_r$—O—(CH$_2$)$_m$.

If in the structure (A) G$_0$=CH, then each of R$^3$ and R$^4$ can be one of H, C$_1$-C$_6$ alkyl, C$_1$-C$_6$ substituted or unsubstituted hydroxyalkyl or aminoalkyl, C$_1$-C$_6$ substituted or unsubstituted branched alkyl, substituted or unsubstituted aryl, C$_1$-C$_6$ substituted or unsubstituted heterocycle connected through carbon or nitrogen, or substituted or unsubstituted heteroaryl connected through carbon or nitrogen, or R$^3$ and R$^4$ taken together can form a moiety such as one of (CHR$^9$)$_r$—(CHR$^9$)$_m$—(CHR$^9$)$_p$, (CHR$^9$)$_r$—S—(CHR$^9$)$_m$, (CHR$^9$)$_r$—SO—(CHR$^9$)$_m$, (CHR$^9$)$_r$—SO$_2$—(CHR$^9$)$_m$, (CHR$^9$)$_r$—NR$^9$—(CHR$^9$)$_m$, or (CHR$^9$)$_r$—O—(CHR$^9$)$_m$.

Further, in the structure (A) G can be N or CR$^6$, and each G is independent of each other G, with the further proviso that not more than two groups G can be N, with the further proviso that for each CR$^6$, each R$^6$ is independent of each other group R$^6$.

Further, in the structure (A) R$^5$ is methyl and the moiety Q is as shown below

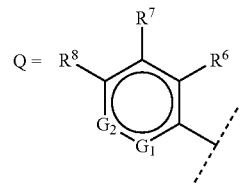

In the moiety Q, each of R$^6$, R$^7$, R$^8$ can be one of H, C$_1$-C$_6$ substituted or unsubstituted alkyl, C$_1$-C$_6$ substituted or unsubstituted alkenyl, C$_1$-C$_6$ substituted or unsubstituted alkynyl, C$_1$-C$_6$ substituted or unsubstituted hydroxyalkyl or aminoalkyl, C$_1$-C$_6$ substituted or unsubstituted branched alkyl, C$_1$-C$_6$ substituted or unsubstituted cycloalkyl, substituted or unsubstituted aryl connected through carbon or a heteroatom, substituted or unsubstituted heteroaryl connected through carbon or a heteroatom, C$_1$-C$_6$ alkoxy, a halogen, CF$_3$, —OCF$_3$, CHR$^3$R$^4$, SR$^3$, SOR$^3$, SO$_2$R$^3$, SO$_2$NR$^3$R$^4$, SO$_3$R$^3$, POR$^3$, PO$_2$R$^3$, PO$_2$NR$^3$R$^4$, PO$_2$CR$^3$R$^4$, PO$_3$R$^3$, NR$^3$R$^4$, NO$_2$, CN, OH, CONR$^3$R$^4$, COR$^3$, COOR$^3$, NR$^3$COR$^4$, NR$^3$CONR$^3$R$^4$, OCONR$^3$R$^4$, CSNR$^3$R$^4$, CSR$^3$, NR$^3$CSNR$^3$R$^4$, SCONR$^3$R$^4$, SCSNR$^3$R$^4$, or SCSNR$^3$R$^4$; or any of R$^6$ and R$^7$ taken together, or R$^7$ and R$^8$ taken together, or R$^6$ and R$^8$ taken together can form a moiety independently selected from any of —HN—CH=CH—, —HN—N=CH—, —HN—N=N—, —O(CH$_2$)$_n$O—, —S(CH$_2$)$_n$S—, —N=CH—S—, —CH=N—O—, —CH=N—S—, —N=CH—O—, —C=N—O—, —C=N—O—, —CH=CH—CH=CH—, —N=CH—CH=CH—, —CH=N—CH=CH—, —O—CH=CH, and —S—CH=CH—; or $R^3$ and $R^4$ taken together can form a moiety such as one of $(CHR^9)_r$—$(CHR^9)_m$—$(CHR^9)_p$, $(CHR^9)_r$—S—$(CHR^9)_m$, $(CHR^9)_r$—SO—$(CHR^9)_m$, $(CHR^9)_r$—$SO_2$—$(CHR^9)_m$, $(CHR^9)_r$—$NR^9$—$(CHR^9)_m$, or $(CHR^9)_r$—O—$(CHR^9)_m$.

Further, in the structure (A), A can be one of O, $NR^3$, $CR^3R^4$, S, SO, and $SO_2$; and in the moiety Q, $G_1$ can be any of CH, N, NH, S, and O, and $G_2$ can be any of $CR^7$, N, NH, S, and O, with each group $R^7$ being independent of every other group $R^7$; and if $G_1$ or $G_2$ is NH, S, or O, then Q is a five membered heteroaromatic ring, optionally fused to a six member aromatic or non-aromatic ring; and if $G_1$ or $G_2$ is N, then Q is a five or a six membered aromatic ring, optionally fused to a six member aromatic or non-aromatic ring, with the further proviso that X or $G_0$ includes at least one heteroatom included with X and selected from O, S and N, or $G_0$ comprises at least four non-hydrogen atoms, inclusive of the heteroatom, and $R^3$ and $R^4$, or $R^1$ and $R^9$, or $R^1$ and $R^4$, or $R^9$ and $R^4$ taken together can form an aromatic, heteroaromatic, cyclic or heterocyclic ring system, or if a noncyclic system is present, then more than one heteroatom is present, and if A is $NR_3$, then any of $R_6$, $R_7$ or $R_8$, or any combination thereof independently includes at least two non-hydrogen substituents, or if A is $NR_3$, then Q forms a fused ring from $R_6$ to $R_7$, or from $R_7$ to $R_8$.

Some exemplary compounds described by structure (A) that can be used include, but are not limited to, the following compounds I through CLXII shown below:

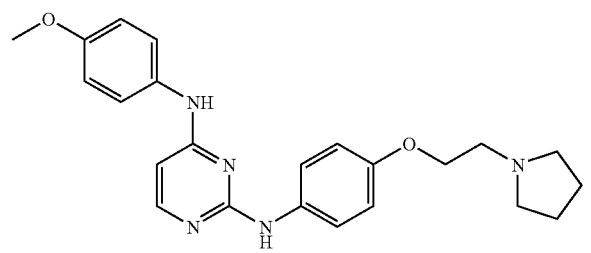

I

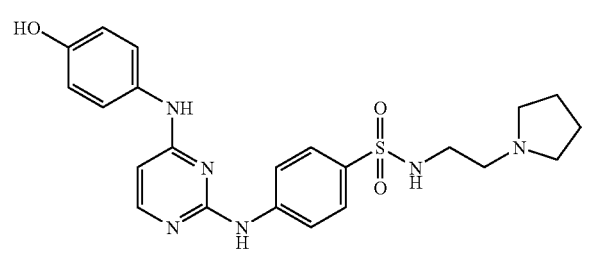

II

III

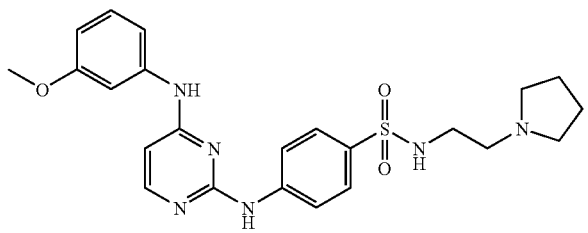

IV

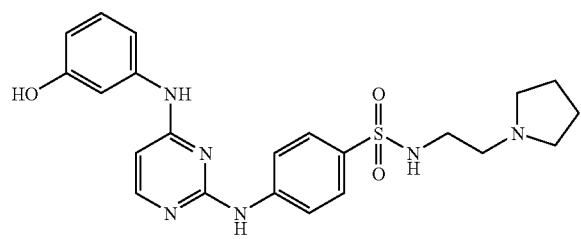

V

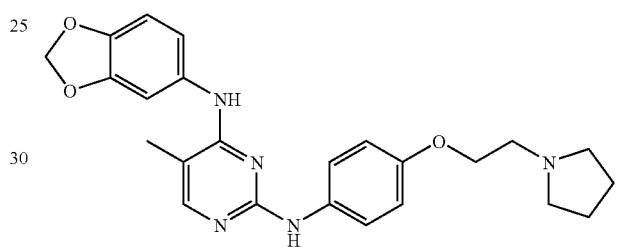

VI

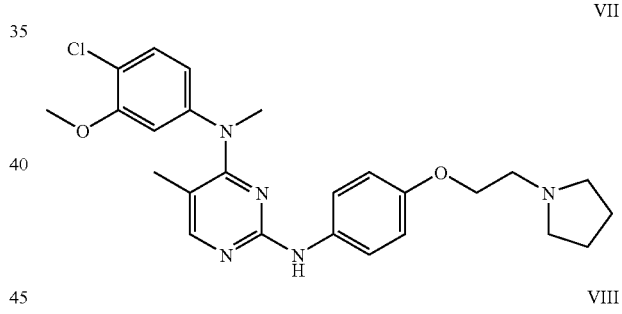

VII

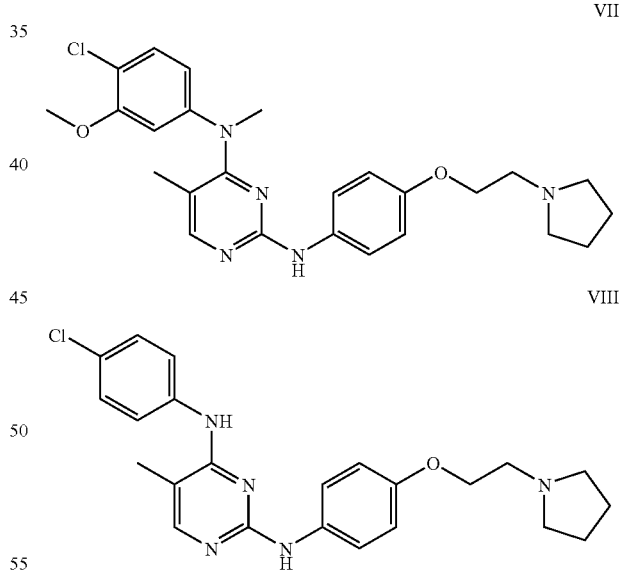

VIII

IX

-continued
X
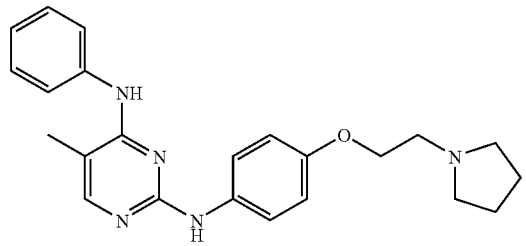
XI
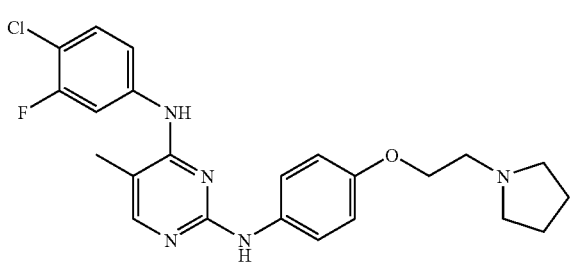
XII
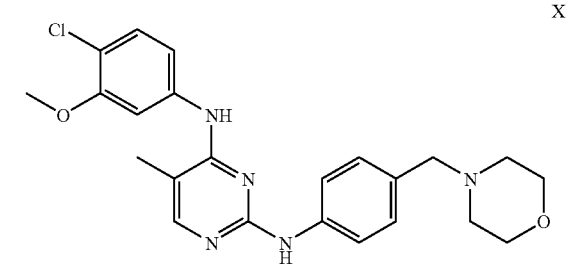
XIII
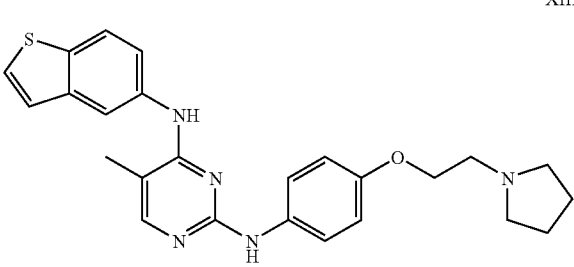
XIV
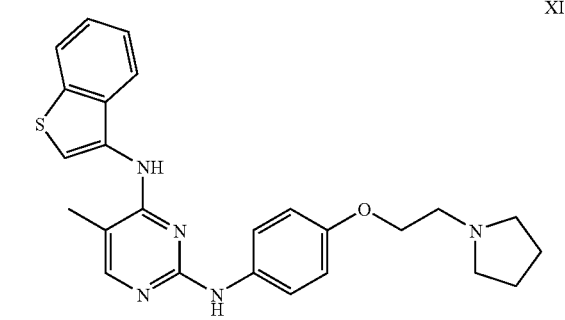
XV
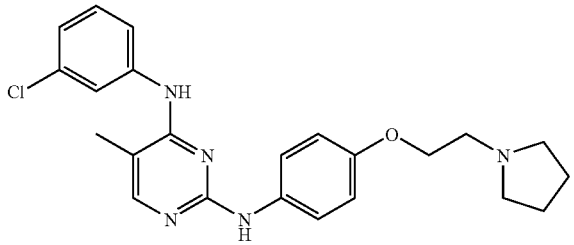
-continued
XVI
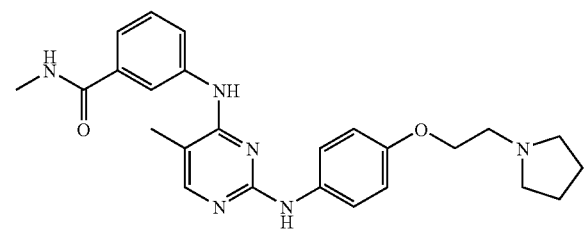
XVII
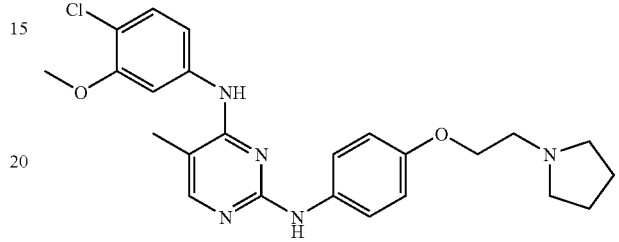
XVIII
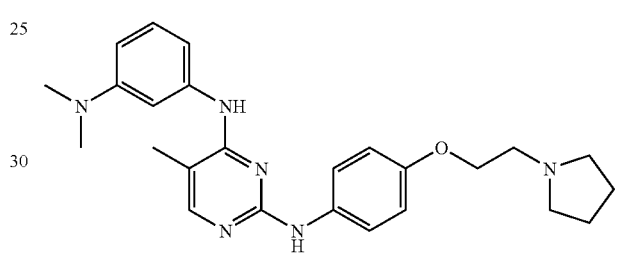
XIX
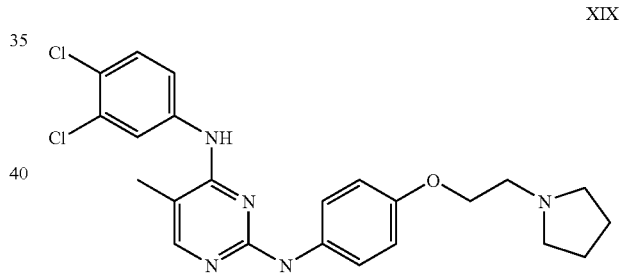
XX
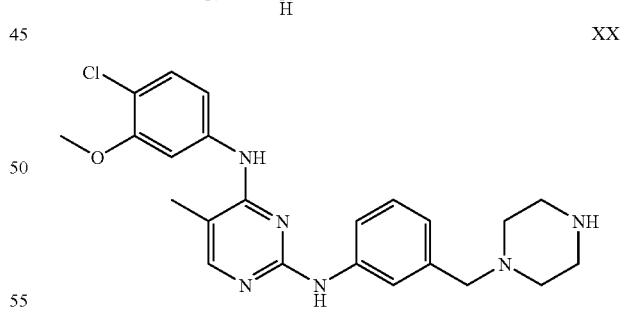
XXI
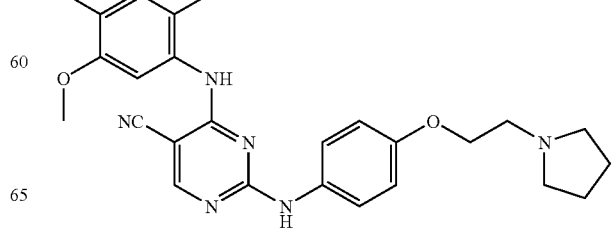

XXII
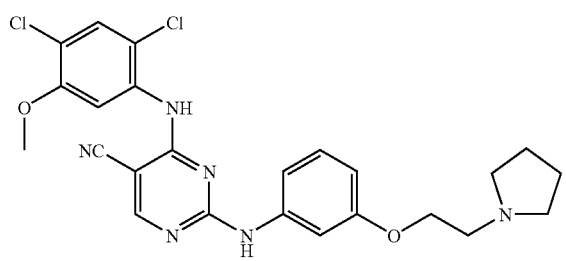
XXVII
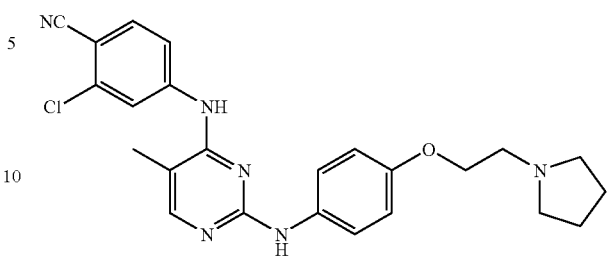
XXIII
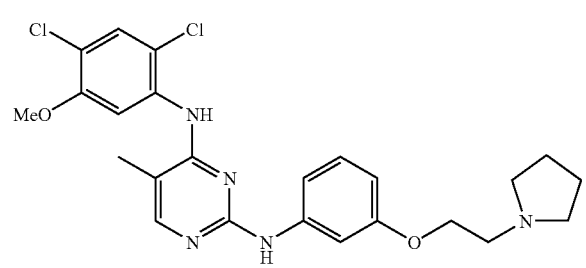
XXVIII
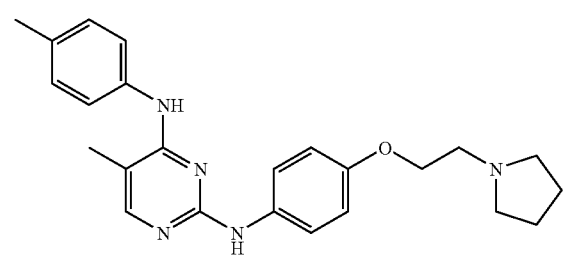
XXIV
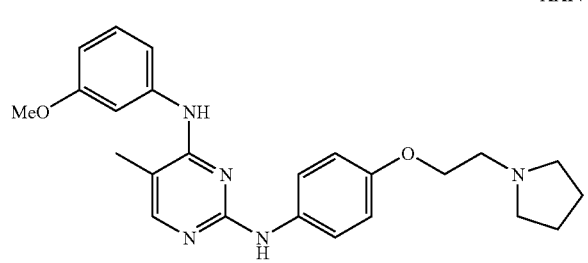
XXIX
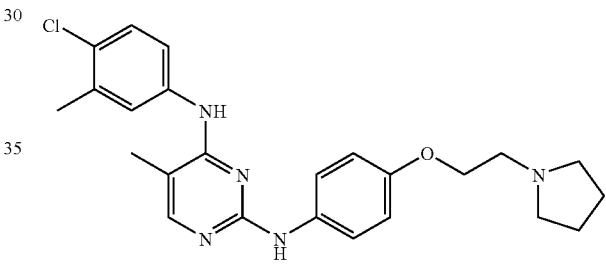
XXV
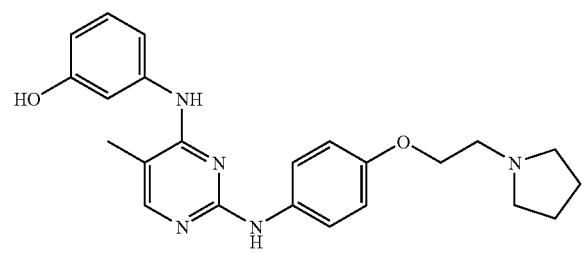
XXX
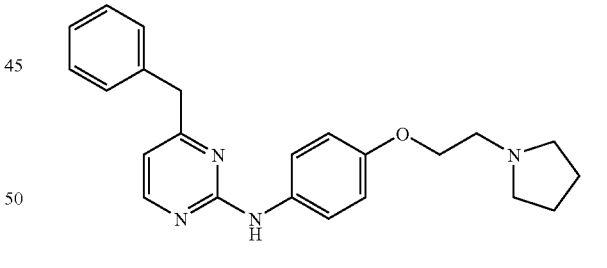
XXVI
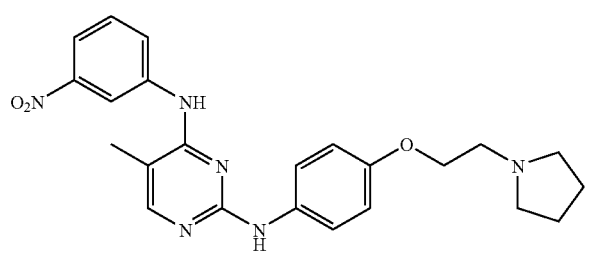
XXXI
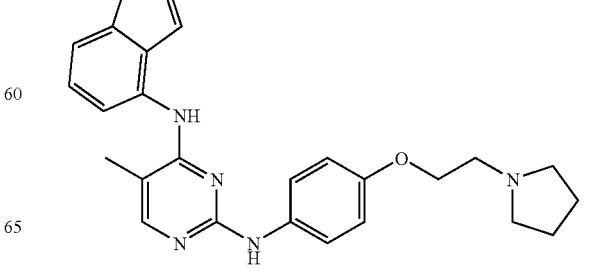

XXXII
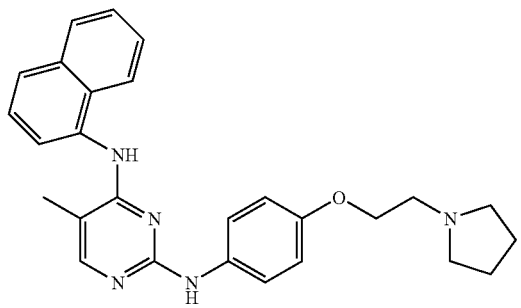
XXXIII
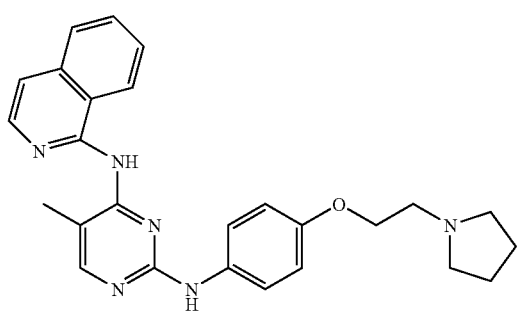
XXXIV
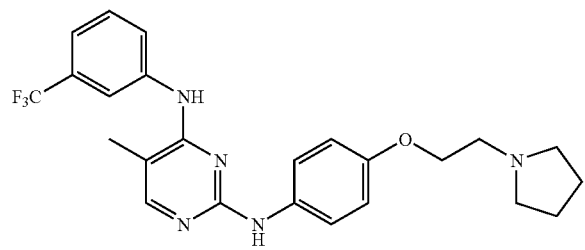
XXXV
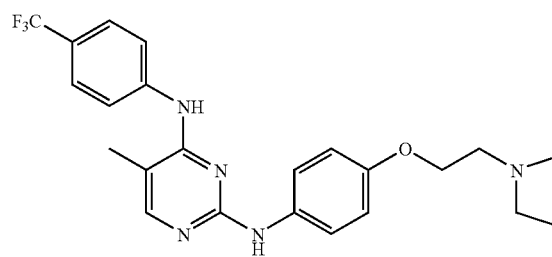
XXXVI
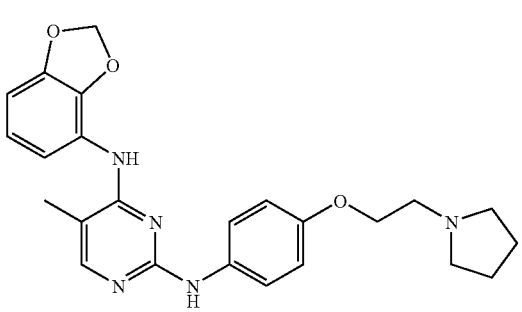
XXXVII
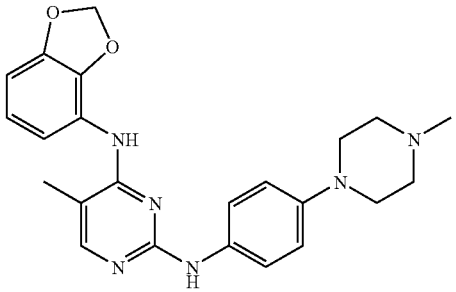
XXXVIII
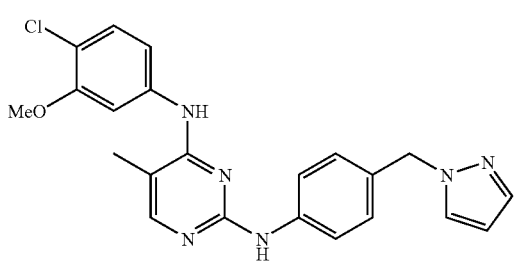
XXXIX
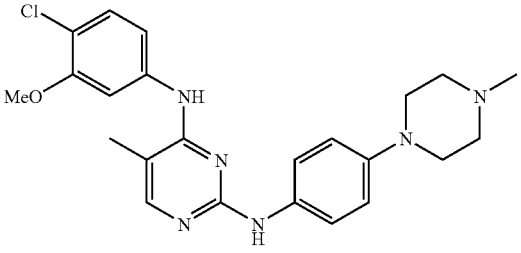
XL
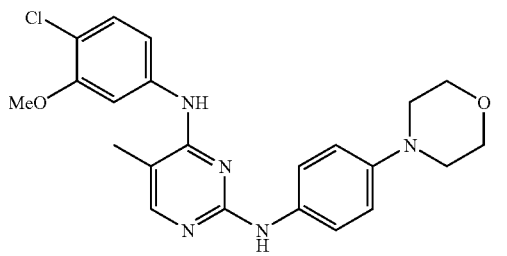
XLI
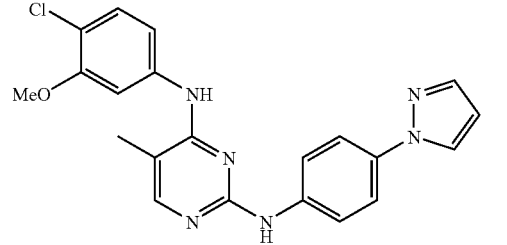
XLII
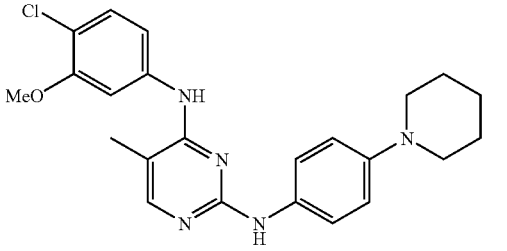

-continued
XLIII
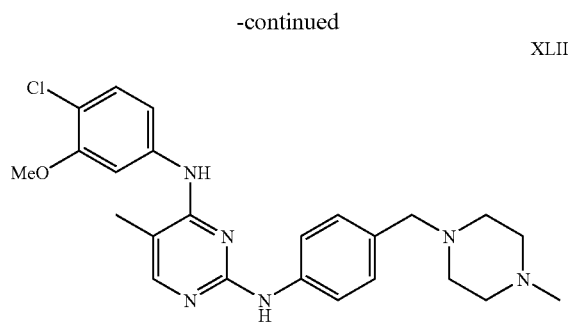
XLIV
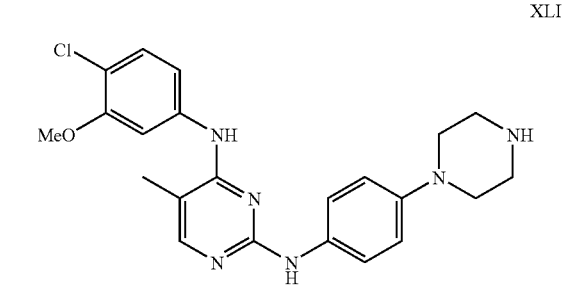
XLV
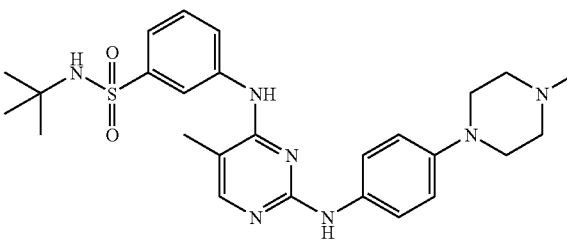
XLVI
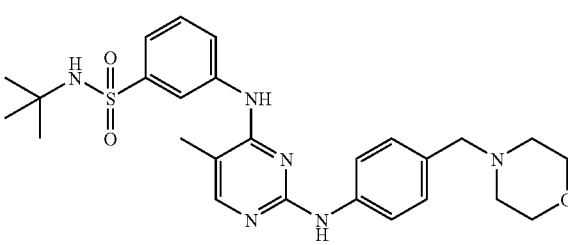
XLVII
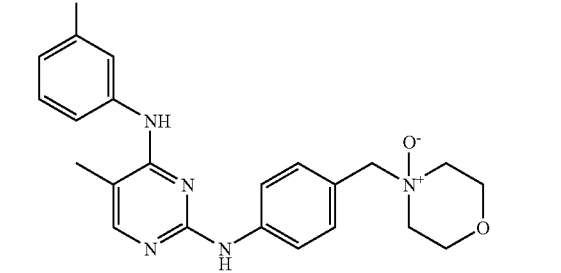
-continued
XLVIII
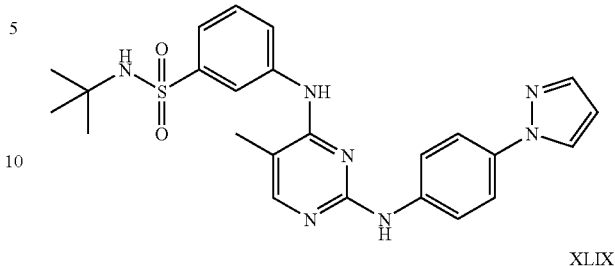
XLIX
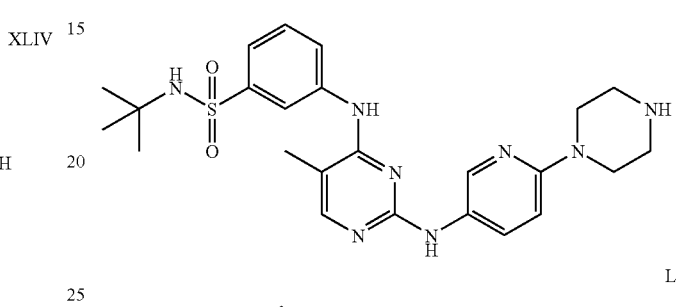
L
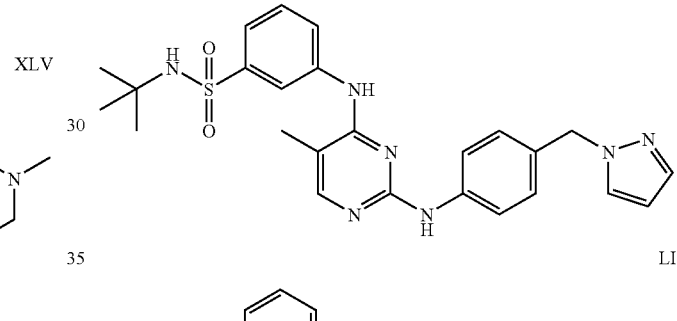
LI
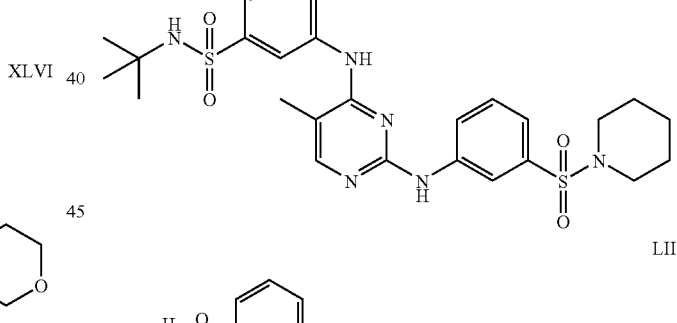
LII
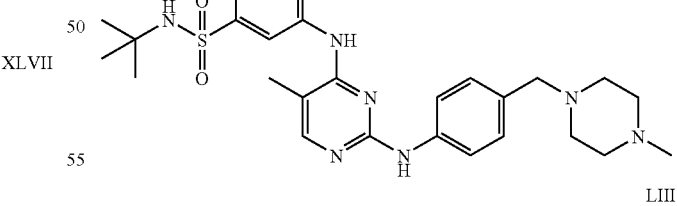
LIII
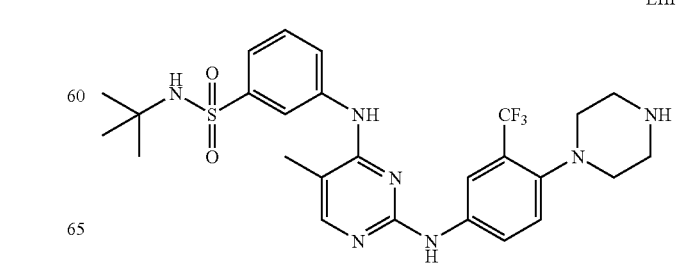

-continued
LIV
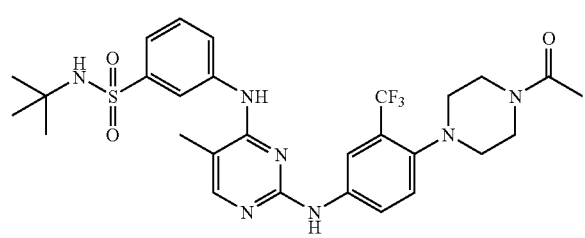
LV
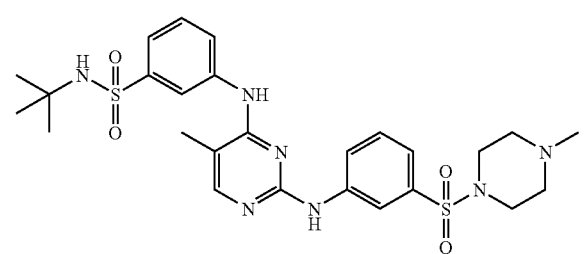
LVI
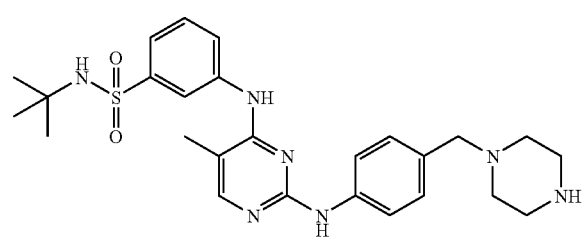
LVII
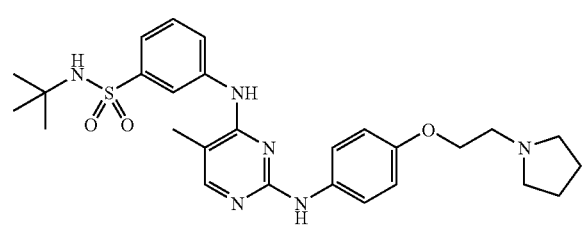
LVIII
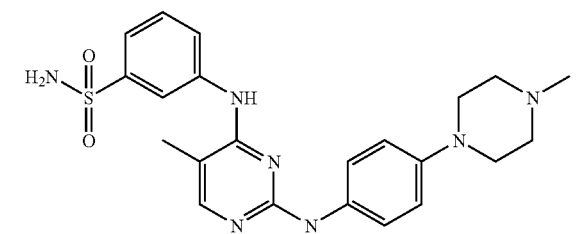
LIX
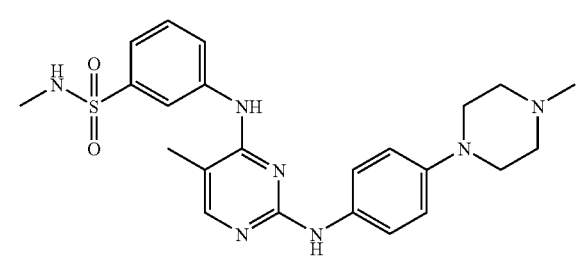
-continued
LX
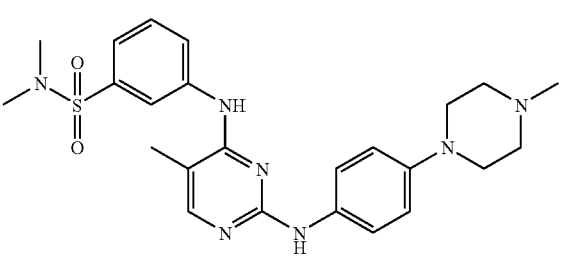
LXI
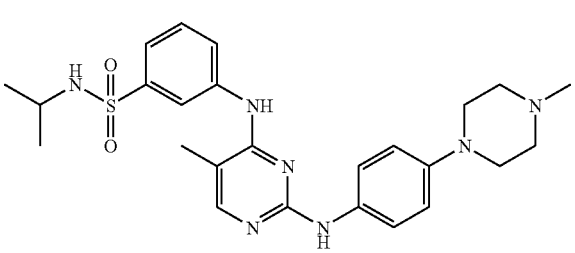
LXII
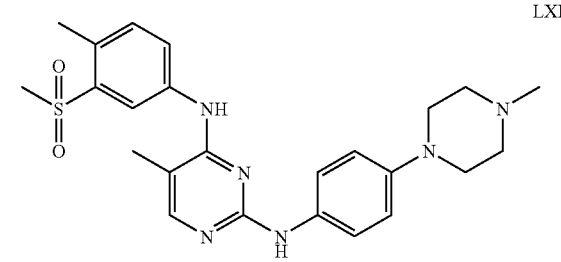
LXIII
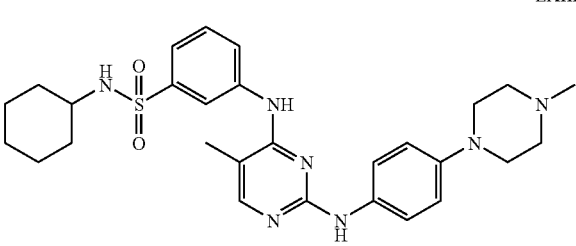
LXIV
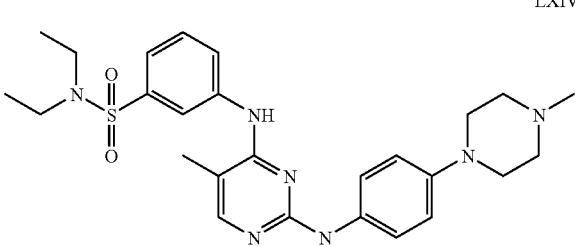
LXV
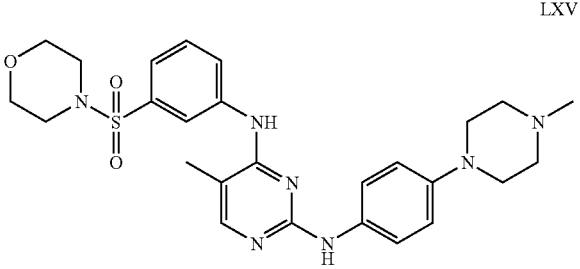

-continued
LXVI
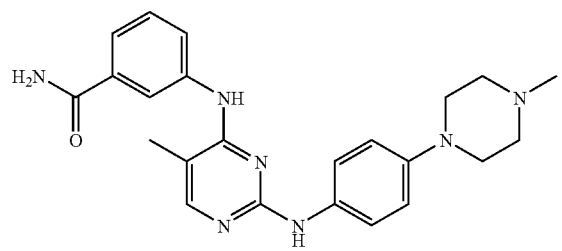
LXVII
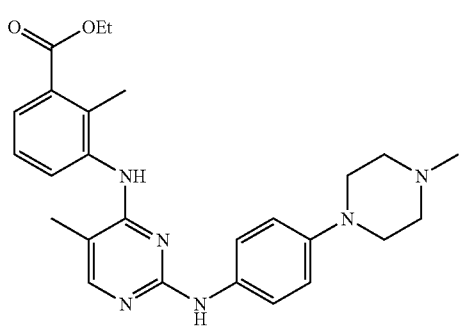
LXVIII
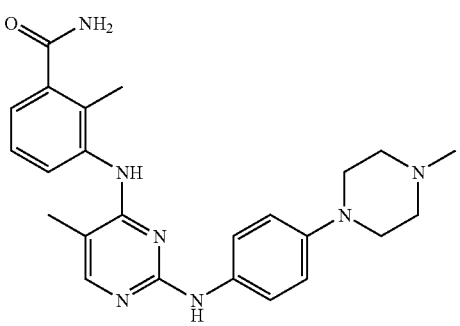
LXIX
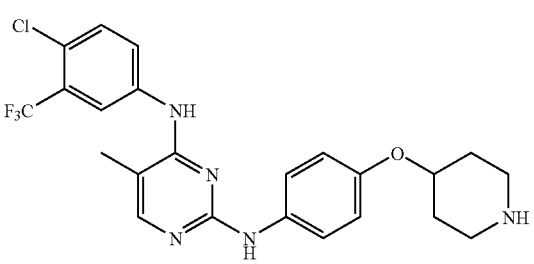
LXX
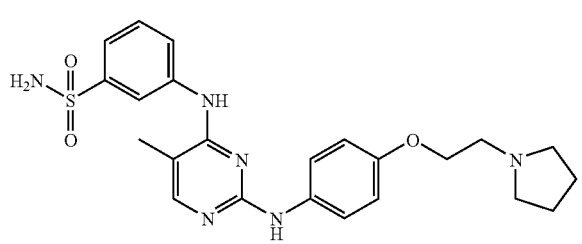
-continued
LXXI
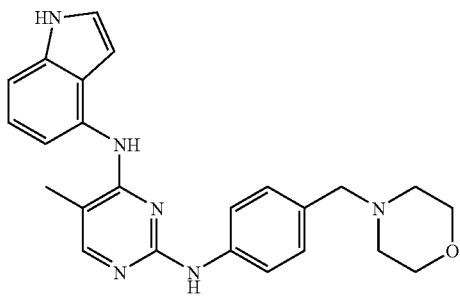
LXXII
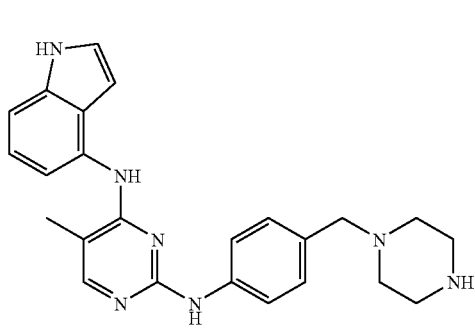
LXXIII
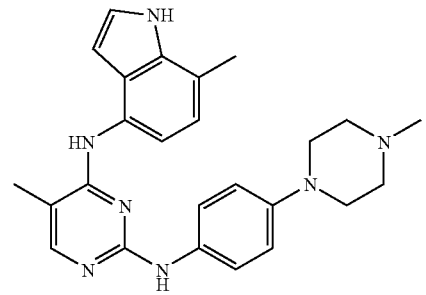
LXXIV
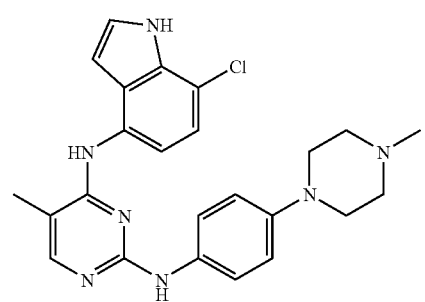
LXXV
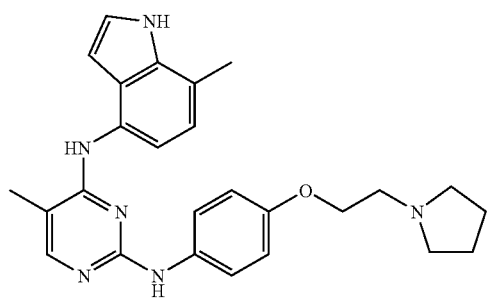

-continued
LXXVI
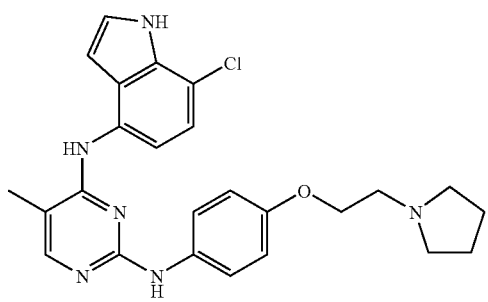
LXXVII
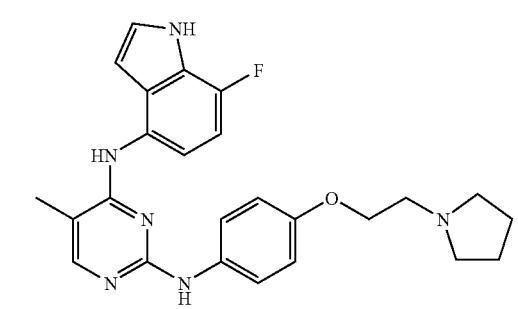
LXXVIII
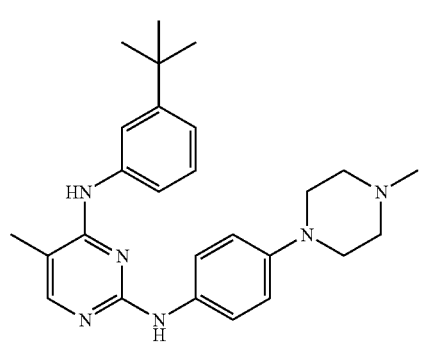
LXXIX
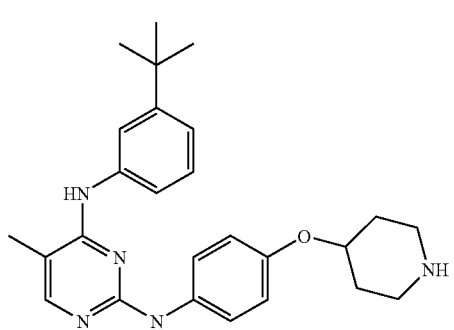
LXXX
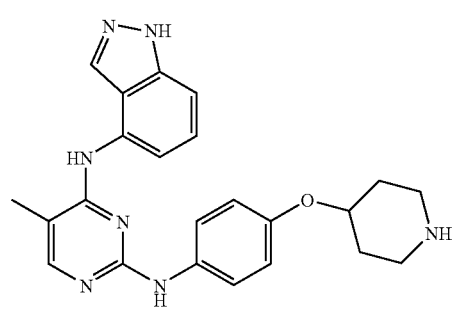
-continued
LXXXI
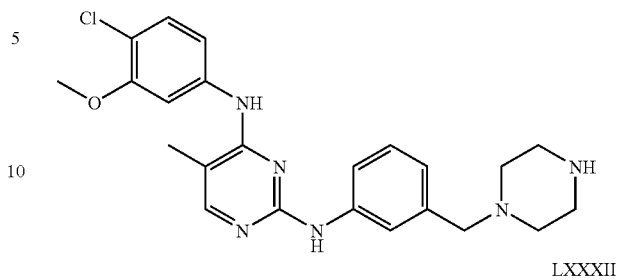
LXXXII
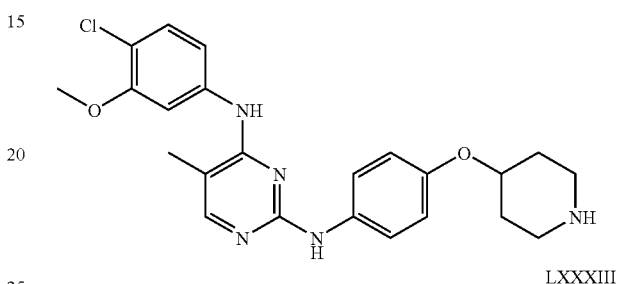
LXXXIII
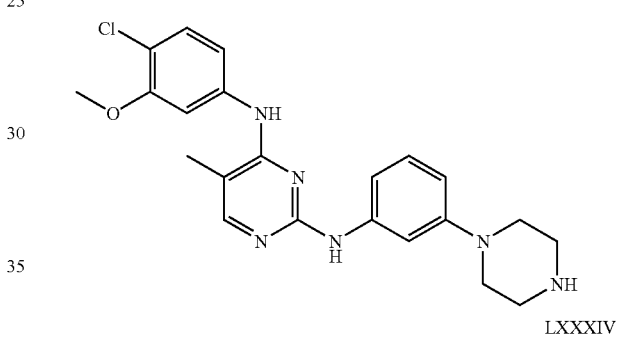
LXXXIV
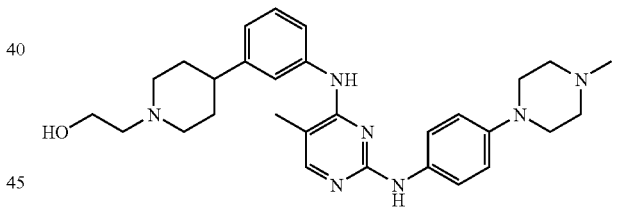
LXXXV
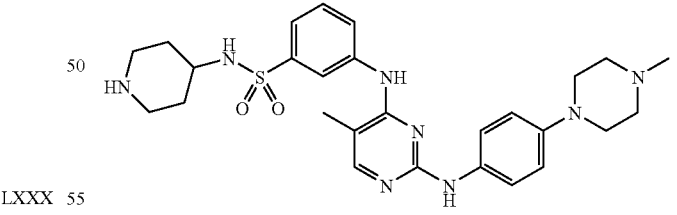
LXXXVI
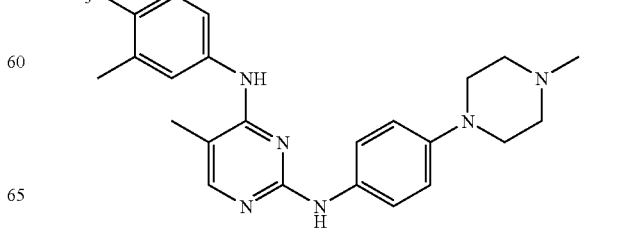

-continued
LXXXVII
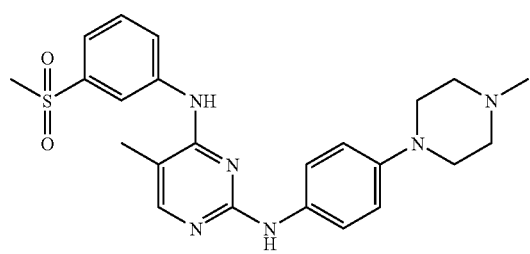
LXXXVIII
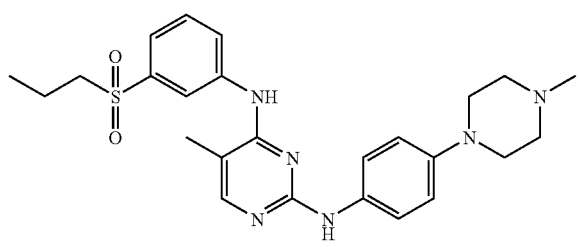
LXXXIX
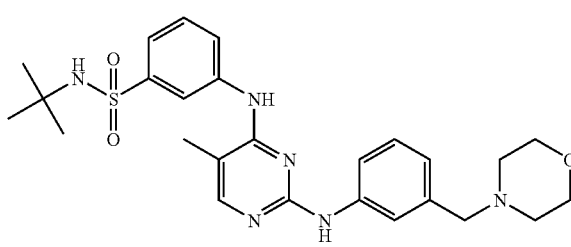
XC
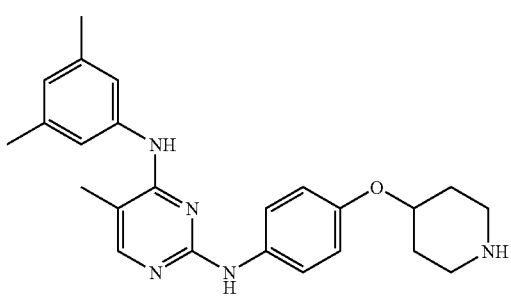
XCI
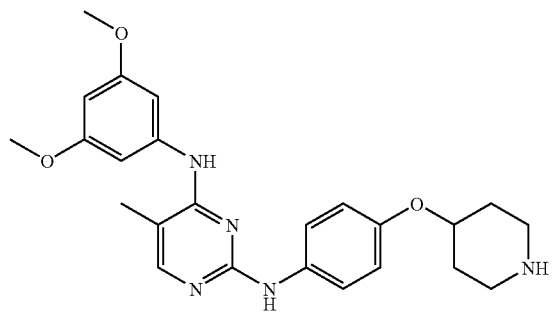
-continued
XCII
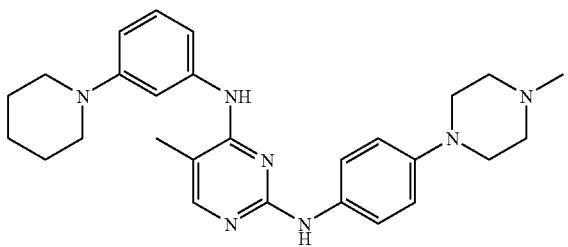
XCIII
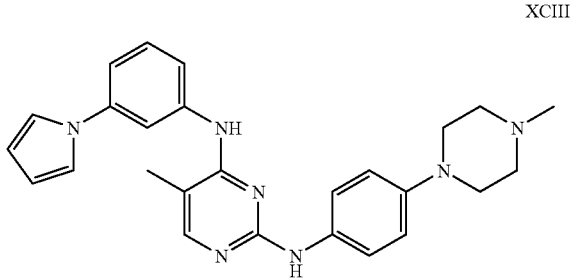
XCIV
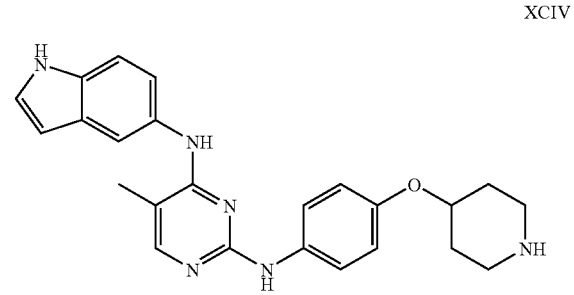
XCV
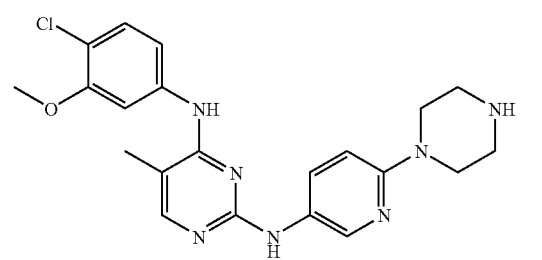
XCVI
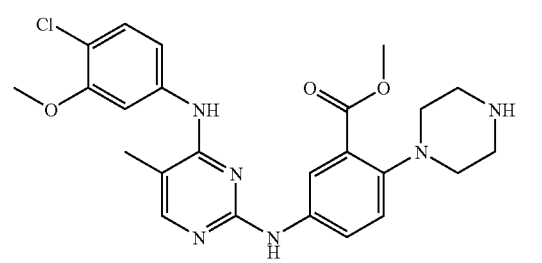

XCVII
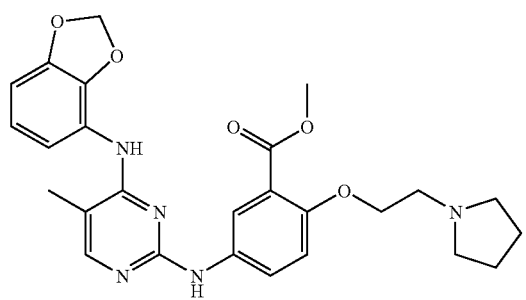
XCVIII
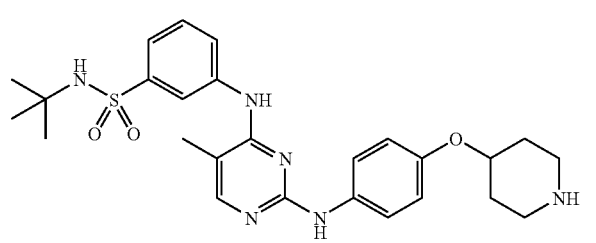
XCIX
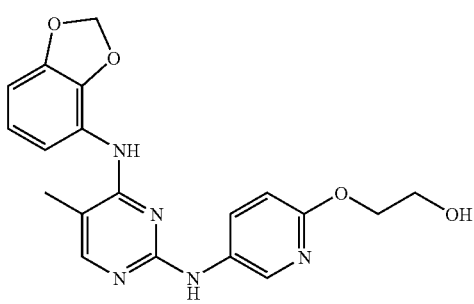
C
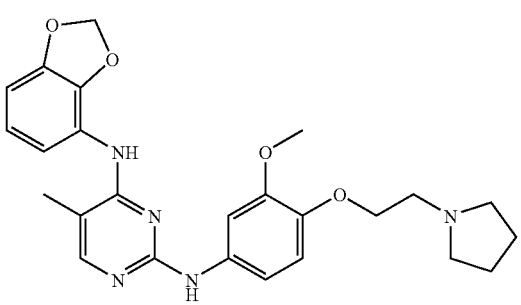
CI
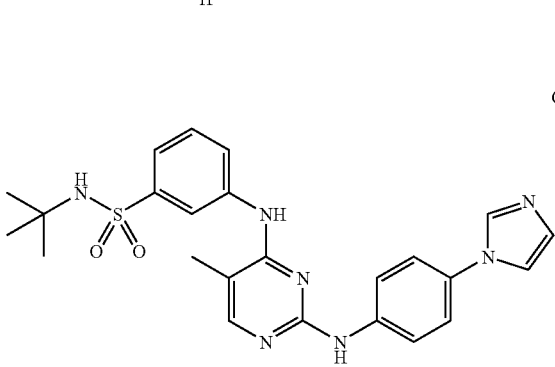
CII
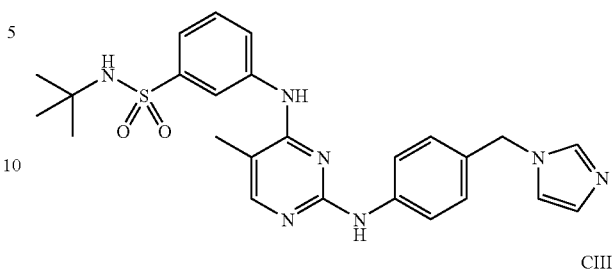
CIII
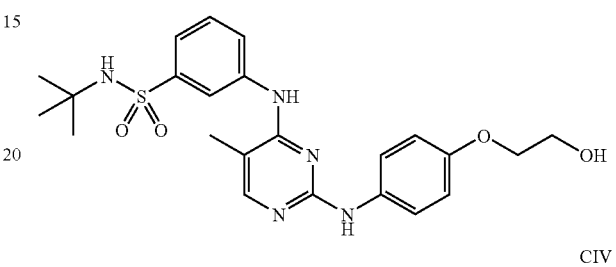
CIV
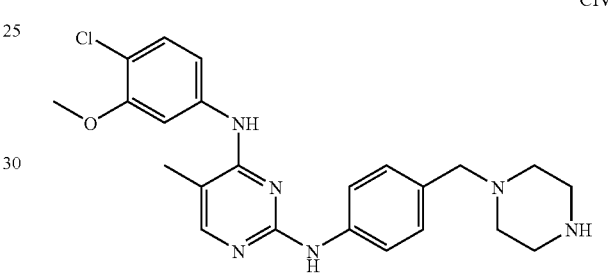
CV
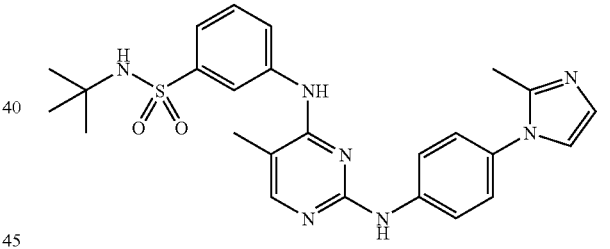
CVI
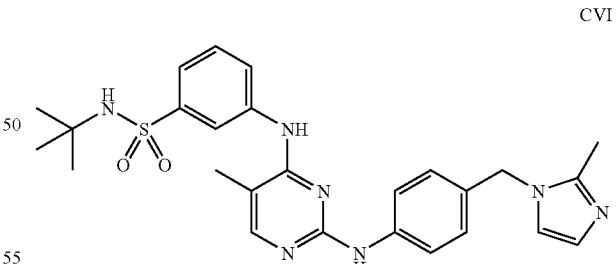
CVII
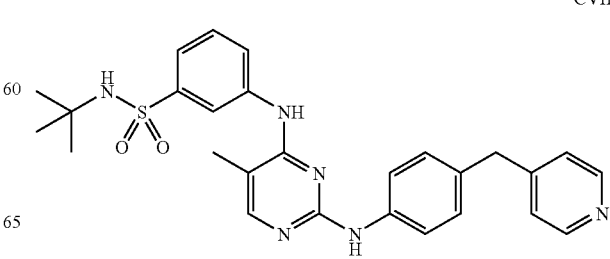

-continued

CVIII

CIX

CX

CXI

CXII

CXIII

CXIV

CXV

CXVI

CXVII

CXVIII

CXIX
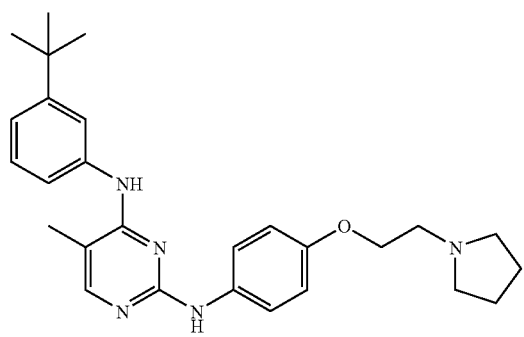
CXXIII
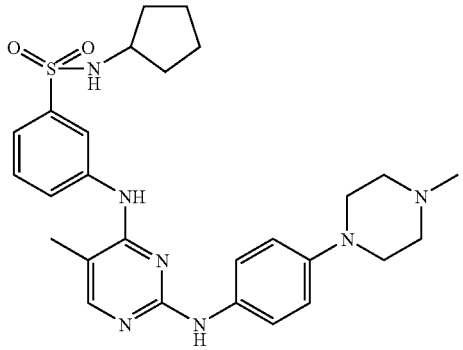
CXX
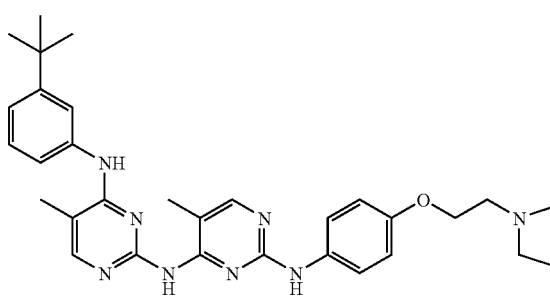
CXXIV
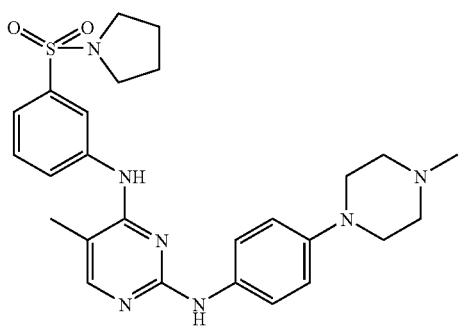
CXXI
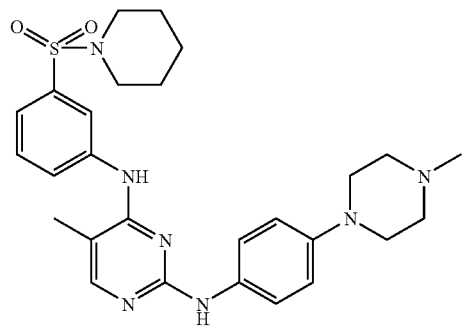
CXXV
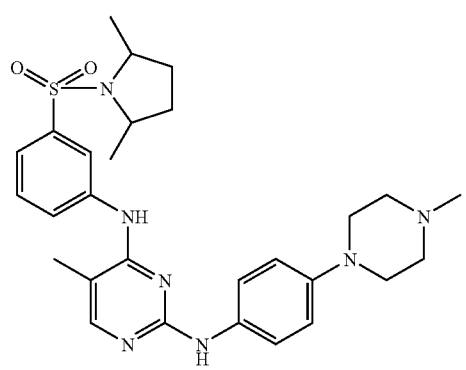
CXXII
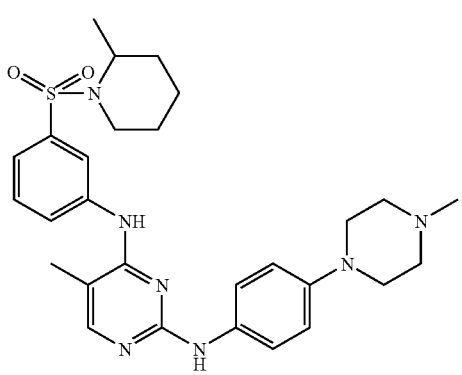
CXXVI
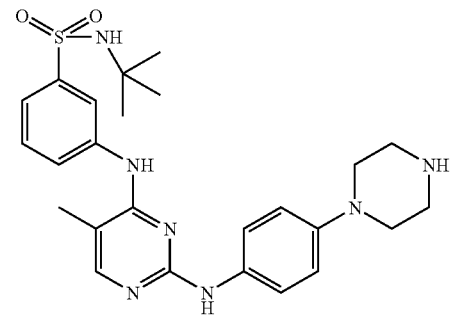

-continued
CXXVII
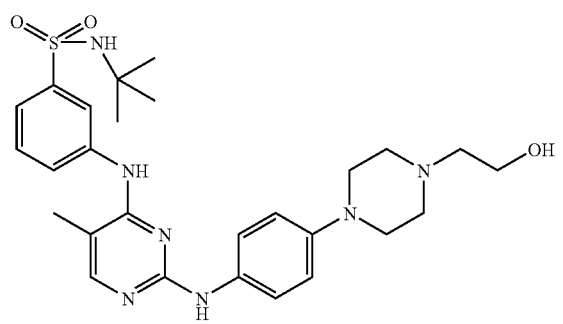
CXXXI
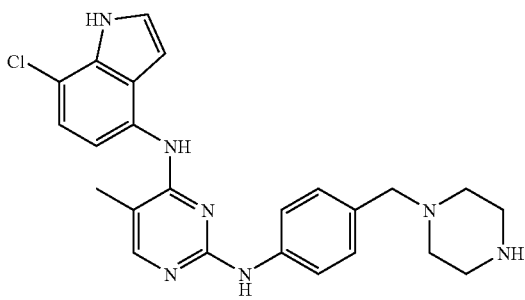
CXXVIII
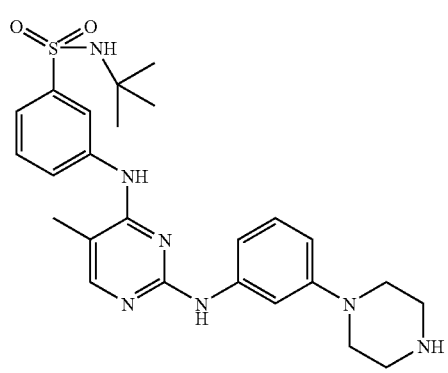
CXXXII
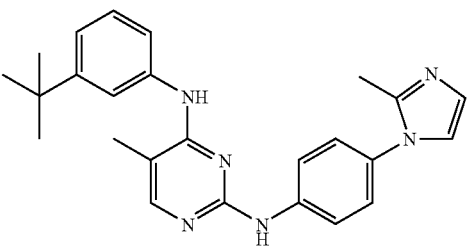
CXXIX
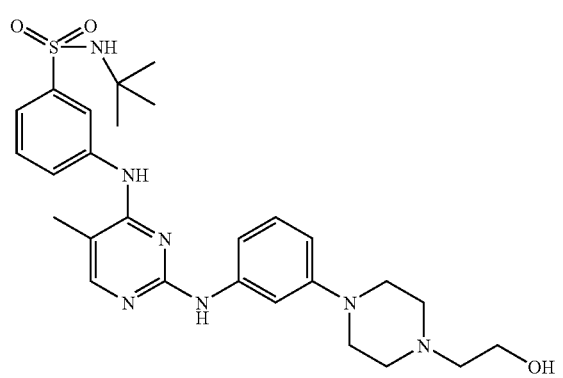
CXXXIII
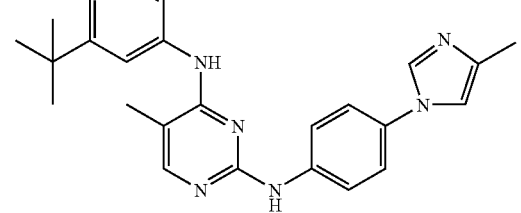
CXXXIV
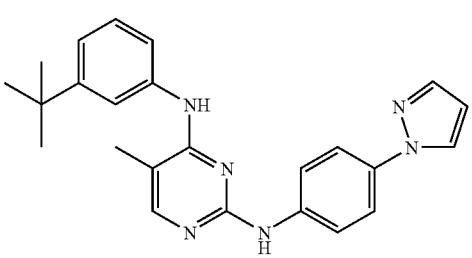
CXXX
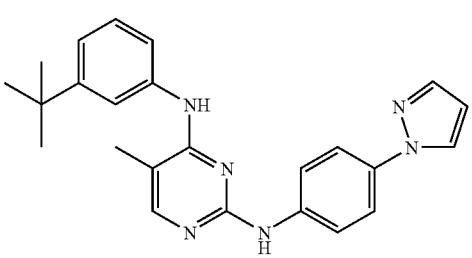
CXXXV
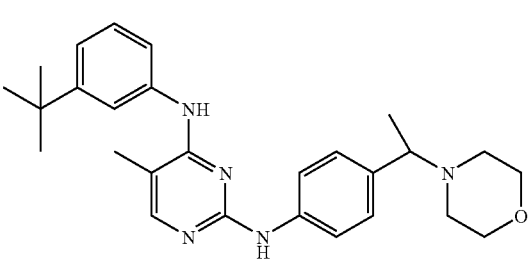

-continued
CXXXVI
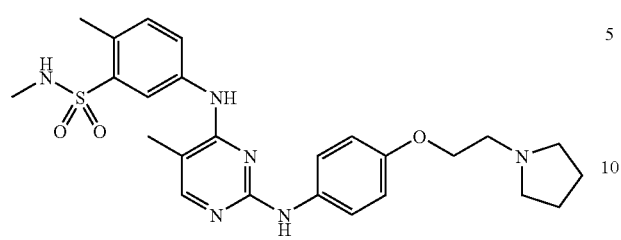
CXXXVII
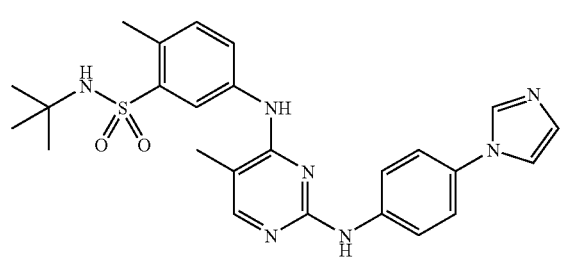
CXXXVIII
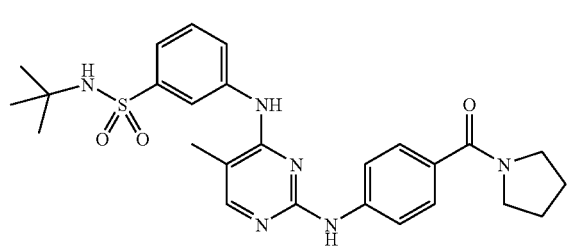
CXXXIX
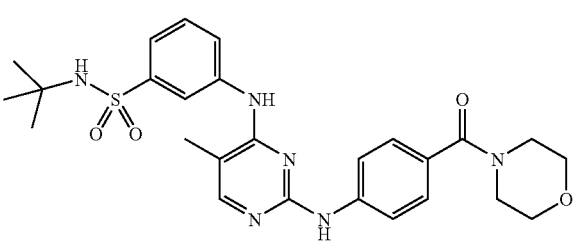
CXL
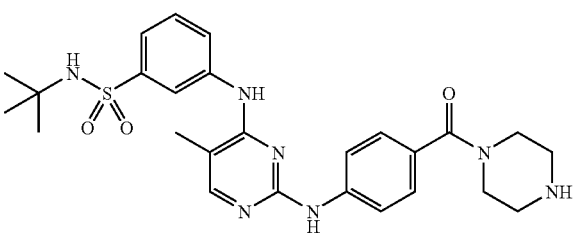
CXLI
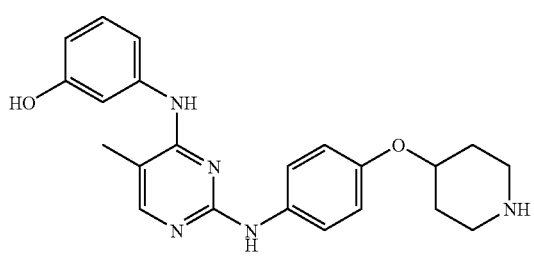
-continued
CXLII
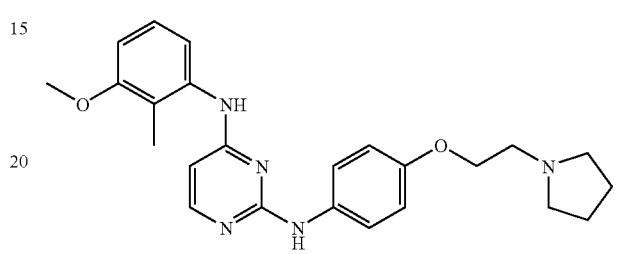
CXLIII
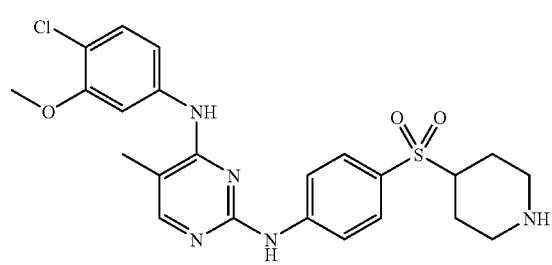
CXLIV
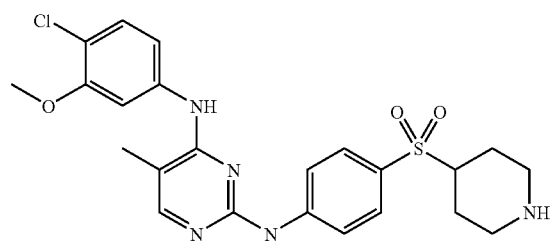
CXLV
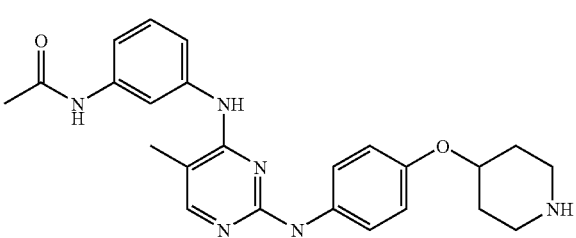
CXLVI
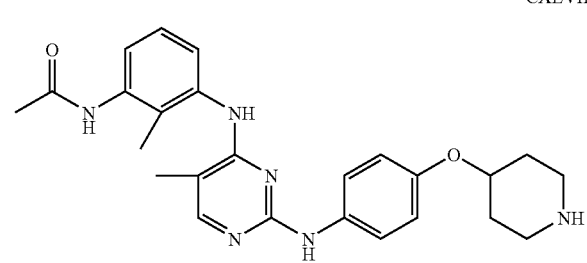

CXLVIII
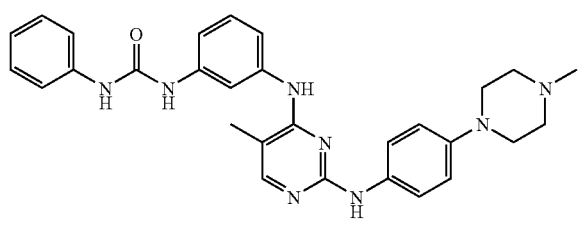
CXLIX
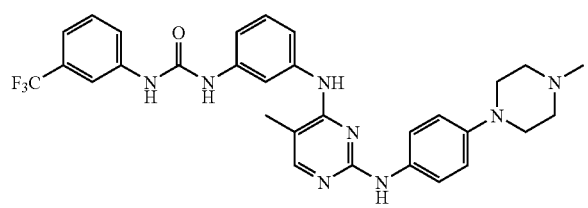
CL
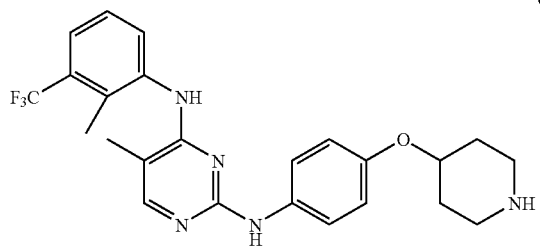
CLI
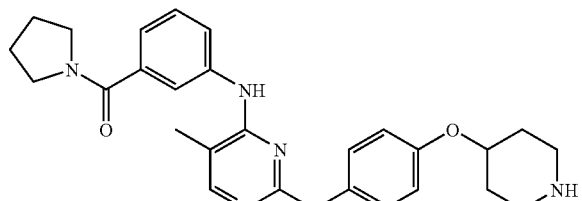
CLII
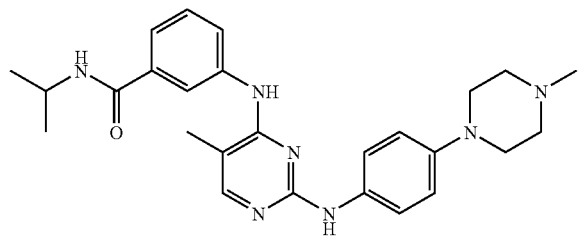
CLIII
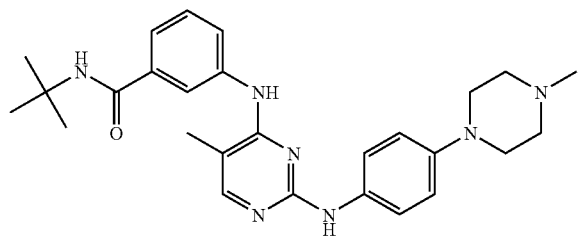
CLIV
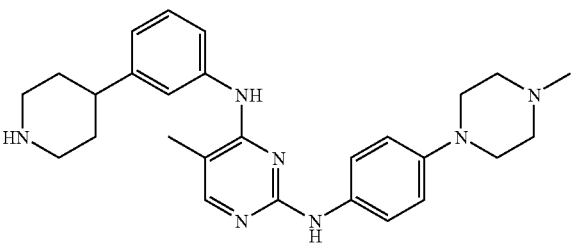
CLV
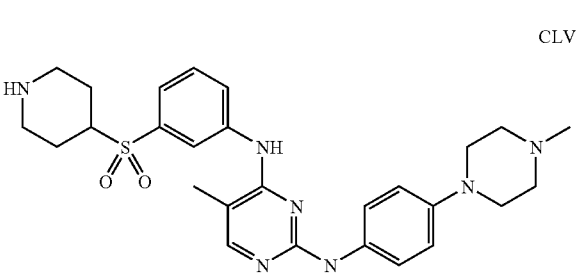
CLVI
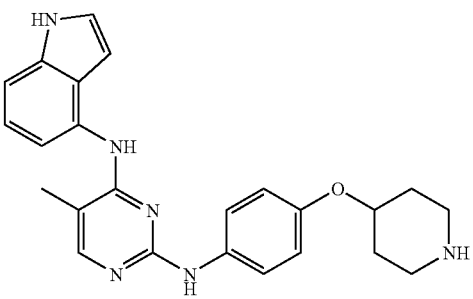
CLVII
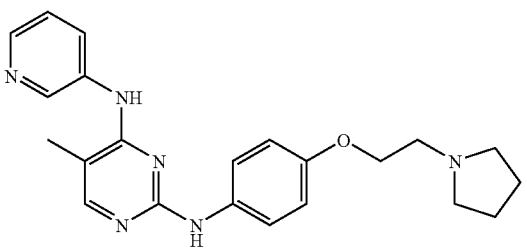
CLVIII
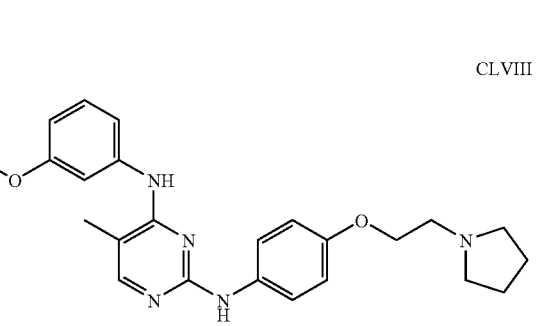

-continued

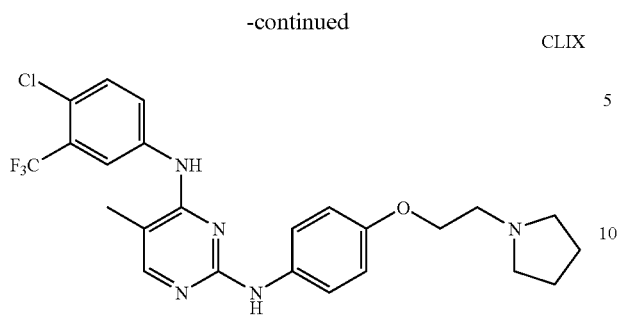

CLIX

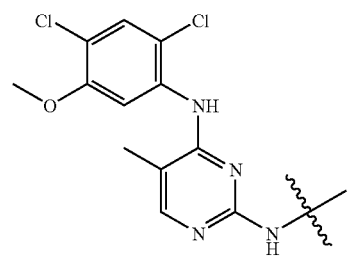

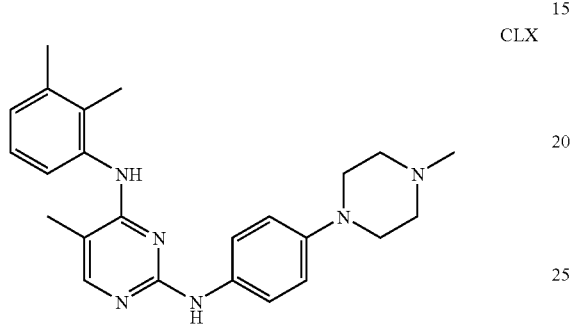

CLX

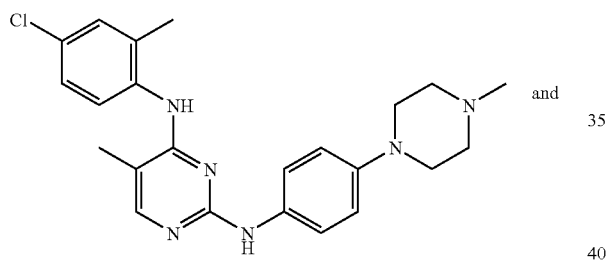

CLXI and

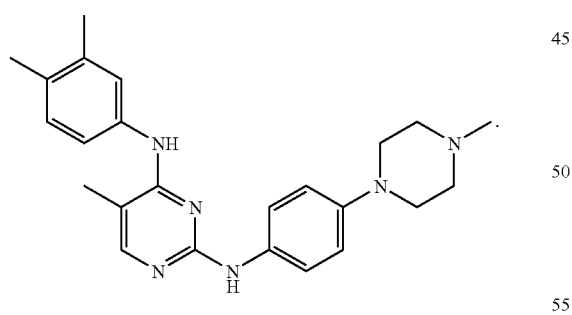

CLXII

According to another embodiment of the invention, compounds having the general structure (Z):

B—C    (Z)

are provided for treatment of various diseases, disorders, and pathologies.

The general structure (Z) includes two chemically connected moieties B and C. The moiety B in the general structure (Z) includes any moiety selected from the following group:

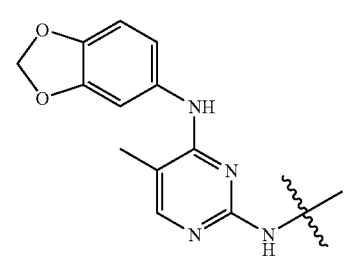

-continued
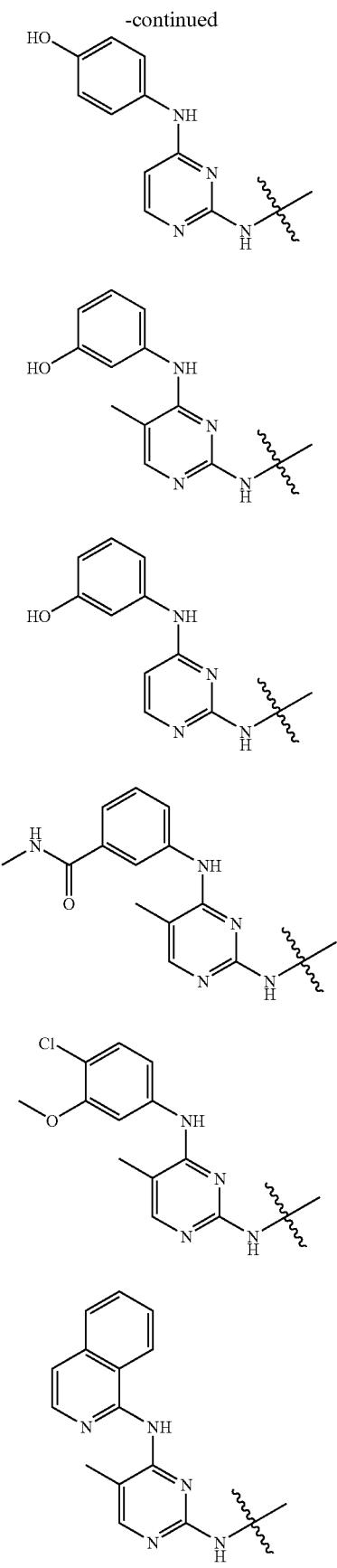
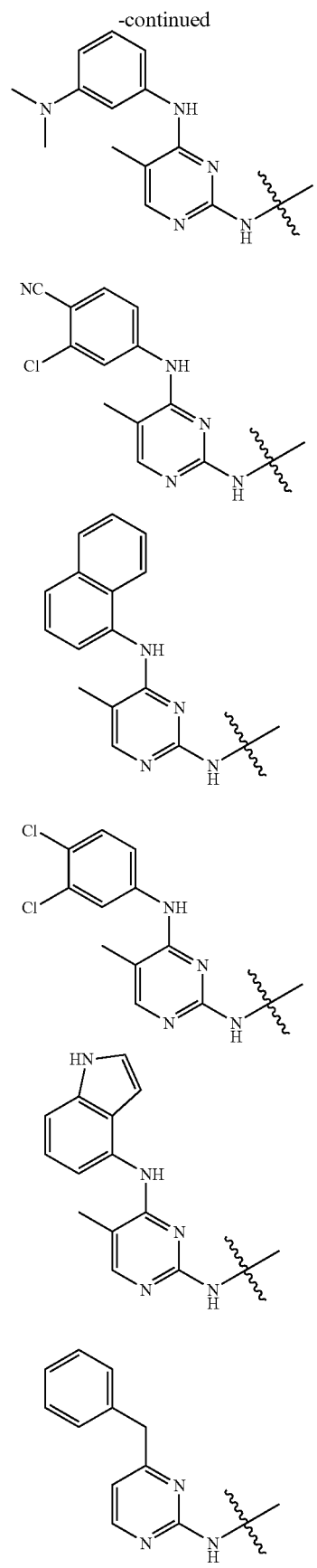

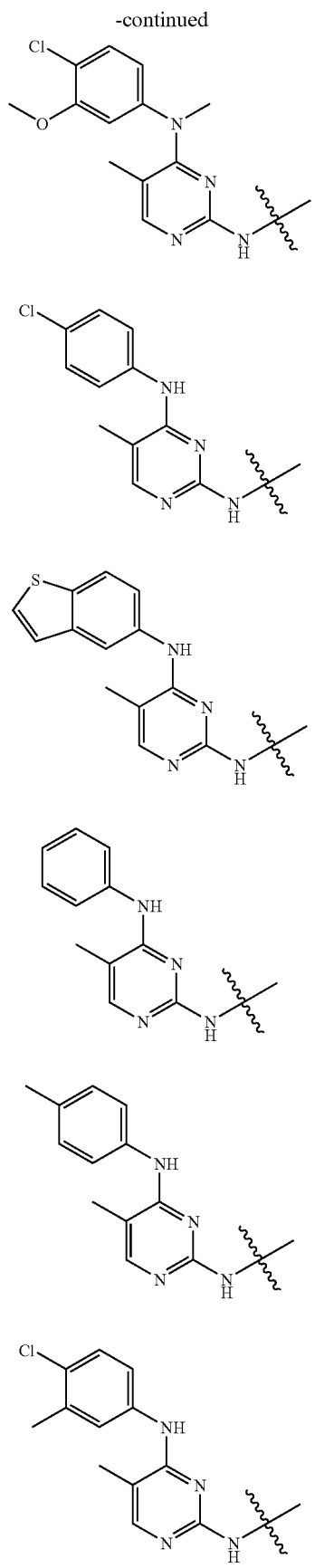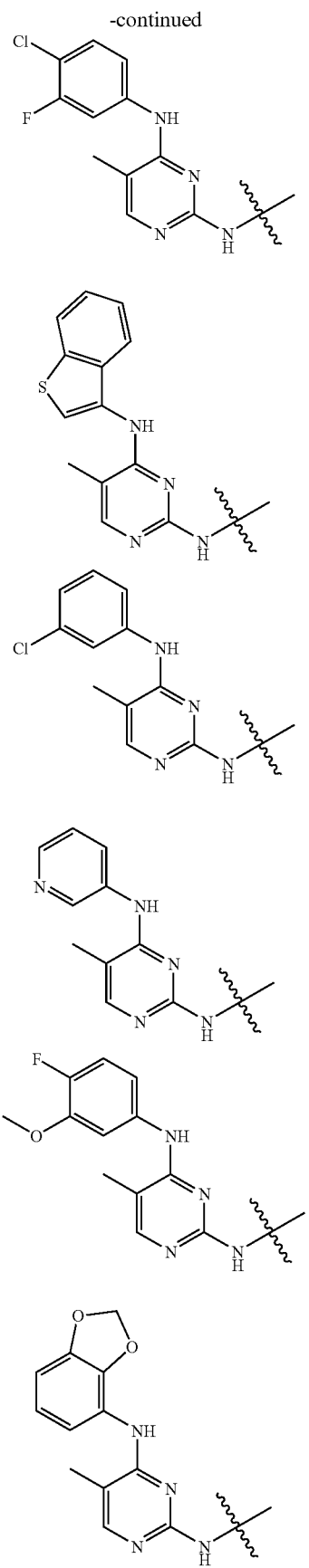

-continued
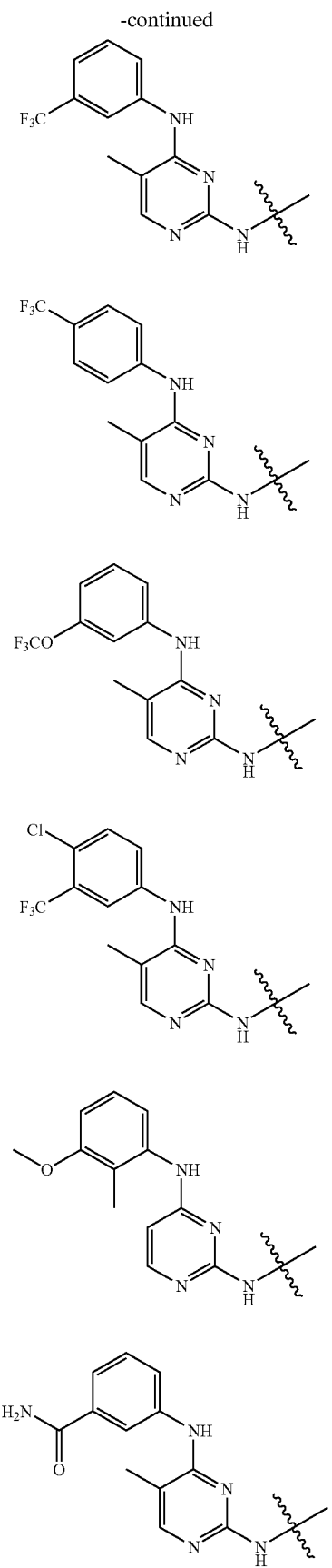
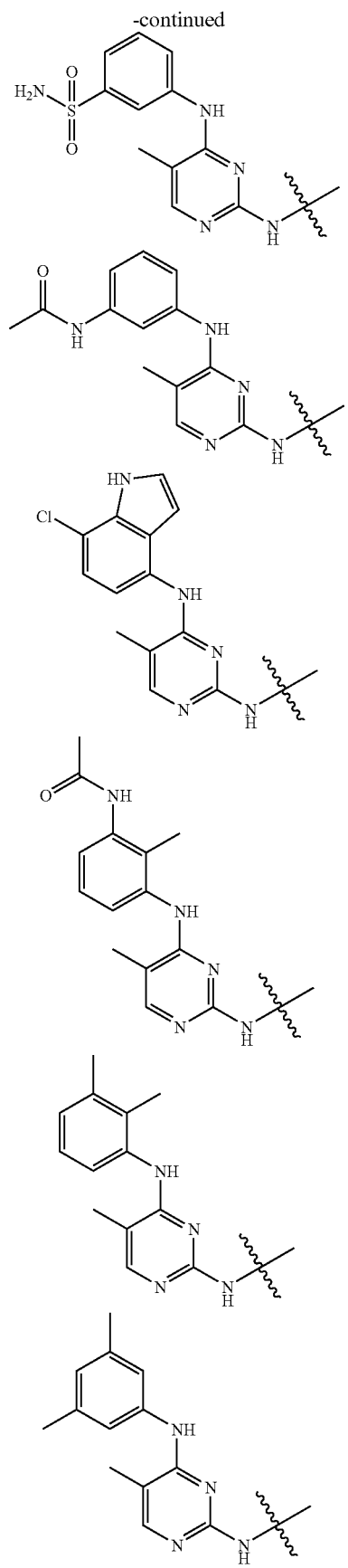

-continued
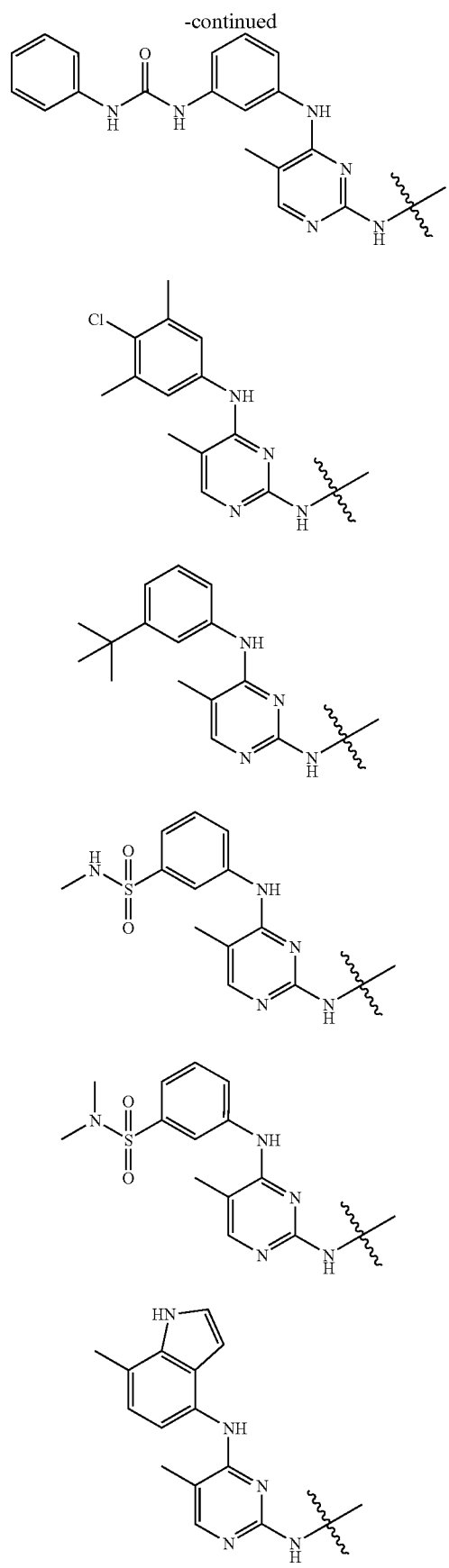
-continued
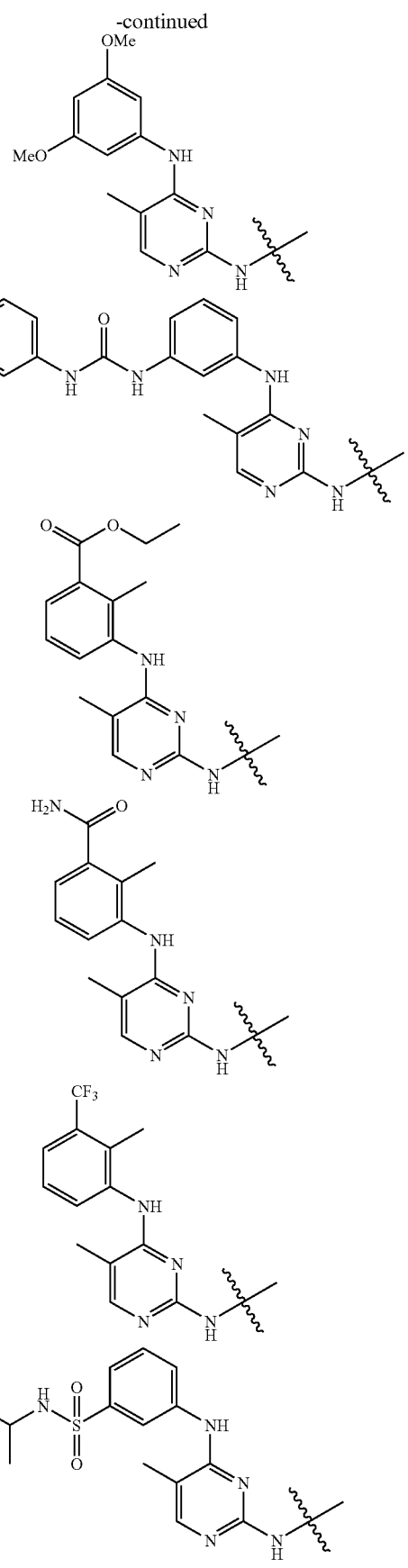

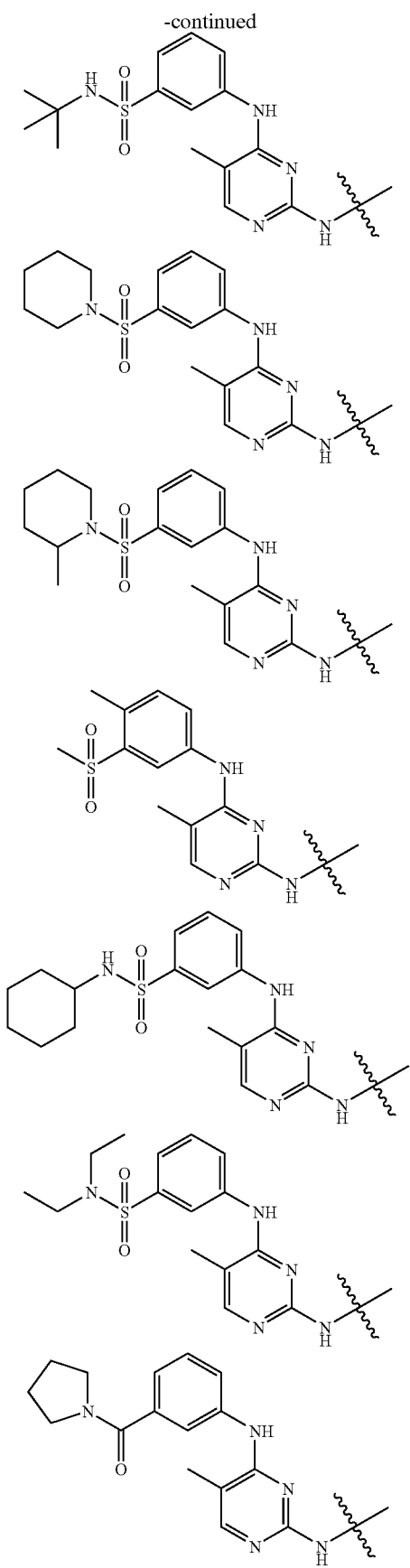

-continued
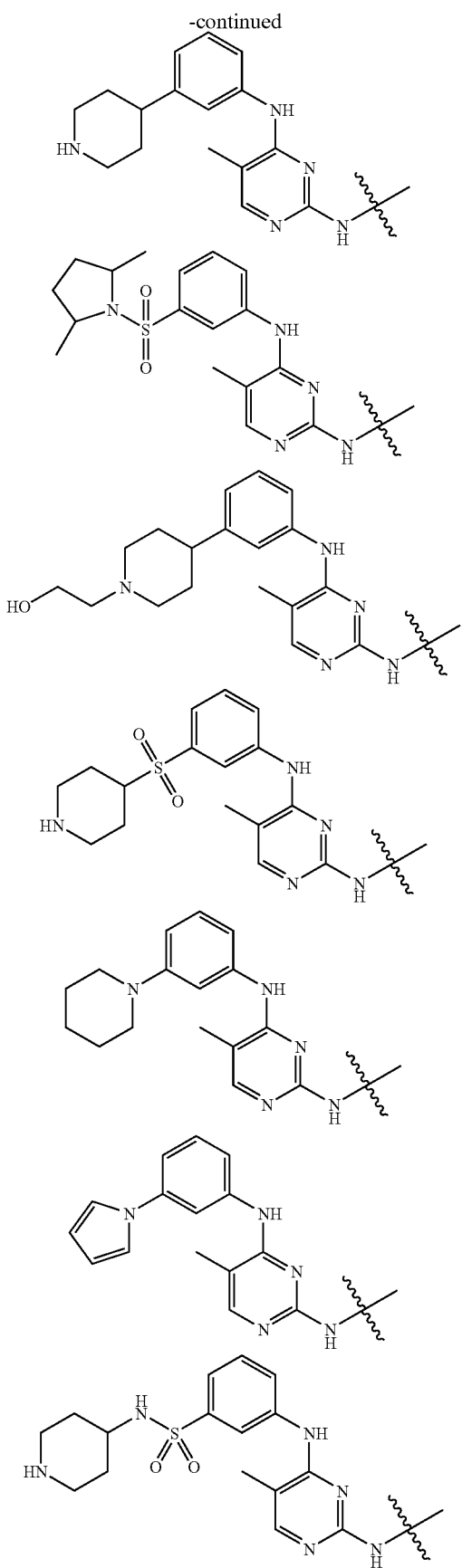
-continued
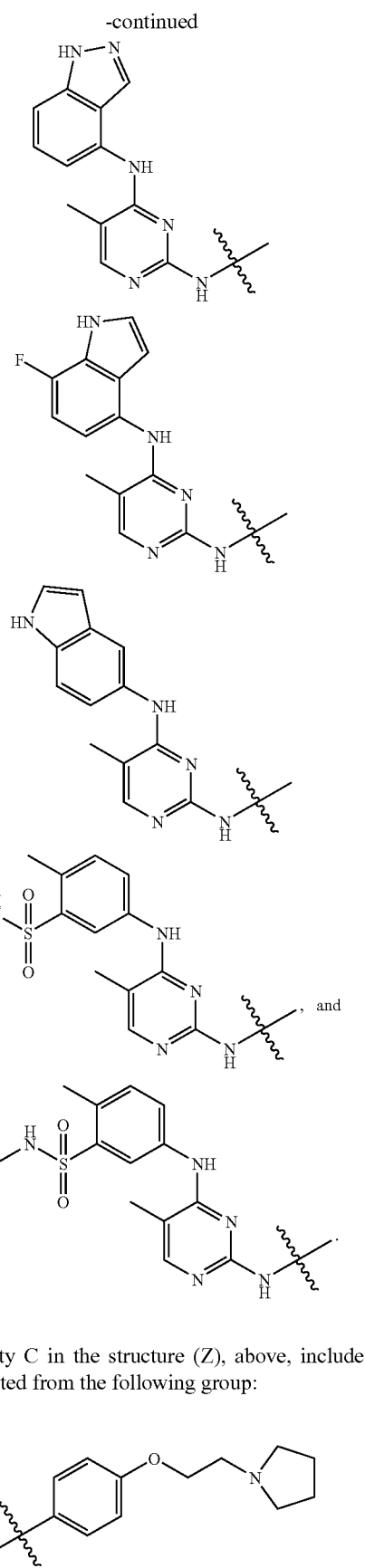
The moiety C in the structure (Z), above, includes any moiety selected from the following group:
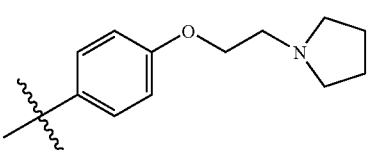

-continued
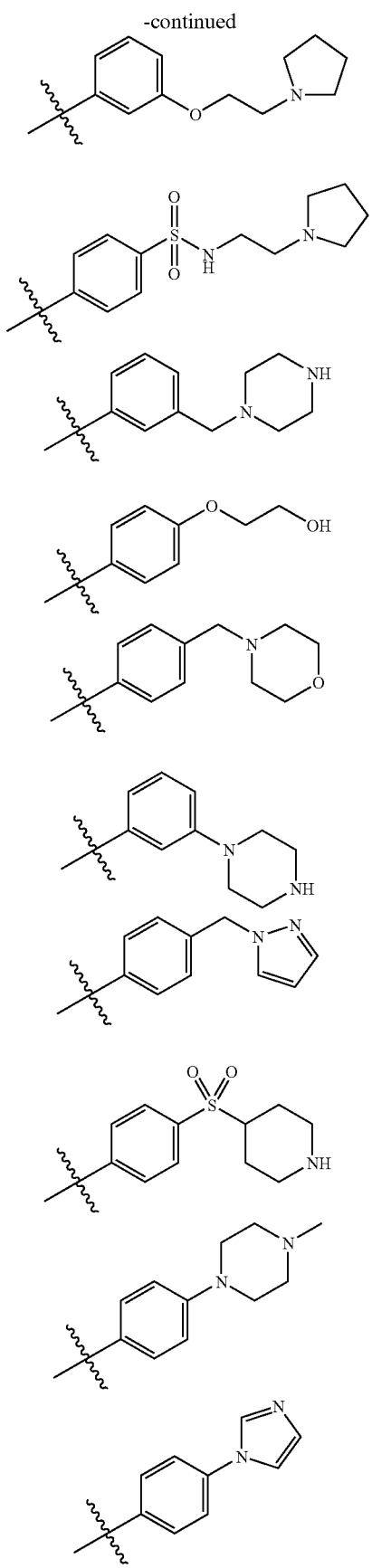
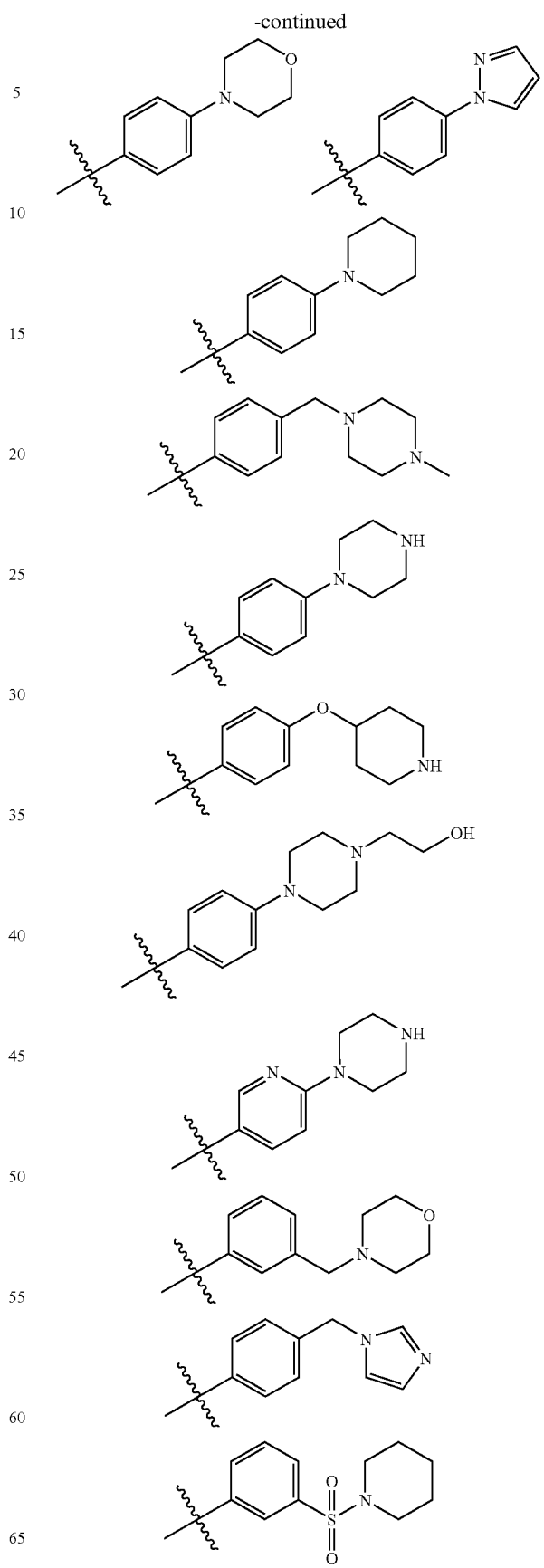

55
-continued
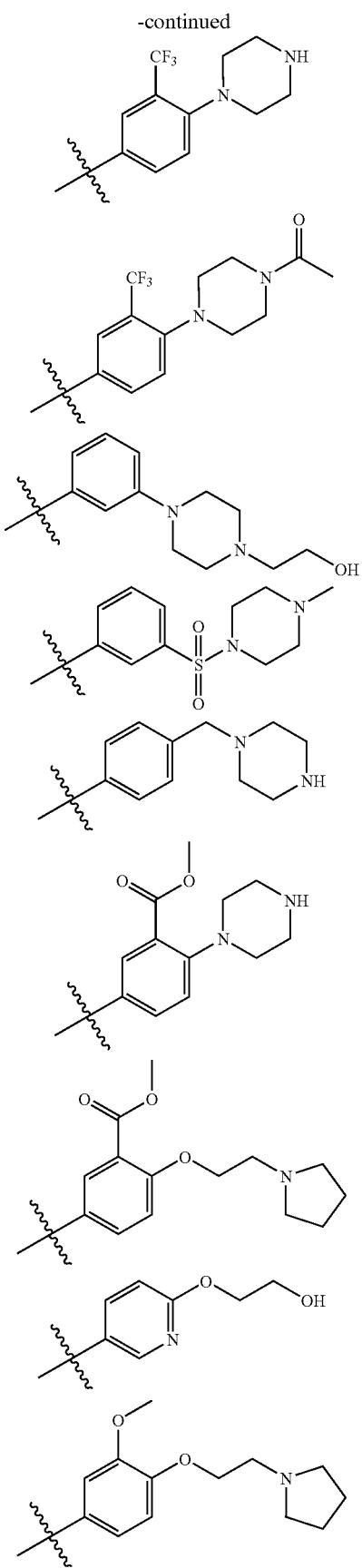
56
-continued
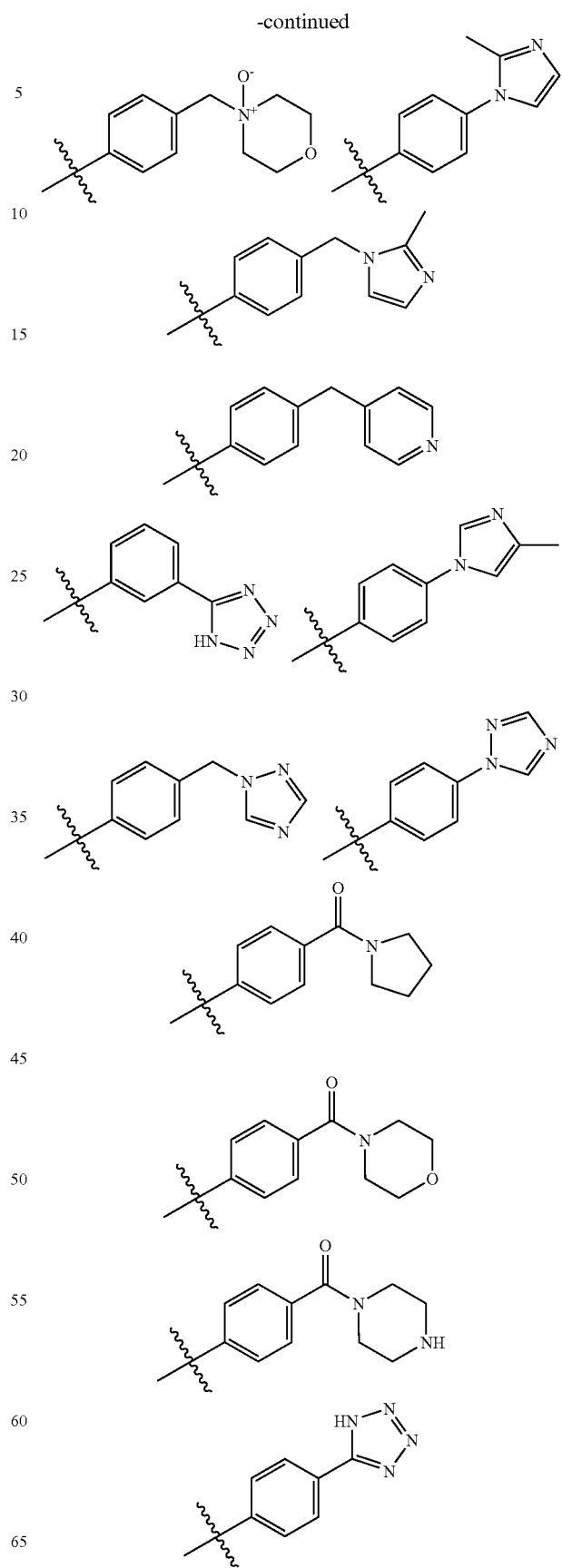

-continued

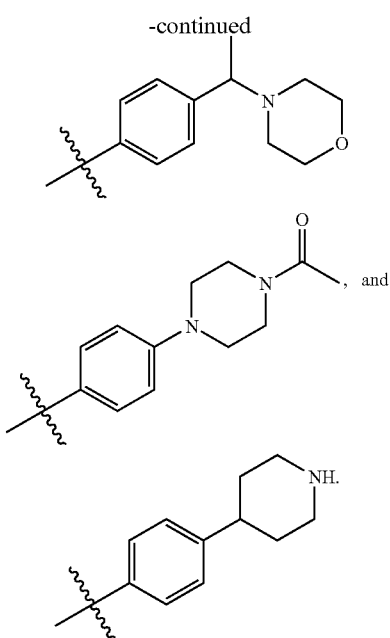

The compounds and methods of the present invention, or pharmaceutically acceptable salts, hydrates, solvates, crystal forms and individual diastereomers thereof, either when administered alone or in combination with other agents (e.g., chemotherapeutic agents or protein therapeutic agents described below) are useful in treating a variety of disorders, including, but not limited to, for example, myeloproliferative disorders, proliferative diabetic retinopathy and other angiogenic-associated disorders including solid tumors and other types of cancer, eye disease, inflammation, psoriasis, and a viral infection. The kinds of cancer that can be treated include, but are not limited to, an alimentary/gastrointestinal tract cancer, colon cancer, liver cancer, skin cancer, breast cancer, ovarian cancer, prostate cancer, lymphoma, leukemia (including acute myelogenous leukemia and chronic myelogenous leukemia), kidney cancer, lung cancer, muscle cancer, bone cancer, bladder cancer or brain cancer.

Some examples of the diseases and disorders that can be treated also include ocular neovasculariaztion, infantile haemangiomas; organ hypoxia, vascular hyperplasia, organ transplant rejection, lupus, multiple sclerosis, rheumatoid arthritis, psoriasis, Type 1 diabetes and complications from diabetes, inflammatory disease, acute pancreatitis, chronic pancreatitis, asthma, allergies, adult respiratory distress syndrome, cardiovascular disease, liver disease, other blood disorders, asthma, rhinitis, atopic, dermatitis, autoimmune thyroid disorders, ulcerative colitis, Crohn's disease, metastatic melanoma, Kaposi's sarcoma, multiple myeloma, conditions associated with cytokines, and other autoimmune diseases including glomerulonephritis, scleroderma, chronic thyroiditis, Graves' disease, autoimmune gastritis, autoimmune hemolytic anemia, autoimmune neutropenia, thrombocytopenia, atopy (e.g., allergic asthma, atopic dermatitis, or allergic rhinitis), chronic active hepatitis, myasthenia gravis, multiple sclerosis, inflammatory bowel disease, graft vs host disease, neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemia, renal ischemia, heart attacks, cardiac hypertrophy, atherosclerosis and arteriosclerosis, organ hypoxia, and platelet aggregation.

Examples of some additional diseases and disorders that can be treated also include cell mediated hypersensitivity (allergic contact dermatitis, hypersensitivity pneumonitis), rheumatic diseases (e.g., systemic lupus erythematosus (SLE), juvenile arthritis, Sjogren's Syndrome, scleroderma, polymyositis, ankylosing spondylitis, psoriatic arthritis), viral diseases (Epstein Barr Virus, Hepatitis B, Hepatitis C, HIV, HTLV1, Vaicella-Zoster Virus, Human Papilloma Virus), food allergy, cutaneous inflammation, and immune suppression induced by solid tumors.

Embodiments of the present invention also provide articles of manufacture that can include a packaging material and a pharmaceutical composition contained within the packaging material. The packaging material can comprise a label which indicates that the pharmaceutical composition can be used for treatment of one or more disorders identified above.

The pharmaceutical composition can include a compound according to the present invention. In addition to a compound of the present invention, the pharmaceutical may also contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

Thus, in one embodiment, the invention provides a pharmaceutical composition including a therapeutic agent and a compound of the invention. The compound is present in a concentration effective to treat, for example, cancer or to treat another disease or disorder described above.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like.

Salts of the invention can include amine salts formed by the protonation of an amino group with inorganic acids such as hydrochloric acid, hydrobromic acid, hydroiodic acid, sulfuric acid, phosphoric acid, and the like. Salts of the invention can also include amine salts formed by the protonation of an amino group with suitable organic acids, such as p-toluenesulfonic acid, acetic acid, methanesulfonic acid and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this embodiment, either alone or in combination with other therapeutic agents, may conveniently be presented in dosage unit form and may be prepared by any of the methods well known in the art of pharmacy. All methods include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one embodiment, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecoline, etoposide, taxane, anthracycline antibiotic, doxorubicin, daunorubicin, carminomycin, epirubicin, idarubicin, mithoxanthrone, 4-dimethoxy-daunomycin, 11-deoxy-daunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve cellular proliferation, an appropriate dosage level can generally be between about 0.01 and about 1000 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody (or therapeutic fragment thereof), a chemotherapeutic or an immunotoxic agent, for treatment of tumors. Illustrative examples of chemotherapeutic agents that can be used for this purpose include doxorubicin, docetaxel, or taxol. It should be further understood that the invention includes combination therapy including a compound of the invention, including but not limited to vasculostatic agents, such as tyrosine, serine or threonine kinase inhibitors, and any chemotherapeutic agent or therapeutic antibody.

C. Examples

The following examples are provided to further illustrate the advantages and features of the present invention, but are not intended to limit the scope of the invention.

Example 1

General Methods

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate ($NaHCO_3$) and sodium chloride (brine) were saturated. Analytical thin layer chromatography (TLC) was carried out on Merck Kieselgel 60 $F_{254}$ plates with visualization by ultraviolet and/or anisaldehyde, potassium permanganate or phosphomolybdic acid dips. Reverse-phase HPLC chromatography was carried out on Gilson 215 liquid handler equipped with Waters SymmetryShield™ RP18 7 μm (40×100 mm) Prep-Pak cartridge. Mobile phase consisted of standard acetonitrile (ACN) and DI Water, each with 0.1% TFA added. Purification was carried out at a flow rate of 40 mL/min. NMR spectra: $^1H$ Nuclear magnetic resonance spectra were recorded at 500 MHz. Data are presented as follows: chemical shift, multiplicity (s=singlet, d=doublet, t=triplet, q=quartet, qn=quintet, dd=doublet of doublets, m=multiplet, br s=broad singlet), coupling constant (J/Hz) and integration. Coupling constants were taken directly from the spectra and are uncorrected. Low resolution mass spectra: Electrospray (ES+) ionization was used. The protonated parent ion (M+H) or fragment of highest mass is quoted. Analytical gradient consisted of 10% ACN in water ramping up to 100% ACN over 5 min unless otherwise stated.

Example 2

$N^4$-(4-Methoxy-phenyl)-pyrimidine-2,4-diamine (Intermediate 1)

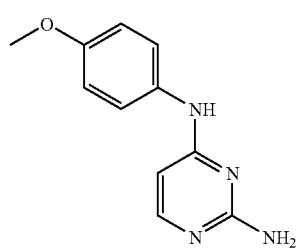

1

A mixture of 4-chloro-pyrimidin-2-ylamine (0.30 g, 2.3 mmol) and 4-methoxy-phenylamine (0.30 g, 2.4 mmol) were suspended in acetic acid (10 mL) and heated at 100° C. for 2 h. The mixture was allowed to cool to room temperature and acetic acid removed under reduced pressure. The residue was taken in water (20 mL) and neutralized to pH~7 with 7M of NaOH solution. The resulting solution was extracted with EtOAc (30 mL) and the organic layer separated. The organic layer was washed with brine, dried over $MgSO_4$ and filtered. The filtrate was concentrated in vacuo and the crude product purified by flash chromatography on silica gel (hexane to EtOAc) to afford the title intermediate 1 (0.23 g, 45%) as a white solid. $^1$H NMR (500 MHz, DMSO-$d_6$): 3.69 (s, 3H), 5.84 (d, J=5.8 Hz, 1H), 6.79 (d, J=9.1 Hz, 2H), 7.63 (d, J=9.1 Hz, 2H), 7.78 (d, J=5.8 Hz, 1H), 8.65 (s, 1H); MS (ESI+): m/z 217 (M+H)$^+$.

Example 3

$N^4$-(4-Methoxy-phenyl)-$N^2$-[4-(2-pyrrolidin-1-yl-ethoxy)-phenyl]-pyrimidine-2,4-diamine (Compound I)

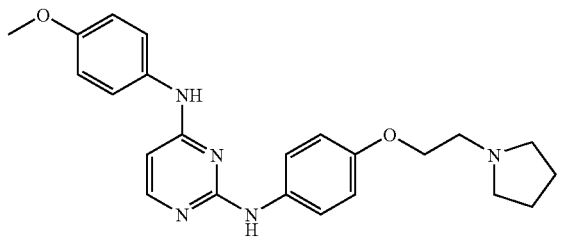

I

To synthesize compound I, intermediate 1 described above and intermediate 2 were used. Intermediate 2, 1-[2-(4-bromophenoxy)-ethyl]-pyrrolidine, shown below is available commercially, and was used as received.

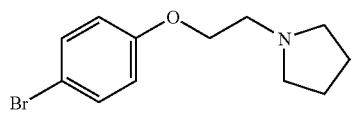

(2)

A suspension of intermediate 1 (74 mg, 0.34 mmol), intermediate 2 (0.10 g, 0.37 mmol), Pd(OAc)$_2$ (5 mg, 0.022 mmol), Xantphos (26 mg, 0.05 mmol) and potassium tert-butoxide (80 mg, 0.71 mmol) in dioxane/DMF (3/1; 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound I (20 mg of TFA salt, 11%) as a brown solid. $^1$H NMR (500 MHz, DMSO-$d_6$): 1.80-1.95 (m, 2H), 1.95-2.10 (m, 2H), 3.05-3.20 (m, 2H), 3.55-3.65 (m, 4H), 3.77 (s, 3H), 4.29 (t, J=4.9 Hz, 2H), 6.30 (d, J=6.8 Hz, 1H), 6.96 (d, J=8.3 Hz, 2H), 6.98 (d, J=8.3 Hz, 2H), 7.41 (d, J=8.8 Hz, 2H), 7.55 (d, J=8.8 Hz, 2H), 7.89 (d, J=6.2 Hz, 1H), 9.87 (br s, 1H), 10.22 (br s, 1H), 10.44 (br s, 1H); MS (ESI+): m/z 406 (M+H)$^+$.

Example 4

4-[4-(4-Methoxy-phenylamino)-pyrimidin-2-ylamino]-N-(2-pyrrolidin-1-yl-ethyl)-benzenesulfonamide (Compound II)

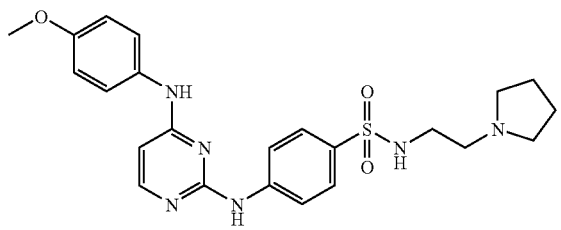

II

To synthesize compound II, intermediate 1 described above and intermediate 3 were used. Intermediate 3, 4-bromo-N-(2-pyrrolidin-1-yl-ethyl)-benzenesulfonamide, the formula of which is shown below, was synthesized from 4-bromophenylsulfonylchloride and 2-aminoethylpyrrolidine, using commonly known synthetic techniques.

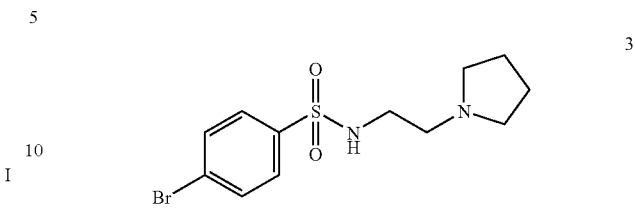

3

A suspension of intermediate 1 described above (70 mg, 0.32 mmol), intermediate 3 (0.12 g, 0.36 mmol), Pd(OAc)$_2$ (5 mg, 0.022 mmol), Xantphos (26 mg, 0.05 mmol) and potassium tert-butoxide (80 mg, 0.71 mmol) in dioxane/DMF (3/1; 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound II (0.16 g of TFA salt, 85%) as a white solid. $^1$H NMR (500 MHz, DMSO-$d_6$): 1.80-1.95 (m, 2H), 1.95-2.05 (m, 2H), 2.95-3.05 (m, 4H), 3.23 (q, J=5.8 Hz, 2H), 3.50-3.60 (m, 2H), 3.79 (s, 3H), 6.41 (d, J=6.8 Hz, 1H), 6.99 (d, J=8.9 Hz, 2H), 7.43 (d, J=8.9 Hz, 2H), 7.71 (d, J=8.6 Hz, 2H), 7.85-7.95 (m, 2H), 7.96 (t, J=6.1 Hz, 1H), 8.02 (d, J=6.2 Hz, 1H), 9.64 (br s, 1H), 10.21 (br s, 1H), 10.71 (br s, 1H); MS (ESI+): m/z 469 (M+H)$^+$.

Example 5

4-[4-(4-Hydroxy-phenylamino)-pyrimidin-2-ylamino]-N-(2-pyrrolidin-1-yl-ethyl)-benzenesulfonamide (Compound III)

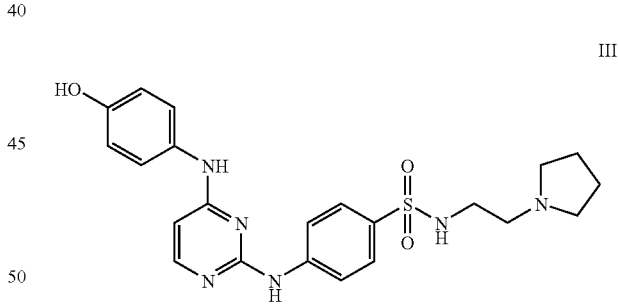

III

To a solution of compound II described above (50 mg, 0.09 mmol) in DCM (6 mL) at room temperature was added BBr$_3$ (0.1 mL) and the mixture stirred at room temperature for 2.5 h. The reaction was quenched with saturated NaHCO$_3$ solution until the pH~7 and the mixture extracted with EtOAc (30 mL). The organic layer was separated and washed with brine, dried over MgSO$_4$ and filtered. The filtrate was concentrated and the resulting solid re-dissolved in minimum of EtOAc. Hexane was added until solid crushed out and the title compound III was filtered as a white solid (25 mg, 64%) without further purification. $^1$H NMR (500 MHz, DMSO-$d_6$): 1.55-1.65 (m, 4H), 2.30-2.40 (m, 4H), 2.43 (t, J=7.0 Hz, 2H), 2.82 (t, J=6.6 Hz, 2H), 6.20 (d, J=5.8 Hz, 1H), 6.70 (d, J=8.8 Hz, 2H), 7.40 (d, J=8.6 Hz, 2H), 7.64 (d, J=8.8 Hz, 2H), 7.92 (d, J=8.4 Hz, 2H), 8.03 (d, J=5.5 Hz, 1H), 8.93 (s, 1H), 9.08 (br s, 1H), 9.70 (s, 1H); MS (ESI+): m/z 455 (M+H)+.

Example 6

4-(4-Chloro-pyrimidin-2-ylamino)-N-(2-pyrrolidin-1-yl-ethyl)-benzenesulfonamide (Intermediate 4)

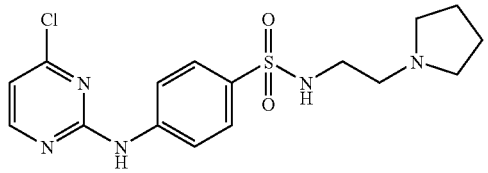

A mixture of 4-chloro-pyrimidin-2-ylamine (1.0 g, 7.8 mmol), above-described intermediate 3 (2.6 g, 7.8 mmol), Pd(OAc)$_2$ (90 mg, 0.40 mmol), Xantphos (0.50 g, 0.86 mmol) and potassium tert-butoxide (2.2 g, 20 mmol) were suspended in dioxane (30 mL) and heated at reflux under the argon atmosphere for 16 h. The mixture was poured into water (30 mL) and extracted with EtOAc (60 mL). The organic layer was separated and washed with brine, dried over MgSO$_4$ and filtered. The filtrate was concentrated in vacuo and the crude product purified by flash chromatography on silica gel (DCM to 25% MeOH/DCM) to afford the title intermediate 4 (0.15 g, 5%) as a brown solid. MS (ESI+): m/z 382 (M+H)+.

Example 7

4-[4-(3-Methoxy-phenylamino)-pyrimidin-2-ylamino]-N-(2-pyrrolidin-1-yl-ethyl)-benzene-sulfonamide (Compound IV)

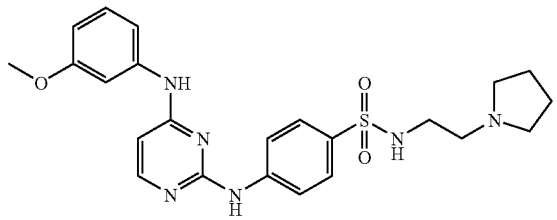

A mixture of the above described intermediate 4 (0.10 g, 0.26 mmol) and 3-methoxy-phenylamine (0.05 mL, 0.45 mmol) were suspended in acetic acid (6 mL) and heated at 100° C. for 1.5 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound IV (55 mg of TFA salt, 36%) as a white solid. $^1$H NMR (500 MHz, DMSO-d$_6$): 1.80-1.90 (m, 2H), 1.95-2.05 (m, 2H), 2.95-3.05 (m, 4H), 3.24 (q, J=6.0 Hz, 2H), 3.50-3.60 (m, 2H), 3.73 (s, 3H), 6.40 (d, J=6.3 Hz, 1H), 6.68 (d, J=7.3 Hz, 1H), 7.18 (d, J=8.2 Hz, 1H), 7.26 (t, J=8.0 Hz, 1H), 7.30 (s, 1H), 7.72 (d, J=8.9 Hz, 2H), 7.91 (t, J=6.1 Hz, 1H), 7.95 (d, J=8.7 Hz, 2H), 8.10 (d, J=6.2 Hz, 1H), 9.59 (br s, 1H), 9.87 (br s, 1H), 10.38 (br s, 1H); MS (ESI+): m/z 469 (M+H)+.

Example 8

4-[4-(3-Hydroxy-phenylamino)-pyrimidin-2-ylamino]-N-(2-pyrrolidin-1-yl-ethyl)-benzene-sulfonamide (Compound V)

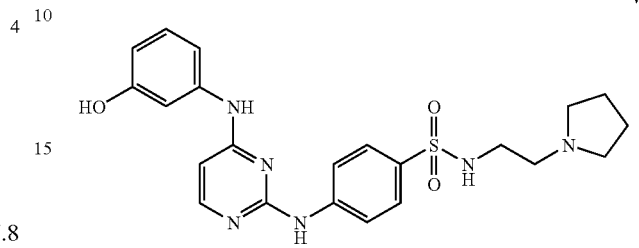

To a solution of the above-described compound IV (30 mg, 0.05 mmol) in DCM (6 mL) at room temperature was added BBr$_3$ (0.1 mL) and the mixture stirred at room temperature for 2.5 h. The reaction was quenched with saturated NaHCO$_3$ solution until the pH~7 and the mixture extracted with EtOAc (30 mL). The organic layer was separated and washed with brine, dried over MgSO$_4$ and filtered. The filtrate was concentrated and the residue purified by HPLC to afford the title compound V (13 mg of TFA salt, 46%) as an off white solid. $^1$H NMR (500 MHz, DMSO-d$_6$): 1.80-1.90 (m, 2H), 1.95-2.05 (m, 2H), 2.95-3.05 (m, 4H), 3.20-3.30 (m, 2H), 6.39 (d, J=6.3 Hz, 1H), 6.53 (d, J=7.2 Hz, 1H), 7.01 (d, J=9.2 Hz, 1H), 7.09 (s, 1H), 7.14 (t, J=8.1 Hz, 1H), 7.73 (d, J=8.8 Hz, 2H), 7.90 (t, J=6.2 Hz, 1H), 7.97 (d, J=8.8 Hz, 2H), 8.08 (d, J=6.4 Hz, 1H), 9.48 (br s, 1H), 9.57 (br s, 1H), 9.86 (br s, 1H), 10.41 (br s, 1H); MS (ESI+): m/z 455 (M+H)+.

Example 9

Benzo[1,3]dioxol-5-yl-(2-chloro-5-methyl-pyrimidin-4-yl)-amine (Intermediate 5)

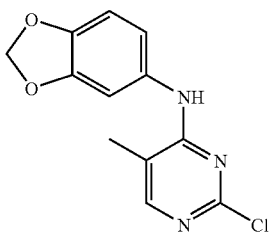

A mixture of 2-chloro-5-methyl-pyrimidin-4-ylamine (0.30 g, 2.1 mmol), 5-bromo-benzo[1,3]dioxole (0.45 g, 2.2 mmol), Pd(OAc)$_2$ (30 mg, 0.13 mmol), Xantphos (0.15 g, 0.26 mmol) and potassium tert-butoxide (0.45 g, 4.0 mmol) were suspended in dioxane (15 mL) and heated at reflux under the argon atmosphere for 16 h. The reaction mixture was cooled to room temperature and diluted with DCM (20 mL). The mixture was filtered and the filtrate concentrated in vacuo. The residue was purified by flash chromatography on silica gel (hexane to 50% EtOAc/hexane) to afford the title intermediate 5 (0.10 g, 18%) as a white solid. MS (ESI+): m/z 264 (M+H)+.

Example 10

N[4]-Benzo[1,3]dioxol-5-yl-5-methyl-N[2]-[4-(2-pyrrolidin-1-yl-ethoxy)-phenyl]-pyrimidine-2,4-diamine (Compound VI)

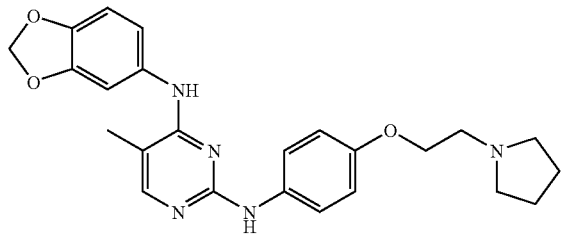

VI

To synthesize compound VI, intermediate 5 described above and intermediate 6 were used. Intermediate 6, 4-(2-pyrrolidin-1-yl-ethoxy)-phenylamine, the formula of which is shown below, was synthesized in two steps, first by alkylation of 4-nitrophenol using 2-chloroethylpyrrolidine, followed by reduction to yield the aniline derivative.

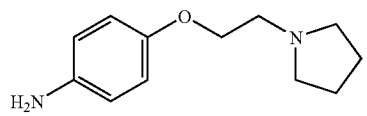

6

Commonly known synthetic techniques were used to synthesize intermediate 6. A mixture of the above-described intermediate 5 (90 mg, 0.34 mmol), intermediate 6 (95 mg, 0.46 mmol), $Pd_2(dba)_3$ (20 mg, 0.02 mmol), Xantphos (30 mg, 0.05 mmol) and cesium carbonate (0.30 g, 0.9 mmol) were suspended in dioxane (10 mL) and heated at reflux under the argon atmosphere for 20 h. The reaction mixture was cooled to room temperature and diluted with DCM (20 mL). The mixture was filtered and the filtrate concentrated in vacuo. The residue was purified by HPLC to afford the title compound VI (40 mg of TFA salt, 21%) as a brown solid. $^1$H NMR (500 MHz, DMSO-$d_6$): 1.85-1.95 (m, 2H), 1.95-2.05 (m, 2H), 2.13 (s, 3H), 3.10-3.20 (m, 2H), 4.26 (t, J=5.0 Hz, 2H), 6.07 (s, 2H), 6.90-7.00 (m, 4H), 7.19 (s, 1H), 7.37 (d, J=9.0 Hz, 2H), 7.84 (s, 1H), 9.60 (br s, 1H), 9.89 (br s, 1H), 10.32 (br s, 1H); MS (ESI+): m/z 434 (M+H)$^+$.

Example 11

(4-Chloro-3-methoxy-phenyl)-(2-chloro-5-methyl-pyrimidin-4-yl)-amine (Intermediate 7)

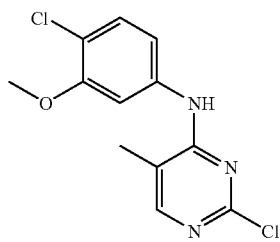

7

A mixture of 2-chloro-5-methyl-pyrimidin-4-ylamine (0.50 g, 3.5 mmol), 4-bromo-1-chloro-2-methoxy-benzene (0.65 mL, 4.8 mmol), $Pd_2(dba)_3$ (0.17 g, 0.19 mmol), Xantphos (0.22 g, 0.38 mmol) and cesium carbonate (2.3 g, 7.1 mmol) were suspended in dioxane (20 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexane to 40% EtOAc/hexane) to afford the title intermediate 7 (0.55 g, 55%) as a yellow solid. $^1$H NMR (500 MHz, DMSO-$d_6$): 2.18 (s, 3H), 3.85 (s, 3H), 7.35 (dd, J=8.6 Hz, J=2.3 Hz, 1H), 7.39 (d, J=8.7 Hz, 1H), 7.56 (d, J=2.3 Hz, 1H), 8.09 (d, J=0.9 Hz, 1H), 8.91 (s, 1H); MS (ESI+): m/z 284 (M+H)$^+$.

Example 12

(4-Chloro-3-methoxy-phenyl)-(2-chloro-5-methyl-pyrimidin-4-yl)-methyl-amine (Intermediate 8)

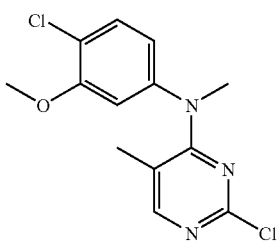

8

A suspension of intermediate 7 (0.50 g, 1.8 mmol) and sodium hydride (60% in mineral oil, 0.15 g, 3.8 mmol) in THF (10 mL) was stirred under the argon atmosphere at 0° C. for 5 min. Methyl iodide (0.15 mL, 2.4 mmol) was syringed at the same temperature to the above mixture. The resulting solution was stirred from 0° C. to room temperature over 15 min and further stirred at room temperature for additional 17 h. The reaction was quenched with water (10 mL) and then extracted with EtOAc (30 mL). The organic layer was separated and washed with brine, dried over $MgSO_4$ and filtered. The filtrate was concentrated and the residue purified by flash chromatography on silica gel (hexane to 20% EtOAc/hexane) to afford the title intermediate 8 (0.20 g, 38%) as a white solid. MS (ESI+): m/z 298 (M+H)$^+$.

Example 13

N[2]-(4-(2-(pyrrolidin-1-yl)ethoxy)phenyl)-N[4]-(4-chloro-3-methoxyphenyl)-N[4],5-dimethylpyrimidine-2,4-diamine (Compound VII)

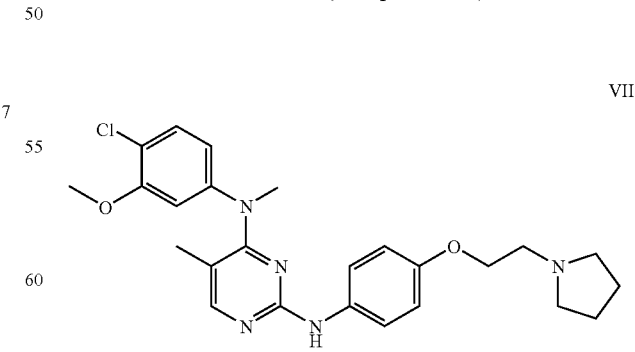

VII

A mixture of intermediate 8 (0.15 g, 0.49 mmol) and intermediate 6 (0.15 g, 0.73 mmol), each of which intermediates is described above, were suspended in acetic acid (8 mL) and heated at 100° C. for 17 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound VII (0.14 g of TFA salt, 49%) as a white solid. $^1$H NMR (500 MHz, DMSO-d$_6$): 1.85-1.95 (m, 2H), 2.00-2.10 (m, 2H), 3.08-3.18 (m, 2H), 3.46 (s, 3H), 3.55-3.65 (m, 4H), 3.85 (s, 3H), 4.27 (t, J=5.0 Hz, 2H), 6.86 (d, J=7.4 Hz, 1H), 7.01 (d, J=9.0 Hz, 2H), 7.15 (s, 1H), 7.46 (d, J=8.4 Hz, 1H), 7.58 (d, J=8.9 Hz, 2H), 7.83 (s, 1H), 9.85 (br s, 1H), 10.04 (br s, 1H), 10.32 (br s, 1H); MS (ESI+): m/z 468 (M+H)$^+$.

Example 14

(2-Chloro-5-methyl-pyrimidin-4-yl)-(4-chloro-phenyl)-amine (Intermediate 9)

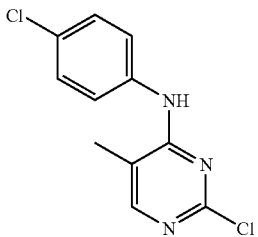

9

A mixture of 2-chloro-5-methyl-pyrimidin-4-ylamine (0.30 g, 2.1 mmol), 1-bromo-4-chloro-benzene (0.60 g, 3.1 mmol), Pd$_2$(dba)$_3$ (95 mg, 0.10 mmol), Xantphos (0.12 g, 0.20 mmol) and cesium carbonate (1.3 g, 4.0 mmol) were suspended in dioxane (20 mL) and heated at reflux under the argon atmosphere for 4 h. The reaction mixture was cooled to room temperature and diluted with DCM (20 mL). The mixture was filtered and the filtrate concentrated in vacuo. The residue was purified by flash chromatography on silica gel (hexane to 30% EtOAc/hexane) to afford the title intermediate 9 (0.15 g, 28%) as a pale yellow solid. MS (ESI+): m/z 254 (M+H)$^+$.

Example 15

N$^4$-(4-Chloro-phenyl)-5-methyl-N$^2$-[4-(2-pyrrolidin-1-yl-ethoxy)-phenyl]-pyrimidine-2,4-diamine (Compound VIII)

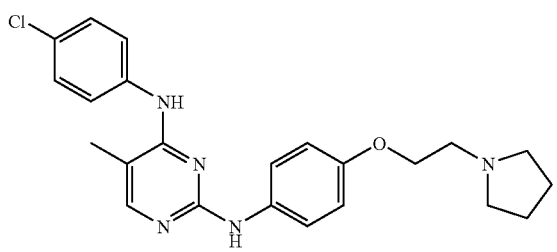

VIII

A mixture of the above-described intermediates 9 (0.15 g, 0.60 mmol) and 6 (0.20 g, 0.97 mmol) was suspended in acetic acid (8 mL) and heated at 100° C. for 6 h. The mixture was allowed to cool to room temperature and acetic acid removed under reduced pressure. The residue was taken in water (15 mL) and neutralized to pH~7 with 7M of NaOH solution. The resulting brown solid was filtered and further purified by HPLC to afford the title compound VIII (38 mg of TFA salt, 12%) as a brown oil. $^1$H NMR (500 MHz, DMSO-d$_6$): 1.80-1.95 (m, 2H), 2.00-2.10 (m, 2H), 2.15 (s, 3H), 3.10-3.20 (m, 2H), 3.55-3.65 (m, 4H), 3.77 (s, 3H), 4.28 (t, J=5.0 Hz, 2H), 6.95 (d, J=9.0 Hz, 2H), 7.38 (d, J=8.9 Hz, 2H), 7.42 (d, J=8.9 Hz, 2H), 7.62 (d, J=8.8 Hz, 2H), 7.90 (s, 1H), 9.48 (br s, 1H), 9.84 (br s, 1H), 10.10 (br s, 1H); MS (ESI+): m/z 424 (M+H)$^+$.

Example 16

2-(4-Amino-phenoxy)-ethanol (Intermediate 10)

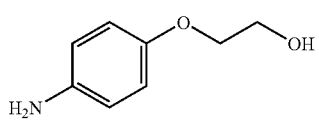

10

A solution of 2-(4-nitro-phenoxy)-ethanol (2.1 g, 12 mmol) in MeOH (30 mL) was flushed with argon and then charged with Pd/C (10% by wt). The mixture was evacuated under house vacuum and then refilled with hydrogen from hydrogen balloon. The cycle was repeated again and the mixture stirred at room temperature for 2 h. The heterogeneous reaction mixture was filtered through a pad of Celite, washed with MeOH and concentrated in vacuo to furnish the title intermediate 10 (1.8 g, 99%) as a brown solid. MS (ESI+): m/z 154 (M+H)$^+$.

Example 17

2-{4-[4-(4-Chloro-3-methoxy-phenylamino)-5-methyl-pyrimidin-2-ylamino]-phenoxy}-ethanol (Compound IX)

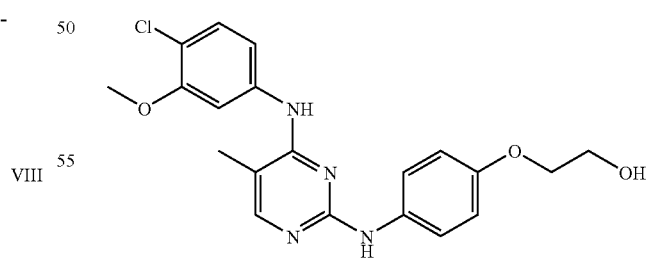

IX

A suspension of the above described intermediates 7 (50 mg, 0.17 mmol), 10 (40 mg, 0.26 mmol), Pd$_2$(dba)$_2$ (8 mg, 0.01 mmol), Xantphos (10 mg, 0.02 mmol) and cesium carbonate (0.13 g, 0.40 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (hexane to EtOAc) to afford the title compound IX (14 mg, 21%) as a light brown solid. $^1$H NMR (500 MHz, DMSO-$d_6$): 2.10 (s, 3H), 3.69 (t, J=5.3 Hz, 2H), 3.75 (s, 3H), 3.92 (t, J=5.1 Hz, 2H), 4.83 (t, J=5.6 Hz, 1H), 6.78 (d, J=9.0 Hz, 2H), 7.29 (d, J=8.5 Hz, 1H), 7.43 (dd, J=8.6 Hz, J=2.2 Hz, 1H), 7.48 (d, J=2.3 Hz, 1H), 7.52 (d, J=9.0 Hz, 2H), 7.88 (s, 1H), 8.31 (s, 1H), 8.80 (s, 1H); MS (ESI+): m/z 401 (M+H)$^+$.

Example 18

5-Methyl-$N^2$-[4-(2-pyrrolidin-1-yl-ethoxy)-phenyl]-pyrimidine-2,4-diamine (Intermediate 11)

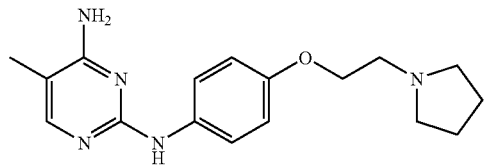

11

A mixture of 2-chloro-5-methyl-pyrimidin-4-ylamine (0.13 g, 0.87 mmol) and the above described intermediate 6 (0.30 g, 1.5 mmol) were suspended in acetic acid (8 mL) and heated at 100° C. for 2 h. The mixture was allowed to cool to room temperature and acetic acid removed under reduced pressure. The residue was taken in water (15 mL) and neutralized to pH~7 with 7M of NaOH solution. The resulting solid was filtered (30 mg) and washed with ether. The filtrate was extracted with EtOAc (30 mL) and the organic layer separated. The organic layer was washed with brine, dried over MgSO$_4$ and filtered. The filtrate was concentrated to afford the additional solid (0.2 g), which were combined with the first batch and afforded the title intermediate 11 (0.23 g, 85%) as a light brown solid. $^1$H NMR (500 MHz, DMSO-$d_6$): 1.65-1.70 (m, 4H), 1.89 (s, 3H), 2.74 (t, J=6.0 Hz, 2H), 3.98 (t, J=6.1 Hz, 2H), 6.30 (s, 2H), 6.78 (d, J=9.1 Hz, 2H), 7.62 (d, J=9.1 Hz, 2H), 7.64 (s, 1H), 8.50 (s, 1H); MS (ESI+): m/z 314 (M+H)$^+$.

Example 19

5-Methyl-$N^4$-phenyl-$N^2$-[4-(2-pyrrolidin-1-yl-ethoxy)-phenyl]-pyrimidine-2,4-diamine (Compound X)

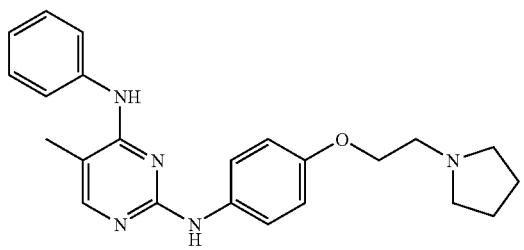

X

A suspension of the above-described intermediate 11 (25 mg, 0.08 mmol), bromobenzene (0.05 mL, 0.50 mmol), Pd$_2$(dba)$_2$ (5 mg, 0.006 mmol), Xantphos (10 mg, 0.02 mmol) and cesium carbonate (70 mg, 0.21 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 30% MeOH/DCM) to afford the title compound X (10 mg, 32%) as alight brown solid. $^1$H NMR (500 MHz, DMSO-$d_6$): 1.65-1.72 (m, 4H), 2.10 (s, 3H), 2.48-2.58 (m, 4H), 2.75-2.82 (m, 2H), 4.00 (t, J=5.9 Hz, 2H), 6.77 (d, J=9.0 Hz, 2H), 7.04 (t, J=7.3 Hz, 1H), 7.32 (t, J=7.9 Hz, 2H), 7.54 (d, J=9.0 Hz, 2H), 7.71 (d, J=7.8 Hz, 2H), 7.84 (s, 1H), 8.20 (s, 1H), 8.76 (s, 1H); MS (ESI+): m/z 390 (M+H)$^+$.

Example 20

(4-Chloro-3-fluoro-phenyl)-(2-chloro-5-methyl-pyrimidin-4-yl)-amine (Intermediate 12)

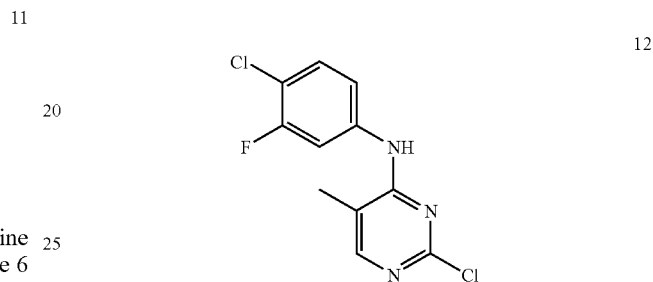

12

A mixture of 2-chloro-5-methyl-pyrimidin-4-ylamine (0.50 g, 3.5 mmol), 4-Bromo-1-chloro-2-fluoro-benzene (1.0 g, 4.8 mmol), Pd$_2$(dba)$_3$ (0.16 g, 0.17 mmol), Xantphos (0.20 g, 0.34 mmol) and cesium carbonate (2.3 g, 7.0 mmol) were suspended in dioxane (25 mL) and heated at reflux under the argon atmosphere for 15 h. The reaction mixture was cooled to room temperature and diluted with DCM (30 mL). The mixture was filtered and the filtrate concentrated in vacuo. The residue was purified by flash chromatography on silica gel (hexane to 40% EtOAc/hexane) to afford the title intermediate 12 (0.75 g, 80%) as an off white solid. MS (ESI+): m/z 272 (M+H)$^+$.

Example 21

$N^4$-(4-Chloro-3-fluoro-phenyl)-5-methyl-$N^2$-[4-(2-pyrrolidin-1-yl-ethoxy)-phenyl]-pyrimidine-2,4-diamine (Compound XI)

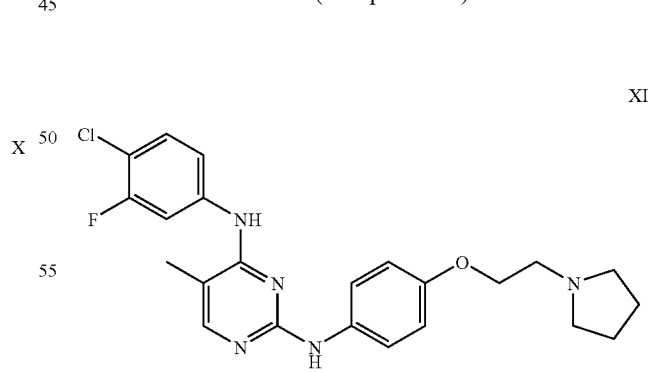

XI

A mixture of the above-described intermediates 12 (0.20 g, 0.74 mmol) and 6 (0.20 g, 0.97 mmol) was suspended in acetic acid (8 mL) and heated at 100° C. for 6 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by flash chromatography on silica gel (DCM to 30% MeOH/DCM) to afford the title compound XI (90 mg, 28%) as a white solid. $^1$H NMR (500 MHz, DMSO-d$_6$): 1.65-1.71 (m, 4H), 2.10 (s, 3H), 2.45-2.55 (m, 4H), 2.77 (t, J=6.0 Hz, 2H), 4.01 (t, J=6.0 Hz, 2H), 6.82 (d, J=9.0 Hz, 2H), 7.44 (t, J=8.8 Hz, 1H), 7.50 (d, J=9.0 Hz, 2H), 7.55 (dd, J=8.9 Hz, J=2.0 Hz, 1H), 7.91 (s, 1H), 8.07 (dd, J=12.5 Hz, J=2.0 Hz, 1H), 8.43 (s, 1H), 8.90 (s, 1H); MS (ESI+): m/z 442 (M+H)$^+$.

Example 22

N$^4$-(4-Chloro-3-methoxy-phenyl)-5-methyl-N$^2$-(4-morpholin-4-ylmethyl-phenyl)-pyrimidine-2,4-diamine (Compound XII)

XII

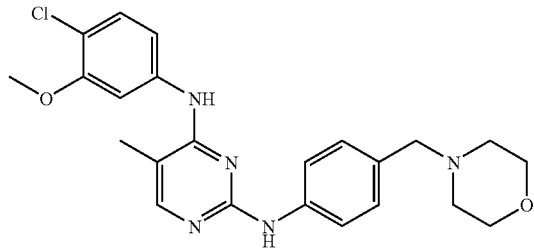

A suspension of the above-described intermediate 7 (50 mg, 0.17 mmol), 4-morpholin-4-ylmethyl-phenylamine (50 mg, 0.26 mmol), Pd$_2$(dba)$_2$ (8 mg, 0.009 mmol), Xantphos (10 mg, 0.02 mmol) and cesium carbonate (0.13 g, 0.40 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound XII (40 mg of TFA salt, 43%) as a pale yellow solid. $^1$H NMR (500 MHz, DMSO-d$_6$): 2.16 (s, 3H), 3.05-3.15 (m, 2H), 3.10-3.20 (m, 2H), 3.60-3.70 (m, 2H), 3.90-4.00 (m, 2H), 4.28 (s, 2H), 4.01 (t, J=6.0 Hz, 2H), 7.25-7.35 (m, 3H), 7.35-7.41 (m, 2H), 7.65 (d, J=8.3 Hz, 2H), 7.98 (s, 1H), 9.10 (br s, 1H), 9.86 (br s, 1H), 9.95 (br s, 1H); MS (ESI+): m/z 440 (M+H)$^+$.

Example 23

Benzo[b]thiophen-5-yl-(2-chloro-5-methyl-pyrimidin-4-yl)-amine (Intermediate 13)

13

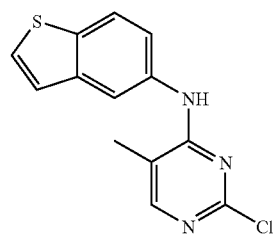

A mixture of 2-chloro-5-methyl-pyrimidin-4-ylamine (0.30 g, 2.1 mmol), 5-bromo-benzo[b]thiophene (0.6 g, 2.8 mmol), Pd$_2$(dba)$_3$ (95 mg, 0.10 mmol), Xantphos (0.12 g, 0.20 mmol) and cesium carbonate (1.3 g, 4.0 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by flash chromatography on silica gel (hexane to 30% EtOAc/hexane) to afford the title intermediate 13 (0.23 g, 40%) as a white solid. MS (ESI+): m/z 276 (M+H)$^+$.

Example 24

N$^4$-Benzo[b]thiophen-5-yl-5-methyl-N$^2$-[4-(2-pyrrolidin-1-yl-ethoxy)-phenyl]-pyrimidine-2,4-diamine (Compound XIII)

XIII

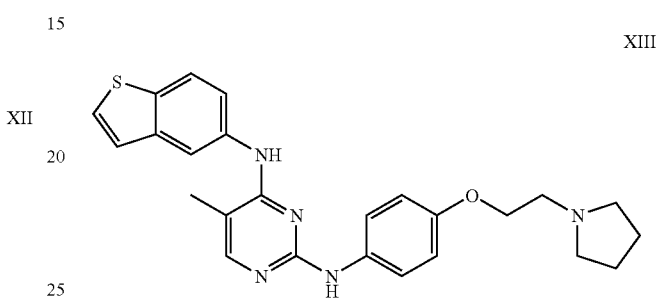

A mixture of the above-described intermediates 13 (0.23 g, 0.83 mmol) and 6 (0.35 g, 1.7 mmol) were suspended in acetic acid (8 mL) and heated at 100° C. for 1 d. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by flash chromatography on silica gel (DCM to 15% MeOH/DCM) to afford the title compound XIII (0.13 g, 35%) as a white solid. $^1$H NMR (500 MHz, DMSO-d$_6$): 1.65-1.75 (m, 4H), 2.12 (s, 3H), 2.50-2.62 (m, 4H), 2.75-2.85 (m, 2H), 3.99 (t, J=5.9 Hz, 2H), 6.70 (d, J=9.0 Hz, 2H), 7.36 (d, J=5.4 Hz, 1H), 7.51 (d, J=9.1 Hz, 2H), 7.61 (dd, J=8.7 Hz, J=2.0 Hz, 1H), 7.74 (d, J=5.4 Hz, 1H), 7.85 (d, J=0.8 Hz, 1H), 7.92 (d, J=8.6 Hz, 1H), 8.29 (d, J=1.7 Hz, 1H), 8.34 (s, 1H), 8.76 (s, 1H); MS (ESI+): m/z 446 (M+H)$^+$.

Example 25

Benzo[b]thiophen-3-yl-(2-chloro-5-methyl-pyrimidin-4-yl)-amine (Intermediate 14)

14

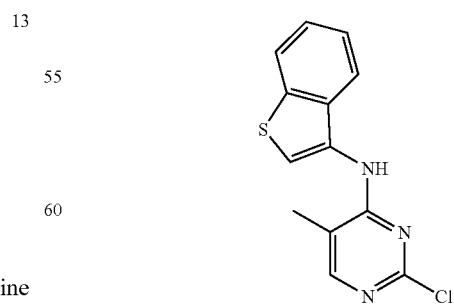

A mixture of 2-chloro-5-methyl-pyrimidin-4-ylamine (0.30 g, 2.1 mmol), 3-bromo-benzo[b]thiophene (0.6 g, 2.8 mmol), Pd$_2$(dba)$_3$ (95 mg, 0.10 mmol), Xantphos (0.12 g, 0.20 mmol) and cesium carbonate (1.3 g, 4.0 mmol) were suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by flash chromatography on silica gel (hexane to 30% EtOAc/hexane) to afford the title intermediate 14 (65 mg, 11%) as a yellow solid. MS (ESI+): m/z 276 (M+H)$^+$.

Example 26

N$^4$-Benzo[b]thiophen-3-yl-5-methyl-N$^2$-[4-(2-pyrrolidin-1-yl-ethoxy)-phenyl]-pyrimidine-2,4-diamine (Compound XIV)

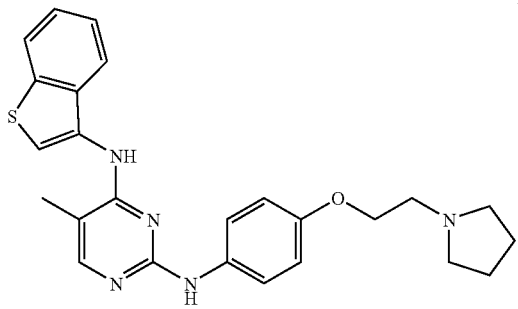

XIV

A mixture of the above-described intermediates 14 (50 mg, 0.18 mmol) and 6 (0.10 g, 0.48 mmol) was suspended in acetic acid (8 mL) and heated at 100° C. for 15 h. The mixture was allowed to cool to room temperature and acetic acid removed under reduced pressure. The residue was taken in water (10 mL) and neutralized to pH~7 with 7M of NaOH solution. The resulting solution was extracted with EtOAc (20 mL) and the organic layer separated. The organic layer was washed with brine, dried over MgSO$_4$ and filtered. The filtrate was concentrated in vacuo and the crude product purified by flash chromatography on silica gel (DCM to 15% MeOH/DCM) to afford the title compound XIV (10 mg, 13%) as an off white solid. $^1$H NMR (500 MHz, DMSO-d$_6$): 1.70-1.80 (m, 4H), 2.19 (s, 3H), 2.65-2.80 (m, 4H), 2.85-3.00 (m, 2H), 3.98-4.03 (m, 2H), 6.63 (d, J=8.8 Hz, 2H), 7.37 (d, J=8.6 Hz, 2H), 7.38-7.45 (m, 2H), 7.79-7.83 (m, 1H), 7.87 (s, 1H), 7.90-8.03 (m, 1H), 8.33 (s, 1H), 8.78 (s, 1H); MS (ESI+): m/z 446 (M+H)$^+$.

Example 27

(2-Chloro-5-methyl-pyrimidin-4-yl)-(3-chloro-phenyl)-amine (Intermediate 15)

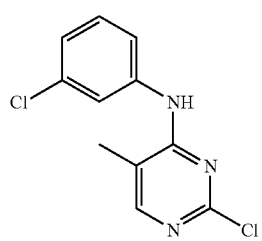

15

A mixture of 2-chloro-5-methyl-pyrimidin-4-ylamine (0.30 g, 2.1 mmol), 1-bromo-3-chloro-benzene (0.60 g, 3.1 mmol), Pd$_2$(dba)$_3$ (95 mg, 0.10 mmol), Xantphos (0.12 g, 0.20 mmol) and cesium carbonate (1.3 g, 4.0 mmol) was suspended in dioxane (20 mL) and heated at reflux under the argon atmosphere for 4 h. The reaction mixture was cooled to room temperature and diluted with DCM (20 mL). The mixture was filtered and the filtrate concentrated in vacuo. The residue was purified by flash chromatography on silica gel (hexane to 40% EtOAc/hexane) to afford the title intermediate 15 (0.30 g, 56%) as a pale yellow solid. MS (ESI+): m/z 254 (M+H)$^+$.

Example 28

N$^4$-(3-Chloro-phenyl)-5-methyl-N$^2$-[4-(2-pyrrolidin-1-yl-ethoxy)-phenyl]-pyrimidine-2,4-diamine (Compound XV)

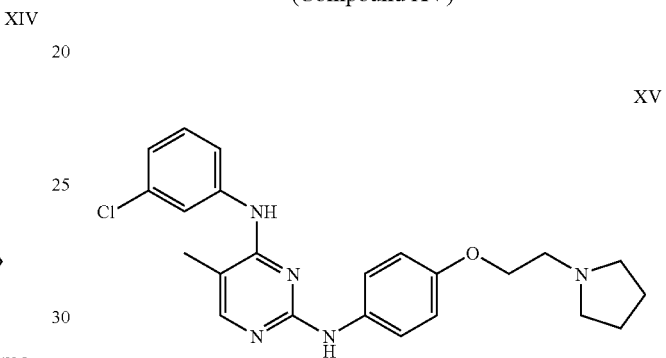

XV

A mixture of the above-described intermediates 15 (0.15 g, 0.59 mmol) and 6 (0.25 g, 1.2 mmol) was suspended in acetic acid (8 mL) and heated at 100° C. for 21 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by flash chromatography on silica gel (DCM to 10% MeOH/DCM) to afford the title compound XV (60 mg, 24%) as a white solid. $^1$H NMR (500 MHz, DMSO-d$_6$): 1.65-1.72 (m, 4H), 2.10 (s, 3H), 2.50-2.60 (m, 4H), 2.78-2.83 (m, 2H), 4.01 (t, J=5.9 Hz, 2H), 6.81 (d, J=9.1 Hz, 2H), 7.05-7.08 (m, 1H), 7.32 (t, J=8.1 Hz, 1H), 7.52 (d, J=9.0 Hz, 2H), 7.71 (d, J=8.3 Hz, 1H), 7.85 (t, J=2.1 Hz, 1H), 7.89 (d, J=0.7 Hz, 1H), 8.33 (s, 1H), 8.86 (s, 1H); MS (ESI+): m/z 424 (M+H)$^+$.

Example 29

3-Bromo-N-methyl-benzamide (Intermediate 16)

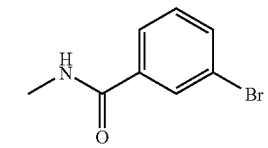

16

A solution of 3-bromo-benzoyl chloride (2.93 g, 13.3 mmol, 1 eq) in 30 mL THF was stirred vigorously and treated with 2.0M methylamine in THF (15 mL, 29.4 mmol, 2.2 eq). A white precipitate was observed and the reaction was allowed to stir for 20 minutes. Reaction was then poured onto ethyl acetate (100 mL) and washed with water (2×150 mL) and brine (1×150 mL). Organic phase cut from aqueous phase and dried over sodium sulfate, filtered and evaporated to afford the title intermediate 16 as a white powder. (2.29 g, 82% yield).

Example 30

3-(2-Chloro-5-methyl-pyrimidin-4-ylamino)-N-methyl-benzamide (Intermediate 17)

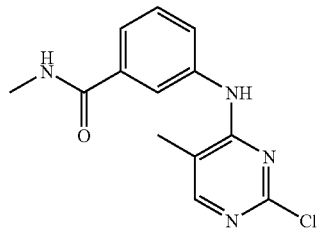

17

In a dry 50 mL round bottom flask, 2-chloro-5-methyl-pyrimidin-4-ylamine (0.3 g, 2.09 mmol, 1 equiv), 3-bromo-N-methyl-benzamide (0.489 g, 2.29 mmol, 1.1 equiv), cesium carbonate (2.04 g, 6.27 mmol, 3 equiv), 4,5-bis(diphenylphosphino)-9,9-dimethyl xanthene (0.242 g, 0.418 mmol, 0.2 equiv) and tris(dibenzylideneacetone) dipalladium (0.191 g, 0.209 mmol, 0.1 equiv) were combined. Reactants were diluted with dioxane (20 mL), flushed with argon and outfitted with reflux condenser. Reaction was heated to reflux for 16 hours. Reaction was then transferred into centrifuge tube, spun down, decanted and evaporated. Resulting yellow solids were diluted with DCM and adsorbed onto silica gel. Chromatography (gradient of 50% ethyl acetate in hexanes up to 100% ethyl acetate) afforded the title intermediate 17 as a pale yellow powder (0.25 g, 43% yield). MS (ESI+): 277.01 (M+H), r.t.=1.92 min.

Example 31

N-Methyl-3-{5-methyl-2-[4-(2-pyrrolidin-1-yl-ethoxy)-phenylamino]-pyrimidin-4-ylamino}-benzamide TFA salt (Compound XVI)

XVI

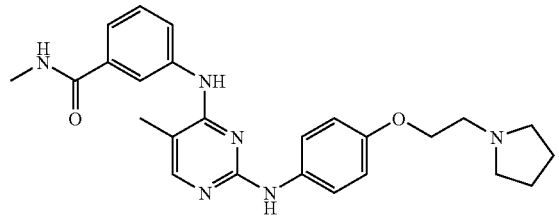

The above-described intermediate 17 (0.068 g, 0.246 mmol, 1 eq), 4-(2-Pyrrolidin-1-yl-ethoxy)-phenylamine (0.061 g, 0.296 mmol, 1.2 eq), cesium carbonate (0.241 g, 0.74 mmol, 3 equiv), 4,5-bis(diphenylphosphino)-9,9-dimethyl xanthene (0.029 g, 0.05 mmol, 0.2 equiv) and tris(dibenzylideneacetone) dipalladium (0.023 g, 0.025 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title product XVI (0.084 g, 76%). MS (ESI+): 447.20 (M+H), r.t.=1.53 min. $^1$H NMR (DMSO-d$_6$): δ 1.87-1.91 (m, 2H), 2.02-2.06 (m, 2H), 2.16 (s, 3H), 2.79 (d, J=4.6 Hz, 3H), 3.11-3.15 (m, 2H), 3.57-3.61 (m, 5H), 4.23 (t, J=5.0 Hz, 3H), 6.84 (d, J=8.8 Hz, 2H), 7.34 (d, J=8.9 Hz, 2H), 7.47 (t, J=7.9 Hz, 1H), 7.68-7.70 (m, 2H), 7.93 (s, 1H), 8.00 (s, 1H), 8.46-8.47 (m, 1H), 9.80 (bs, 1H), 9.93 (bs, 1H) 10.41 (bs, 1H).

Example 32

$N^4$-(4-Chloro-3-methoxy-phenyl)-5-methyl-$N^2$-[4-(2-pyrrolidin-1-yl-ethoxy)-phenyl]-pyrimidine-2,4-diamine TFA salt (Compound XVII)

XVII

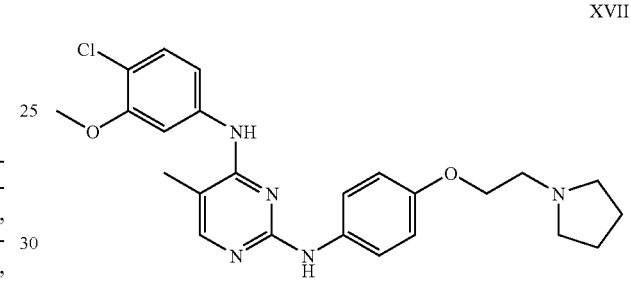

The above-described intermediate 7 (0.083 g, 0.293 mmol, 1 eq), 4-(2-Pyrrolidin-1-yl-ethoxy)-phenylamine (0.073 g, 0.352 mmol, 1.2 eq), cesium carbonate (0.287 g, 0.879 mmol, 3 equiv), 4,5-bis(diphenylphosphino)-9,9-dimethyl xanthene (0.034 g, 0.059 mmol, 0.2 equiv) and tris(dibenzylideneacetone) dipalladium (0.027 g, 0.029 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title product XVII (0.1 g, 75%). MS (ESI+): 454.13 (M+H), r.t.=1.82 min. $^1$H NMR (DMSO-d$_6$): δ 1.87-1.90 (m, 2H), 2.02-2.05 (m, 2H), 2.15 (s, 3H), 3.11-3.14(m, 2H), 3.58-3.61 (m, 5H), 3.70 (s, 3H), 4.26 (t, J=5.0 Hz, 3H), 6.91 (d, J=8.9 Hz, 2H), 7.23 (m, 1H), 7.34-7.4 (m, 4H), 7.93 (s, 1H), 9.63 (bs, 1H), 9.96 (bs, 1H) 10.40 (bs, 1H).

Example 33

N-(2-Chloro-5-methyl-pyrimidin-4-yl)-N',N'-dimethyl-benzene-1,3-diamine (Intermediate 18)

18

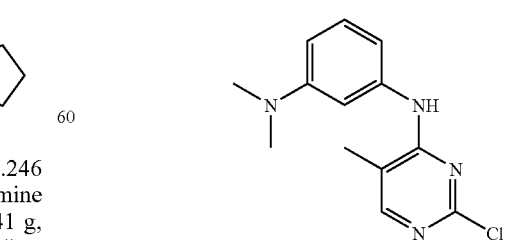

2-Chloro-5-methyl-pyrimidin-4-ylamine (0.343 g, 2.38 mmol, 1 equiv), (3-bromo-phenyl)-dimethyl-amine (0.524 g, 2.62 mmol, 1.1 equiv), cesium carbonate (2.3 g, 7.15 mmol, 3 equiv), 4,5-bis(diphenylphosphino)-9,9-dimethyl xanthene (0.276 g, 0.476 mmol, 0.2 equiv) and tris(dibenzylideneacetone) dipalladium (0.218 g, 0.238 mmol, 0.1 equiv) were combined in 30 ml microwave vessel. Reactants were then diluted with 12 ml dioxane and microwaved for 25 minutes at 160° C. Reaction vessel was then spun down, decanted and evaporated to dryness. Resulting solids were diluted with DCM and adsorbed onto silica gel. Chromatography (gradient of 0% methanol in DCM up to 25% methanol in DCM) afforded the title intermediate 18 as orange solid (0.184 g, 29% yield). MS (ESI+): 263.02 (M+H), r.t.=1.72 min.

Example 34

$N^4$-(3-Dimethylamino-phenyl)-5-methyl-$N^2$-[4-(2-pyrrolidin-1-yl-ethoxy)-phenyl]-pyrimidine-2,4-diamine TFA salt (Compound XVIII)

XVIII

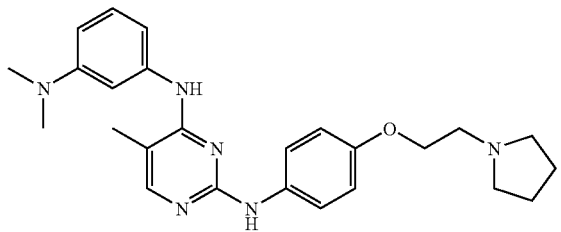

The above-described intermediate 18 (0.092 g, 0.35 mmol, 1 eq), 4-(2-pyrrolidin-1-yl-ethoxy)-phenylamine (0.087 g, 0.42 mmol, 1.2 eq), cesium carbonate (0.343 g, 1.05 mmol, 3 equiv), 4,5-bis(diphenyl phosphino)-9,9-dimethyl xanthene (0.041 g, 0.0702 mmol, 0.2 equiv) and tris(dibenzylideneacetone) dipalladium (0.032 g, 0.035 mmol, 0.1 equiv) were combined in a 15 ml microwave vessel. Reactants were then diluted with 7 ml dioxane and microwaved for 15 minutes at 160° C. Reaction vessel was then spun down, decanted and evaporated to dryness. HPLC purification provided the TFA salt of the title compound XVIII (0.035 g, 23%). MS (ESI+): 433.21 (M+H), r.t.=1.52 min. $^1$H NMR (DMSO-$d_6$): δ 1.87-1.90 (m, 2H), 2.03-2.06 (m, 2H), 2.15 (s, 3H), 2.87 (s, 6H), 3.12-3.15 (m, 2H), 3.57-3.60 (m, 4H), 3.70 (s, 3H), 4.25 (t, J=5.0 Hz, 3H), 6.34 (dd, J=8.4 Hz, J=2.3 Hz, 1H), 6.82-6.90 (m, 4H), 7.20 (t, J=8.0 Hz, 1H), 7.39 (d, J=9.1 Hz, 2H), 7.85 (s, 1H), 9.63 (bs, 1H), 9.90 (bs, 1H) 10.39 (bs, 1H).

Example 35

(2-Chloro-5-methyl-pyrimidin-4-yl)-(3,4-dichloro-phenyl)-amine (Intermediate 19)

19

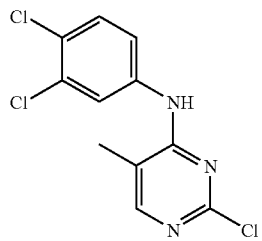

2-chloro-5-methyl-pyrimidin-4-ylamine (0.408 g, 2.83 mmol, 1 equiv), 4-Bromo-1,2-dichloro-benzene (0.704 g, 3.12 mmol, 1.1 equiv), cesium carbonate (2.8 g, 8.49 mmol, 3 equiv), 4,5-bis(diphenylphosphino)-9,9-dimethyl xanthene (0.328 g, 0.57 mmol, 0.2 equiv) and tris(dibenzylideneacetone) dipalladium (0.26 g, 0.283 mmol, 0.1 equiv) were combined in 30 ml microwave vessel. Reactants were then diluted with 12 ml dioxane and microwaved for 25 minutes at 160° C. Reaction vessel was then spun down, decanted and evaporated to dryness. Resulting solids were diluted with DCM and adsorbed onto silica gel. Chromatography (gradient of 15% ethyl acetate in hexanes up to 80% ethyl acetate in hexanes) afforded the title intermediate 19 as a pale yellow powder (0.366 g, 45% yield). MS (ESI+): 287.97 (M+H), r.t.=3.12 min.

Example 36

$N^4$-(3,4-Dichloro-phenyl)-5-methyl-$N^2$-[4-(2-pyrrolidin-1-yl-ethoxy)-phenyl]-pyrimidine-2,4-diamine TFA salt (Compound XIX)

XIX

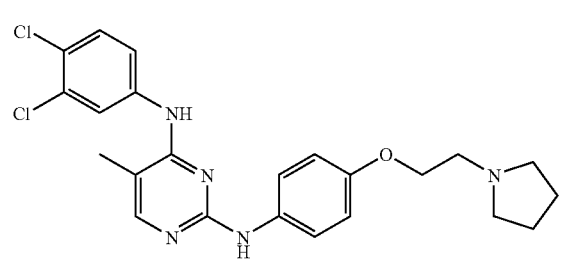

The above-described intermediate 19 (0.09 g, 0.313 mmol, 1 eq), 4-(2-pyrrolidin-1-yl-ethoxy)-phenylamine (0.078 g, 0.376 mmol, 1.2 eq), cesium carbonate (0.307 g, 0.941 mmol, 3 equiv), 4,5-bis(diphenylphosphino)-9,9-dimethyl xanthene (0.036 g, 0.063 mmol, 0.2 equiv) and tris(dibenzylideneacetone) dipalladium (0.029 g, 0.0314 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification provided the TFA salt of the title compound XIX (0.056 g, 39%). MS (ESI+): 458.1 (M+H), r.t.=1.93 min. $^1$H NMR (DMSO-$d_6$): δ 1.87-1.91 (m, 2H), 2.03-2.06 (m, 2H), 2.14 (s, 3H), 3.12-3.15 (m, 3H), 3.57-3.60 (m, 4H), 4.26 (t, J=5.0 Hz, 2H), 6.97 (d, J=9.0 Hz, 1H), 7.40 (d, J=9 Hz, 2H), 7.60 (s, 2H), 7.97 (d, J=15.35 Hz, 2H), 9.46 (bs, 1H), 9.89 (bs, 1H) 10.17 (bs, 1H).

Example 37

4-{3-[4-(4-Chloro-3-methoxy-phenylamino)-5-methyl-pyrimidin-2-ylamino]-benzyl}-piperazine-1-carboxylic acid tert-butyl ester (Intermediate 20)

20

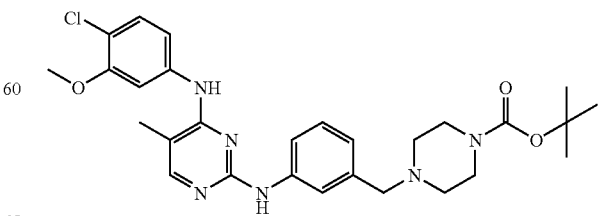

(4-Chloro-3-methoxy-phenyl)-(2-chloro-5-methyl-pyrimidin-4-yl)-amine (0.092 g, 0.325 mmol, 1 eq), 4-(3-aminobenzyl)-piperazine-1-carboxylic acid tert-butyl ester (0.114 g, 0.39 mmol, 1.2 eq), cesium carbonate (0.318 g, 0.975 mmol, 3 equiv), 4,5-bis(diphenylphosphino)-9,9-dimethyl xanthene (0.038 g, 0.065 mmol, 0.2 equiv) and tris(dibenzylideneacetone) dipalladium (0.03 g, 0.0325 mmol, 0.1 equiv) were combined in a 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title intermediate 20 (0.075 g, 43%). MS (ESI+): 539.32 (M+H), r.t.=2.09 min.

Example 38

N$^4$-(4-Chloro-3-methoxy-phenyl)-5-methyl-N$^2$-(3-piperazin-1-ylmethyl-phenyl)-pyrimidine-2,4-diamine TFA salt (Compound XX)

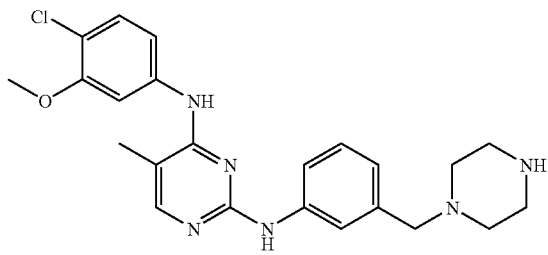

XX

A stirring solution of the above-described intermediate 20 (0.075 g, 0.14 mmol, 1 eq) in DCM (6 ml) was treated with TFA (2 ml). After 2 h, reaction solvents were evaporated and resulting residue triturated with ether to afford the title compound XX as white, hygroscopic solids, TFA salt. (0.05 g, 82%). MS (ESI+): 439.13 (M+H), r.t.=1.67 min. $^1$H NMR (DMSO-d$_6$): δ 2.17 (s, 3H), 2.89 (bs, 4H), 3.2 (bs, 4H), 3.68 (s, 3H), 3.82 (bs, 3H), 7.16-7.20 (m, 2H), 7.28 (t, J=7.7 Hz, 1H), 7.33 (d, J=2.3 Hz, 1H), 7.39 (s, 1H), 7.42 (d, J=8.5 Hz, 1H), 7.49-7.51 (m, 1H), 7.98 (s, 1H), 8.87 (bs, 1H), 9.79 (bs, 1H) 10.57 (bs, 1H).

Example 39

2-(4-(2-(Pyrrolidin-1-yl)ethoxy)phenylamino)-4-aminopyrimidine-5-carbonitrile (Intermediate 21)

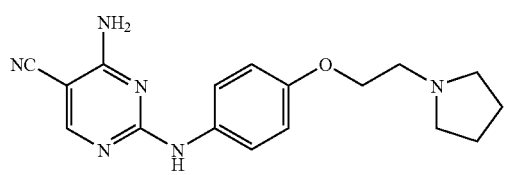

21

To a solution of 2,4-diaminopyrimidine-5-carbonitrile (135 mg, 1.00 mmol) in 1,4-dioxane (20 mL) was added 1-(2-(4-bromophenoxy)ethyl)pyrrolidine (270 mg, 1.0 mmol), Cs$_2$CO$_3$ (1.3 g, 4.0 mmol), Pd$_2$(dba)$_3$ (92 mg, 0.1 mmol), and 4,5-bis(diphenylphosphino)-9,9-dimethyxanthene (Xant Phos, 174 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (50 mL) was added, the solid was collected by filtration. The crude product was purified by HPLC and afforded the title intermediate 21 (32 mg, 10%).

Example 40

4-(2,4-Dichloro-5-methoxyphenylamino)-2-(4-(2-(pyrrolidin-1-yl)ethoxy)phenyl-amino)pyrimidine-5-carbonitrile (Compound XXI)

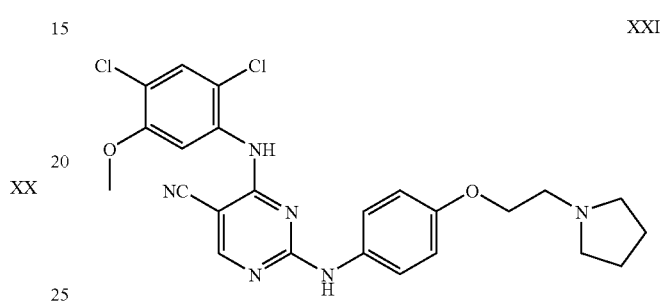

XXI

To a solution of the above-described intermediate 21 (32 mg, 0.1 mmol) in 1,4-dioxane (10 mL) was added 1-bromo-2,4-dichloro-5-methoxybenzene (28 mg, 0.11 mmol), Cs$_2$CO$_3$ (97 mg, 0.3 mmol), Pd$_2$(dba)$_3$ (7 mg, 0.0074 mmol), and 4,5-bis(diphenylphosphino)-9,9-dimethyxanthene (Xant Phos, 13 mg, 0.022 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by chromatograph (SiO$_2$/CH$_2$Cl$_2$, then CH$_2$Cl$_2$:MeOH:NH$_3$.H$_2$O=100:10:1) and afforded the title compound XXI (35 mg, 67%). $^1$H NMR (500 MHz, DMSO-d$^6$): 1.88-1.90 (m, 2H); 2.00-2.03 (m, 2H); 3.07-3.11 (m, 2H); 3.54-3.56 (m, 4H); 3.81 (s, 3H); 4.25 (br, 2H); 6.68 (br, 2H); 7.32 (br, 2H); 7.33 (s, 1H); 7.75 (s, 1H); 8.50 (s, 1H); 9.73 (br, 1H); 9.94 (br, 1H); 10.60 (br, 1H). MS (EI): 499.0.

Example 41

2-(3-(2-(Pyrrolidin-1-yl)ethoxy)phenylamino)-4-aminopyrimidine-5-carbonitrile (Intermediate 22)

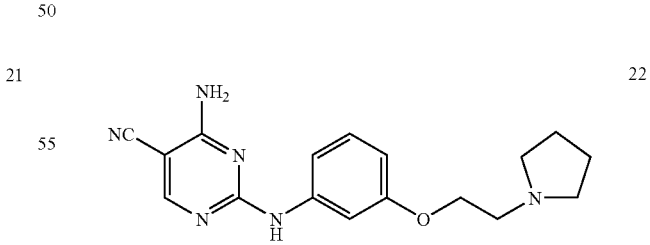

22

To a solution of 2,4-diaminopyrimidine-5-carbonitrile (145 mg, 1.07 mmol) in 1,4-dioxane (20 mL) was added 1-(2-(3-bromophenoxy)ethyl)pyrrolidine (290 mg, 1.07 mmol), Cs$_2$CO$_3$ (1.43 g, 4.4 mmol), Pd$_2$(dba)$_3$ (92 mg, 0.1 mmol), and 4,5-bis(diphenylphosphino)-9,9-dimethyxanthene (Xant Phos, 174 mg, 0.3 mmol). The mixture was heated under reflux for 4 h under Ar. The solid was filtered off

85 and the filtrate washed with brine (1×100 mL). The organic solution was separated and dried (Na$_2$SO$_4$). The solvent was removed until 5 mL and hexane (50 mL) was added, the solid was collected by filtration. The crude product was purified by HPLC and afforded the title intermediate 22 (55 mg, 16%).

Example 42

4-(2,4-Dichloro-5-methoxyphenylamino)-2-(3-(2-(pyrrolidin-1-yl)ethoxy)phenyl-amino)pyrimidine-5-carbonitrile (Compound XXII)

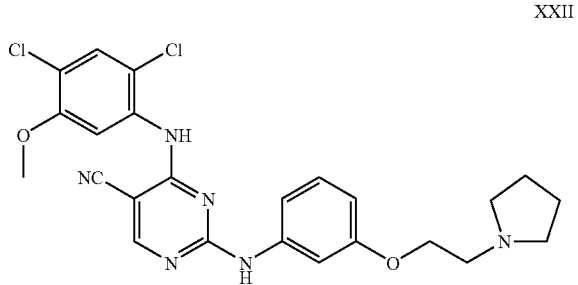

XXII

To a solution of the above-described intermediate 22 (50 mg, 0.15 mmol) in 1,4-dioxane (10 mL) was added 1-bromo-2,4-dichloro-5-methoxybenzene (44 mg, 0.17 mmol), Cs$_2$CO$_3$ (200 mg, 0.62 mmol), Pd$_2$(dba)$_3$ (14 mg, 0.015 mmol), and 4,5-bis(diphenylphosphino)-9,9-dimethyxanthene (Xant Phos, 27 mg, 0.05 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXII (6 mg, 8%). $^1$H NMR (500 MHz, DMSO-d$^6$): 1.87-1.89 (m, 2H); 1.90-2.03 (m, 2H); 3.04-3.08 (m, 2H); 3.52-3.56 (m, 4H); 3.80 (s, 3H); 4.23 (br, 2H); 6.62 (d, J=6.4 Hz, 2H); 6.97 (br, 1H); 7.14 (br, 2H); 7.34 (s, 1H); 7.74 (s, 1H); 8.54 (s, 1H); 9.70 (br, 1H); 9.95 (br, 1H); 10.83 (br, 1H). MS (EI): 499.0.

Example 43

2-Chloro-N-(2,4-dichloro-5-methoxyphenyl)-5-methylpyrimidin-4-amine (Intermediate 23)

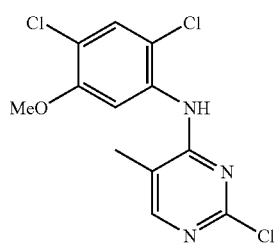

23

To a solution of 2-chloro-5-methylpyrimidin-4-amine (44.8 mg, 0.31 mmol) in 1,4-dioxane (20 mL) was added 1-bromo-2,4-dichloro-5-methoxybenzene (96 mg, 0.37 mmol), Cs$_2$CO$_3$ (408 mg, 1.25 mmol), Pd$_2$(dba)$_3$ (37 mg, 0.04 mmol), and 4,5-bis(diphenylphosphino)-9,9-dimethyxanthene (Xant Phos, 70 mg, 0.12 mmol). The mixture was heated under reflux for 4 h under Ar. The solid was filtered off and the filtrate washed with brine (1×100 mL). The organic solution was separated and dried (Na$_2$SO$_4$). The solvent was removed in vacuo. The crude product was used for next reaction without purification.

Example 44

N$^2$-(3-(2-(pyrrolidin-1-yl)ethoxy)phenyl)-N$^4$-(2,4-dichloro-5-methoxyphenyl)-5-methylpyrimidine-2,4-diamine (Compound XXIII)

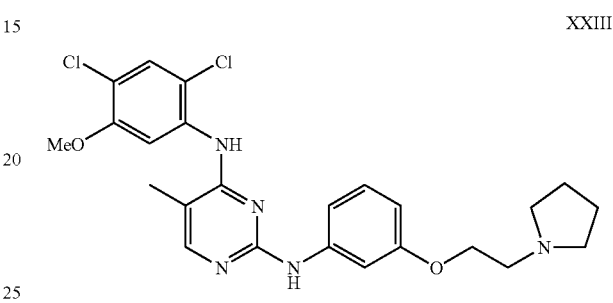

XXIII

To a solution of the above-described intermediate 23 in 1,4-dioxane (10 mL) was added 3-(2-(pyrrolidin-1-yl)ethoxy)benzenamine (77.3 mg, 0.38 mmol), Cs$_2$CO$_3$ (488 mg, 1.25 mmol), Pd$_2$(dba)$_3$ (28 mg, 0.03 mmol), and 4,5-bis(diphenylphosphino)-9,9-dimethyxanthene (Xant Phos, 53 mg, 0.09 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXIII (25 mg, 15%).

$^1$H NMR (500 MHz, DMSO-d$^6$): 1.87-1.89 (m, 2H); 1.90-2.03 (m, 2H); 2.18 (s, 3H); 3.04-3.08 (m, 2H); 3.52-3.56 (m, 4H); 3.80 (s, 3H); 4.24 (t, J=5.0 Hz, 2H); 6.71 (d, J=7.65 Hz, 1H); 6.91 (s, 1H); 6.96 (d, J=8.5 Hz, 1H); 7.02 (t, J=8.2 Hz, 1H); 7.37 (s, 1H); 7.83 (s, 1H); 8.02 (s, 1H); 10.09 (br, 1H); 10.66 (br, 1H); 10.82 (br, 1H). MS (EI): 488.2.

Example 45

2-Chloro-N-(3-methoxyphenyl)-5-methylpyrimidin-4-amine (Intermediate 24)

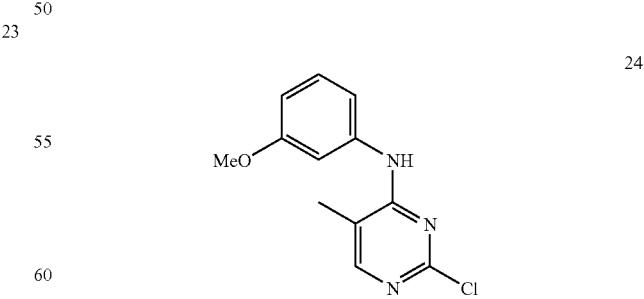

24

To a solution of 2-chloro-5-methylpyrimidin-4-amine (320 mg, 2.23 mmol) in 1,4-dioxane (40 mL) was added 1-bromo-3-methoxybenzene (458.5 mg, 2.45 mmol), Cs$_2$CO$_3$ (2.9 g, 8.9 mmol), Pd$_2$(dba)$_3$ (201 mg, 0.22 mmol), and 4,5-bis(diphenylphosphino)-9,9-dimethyxanthene (Xant Phos, 382 mg, 0.66 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 24 (500 mg, 90%), was used for next reaction without further purification.

Example 46

N$^2$-(4-(2-(pyrrolidin-1-yl)ethoxy)phenyl)-N$^4$-(3-methoxyphenyl)-5-methyl-pyrimidine-2,4-diamine (Compound XXIV)

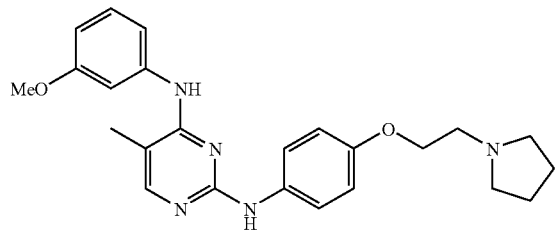

XXIV

To a solution of the above-described intermediate 24 (240 mg, 0.96 mmol) in 1,4-dioxane (20 mL) was added 4-(2-(pyrrolidin-1-yl)ethoxy)benzenamine (200 mg, 0.96 mmol), Cs$_2$CO$_3$ (1.3 mg, 4.0 mmol), Pd$_2$(dba)$_3$ (82 mg, 0.09 mmol), and 4,5-bis(diphenylphosphino)-9,9-dimethyxanthene (Xant Phos, 156 mg, 0.27 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXIV (85 mg, 20%). $^1$H NMR (500 MHz, DMSO-d$^6$): 1.89-1.91 (m, 2H); 1.98-2.05 (m, 2H); 2.16 (s, 3H); 3.07-3.12 (m, 2H); 3.52-3.56 (m, 4H); 3.73 (s, 3H); 4.33 (t, J=4.5 Hz, 2H); 6.83-6.85 (m, 1H); 6.91 (d, J=8.8 Hz, 2H); 7.17 (s, 1H); 7.34 (d, J=8.8 Hz, 2H); 7.41 (t, J=7.7 Hz, 1H); 7.56 (d, J=7.7 Hz, 1H); 7.89 (s, 1H); 9.75 (s, 1H); 10.51 (s, 1H); 10.96 (br, 1H). MS (EI): 420.2.

Example 47

3-(2-(4-(2-(Pyrrolidin-1-yl)ethoxy)phenylamino)-5-methylpyrimidin-4-ylamino)-phenol (Compound XXV)

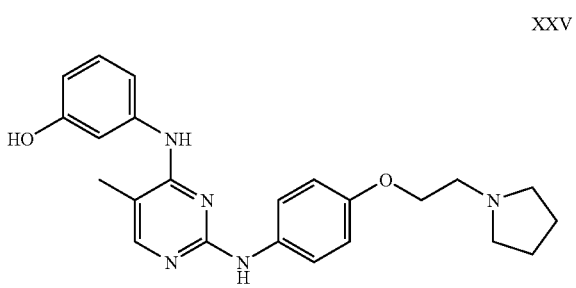

XXV

To a solution of the above-described compound XXIV (50 mg, 0.1 mmol) in anhydrous CH$_2$Cl$_2$ (10 mL) was added 1.0 M BBr$_3$ in CH$_2$Cl$_2$ (0.3 mL, 0.3 mmol). The mixture was stirred for 3 h at room temperature. The saturated NaHCO$_3$ (20 mL) was added and organic layer was separated. The aqueous was extracted with CH$_2$Cl$_2$ (3×10 mL). Combined organic solution was dried (Na$_2$SO$_4$). The product was purified by HPLC and afforded the title compound XXV (17 mg, 35%) as yellow solid. $^1$H NMR (500 MHz, DMSO-d$^6$): 1.89 (br, 2H); 2.00 (br, 2H); 2.14 (s, 3H); 3.09 (br, 2H); 3.42 (br, 4H); 4.33 (br, 2H); 6.72 (d, J=7.1 Hz, 1H); 6.91 (d, J=8.4 Hz, 2H); 6.96 (d, J=7.6 Hz, 1H); 7.00 (s, 1H); 7.18 (t, J=8.0 Hz, 1H); 7.38 (d, J=8.6 Hz, 2H); 7.88 (s, 1H); 9.70 (s, 1H); 9.74 (s, 1H); 10.55 (s, 1H); 11.09 (br, 1H). MS (EI): 406.2.

Example 48

2-Chloro-5-methyl-N-(3-nitrophenyl)pyrimidin-4-amine (Intermediate 25)

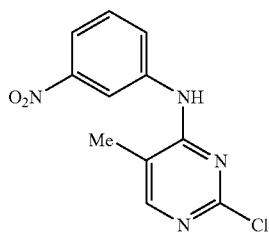

To a solution of 2-chloro-5-methylpyrimidin-4-amine (232 mg, 1.61 mmol) in 1,4-dioxane (40 mL) was added 1-bromo-3-nitrobenzene (359 mg, 1.78 mmol), Cs$_2$CO$_3$ (2.1 g, 6.4 mmol), Pd$_2$(dba)$_3$ (146 mg, 0.16 mmol), and 4,5-bis(diphenylphosphino)-9,9-dimethyxanthene (Xant Phos, 278 mg, 0.48 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 25, was used for next reaction without further purification.

Example 49

N$^2$-(4-(2-(pyrrolidin-1-yl)ethoxy)phenyl)-5-methyl-N$^4$-(3-nitrophenyl)pyrimidine-2,4-diamine (Compound XXVI)

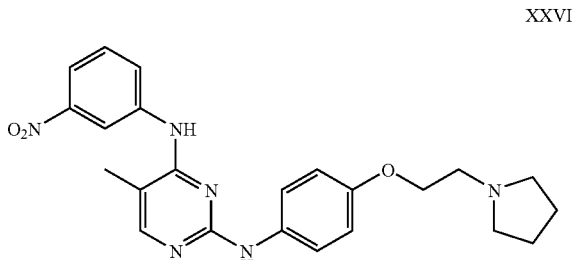

XXVI

To a solution of the above-described intermediate 25 in 1,4-dioxane (40 mL) was added 4-(2-(pyrrolidin-1-yl)ethoxy)benzenamine (367 mg, 1.78 mmol), Cs$_2$CO$_3$ (2.1 g, 6.4 mmol), Pd$_2$(dba)$_3$ (146 mg, 0.16 mmol), and 4,5-bis (diphenylphosphino)-9,9-dimethyxanthene (Xant Phos, 218 mg, 0.48 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXVI (51 mg, 7%).

$^1$H NMR (500 MHz, DMSO-d$^6$): 1.89-1.92 (m, 2H); 1.98-2.05 (m, 2H); 2.21 (s, 3H); 3.10-3.12 (m, 2H); 3.52-3.57 (m, 4H); 4.33 (t, J=4.8 Hz, 2H); 6.90 (d, J=8.9 Hz, 2H); 7.32 (d, J=8.9 Hz, 2H); 7.67 (t, J=8.2 Hz, 1H); 7.99 (s, 1H); 7.56 (dd, J=8.4 Hz, J=1.8 Hz, 1H); 8.09 (d, J=7.4 Hz, 1H); 8.45 (s, 1H); 10.14 (s, 1H); 10.60 (s, 1H); 11.17 (br, 1H). MS (EI): 435.2.

Example 50

4-(2-Chloro-5-methylpyrimidin-4-ylamino)-2-chlorobenzonitrile (Intermediate 26)

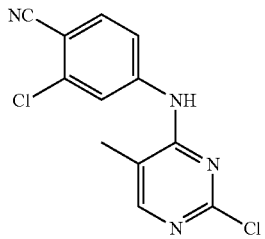

26

To a solution of 2-chloro-5-methylpyrimidin-4-amine (144 mg, 1.0 mmol) in 1,4-dioxane (20 mL) was added 4-bromo-2-chlorobenzonitrile (217 mg, 1.0 mmol), Cs$_2$CO$_3$ (1.3 g, 4.0 mmol), Pd$_2$(dba)$_3$ (91 mg, 0.1 mmol), and 4,5-bis(diphenylphosphino)-9,9-dimethyxanthene (Xant Phos, 173 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 26, was used for next reaction without further purification.

Example 51

4-(2-(4-(2-(pyrrolidin-1-yl)ethoxy)phenylamino)-5-methylpyrimidin-4-ylamino)-2-chlorobenzonitrile (Compound XXVII)

XXVII

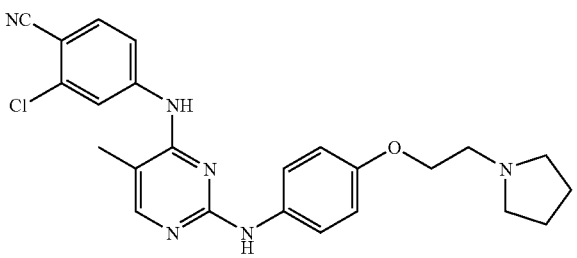

To a solution of the above-described intermediate 26 (140 mg, 0.5 mmol) in 1,4-dioxane (20 mL) was added 4-(2-(pyrrolidin-1-yl)ethoxy)benzenamine (113 mg, 0.55 mmol), Cs$_2$CO$_3$ (660 mg, 2.0 mmol), Pd$_2$(dba)$_3$ (46 mg, 0.05 mmol), and 4,5-bis(diphenylphosphino)-9,9-dimethyxanthene (Xant Phos, 87 mg, 0.15 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXVII (11.5 mg, 5%) as a yellow solid. $^1$H NMR (500 MHz, DMSO-d$^6$): 1.89-1.92 (m, 2H); 1.98-2.05 (m, 2H); 2.20 (s, 3H); 3.08-3.13 (m, 2H); 3.56-3.59 (m, 4H); 4.36 (t, J=4.9 Hz, 2H); 7.03 (d, J=9.0 Hz, 2H); 7.40 (d, J=9.0 Hz, 2H); 7.87 (br, 1H); 7.92 (d, J=8.6 Hz, 1H); 8.03 (s, 1H); 8.16 (s, 1H); 9.82 (br, 1H); 10.37 (br, 1H); 10.90 (br, 1H). MS (EI): 449.1.

Example 52

N$^2$-(4-(2-(pyrrolidin-1-yl)ethoxy)phenyl)-5-methyl-N$^4$-p-tolylpyrimidine-2,4-diamine (Compound XXVIII)

XXVIII

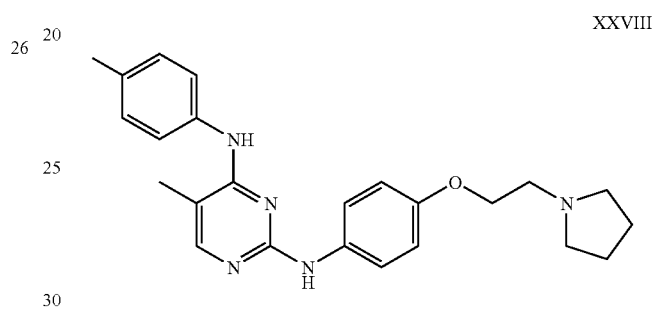

To a solution of the above-described intermediate 11 (50 mg, 0.16 mmol) in 1,4-dioxane (20 mL) was added 1-bromo-4-methylbenzene (28 mg, 0.16 mmol), Cs$_2$CO$_3$ (210 mg, 0.64 mmol), Pd$_2$(dba)$_3$ (10 mg, 0.01 mmol), and 4,5-bis(diphenylphosphino)-9,9-dimethyxanthene (Xant Phos, 18 mg, 0.03 mmol). The mixture was heated under reflux for 4 h under Ar. The solid was filtered off. The solvent was removed in vacuo. The crude product was purified by HPLC and afforded the title compound XXVIII (15.7 mg, 6%) as a yellow solid. $^1$H NMR (500 MHz, DMSO-d$^6$): 1.85-1.89 (m, 2H); 1.96-2.01 (m, 2H); 2.12 (s, 3H); 2.31 (s, 3H); 3.04-3.08 (m, 2H); 3.51-3.55 (m, 4H); 4.32 (br, 2H); 6.89 (br, 2H); 7.18 (br, 2H); 7.31 (br, 2H); 7.41 (br, 2H); 7.84 (s, 1H); 9.71 (s, 1H); 10.46 (s, 1H); 11.13 (br, 1H). MS (EI): 404.2.

Example 53

N$^2$-(4-(2-(pyrrolidin-1-yl)ethoxy)phenyl)-N$^4$-(4-chloro-3-methylphenyl)-5-methylpyrimidine-2,4-diamine (Compound XXIX)

XXIX

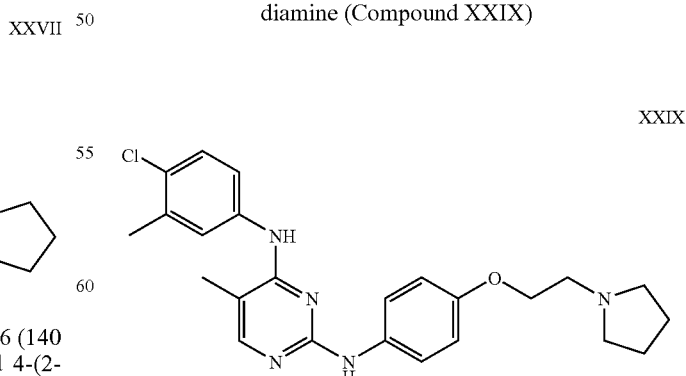

To a solution of the above-described intermediate 11 (80 mg, 0.25 mmol) in 1,4-dioxane (20 mL) was added 4-bromo-1-chloro-2-methylbenzene (63 mg, 0.30 mmol), Cs$_2$CO$_3$ (326 mg, 1.0 mmol), Pd$_2$(dba)$_3$ (18 mg, 0.02 mmol), and 4,5-bis(diphenylphosphino)-9,9-dimethyxanthene (Xant Phos, 36 mg, 0.06 mmol). The mixture was heated under reflux for 4 h under Ar. The solid was filtered off. The solvent was removed in vacuo. The crude product was purified by HPLC and afforded the title compound XXIX (17.5 mg, 15%) as a yellow solid. $^1$H NMR (500 MHz, DMSO-d$^6$): 1.85-1.89 (m, 2H); 1.96-2.01 (m, 2H); 2.12 (s, 3H); 2.25 (s, 3H); 3.04-3.08 (m, 2H); 3.51-3.55 (m, 4H); 4.32 (br, 2H); 6.91 (br, 2H); 7.04 (br, 1H); 7.31 (br, 1H); 7.41 (br, 2H); 7.58 (s, 1H); 7.89 (br, 1H); 9.75 (s, 1H); 10.54 (s, 1H); 11.13 (br, 1H). MS (EI): 438.1.

Example 54

N-(4-(2-(pyrrolidin-1-yl)ethoxy)phenyl)-4-benzyl-5-methylpyrimidin-2-amine (Compound XXX)

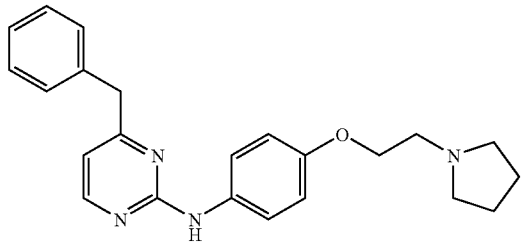

XXX

To a solution of 4-benzyl-2-chloropyrimidine (286 mg, 1.4 mmol) in 1,4-dioxane (20 mL) was added 4-(2-(pyrrolidin-1-yl)ethoxy)benzenamine (288 mg, 1.4 mmol), Cs$_2$CO$_3$ (1.82 g, 5.6 mmol), Pd$_2$(dba)$_3$ (92 mg, 0.1 mmol), and 4,5-bis(diphenylphosphino)-9,9-dimethyxanthene (Xant Phos, 173 mg, 0.3 mmol). The mixture was heated under reflux for 4 h under Ar. The solid was filtered off. The solvent was removed in vacuo. The crude product was purified by HPLC and afforded the title compound XXX (42 mg, 10%) as a yellow solid. $^1$H NMR (500 MHz, DMSO-d$^6$): 1.89 (br, 2H); 2.00 (br, 2H); 3.09 (br, 2H); 3.54 (br, 4H); 4.31 (br, 2H); 6.71 (d, J=5.0 Hz, 1H); 6.93 (d, J=8.8 Hz, 2H); 7.24 (m, 1H); 7.32 (m, 4H); 7.62 (d, J=8.8 Hz, 2H); 8.32 (d, J=5.0 Hz, 1H); 9.66 (s, 1H); 10.92 (br, 1H). MS (EI): 375.2.

Example 55

4-((1H-indol-4-yl)methyl)-N-(4-(2-(pyrrolidin-1-yl)ethoxy)phenyl)-5-methylpyrimidin-2-amine (Compound XXXI)

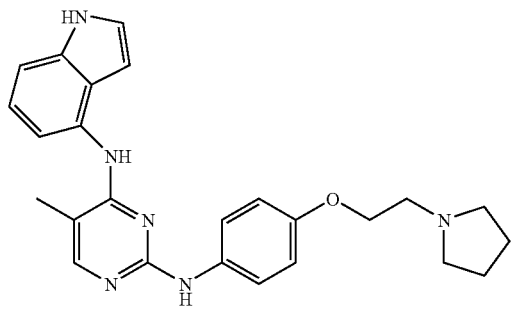

XXXI

To a solution of the above-described intermediate 11 (460 mg, 1.46 mmol) in 1,4-dioxane (20 mL) was added 4-bromo-1H-indole (288 mg, 1.46 mmol), Cs$_2$CO$_3$ (1.95 g, 6.0 mmol), Pd$_2$(dba)$_3$ (128 mg, 0.14 mmol), and 4,5-bis(diphenylphos-phino)-9,9-dimethyxanthene (Xant Phos, 243 mg, 0.42 mmol). The mixture was heated under reflux for overnight under Ar. The solid was filtered off. The solvent was removed in vacuo. The crude product was purified by HPLC and afforded the title compound XXXI (66 mg, 10%) as a yellow solid. $^1$H NMR (500 MHz, DMSO-d$^6$): 1.87 (br, 2H); 1.98-2.05 (m, 2H); 2.21 (s, 3H); 3.15 (br, 2H); 3.52 (br, 2H); 3.69 (br, 2H), 4.24 (br, 2H); 6.33 (s, 1H); 6.60 (br, 2H); 6.82 (br, 1H); 6.92 (br, 1H); 7.02 (br, 2H); 7.16 (br, 1H); 7.26 (br, 1H); 7.43 (m, 1H); 7.88 (m, 1H); 10.11 (s, 1H); 11.40 (s, 1H). MS (EI): 429.1.

Example 56

2-Chloro-5-methyl-N-(naphthalen-1-yl)pyrimidin-4-amine (Intermediate 27)

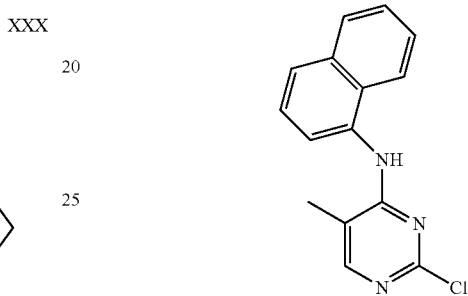

27

To a solution of 2-chloro-5-methylpyrimidin-4-amine (144 mg, 1.0 mmol) in 1,4-dioxane (40 mL) was added 1-bromonaphthalene (227 mg, 1.1 mmol), Cs$_2$CO$_3$ (1.3 g, 4.0 mmol), Pd$_2$(dba)$_3$ (91 mg, 0.1 mmol), and 4,5-bis(diphenylphosphino)-9,9-dimethyxanthene (Xant Phos, 183 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 27, was used for next reaction without further purification.

Example 57

N-(4-(2-(pyrrolidin-1-yl)ethoxy)phenyl)-5-methyl-4-(naphthalen-1-yl)pyrimidin-2-amine (Compound XXXII)

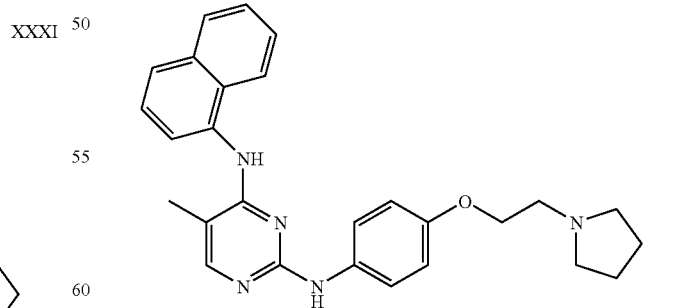

XXXII

To a solution of the above-described intermediate 27 (235 mg, 0.87 mmol) in 1,4-dioxane (20 mL) was added 4-(2-(pyrrolidin-1-yl)ethoxy)benzenamine (183 mg, 0.87 mmol), Cs$_2$CO$_3$ (1.3 g, 4.0 mmol), Pd$_2$(dba)$_3$ (46 mg, 0.05 mmol), and 4,5-bis(diphenylphosphino)-9,9-dimethyxanthene (Xant Phos, 87 mg, 0.15 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXXII (89 mg, 21%) as a yellow solid. $^1$H NMR (500 MHz, DMSO-d$^6$): 1.88-1.90 (m, 2H); 1.97-2.03 (m, 2H); 2.30 (s, 3H); 3.03-3.08 (m, 2H); 3.50-3.53 (m, 4H); 4.21 (t, J=4.9 Hz, 2H); 6.50 (d, J=7.2 Hz, 2H); 6.82 (d, J=8.6 Hz, 2H); 7.54 (d, J=7.8 Hz, 2H); 7.57-7.61 (m, 1H); 7.63 (t, J=7.4 Hz, 1H); 7.89 (d, J=8.3 Hz, 2H); 7.95 (s, 1H); 8.02 (d, J=8.3 Hz, 1H); 8.08 (d, J=7.7 Hz, 1H); 10.37 (s, 1H); 10.43 (s, 1H); 10.93 (br, 1H). MS (EI): 440.1.

Example 58

1-(2-Chloro-5-methylpyrimidin-4-yl)isoquinoline (Intermediate 28)

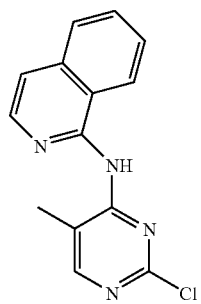

28

To a solution of 2-chloro-5-methylpyrimidin-4-amine (144 mg, 1.0 mmol) in 1,4-dioxane (40 mL) was added 1-chloroisoquinoline (164 mg, 1.0 mmol), Cs$_2$CO$_3$ (1.3 g, 4.0 mmol), Pd$_2$(dba)$_3$ (91 mg, 0.1 mmol), and 4,5-bis(diphenylphosphino)-9,9-dimethyxanthene (Xant Phos, 183 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 28, was used for next reaction without further purification.

Example 59

N-(4-(2-(pyrrolidin-1-yl)ethoxy)phenyl)-4-(isoquinolin-1-yl)-5-methylpyrimidin-2-amine (Compound XXXIII)

XXXIII

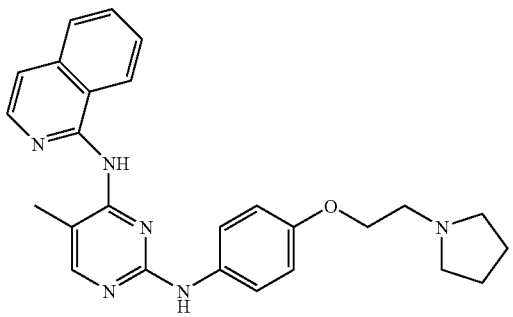

To a solution of the above-described intermediate 28 (90 mg, 0.33 mmol) in 1,4-dioxane (20 mL) was added 4-(2-(pyrrolidin-1-yl)ethoxy)benzenamine (76 mg, 0.37 mmol), Cs$_2$CO$_3$ (391 mg, 1.2 mmol), Pd$_2$(dba)$_3$ (28 mg, 0.03 mmol), and 4,5-bis(diphenylphosphino)-9,9-dimethyxanthene (Xant Phos, 52 mg, 0.09 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXXIII (21 mg, 15%) as a yellow solid. $^1$H NMR (500 MHz, DMSO-d$^6$): 1.64-1.70 (m, 6H); 2.23 (s, 3H); 2.78 (t, J=5.9 Hz, 2H); 4.04 (t, J=5.9 Hz, 2H); 6.38 (d, J=7.2 Hz, 1H); 6.93 (d, J=9.0 Hz, 2H); 6.97 (d, J=7.2 Hz, 1H); 7.45 (br, 1H); 7.57 (d, J=8.8 Hz, 1H); 7.58-7.62 (m, 1H); 7.70-7.78 (m, 2H); 8.04 (s, 1H); 8.75 (d, J=8.1 Hz, 1H); 9.06 (s, 1H); 9.19 (s, 1H). MS (EI): 441.2.

Example 60

N$^2$-(4-(2-(pyrrolidin-1-yl)ethoxy)phenyl)-N$^4$-(3-(trifluoromethyl)phenyl)-5-methylpyrimidine-2,4-diamine (Compound XXXIV)

XXXIV

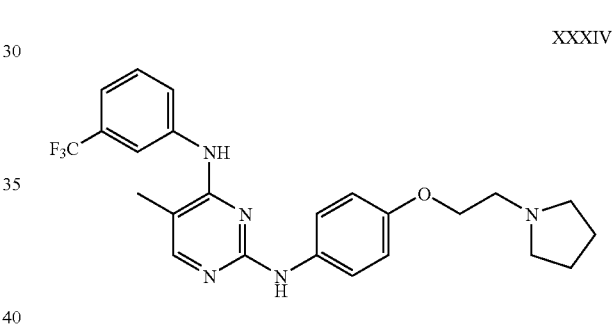

A mixture of 2-chloro-5-methyl-pyrimidin-4-ylamine (143 mg, 1.0 mmol), 1-bromo-3-(trifluoromethyl)benzene (225 mg, 1.0 mmol), Pd$_2$(dba)$_3$ (9.0 mg, 0.01 mmol), Xantphos (12 mg, 0.02 mmol) and cesium carbonate (650 mg, 2.0 mmol) were suspended in dioxane (15 mL) and heated at reflux under the argon atmosphere for 15 h. The reaction mixture was cooled to room temperature and diluted with DCM (30 mL). The mixture was filtered and the filtrate concentrated in vacuo. The residue on purification using HPLC gave N$^4$-(3-(trifluoromethyl)phenyl)-5-methylpyrimidine-2,4-diamine as an off white solid (192 mg, 67%). MS (ESI+): m/z 288 (M+H)$^+$. A mixture of N$^4$-(3-(trifluoromethyl)phenyl)-5-methylpyrimidine-2,4-diamine (28.7 mg, 0.1 mmol) and 4-(2-(pyrrolidin-1-yl)ethoxy)benzenamine (22 mg, 0.12 mmol) were dissolved in acetic acid (5 mL) and heated under microwave at 150° C. for 10 min. The mixture was cooled to room temperature and acetic acid removed under reduced pressure. The residue was purified by HPLC to afford the title compound XXXIV as brown solid (16 mg, 35%). $^1$H NMR (500 MHz, DMSO-d$_6$): 1.65-1.71 (m, 4H), 2.11 (s, 3H), 2.45-2.55 (m, 4H), 2.74 (t, J=6.0 Hz, 2H), 3.98 (t, J=6.0 Hz, 2H), 6.76 (d, J=9.0 Hz, 2H), 7.35 (d, J=5.1 Hz, 1H), 7.45-7.57 (m, 3H), 7.9-7.97 (m, 2H), 8.20 (d, J=7.6 Hz, 1H), 8.41(s, 1H), 8.85 (s, 1H), m/z 458 (M+H)$^+$.

Example 61

2-chloro-N-(4-(trifluoromethyl)phenyl)-5-methylpyrimidin-4-amine (Intermediate 29)

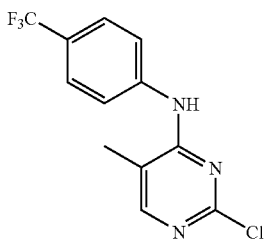

29

A suspension of 2-chloro-5-methylpyrimidin-4-amine (159 μL, 1.2 mmol), 1-bromo-4-(trifluoromethyl)benzene (150 mg, 1.0 mmol), potassium tert-butoxide (224 mg, 2.0 mmol), Xantphos (120 mg, 0.2 mmol), and palladium acetate (26 mg, 0.1 mmol) was sealed in a microwave reaction tube and irradiated at 160° C. for 15 min. The mixture was allowed to cool to room temperature, the solids were filtered using DCM to rinse, and the solution was concentrated under reduced pressure. The residue was purified by flash chromatography on silica gel (hexane to EtOAc) to afford the title intermediate 29 (128.7 mg, 43%) as a white solid. MS (ESI+): m/z 288 (M+H)$^+$.

Example 62

$N^2$-(4-(2-(pyrrolidin-1-yl)ethoxy)phenyl)-$N^4$-(4-(trifluoromethyl)phenyl)-5-methylpyrimidine-2,4-diamine (Compound XXXV)

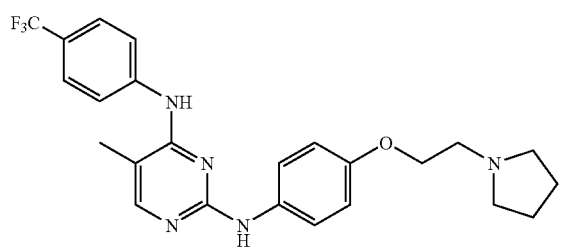

XXXV

A mixture of the above-described intermediates 29 (128 mg, 0.5 mmol) and 6 (212 mg, 1.0 mmol) were suspended in acetic acid (5 mL) and heated at 75° C. for 18 h. The mixture was allowed to cool to room temperature and acetic acid removed under reduced pressure. The residue was basified with sat., aq NaHCO$_3$ (50 mL) and extracted with DCM (2×50 mL). The organic layer was concentrated in vacuo and the crude product purified by reverse phase flash chromatography on C18 (water to CH$_3$CN, 0.1% TFA). The aqueous fractions were neutralized with sat, aq NaHCO$_3$ and extracted with EtOAc. The organics were concentrated in vacuo and the residue taken up in DCM. HCl in dioxane was added along with ether and the resulting solid filtered to afford the hydrochloride salt of the title compound XXXV (166 mg, 70%) as a grey solid. $^1$H NMR (500 MHz, DMSO-d$_6$): 1.80-1.95 (m, 2H), 1.95-2.10 (m, 2H), 2.19 (s, 3H), 3.05-3.20 (m, 2H), 3.55-3.65 (m, 6H), 4.33 (t, J=4.7 Hz, 2H), 6.97 (d, J=8.7 Hz, 2H), 7.34 (d, J=8.8 Hz, 2H), 7.73 (d, J=8.5 Hz, 2H), 7.83 (d, J=8.0 Hz, 2H), 7.94 (s, 1H), 9.92 (br s, 1H), 10.44 (br s, 1H), 10.85 (br s, 1H); MS (ESI+): m/z 458.5 (M+H)$^+$.

Example 63

Benzo[1,3]dioxol-4-yl-(2-chloro-5-methyl-pyrimidin-4-yl)-amine (Intermediate 30)

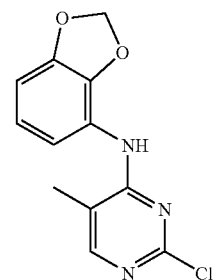

30

A mixture of 2-chloro-5-methyl-pyrimidin-4-ylamine (1.4 g, 9.7 mmol), 4-bromo-benzo[1,3]dioxole (2.0 g, 10 mmol), Pd$_2$(dba)$_3$ (0.80 g, 0.87 mmol), Xantphos (1.0 g, 1.7 mmol) and cesium carbonate (6.3 g, 19 mmol) was suspended in dioxane (40 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexanes to 50% EtOAc/hexanes) to afford the title compound (1.0 g, 39%) as a white solid. $^1$H NMR (500 MHz, DMSO-d$_6$): δ 2.13 (s, 3H), 5.99 (s, 2H), 6.80-6.90 (m, 3H), 8.01 (s, 1H), 8.92 (s, 1H). MS (ES+): m/z 264 (M+H)$^+$.

Example 64

$N^4$-Benzo[1,3]dioxol-4-yl-5-methyl-$N^2$-[4-(2-pyrrolidin-1-yl-ethoxy)-phenyl]-pyrimidine-2,4-diamine (Compound XXXVI)

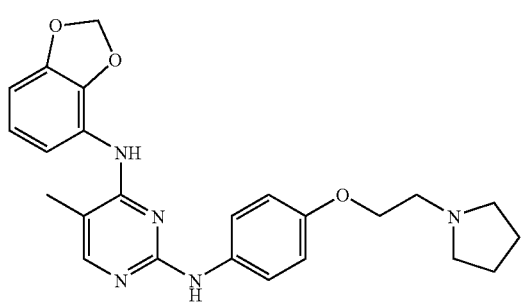

XXXVI

A mixture of intermediate 30 (0.25 g, 0.95 mmol) and 4-(2-pyrrolidin-1-yl-ethoxy)-phenylamine (0.40 g, 1.9 mmol) in acetic acid (15 mL) was heated at 100° C. for 20 h. The mixture was allowed to cool to room temperature and acetic acid removed under reduced pressure. The residue was taken in water (20 mL) and neutralized to pH~7 with 10% NaOH solution. The resulting solution was extracted with EtOAc (2×30 mL) and the organic layer separated. The organic layer was washed with brine, dried over anhydrous Na₂SO₄ and filtered. The filtrate was concentrated in vacuo and the crude product purified by flash chromatography on silica gel (DCM to 20% MeOH/DCM) to afford the title compound (0.14 g, 34%) as a white solid.

¹H NMR (500 MHz, DMSO-d₆): δ 1.65-1.75 (m, 4H), 2.06 (s, 3H), 2.55-2.65 (m, 4H), 2.78-2.88 (m, 2H), 3.98 (t, J=5.8 Hz, 2H), 5.89 (s, 2H), 6.65 (d, J=9.0 Hz, 2H), 6.79-6.84 (m, 2H), 6.89 (dd, J=7.7, 1.7 Hz, 1H), 7.45 (d, J=9.1 Hz, 2H), 7.81 (s, 1H), 8.23 (s, 1H), 8.73 (s, 1H). MS (ES+): m/z 434 (M+H)⁺.

Example 65

N⁴-Benzo[1,3]dioxol-4-yl-5-methyl-N²-[4-(4-methyl-piperazin-1-yl)-phenyl]-pyrimidine-2,4-diamine (Compound XXXVII)

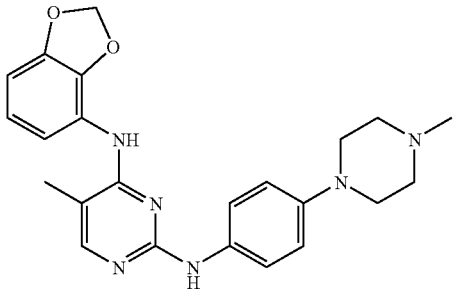

XXXVII

A mixture of intermediate 30 (0.10 g, 0.38 mmol) and 4-(4-methyl-piperazin-1-yl)-phenylamine (0.12 g, 0.51 mmol) in acetic acid (3 mL) was sealed in a microwave reaction tube and irradiated with microwave at 150° C. for 15 min. After cooling to room temperature, the cap was removed and the mixture concentrated. The residue was taken in water (20 mL) and the mixture was neutralized with 10% NaOH solution until solid precipitated. The solid was filtered and then purified by flash chromatography on silica gel (DCM to 15% MeOH/DCM) to afford the title compound (22 mg, 14%) as a light red solid.

¹H NMR (500 MHz, DMSO-d₆): δ 2.06 (s, 3H), 2.21 (s, 3H), 2.44 (t, J=4.8 Hz, 4H), 2.97 (t, J=4.9 Hz, 4H), 5.89 (s, 2H), 6.67 (d, J=9.1 Hz, 2H), 6.80-6.86 (m, 2H), 6.91 (dd, J=7.6, 1.7 Hz, 1H), 7.41 (d, J=9.0 Hz, 2H), 7.79 (s, 1H), 8.17 (s, 1H), 8.63 (s, 1H). MS (ES+): m/z 419 (M+H)⁺.

Example 66

(4-Chloro-3-methoxy-phenyl)-(2-chloro-5-methyl-pyrimidin-4-yl)-amine (Intermediate 31)

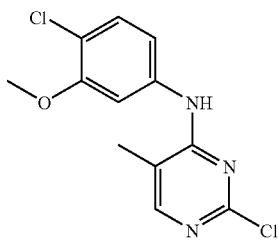

31

A mixture of 2-chloro-5-methyl-pyrimidin-4-ylamine (0.50 g, 3.5 mmol), 4-bromo-1-chloro-2-methoxy-benzene (0.65 mL, 4.8 mmol), Pd₂(dba)₃ (0.17 g, 0.19 mmol), Xantphos (0.22 g, 0.38 mmol) and cesium carbonate (2.3 g, 7.1 mmol) was suspended in dioxane (20 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexanes to 40% EtOAc/hexanes) to afford the title compound (0.55 g, 55%) as a yellow solid.

¹H NMR (500 MHz, DMSO-d₆): δ 2.18 (s, 3H), 3.85 (s, 3H), 7.35 (dd, J=8.6, 2.3 Hz, 1H), 7.39 (d, J=8.7 Hz, 1H), 7.56 (d, J=2.3 Hz, 1H), 8.09 (d, J=0.9 Hz, 1H), 8.91 (s, 1H). MS (ES+): m/z 284 (M+H)⁺.

Example 67

N⁴-(4-Chloro-3-methoxy-phenyl)-5-methyl-N²-(4-pyrazol-1-ylmethyl-phenyl)-pyrimidine-2,4-diamine (Compound XXXVIII)

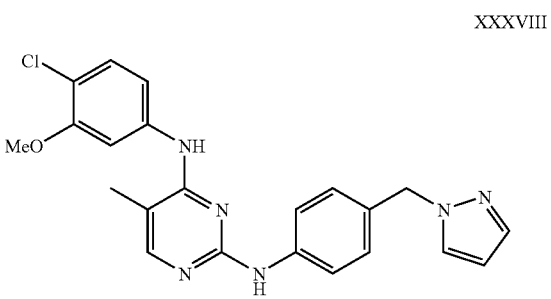

XXXVIII

A suspension of intermediate 31 (0.20 g, 0.70 mmol), 4-pyrazol-1-ylmethyl-phenylamine (0.14 g, 0.81 mmol), Pd₂(dba)₃ (40 mg, 0.044 mmol), Xantphos (50 mg, 0.086 mmol) and cesium carbonate (0.50 g, 1.5 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO₃ solution (40 mL). The combined aqueous layers were extracted with EtOAc (2×30 mL) and the combined organic layers washed with brine, dried over anhydrous Na₂SO₄ and filtered. The filtrate was concentrated and the resulting solid was dissolved in minimum amount of EtOAc and hexanes added until solid precipitated. After filtration, the title compound was obtained as an off white solid (0.13 g, 44%).

¹H NMR (500 MHz, DMSO-d₆): δ 2.11 (s, 3H), 3.74 (s, 3H), 5.22 (s, 2H), 6.25 (t, J=2.1 Hz, 1H), 7.08 (d, J=8.6 Hz, 2H), 7.27 (d, J=9.3 Hz, 1H), 7.40-7.45 (m, 3H), 7.60 (d, J=8.6 Hz, 2H), 7.75 (d, J=1.8 Hz, 1H), 7.91 (s, 1H), 8.36 (s, 1H), 9.04 (s, 1H) MS (ES+): m/z 421 (M+H)⁺.

Example 68

5-Methyl-N²-[4-(4-methyl-piperazin-1-yl)-phenyl]-pyrimidine-2,4-diamine (Intermediate 32)

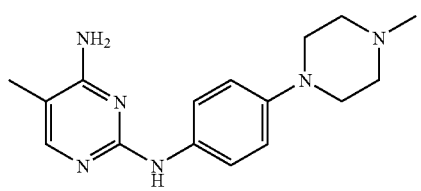

A mixture of 2-chloro-5-methyl-pyrimidin-4-ylamine (1.0 g, 6.9 mmol) and 4-(4-methyl-piperazin-1-yl)-phenylamine (1.5 mL, 7.8 mmol) in acetic acid (15 mL) was heated at 100° C. for 2.5 h. The mixture was allowed to cool to room temperature and acetic acid removed under reduced pressure. The residue was taken in water (20 mL) and the mixture was neutralized with 10% NaOH solution until solid precipitated. After filtration and washed with water, the title compound was obtained as a grey solid (1.3 g, 63%).

$^1$H NMR (500 MHz, DMSO-$d_6$): δ 1.88 (s, 3H), 2.21 (s, 3H), 2.21 (s, 3H), 2.44 (t, J=4.8 Hz, 4H), 3.00 (t, J=4.8 Hz, 4H), 6.27 (s, 2H), 6.79 (d, J=9.0 Hz, 2H), 7.57 (d, J=9.0 Hz, 2H), 7.63 (s, 1H), 8.42 (s, 1H). MS (ES+): m/z 299 (M+H)$^+$.

Example 69

N⁴-(4-Chloro-3-methoxy-phenyl)-5-methyl-N²-[4-(4-methyl-piperazin-1-yl)-phenyl]-pyrimidine-2,4-diamine (Compound XXXIX)

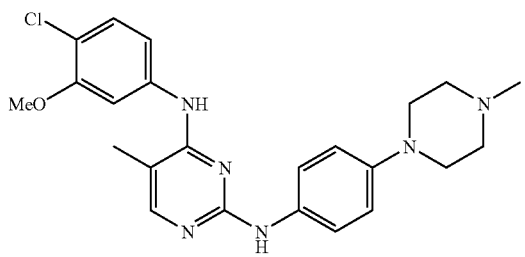

A suspension of intermediate 32 (0.30 g, 1.0 mmol), 4-bromo-1-chloro-2-methoxy-benzene (0.20 mL, 1.5 mmol), Pd$_2$(dba)$_3$ (50 mg, 0.055 mmol), Xantphos (65 mg, 0.11 mmol) and cesium carbonate (0.70 g, 2.1 mmol) in dioxane/DMF (3/1, 8 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as an off white solid (0.20 g, 46%).

$^1$H NMR (500 MHz, DMSO-$d_6$): δ 2.09 (s, 3H), 2.21 (s, 3H), 2.45 (t, J=4.9 Hz, 4H), 3.02 (t, J=4.9 Hz, 4H), 3.73 (s, 3H), 6.79 (d, J=9.1 Hz, 2H), 7.27 (d, J=8.6 Hz, 1H), 7.42-7.47 (m, 3H), 7.49 (d, J=2.3 Hz, 1H), 7.86 (s, 1H), 8.28 (s, 1H), 8.72 (s, 1H). MS (ES+): m/z 439 (M+H)$^+$.

Example 70

N⁴-(4-Chloro-3-methoxy-phenyl)-5-methyl-N²-(4-morpholin-4-yl-phenyl)-pyrimidine-2,4-diamine (Compound XL)

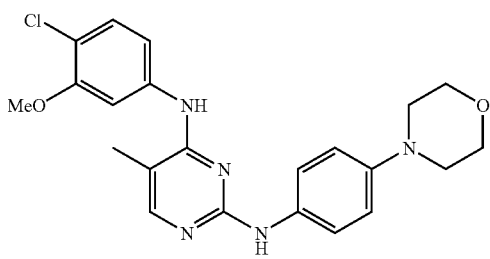

A mixture of intermediate 31 (0.10 g, 0.35 mmol) and 4-morpholin-4-yl-phenylamine (80 mg, 0.45 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture was neutralized with 10% NaOH solution until solid precipitated. The solid was filtered and then purified by flash chromatography on silica gel (DCM to 10% MeOH/DCM) to afford the title compound (55 mg, 37%) as a light brown solid.

$^1$H NMR (500 MHz, DMSO-$d_6$): δ 2.10 (s, 3H), 3.00 (t, J=4.8 Hz, 4H), 3.71-3.76 (m, 7H), 6.80 (d, J=9.0 Hz, 2H), 7.28 (d, J=8.6 Hz, 1H), 7.45 (dd, J=8.7, 2.2 Hz, 1H), 7.47-7.50 (m, 3H), 7.87 (s, 1H), 8.29 (s, 1H), 8.75 (s, 1H). MS (ES+): m/z 426 (M+H)$^+$.

Example 71

N⁴-(4-Chloro-3-methoxy-phenyl)-5-methyl-N²-(4-pyrazol-1-yl-phenyl)-pyrimidine-2,4-diamine (Compound XLI)

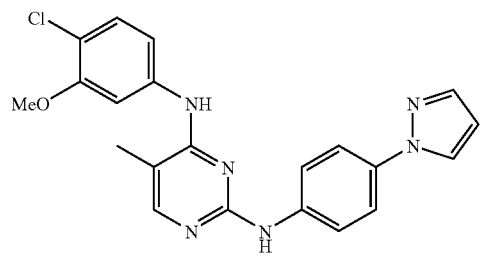

A mixture of intermediate 31 (90 mg, 0.32 mmol) and 4-pyrazol-1-yl-phenylamine (70 mg, 0.44 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture neutralized with 10% NaOH solution until solid precipitated. The solid was filtered and then purified by HPLC. The corrected fractions were combined and concentrated to afford the title compound (40 mg of TFA salt, 24%) as a white solid.

$^1$H NMR (500 MHz, DMSO-d$_6$): δ 2.17 (s, 3H), 3.75 (s, 3H), 6.54 (t, J=1.9 Hz, 1H), 7.30 (d, J=6.6 Hz, 1H), 7.39 (d, J=2.1 Hz, 1H), 7.40 (d, J=8.6 Hz, 1H), 7.59 (d, J=8.9 Hz, 2H), 7.71 (d, J=8.9 Hz, 2H), 7.73 (d, J=1.6 Hz, 1H), 7.93 (s, 1H), 8.41 (d, J=2.5 Hz, 1H), 9.41 (s, 1H), 10.05 (s, 1H). MS (ES+): m/z 407 (M+H)$^+$.

Example 72

N$^4$-(4-Chloro-3-methoxy-phenyl)-5-methyl-N$^2$-(4-piperidin-1-yl-phenyl)-pyrimidine-2,4-diamine (XLII)

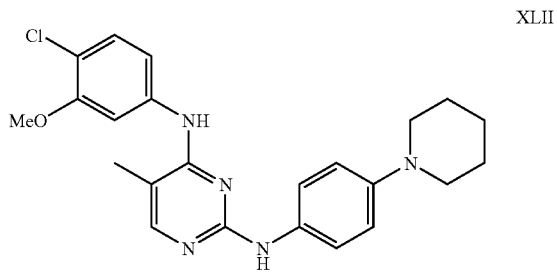

XLII

A mixture of intermediate 31 (0.11 g, 0.39 mmol) and 4-piperidin-1-yl-phenylamine (90 mg, 0.51 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture neutralized with 10% NaOH solution until solid precipitated. The solid was filtered and then purified by flash chromatography on silica gel (hexanes to 70% EtOAc/hexanes)to afford the title compound (10 mg, 6%) as a light brown solid.

$^1$H NMR (500 MHz, DMSO-d$_6$): δ 1.48-1.53 (m, 2H), 1.59-1.65 (m, 4H), 2.09 (s, 3H), 3.00 (t, J=5.4 Hz, 4H), 3.73 (s, 3H), 6.78 (d, J=9.0 Hz, 2H), 7.27 (d, J=8.7 Hz, 1H), 7.40-7.47 (m, 3H), 7.50 (d, J=2.2 Hz, 1H), 7.86 (s, 1H), 8.28 (s, 1H), 8.71 (s, 1H). MS (ES+): m/z 424 (M+H)$^+$.

Example 73

N$^4$-(4-Chloro-3-methoxy-phenyl)-5-methyl-N$^2$-[4-(4-methyl-piperazin-1-ylmethyl)-phenyl]-pyrimidine-2,4-diamine (XLIII)

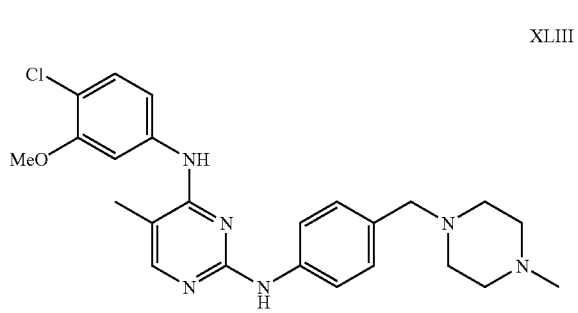

XLIII

A suspension of intermediate 31 (50 mg, 0.18 mmol), 4-(4-methyl-piperazin-1-ylmethyl)-phenylamine (50 mg, 0.24 mmol), Pd$_2$(dba)$_3$ (10 mg, 0.011 mmol), Xantphos (13 mg, 0.022 mmol) and cesium carbonate (0.12 g, 0.37 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 10% MeOH/DCM)to afford the title compound (35 mg, 44%) as an off white solid.

$^1$H NMR (500 MHz, DMSO-d$_6$): δ 2.11 (s, 3H), 2.15 (s, 3H), 2.20-2.45 (m, 8H), 3.35 (s, 2H), 3.75 (s, 3H), 7.07 (d, J=8.5 Hz, 2H), 7.28 (d, J=8.5 Hz, 1H), 7.44 (dd, J=8.7, 2.3 Hz, 1H), 7.47 (d, J=2.3 Hz, 1H), 7.57 (d, J=8.5 Hz, 2H), 7.91 (s, 1H), 8.36 (s, 1H), 8.98 (s, 1H). MS (ES+): m/z 453 (M+H)$^+$.

Example 74

N$^4$-(4-Chloro-3-methoxy-phenyl)-5-methyl-N$^2$-(4-piperazin-1-yl-phenyl)-pyrimidine-2,4-diamine (Compound XLIV)

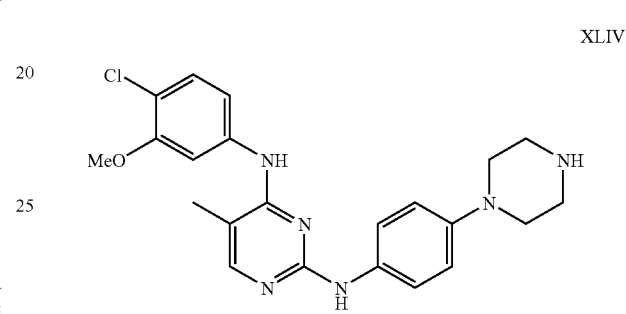

XLIV

A mixture of intermediate 31 (0.20 g, 0.70 mmol) and 4-(4-amino-phenyl)-piperazine-1-carboxylic acid tert-butyl ester (0.22 g, 0.79 mmol) in acetic acid (4 mL) was sealed in a microwave reaction tube and irradiated with microwave at 150° C. for 15 min. After cooling to room temperature, the cap was removed and the mixture concentrated. The residue was purified by HPLC and the corrected fractions combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as an off white solid (0.10 g, 33%).

$^1$H NMR (500 MHz, DMSO-d$_6$): δ 2.10 (s, 3H), 3.16 (s, 8H), 3.73 (s, 3H), 6.83 (d, J=9.0 Hz, 2H), 7.29 (d, J=8.8 Hz, 1H), 7.44 (dd, J=8.7, 2.1 Hz, 1H), 7.49-7.52 (m, 3H), 7.88 (s, 1H), 8.32 (s, 1H), 8.81 (s, 1H) MS (ES+): m/z 425 (M+H)$^+$.

Example 75

N-tert-Butyl-3-{5-methyl-2-[4-(4-methyl-piperazin-1-yl)-phenylamino]-pyrimidin-4-ylamino}-benzene-sulfonamide (Compound XLV)

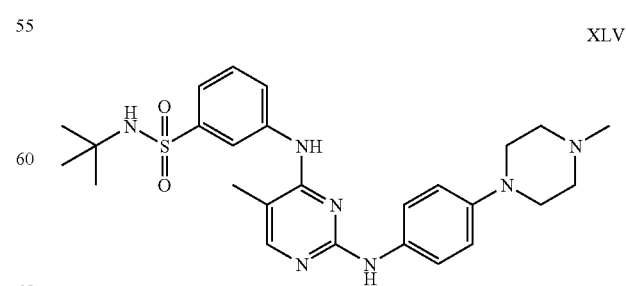

XLV

A suspension of intermediate 32 (0.30 g, 1.0 mmol), 3-bromo-N-tert-butyl-benzenesulfonamide (0.35 g, 1.2 mmol), Pd$_2$(dba)$_3$ (60 mg, 0.066 mmol), Xantphos (70 mg, 0.12 mmol) and cesium carbonate (0.70 g, 2.1 mmol) in dioxane/DMF (3/1, 8 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/7, 40 mL). After filtration, the title compound was obtained as an off white solid (0.30 g, 59%).

$^1$H NMR (500 MHz, DMSO-d$_6$): δ 1.12 (s, 9H), 2.11 (s, 3H), 2.22 (s, 3H), 2.45 (t, J=4.7 Hz, 4H), 3.02 (t, J=4.8 Hz, 4H), 6.81 (d, J=9.1 Hz, 2H), 7.45-7.52 (m, 4H), 7.56 (s, 1H), 7.89 (s, 1H), 8.10-8.16 (m, 2H), 8.51 (s, 1H), 8.70 (s, 1H) MS (ES+): m/z 510 (M+H)$^+$.

Example 76

N-tert-Butyl-3-(2-chloro-5-methyl-pyrimidin-4-ylamino)-benzenesulfonamide (Intermediate 33)

33

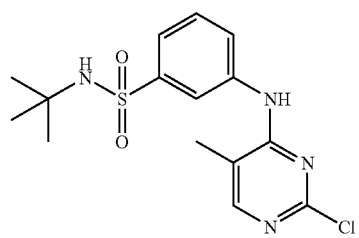

A mixture of 2-chloro-5-methyl-pyrimidin-4-ylamine (0.4 g, 2.8 mmol), 3-bromo-N-tert-butyl-benzenesulfonamide (1.0 g, 3.4 mmol), Pd$_2$(dba)$_3$ (0.17 g, 0.19 mmol), Xantphos (0.2 g, 3.5 mmol) and cesium$^{carbonate}$ (2.0 g, 6.1 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was dissolved in EtOAc and hexanes added until solid precipitated. After filtration, the title compound (1.2 g, 98%) was obtained as a light brown solid. It was used in the next step without purification. MS (ES+): m/z 355 (M+H)$^+$.

Example 77

N-tert-Butyl-3-[5-methyl-2-(4-morpholin-4-ylmethyl-phenylamino)-pyrimidin-4-ylamino]-benzenesulfonamide (Compound XLVI)

XLVI

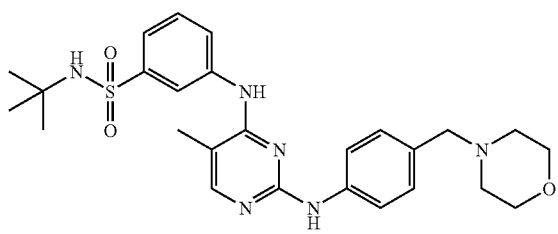

A mixture of intermediate 33 (0.50 g, 1.4 mmol), 4-morpholin-4-ylmethyl-phenylamine (0.35 g, 1.8 mmol), Pd$_2$(dba)$_3$ (0.10 g, 0.11 mmol), Xantphos (0.12 g, 0.21 mmol) and cesium carbonate (1.0 g, 3.1 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by HPLC and the corrected fractions combined and poured into saturated NaHCO$_3$ solution (50 mL). The combined aqueous layers were extracted with EtOAc (2×50 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as an off white solid (0.23 g, 31%).

$^1$H NMR (500 MHz, DMSO-d$_6$): δ 1.12 (s, 9H), 2.13 (s, 3H), 2.28-2.34 (m, 4H), 3.35 (s, 2H), 3.55 (t, J=4.8 Hz, 4H), 7.10 (d, J=8.5 Hz, 2H), 7.45-7.52 (m, 2H), 7.57 (s, 1H), 7.59 (d, J=8.5 Hz, 2H), 7.94 (s, 1H), 8.10 (s, 1H), 8.13-8.16 (m, 1H), 8.58 (s, 1H), 8.95 (s, 1H). MS (ES+): m/z 511 (M+H)$^+$.

Example 78

N-tert-Butyl-3-{5-methyl-2-[4-(4-oxy-morpholin-4-ylmethyl)-phenylamino]-pyrimidin-4-ylamino}-benzenesulfonamide (Compound XLVII)

XLVII

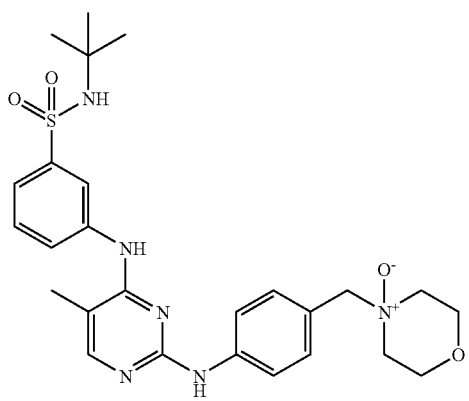

A solution of the above-described compound XLVI (30 mg, 0.06 mmol) and 3-chloroperbenzoic acid (77%, 14 mg, 0.06 mmol) in chloroform (30 mL) was stirred at room temperature for 1 hour. The solvent was removed by rotovap and the resulting mixture was purified by silica gel with 20% CH$_3$OH/CHCl$_3$ as an eluent to afford the title compound as an off-white solid (15 mg, 48%).

$^1$H NMR (500 MHz, DMSO-d$_6$): δ 1.12 (s, 9H), 2.14 (s, 3H), 2.71 (d, J=10.9 Hz, 2H), 3.63 (d, J=9.9 Hz, 2H), 4.08 (t, J=11.6 Hz, 2H), 4.28 (s, 2H), 7.38 (d, J=8.5 Hz, 2H), 7.50 (d, J=5.0 Hz, 2H), 7.61 (s, 1H), 7.66 (d, J=8.5 Hz, 2H), 7.96 (s, 1H), 8.13 (m, 2H), 8.63 (s, 1H), 9.13 (s, 1H). MS (ES+): m/z 527 (M+H)$^+$.

Example 79

N-tert-Butyl-3-[5-methyl-2-(4-pyrazol-1-yl-phenylamino)-pyrimidin-4-ylamino]-benzenesulfonamide (Compound XLVIII)

XLVIII

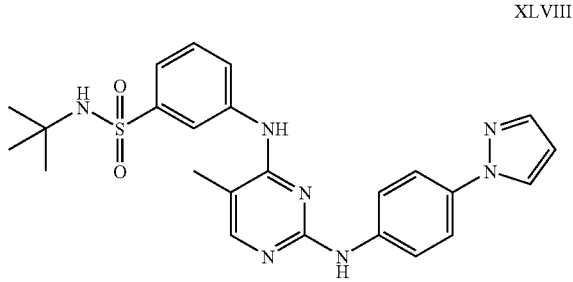

A mixture of intermediate 33 (0.10 g, 0.28 mmol) and 4-pyrazol-1-yl-phenylamine (50 mg, 0.31 mmol) in acetic acid (3 mL) was sealed in a microwave reaction tube and irradiated with microwave at 130° C. for 15 min. After cooling to room temperature, the cap was removed and the mixture concentrated. The residue was taken up in water (20 mL) and neutralized with 10% NaOH solution until solid precipitated. The brown solid was filtered and then purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (15 mg, 11%).

$^1$H NMR (500 MHz, DMSO-d$_6$): δ 1.12 (s, 9H), 2.15 (s, 3H), 6.49 (t, J=2.2 Hz, 1H), 7.50-7.55 (m, 2H), 7.58 (s, 1H), 7.62 (d, J=9.1 Hz, 2H), 7.68 (d, J=1.3 Hz, 1H), 7.77 (d, J=9.1 Hz, 2H), 7.96 (s, 1H), 8.11 (s, 1H), 8.13-8.16 (m, 1H), 8.33 (d, J=2.5 Hz, 1H), 8.64 (s, 1H), 9.17 (s, 1H). MS (ES+): m/z 478 (M+H)$^+$.

Example 80

N-tert-Butyl-3-[5-methyl-2-(6-piperazin-1-yl-pyridin-3-ylamino)-pyrimidin-4-ylamino]-benzenesulfonamide (Compound XLIX)

XLIX

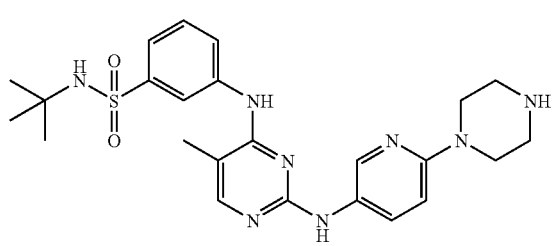

A mixture of intermediate 33 (0.10 g, 0.28 mmol) and 4-(5-amino-pyridin-2-yl)-piperazine-1-carboxylic acid tert-butyl ester (90 mg, 0.32 mmol) in acetic acid (3 mL) was sealed in a microwave reaction tube and irradiated with microwave at 130° C. for 15 min. After cooling to room temperature, the cap was removed and the mixture concentrated. The residue was dissolved in DCM (5 mL) and 30% TFA/DCM (6 mL) added. The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (10 mg, 7%).

$^1$H NMR (500 MHz, DMSO-d$_6$): δ 1.12 (s, 9H), 2.11 (s, 3H), 2.83 (t, J=5.0 Hz, 4H), 3.28-3.33 (m, 4H), 6.73 (d, J=9.1 Hz, 1H), 7.40-7.49 (m, 2H), 7.57 (s, 1H), 7.86 (dd, J=9.1, 2.7 Hz, 1H), 7.88 (s, 1H), 8.10-8.16 (m, 2H), 8.28 (d, J=2.5 Hz, 1H), 8.53 (s, 1H), 8.72 (s, 1H). MS (ES+): m/z 497 (M+H)$^+$.

Example 81

N-tert-Butyl-3-[5-methyl-2-(4-pyrazol-1-ylmethyl-phenylamino)-pyrimidin-4-ylamino]-benzenesulfonamide (Compound L)

L

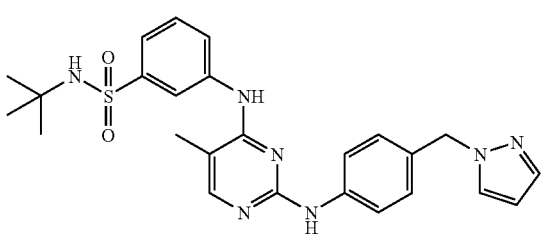

A mixture of intermediate 33 (0.10 g, 0.28 mmol) and 4-pyrazol-1-ylmethyl-phenylamine (50 mg, 0.29 mmol) in acetic acid (3 mL) was sealed in a microwave reaction tube and irradiated with microwave at 130° C. for 15 min. After cooling to room temperature, the cap was removed and the mixture concentrated. The residue was purified by HPLC and the corrected fractions combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (12 mg, 9%).

$^1$H NMR (500 MHz, DMSO-d$_6$): δ 1.12 (s, 9H), 2.13 (s, 3H), 5.21 (s, 2H), 6.24 (t, J=1.9 Hz, 1H), 7.08 (d, J=8.5 Hz, 2H), 7.27-7.50 (m, 3H), 7.56 (s, 1H), 7.60 (d, J=8.4 Hz, 2H), 7.75 (d, J=2.1 Hz, 1H), 7.94 (s, 1H), 8.14 (d, J=7.9 Hz, 1H), 8.59 (s, 1H), 9.01 (s, 1H). MS (ES+): m/z 492 (M+H)$^+$.

Example 82

5-Methyl-N$^2$-[3-(piperidine-1-sulfonyl)-phenyl]-pyrimidine-2,4-diamine (Intermediate 34)

34

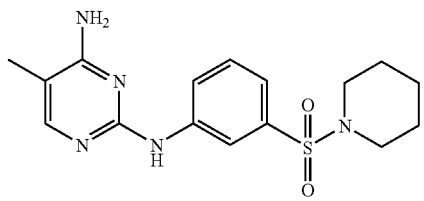

A mixture of 2-chloro-5-methyl-pyrimidin-4-ylamine (0.25 g, 1.74 mmol) and 3-(piperidine-1-sulfonyl)-phenylamine (0.50 g, 2.1 mmol) in acetic acid (4 mL) was sealed in a microwave reaction tube and irradiated with microwave at 130° C. for 15 min. After cooling to room temperature, the cap was removed and the mixture concentrated. The residue was taken in water (20 mL) and pH adjusted to ~9 with 10% NaOH solution. The resulting solution was extracted with EtOAc (2×30 mL) and the organic layer separated. The combined organic layers were washed with brine, dried over anhydrous Na$_2$SO$_4$ and filtered. The filtrate was concentrated in vacuo and the crude product (~0.6 g) used in the next step without purification. MS (ES+): m/z 348 (M+H)$^+$.

Example 83

N-tert-Butyl-3-{5-methyl-2-[3-(piperidine-1-sulfonyl)-phenylamino]-pyrimidin-4-ylamino}-benzenesulfonamide (Compound LI)

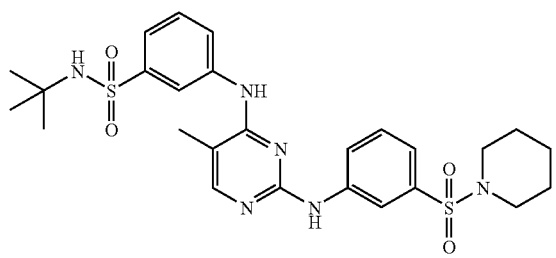

LI

A suspension of intermediate 34 (0.10 g, 0.29 mmol), 3-bromo-N-tert-butyl-benzenesulfonamide (84 mg, 0.29 mmol), Pd$_2$(dba)$_3$ (15 mg, 0.016 mmol), Xantphos (20 mg, 0.035 mmol) and cesium carbonate (0.18 g, 0.55 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (20 mg, 12%).

$^1$H NMR (500 MHz, DMSO-d$_6$): δ 1.12 (s, 9H), 1.30-1.40 (m, 2H), 1.50-1.56 (m, 4H), 2.16 (s, 3H), 2.88 (t, J=5.3 Hz, 4H), 7.17 (d, J=7.8 Hz, 1H), 7.43 (t, J=8.0 Hz, 1H), 7.59-7.60 (m, 2H), 7.58 (s, 1H), 8.13 (s, 1H), 7.16 (dd, J=7.9, 1.9 Hz, 1H), 8.18-8.22 (m, 1H), 8.67 (s, 1H), 9.37 (s, 1H). MS (ES+): m/z 559 (M+H)$^+$.

Example 84

N-tert-Butyl-3-{5-methyl-2-[4-(4-methyl-piperazin-1-ylmethyl)-phenylamino]-pyrimidin-4-ylamino}-benzenesulfonamide (Compound LII)

LII

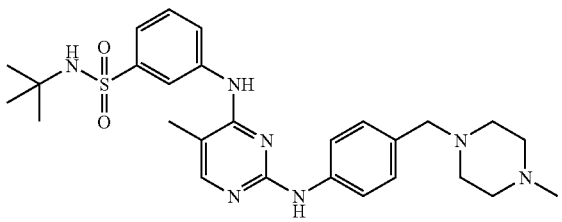

A suspension of intermediate 33 (0.10 g, 0.28 mmol), 4-(4-methyl-piperazin-1-ylmethyl)-phenylamine (65 mg, 0.32 mmol), Pd$_2$(dba)$_3$ (20 mg, 0.022 mmol), Xantphos (25 mg, 0.043 mmol) and cesium carbonate (0.18 g, 0.55 mmol) in dioxane/DMF (3/1, 4 mL) was sealed in a microwave reaction tube and irradiated with microwave at 170° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (53 mg, 36%).

$^1$H NMR (500 MHz, DMSO-d$_6$): δ 1.12 (s, 9H), 2.13 (s, 3H), 2.15 (s, 3H), 2.20-2.45 (m, 4H), 3.25-3.40 (m, 6H), 7.08 (d, J=8.6 Hz, 2H), 7.45-7.52 (m, 2H), 7.56 (s, 1H), 7.57 (d, J=8.6 Hz, 2H), 7.94 (s, 1H), 8.09 (s, 1H), 8.13-8.16 (m, 1H), 8.58 (s, 1H), 8.94 (s, 1H). MS (ES+): m/z 524 (M+H)$^+$.

Example 85

N-tert-Butyl-3-[5-methyl-2-(4-piperazin-1-yl-3-trifluoromethyl-phenylamino)-pyrimidin-4-ylamino]-benzenesulfonamide (Compound LIII)

LIII

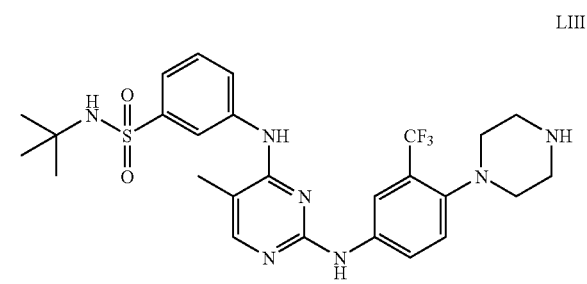

A mixture of intermediate 33 (0.10 g, 0.28 mmol), 4-(4-amino-2-trifluoromethyl-phenyl)-piperazine-1-carboxylic acid tert-butyl ester (0.1 g, 0.29 mmol), Pd$_2$(dba)$_3$ (20 mg, 0.022 mmol), Xantphos (25 mg, 0.043 mmol) and cesium carbonate (0.18 g, 0.55 mmol) in dioxane/DMF (3/1, 4 mL) was sealed in a microwave reaction tube and irradiated with microwave at 170° C. for 15 min. After cooling to room temperature, the cap was removed and the resulting mixture filtered. The filtered solid was washed with DCM and the filtrate concentrated. The residue was dissolved in DCM (5 mL) and 50% TFA/DCM (6 mL) added. The mixture was stirred at room temperature for 2 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (42 mg, 26%).

$^1$H NMR (500 MHz, DMSO-d$_6$): δ 1.12 (s, 9H), 2.14 (s, 3H), 2.70-2.75 (m, 4H), 2.80-2.85 (m, 4H), 7.36 (d, J=8.5 Hz, 2H), 7.45-7.52 (m, 2H), 7.55 (s, 1H), 7.90-8.00 (m, 3H), 8.07 (s, 1H), 8.15 (d, J=7.6 Hz, 1H), 8.63 (s, 1H), 9.22 (s, 1H) MS (ES+): m/z 564 (M+H)$^+$.

Example 86

3-{2-[4-(4-Acetyl-piperazin-1-yl)-3-trifluoromethyl-phenylamino]-5-methyl-pyrimidin-4-ylamino}-N-tert-butyl-benzenesulfonamide (Compound LIV)

LIV

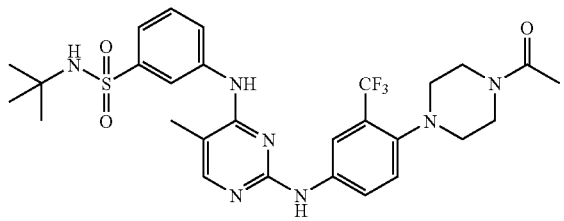

A mixture of intermediate 33 (0.10 g, 0.28 mmol), 1-[4-(4-amino-2-trifluoromethyl-phenyl)-piperazin-1-yl]-ethanone (0.1 g, 0.35 mmol), Pd$_2$(dba)$_3$ (15 mg, 0.016 mmol), Xantphos (20 mg, 0.035 mmol) and cesium carbonate (0.20 g, 0.61 mmol) in dioxane/DMF (3/1, 4 mL) was sealed in a microwave reaction tube and irradiated with microwave at 160° C. for 15 min. After cooling to room temperature, the cap was removed and the resulting mixture filtered. The filtered solid was washed with DCM and the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (64 mg, 38%).

$^1$H NMR (500 MHz, DMSO-d$_6$): δ 1.12 (s, 9H), 2.04 (3, H), 2.14 (s, 3H), 2.73 (t, J=4.9 Hz, 2H), 2.79 (t, J=4.7 Hz, 2H), 3.50-3.60 (m, 4H), 7.40 (d, J=8.7 Hz, 2H), 7.45-7.52 (m, 2H), 7.56 (s, 1H), 7.90-8.00 (m, 3H), 8.07 (s, 1H), 8.14 (d, J=7.2 Hz, 1H), 8.64 (s, 1H), 9.26 (s, 1H). MS (ES+): m/z 606 (M+H)$^+$.

Example 87

5-Methyl-N$^2$-[3-(4-methyl-piperazine-1-sulfonyl)-phenyl]-pyrimidine-2,4-diamine (Intermediate 35)

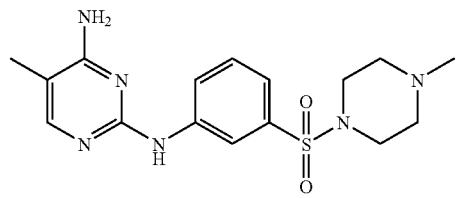

A mixture of 2-chloro-5-methyl-pyrimidin-4-ylamine (0.25 g, 1.74 mmol) and 3-(4-methyl-piperazine-1-sulfonyl)-phenylamine (0.50 g, 2.0 mmol) in acetic acid (4 mL) was sealed in a microwave reaction tube and irradiated with microwave at 130° C. for 15 min. After cooling to room temperature, the cap was removed and the mixture concentrated. The residue was taken in water (20 mL) and pH adjusted to ~9 with 10% NaOH solution. The resulting solution was extracted with EtOAc (2×30 mL) and the organic layer separated. The combined organic layers were washed with brine, dried over anhydrous Na$_2$SO$_4$ and filtered. The filtrate was concentrated in vacuo and the crude product (~0.42 g) used in the next step without purification. MS (ES+): m/z 363 (M+H)$^+$.

Example 88

N-tert-Butyl-3-{5-methyl-2-[3-(4-methyl-piperazine-1-sulfonyl)-phenylamino]-pyrimidin-4-ylamino}-benzenesulfonamide (Compound LV)

LV

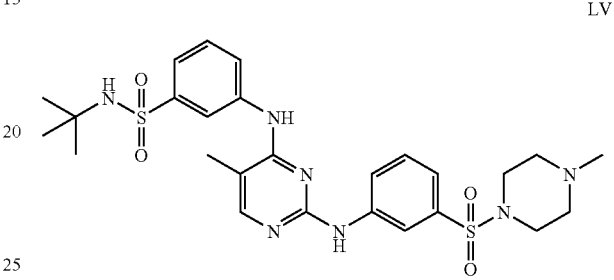

A suspension of intermediate 35 (0.10 g, 0.28 mmol), 3-bromo-N-tert-butyl-benzenesulfonamide (80 mg, 0.27 mmol), Pd$_2$(dba)$_3$ (15 mg, 0.016 mmol), Xantphos (20 mg, 0.035 mmol) and cesium carbonate (0.18 g, 0.55 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (10 mg, 6%).

$^1$H NMR (500 MHz, DMSO-d$_6$): δ 1.12 (s, 9H), 2.13 (s, 3H), 2.16 (s, 3H), 2.33-2.40 (m, 4H), 2.85-2.94 (m, 4H), 7.18 (d, J=8.1 Hz, 1H), 7.44 (t, J=8.0 Hz, 1H), 7.49-7.54 (m, 2H), 7.58 (s, 1H), 8.00-8.03 (m, 2H), 8.13 (s, 1H), 8.15 (dd, J=8.6, 1.6 Hz, 1H), 8.18-8.23 (m, 1H), 8.66 (s, 1H), 9.38 (s, 1H). MS (ES+): m/z 574 (M+H)$^+$.

Example 89

N-tert-Butyl-3-[5-methyl-2-(4-piperazin-1-ylmethyl-phenylamino)-pyrimidin-4-ylamino]-benzene-sulfonamide (Compound LVI)

LVI

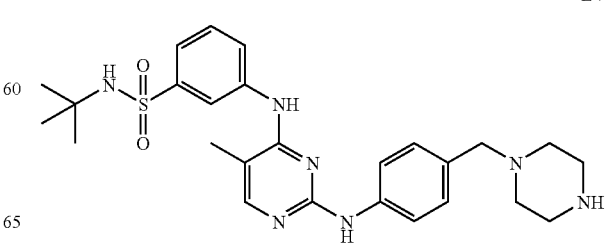

A mixture of intermediate 33 (0.10 g, 0.28 mmol), 4-(4-amino-benzyl)-piperazine-1-carboxylic acid tert-butyl ester (0.1 g, 0.34 mmol), Pd$_2$(dba)$_3$ (15 mg, 0.016 mmol), Xantphos (20 mg, 0.035 mmol) and cesium carbonate (0.20 g, 0.61 mmol) in dioxane/DMF (3/1, 4 mL) was sealed in a microwave reaction tube and irradiated with microwave at 170° C. for 15 min. After cooling to room temperature, the cap was removed and the resulting mixture filtered. The filtered solid was washed with DCM and the filtrate concentrated. The residue was dissolved in DCM (6 mL) and TFA (3 mL) added. The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid triturated in hexanes/EtOAc (10/1, 55 mL). After filtration, the title compound was obtained as a white solid (32 mg, 22%).

$^1$H NMR (500 MHz, DMSO-d$_6$): δ 1.12 (s, 9H), 2.13 (s, 3H), 2.30-2.40 (m, 4H), 2.85 (t, J=4.7 Hz, 4H), 3.38 (s, 2H), 7.09 (d, J=8.5 Hz, 2H), 7.45-7.52 (m, 2H), 7.56 (s, 1H), 7.59 (d, J=8.5 Hz, 2H), 7.94 (s, 1H), 8.10 (s, 1H), 8.13-8.16 (m, 1H), 8.59 (s, 1H), 8.96 (s, 1H). MS (ES+): m/z 510 (M+H)$^+$.

Example 90

N-tert-Butyl-3-{5-methyl-2-[4-(2-pyrrolidin-1-yl-ethoxy)-phenylamino]-pyrimidin-4-ylamino}-benzenesulfonamide (Compound LVII)

LVII

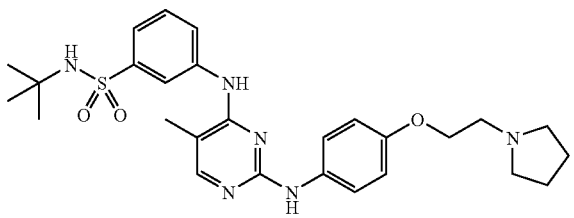

A mixture of intermediate 33 (0.10 g, 0.28 mmol) and 4-(2-pyrrolidin-1-yl-ethoxy)-phenylamine (0.10 g, 0.49 mmol) in acetic acid (3 mL) was sealed in a microwave reaction tube and irradiated with microwave at 150° C. for 20 min. After cooling to room temperature, the cap was removed and the mixture concentrated. The residue was purified by HPLC and the corrected fractions combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (40 mg, 27%).

$^1$H NMR (500 MHz, DMSO-d$_6$): δ 1.12 (s, 9H), 1.65-1.70 (m, 4H), 2.12 (s, 3H), 2.45-2.55 (m, 4H), 2.76 (t, J=5.8 Hz, 2H), 3.99 (t, J=6.0 Hz, 2H), 6.79 (d, J=9.0 Hz, 2H), 7.46-7.53 (m, 4H), 7.56 (s, 1H), 7.90 (s, 1H), 8.10-8.15 (m, 2H), 8.53 (s, 1H), 8.77 (s, 1H). MS (ES+): m/z 525 (M+H)$^+$.

Example 91

3-{5-Methyl-2-[4-(4-methyl-piperazin-1-yl)-phenylamino]-pyrimidin-4-ylamino}-benzenesulfonamide (Compound LVIII)

LVIII

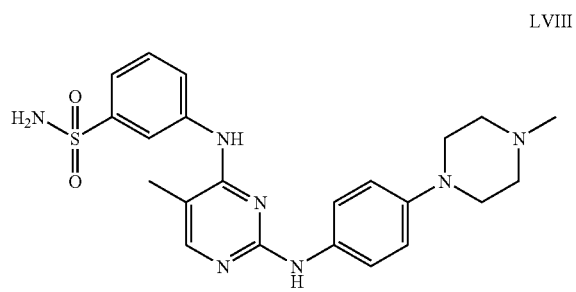

A suspension of intermediate 32 (0.10 g, 0.33 mmol), 3-bromo-benzenesulfonamide (0.10 g, 0.42 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated to afford the title compound as a grey solid (10 mg, 7%).

$^1$H NMR (500 MHz, DMSO-d$_6$): δ 2.10 (s, 3H), 2.22 (s, 3H), 2.44 (t, J=4.9 Hz, 4H), 3.03 (t, J=4.9 Hz, 4H), 6.81 (d, J=9.0 Hz, 2H), 7.34 (s, 2H), 7.45-7.50 (m, 4H), 7.89 (s, 1H), 8.06 (s, 1H), 8.13-8.18 (m, 1H), 8.54 (s, 1H), 8.70 (s, 1H). MS (ES+): m/z 454 (M+H)$^+$.

Example 92

N-Methyl-3-{5-methyl-2-[4-(4-methyl-piperazin-1-yl)-phenylamino]-pyrimidin-4-ylamino}-benzenesulfonamide (Compound LIX)

LIX

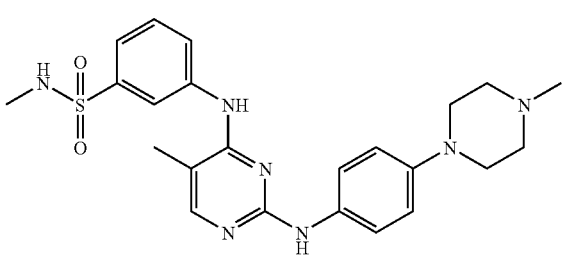

A suspension of intermediate 32 (0.10 g, 0.33 mmol), 3-bromo-N-methyl-benzenesulfonamide (0.11 g, 0.44 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of DCM/Et$_2$O (1/5, 30 mL). After filtration, the title compound was obtained as a light brown solid (65 mg, 42%).

$^1$H NMR (500 MHz, DMSO-d$_6$): δ 2.11 (s, 3H), 2.23 (s, 3H), 2.44 (d, J=5.0 Hz, 3H), 2.45-2.50 (m, 4H), 3.03 (t, J=4.9 Hz, 4H), 6.81 (d, J=9.1 Hz, 2H), 7.40-7.43 (m, 2H), 7.46 (d, J=9.1 Hz, 2H), 7.52 (t, J=8.0 Hz, 1H), 7.89 (s, 1H), 7.94 (t, J=1.8 Hz, 1H), 8.29 (br d, J=8.3 Hz, 1H), 8.56 (s, 1H), 8.72 (s, 1H). MS (ES+): m/z 468 (M+H)$^+$.

Example 93

N,N-Dimethyl-3-{5-methyl-2-[4-(4-methyl-piperazin-1-yl)-phenylamino]-pyrimidin-4-ylamino}-benzenesulfonamide (Compound LX)

LX

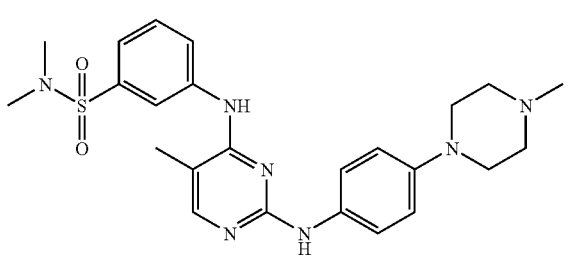

A suspension of intermediate 32 (0.13 g, 0.43 mmol), 3-bromo-N,N-dimethyl-benzenesulfonamide (0.14 g, 0.53 mmol), Pd$_2$(dba)$_3$ (25 mg, 0.027 mmol), Xantphos (30 mg, 0.052 mmol) and cesium carbonate (0.33 g, 1.0 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as an off white solid (60 mg, 29%).

$^1$H NMR (500 MHz, DMSO-d$_6$): δ 2.17 (s, 3H), 2.23 (s, 3H), 2.44 (d, J=5.0 Hz, 3H), 2.45-2.50 (m, 4H), 2.63 (s, 6H), 3.03 (t, J=4.9 Hz, 4H), 6.81 (d, J=9.1 Hz, 2H), 7.36 (d, J=8.0 Hz, 1H), 7.45 (d, J=9.1 Hz, 2H), 7.54 (t, J=8.0 Hz, 1H), 7.84 (t, J=1.9 Hz, 1H), 7.90 (s, 1H), 8.46 (br d, J=7.8 Hz, 1H), 8.57 (s, 1H), 8.74 (s, 1H). MS (ES+): m/z 482 (M+H)$^+$.

Example 94

N-Isopropyl-3-{5-methyl-2-[4-(4-methyl-piperazin-1-yl)-phenylamino]-pyrimidin-4-ylamino}-benzenesulfonamide (Compound LXI)

LXI

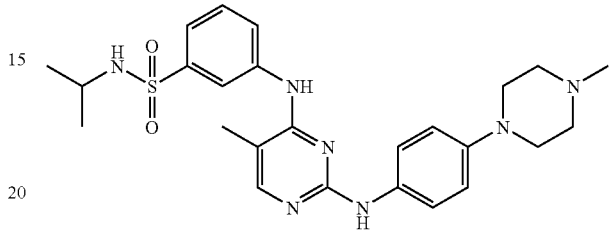

A suspension of intermediate 32 (0.10 g, 0.33 mmol), 3-bromo-N-isopropyl-benzenesulfonamide (0.11 g, 0.39 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (47 mg, 29%).

$^1$H NMR (500 MHz, DMSO-d$_6$): δ 0.98 (d, J=6.6 Hz, 6H), 2.11 (s, 3H), 2.24 (s, 3H), 2.45-2.50 (m, 4H), 3.03 (t, J=4.8 Hz, 4H), 3.20-3.27 (m, 1H), 6.80 (d, J=9.0 Hz, 2H), 7.40-7.52 (m, 4H), 7.59 (d, J=7.1 Hz, 1H), 7.89 (s, 1H), 8.21 (br d, J=7.9 Hz, 1H), 8.53 (s, 1H), 8.71 (s, 1H). MS (ES+): m/z 496 (M+H)$^+$.

Example 95

N$^4$-(3-Methanesulfonyl-4-methyl-phenyl)-5-methyl-N$^2$-[4-(4-methyl-piperazin-1-yl)-phenyl]-pyrimidine-2,4-diamine (Compound LXII)

LXII

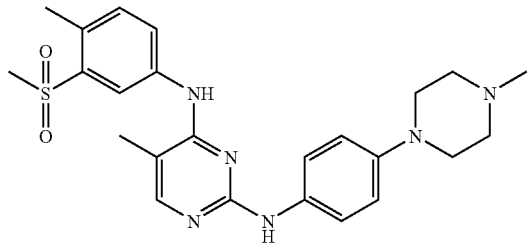

A suspension of intermediate 32 (0.10 g, 0.33 mmol), 4-bromo-2-methanesulfonyl-1-methyl-benzene (0.10 g, 0.40 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as a light brown solid (41 mg, 27%).

$^1$H NMR (500 MHz, DMSO-d$_6$): δ 2.09 (s, 3H), 2.22 (s, 3H), 2.45 (t, J=4.7 Hz, 4H), 2.61 (s, 3H), 3.03 (t, J=4.9 Hz, 4H), 3.20 (s, 3H), 6.80 (d, J=9.1 Hz, 2H), 7.35 (d, J=8.5 Hz, 1H), 7.44 (d, J=9.0 Hz, 2H), 7.87 (s, 1H), 8.05 (d, J=2.4 Hz, 1H), 8.21 (br d, J=7.0 Hz, 1H), 8.55 (s, 1H), 8.71 (s, 1H). MS (ES+): m/z 467 (M+H)$^+$.

Example 96

N-Cyclohexyl-3-{5-methyl-2-[4-(4-methyl-piperazin-1-yl)-phenylamino]-pyrimidin-4-ylamino}-benzenesulfonamide (Compound LXIII)

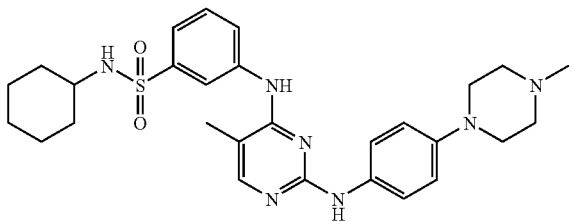

LXIII

A suspension of intermediate 32 (0.10 g, 0.33 mmol), 3-bromo-N-cyclohexyl-benzenesulfonamide (0.13 g, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (45 mg, 25%).

$^1$H NMR (500 MHz, DMSO-d$_6$): δ 1.07-1.17 (m, 6H), 1.53-1.63 (m, 4H), 2.11 (s, 3H), 2.22 (s, 3H), 2.45 (t, J=4.7 Hz, 4H), 2.90-3.00 (m, 1H), 3.02 (t, J=4.8 Hz, 4H), 6.80 (d, J=9.1 Hz, 2H), 7.43-7.53 (m, 4H), 7.65 (d, J=7.3 Hz, 1H), 7.89 (s, 1H), 8.05 (s, 1H), 8.18 (br d, J=7.7 Hz, 1H), 8.52 (s, 1H), 8.71 (s, 1H). MS (ES+): m/z 536 (M+H)$^+$.

Example 97

N,N-Diethyl-3-{5-methyl-2-[4-(4-methyl-piperazin-1-yl)-phenylamino]-pyrimidin-4-ylamino}-benzenesulfonamide (Compound LXIV)

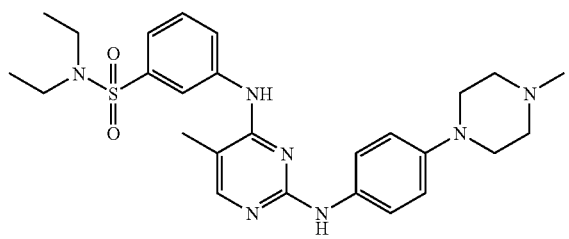

LXIV

A suspension of intermediate 32 (0.10 g, 0.33 mmol), 3-bromo-N,N-diethyl-benzenesulfonamide (0.12 g, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (45 mg, 27%).

$^1$H NMR (500 MHz, DMSO-d$_6$): δ 1.06 (t, J=7.1 Hz, 6H), 2.11 (s, 3H), 2.22 (s, 3H), 2.44 (t, J=4.7 Hz, 4H), 3.03 (t, J=4.8 Hz, 4H), 3.16 (q, J=7.1 Hz, 4H), 6.80 (d, J=9.1 Hz, 2H), 7.39 (d, J=8.1 Hz, 1H), 7.45 (d, J=9.0 Hz, 2H), 7.50 (t, J=8.1 Hz, 1H), 7.89 (t, J=1.9 Hz, 1H), 7.89 (s, 1H), 8.39 (br d, J=7.9 Hz, 1H), 8.53 (s, 1H), 8.74 (s, 1H). MS (ES+): m/z 510 (M+H)$^+$.

Example 98

5-Methyl-N$^2$-[4-(4-methyl-piperazin-1-yl)-phenyl]-N$^4$-[3-(morpholine-4-sulfonyl)-phenyl]-pyrimidine-2,4-diamine (Compound LXV)

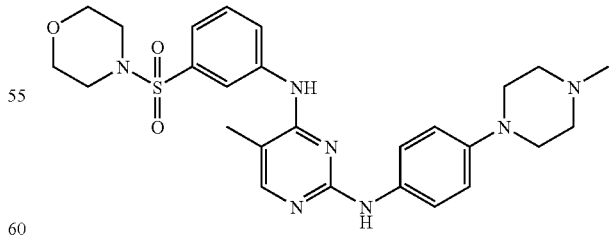

LXV

A suspension of intermediate 32 (0.10 g, 0.33 mmol), 4-(3-bromo-benzenesulfonyl)-morpholine (0.12 g, 0.39 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min.

After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as a light red solid (90 mg, 52%).

$^1$H NMR (500 MHz, DMSO-d$_6$): δ 2.12 (s, 3H), 2.22 (s, 3H), 2.45 (t, J=4.8 Hz, 4H), 2.89 (t, J=4.6 Hz, 4H), 3.03 (t, J=4.8 Hz, 4H), 3.64 (t, J=4.7 Hz, 4H), 6.81 (d, J=9.1 Hz, 2H), 7.35 (d, J=8.1 Hz, 1H), 7.45 (d, J=9.0 Hz, 2H), 7.56 (t, J=8.1 Hz, 1H), 7.84 (t, J=1.9 Hz, 1H), 7.91 (s, 1H), 8.47 (br d, J=8.4 Hz, 1H), 8.59 (s, 1H), 8.75 (s, 1H). MS (ES+): m/z 524 (M+H)$^+$.

Example 99

3-{5-Methyl-2-[4-(4-methyl-piperazin-1-yl)-phenylamino]-pyrimidin-4-ylamino}-benzoic acid ethyl ester (Intermediate 36)

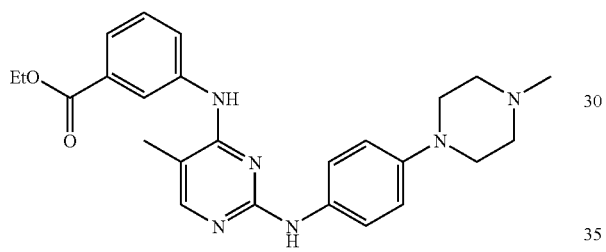

A suspension of intermediate 32 (0.10 g, 0.33 mmol), 3-bromo-benzoic acid ethyl ester (0.07 mL, 0.44 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 10% MeOH/DCM) to afford the title compound (0.10 g, 68%). MS (ES+): m/z 447 (M+H)$^+$.

Example 100

3-{5-Methyl-2-[4-(4-methyl-piperazin-1-yl)-phenylamino]-pyrimidin-4-ylamino}-benzamide (Compound LXVI)

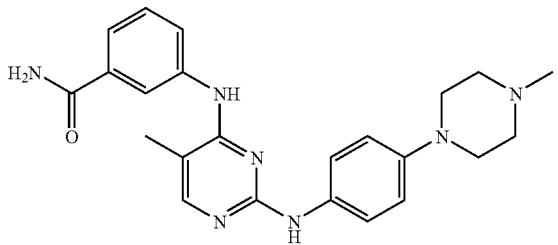

A mixture of intermediate 36 (0.10 g, 0.22 mmol) in concentrated NH$_4$OH was sealed in a reaction tube and heated at 50° C. for 3 d. The mixture was poured into water (15 mL) and extracted with EtOAc (2×30 mL). The combined organic layers were washed with brine, dried over anhydrous Na$_2$SO$_4$ and filtered. The filtrate was concentrated and the residue purified by HPLC. The corrected fractions were combined and poured into saturated NaHCO$_3$ solution (30 mL). The aqueous layer was extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as a white solid (10 mg, 11%).

$^1$H NMR (500 MHz, DMSO-d$_6$): δ 2.10 (s, 3H), 2.22 (s, 3H), 2.40-2.50 (m, 4H), 2.95-3.05 (m, 4H), 6.75 (d, J=9.1 Hz, 2H), 7.30-7.40 (m, 2H), 7.45 (d, J=9.1 Hz, 2H), 7.53-7.58 (m, 1H), 7.85 (s, 1H), 7.90 (br s, 2H), 8.03 (s, 1H), 8.37 (s, 1H), 8.71 (s, 1H). MS (ES+): m/z 418 (M+H)$^+$.

Example 101

2-Methyl-3-{5-methyl-2-[4-(4-methyl-piperazin-1-yl)-phenylamino]-pyrimidin-4-ylamino}-benzoic acid ethyl ester (Compound LXVII)

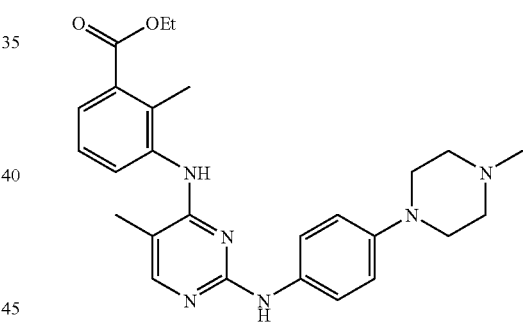

A suspension of intermediate 32 (0.10 g, 0.33 mmol), 3-bromo-2-methyl-benzoic acid ethyl ester (0.10 mL, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by flash chromatography on silica gel (DCM to 30% MeOH and 1% TEA in DCM) to afford the title compound (0.14 g, 92%) as a light brown oil.

$^1$H NMR (500 MHz, DMSO-d$_6$): δ 1.32 (t, J=7.1 Hz, 3H), 2.10 (s, 3H), 2.21 (s, 3H), 2.32 (s, 3H), 2.40-2.45 (m, 4H), 2.94 (t, J=4.8 Hz, 4H), 4.30 (q, J=7.1 Hz, 2H), 6.57 (d, J=9.1 Hz, 2H), 7.25 (d, J=8.9 Hz, 2H), 7.35 (t, J=7.8 Hz, 1H), 7.48 (dd, J=7.9, 1.0 Hz, 1H), 7.70 (dd, J=7.8, 1.1 Hz, 1H), 7.78 (s, 1H), 8.23 (s, 1H), 8.58 (s, 1H). MS (ES+): m/z 461 (M+H)$^+$.

Example 102

2-Methyl-3-{5-methyl-2-[4-(4-methyl-piperazin-1-yl)-phenylamino]-pyrimidin-4-ylamino}-benzamide (Compound LXVIII)

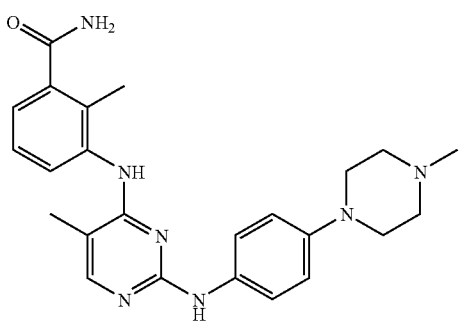

LXVIII

To a mixture of the above-described compound LXVII (0.10 g, 0.22 mmol) and formamide (0.05 mL, 1.3 mmol) in DMF (5 mL) at 100° C. was added NaOMe (0.10 g, 0.46 mmol) under the argon atmosphere. The mixture was stirred at the same temperature for 2 h and then at room temperature for additional 15 h. The mixture was poured into water (15 mL) and extracted with EtOAc (2×15 mL). The combined organic layers were washed with brine, dried over anhydrous $Na_2SO_4$ and filtered. The filtrate was concentrated and the residue purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and the residue triturated in a mixture of EtOAc/hexanes (1/5, 30 mL). After filtration, the title compound was obtained as a white solid (20 mg, 21%).

$^1$H NMR (500 MHz, DMSO-$d_6$): δ 2.09 (s, 3H), 2.21 (s, 3H), 2.23 (s, 3H), 2.40-2.45 (m, 4H), 2.97 (t, J=4.8 Hz, 4H), 6.69 (d, J=9.1 Hz, 2H), 7.24-7.28 (m, 2H), 7.35 (d, J=9.0 Hz, 2H), 7.39-7.43 (m, 2H), 7.69 (s, 1H), 7.78 (s, 1H), 8.01 (s, 1H), 8.53 (s, 1H). MS (ES+): m/z 432 (M+H)$^+$.

Example 103

(2-Chloro-5-methyl-pyrimidin-4-yl)-(4-chloro-3-trifluoromethyl-phenyl)-amine (Intermediate 37)

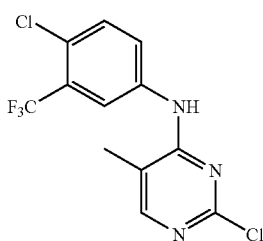

37

A mixture of 2-chloro-5-methyl-pyrimidin-4-ylamine (0.30 g, 2.1 mmol), 4-bromo-1-chloro-2-trifluoromethyl-benzene (0.40 mL, 2.7 mmol), $Pd_2(dba)_3$ (0.10 g, 0.11 mmol), Xantphos (0.13 g, 0.22 mmol) and cesium carbonate (1.5 g, 4.6 mmol) in dioxane/DMF (6/1, 7 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (hexanes to 50% EtOAc/hexanes) to afford the title compound (0.65 g, 96%) as a white solid. MS (ES+): m/z 322 (M+H)$^+$.

Example 104

$N^4$-(4-Chloro-3-trifluoromethyl-phenyl)-5-methyl-$N^2$-[4-(piperidin-4-yloxy)-phenyl]-pyrimidine-2,4-diamine (Compound LXIX)

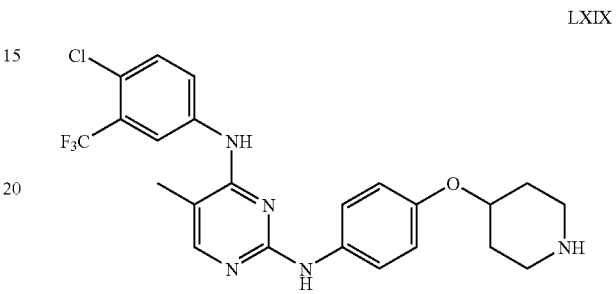

LXIX

A mixture of intermediate 37 (0.10 g, 0.31 mmol) and 4-(4-amino-phenoxy)-piperidine-1-carboxylic acid tert-butyl ester (0.12 g, 0.41 mmol) in acetic acid (3 mL) was sealed in a microwave reaction tube and irradiated with microwave at 150° C. for 15 min. After cooling to room temperature, the cap was removed and the mixture concentrated. The residue was taken in water (20 mL) and neutralized with 10% NaOH solution until solid precipitated. The resulting solid was filtered and purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated to afford the title compound as a white solid (30 mg, 20%).

$^1$H NMR (500 MHz, DMSO-$d_6$): δ 1.69-1.77 (m, 2H), 2.00-2.04 (m, 2H), 2.11 (s, 3H), 2.90-3.00 (m, 2H), 3.10-3.20 (m, 2H), 4.40-4.48 (m, 1H), 6.84 (d, J=9.0 Hz, 2H), 7.49 (d, J=9.0 Hz, 2H), 7.58 (d, J=8.8 Hz, 1H), 7.94 (s, 1H), 8.12 (d, J=2.6 Hz, 1H), 8.21 (br d, J=8.2 Hz, 1H), 8.64 (s, 1H), 8.93 (s, 1H). MS (ES+): m/z 478 (M+H)$^+$.

Example 105

5-Methyl-$N^2$-[4-(2-pyrrolidin-1-yl-ethoxy)-phenyl]-pyrimidine-2,4-diamine (Intermediate 38)

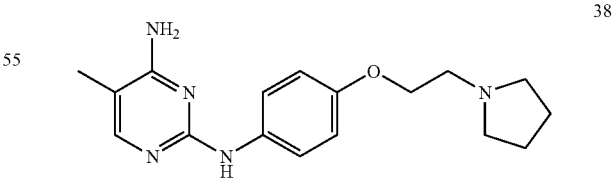

38

A mixture of 2-chloro-5-methyl-pyrimidin-4-ylamine (0.50 g, 3.5 mmol) and 4-(2-pyrrolidin-1-yl-ethoxy)-phenylamine (1.1 g, 5.3 mmol) in acetic acid (8 mL) was sealed in a microwave reaction tube and irradiated with microwave at 150° C. for 15 min. After cooling to room temperature, the cap was removed and the mixture concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous $Na_2SO_4$ and filtered. The filtrate was concentrated to afford the title compound as a grey solid (0.80 g, 73%). It was used in the next step without purification. MS (ES+): m/z 314 (M+H)+.

Example 106

3-{5-Methyl-2-[4-(2-pyrrolidin-1-yl-ethoxy)-phenylamino]-pyrimidin-4-ylamino}-benzenesulfonamide (Compound LXX)

LXX

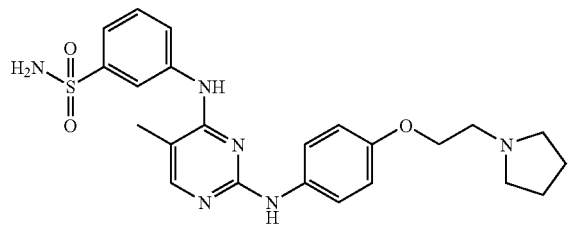

A mixture of intermediate 38 (0.10 g, 0.32 mmol), 3-bromo-benzenesulfonamide (0.10 g, 0.42 mmol), $Pd_2(dba)_3$ (20 mg, 0.022 mmol), Xantphos (25 mg, 0.043 mmol) and cesium carbonate (0.20 g, 0.61 mmol) in dioxane/DMF (3/1, 4 mL) was sealed in a microwave reaction tube and irradiated with microwave at 170° C. for 25 min. After cooling to room temperature, the cap was removed and the resulting mixture filtered and the filtered solid washed with DCM. The filtrate was concentrated and the residue purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and solid triturated in a mixture of EtOAc/hexanes (1/10, 33 mL). After filtration, the title compound was obtained as a white solid (11 mg, 7%).
$^1$H NMR (500 MHz, DMSO-$d_6$): δ 1.65-1.72 (m, 4H), 2.11 (s, 3H), 2.49-2.52 (m, 4H), 2.75-2.80 (m, 2H), 4.00 (t, J=5.9 Hz, 2H), 6.80 (d, J=9.0 Hz, 2H), 7.34 (s, 2H), 7.45-7.50 (m, 2H), 7.52 (d, J=9.0 Hz, 2H), 7.90 (s, 1H), 8.05 (s, 1H), 8.10-8.15 (m, 1H), 8.57 (s, 1H), 8.77 (s, 1H). MS (ES+): m/z 469 (M+H)+.

Example 107

5-Methyl-$N^2$-(4-morpholin-4-ylmethyl-phenyl)-pyrimidine-2,4-diamine (Intermediate 39)

39

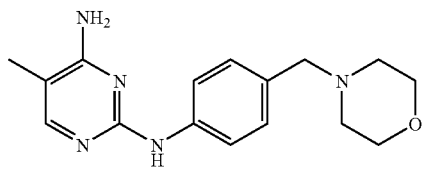

A mixture of 2-chloro-5-methyl-pyrimidin-4-ylamine (0.40 g, 2.8 mmol) and 4-morpholin-4-ylmethyl-phenylamine (0.60 g, 3.1 mmol) in acetic acid (15 mL) was heated at 70° C. for 17 h. After cooling to room temperature, the mixture was concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous $Na_2SO_4$ and filtered. The filtrate was concentrated to afford the title compound as a brown syrup (0.70 g, 83%). It was used in the next step without purification. MS (ES+): m/z 300 (M+H)+

Example 108

$N^4$-(1H-Indol-4-yl)-5-methyl-$N^2$-(4-morpholin-4-ylmethyl-phenyl)-pyrimidine-2,4-diamine (Compound LXXI)

LXXI

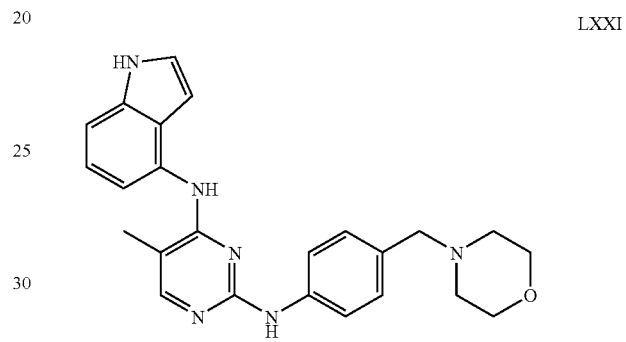

A mixture of intermediate 39 (0.40 g, 1.3 mmol), 4-bromo-1-triisopropylsilanyl-1H-indole (0.50 g, 1.4 mmol), $Pd_2(dba)_3$ (0.10 g, 0.11 mmol), Xantphos (0.12 g, 0.21 mmol) and cesium carbonate (0.90 g, 2.8 mmol) was suspended in dioxane (20 mL) and heated at reflux under the argon atmosphere for 4 h. The reaction mixture was cooled to room temperature and diluted with DCM (30 mL). The mixture was filtered and the filtrate concentrated in vacuo. The residue was purified by flash chromatography on silica gel (hexanes to EtOAc) to afford the TIPS protected precursor as a yellow oil.

To the above TIPS protected precursor (50 mg, 0.088 mmol) in THF (5 mL) was added TBAF (0.5 mL, 1M in THF). The mixture was stirred at room temperature for 1 h and then poured into water (20 mL). The aqueous layer was extracted with EtOAc (2×20 mL) and the combined organic layers washed with brine, dried over anhydrous $Na_2SO_4$ and filtered. The filtrate was concentrated and the residue purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and solid dissolved in minimum amount of EtOAc and then hexanes added until solid precipitated. After filtration, the title compound was obtained as a light brown solid (6 mg, 1% overall yield).
$^1$H NMR (500 MHz, DMSO-$d_6$): δ 2.17 (s, 3H), 2.25-2.30 (m, 4H), 3.29 (s, 2H), 3.54 (t, J=4.5 Hz, 4H), 6.40 (t, J=2.2 Hz, 1H), 6.89 (d, J=8.5 Hz, 2H), 7.09 (t, J=7.8 Hz, 1H), 7.25 (d, J=8.0 Hz, 1H), 7.27 (t, J=2.8 Hz, 1H), 7.30 (d, J=7.5 Hz, 1H), 7.43 (d, J=8.5 Hz, 2H), 7.85 (s, 1H), 8.14 (s, 1H), 8.77 (s, 1H), 11.10 (s, 1H). MS (ES+): m/z 415 (M+H)+.

Example 109

4-[4-(4-Amino-5-methyl-pyrimidin-2-ylamino)-benzyl]-piperazine-1-carboxylic acid tert-butyl ester (Intermediate 40)

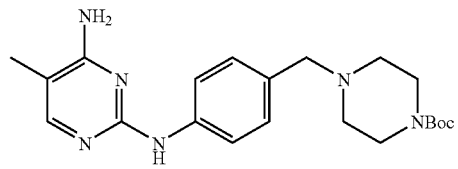

A mixture of 2-chloro-5-methyl-pyrimidin-4-ylamine (0.35 g, 2.4 mmol) and 4-(4-amino-benzyl)-piperazine-1-carboxylic acid tert-butyl ester (0.80 g, 2.8 mmol) in acetic acid (20 mL) was heated at 70° C. for 1 d. After cooling to room temperature, the mixture was concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous $Na_2SO_4$ and filtered. The filtrate was concentrated and the title compound used in the next step without purification. MS (ES+): m/z 399 $(M+H)^+$.

Example 110

$N^4$-(1H-Indol-4-yl)-5-methyl-$N^2$-(4-piperazin-1-ylmethyl-phenyl)-pyrimidine-2,4-diamine (Compound LXXII)

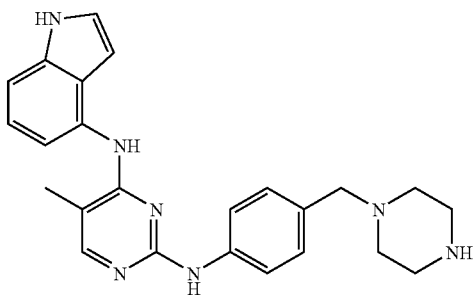

A mixture of intermediate 40 (0.78 g, 2.0 mmol), 4-bromo-1-triisopropylsilanyl-1H-indole (0.70 g, 2.0 mmol), $Pd_2(dba)_3$ (0.15 g, 0.16 mmol), Xantphos (0.19 g, 0.32 mmol) and cesium carbonate (1.3 g, 4.0 mmol) was suspended in dioxane (20 mL) and heated at reflux under the argon atmosphere for 4.5 h. The reaction mixture was cooled to room temperature, filtered and the filtered solid was with DCM (30 mL). The filtrate was concentrated and the residue purified by flash chromatography on silica gel (hexanes to 30% EtOAc/hexanes) to afford the TIPS protected precursor.

To the above TIPS protected precursor (0.10 g, 0.15 mmol) in DCM (8 mL) was added TFA (2 mL). The mixture was stirred at room temperature for 2 h and then concentrated. The residue was purified by HPLC and the corrected fractions combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and solid triturated in a mixture of EtOAc/hexanes (1/5, 30 mL). After filtration, the title compound was obtained as a white solid (25 mg, 3% overall yield).

$^1$H NMR (500 MHz, DMSO-$d_6$): δ 2.17 (s, 3H), 2.20-2.30 (m, 4H), 2.73 (t, J=4.6 Hz, 4H), 3.28 (s, 2H), 6.41 (t, J=2.2 Hz, 1H), 6.89 (d, J=8.5 Hz, 2H), 7.09 (t, J=7.8 Hz, 1H), 7.24 (d, J=8.3 Hz, 1H), 7.27 (t, J=2.8 Hz, 1H), 7.31 (d, J=7.5 Hz, 1H), 7.44 (d, J=8.5 Hz, 2H), 7.85 (s, 1H), 8.13 (s, 1H), 8.77 (s, 1H), 11.10 (s, 1H) MS (ES+): m/z 414 $(M+H)^+$.

Example 111

5-Methyl-$N^4$-(7-methyl-1H-indol-4-yl)-$N^2$-(4-(4-methylpiperazin-1-yl)phenyl)pyrimidine-2,4-diamine (Compound LXXIII)

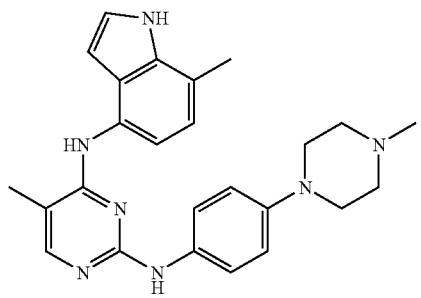

A mixture of intermediate 32 (674 mg, 2.25 mmol), 4-bromo-7-methyl-1H-indole (522 mg, 2.48 mmol), $Pd_2(dba)_3$ (182 mg, 0.2 mmol), Xantphos (360 mg, 0.6 mmol) and cesium carbonate (2.6 g, 8 mmol) was suspended in dioxane (50 mL) and heated at reflux under the argon atmosphere for 20 h. The mixture was filtered and the filtrate concentrated in vacuo. The residue was purified by HPLC to afford the title compound (136 mg of HCl salt, 13%) as a white solid.

$^1$H NMR (500 MHz, DMSO-$d_6$): δ 2.21 (s, 3H), 2.55 (s, 3H), 2.80 (d, J=4.6 Hz, 3H), 3.00-3.05 (m, 2H), 3.10-3.16 (m, 2H), 3.45-3.48 (m, 2H), 3.64-3.66 (m, 2H), 6.33-6.34 (m, 1H), 6.63 (br, 2H), 6.92-6.97 (m, 4H), 7.35 (t, J=2.7 Hz, 1H), 7.83 (s, 1H), 10.04 (s, 1H), 10.24 (s, 1H), 11.08 (br s, 1H), 11.34 (s, 1H), 12.12 (br s, 1H). MS (ES+): m/z 428 $(M+H)^+$.

Example 112

$N^4$-(7-Chloro-1H-indol-4-yl)-5-methyl-$N^2$-(4-(4-methylpiperazin-1-yl)phenyl)pyrimidine-2,4-diamine (Compound LXXIV)

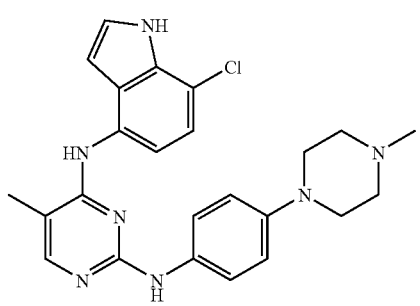

A mixture of intermediate 32 (298 mg, 1.0 mmol), 4-bromo-7-chloro-1H-indole (231 mg, 1.04 mmol), $Pd_2(dba)_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (251 mg of HCl salt, 51%) as a white solid.

$^1$H NMR (500 MHz, DMSO-d$_6$): δ 2.21 (s, 3H), 2.80 (d, J=4.6 Hz, 3H), 3.01-3.05 (m, 2H), 3.08-3.13 (m, 2H), 3.46-3.48 (m, 2H), 3.65-3.67 (m, 2H), 6.46-6.47 (m, 1H), 6.64 (br s, 1H), 6.93 (d, J=8.9 Hz, 2H), 7.05 (d, J=8.1 Hz, 2H), 7.25 (d, J=8.0 Hz, 2H), 7.43-7.44 (m, 1H), 7.87 (s, 1H), 10.13 (s, 1H), 10.27 (s, 1H), 11.00 (br s, 1H), 11.70 (s, 1H), 12.23 (br s, H). MS (ES+): m/z 448 (M+H)$^+$.

Example 113

N$^2$-(4-(2-(Pyrrolidin-1-yl)ethoxy)phenyl)-5-methyl-N$^4$-(7-methyl-1H-indol-4-yl)pyrimidine-2,4-diamine (Compound LXXV)

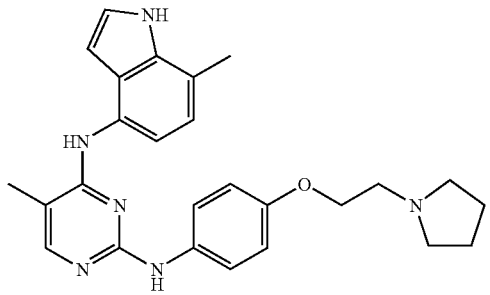

LXXV

A mixture of intermediate 38 (410 mg, 1.3 mmol), 4-bromo-7-methyl-1H-indole (275 mg, 1.3 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (92 mg of HCl salt, 15%) as a white solid.

$^1$H NMR (500 MHz, DMSO-d$_6$): δ 1.88-1.90 (m, 2H), 1.93-2.02 (m, 2H), 2.21 (s, 3H), 2.55 (s, 3H), 3.06-3.10 (m, 2H), 3.51-3.54 (m, 4H), 4.26 (t, J=4.9 Hz, 2H), 6.33-6.34 (m, 1H), 6.61 (br d, 2H), 6.93-6.95 (m, 2H), 7.03 (d, J=8.9 Hz, 2H), 7.34 (t, J=2.8 Hz, 1H), 7.85 (s, 1H), 10.07 (s, 1H), 10.33 (s, 1H), 10.91 (br s, 1H), 11.34 (s, 1H), 12.15 (br s, H). MS (ES+): m/z 443 (M+H)$^+$.

Example 114

N$^2$-(4-(2-(Pyrrolidin-1-yl)ethoxy)phenyl)-5-methyl-N$^4$-(7-chloro-1H-indol-4-yl)pyrimidine-2,4-diamine (Compound LXXVI)

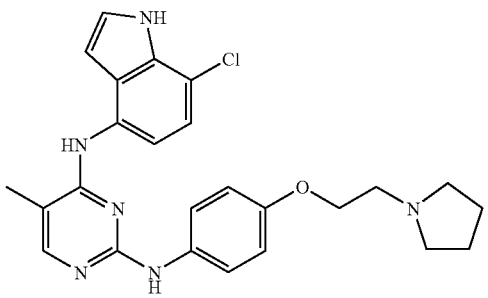

LLXVI

A mixture of intermediate 38 (270 mg, 0.86 mmol), 4-bromo-7-chloro-1H-indole (198 mg, 0.86 mmol), Pd$_2$(dba)$_3$ (72 mg, 0.08 mmol), Xantphos (140 mg, 0.24 mmol) and cesium carbonate (1.3 g, 4 mmol) was suspended in dioxane (50 mL) and heated at reflux under the argon atmo-sphere for 20 h. The mixture was filtered and the filtrate concentrated in vacuo. The residue was purified by HPLC to afford the title compound (33 mg of HCl salt, 8%) as a white solid.

$^1$H NMR (500 MHz, DMSO-d$_6$): δ 1.88-1.90 (m, 2H), 1.93-2.02 (m, 2H), 2.22 (s, 3H), 3.06-3.10 (m, 2H), 3.51-3.54 (m, 4H), 4.27 (t, J=4.9 Hz, 2H), 6.46-6.47 (m, 1H), 6.63 (br d, 2H), 6.95 (d, J=8.2 Hz, 2H), 7.06 (d, J=8.0 Hz, 1H), 7.25 (d, J=8.0 Hz, 1H), 7.43 (t, J=2.8 Hz, 1H), 7.90 (s, 1H), 10.13 (s, 1H), 10.40 (s, 1H), 10.94 (br s, 1H), 11.70 (s, 1H), 12.33 (br s, H). MS (ES+): m/z 463 (M+H)$^+$.

Example 115

N$^2$-(4-(2-(Pyrrolidin-1-yl)ethoxy)phenyl)-5-methyl-N$^4$-(7-fluoro-1H-indol-4-yl)pyrimidine-2,4-diamine (Compound LXXVII)

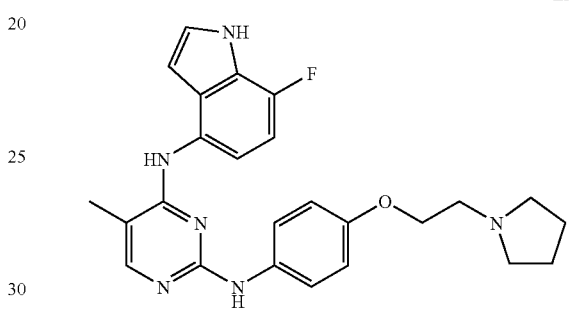

LXXVII

A mixture of intermediate 38 (413 mg, 1.3 mmol), 4-bromo-7-fluoro-1H-indole (310 mg, 1.45 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (10 mg of HCl salt, 1.5%) as a brown solid.

$^1$H NMR (500 MHz, DMSO-d$_6$): δ 1.88-1.90 (m, 2H), 1.93-2.02 (m, 2H), 2.21 (s, 3H), 3.06-3.10 (m, 2H), 3.51-3.56 (m, 4H), 4.26 (t, J=4.9 Hz, 2H), 6.42-6.43 (m, 1H), 6.63 (br d, 2H), 6.95-7.04 (m, 3H), 7.35 (d, J=8.9 Hz, 1H), 7.42 (t, J=2.8 Hz, 1H), 7.89 (s, 1H), 10.08 (s, 1H), 10.41 (s, 1H), 10.90 (br s, 1H), 11.85 (s, 1H), 12.33 (br s, H). MS (ES+): m/z 447 (M+H)$^+$.

Example 116

N$^4$-(3-tert-Butylphenyl)-5-methyl-N$^2$-(4-(4-methylpiperazin-1-yl)phenyl)pyrimidine-2,4-diamine (Compound LXXVIII)

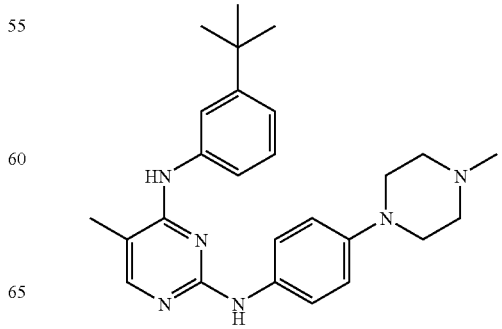

LXXVIII

A mixture of intermediate 32 (298 mg, 1.0 mmol), 1-tert-butyl-3-bromobenzene (256 mg, 1.2 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (27 mg of HCl salt, 6%) as a white solid.

$^1$H NMR (500 MHz, DMSO-d$_6$): δ 1.25 (s, 9H), 2.16 (s, 3H), 2.80 (d, J=4.6 Hz, 3H), 3.04-3.16 (m, 4H), 3.47-3.49 (m, 2H), 3.65-3.67 (m, 2H), 6.90 (d, J=8.9 Hz, 2H), 7.26 (d, J=9.0 Hz, 2H), 7.28-7.35 (m, 2H), 7.45 (t, J=1.8 Hz, 1H), 7.50 (d, J=7.8 Hz, 1H), 7.86 (s, 1H), 9.70 (s, 1H), 10.37 (s, 1H), 11.01 (br s, 1H), 12.34 (br s, H). MS (ES+): m/z 431 (M+H)$^+$.

Example 117

N—(3-tert-Butylphenyl)-2-chloro-5-methylpyrimidin-4-amine (Intermediate 41)

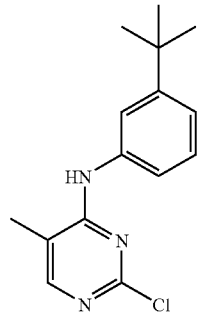

A mixture of 2-chloro-5-methylpyrimidin-4-amine (670 mg, 4.7 mmol), 1-tert-butyl-3-bromobenzene (1.5 g, 7 mmol), Pd$_2$(dba)$_3$ (366 mg, 0.4 mmol), Xantphos (695 mg, 1.2 mmol) and cesium carbonate (6.2 g, 19 mmol) was suspended in dioxane (150 mL) and heated at reflux under the argon atmosphere for 20 h. The mixture was filtered and the filtrate concentrated in vacuo. The residue was dissolved in EtOAc (10 mL) and added hexanes (100 mL). The solid was collected by filtration and washed with hexanes to afford the crude title compound (1.2 g, 99%) as a yellow solid.

Example 118

N$^4$-(3-tert-Butylphenyl)-5-methyl-N$^2$-(4-(piperidin-4-yloxy)phenyl)pyrimidine-2,4-diamine (Compound LXXIX)

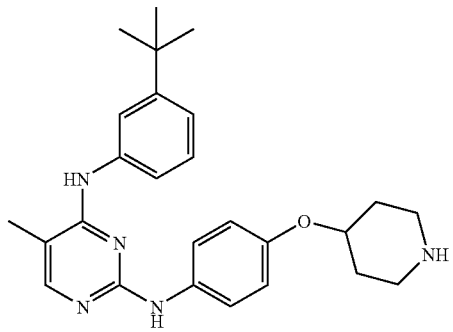

A mixture of intermediate 41 (740 mg, 2.68 mmol) and tert-butyl 4-(4-aminophenoxy)piperidine-1-carboxylate (500 mg, 1.71 mmol) was suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (276 mg of HCl salt, 35%) as a yellow solid.

$^1$H NMR (500 MHz, DMSO-d$_6$): δ 1.22 (s, 9H), 1.77-1.81 (m, 2H), 2.03-2.07 (m, 2H), 2.14 (s, 3H), 3.00-3.04 (m, 2H), 3.18 (br s, 2H), 4.56-4.57 (m, 1H), 6.86 (d, J=8.9 Hz, 2H), 7.26-7.31 (m, 4H), 7.40 (s, 1H), 7.44 (d, J=7.5 Hz, 1H), 7.84 (s, 1H), 8.93 (br s, 1H), 8.99 (br s, 1H), 9.67 (s, 1H), 10.31 (s, 1H). MS (ES+): m/z 432 (M+H)$^+$.

Example 119 tert-Butyl 4-(4-(4-amino-5-methylpyrimidin-2-ylamino)phenoxy)piperidine-1-carboxylate (Intermediate 42)

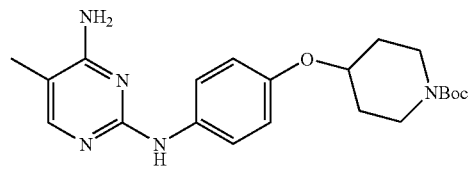

A mixture of 2-chloro-5-methylpyrimidin-4-amine (540 mg, 3.7 mmol), tert-butyl 4-(4-aminophenoxy)piperidine-1-carboxylate (1.1 g, 3.7 mmol) was suspended in acetic acid (20 mL) and heated at 70° C. for 1 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo to afford the title compound (1.4 g, 95%) as a yellow solid.

Example 120

N$^4$-(1H-Indazol-4-yl)-5-methyl-N$^2$-(4-(piperidin-4-yloxy)phenyl)pyrimidine-2,4-diamine (Compound LXXX)

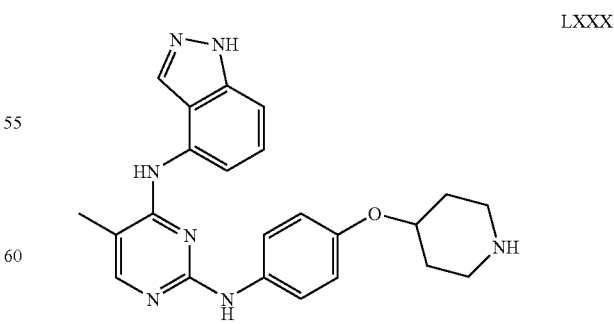

A mixture of intermediate 42 (480 mg, 1.2 mmol), 4-bromo-1H-indazole (236 mg, 1.2 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL)

and heated at reflux under the argon atmosphere for 20 h. The mixture was filtered and the filtrate concentrated in vacuo. The residue was purified by HPLC to afford the title compound (4 mg of HCl salt, 1.2%) as a yellow solid.

$^1$H NMR (500 MHz, DMSO-d$_6$): δ 1.75-1.80 (m, 2H), 2.02-2.07 (m, 2H), 2.24 (s, 3H), 3.05-3.09 (m, 2H), 3.17-3.21 (m, 2H), 4.52 (br s, 1H), 6.63 (d, J=8.6 Hz, 2H), 7.01 (d, J=8.6 Hz, 2H), 7.14 (d, J=7.3 Hz, 2H), 7.38-7.44 (m, 2H), 7.62 (d, J=8.9 Hz, 2H), 7.92 (s, 1H), 8.02 (s, 1H), 9.00 (br s, 1H), 9.04 (br s, 1H), 10.20 (s, 1H), 10.33 (s, 1H). MS (ES+): m/z 416 (M+H)$^+$.

Example 121

4-{3-[4-(4-Chloro-3-methoxy-phenylamino)-5-methyl-pyrimidin-2-ylamino]-benzyl}-piperazine-1-carboxylic acid tert-butyl ester (Intermediate 43)

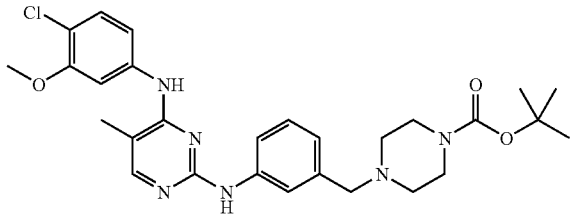

43

A mixture of intermediate 31 (0.092 g, 0.33 mmol), 4-(3-amino-benzyl)-piperazine-1-carboxylic acid tert-butyl ester (0.11 g, 0.39 mmol), Pd$_2$(dba)$_3$ (0.03 g, 0.033 mmol), Xantphos (0.038 g, 0.065 mmol) and cesium carbonate (0.32 g, 0.98 mmol) was suspended in dioxane (5 mL) and microwaved at 160° C. for 15 min. The reaction mixture was cooled to room temperature and centrifuged down. The reaction was decanted and the organic phase concentrated in vacuo. The residue was purified by HPLC to afford the title compound (0.075 g, 43%) as a brown solid.

Example 122

N$^4$-(4-Chloro-3-methoxy-phenyl)-5-methyl-N$^2$-(3-piperazin-1-ylmethyl-phenyl)-pyrimidine-2,4-diamine (Compound LXXXI)

LXXXI

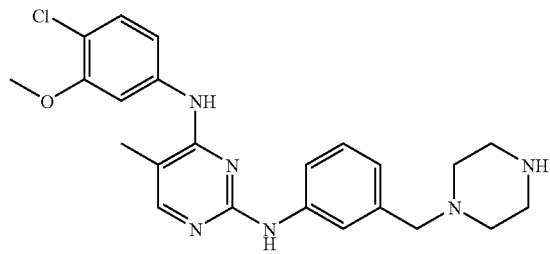

A solution of intermediate 43 (0.075 g, 0.14 mmol) in DCM (8 mL) was treated with TFA (2 mL). After 2 h of stirring, solvents were removed and resulting residue was triturated with diethyl ether resulting in white hygroscopic powder (0.05 g, 82%).

$^1$H NMR (500 MHz, DMSO-d$_6$): δ 2.17 (s, 3H), 2.89 (br s, 4H), 3.2 (br s, 4H), 3.68 (s, 4H), 3.82 (br s, 3H), 7.16-7.19 (m, 2H), 7.28 (t, J=7.9 Hz, 1H), 7.33 (d, J=2.3 Hz, 1H), 7.39 (s, 1H), 7.43 (d, J=8.5 Hz, 1H), 7.49 (d, 8.6 Hz, 1H), 7.98 (s, 1H), 8.8 (br s, 2H), 9.78 (br s, 1H), 10.57 (br s, 1H). MS (ES+): m/z 439 (M+H)$^+$.

Example 123

N$^4$-(4-Chloro-3-methoxy-phenyl)-5-methyl-N$^2$-[4-(piperidin-4-yloxy)-phenyl]-pyrimidine-2,4-diamine (Compound LXXXII)

LXXXII

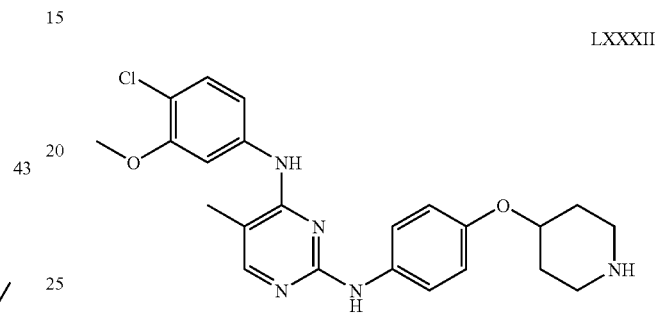

A mixture of intermediate 31 (0.66 g, 2.3 mmol) and 4-(4-amino-phenoxy)-piperidine-1-carboxylic acid tert-butyl ester (0.88 mg, 3.0 mmol) in acetic acid (15 mL) was microwaved at 160° C. for 15 min. The mixture was allowed to cool to room temperature and acetic acid removed under reduced pressure. The residue was taken in water (20 mL) and the mixture was neutralized with 10% NaOH solution until solid precipitated. Filtration followed by column chromatography yielded the title compound as beige solids (0.51 g, 50%).

$^1$H NMR (500 MHz, DMSO-d$_6$): δ 1.37-1.44 (m, 2H), 1.86-1.89 (m, 2H), 2.09 (s, 3H), 2.50-2.56 (m, 2H), 2.91-2.95 (m, 2H), 3.16 (s, 3H), 3.32 (br s, 3H), 3.72 (s, 3H), 4.09 (br s, 1H), 4.21-4.26 (m, 1H), 6.77 (d, J=9 Hz, 2H), 7.27 (d, J=8.5 Hz, 1H), 7.40-7.42 (m, 1H), 7.46-7.49 (m, 3H), 7.87 (s, 1H), 8.31 (s, 1H), 8.78 (s, 1H). MS (ES+): m/z 440 (M+H)$^+$.

Example 124

4-{3-[4-(4-Chloro-3-methoxy-phenylamino)-5-methyl-pyrimidin-2-ylamino]-phenyl}-piperazine-1-carboxylic acid tert-butyl ester (Intermediate 44)

44

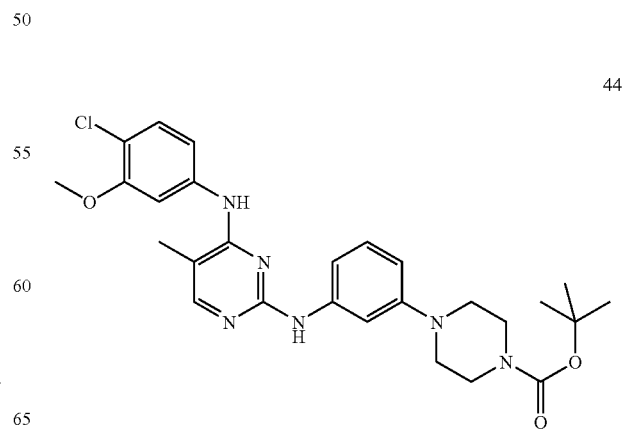

A mixture of intermediate 31 (0.13 g, 0.46 mmol) and 4-(3-amino-phenyl)-piperazine-1-carboxylic acid tert-butyl ester (0.19 mg, 0.68 mmol) in acetic acid (8 mL) was heated at 80° C. for 15 h. The mixture was allowed to cool to room temperature and acetic acid removed under reduced pressure. The residue was taken up in water (20 mL) and the mixture was neutralized with 10% NaOH solution. This was then extracted with ethyl acetate, washed with brine and evaporated to oily residue. Column chromatography yielded the title compound as white solids (0.12 g, 48%).

Example 125

$N^4$-(4-Chloro-3-methoxy-phenyl)-5-methyl-$N^2$-(3-piperazin-1-yl-phenyl)-pyrimidine-2,4-diamine (Compound LXXXIII)

LXXXIII

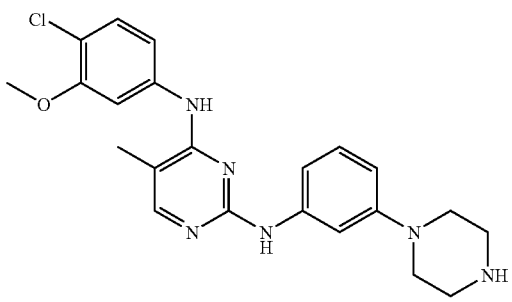

A solution of intermediate 44 (0.11 g, 0.21 mmol) in DCM (8 mL) was treated with TFA (1 mL). After 3 h of stirring, solvents were removed and resulting residue was taken up in ethyl acetate and washed with 10% sodium bicarbonate solution. Organic phase then dried over sodium sulfate, filtered and evaporated to white powder. This was diluted with DCM (5 mL) and treated with 4M HCl in dioxane (0.5 mL). Solvents were immediately removed affording HCL salt of title compound as white solids (0.06 g, 67%).

$^1$H NMR (500 MHz, DMSO-$d_6$): δ 2.18 (s, 3H), 3.12 (br s, 4H), 3.22 (br s, 4H), 3.65 (s, 3H), 6.80 (d, J=8.1 Hz, 1H), 6.95 (s, 2H), 7.14 (t, J=8.2 Hz, 1H), 7.23 (d, J=7.0 Hz, 1H), 7.37-7.40 (m, 2H), 7.95 (s, 1H), 9.33 (br s, 2H), 9.88 (s, 1H), 10.62 (s, 1H). MS (ES+): m/z 425 (M+H)$^+$.

Example 126

2-[4-(3-Bromo-phenyl)-piperidin-1-yl]-ethanol (Intermediate 45)

45

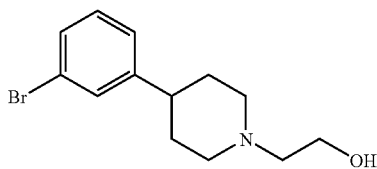

4-(3-Bromo-phenyl)-piperidine (1.2 g, 4.8 mmol) and 2-bromoethanol (0.72 mL, 10 mmol) were diluted with DMF (20 mL) and treated with potassium carbonate (2.7 g, 20 mmol). These were stirred at ambient temperature for 18 then poured onto water and extracted with ethyl acetate. Organic phase then washed with brine, dried over sodium sulfate, filtered and evaporated to clear oil (0.6 g, 44%).

Example 127

2-[4-(3-{5-Methyl-2-[4-(4-methyl-piperazin-1-yl)-phenylamino]-pyrimidin-4-ylamino}-phenyl)-piperidin-1-yl]-ethanol (Compound LXXXIV)

LXXXIV

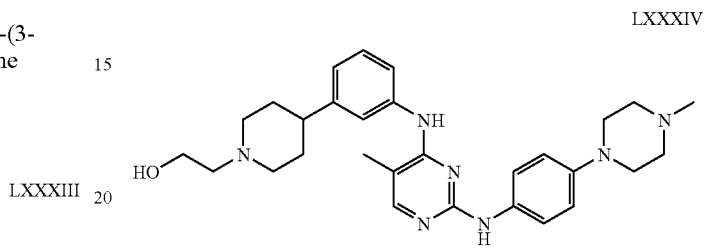

A mixture of intermediate 32 (0.11 g, 0.38 mmol), intermediate 45 (0.21 g, 0.75 mmol), $Pd_2(dba)_3$ (0.034 g, 0.037 mmol), Xantphos (0.043 g, 0.075 mmol) and cesium carbonate (0.37 g, 1.1 mmol) was suspended in dioxane (10 mL) and microwaved at 160° C. for 15 min. The reaction mixture was cooled to room temperature and centrifuged down. The reaction was decanted and the organic phase concentrated in vacuo. The residue was purified by HPLC to afford the title compound (0.075 g, 43%) as a purple solid (0.02 g, 11%).

$^1$H NMR (500 MHz, DMSO-$d_6$): δ 1.60-1.67 (m, 2H), 1.73 (d, J=11.3 Hz, 2H), 2.02-2.07 (m, 2H), 2.08 (s, 3H), 2.21 (s, 3H), 2.39-2.45 (m, 7H), 2.95 (d, J=11.4 Hz, 2H), 3.00 (t, J=4.66 Hz, 4H), 3.50 (t, J=6.44 Hz, 2H), 6.76 (d, J=9 Hz, 2H), 6.92 (d, J=8.5 Hz, 1H), 7.22 (t, J=7.8 Hz, 1H), 7.45-7.49 (m, 3H), 7.66 (d, J=7.7 Hz, 1H), 7.82 (s, 1H), 8.09 (s, 1H), 8.67 (s, 1H). MS (ES+): m/z 502 (M+H)$^+$.

Example 128

4-(3-Bromo-benzenesulfonylamino)-piperidine-1-carboxylic acid tert-butyl ester (Intermediate 46)

46

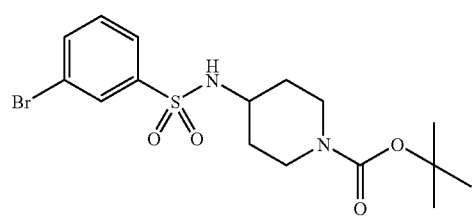

3-Bromo-benzenesulfonyl chloride (2.2 g, 8.7 mmol) and 4-amino-piperidine-1-carboxylic acid tert-butyl ester (2 g, 10 mmol) were combined and diluted with DCM (50 mL) and TEA (3.6 mL, 26 mmol). After 16 h, reaction was poured into separatory funnel and washed with water. Organic phase was then washed with brine, dried over sodium sulfate, filtered and evaporated to clear oil which solidified upon standing (3.6 g, 98%).

Example 129

4-(3-{5-Methyl-2-[4-(4-methyl-piperazin-1-yl)-phenylamino]-pyrimidin-4-ylamino}-benzenesulfonylamino)-piperidine-1-carboxylic acid tert-butyl ester (Intermediate 47)

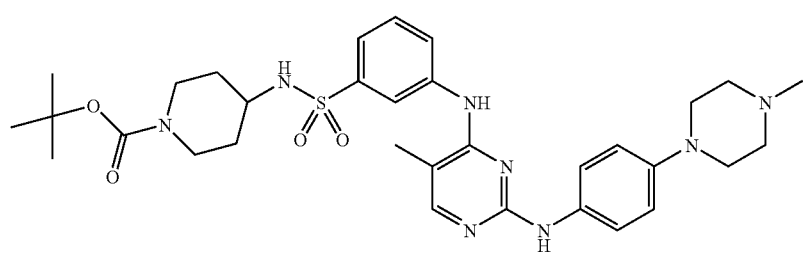

47

A mixture of intermediate 32 (0.15 g, 0.518 mmol), intermediate 46 (0.28 g, 0.67 mmol), Pd$_2$(dba)$_3$ (0.024 g, 0.026 mmol), Xantphos (0.03 g, 0.052 mmol) and cesium carbonate (0.34 g, 1 mmol) was suspended in dioxane (10 mL) and microwaved at 160° C. for 15 min. The reaction mixture was cooled to room temperature and centrifuged down. The reaction was decanted onto ice. Resulting precipitate dried and carried on directly for deprotection step (0.2 g).

Example 130

3-{5-Methyl-2-[4-(4-methyl-piperazin-1-yl)-phenylamino]-pyrimidin-4-ylamino}-N-piperidin-4-yl-benzenesulfonamide (Compound LXXXV)

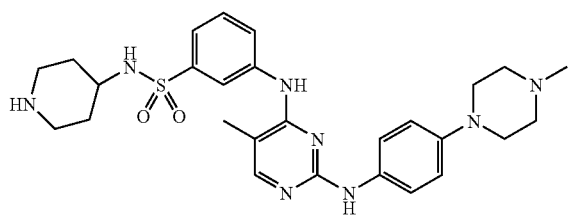

LXXXV

Intermediate 47 (0.2 g, 0.32 mmol) was diluted with DCM (10 mL) and treated with TFA (0.3 mL). After 3 h, reaction solvents removed and resulting residue was purified by HPLC (0.01 g, 6%).

$^1$H NMR (500 MHz, DMSO-d$_6$): δ 1.30-1.35 (m, 2H), 1.56-1.58 (m, 2H), 1.98 (s, 2H), 2.11 (s, 3H), 2.21 (s, 3H), 2.43-2.45 (m, 4H), 2.84-2.87 (m, 2H), 3.02 (t, J=4.6 Hz, 2H), 6.80 (d, J=9 Hz, 2H), 7.45-7.51 (m, 4H), 7.78 (br s, 1H), 7.88 (s, 1H), 8.05 (s, 1H), 8.20 (d, J=7.6 Hz, 1H), 8.53 (s, 1H), 8.71 (s, 1H). MS (ES+): m/z 537 (M+H)$^+$.

Example 131

N$^4$-(4-(Trifluoromethyl)-3-methylphenyl)-5-methyl-N$^2$-(4-(4-methylpiperazin-1-yl)phenyl)pyrimidine-2,4-diamine hydrochloride (Compound LXXXVI)

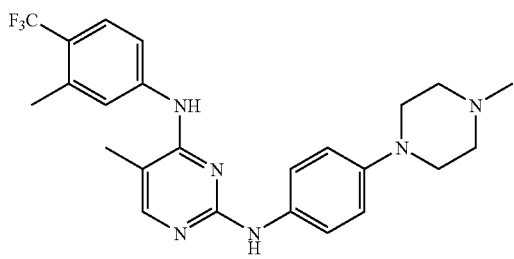

LXXXVI

A suspension of intermediate 32 (0.12 g, 0.40 mmol), 1-bromo-3-(trifluoromethyl)-2-methylbenzene (0.14 g, 0.59 mmol), Pd$_2$(dba)$_3$ (37 mg, 0.04 mmol), Xantphos (47 mg, 0.08 mmol) and cesium carbonate (0.39 g, 1.20 mmol) in dioxane (20 mL) was degassed with argon for 2 min then refluxed in a sealed tube for overnight. After cooling to room temperature, the solvent was removed by rotovap and the resulting mixture was purified by silica gel with 10% CH$_3$OH/CHCl$_3$ as an eluent to afford the title compound as a white solid. The white was dissolved in CHCl$_3$ (30 mL) and titrated with 2 M HCl in dioxane to pH 1. The solvent was removed by rotovap and the solid was recrystalized from acetone (25 mg, 13%).

$^1$H NMR (500 MHz, DMSO-d$_6$): δ 2.20 (s, 3H), 2.26 (s, 3H), 2.77 (d, J=4.5 Hz, 3H), 3.00-3.20 (m, 4H), 3.45 (d, J=11.6 Hz, 2H), 3.63 (d, J=12.2 Hz, 2H), 6.71 (d, J=8.1 Hz, 2H), 7.05 (d, J=9.0 Hz, 2H), 7.55 (t, J=7.9 Hz, 1H), 7.63 (d, J=7.8 Hz, 1H), 7.77 (d, J=7.77 Hz, 1H), 7.94 (s, 1H), 10.13 (s, 1H), 10.60 (s, 1H), 11.28 (s, 1H). MS (ES+): m/z 457 (M+H)$^+$.

Example 132

5-Methyl-$N^2$-(4-(4-methylpiperazin-1-yl)phenyl)-$N^4$-(3-(methylsulfonyl)phenyl)-pyrimidine-2,4-diamine (Compound LXXXVII)

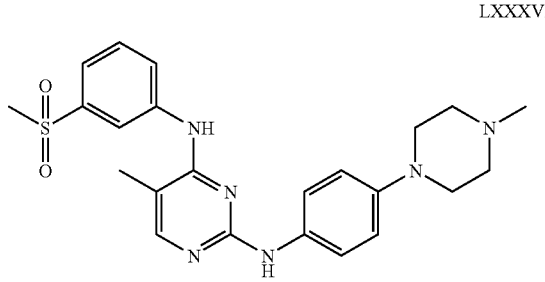

LXXXVII

A suspension of intermediate 32 (0.13 g, 0.44 mmol), 1-bromo-3-(methylsulfonyl)benzene (0.24 g, 1.0 mmol), Pd$_2$(dba)$_3$ (40 mg, 0.04 mmol), Xantphos (50 mg, 0.08 mmol) and cesium carbonate (0.43 g, 1.32 mmol) in dioxane (50 mL) was degassed with argon for 2 min then refluxed for overnight. After cooling to room temperature, the solvent was removed by rotovap and the resulting mixture was purified by silica gel with 30% CH$_3$OH/CHCl$_3$ as an eluent to afford the title compound as pale yellow solid (35 mg, 15%).

$^1$H NMR (500 MHz, DMSO-d$_6$): δ 2.11 (s, 3H), 2.23 (s, 3H), 2.46 (br s, 4H), 3.03 (t, J=4.4 Hz, 4H), 3.19 (s, 3H), 6.81 (d, J=9.0 Hz, 2H), 7.45 (d, J=8.9 Hz, 2H), 7.5-7.6 (m, 2H), 7.91 (s, 1H), 8.05 (s, 1H), 8.36 (d, J=6.7 Hz, 1H), 8.60 (s, 1H), 8.77 (s, 1H). MS (ES+): m/z 453 (M+H)$^+$.

Example 133

1-Bromo-3-(propylsulfonyl)benzene (Intermediate 48)

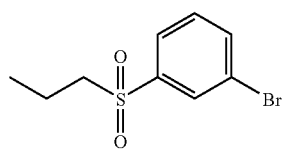

48

To a solution of 3-bromobenzenethiol (0.50 g, 2.6 mmol) in dioxane (50 mL) was added 1-iodopropane (1.1 g, 6.5 mmol) and cesium carbonate (2.2 g, 6.8 mmol) was stirred at reflux until all 3-bromobenzenethiol reacted. The reaction was quenched with saturated NaHCO$_3$ solution (25 mL) and the mixture extracted with CHCl$_3$ (60 mL). The product in the CHCl$_3$ was refluxed with mCPBA (2.9 g, 13 mmol) until all starting reacted. The organic layer was washed with 2M NaOH to remove the excess of mCPBA, dried over Na$_2$SO$_4$ and filtered. The filtrate was concentrated and the crude product was purified with silica gel column with 1:1 hexanes/CHCl$_3$ as an eluent to yield colorless oil (0.30 g, 43% in 2-steps).

$^1$H NMR (500 MHz, DMSO-d$_6$): 0.92 (t, J=7.4 Hz, 3H), 1.52-1.60 (m, 2H), 3.35-3.38 (m, 2H), 7.63 (t, J=8.0 Hz, 1H), 7.88-7.91 (m, 1H), 7.95-7.98 (m, 1H), 8.04 (t, J=1.8 Hz, 1H).

Example 134

5-Methyl-$N^2$-(4-(4-methylpiperazin-1-yl)phenyl)-$N^4$-(3-(propylsulfonyl)phenyl)-pyrimidine-2,4-diamine hydrochloride (Compound LXXXVIII)

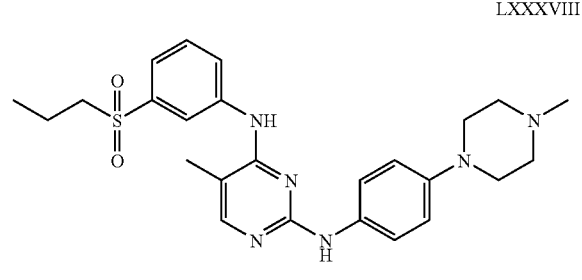

LXXXVIII

A suspension of intermediate 32 (0.25 g, 0.84 mmol), intermediate 48 (0.26 g, 1 mmol), Pd$_2$(dba)$_3$ (8 mg, 0.01 mmol), Xantphos (16 mg, 0.03 mmol) and cesium carbonate (0.82 g, 2.52 mmol) in dioxane (50 mL) was degassed with argon for 2 min then refluxed for overnight. After cooling to room temperature, the solvent was removed by rotovap and the resulting mixture was purified by silica gel with 10% CH$_3$OH/CHCl$_3$ as an eluent to afford the title compound as a white solid. The white was dissolved in CHCl$_3$ (30 mL) and titrated with 2 M HCl in dioxane to pH 1. The solvent was removed by rotovap and the solid was recrystalized from methanol (65 mg, 15%).

$^1$H NMR (500 MHz, DMSO-d$_6$): 0.90 (t, J=7.4 Hz, 3H), 1.50-1.60 (m, 2H), 2.18 (s, 3H), 2.81 (s, 3H), 3.00-3.13 (m, 4H), 3.27 (t, J=7.7 Hz, 2H), 3.48 (d, J=10.9 Hz, 2H), 3.75 (d, J=11.4 Hz, 2H), 6.95 (d, J=8.8 Hz, 2H), 7.27 (d, J=8.9 Hz, 2H), 7.64 (t, J=8.0 Hz, 1H), 7.73 (d, J=7.8 Hz, 1H), 7.93 (s, 1H), 8.00 (s, 1H), 8.07 (s, 1H), 9.92 (s, 1H), 10.36 (s, 1H), 10.99 (s, 1H). MS (ES+): m/z 481 (M+H)$^+$.

Example 135

3-(Morpholinomethyl)benzenamine (Intermediate 49)

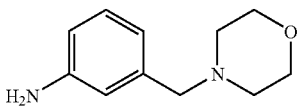

49

Zinc chloride (0.1 g, 0.73 mmol) was added to the solution of 3-nitrobenzaldehyde (5.9 g, 39.02 mmol), morpholine (3.4 g, 39.02 mmol), sodium cyanoborohydride (2.7 g, 43 mmol) in methanol (50 mL) at room temperature. The solution was heated to reflux for 1 hour. After cooling down, the reaction was quenched by water (2 mL) and the methanol was removed by rotovap. The crude product was dissolved in 2M NaOH (50 mL) and extracted by CHCl$_3$, dried over Na$_2$SO$_4$ and filtered. The filtrate was concentrated under vacuum.

The above crude product in methanol (200 mL) was reduced by Raney Ni and hydrazine at room temperature. The reaction was monitored by TLC in ethyl acetate. After all starting material reacted, the methanol was removed by rotovap. The crude was purified by silica gel with ethyl acetate as an eluent to yield a white solid (1.5 g, 50% in 2-steps).

$^1$H NMR (500 MHz, DMSO-d$_6$): 2.31 (s, 4H), 3.28 (s, 2H), 3.56 (t, J=4.6 Hz, 4H), 4.97 (s, 2H), 6.40-6.45 (m, 2H), 6.53 (t, J=1.8 Hz, 1H), 6.93 (t, J=7.7 Hz, 1H).

Example 136

5-Methyl-N$^2$-(3-(morpholinomethyl)phenyl)pyrimidine-2,4-diamine (Intermediate 50)

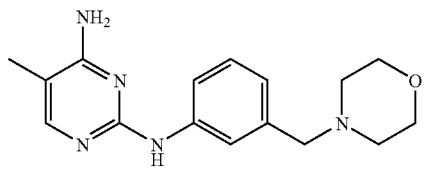

50

A mixture of 2-chloro-5-methylpyrimidin-4-amine (0.17 g, 1.17 mmol) and intermediate 49 (0.25 g, 1.30 mmol) was suspended in acetic acid (10 mL) and heated at 100° C. for 2 h. The mixture was allowed to cool to room temperature and acetic acid removed under reduced pressure. The residue was taken in water (20 mL) and neutralized to pH~8. The resulting solution was extracted with CHCl$_3$ (100 mL) and the organic layer separated. The organic layer was washed with brine, dried over Na$_2$SO$_4$ and filtered. The filtrate was concentrated in vacuo and the crude product purified by silica gel column with 10% CH$_3$OH/EtOAc as an eluent to afford the title compound as oil (0.15 g, 43%).

$^1$H NMR (500 MHz, DMSO-d$_6$): 1.91 (s, 3H), 2.35 (s, 4H), 3.17 (s, 2H), 3.57 (t, J=4.4 Hz, 4H), 6.37 (s, 2H), 6.78 (d, J=7.5 Hz, 1H), 7.13 (t, J=7.8 Hz, 1H), 7.59 (s, 1H), 7.69 (s, 1H), 7.74 (d, J=9.3 Hz, 1H), 8.68 (s, 1H).

Example 137

N-tert-Butyl-3-[5-methyl-2-(3-morpholin-4-ylmethyl-phenylamino)-pyrimidin-4-ylamino]-benzenesulfonamide hydrochloride (Compound LXXXIX)

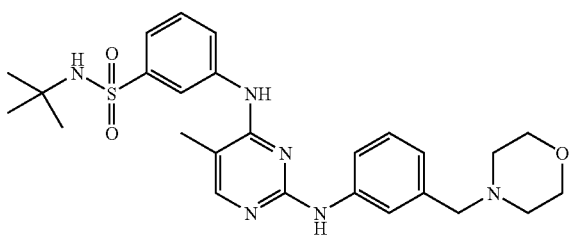

LXXXIX

A suspension of intermediate 50 (1.0 g, 3.42 mmol), 3-bromo-N-tert-butyl-benzenesulfonamide (1.28 g, 4.28 mmol), Pd$_2$(dba)$_3$ (30 mg, 0.03 mmol), Xantphos (40 mg, 0.07 mmol) and cesium carbonate (3.34 g, 10.24 mmol) in dioxane (50 mL) was degassed with argon for 2 min then refluxed for overnight. After cooling to room temperature, the solvent was removed by rotovap and the resulting mixture was purified by silica gel with 10% CH$_3$OH/CHCl$_3$ as an eluent to afford the title compound as a white solid. The white was dissolved in hot dioxane (150 mL) and titrated with 2 M HCl in dioxane to pH 1. The solvent was removed by rotovap and the solid was recrystalized from methanol (0.15 g, 8%).

$^1$H NMR (500 MHz, DMSO-d$_6$): 1.08 (s, 9H), 2.20 (s, 3H), 3.0-3.2 (m, 4H), 3.7-4.0 (m, 4H), 4.23 (s, 2H), 7.33 (t, J=7.9 Hz, 1H), 7.38 (d, J=7.7 Hz, 1H), 7.48 (s, 1H), 7.55-7.65 (m, 3H), 7.71 (d, J=7.9 Hz, 1H), 7.90 (d, J=7.4 Hz, 1H), 8.01 (s, 1H), 9.96 (br s, 1H), 10.61 (br s, 1H), 11.31 (br s, 1H). MS (ES+): m/z 511 (M+H)$^+$.

Example 138

2-Chloro-5-methyl-N-(3,5-dimethylphenyl)pyrimidin-4-amine (Intermediate 51)

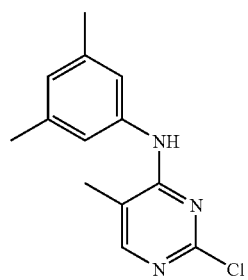

51

A mixture of 1-bromo-3,5-dimethylbenzene (104 μL, 0.77 mmol), 2-chloro-5-methyl-pyrimidin-4-ylamine (104 mg, 0.72 mmol), Pd(OAC)$_2$ (15 mg, 0.07 mmol), Xantphos (83 mg, 0.14 mmol) and potassium tert-butoxide (159 mg, 1.42 mmol) in dioxane (8 mL) was microwaved at 160° C. for 20 min. The reaction mixture was cooled to room temperature and filtered rinsing with DCM and methanol. The filtrate was concentrated and purified using gradient flash chromatography (0-100% ethyl acetate in hexanes) to afford the title compound as a yellow oil (89 mg, 50%). MS (ES+): m/z 248 (M+H)$^+$.

Example 139

5-Methyl-N$^4$-(3,5-dimethylphenyl)-N$^2$-(4-(piperidin-4-yloxy)phenyl)pyrimidine-2,4-diamine (Compound XC)

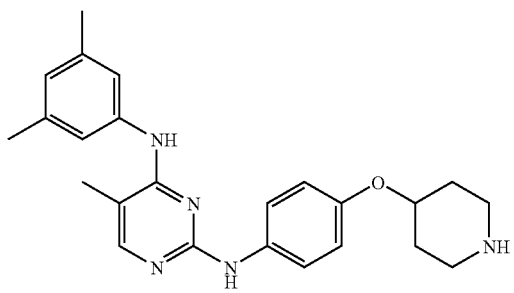

XC

A mixture of intermediate 51 (89 mg, 0.36 mmol), and 4-(4-amino-phenoxy)-piperidine-1-carboxylic acid tert-butyl ester (139 mg, 0.47 mmol) in acetic acid was stirred at room temperature for 16 h, then heated to 95° C. for 2 h. The reaction mixture was concentrated in vacuo, and purified by preparative HPLC. The product was basified with NaHCO$_3$ (aq)(10 mL) and extracted with ethyl acetate (3×30 mL). The combined organic layers were washed with brine (5 mL), dried (Na$_2$SO$_4$), and concentrated. The freebase was taken up in MeOH (5 mL) and conc HCl (5 drops) and after 2 min was concentrated in vacuo in the presence of DCM and hexanes to afford the HCl salt of the title compound as an off-white solid (63 mg, 40%).

¹H NMR (500 MHz, DMSO-d₆): δ 1.72-1.83 (m, 2H), 2.02-2.08 (m, 2H), 2.14 (d, J=0.6 Hz, 3H), 2.24 (s, 6H), 3.04-3.15 (m, 2H), 3.21-3.31 (m, 2H), 4.57-4.60 (m, 1H), 6.85 (s, 1H), 6.91 (d, J=8.9 Hz, 2H), 7.20 (s, 2H), 7.37 (d, J=8.9 Hz, 2H), 7.85 (s, 1H), 8.50 (br s, 1H), 8.56 (br s, 1H), 9.36 (br s, 1H), 10.10 (br s, 1H). MS (ES+): m/z 404 (M+H)⁺.

Example 140

2-Chloro-N-(3,5-dimethoxyphenyl)-5-methylpyrimidin-4-amine (Intermediate 52)

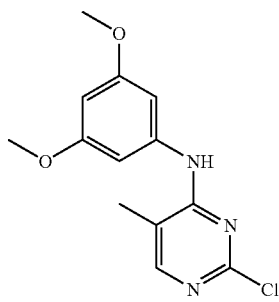

52

A mixture of 1-bromo-3,5-dimethoxybenzene (436 mg, 2.01 mmol), 2-chloro-5-methyl-pyrimidin-4-ylamine (287 mg, 2.00 mmol), Pd(OAc)₂ (44 mg, 0.20 mmol), Xantphos (237 mg, 0.41 mmol) and potassium tert-butoxide (448 mg, 3.99 mmol) in dioxane (15 mL) and DMF (5 mL) was microwaved at 160° C. for 20 min. The reaction mixture was cooled to room temperature and filtered rinsing with DCM and methanol. The filtrate was concentrated and purified using gradient flash chromatography (0-100% ethyl acetate in hexanes) to afford the title compound as a yellow solid (182 mg, 33%).

¹H NMR (500 MHz, DMSO-d₆): δ 2.17 (s, 3H), 3.74 (s, 6H), 6.27 (t, J=2.2 Hz, 1H), 6.99 (d, J=2.2 Hz, 2H), 8.06 (s, 1H), 8.71 (s, 1H). MS (ES+): m/z 280 (M+H)⁺.

Example 141

N⁴-(3,5-Dimethoxyphenyl)-5-methyl-N²-(4-(piperidin-4-yloxy)phenyl)pyrimidine-2,4-diamine (Compound XCI)

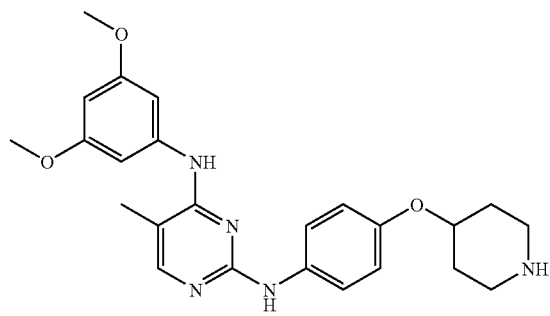

XCI

A mixture of intermediate 52 (100 mg, 0.36 mmol), and 4-(4-amino-phenoxy)-piperidine-1-carboxylic acid tert-butyl ester (106 mg, 0.36 mmol) in acetic acid was heated to 95° C. for 2 h. The reaction mixture was concentrated in vacuo, and purified by preparative HPLC to afford the TFA salt of the title compound as a tan solid (75 mg, 39%).

¹H NMR (500 MHz, DMSO-d₆): δ 1.74-1.83 (m, 2H), 2.03-2.11 (m, 2H), 2.15 (s, 3H), 3.06-3.15 (m, 2H), 3.21-3.30 (m, 2H), 3.69 (s, 6H), 4.57-4.60 (m, 1H), 6.39 (t, J=2.2 Hz, 1H), 6.80 (d, J=2.2 Hz, 2H), 6.89 (d, J=8.9 Hz, 2H), 7.37 (d, J=9.0 Hz, 2H), 7.86 (s, 1H), 8.53 (br s, 1H), 8.58 (br s, 1H), 9.49 (br s, 1H), 10.24 (br s, 1H). MS (ES+): m/z 436 (M+H)⁺.

Example 142

5-Methyl-N²-(4-(4-methylpiperazin-1-yl)phenyl)-N⁴-(3-(piperidin-1-yl)phenyl)pyrimidine-2,4-diamine (Compound XCII)

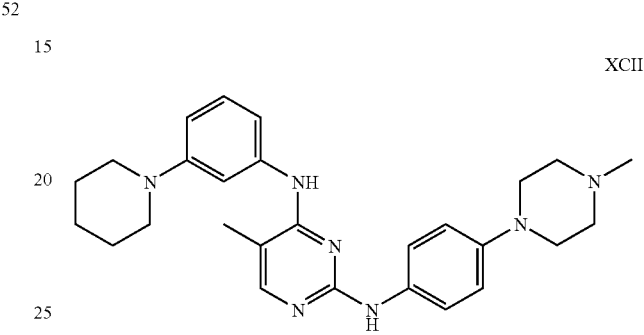

XCII

A mixture of 1-(3-bromophenyl)piperidine (91 mg, 0.38 mmol), intermediate 32 (99 mg, 0.33 mmol), Pd₂(dba)₃ (15 mg, 0.02 mmol), Xantphos (24 mg, 0.04 mmol) and cesium carbonate (219 mg, 0.67 mmol) in dioxane (4 mL) was microwaved at 160° C. for 15 min. The reaction mixture was cooled to room temperature, concentrated in vacuo, taken up in methanol, and filtered rinsing with DCM and methanol. The filtrate was concentrated and purified by preparative HPLC to afford the TFA salt of the title compound as an off-white solid (14 mg, 8%).

¹H NMR (500 MHz, DMSO-d₆): δ 1.47-1.53 (m, 2H), 1.56-1.61 (m, 4H), 2.07 (s, 3H), 2.21 (s, 3H), 2.44 (t, J=4.9 Hz, 4H), 3.01 (t, J=4.9 Hz, 4H), 3.08 (t, J=5.4 Hz, 4H), 6.63 (dd, J=8.2, 2.3 Hz, 1H), 6.76 (d, J=9.0 Hz, 2H), 7.12 (t, J=8.3 Hz, 1H), 7.14 (s, 1H), 7.27 (d, J=7.6 Hz, 1H), 7.50 (d, J=9.0 Hz, 2H), 7.81 (s, 1H), 8.00 (s, 1H), 8.67 (s, 1H). MS (ES+): m/z 458 (M+H)⁺.

Example 143

N⁴-(3-(1H-Pyrrol-1-yl)phenyl)-5-methyl-N²-(4-(4-methylpiperazin-1-yl)phenyl)pyrimidine-2,4-diamine (Compound XCIII)

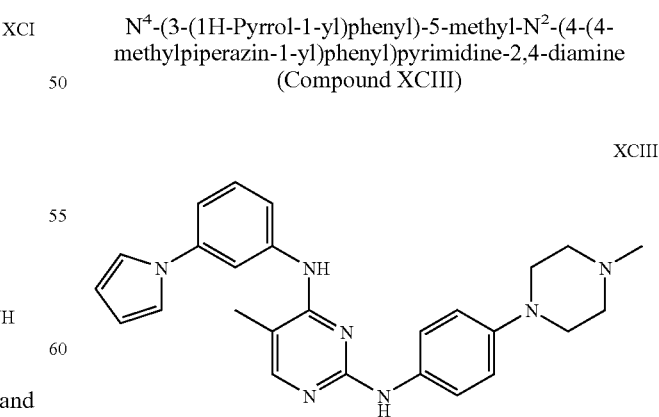

XCIII

A mixture of 1-(3-bromophenyl)-1H-pyrrole (86 mg, 0.39 mmol), intermediate 32 (99 mg, 0.33 mmol), Pd₂(dba)₃ (16 mg, 0.02 mmol), Xantphos (26 mg, 0.05 mmol) and cesium carbonate (215 mg, 0.66 mmol) in dioxane (4 mL) was microwaved at 160° C. for 15 min. The reaction mixture was cooled to room temperature, concentrated in vacuo, taken up in methanol, and filtered rinsing with DCM and methanol. The filtrate was concentrated and purified by preparative HPLC to afford the TFA salt of the title compound as an off-white solid (32 mg, 18%).

$^1$H NMR (500 MHz, DMSO-$d_6$): δ 2.11 (s, 3H), 2.21 (s, 3H), 2.42 (t, J=4.9 Hz, 4H), 2.95 (t, J=4.9 Hz, 4H), 6.24 (t, J=2.2 Hz, 2H), 6.58 (d, J=8.9 Hz, 2H), 7.23 (dd, J=7.8, 1.8 Hz, 1H), 7.31 (t, J=2.2 Hz, 2H), 7.37 (t, J=8.1 Hz, 1H), 7.43 (d, J=9.0 Hz, 2H), 7.60 (d, J=8.8 Hz, 1H), 7.86 (t, J=2.2 Hz, 1H), 7.87 (s, 1H), 8.30 (s, 1H), 8.74 (s, 1H). MS (ES+): m/z 440 (M+H)$^+$.

Example 144

5-{2-[4-(1-tert-Butoxycarbonyl-piperidin-4-yloxy)-phenylamino]-5-methyl-pyrimidin-4-ylamino}-indole-1-carboxylic acid tert-butyl ester
(Intermediate 53)

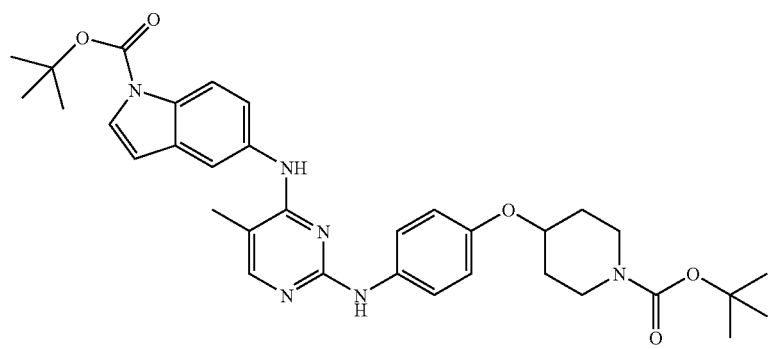

53

A mixture of tert-butyl 5-bromo-1H-indole-1-carboxylate (161 mg, 0.54 mmol), intermediate 42 (202 mg, 0.50 mmol), Pd$_2$(dba)$_3$ (29 mg, 0.03 mmol), Xantphos (36 mg, 0.07 mmol) and cesium carbonate (321 mg, 0.98 mmol) in dioxane (5 mL) was microwaved at 160° C. for 20 min. The reaction mixture was cooled to room temperature and filtered rinsing with DCM. The filtrate was concentrated and purified by gradient flash chromatography (0-20% MeOH in DCM) to afford the title compound as a light-brown solid (290 mg, 94%). MS (ES+): m/z 615 (M+H)$^+$.

Example 145

N$^4$-(1H-Indol-5-yl)-5-methyl-N$^2$-(4-(piperidin-4-yloxy)phenyl)pyrimidine-2,4-diamine
(Compound XCIV)

XCIV

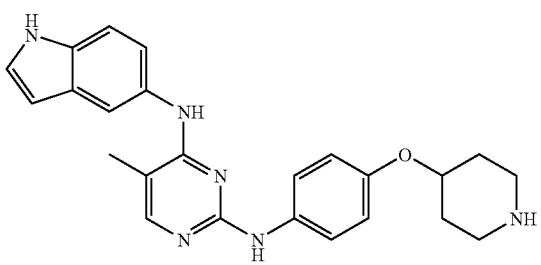

To a solution of acetyl chloride (670 μL, 9.42 mmol) in methanol (22 mL) was added intermediate 53 (290 mg, 0.47 mmol), and the reaction mixture was heated to 60° C. for 4 h. The mixture was concentrated in vacuo and purified by preparative HPLC to afford the TFA salt of the title compound as a brown solid (6 mg, 2%).

$^1$H NMR (500 MHz, DMSO-$d_6$): δ 1.70-1.78 (m, 2H), 1.98-2.07 (m, 2H), 2.16 (s, 3H), 3.02-3.11 (m, 2H), 3.21-3.30 (m, 2H), 4.44-4.53 (m, 1H), 6.43 (s, 1H), 6.75 (d, J=8.2 Hz, 2H), 7.16 (d, J=8.4 Hz, 1H), 7.31 (d, J=8.7 Hz, 2H), 7.40-7.42 (m, 2H), 7.71 (s, 1H), 7.78 (s, 1H), 8.48 (br s, 1H), 8.54 (br s, 1H), 9.65 (br s, 1H), 9.99 (br s, 1H), 11.18 (s, 1H). MS (ES+): m/z 415 (M+H)$^+$.

Example 146

N4-(4-Chloro-3-methoxy-phenyl)-5-methyl-N2-(6-piperazin-1-yl-pyridin-3-yl)-pyrimidine-2,4-diamine
(Compound XCV)

XCV

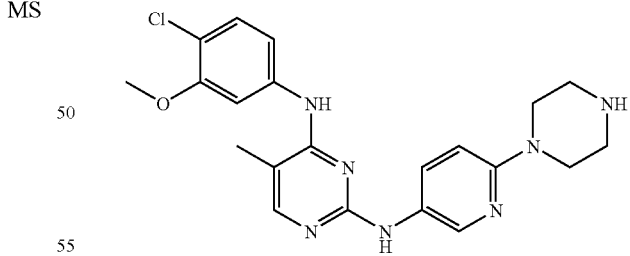

A mixture of intermediate 31 (0.10 g, 0.35 mmol), 4-(5-amino-pyridin-2-yl)-piperazine-1-carboxylic acid tert-butyl ester (0.10 g, 0.36 mmol), Pd$_2$(dba)$_3$ (30 mg, 0.033 mmol), Xantphos (35 mg, 0.06 mmol) and cesium carbonate (0.23 g, 0.71 mmol) in dioxane/DMF (3/1, 4 mL) was sealed in a microwave reaction tube and irradiated with microwave at 170° C. for 30 min. After cooling to room temperature, the cap was removed and the resulting mixture filtered. The filtered solid was washed with DCM and the filtrate concentrated. The residue was purified by flash chromatography on silica gel (hexanes to EtOAc) to afford the Boc-protected precursor. To a solution of the precursor in DCM (5 mL) was added TFA (3 mL). The mixture was stirred at room temperature for 30 min, concentrated and the residue purified by HPLC. The corrected fractions were combined and poured into saturated NaHCO₃ solution (30 mL). The combined aqueous layers were extracted with EtOAc (2×30 mL) and the combined organic layers washed with brine, dried over anhydrous Na₂SO₄ and filtered. The filtrate was concentrated and the resulting solid triturated in a mixture of hexanes/EtOAc (10/1, 55 mL). After filtration, the title compound was obtained as a white solid (20 mg, 13%).

¹H NMR (500 MHz, DMSO-d₆): δ 2.09 (s, 3H), 2.81 (t, J=5.0 Hz, 4H), 3.29-3.31 (m, 4H), 3.73 (s, 3H), 6.70 (d, J=9.1 Hz, 1H), 7.26 (d, J=8.6 Hz, 1H), 7.42 (d, J=9.1 Hz, 1H), 7.49 (d, J=2.2 Hz, 1H), 7.76 (dd, J=9.1, 2.6 Hz, 1H), 7.86 (s, 1H), 8.29 (s, 1H), 8.31 (d, J=2.6 Hz, 1H), 8.71 (s, 1H). MS (ES+): m/z 426 (M+H)⁺.

Example 147

4-(4-Amino-2-methoxycarbonyl-phenyl)-piperazine-1-carboxylic acid tert-butyl ester (Intermediate 54)

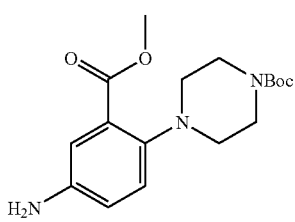

54

To a solution of 4-(2-methoxycarbonyl-4-nitro-phenyl)-piperazine-1-carboxylic acid tert-butyl ester (1.0 g, 2.7 mmol) in MeOH (30 mL) was added 10 wt % Pd/C (0.1 equiv by wt) under argon atmosphere. The mixture was evacuated and then refilled with hydrogen (3 cycles) and stirred at room temperature for 2 h. The heterogeneous reaction mixture was filtered through a pad of Celite, washed with MeOH and concentrated in vacuo. The crude amino-compound was used in the next step without purification. MS (ES+): m/z 336 (M+H)⁺.

Example 148

5-[4-(4-Chloro-3-methoxy-phenylamino)-5-methyl-pyrimidin-2-ylamino]-2-piperazin-1-yl-benzoic acid methyl ester (Compound XCVI)

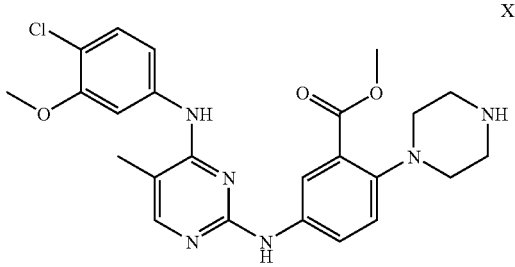

XCVI

A mixture of intermediate 31 (0.10 g, 0.35 mmol), intermediate 54 (0.14 g, 0.42 mmol), Pd₂(dba)₃ (30 mg, 0.033 mmol), Xantphos (35 mg, 0.06 mmol) and cesium carbonate (0.23 g, 0.71 mmol) was suspended in dioxane (15 mL) and heated at reflux under the argon atmosphere for 2.5 h. The reaction mixture was cooled to room temperature and diluted with DCM (30 mL). The mixture was filtered and the filtrate concentrated. The residue was purified by flash chromatography on silica gel (hexanes to 60% EtOAc/hexanes) to afford the Boc-protected precursor. To a solution of the precursor in DCM (5 mL) was added TFA (2 mL). The mixture was stirred at room temperature for 1 h, concentrated and the residue purified by HPLC. The corrected fractions were combined and poured into saturated NaHCO₃ solution (30 mL). The combined aqueous layers were extracted with EtOAc (2×30 mL) and the combined organic layers washed with brine, dried over anhydrous Na₂SO₄ and filtered. The filtrate was concentrated and then taken up in minimum amount of EtOAc. Hexanes were added until solid precipitated. After filtration, the title compound was obtained as a white solid (40 mg, 24%).

¹H NMR (500 MHz, DMSO-d₆): δ 2.11 (s, 3H), 2.80-2.90 (m, 8H), 3.73 (s, 3H), 3.74 (s, 3H), 6.98 (d, J=8.9 Hz, 1H), 7.25 (d, J=8.5 Hz, 1H), 7.40-7.48 (m, 2H), 7.69 (dd, J=8.9, 2.6 Hz, 1H), 7.90 (d, J=2.6 Hz, 1H), 7.91 (s, 1H), 8.36 (s, 1H), 9.04 (s, 1H). MS (ES+): m/z 483 (M+H)⁺.

Example 149

5-Amino-2-(2-pyrrolidin-1-yl-ethoxy)-benzoic acid methyl ester (Intermediate 55)

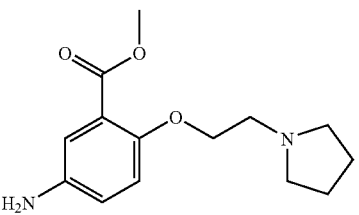

55

A suspension of 5-amino-2-hydroxy-benzoic acid methyl ester (1.0 g, 6.0 mmol), 1-(2-chloro-ethyl)-pyrrolidine hydrochloride (1.2 g, 7.1 mmol) and cesium carbonate (5.0 g, 15 mmol) in DMF (40 mL) was heated at 60° C. for 17 h. The mixture was allowed to cool to room temperature, poured into water (60 mL) and extracted with EtOAc (2×50 mL). The combined extracts were washed with brine, dried over anhydrous Na₂SO₄ and filtered. The filtrate was concentrated and the residue purified by flash chromatography on silica gel (DCM to 30% MeOH/DCM) to afford the title compound (0.2 g, 13%) as a light brown solid. MS (ES+): m/z 265 (M+H)⁺.

Example 150

5-[4-(Benzo[1,3]dioxol-4-ylamino)-5-methyl-pyrimidin-2-ylamino]-2-(2-pyrrolidin-1-yl-ethoxy)-benzoic acid methyl ester (Compound XCVII)

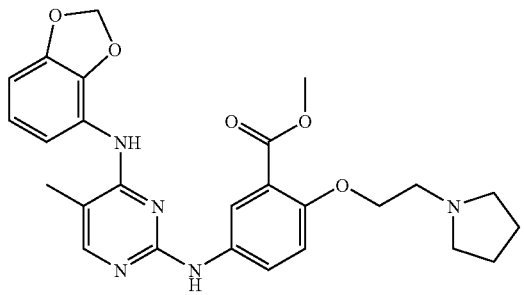

XCVII

A mixture of intermediate 30 (0.15 g, 0.57 mmol), intermediate 55 (0.20 g, 0.75 mmol), Pd$_2$(dba)$_3$ (50 mg, 0.055 mmol), Xantphos (60 mg, 0.10 mmol) and cesium carbonate (0.30 g, 0.92 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (30 mg, 11%).

$^1$H NMR (500 MHz, DMSO-d$_6$): δ 1.65-1.72 (m, 4H), 2.07 (s, 3H), 2.50-2.62 (m, 4H), 2.75-2.85 (m, 2H), 3.73 (s, 3H), 4.02 (t, J=5.8 Hz, 2H), 5.88 (s, 2H), 6.78-6.88 (m, 3H), 6.92 (dd, J=8.0, 2.1 Hz, 1H), 7.75-7.80 (m, 2H), 7.83 (s, 1H), 8.22 (s, 1H), 8.89 (s, 1H). MS (ES+): m/z 492 (M+H)$^+$.

Example 151

N-tert-Butyl-3-{5-methyl-2-[4-(piperidin-4-yloxy)-phenylamino]-pyrimidin-4-ylamino}-benzene-sulfonamide (Compound XCVIII)

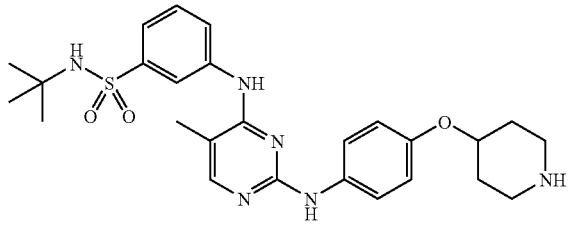

XCVIII

A mixture of intermediate 33 (0.15 g, 0.42 mmol) and 4-(4-amino-phenoxy)-piperidine-1-carboxylic acid tert-butyl ester (0.15 g, 0.51 mmol) in acetic acid (3 mL) was sealed in a microwave reaction tube and irradiated with microwave at 150° C. for 20 min. After cooling to room temperature, the cap was removed and the mixture concentrated. The residue was taken in water (20 mL) and the pH adjusted with 10% NaOH solution until solid precipitated. The solid was filtered and then purified by HPLC. The corrected fractions were combined, poured into saturated NaHCO$_3$ solution (30 mL) and extracted with EtOAc (2×30 mL). The combined extracts were washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (20 mg, 9%).

$^1$H NMR (500 MHz, DMSO-d$_6$): δ 1.12 (s, 9H), 1.65-1.73 (m, 2H), 1.95-2.05 (m, 2H), 2.12 (s, 3H), 2.89-2.95 (m, 2H), 3.10-3.20 (m, 2H), 4.40-4.45 (m, 1H), 6.84 (d, J=9.1 Hz, 2H), 7.45-7.60 (m, 6H), 7.90 (s, 1H), 8.10-8.15 (m, 2H), 8.55 (s, 1H), 8.81 (s, 1H). MS (ES+): m/z 511 (M+H)$^+$.

Example 152

2-(5-Amino-pyridin-2-yloxy)-ethanol
(Intermediate 56)

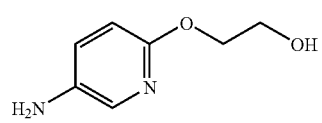

56

To a solution of 2-(5-nitro-pyridin-2-yloxy)-ethanol (1.0 g, 5.4 mmol) in MeOH (30 mL) was added 10 wt % Pd/C (0.1 equiv by wt) under argon atmosphere. The mixture was evacuated and then refilled with hydrogen (3 cycles) and stirred at room temperature for 1 h. The heterogeneous reaction mixture was filtered through a pad of Celite, washed with MeOH and concentrated in vacuo. The crude amino-compound was used in the next step without purification. MS (ES+): m/z 155 (M+H)$^+$.

Example 153

2-{5-[4-(Benzo[1,3]dioxol-4-ylamino)-5-methyl-pyrimidin-2-ylamino]-pyridin-2-yloxy}-ethanol (Compound XCIX)

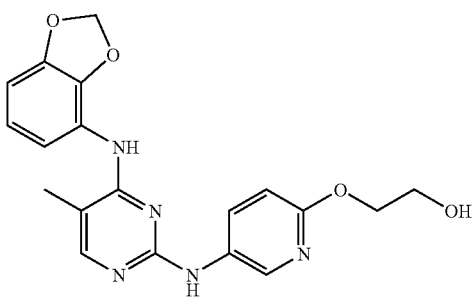

XCIX

A mixture of intermediate 30 (0.10 g, 0.38 mmol), intermediate 56 (0.10 g, 0.65 mmol), Pd$_2$(dba)$_3$ (30 mg, 0.033 mmol), Xantphos (35 mg, 0.06 mmol) and cesium carbonate (0.26 g, 0.80 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (50 mg, 35%).

$^1$H NMR (500 MHz, DMSO-d$_6$): δ 2.06 (s, 3H), 3.66 (q, J=5.4 Hz, 2H), 4.15 (t, J=5.2 Hz, 2H), 4.77 (t, J=5.5 Hz, 2H), 5.91 (s, 2H), 6.52 (d, J=9.0 Hz, 1H), 6.78-6.90 (m, 3H), 7.82 (s, 1H), 7.96 (dd, J=8.9, 2.7 Hz, 1H), 8.22 (d, J=2.6 Hz, 1H), 8.27 (s, 1H), 8.84 (s, 1H). MS (ES+): m/z 382 (M+H)$^+$.

Example 154

1-[2-(2-Methoxy-4-nitro-phenoxy)-ethyl]-pyrrolidine (Intermediate 57)

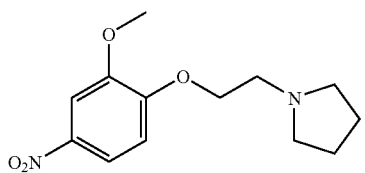

57

A suspension of potassium 2-methoxy-4-nitro-phenolate (2.0 g, 9.7 mmol), 1-(2-chloro-ethyl)-pyrrolidine hydrochloride (2.0 g, 12 mmol) and cesium carbonate (7.0, 22 mmol) in DMF (35 mL) was heated at 80° C. for 16 h. The mixture was allowed to cool to room temperature, poured into water (60 mL) and extracted with EtOAc (2×50 mL). The combined extracts were washed with brine, dried over anhydrous Na$_2$SO$_4$ and filtered. The filtrate was concentrated and used in the next step without purification.

MS (ES+): m/z 267 (M+H)$^+$.

Example 155

3-Methoxy-4-(2-pyrrolidin-1-yl-ethoxy)-phenylamine (Intermediate 58)

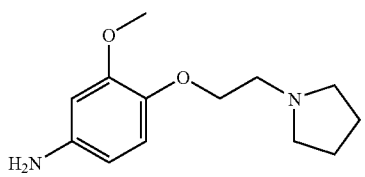

58

To a solution of intermediate 57 (1.7 g, 6.4 mmol) in MeOH (30 mL) was added 10 wt % Pd/C (0.1 equiv by wt) under argon atmosphere. The mixture was evacuated and then refilled with hydrogen (3 cycles) and stirred at room temperature for 1 h. The heterogeneous reaction mixture was filtered through a pad of Celite, washed with MeOH and concentrated in vacuo. The crude amino-compound was used in the next step without purification. MS (ES+): m/z 237 (M+H)$^+$.

Example 156

N$^4$-Benzo[1,3]dioxol-4-yl-N$^2$-[3-methoxy-4-(2-pyrrolidin-1-yl-ethoxy)-phenyl]-5-methyl-pyrimidine-2,4-diamine (Compound C)

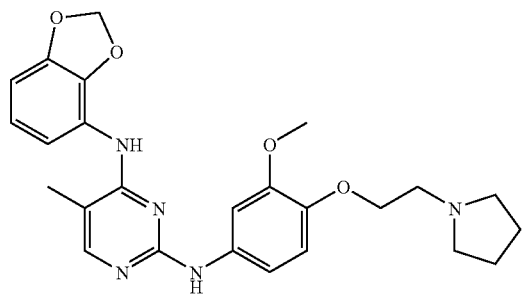

C

A mixture of intermediate 30 (0.10 g, 0.38 mmol), intermediate 58 (0.11 g, 0.46 mmol), Pd$_2$(dba)$_3$ (30 mg, 0.033 mmol), Xantphos (35 mg, 0.06 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (50 mg, 28%).

$^1$H NMR (500 MHz, DMSO-d$_6$): δ 1.65-1.72 (m, 4H), 2.06 (s, 3H), 2.50-2.62 (m, 4H), 2.75-2.85 (m, 2H), 3.50 (s, 3H), 3.94 (t, J=6.1 Hz, 2H), 5.84 (s, 2H), 6.67 (d, J=8.8 Hz, 1H), 6.78 (dd, J=7.8, 1.1 Hz, 1H), 6.83 (t, J=7.9 Hz, 1H), 6.92 (dd, J=8.1, 1.1 Hz, 1H), 7.14 (dd, J=8.7, 2.4 Hz, 1H), 7.23 (d, J=2.4 Hz, 1H), 7.83 (s, 1H), 8.21 (s, 1H), 8.69 (s, 1H). MS (ES+): m/z 464 (M+H)$^+$.

Example 157

N-tert-Butyl-3-[2-(4-imidazol-1-yl-phenylamino)-5-methyl-pyrimidin-4-ylamino]-benzenesulfonamide (Compound CI)

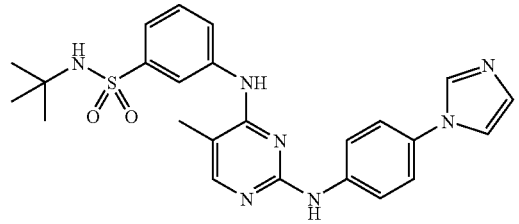

CI

A mixture of intermediate 33 (0.40 g, 1.1 mmol), 4-imidazol-1-yl-phenylamine (0.20 g, 1.3 mmol), Pd$_2$(dba)$_3$ (0.10 g, 0.11 mmol), Xantphos (0.12 g, 0.21 mmol) and cesium carbonate (0.80 g, 2.5 mmol) in dioxane/DMF (3/1, 8 mL) was sealed in a microwave reaction tube and irradiated with microwave at 160° C. for 30 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (40 mL). The combined aqueous layers were extracted with EtOAc (2×40 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (0.15 g, 28%).

$^1$H NMR (500 MHz, DMSO-d$_6$): δ 1.12 (s, 9H), 2.15 (s, 3H), 7.07 (s, 1H), 7.43 (d, J=9.0 Hz, 2H), 7.50-7.60 (m, 3H), 7.61 (s, 1H), 7.79 (d, J=9.0 Hz, 2H), 7.98 (s, 1H), 8.08-8.13 (m, 3H), 8.64 (s, 1H), 9.19 (s, 1H). MS (ES+): m/z 478 (M+H)$^+$.

Example 158

N-tert-Butyl-3-[2-(4-imidazol-1-ylmethyl-phenylamino)-5-methyl-pyrimidin-4-ylamino]-benzenesulfonamide (Compound CII)

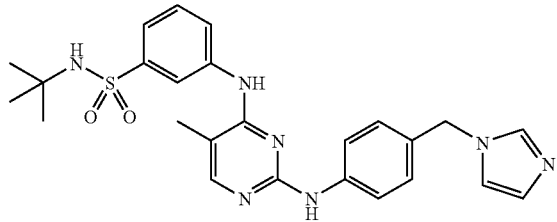

CII

A mixture of intermediate 33 (0.10 g, 0.28 mmol), 4-imidazol-1-ylmethyl-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (40 mg, 29%).

$^1$H NMR (500 MHz, DMSO-d$_6$): δ 1.12 (s, 9H), 2.13 (s, 3H), 5.07 (s, 2H), 6.89 (s, 1H), 7.12 (d, J=8.6 Hz, 2H), 7.15 (s, 1H), 7.46 (t, J=7.9 Hz, 1H), 7.49-7.52 (m, 1H), 7.56 (s, 1H), 7.63 (d, J=8.6 Hz, 2H), 7.72 (s, 1H), 7.94 (s, 1H), 8.09 (s, 1H), 8.14 (d, J=8.1 Hz, 1H), 8.60 (s, 1H), 9.02 (s, 1H). MS (ES+): m/z 492 (M+H)$^+$.

Example 159

2-(4-Amino-phenoxy)-ethanol (Intermediate 59)

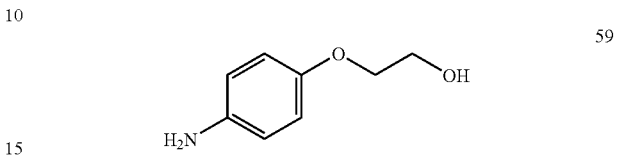

59

A solution of 2-(4-nitro-phenoxy)-ethanol (2.1 g, 12 mmol) in MeOH (30 mL) was flushed with argon and then charged with 10 wt % Pd/C (0.1 equiv by wt). The mixture was evacuated under house vacuum and then refilled with hydrogen from hydrogen balloon. The cycle was repeated again and the mixture stirred at room temperature for 2 h. The heterogeneous reaction mixture was filtered through a pad of Celite, washed with MeOH and concentrated in vacuo to furnish the title compound (1.8 g, 99%) as a brown solid. MS (ES+): m/z 154 (M+H)$^+$.

Example 160

N-tert-Butyl-3-{2-[4-(2-hydroxy-ethoxy)-phenylamino]-5-methyl-pyrimidin-4-ylamino}-benzenesulfonamide (Compound CIII)

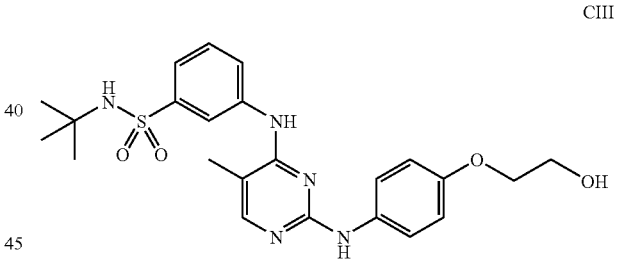

CIII

A mixture of intermediate 33 (0.10 g, 0.28 mmol), intermediate 59 (55 mg, 0.36 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (15 mg, 11%).

$^1$H NMR (500 MHz, DMSO-d$_6$): δ 1.12 (s, 9H), 2.12 (s, 3H), 3.69 (q, J=5.2 Hz, 2H), 3.91 (t, J=5.1 Hz, 2H), 4.82 (t, J=5.5 Hz, 2H), 6.80 (d, J=9.1 Hz, 2H), 7.45-7.50 (m, 2H), 7.52 (d, J=9.0 Hz, 2H), 7.55 (s, 1H), 7.90 (s, 1H), 8.08-8.15 (m, 2H), 8.53 (s, 1H), 8.77 (s, 1H). MS (ES+): m/z 472 (M+H)+.

Example 161

N4-(4-Chloro-3-methoxy-phenyl)-5-methyl-N2-(4-piperazin-1-ylmethyl-phenyl)-pyrimidine-2,4-diamine (Compound CIV)

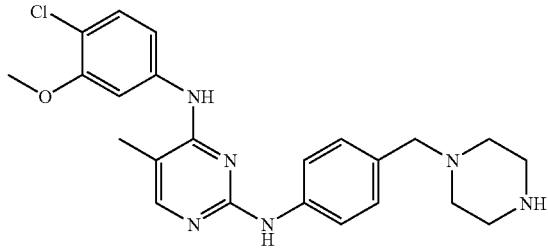

CIV

A mixture of intermediate 31 (0.10 g, 0.35 mmol), 4-(4-amino-benzyl)-piperazine-1-carboxylic acid tert-butyl ester (0.12 g, 0.41 mmol), Pd$_2$(dba)$_3$ (30 mg, 0.033 mmol), Xantphos (35 mg, 0.06 mmol) and cesium carbonate (0.23 g, 0.71 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM and the filtrate concentrated. The residue was purified by flash chromatography on silica gel (hexanes to 60% EtOAc/hexanes) to afford the Boc-protected precursor. To a solution of the precursor in DCM (5 mL) was added TFA (3 mL). The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (13 mg, 9%).

$^1$H NMR (500 MHz, DMSO-d$_6$): δ 2.11 (s, 3H), 2.30-2.40 (m, 4H), 2.83 (t, J=4.8 Hz, 4H), 3.37 (s, 2H), 3.75 (s, 3H), 7.08 (d, J=8.6 Hz, 2H), 7.29 (d, J=8.6 Hz, 1H), 7.43 (dd, J=8.6, 2.2 Hz, 1H), 7.47 (d, J=2.2 Hz, 1H), 7.59 (d, J=8.6 Hz, 2H), 7.91 (s, 1H), 8.37 (s, 1H), 8.99 (s, 1H). MS (ES+): m/z 439 (M+H)+.

Example 162

N-tert-Butyl-3-{5-methyl-2-[4-(2-methyl-imidazol-1-yl)-phenylamino]-pyrimidin-4-ylamino}-benzenesulfonamide (Compound CV)

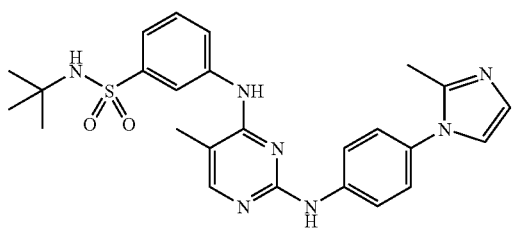

CV

A mixture of intermediate 33 (0.10 g, 0.28 mmol), 4-(2-methyl-imidazol-1-yl)-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (30 mg, 22%).

$^1$H NMR (500 MHz, DMSO-d$_6$): δ 1.11 (s, 9H), 2.15 (s, 3H), 2.24 (s, 3H), 6.87 (d, J=1.2 Hz, 1H), 7.18 (d, J=1.3 Hz, 1H), 7.22 (d, J=8.9 Hz, 2H), 7.50-7.55 (m, 2H), 7.56 (s, 1H), 7.79 (d, J=8.9 Hz, 2H), 7.98 (s, 1H), 8.07-8.10 (m, 2H), 8.65 (s, 1H), 9.26 (s, 1H). MS (ES+): m/z 492 (M+H)+.

Example 163

N-tert-Butyl-3-{5-methyl-2-[4-(2-methyl-imidazol-1-ylmethyl)-phenylamino]-pyrimidin-4-ylamino}-benzenesulfonamide (Compound CVI)

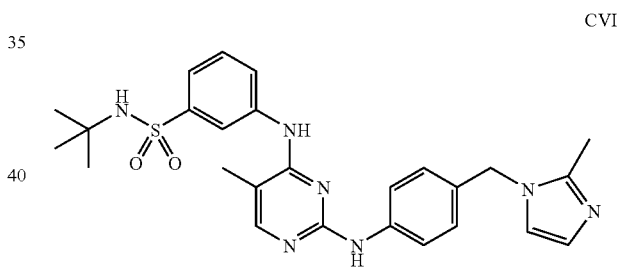

CVI

A mixture of intermediate 33 (0.10 g, 0.28 mmol), 4-(2-methyl-imidazol-1-ylmethyl)-phenylamine (65 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (30 mg, 21%).

$^1$H NMR (500 MHz, DMSO-d$_6$): δ 1.12 (s, 9H), 2.13 (s, 3H), 2.24 (s, 3H), 5.01 (s, 2H), 6.73 (d, J=1.2 Hz, 1H), 7.01 (d, J=8.6 Hz, 2H), 7.07 (d, J=1.1 Hz, 1H), 7.44 (t, J=7.9 Hz, 1H), 7.48-7.51 (m, 1H), 7.56 (s, 1H), 7.62 (d, J=8.6 Hz, 2H), 7.94

Example 164

N-tert-Butyl-3-[5-methyl-2-(4-pyridin-4-ylmethyl-phenylamino)-pyrimidin-4-ylamino]-benzene-sulfonamide (Compound CVII)

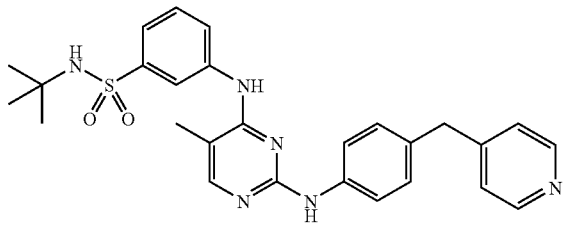

CVII

A mixture of intermediate 33 (0.10 g, 0.28 mmol), 4-Pyridin-4-ylmethyl-phenylamine (65 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (45 mg, 32%).

$^1$H NMR (500 MHz, DMSO-d$_6$): δ 1.11 (s, 9H), 2.13 (s, 3H), 3.87 (s, 2H), 7.07 (d, J=8.6 Hz, 2H), 7.22 (d, J=6.0 Hz, 2H), 7.43 (t, J=7.9 Hz, 1H), 7.47-7.50 (m, 1H), 7.56 (d, J=6.3 Hz, 2H), 7.58 (s, 1H), 7.93 (s, 1H), 8.09 (s, 1H), 8.13 (d, J=8.0 Hz, 1H), 8.44 (d, J=5.8 Hz, 2H), 8.58 (s, 1H), 8.94 (s, 1H). MS (ES+): m/z 503 (M+H)$^+$.

Example 165

N-tert-Butyl-3-[5-methyl-2-(4-morpholin-4-yl-phenylamino)-pyrimidin-4-ylamino]-benzenesulfonamide (Compound CVIII)

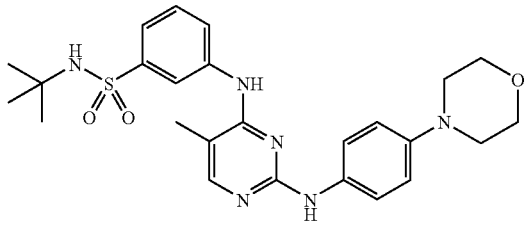

CVIII

A mixture of intermediate 33 (0.10 g, 0.28 mmol), 4-morpholin-4-yl-phenylamine (60 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a grey solid (45 mg, 32%).

$^1$H NMR (500 MHz, DMSO-d$_6$): δ 1.12 (s, 9H), 2.12 (s, 3H), 3.00 (t, J=4.8 Hz, 4H), 3.73 (t, J=4.8 Hz, 4H), 6.82 (d, J=9.1 Hz, 2H), 7.45-7.52 (m, 4H), 7.56 (s, 1H), 7.89 (s, 1H), 8.10-8.17 (m, 2H), 8.52 (s, 1H), 8.73 (s, 1H). MS (ES+): m/z 497 (M+H)$^+$.

Example 166

N-tert-Butyl-3-[5-methyl-2-(4-[1,2,4]triazol-1-ylmethyl-phenylamino)-pyrimidin-4-ylamino]-benzene-sulfonamide (Compound CIX)

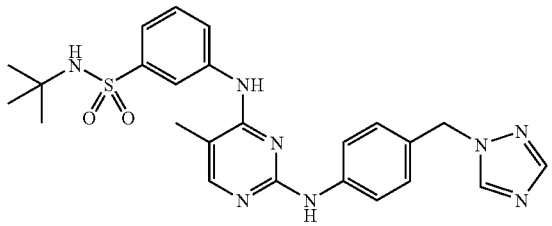

CIX

A mixture of intermediate 33 (0.10 g, 0.28 mmol), 4-[1,2,4]triazol-1-ylmethyl-phenylamine (60 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (37 mg, 27%).

$^1$H NMR (500 MHz, DMSO-d$_6$): δ 1.17 (s, 9H), 2.13 (s, 3H), 5.29 (s, 2H), 7.14 (d, J=8.6 Hz, 2H), 7.46 (t, J=7.8 Hz, 1H), 7.48-7.51 (m, 1H), 7.56 (s, 1H), 7.63 (d, J=8.6 Hz, 2H), 7.94 (s, 1H), 7.95 (s, 1H), 8.08 (s, 1H), 8.13 (d, J=8.0 Hz, 1H), 8.59 (s, 1H), 8.60 (s, 1H), 9.04 (s, 1H). MS (ES+): m/z 493 (M+H)$^+$.

Example 167

N-tert-Butyl-3-{5-methyl-2-[4-(4-methyl-imidazol-1-yl)-phenylamino]-pyrimidin-4-ylamino}-benzene-sulfonamide (Compound CX)

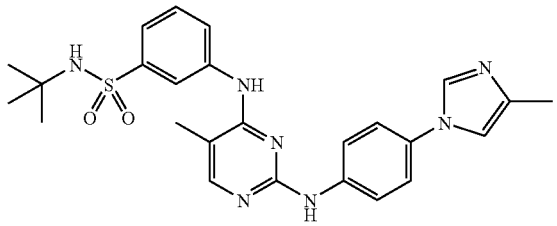

CX

A mixture of intermediate 33 (0.10 g, 0.28 mmol), 4-(4-methyl-imidazol-1-yl)-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (20 mg, 15%).

$^1$H NMR (500 MHz, DMSO-d$_6$): δ 1.12 (s, 9H), 2.15 (s, 3H), 2.16 (s, 3H), 7.30 (s, 1H), 7.38 (d, J=9.0 Hz, 2H), 7.50-7.56 (m, 2H), 7.57 (s, 1H), 7.76 (d, J=9.0 Hz, 2H), 7.96 (s, 1H), 7.97 (s, 1H), 8.09-8.13 (m, 2H), 8.63 (s, 1H), 9.16 (s, 1H). MS (ES+): m/z 492 (M+H)$^+$.

Example 168

N-tert-Butyl-3-[5-methyl-2-(4-[1,2,4]triazol-1-yl-phenylamino)-pyrimidin-4-ylamino]-benzene-sulfonamide (Compound CXI)

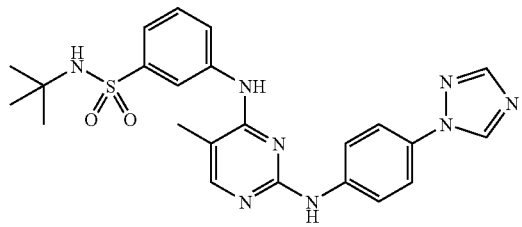

CXI

A mixture of intermediate 33 (0.10 g, 0.28 mmol), 4-[1,2,4]triazol-1-yl-phenylamine (55 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (40 mg, 29%).

$^1$H NMR (500 MHz, DMSO-d$_6$): δ 1.12 (s, 9H), 2.15 (s, 3H), 7.50-7.58 (m, 3H), 7.63 (d, J=9.1 Hz, 2H), 7.83 (d, J=9.0 Hz, 2H), 7.99 (s, 1H), 8.09 (s, 1H), 8.10-8.15 (m, 1H), 8.17 (s, 1H), 8.66 (s, 1H), 9.12 (s, 1H), 9.27 (s, 1H). MS (ES+): m/z 479 (M+H)$^+$.

Example 169

N-tert-Butyl-3-{5-methyl-2-[3-(1H-tetrazol-5-yl)-phenylamino]-pyrimidin-4-ylamino}-benzene-sulfonamide (Compound CXII)

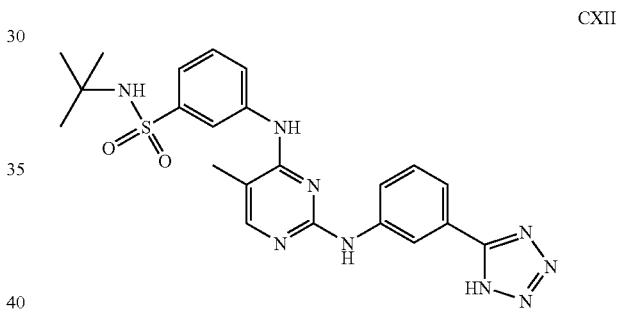

CXII

A mixture of intermediate 33 (0.10 g, 0.28 mmol), 3-(1H-tetrazol-5-yl)-phenylamine (55 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (15 mg, 11%).

$^1$H NMR (500 MHz, DMSO-d$_6$): δ 1.13 (s, 9H), 2.15 (s, 3H), 7.26 (t, J=7.9 Hz, 1H), 7.38 (t, J=8.0 Hz, 1H), 7.44 (dd, J=7.9, 1.1 Hz, 1H), 7.50 (d, J=7.6 Hz, 1H), 7.58 (s, 1H), 7.79 (dd, J=8.1, 1.4 Hz, 1H), 7.98 (s, 1H), 8.16 (s, 1H), 8.22 (s, 1H), 8.27 (d, J=7.8 Hz, 1H), 8.57 (s, 1H), 9.08 (s, 1H). MS (ES+): m/z 480 (M+H)$^+$.

Example 170

4-(1H-Tetrazol-5-yl)-phenylamine (Intermediate 60)

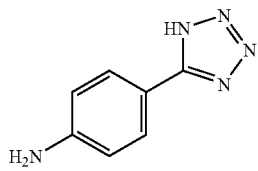

To a solution of 5-(4-nitro-phenyl)-1H-tetrazole (1.0 g, 5.2 mmol) in MeOH (30 mL) was added 10 wt % Pd/C (0.1 equiv by wt) under argon atmosphere. The mixture was evacuated, refilled with hydrogen (3 cycles) and stirred at room temperature for 1.5 h. The heterogeneous reaction mixture was filtered through a pad of Celite, washed with MeOH and concentrated in vacuo. The crude amino-compound was used in the next step without purification. MS (ES+): m/z 162 (M+H)$^+$.

Example 171

N-tert-Butyl-3-{5-methyl-2-[4-(1H-tetrazol-5-yl)-phenylamino]-pyrimidin-4-ylamino}-benzene-sulfonamide (Compound CXIII)

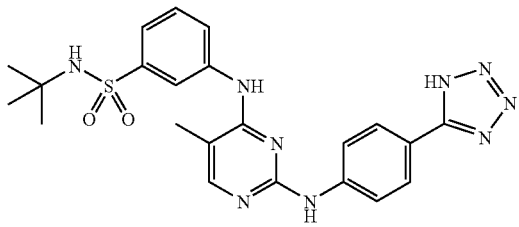

A mixture of intermediate 33 (0.10 g, 0.28 mmol), intermediate 60 (60 mg, 0.37 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1; 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (15 mg, 11%).

$^1$H NMR (500 MHz, DMSO-d$_6$): δ 1.13 (s, 9H), 2.16 (s, 3H), 7.52-7.56 (m, 2H), 7.57 (s, 1H), 7.83 (s, 4H), 8.01 (s, 1H), 8.08 (s, 1H), 8.13-8.19 (m, 1H), 8.69 (s, 1H), 9.34 (s, 1H). MS (ES+): m/z 480 (M+H)$^+$.

Example 172

3-{2-[4-(4-Acetyl-piperazin-1-yl)-phenylamino]-5-methyl-pyrimidin-4-ylamino}-N-tert-butyl-benzene-sulfonamide (Compound CXIV)

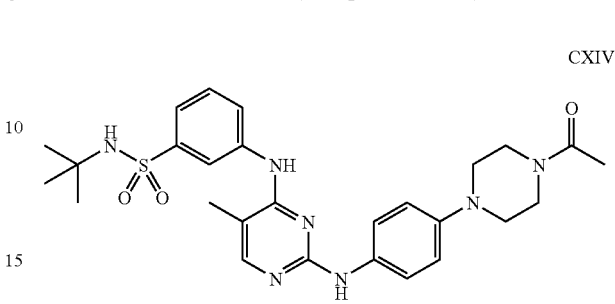

A mixture of intermediate 33 (0.10 g, 0.28 mmol), 1-[4-(4-amino-phenyl)-piperazin-1-yl]-ethanone (80 mg, 0.36 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (55 mg, 37%).

$^1$H NMR (500 MHz, DMSO-d$_6$): δ 1.12 (s, 9H), 2.04 (s, 3H), 2.12 (s, 3H), 2.97 (t, J=5.2 Hz, 2H), 3.03 (t, J=5.1 Hz, 2H), 3.57 (q, J=5.4 Hz, 4H), 6.85 (d, J=9.0 Hz, 2H), 7.46-7.52 (m, 4H), 7.56 (s, 1H), 7.90 (s, 1H), 8.10-8.17 (m, 2H), 8.52 (s, 1H), 8.75 (s, 1H). MS (ES+): m/z 538 (M+H)$^+$.

Example 173

N-tert-Butyl-3-{5-methyl-2-[4-(1-morpholin-4-yl-ethyl)-phenylamino]-pyrimidin-4-ylamino}-benzene-sulfonamide (Compound CXV)

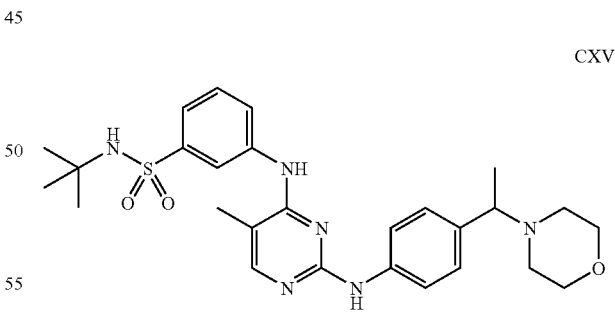

A mixture of intermediate 33 (0.10 g, 0.28 mmol), 4-(1-morpholin-4-yl-ethyl)-phenylamine (80 mg, 0.39 mmol), Pd$_2$(dba)$_3$ (30 mg, 0.033 mmol), Xantphos (35 mg, 0.061 mmol) and cesium carbonate (0.26 g, 0.80 mmol) in dioxane (4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na₂SO₄ and filtered. The filtrate was concentrated and then taken up in minimum amount of EtOAc. Hexanes were added until solid precipitated. After filtration, the title compound was obtained as a white solid (40 mg, 27%).

¹H NMR (500 MHz, DMSO-d₆): δ 1.12 (s, 9H), 1.25 (d, J=6.6 Hz, 3H), 2.13 (s, 3H), 2.20-2.30 (m, 2H), 2.30-2.40 (m, 2H), 3.24 (q, J=6.6 Hz, 1H), 3.54 (t, J=4.4 Hz, 4H), 7.10 (d, J=8.5 Hz, 2H), 7.45-7.52 (m, 2H), 7.55 (s, 1H), 7.57 (d, J=8.5 Hz, 2H), 7.93 (s, 1H), 8.09 (s, 1H), 8.15 (d, J=7.7 Hz, 1H), 8.57 (s, 1H), 8.92 (s, 1H). MS (ES+): m/z 525 (M+H)⁺.

Example 174

N⁴-(1H-Indol-4-yl)-5-methyl-N²-(4-(4-methylpiperazin-1-yl)phenyl)pyrimidine-2,4-diamine
(Compound CXVI)

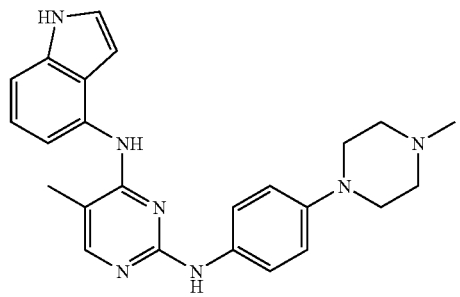

CXVI

A mixture of intermediate 32 (270 mg, 0.9 mmol), 4-bromo-1H-indole (196 mg, 0.9 mmol), Pd₂(dba)₃ (91 mg, 0.09 mmol), Xantphos (157 mg, 0.27 mmol) and cesium carbonate (1.2 g, 3.6 mmol) were suspended in dioxane (100 mL) and heated at reflux under the argon atmosphere for 20 h. The mixture was filtered and the filtrate concentrated in vacuo. The residue was purified by HPLC to afford the title compound (55 mg of HCl salt, 14%) as a white solid.

¹H NMR (500 MHz, DMSO-d₆): δ 2.22 (s, 3H), 2.79 (d, J=4.3 Hz, 3H), 2.98-3.03 (m, 2H), 3.08-3.14 (m, 2H), 3.46-3.48 (m, 2H), 3.64-3.66 (m, 2H), 6.35-6.36 (m, 1H), 6.63 (br d, J=8.0 Hz, 1H), 6.98 (d, J=9.1 Hz, 2H), 7.05 (d, J=7.4 Hz, 1H), 7.16 (t, J=7.6 Hz, 1H), 7.36 (t, J=2.8 Hz, 2H), 7.43 (d, J=8.0 Hz, 1H), 7.86 (s, 1H), 10.07 (s, 1H), 10.27 (s, 1H), 11.00 (br s, 1H), 11.38 (s, 1H), 12.16 (br s, H). MS (ES+): m/z 414 (M+H)⁺.

Example 175

2-Chloro-5-methyl-N-(2,3-dimethylphenyl)pyrimidin-4-amine (Intermediate 61)

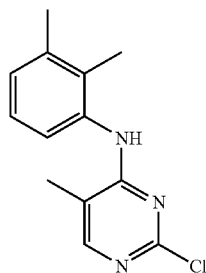

61

A mixture of 2-chloro-5-methylpyrimidin-4-amine (143.6 mg, 1 mmol), 1-bromo-2,3-dimethylbenzene (222 mg, 1.2 mmol), Pd₂(dba)₃ (92 mg, 0.1 mmol), Xantphos (174 mg, 0.3 mmol) and cesium carbonate (1.3 g, 4 mmol) were suspended in dioxane (150 mL) and heated at reflux under the argon atmosphere for 20 h. The mixture was filtered and the filtrate concentrated in vacuo. The residue was dissolved in EtOAc (10 mL) and added hexanes (100 mL). The solid was collected by filtration and washed with hexanes to afford the crude title compound as a yellow solid.

Example 176

5-Methyl-N⁴-(2,3-dimethylphenyl)-N²-(4-(piperidin-4-yloxy)phenyl)pyrimidine-2,4-diamine
(Compound CXVII)

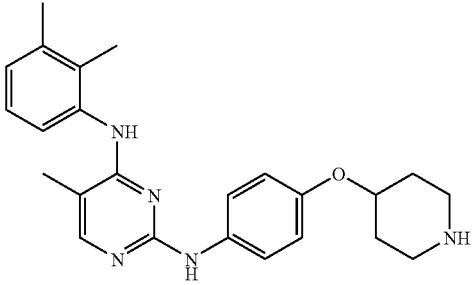

CXVII

A mixture of intermediate 61 (1.0 mmol) and tert-butyl 4-(4-aminophenoxy)piperidine-1-carboxylate (292.4 mg, 1.0 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO₄ and filtered. The filtrate was concentrated in vacuo and the crude product purified by HPLC to afford the title compound (105 mg of HCl salt, 24%) as a yellow solid.

¹H NMR (500 MHz, DMSO-d₆): δ 1.76-1.83 (m, 2H), 2.03 (s, 3H), 2.05-2.09 (m, 2H), 2.17 (s, 3H), 2.30 (s, 3H), 3.02-3.05 (m, 2H), 3.18 (br s, 2H), 4.53-4.56 (m, 1H), 6.72 (d, J=8.5 Hz, 2H), 7.11-7.14 (m, 3H), 7.19-7.24 (m, 2H), 7.87 (s, 1H), 9.06 (br s, 1H), 9.13 (br s, 1H), 9.92 (s, 1H), 10.43 (s, 1H). MS (ES+): m/z 404 (M+H)⁺.

Example 177

N⁴-(4-Chloro-3,5-dimethylphenyl)-5-methyl-N²-(4-(4-methylpiperazin-1-yl)phenyl)pyrimidine-2,4-diamine (Compound CXVIII)

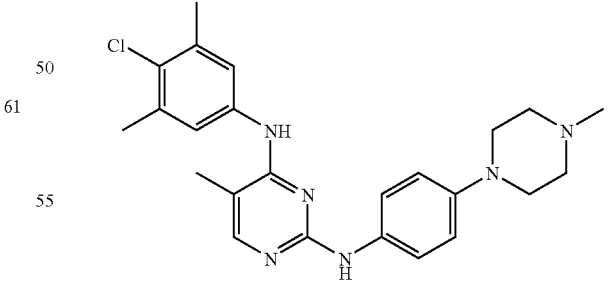

CXVIII

A mixture of intermediate 32 (240 mg, 0.8 mmol), 5-bromo-2-chloro-1,3-dimethylbenzene (212 mg, 0.96 mmol), Pd₂(dba)₃ (92 mg, 0.1 mmol), Xantphos (170 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (63 mg of HCl salt, 17%) as a white solid.

$^1$H NMR (500 MHz, DMSO-d$_6$): δ 2.15 (s, 3H), 2.17 (s, 3H), 2.80 (d, J=4.5 Hz, 3H), 3.06-3.14 (m, 4H), 3.48-3.52 (m, 2H), 3.75-3.77 (m, 2H), 6.93 (d, J=8.9 Hz, 2H), 7.29 (d, J=8.9 Hz, 2H), 7.46 (s, 2H), 7.90 (s, 1H), 9.65 (s, 1H), 10.49 (s, 1H), 11.13 (br s, 2H). MS (ES+): m/z 437 (M+H)$^+$.

Example 178

N$^2$-(4-(2-(Pyrrolidin-1-yl)ethoxy)phenyl)-N$^4$-(3-tert-butylphenyl)-5-methyl-pyrimidine-2,4-diamine (Compound CXIX)

CXIX

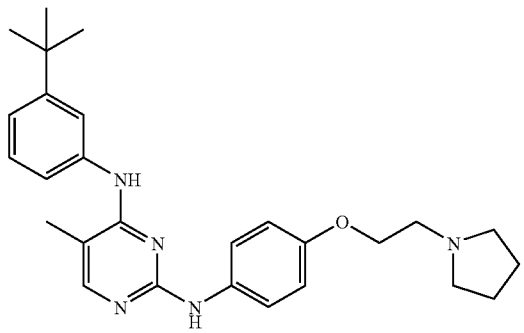

A mixture of intermediate 41 (365 mg, 1.32 mmol) and 4-(2-(pyrrolidin-1-yl)ethoxy)benzenamine (410 mg, 1.98 mmol) were suspended in acetic acid (20 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (127 mg of HCl salt, 20%) as a white solid.

$^1$H NMR (500 MHz, DMSO-d$_6$): δ 1.89-1.91 (m, 2H), 1.98-2.02 (m, 2H), 2.17 (s, 3H), 3.07-3.12 (m, 2H), 3.52-3.57 (m, 4H), 4.32 (t, J=4.8 Hz, 2H), 6.90 (d, J=8.9 Hz, 2H), 7.29-7.38 (m, 4H), 7.43-7.44 (m, 1H), 7.48 (d, J=7.9 Hz, 1H), 7.89 (s, 1H), 9.75 (s, 1H), 10.51 (s, 1H), 11.07 (br, 1H). MS (ESI+): m/z 446 (M+H)$^+$.

Example 179

N$^2$-(4-(2-(Pyrrolidin-1-yl)ethoxy)phenyl)-N$^4$-(4-(3-tert-butylphenylamino)-5-methylpyrimidin-2-yl)-5-methylpyrimidine-2,4-diamine (Compound CXX)

CXX

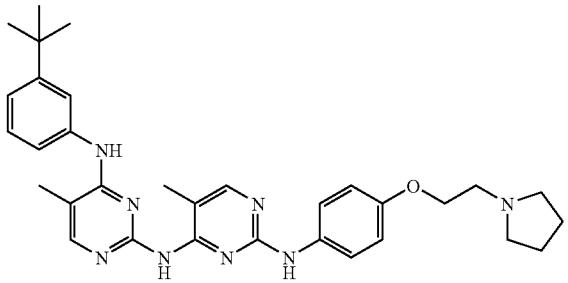

A mixture of intermediate 41 (210 mg, 0.67 mmol), intermediate 38 (185 mg, 0.67 mmol), Pd$_2$(dba)$_3$ (55 mg, 0.06 mmol), Xantphos (104 mg, 0.18 mmol) and cesium carbonate (782 g, 2.4 mmol) were suspended in dioxane (50 mL) and heated at reflux under the argon atmosphere for 20 h. The mixture was filtered and the filtrate concentrated in vacuo. The residue was purified by HPLC to afford the title compound (94 mg of HCl salt, 24%) as a yellow solid.

$^1$H NMR (500 MHz, DMSO-d$_6$): δ 1.29 (s, 9H), 1.84-1.88 (m, 2H), 1.94-2.01 (m, 2H), 2.14 (s, 3H), 2.27 (s, 3H), 3.06-3.10 (m, 2H), 3.51-3.56 (m, 4H), 4.29 (t, J=4.9 Hz, 2H), 6.97 (d, J=9.1 Hz, 2H), 7.27 (d, J=8.6 Hz, 2H), 7.34 (t, J=7.9 Hz, 2H), 7.57 (t, J=1.9 Hz, 2H), 7.65 (d, J=9.1 Hz, 1H), 7.72 (d, J=8.6 Hz, 2H), 8.15 (s, 1H), 8.39 (s, 1H), 9.82 (s, 1H), 10.21 (br s, 1H), 10.68 (br s, 1H), 10.93 (br s, 1H). MS (ES+): m/z 553 (M+H)$^+$.

Example 180

5-Methyl-N$^2$-[4-(4-methyl-piperazin-1-yl)-phenyl]-N$^4$-[3-(piperidine-1-sulfony)-phenyl]-pyrimidine-2,4-diamine (Compound CXXI)

CXXI

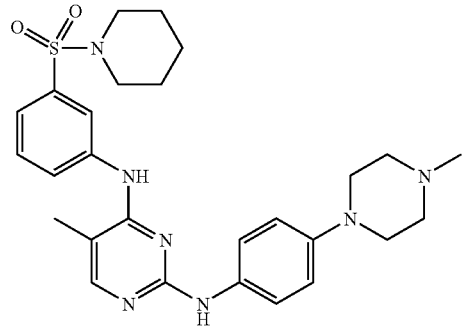

A mixture of intermediate 32 (150 mg, 0.5 mmol), 1-(3-bromo-benzenesulfonyl)-piperidine (152 mg, 0.5 mmol), Pd$_2$(dba)$_3$ (46 mg, 0.05 mmol), Xantphos (87 mg, 0.15 mmol) and cesium carbonate (652 mg, 2 mmol) were suspended in dioxane (20 mL) and heated at reflux under the argon atmosphere for 20 h. The mixture was filtered and the filtrate concentrated in vacuo. The residue was purified by HPLC to afford the title compound (84 mg of HCl salt, 37%) as a white solid.

$^1$H NMR (500 MHz, DMSO-d$_6$): δ 1.30-1.34 (m, 2H), 1.50-1.55 (m, 4H), 2.17 (s, 3H), 2.81 (d, J=4.5 Hz, 3H), 2.88 (t, J=5.3 Hz, 4H), 3.04-3.16 (m, 4H), 3.47-3.51 (m, 2H), 3.75-3.77 (m, 2H), 6.33-6.34 (m, 1H), 6.95 (d, J=9.0 Hz, 2H), 7.25 (d, J=9.0 Hz, 2H), 7.56-7.63 (m, 2H), 7.83 (t, J=1.7 Hz, 1H), 7.92 (s, 1H), 8.05 (d, J=9.3 Hz, 1H), 9.94 (s, 1H), 10.38 (s, 1H), 10.88 (br s, 1H). MS (ES+): m/z 522 (M+H)$^+$.

Example 181

5-Methyl-N$^2$-[4-(4-methyl-piperazin-1-yl)-phenyl]-N$^4$-[3-(2-methyl-piperidine-1-sulfony)-phenyl]-pyrimidine-2,4-diamine (Compound CXXII)

CXXII

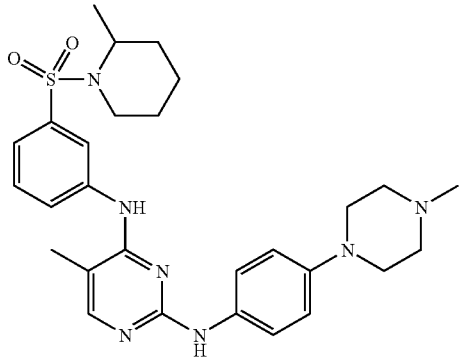

A mixture of intermediate 32 (161 mg, 0.54 mmol), 1-(3-bromo-benzenesulfonyl)-2-methyl-piperidine (172 mg, 0.54 mmol), Pd$_2$(dba)$_3$ (46 mg, 0.05 mmol), Xantphos (87 mg, 0.15 mmol) and cesium carbonate (652 mg, 2 mmol) were suspended in dioxane (20 mL) and heated at reflux under the argon atmosphere for 20 h. The mixture was filtered and the filtrate concentrated in vacuo. The residue was purified by HPLC to afford the title compound (10 mg of HCl salt, 3%) as a white solid.

$^1$H NMR (500 MHz, DMSO-d$_6$): δ 0.98 (d, J=6.9 Hz, 3H), 1.15-1.21 (m, 1H), 1.36-1.40 (m, 3H), 1.47-1.53 (m, 2H), 2.18 (s, 3H), 2.80 (d, J=4.5 Hz, 3H), 2.94-2.99 (m, 1H), 3.05-3.16 (m, 4H), 3.47-3.49 (m, 2H), 3.59-3.61 (m, 2H), 3.73-3.76 (m, 2H), 4.08-4.10 (m, 1H), 6.93 (d, J=8.9 Hz, 2H), 7.25 (d, J=8.9 Hz, 2H), 7.58 (t, J=8.0 Hz, 1H), 7.65 (d, J=8.0 Hz, 1H), 7.92 (d, J=7.1 Hz, 2H), 7.96 (br, 1H), 9.95 (s, 1H), 10.45 (s, 1H), 11.00 (br s, 1H). MS (ES+): m/z 536 (M+H)$^+$.

Example 182

N-Cyclopentyl-3-{5-methyl-2-[4-(4-methyl-piperazin-1-yl)-phenylamino]-pyrimidine-4-ylamino}-benzenesulfonamide (Compound CXXIII)

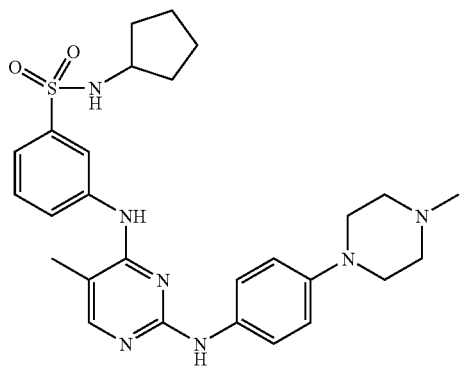

CXXIII

A mixture of intermediate 32 (229 mg, 0.78 mmol), 3-bromo-N-cyclopentyl-benzenesulfonamide (280 mg, 0.92 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (130 mg of HCl salt, 25%) as a white solid.

$^1$H NMR (500 MHz, DMSO-d$_6$): δ 1.27-1.36 (m, 4H), 1.36-1.58 (m, 4H), 2.18 (s, 3H), 2.80 (d, J=4.6 Hz, 3H), 3.05-3.15 (m, 4H), 3.36-3.42 (m, 1H), 3.47-3.49 (m, 2H), 3.74-3.76 (m, 2H), 6.94 (d, J=8.7 Hz, 2H), 7.26 (d, J=8.9 Hz, 2H), 7.59 (t, J=8.0 Hz, 1H), 7.68 (d, J=8.0 Hz, 1H), 7.75 (d, J=7.1 Hz, 2H), 7.92 (br, 2H), 7.93 (br, 1H), 9.96 (s, 1H), 10.45 (s, 1H), 11.98 (br s, 1H). MS (ES+): m/z 522 (M+H)$^+$.

Example 183

5-Methyl-N$^2$-[4-(4-methyl-piperazin-1-yl)-phenyl]-N$^4$-[3-(pyrrolidine-1-sulfony)phenyl]-pyrimidine-2,4-diamine (Compound CXXIV)

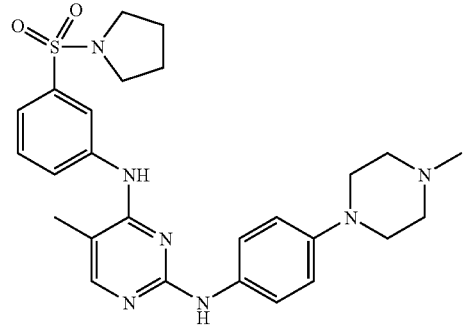

CXXIV

A mixture of intermediate 32 (298 mg, 1.0 mmol), 1-(3-bromo-benzenesulfonyl)-pyrrolidine (360 mg, 1.24 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (200 mg of HCl salt, 37%) as a white solid.

$^1$H NMR (500 MHz, DMSO-d$_6$): δ 1.61-1.65 (m, 4H), 2.19 (s, 3H), 2.80 (br, 3H), 3.06-3.16 (m, 10H), 3.74-3.77 (br, 2H), 6.94 (d, J=9.0 Hz, 2H), 7.26 (d, J=9.0 Hz, 2H), 7.60 (t, J=8.0 Hz, 1H), 7.65 (d, J=8.0 Hz, 1H), 7.91 (t, J=1.7 Hz, 1H), 7.93 (s, 1H), 8.05 (d, J=7.5 Hz, 1H), 9.95 (s, 1H), 10.43 (s, 1H), 11.07 (br s, 1H). MS (ES+): m/z 508 (M+H)$^+$.

Example 184

N$^4$-[3-(2,5-Dimethyl-pyrrolidine-1-sulfonyl)-phenyl]-5-methyl-N$^2$-[4-(4-methyl-piperazin-1-yl)-phenyl]-pyrimidine-2,4-diamine (Compound CXXV)

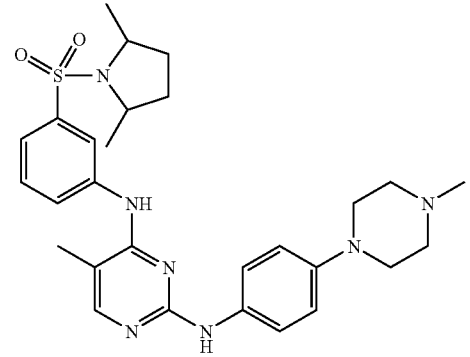

CXXV

A mixture of intermediate 32 (298 mg, 1.0 mmol), 1-(3-bromo-benzenesulfonyl)-2,5-dimethyl-pyrrolidine (318 mg, 1.0 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (100 mg of HCl salt, 17%) as a white solid.

$^1$H NMR (500 MHz, DMSO-d$_6$): δ 1.26 (s, 3H), 1.27 (s, 3H), 1.45-1.48 (m, 4H), 2.19 (s, 3H), 2.80 (d, J=4.6 Hz, 3H), 3.06-3.15 (m, 4H), 3.47-3.50 (m, 2H), 3.60-3.64 (m, 2H), 3.74-3.76 (m, 2H), 6.94 (d, J=9.0 Hz, 2H), 7.25 (d, J=9.0 Hz, 2H), 7.59 (t, J=8.0 Hz, 1H), 7.68 (d, J=7.6 Hz, 1H), 7.93 (br, 2H), 8.02 (br, 1H), 9.97 (s, 1H), 10.47 (s, 1H), 11.07 (br s, 1H). MS (ES+): m/z 536 (M+H)$^+$.

Example 185

N-tert-Butyl-3-[5-methyl-2-(4-piperazin-1-yl-phenylamino)-pyrimidin-4-ylamino]-benzenesulfonamide (Compound CXXVI)

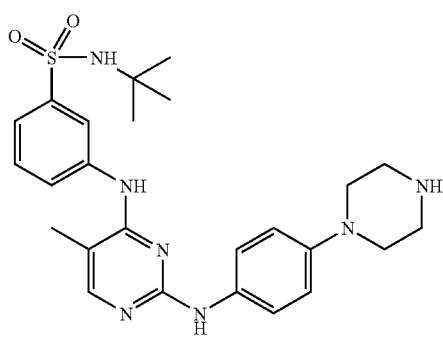

CXXVI

A mixture of intermediate 33 (355 mg, 1.0 mmol), tert-butyl 4-(4-aminophenyl)piperazine-1-carboxylate (278 mg, 1.0 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was dissolved in CH$_2$Cl$_2$ (10 mL) and trifuloroacetic acid (2 mL) was added. The mixture was stirred for 4 h at room temperature before 10% NaOH was added. The organic layer was separated and aqueous was extracted with CH$_2$Cl$_2$ (10 mL×2). The combined organic layers were dried (Na$_2$SO$_4$). The solvent was removed in vacuo. The residue was purified by HPLC to afford the title compound (62 mg, 12%) as a white solid.

$^1$H NMR (500 MHz, DMSO-d$_6$): δ 1.10 (s, 9H), 2.18 (s, 3H), 3.20 (br, 4H), 3.33 (br, 4H), 6.94 (d, J=9.0 Hz, 2H), 7.25 (d, J=9.0 Hz, 2H), 7.57 (t, J=8.0 Hz, 1H), 7.63 (s, 1H), 7.71 (d, J=8.1 Hz, 1H), 7.87 (br, 1H), 7.92 (br, 1H), 7.96 (br, 1H), 9.30 (br, 1H), 9.96 (s, 1H), 10.46 (s, 1H). MS (ES+): m/z 496 (M+H)$^+$.

Example 186

N-tert-Butyl-3-(2-{4-[4-(2-hydroxy-ethyl)-piperazin-1-yl]-phenylamino}-[5-methyl-pyrimidin-4-ylamino]-benzenesulfonamide (Compound CXXVII)

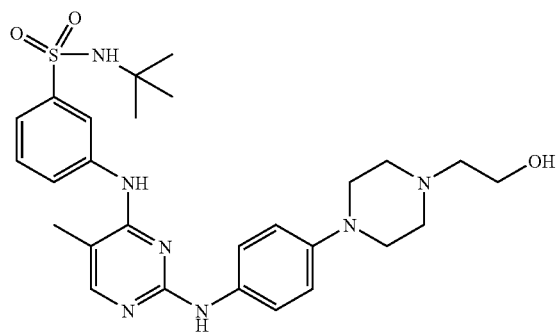

CXXVII

The above-described compound CXXVI (31 mg, 0.06 mmol) was dissolved in DMF (10 mL) followed by adding 2-bromoethanol (16 mg, 0.13 mmol) and diisopropylethylamine (33 mg, 0.25 mmol). The mixture was stirred for 48 h at room temperature. Solvent was removed in vacuo and residue was dissolved in EtOAc (20 mL). The solution was washed with saturated NaHCO$_3$ and brine. The combined organic layers were dried and concentrated until 2 mL solution followed by adding Et$_2$O (20 mL). The solid was collected by centrifugation and transferred to its HCl salt (10.7 mg, 30%).

$^1$H NMR (500 MHz, DMSO-d$_6$): δ 1.09 (s, 9H), 2.17 (s, 3H), 3.12-3.23 (m, 4H), 3.56-3.60 (m, 2H), 3.69-3.74 (m, 2H), 3.83 (br, 2H), 4.13 (br, 2H), 6.94 (d, J=9.0 Hz, 2H), 7.25 (d, J=9.0 Hz, 2H), 7.57 (t, J=8.0 Hz, 1H), 7.63 (s, 1H), 7.71 (d, J=8.1 Hz, 1H), 7.87 (br, 1H), 7.93 (br, 1H), 7.95 (br, 1H), 9.98 (s, 1H), 10.53 (s, 1H), 10.75 (br, 1H). MS (ES+): m/z 540 (M+H)$^+$.

Example 187

N-tert-Butyl-3-[5-methyl-2-(3-piperazin-1-yl-phenylamino)-pyrimidin-4-ylamino]-benzenesulfonamide (Compound CXXVIII)

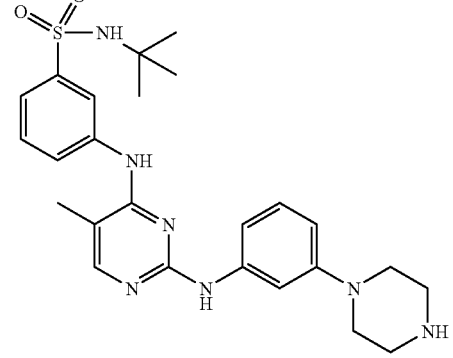

CXXVIII

A mixture of intermediate 33 (240 mg, 0.67 mmol), tert-butyl 4-(3-aminophenyl)piperazine-1-carboxylate (166 mg, 0.6 mmol), Pd$_2$(dba)$_3$ (55 mg, 0.06 mmol), Xantphos (104 mg, 0.18 mmol) and cesium carbonate (782 mg, 2.4 mmol) were suspended in dioxane (100 mL) and heated at reflux under the argon atmosphere for 20 h. The mixture was filtered and the filtrate concentrated in vacuo. The residue was dissolved in CH$_2$Cl$_2$ (10 mL) and trifuloroacetic acid (2 mL) was added. The mixture was stirred for 4 h at room temperature before 10% NaOH was added. The organic layer was separated and aqueous was extracted with CH$_2$Cl$_2$ (10 mL×2). The combined organic layers were dried (Na$_2$SO$_4$). The solvent was removed in vacuo. The residue was purified by HPLC to afford the title compound (18 mg, 6%) as a white solid.

$^1$H NMR (500 MHz, DMSO-d$_6$): δ 1.10 (s, 9H), 2.19 (s, 3H), 3.17 (br, 4H), 3.27-3.29 (m, 4H), 6.80 (d, J=8.1 Hz, 1H), 6.87 (br, 1H), 6.96 (d, J=8.1 Hz, 1H), 7.16 (t, J=8.1 Hz, 1H), 7.53 (t, J=8.3 Hz, 1H), 7.61 (s, 1H), 7.70 (d, J=7.8 Hz, 1H), 7.94 (br, 3H), 9.19 (br, 2H), 9.93 (s, 1H), 10.48 (s, 1H). MS (ES+): m/z 496 (M+H)$^+$.

Example 188

N-tert-Butyl-3-(2-{3-[4-(2-hydroxy-ethyl)-piperazin-1-yl]-phenylamino}-[5-methyl-pyrimidin-4-ylamino]-benzenesulfonamide (Compound CXXIX)

CXXIX

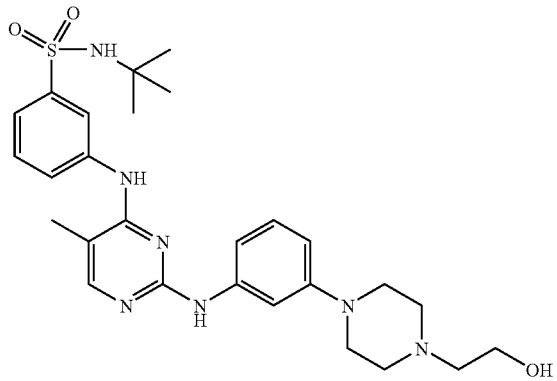

The above-described compound CXXVI (12 mg, 0.024 mmol) was dissolved in DMF (10 mL) followed by adding 2-bromoethanol (6.1 mg, 0.048 mmol) and diisopropylethylamine (12 mg, 0.092 mmol). The mixture was stirred for 48 h at room temperature. Solvent was removed in vacuo and residue was dissolved in EtOAc (20 mL). The solution was washed with saturated NaHCO$_3$ and brine. The combined organic layers were dried and concentrated until 2 mL solution followed by adding Et$_2$O (20 mL). The solid was collected by centrifugation and transferred to its HCl salt (7 mg, 51%).

$^1$H NMR (500 MHz, DMSO-d$_6$): δ 1.09 (s, 9H), 2.19 (s, 3H), 3.12-3.22 (m, 4H), 3.56-3.60 (m, 2H), 3.69-3.74 (m, 2H), 3.81 (br, 2H), 4.12 (br, 2H), 6.80 (br, 1H), 6.88 (br, 1H), 6.96 (br, 1H), 7.16 (br, 1H), 7.57 (br, 1H), 7.60 (s, 1H), 7.69 (d, J=7.8 Hz, 1H), 7.94 (br, 3H), 9.94 (s, 1H), 10.49 (s, 1H). MS (ES+): m/z 540 (M+H)$^+$.

Example 189

N$^2$-(4-(1H-Pyrazol-1-yl)phenyl)-N$^4$-(3-tert-butylphenyl)-5-methylpyrimidine-2,4-diamine (Compound CXXX)

CXXX

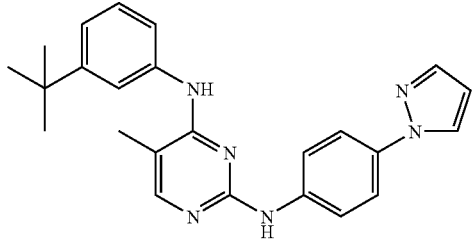

A mixture of intermediate 41 (580 mg, 2.1 mmol) and 4-(1H-pyrazol-1-yl)benzenamine (335 mg, 2.1 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (31 mg, 4%) as a yellow solid.

$^1$H NMR (500 MHz, DMSO-d$_6$): δ 1.24 (s, 9H), 2.18 (s, 3H), 6.53 (t, J=2.0 Hz, 1H), 7.33 (d, J=8.0 Hz, 1H), 7.38 (t, J=7.9 Hz, 1H), 7.44 (s, 1H), 7.47 (d, J=8.2 Hz, 1H), 7.50 (d, J=8.9 Hz, 2H), 7.67 (d, J=8.9 Hz, 2H), 7.73 (s, 1H), 7.95 (s, 1H), 8.43 (d, J=2.4 Hz, 1H), 9.81 (br s, 1H), 10.67 (s, 1H). MS (ES+): m/z 399 (M+H)$^+$.

Example 190

N$^4$-(7-Chloro-1H-indol-4-yl)-5-methyl-N$^2$-(4-((piperazin-1-yl)methyl)phenyl)-pyrimidine-2,4-diamine (Compound CXXXI)

CXXXI

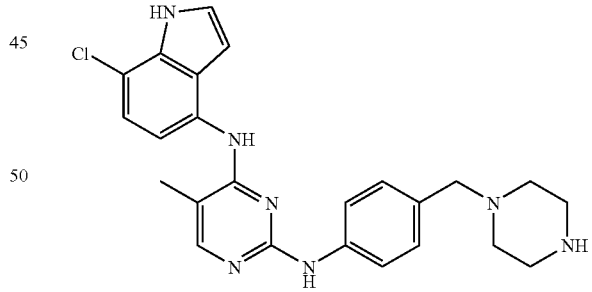

A mixture of intermediate 40 (150 mg, 0.37 mmol), 4-bromo-7-chloro-1H-indole (87 mg, 0.37 mmol), Pd$_2$(dba)$_3$ (38 mg, 0.04 mmol), Xantphos (76 mg, 0.12 mmol) and cesium carbonate (521 mg, 1.6 mmol) were suspended in dioxane (50 mL) and heated at reflux under the argon atmosphere for 20 h. The mixture was filtered and the filtrate concentrated in vacuo. The residue was dissolved in CH$_2$Cl$_2$ (10 mL) and trifuloroacetic acid (2 mL) was added. The mixture was stirred for 4 h at room temperature before 10% NaOH was added. The organic layer was separated and aqueous was extracted with CH$_2$Cl$_2$ (10 mL×2). The combined organic layers were dried (Na$_2$SO$_4$). The solvent was removed in vacuo. The residue was purified by HPLC to afford the title compound (26 mg, 15%) as a white solid.

$^1$H NMR (500 MHz, DMSO-d$_6$): δ 2.21 (s, 3H), 3.30 (br, 4H), 3.50 (br, 4H), 4.42 (br, 2H), 6.91 (s, 1H), 7.11 (d, J=8.3 Hz, 1H), 7.40 (d, J=7.5 Hz, 1H), 7.42 (t, J=2.7 Hz, 1H), 7.70 (br, 4H), 8.03 (s, 1H), 9.87 (br, 1H), 9.95 (s, 1H), 10.64 (s, 1H), 11.64 (s, 1H). MS (ES+): m/z 448 (M+H)$^+$.

Example 191

N$^4$-(3-tert-Butylphenyl)-5-methyl-N$^2$-(4-(2-methyl-1H-imidazol-1-yl)phenyl)-pyrimidine-2,4-diamine (Compound CXXXII)

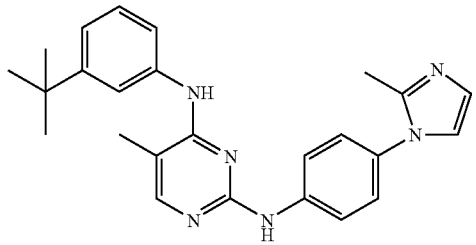

CXXXII

A mixture of intermediate 41 (180 mg, 0.65 mmol) and 4-(2-methyl-1H-imidazol-1-yl)benzenamine (113 mg, 0.65 mmol), Pd$_2$(dba)$_3$ (55 mg, 0.06 mmol), Xantphos (104 mg, 0.18 mmol) and cesium carbonate (782 mg, 2.4 mmol) were suspended in dioxane (100 mL) and heated at reflux under the argon atmosphere for 20 h. The mixture was filtered and the filtrate concentrated in vacuo. The residue was purified by HPLC to afford the title compound (78 mg of HCl salt, 27%) as a white solid.

$^1$H NMR (500 MHz, DMSO-d$_6$): δ 1.26 (s, 9H), 2.21 (s, 3H), 2.50 (s, 3H), 7.31-7.36 (m, 1H), 7.40 (t, J=7.8 Hz, 1H), 7.44 (d, J=8.9 Hz, 2H), 7.47 (d, J=8.0 Hz, 2H), 7.65 (d, J=8.9 Hz, 2H), 7.75 (d, J=2.1 Hz, 1H), 7.79 (d, J=2.1 Hz, 2H), 8.03 (s, 1H), 10.02 (s, 1H), 11.26 (s, 1H). MS (ES+): m/z 413 (M+H)$^+$.

Example 192

4-(4-Methyl-1H-imidazol-1-yl)benzenamine (Intermediate 62)

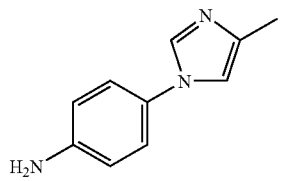

62

To a solution of 1-fluoro-4-nitrobenzene (1.7 g, 12 mmol) in DMF (100 mL) was added 4-methyl-1H-imidazole (0.82 g, 10 mmol) and K$_2$CO$_3$ (11 g, 80 mmol). The mixture was heated at reflux under the argon atmosphere for 20 h. The mixture was filtered and the filtrate concentrated in vacuo. The residue was dissolved in EtOAc (100 mL) and washed with brine (100 mL×2). The organic layer was dried and concentrated. The solid was dissolved in MeOH and bubbled with Ar for 2 min. before adding 10% Pd—C. The hydrogenation was finished in 4 h. The catalyst was removed by filtration and solvent was removed in vacuo to afford title compound (1.5 g, 87%) as brown solid.

Example 193

N$^4$-(3-tert-Butylphenyl)-5-methyl-N$^2$-(4-(4-methyl-1H-imidazol-1-yl)phenyl) pyrimidine-2,4-diamine (Compound CXXXIII)

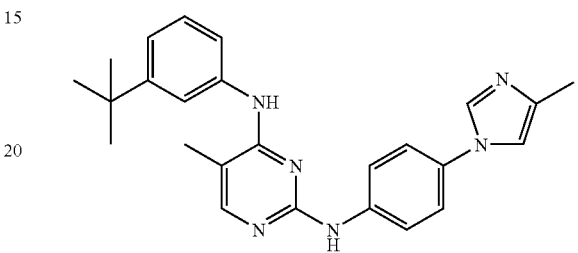

CXXXIII

A mixture of intermediate 41 (318 mg, 1.15 mmol) and intermediate 62 (200 mg, 1.15 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (66 mg of HCl salt, 20%) as a white solid.

$^1$H NMR (500 MHz, DMSO-d$_6$): δ 1.26 (s, 9H), 2.19 (s, 3H), 2.36 (s, 3H), 7.30 (d, J=7.9 Hz, 1H), 7.41 (d, J=7.9 Hz, 1H), 7.44 (t, J=1.8 Hz, 1H), 7.54 (d, J=7.9 Hz, 1H), 7.59 (d, J=9.0 Hz, 2H), 7.68 (d, J=9.0 Hz, 2H), 7.94 (s, 1H), 7.99 (s, 1H), 9.53 (d, J=1.3 Hz, 1H), 9.72 (br s, 1H), 10.81(br s, 1H). MS (ES+): m/z 413 (M+H)$^+$.

Example 194 tert-Butyl 4-(4-aminophenyl)piperidine-1-carboxylate (Intermediate 63)

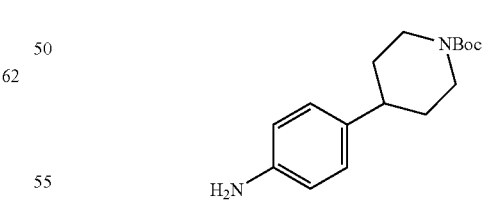

63

To a solution of 4-(4-nitrophenyl)piperidine (412 mg, 2 mmol) in CH2Cl2 (100 mL) was added di-tert-butyl carbonate (480 mg, 2.2 mmol) and N,N-dimethylpyridin-4-amine (50 mg, 0.4 mmol). The mixture was stirred for 20 h at room temperature. The mixture was added saturated NaHCO3 (100 mL). The organic layer was separated and aqueous was extracted with CH2Cl2 (50 mL×2). The combined organic solution was dried and concentrated in vacuo. The residue was dissolved in MeOH and bubbled with Ar for 2 min. before adding 10% Pd—C. The hydrogenation was finished in 4 h.

The catalyst was removed by filtration and solvent was removed in vacuo to afford title compound (460 mg, 83%) as white solid.

Example 195

N⁴-(3-tert-Butylphenyl)-5-methyl-N²-(4-(piperidin-4-yl)phenyl)pyrimidine-2,4-diamine (Compound CXXXIV)

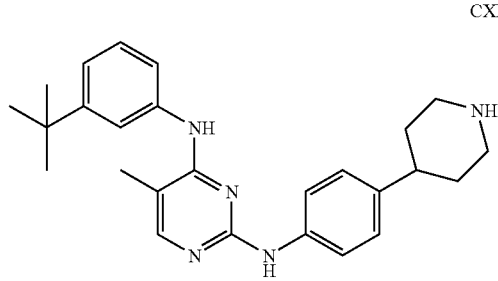

CXXXIV

A mixture of intermediate 41 (170 mg, 0.6 mmol) and intermediate 63 (170 mg, 0.6 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO₄ and filtered. The filtrate was concentrated in vacuo and the crude product purified by HPLC to afford the title compound (8 mg, 3%) as a white solid.

$^1$H NMR (500 MHz, DMSO-d₆): δ 1.26 (s, 9H), 1.76-1.88 (m, 4H), 2.17 (s, 3H), 2.76-2.81 (m, 1H), 2.93-3.00 (m, 2H), 3.36-3.40 (m, 2H), 7.07 (d, J=8.5 Hz, 1H), 7.30-7.36 (m, 4H), 7.44 (s, 1H), 7.46 (d, J=8.7 Hz, 1H), 7.91 (s, 1H), 8.84 (br s, 1H), 8.92 (br s, 1H), 9.73 (s, 1H), 10.45 (s, 1H). MS (ES+): m/z 416 (M+H)⁺.

Example 196

N⁴-(3-tert-Butylphenyl)-5-methyl-N²-(4-(1-morpholinoethyl)phenyl)pyrimidine-2,4-diamine (Compound CXXXV)

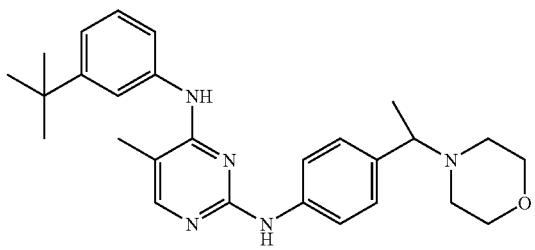

CXXXV

A mixture of intermediate 41 (276 mg, 1.0 mmol) and 4-(1-morpholinoethyl)benzenamine (210 mg, 1.0 mmol), Pd₂(dba)₃ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (17 mg of HCl salt, 4%) as a yellow solid.

$^1$H NMR (500 MHz, DMSO-d₆): δ 1.26 (s, 9H), 1.66 (d, J=6.8 Hz, 3H), 2.19 (s, 3H), 2.79 (br, 2H), 2.92 (br, 1H), 3.61-3.64 (m, 2H), 3.77-3.82 (m, 2H), 3.94-3.99 (m, 2H), 7.32 (d, J=7.8 Hz, 1H), 7.42 (t, J=1.9 Hz, 1H), 7.43 (d, J=7.8 Hz, 1H), 7.46-7.52 (m, 5H), 7.97 (s, 1H), 9.86 (s, 1H), 10.78 (s, 1H), 11.72(br s, 1H). MS (ES+): m/z 446 (M+H)⁺.

Example 197

5-Bromo-2-methyl-benzenesulfonyl chloride (Intermediate 64)

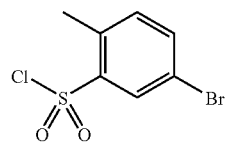

64

Bromide (1.99 g, 11.61 mmol) was stirred vigorously and treated with chlorosulfonic acid (1.55 mL, 23.22 mmol). Once addition was complete, resulting red syrup was heated to 60° C. Reaction TLC after 10 min showed no starting material and reaction was quenched by pouring onto ice. Product was extracted by washing with EtOAc (2×150 mL). Organic phase dried over Na₂SO₄, filtered and evaporated to yellow oil (2.2 g, 70%).

Example 198

5-Bromo-2,N-dimethyl-benzenesulfonamide (Intermediate 65)

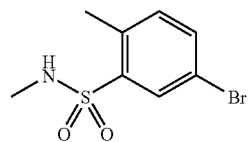

65

A stirring suspension of intermediate 64 (0.43 g, 1.58 mmol) in DCM (5 mL) was treated with 2.0M methylamine solution in THF (2.4 mL, 4.8 mmol). After 16 h reaction solvents were removed and resulting residue diluted with EtOAc (150 mL) and washed with water. Organic phase dried over Na₂SO₄, filtered and evaporated to white solids (0.37 g, 89%).

Example 199

2,N-Dimethyl-5-{5-methyl-2-[4-(2-pyrrolidin-1-yl-ethoxy)-phenylamino]-pyrimidin-4-ylamino}-benzenesulfonamide (Compound CXXXVI)

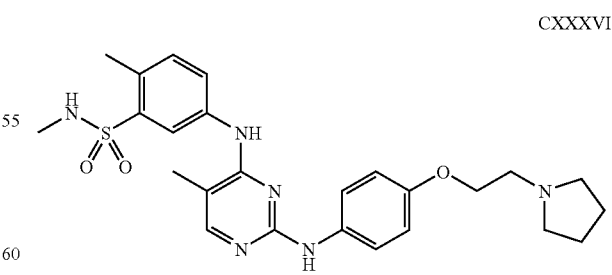

CXXXVI

A mixture of intermediate 65 (0.14 g, 0.52 mmol), intermediate 38 (0.14 g, 0.43 mmol), Pd₂(dba)₃ (0.040 g, 0.043 mmol), Xantphos (0.050 g, 0.087 mmol) and cesium carbonate (0.43 g, 1.3 mmol) were suspended in dioxane (10 mL), sealed in a microwave reaction tube and irradiated with microwaves at 160° C. for 15 min. The reaction mixture was cooled to room temperature and centrifuged down. The reaction was decanted and the organic phase concentrated in vacuo. The residue was purified by HPLC to afford the title compound as a white solid (0.052 g, 24%).

¹H NMR (500 MHz, DMSO-d$_6$): δ 1.66-1.70 (m, 4H), 2.08 (s, 3H), 2.43 (d, J=4.9 Hz, 3H), 2.5 (br s, 4H), 2.78, (t, J=5.7 Hz), 4.00 (t, J=5.9 Hz), 6.79 (d, J=9.0 Hz, 2H), 7.31 (d, J=9.7 Hz, 1H), 7.42 (q, J=9.8 Hz, 1H), 7.49 (d, J=9.0 Hz, 1H), 7.87 (s, 1H), 7.97 (d, J=2.3 Hz, 1H), 8.07-8.09 (m, 1H), 8.49 (s, 1H), 8.75 (s, 1H). MS (ES+): m/z 497 (M+H)⁺.

Example 200

5-Bromo-N-tert-butyl-2-methyl-benzenesulfonamide (Intermediate 66)

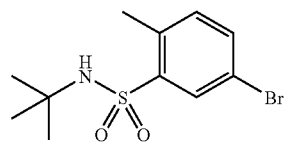

A stirring suspension of intermediate 64 (1.22 g, 4.5 mmol) in DCM (25 mL) was treated with tert-butylamine (1.4 mL, 13.6 mmol). After 16 h, reaction solvents were removed and resulting solids triturated with water. Solids were dried under vacuum overnight (1.3 g, 94%).

Example 201

N-tert-Butyl-5-(2-chloro-5-methyl-pyrimidin-4-ylamino)-2-methyl-benzenesulfonamide (Intermediate 67)

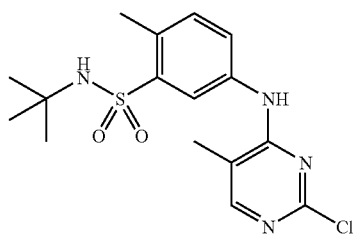

A mixture of intermediate 66 (0.90 g, 2.96 mmol), 2-chloro-5-methyl-pyrimidin-4-ylamine (0.33 g, 2.28 mmol), Pd$_2$(dba)$_3$ (0.21 g, 0.23 mmol), Xantphos (0.264 g, 0.46 mmol) and cesium carbonate (2.2 g, 6.8 mmol) were suspended in dioxane (15 mL), sealed in a microwave reaction tube and irradiated with microwaves at 160° C. for 15 min. The reaction mixture was cooled to room temperature and centrifuged down. The reaction was decanted and the organic phase concentrated in vacuo. The residue was purified on silica gel column to afford the title compound as a white solid (0.12 g, 14%).

Example 202

N-tert-Butyl-5-[2-(4-imidazol-1-yl-phenylamino)-5-methyl-pyrimidin-4-ylamino]-2-methyl-benzenesulfonamide (Compound CXXXVII)

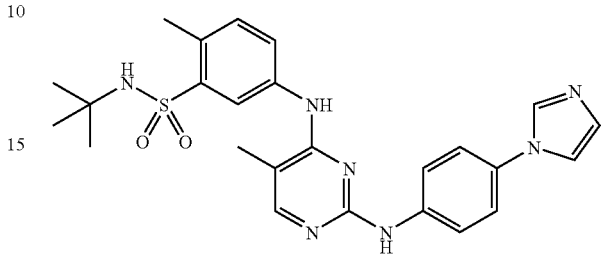

CXXXVII

A mixture of intermediate 67 (0.113 g, 0.31 mmol), 4-imidazol-1-yl-phenylamine (0.059 g, 0.37 mmol), Pd$_2$(dba)$_3$ (0.028 g, 0.03 mmol), Xantphos (0.036 g, 0.06 mmol) and cesium carbonate (0.3 g, 0.92 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.052 g, 24%).

¹H NMR (500 MHz, DMSO-d$_6$): δ 1.11 (s, 9H), 2.13 (s, 3H), 2.58 (s, 3H), 7.07 (s, 1H), 7.34 (d, J=8.5 Hz, 1H), 7.42 (d, J=8.9 Hz, 2H), 7.48 (s, 1H), 7.60 (s, 1H), 7.78 (d, J=8.9 Hz, 2H), 7.94 (s, 1H), 7.98-8.00 (m, 1H), 8.09 (s, 1H), 8.12 (d, J=2.3 Hz, 1H), 8.56 (s, 1H), 9.16 (s, 1H). MS (ES+): m/z 492 (M+H)⁺.

Example 203

N-tert-Butyl-3-{5-methyl-2-[4-(pyrrolidine-1-carbonyl)-phenylamino]-pyrimidin-4-ylamino}-benzenesulfonamide (Compound CXXXVIII)

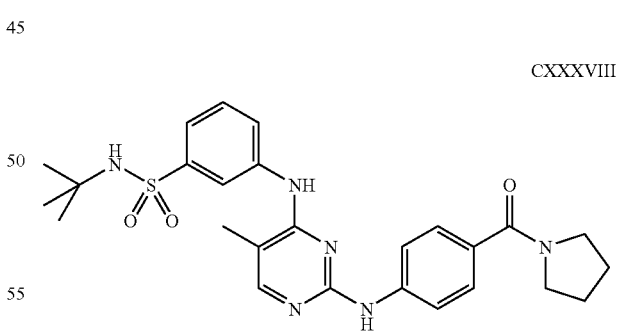

CXXXVIII

A mixture of intermediate 33 (0.11 g, 0.32 mmol), (4-amino-phenyl)-pyrrolidin-1-yl-methanone (0.072 g, 0.38 mmol), Pd$_2$(dba)$_3$ (0.029 g, 0.032 mmol), Xantphos (0.037 g, 0.063 mmol) and cesium carbonate (0.3 g, 0.95 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.040 g, 25%).

<sup>1</sup>H NMR (500 MHz, DMSO-d<sub>6</sub>): δ 1.11 (s, 9H), 1.8 (br s, 4H), 2.14 (s, 3H), 3.44 (t, J=6.6 Hz, 4H), 7.38 (d, J=9.0 Hz, 2H), 7.52-7.54 (m, 2H), 7.56 (s, 1H), 7.70 (d, J=9.8 Hz, 2H), 7.98 (s, 1H), 8.08-8.10 (m, 2H), 8.60 (br s, 1H), 9.24 (s, 1H). MS (ES+): m/z 509 (M+H)$^+$.

Example 204

N-tert-Butyl-3-{5-methyl-2-[4-(morpholine-4-carbonyl)-phenylamino]-pyrimidin-4-ylamino}-benzenesulfonamide (Compound CXXXIX)

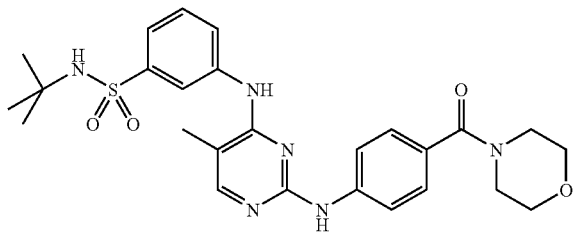

CXXXIX

A mixture of intermediate 33 (0.13 g, 0.37 mmol), (4-amino-phenyl)-morpholin-4-yl-methanone (0.092 g, 0.45 mmol), Pd$_2$(dba)$_3$ (0.034 g, 0.037 mmol), Xantphos (0.043 g, 0.075 mmol) and cesium carbonate (0.37 g, 1.1 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.065 g, 33%).

<sup>1</sup>H NMR (500 MHz, DMSO-d<sub>6</sub>): δ 1.11 (s, 9H), 2.14 (s, 3H), 3.49 (br s, 4H), 3.59 (br s, 4H), 5.75 (s, 1H), 7.25 (d, J=9.0 Hz, 2H), 7.52-7.54 (m, 2H), 7.56 (s, 1H), 7.71 (d, J=9.0 Hz, 2H), 7.98 (s, 1H), 8.06-8.08 (m, 2H), 8.65 (br s, 1H), 9.26 (s, 1H). MS (ES+): m/z 525 (M+H)$^+$.

Example 205

N-tert-Butyl-3-{5-methyl-2-[4-(piperazine-1-carbonyl)-phenylamino]-pyrimidin-4-ylamino}-benzenesulfonamide (Compound CXL)

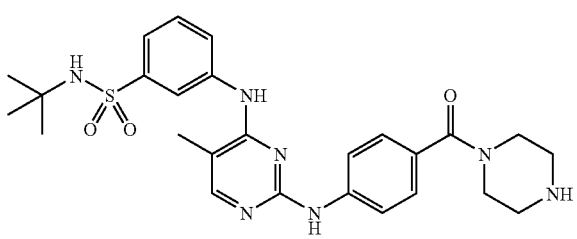

CXL

A mixture of intermediate 33 (0.12 g, 0.33 mmol), 4-(4-amino-benzoyl)-piperazine-1-carboxylic acid tert-butyl ester (0.12 g, 0.45 mmol), Pd$_2$(dba)$_3$ (0.030 g, 0.037 mmol), Xantphos (0.038 g, 0.075 mmol) and cesium carbonate (0.33 g, 1.1 mmol) were suspended in dioxane (6 mL), sealed in a microwave reaction tube and irradiated with microwaves at 160° C. for 15 min. The reaction was decanted and the organic phase concentrated in vacuo. The residue was purified by silica gel chromatography (25%-i 00% EtOAc in Hexanes). Product was then treated with 20 mL of 20% TFA solution in DCM. Solvents then removed by rotary evaporation. Resulting material purified by HPLC to afford the title compound as a white solid (0.045 g, 26%).

<sup>1</sup>H NMR (500 MHz, DMSO-d<sub>6</sub>): δ 1.11 (s, 9H), 2.14 (s, 3H), 2.82 (br s, 4H), 3.48 (br s, 4H), 7.24 (d, J=9.0 Hz, 2H), 7.51-7.53 (m, 2H), 7.55 (s, 1H), 7.71 (d, J=9.0 Hz, 2H), 7.94 (s, 1H), 8.06-8.08 (m, 2H), 8.65 (br s, 1H), 9.25 (s, 1H). MS (ES+): m/z 524 (M+H)$^+$.

Example 206 tert-Butyl 4-(4-(4-(3-methoxyphenylamino)-5-methylpyrimidin-2-ylamino)phenoxy)piperidine-1-carboxylate (Intermediate 68)

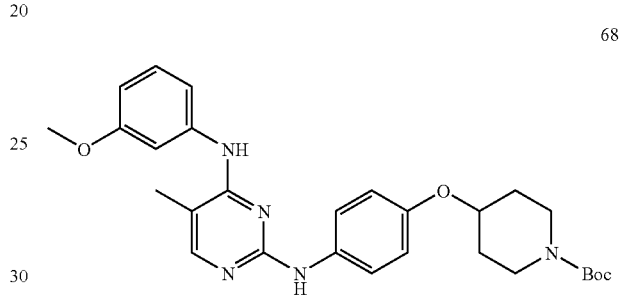

68

A mixture of 1-bromo-3-methoxybenzene (69.5 µL, 0.56 mmol), intermediate 42 (205 mg, 0.51 mmol), Pd$_2$(dba)$_3$ (23 mg, 0.03 mmol), Xantphos (33 mg, 0.06 mmol) and cesium carbonate (359 mg, 1.10 mmol) in dioxane (3 mL) was irradiated in the microwave at 160° C. for 20 min. The reaction mixture was cooled to room temperature, filtered and the filtrate rinsed with DCM and MeOH. The combined liquids were concentrated in vacuo, and purified using gradient flash chromatography (0-100% ethyl acetate in hexanes) to afford the title compound as a beige solid (215 mg, 83%).

Example 207

3-(2-(4-(Piperidin-4-yloxy)phenylamino)-5-methylpyrimidin-4-ylamino)phenol (Compound CXLI)

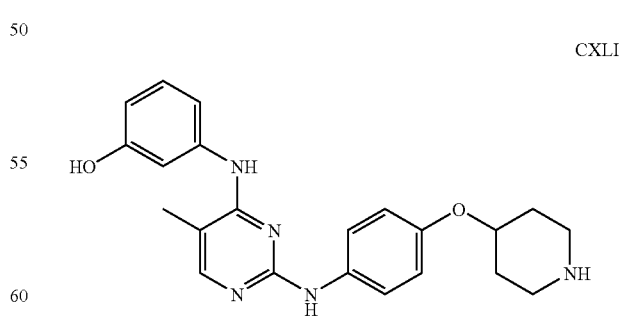

CXLI

To a mixture of intermediate 68 (215 mg, 0.42 mmol) in DCM (4 mL) was added BBr$_3$ (120 µL, 1.27 mmol) and stirred at room temperature for 64 h. The reaction was quenched with MeOH and concentrated in vacuo. The residue was purified by preparative HPLC and the fractions concentrated in vacuo to afford the TFA salt of the title compound (116 mg, 56%). The TFA salt was taken up in MeOH and passed through SPE PL-HCO₃ MP-Resin cartridges, concentrated in vacuo, triturated with ether, and filtered to provide the title compound as a white solid (31 mg, 69% recovery).
$^1$H NMR (500 MHz, DMSO-$d_6$): δ 1.51-1.60 (m, 2H), 1.90-1.98 (m, 2H), 2.07 (s, 3H), 2.70-2.78 (m, 2H), 3.02-3.09 (m, 2H), 4.28-4.36 (m, 1H), 6.48 (dd, J=8.1, 2.2 Hz, 1H), 6.79 (d, J=9.1 Hz, 2H), 7.06-7.11 (m, 2H), 7.16 (d, J=8.5 Hz, 1H), 7.57 (d, J=9.1 Hz, 2H), 7.82 (s, 1H), 8.08 (s, 1H), 8.73 (s, 1H), 9.27 (br s, 1H). MS (ES+): m/z 392 (M+H)⁺.

Example 208

(2-Chloro-5-methyl-pyrimidin-4-yl)-(4-fluoro-3-methoxy-phenyl)-amine (Intermediate 69)

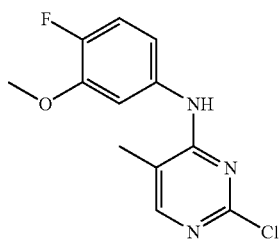

A mixture of 2-chloro-5-methyl-pyrimidin-4-ylamine (1.2 g, 8.1 mmol), 4-bromo-1-fluoro-2-methoxy-benzene (1.8 g, 8.9 mmol), Pd₂(dba)₃ (0.74 g, 0.81 mmol), Xantphos (0.93 g, 1.6 mmol) and cesium carbonate (7.88 g, 24.2 mmol) were suspended in dioxane (60 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel to afford the title compound (0.3 g, 14%) as a beige solid.

Example 209

N⁴-(4-Fluoro-3-methoxy-phenyl)-5-methyl-N²-[4-(2-pyrrolidin-1-yl-ethoxy)-phenyl]-pyrimidine-2,4-diamine (Compound CXLII)

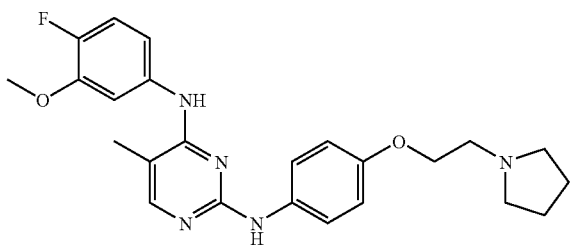

A mixture of intermediate 69 (0.1 g, 0.37 mmol) and 4-(2-pyrrolidin-1-yl-ethoxy)-phenylamine (0.16 g, 0.75 mmol) were suspended in acetic acid (10 mL) and heated to 110° C. for 16 h. The reaction mixture was cooled to room temperature and concentrated in vacuo. The residue was purified by HPLC to afford the title compound (0.03 g, 17%) as green solids. $^1$H NMR (500 MHz, DMSO-$d_6$): δ 1.88 (br s, 2H), 2.0 (br s, 2H), 2.15 (s, 3H), 3.08 (br s, 2H), 3.55 (br s, 4H), 3.7 (s, 3H), 4.32 (br s, 2H), 6.9 (d, J=7.9 Hz, 2H), 7.13 (br s, 1H), 7.21-7.25 (m, 1H), 7.32-7.34 (m, 3H), 7.89 (s, 1H), 9.78 (br s, 1H), 10.48 (br s, 1H), 10.92 (br s, 1H). MS (ES+): m/z 438 (M+H)⁺.

Example 210

(2-Chloro-pyrimidin-4-yl)-(3-methoxy-2-methyl-phenyl)-amine (Intermediate 70)

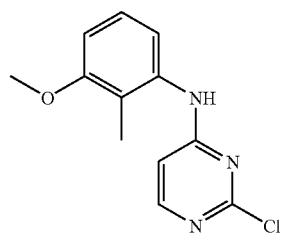

A mixture of 3-methoxy-2-methyl-phenylamine (0.68 g, 5 mmol) and 2,4-dichloro-pyrimidine (0.74 g, 5 mmol) were suspended in ethyl alcohol (10 mL) and stirred at room temperature for 20 h. The reaction mixture was diluted with DCM (50 mL), filtered and concentrated in vacuo. The residue was purified by silica gel column chromatography to afford the title compound (0.085 g, 7%) as yellow solids.

Example 211

N⁴-(3-Methoxy-2-methyl-phenyl)-N²-[4-(2-pyrrolidin-1-yl-ethoxy)-phenyl]-pyrimidine-2,4-diamine (Compound CXLIII)

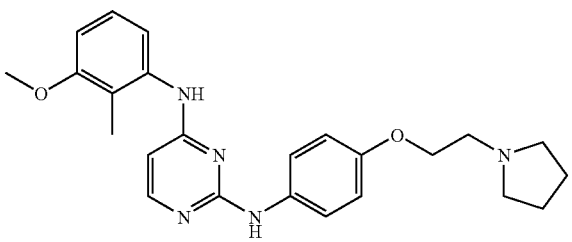

A mixture of intermediate 70 (0.08 g, 0.32 mmol) and 4-(2-pyrrolidin-1-yl-ethoxy)-phenylamine (0.13 g, 0.64 mmol) were suspended in acetic acid (10 mL) and heated to 80° C. for 16 h. The reaction mixture was cooled to room temperature and concentrated in vacuo. The residue was purified by HPLC to afford the title compound (0.03 g, 17%) as grey solids.
$^1$H NMR (500 MHz, DMSO-$d_6$): δ 1.89 (br s, 2H), 2.0 (br s, 4H), 3.08 (br s, 2H), 3.4 (br s, 4H), 3.54 (br s, 4H), 3.83 (s, 3H), 4.31 (br s, 2H), 6.86 (br s, 2H), 6.97 (d, J=8.1 Hz, 2H), 7.26 (t, J=8.1 Hz 1H), 7.34 (br s, 2H), 7.89 (s, 1H), 9.73 (br s, 1H), 10.62 (br s, 2H), 11.01 (br s, 1H). MS (ES+): m/z 420 (M+H)⁺.

Example 212

4-(4-Acetylamino-benzenesulfonyl)-piperidine-1-carboxylic acid tert-butyl ester (Intermediate 71)

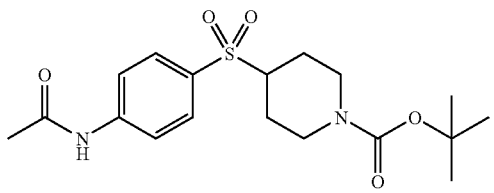

71

A mixture of 4-(4-bromo-benzenesulfonyl)-piperidine-1-carboxylic acid tert-butyl ester (4 g, 9.92 mmol), acetamide (0.88 g, 14.9 mmol), $Pd_2(dba)_3$ (0.46 g, 0.49 mmol), Xantphos (0.56 g, 0.99 mmol) and cesium carbonate (9.7 g, 29.8 mmol) were suspended in dioxane (60 mL) and heated at reflux under the argon atmosphere for 4 h. The reaction mixture was cooled to room temperature and poured onto ice. Resulting yellow solids collected by filtration and dried. Crude product was purified by flash chromatography on silica gel to afford the title compound as a beige solid (3.12 g, 82%).

Example 213

4-(4-Amino-benzenesulfonyl)-piperidine-1-carboxylic acid tert-butyl ester (Intermediate 72)

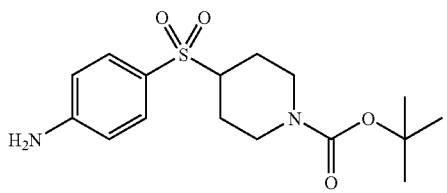

72

A suspension of intermediate 71 (2.6 g, 6.7 mmol) was diluted with 60 mL of Claisen's alkali (88 g KOH dissolved in 63 mL $H_2O$ diluted up to 250 mL with MeOH) and heated to 90° C. After 2 h, reaction was removed from heating, cooled to room temperature and diluted with water (50 mL). Grey solids collected by suction filtration, washed with water and dried overnight (2.2 g, 97%).

Example 214

$N^4$-(4-Chloro-3-methoxy-phenyl)-5-methyl-$N^2$-[4-(piperidine-4-sulfonyl)-phenyl]-pyrimidine-2,4-diamine (Compound CXLIV)

CXLIV

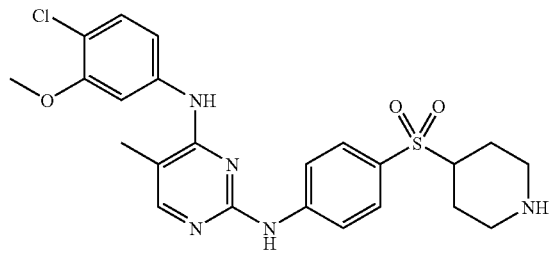

A mixture of intermediate 31 (0.14 g, 0.51 mmol), intermediate 72 (0.19 g, 0.56 mmol), $Pd_2(dba)_3$ (0.046 g, 0.051 mmol), Xantphos (0.59 g, 0.1 mmol) and cesium carbonate (0.5 g, 1.52 mmol) were suspended in dioxane (8 mL) and microwaved at 160° C. for 15 min. The reaction mixture was cooled to room temperature and centrifuged down. Solvents were then decanted and evaporated. Resulting residue was purified by flash chromatography on silica gel to afford the N-protected precursor of title compound. These solids were treated with 20% TFA in DCM solution and immediately evaporated. Residue was dissolved in minimum amount to EtOAc and added dropwise to large excess of diethyl ether. Resulting light yellow powder was collected by filtration and dried (0.16 g, 55%).

$^1$H NMR (500 MHz, DMSO-$d_6$): δ 1.61-1.69 (m, 2H), 1.98-2.01 (m, 2H), 2.16 (s, 3H), 2.86 (q, J=12 Hz, 2H), 3.35 (d, J=12.6 Hz, 2H), 3.64 (tt, J=11.7 Hz, J=3.8 Hz, 1H), 3.79 (s, 3H), 7.34 (dd, J=8.7 Hz, J=2.0 Hz, 1H), 7.39-7.41 (m, 2H), 7.6 (d, J=8.9 Hz, 2H), 7.91 (d, J=8.9 Hz, 2H), 8.02 (s, 1H), 8.19-8.21 (m, 1H), 8.6-8.63 (m, 1H), 8.89 (br s, 1H). MS (ES+): m/z 488 (M+H)$^+$.

Example 215

(4-Chloro-3-methyl-phenyl)-(2-chloro-5-methyl-pyrimidin-4-yl)-amine (Intermediate 73)

73

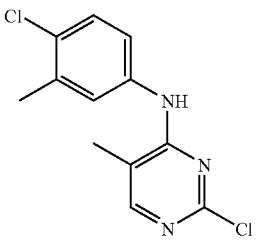

A mixture of 2-chloro-5-methyl-pyrimidin-4-ylamine (0.34 g, 2.34 mmol), 4-bromo-1-chloro-2-methyl-benzene (0.58 g, 2.8 $^{mmol}$), $Pd_2(dba)_3$ (0.21 g, 0.23 mmol), Xantphos (0.47 g, 0.47 mmol) and cesium carbonate (2.3 g, 7 mmol) were suspended in dioxane (9 mL) microwaved at 160° C. for 20 min. The reaction mixture was cooled to room temperature and centrifuged down. Solvents were then decanted and evaporated. Resulting residue was purified by flash chromatography on silica gel to afford title compound as yellow solids (0.24 g, 38%).

Example 216

$N^4$-(4-Chloro-3-methyl-phenyl)-5-methyl-$N^2$-[4-(piperidin-4-yloxy)-phenyl]-pyrimidine-2,4-diamine (Compound CXLV)

CXLV

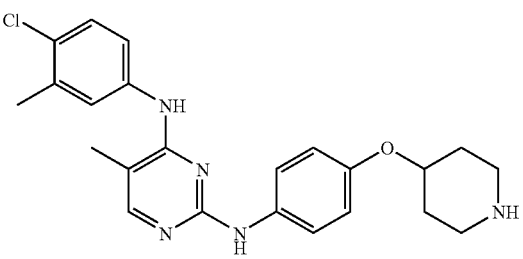

A mixture of intermediate 73 (0.071 g, 0.27 mmol) and 4-(4-amino-phenoxy)-piperidine-1-carboxylic acid tert-butyl ester (0.1 g, 0.35 mmol) were diluted with HOAc (5 mL) and microwaved at 150° C. for 15 min. Solvents then removed and resulting residue purified on HPLC. Title compound isolated as white solids (0.025 g, 22%).

¹H NMR (500 MHz, DMSO-d$_6$): δ 1.76-1.83 (m, 2H), 2.05-2.09 (m, 2H), 2.13 (s, 3H), 2.27 (s, 3H), 3.10 (br s, 2H), 3.16 (br s, 2H), 4.58-4.61 (m, 1H), 6.93 (d, J=9 Hz, 2H), 7.34-7.39 (m, 3H), 7.43-7.45 (m, 1H), 7.59 (s, 1H), 7.87 (s, 1H), 8.51 (br s, 1H), 8.55 (br s, 1H), 9.38 (br s, 1H), 10.0 (br s, 1H). MS (ES+): m/z 424 (M+H)$^+$.

Example 217

N-(3-Bromo-phenyl)-acetamide (Intermediate 74)

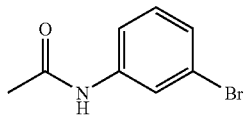

74

A solution of 3-bromo-phenylamine (1.04 g, 6 mmol) was treated with DIEA (2.3 mL, 13.3 mmol) and chilled to zero degrees. Acetyl chloride (0.47 mL, 6.7 mmol) was added dropwise via syringe. Reaction was allowed to return to room temperature and stir for 1 hour. Reaction was then poured onto water and washed once. Organic phase was evaporated to beige solids (1.25 g, 98%).

Example 218

N-[3-(2-Chloro-5-methyl-pyrimidin-4-ylamino)-phenyl]-acetamide (Intermediate 75)

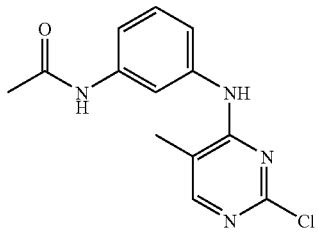

75

A mixture of 2-chloro-5-methyl-pyrimidin-4-ylamine (0.71 g, 4.9 mmol), intermediate 74 (1.25 g, 5.9 mmol), Pd$_2$(dba)$_3$ (0.45 g, 0.49 mmol), Xantphos (0.57 g, 0.98 mmol) and cesium carbonate (4.8 g, 14.7 mmol) were suspended in dioxane (40 mL) refluxed for 18 h. The reaction mixture was then cooled to room temperature, filtered and solvents evaporated. Resulting residue was purified by flash chromatography on silica gel to afford title compound as white solids (0.44, 32%).

Example 219

N-(3-{5-Methyl-2-[4-(piperidin-4-yloxy)-phenylamino]-pyrimidin-4-ylamino}-phenyl)-acetamide (Compound CXLVI)

CXLVI

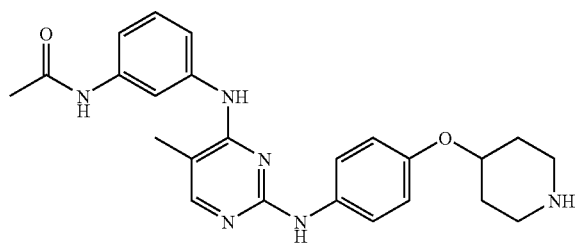

A mixture of intermediate 75 (0.074 g, 0.27 mmol) and 4-(4-amino-phenoxy)-piperidine-1-carboxylic acid tert-butyl ester (0.1 g, 0.35 mmol) were diluted with HOAc (5 mL) and microwaved at 150° C. for 15 min. Solvents then removed and resulting residue purified on HPLC. Title compound isolated as white solids (0.072 g, 62%).

¹H NMR (500 MHz, DMSO-d$_6$): δ 1.74-1.81 (m, 2H), 2.03-2.07 (m, 5H), 2.15 (s, 3H), 3.09 (br s, 2H), 3.24 (br s, 2H), 4.54-4.57 (m, 1H), 6.85 (d, J=8.8 Hz, 2H), 7.22 (d, J=7.7 Hz, 2H), 7.29-7.39 (m, 4H), 7.77 (s, 1H), 7.87 (s, 1H), 8.55 (br s, 1H), 8.60 (br s, 1H), 9.67 (s, 1H), 10.0 (br s, 1H), 10.2 (br s, 1H). MS (ES+): m/z 433 (M+H)$^+$.

Example 220

N-(3-Bromo-2-methyl-phenyl)-acetamide (Intermediate 76)

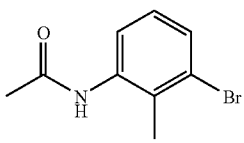

76

A solution of 3-bromo-2-methyl-phenylamine (4.1 g, 21.9 mmol) was treated with DIEA (8.4 mL, 48 mmol) and chilled to zero degrees. Acetyl chloride (1.7 mL, 24.1 mmol) was added dropwise via syringe. Reaction was allowed to return to room temperature and stir for 1 hour. Reaction was then poured onto water and washed once. Organic phase was evaporated to off-white solids. Trituration with hexanes afforded title compound as white solids (4.4 g, 89%).

Example 221

N-[3-(2-Chloro-5-methyl-pyrimidin-4-ylamino)-2-methyl-phenyl]-acetamide (Intermediate 77)

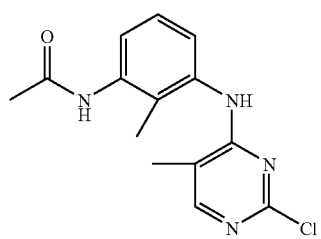

77

A mixture of 2-chloro-5-methyl-pyrimidin-4-ylamine (0.86 g, 5.9 mmol), intermediate 76 (1.6 g, 7.1 mmol), Pd$_2$(dba)$_3$ (0.55 g, 0.59 mmol), Xantphos (0.69 g, 1.2 mmol) and cesium carbonate (5.8 g, 17.8 mmol) were suspended in dioxane (40 mL) refluxed for 16 h. The reaction mixture was then cooled to room temperature, filtered and solvents evaporated. Resulting residue was purified by flash chromatography on silica gel to afford title compound as white solids (0.56 g, 32%).

Example 222

N-(2-Methyl-3-{5-methyl-2-[4-(piperidin-4-yloxy)-phenylamino]-pyrimidin-4-ylamino}-phenyl)-acetamide (Compound CXLVII)

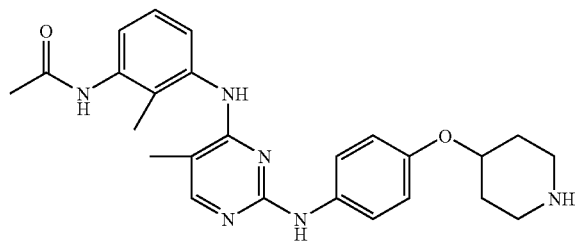

CXLVII

A mixture of intermediate 77 (0.15 g, 0.5 mmol) and 4-(4-Amino-phenoxy)-piperidine-1-carboxylic acid tert-butyl ester (0.19 g, 0.65 mmol) were diluted with HOAc (5 mL) and microwaved at 150° C. for 15 min. Solvents then removed and resulting residue purified on HPLC. Title compound isolated as white solids (0.091 g, 41%).

$^1$H NMR (500 MHz, DMSO-$d_6$): δ 1.71-1.78 (m, 2H), 2.02-2.08 (m, 8H), 2.16 (s, 3H), 3.09 (br s, 2H), 3.24 (br s, 2H), 4.50-4.52 (m, 1H), 6.77 (d, J=8.4 Hz, 2H), 7.09-7.15 (m, 3H), 7.27 (t, J=7.9 Hz, 1H), 7.49 (d, J=8.1 Hz, 1H), 7.86 (s, 1H), 8.54 (br s, 1H), 8.59 (br s, 1H), 9.45 (s, 1H), 9.84 (br s, 1H), 10.34 (br s, 1H). MS (ES+): m/z 447 (M+H)$^+$.

Example 223

5-Methyl-$N^2$-[4-(4-methyl-piperazin-1-yl)-phenyl]-$N^4$-(3-nitro-phenyl)-pyrimidine-2,4-diamine (Intermediate 78)

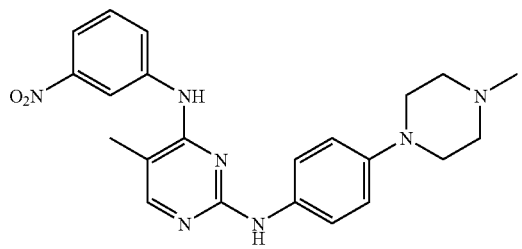

78

A mixture of 1-bromo-3-nitro-benzene (0.77 g, 3.8 mmol), intermediate 32 (0.95 g, 3.2 mmol), Pd$_2$(dba)$_3$ (0.29 g, 0.32 mmol), Xantphos (0.37 g, 0.64 mmol) and cesium carbonate (3.1 g, 9.6 mmol) were suspended in dioxane (40 mL) refluxed for 16 h. The reaction mixture was then cooled to room temperature, filtered and solvents evaporated. Resulting residue was purified by flash chromatography on silica gel to afford title compound as white solids (0.53 g, 40%).

Example 224

$N^4$-(3-Amino-phenyl)-5-methyl-$N^2$-[4-(4-methyl-piperazin-1-yl)-phenyl]-pyrimidine-2,4-diamine (Intermediate 79)

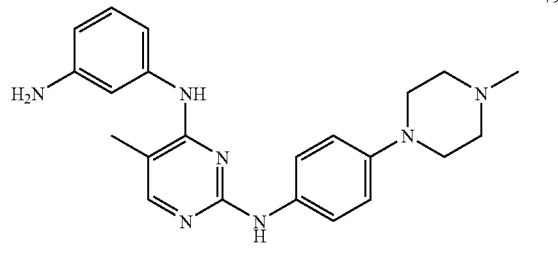

79

Slurry of intermediate 78 (0.23 g, 0.54 mmol) in MeOH (25 mL) was purged with argon and treated with Pd/C 10% wt. (0.18 g). Reaction atmosphere was replaced with hydrogen and stirred for 4 h. Hydrogen balloon was then removed and argon was flushed through reaction before filtration through Celite. Solvents were then evaporated to pale brown solids (0.17 g, 83%).

Example 225

1-(3-{5-Methyl-2-[4-(4-methyl-piperazin-1-yl)-phenylamino]-pyrimidin-4-ylamino}-phenyl)-3-phenyl-urea (Compound CXLVIII)

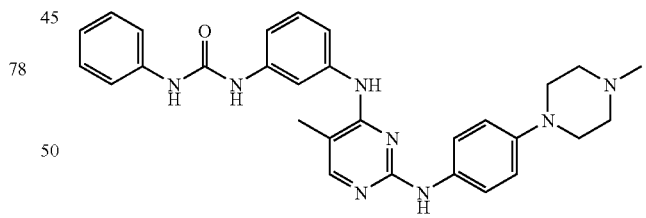

CXLVIII

A suspension of intermediate 79 (0.17 g, 0.45 mmol) in DCM (10 mL) was treated with phenyl isocyanate (0.058 mL, 0.54 mmol) and stirred for 1 hour. Reaction solvents then removed and resulting residue purified by HPLC to provide title compound as white solids (0.075 g, 33%).

$^1$H NMR (500 MHz, DMSO-$d_6$): δ 2.09 (s, 3H), 2.15 (s, 3H), 2.30-2.32 (m, 4H), 2.92-2.94 (m, 4H), 6.74 (d, J=8.4 Hz, 2H), 6.94-6.97 (m, 1H), 7.19-7.28 (m, 5H), 7.45 (d, J=8.8 Hz, 2H), 7.53 (d, J=9.0 Hz, 2H), 7.73 (br s, 1H), 7.83 (s, 1H), 8.23 (s, 1H), 8.68 (s, 1H), 8.74 (s, 1H), 8.78 (s, 1H). MS (ES+): m/z 509 (M+H)$^+$.

Example 226

1-(3-{5-Methyl-2-[4-(4-methyl-piperazin-1-yl)-phenylamino]-pyrimidin-4-ylamino}-phenyl)-3-(3-trifluoromethyl-phenyl)-urea (Compound CXLIX)

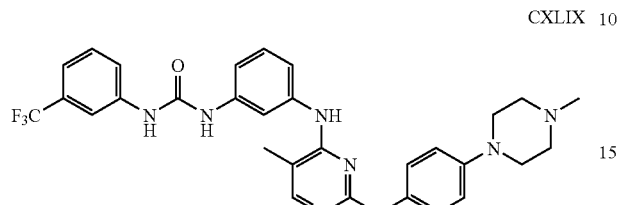

CXLIX

A suspension of intermediate 79 (0.1 g, 0.26 mmol) in DCM (8 mL) was treated with 1-isocyanato-3-trifluoromethyl-benzene (0.043 mL, 0.31 mmol) and stirred for 1 hour. Reaction solvents then removed and resulting residue purified by HPLC to provide title compound as white solids (0.039 g, 26%).

$^1$H NMR (500 MHz, DMSO-$d_6$): δ 2.16 (s, 3H), 2.82 (s, 3H), 2.86 (br s, 2H), 3.08 (br s, 2H), 3.42 (br s, 2H), 3.69 (br s, 2H), 6.88 (d, J=8.4 Hz, 2H), 7.20 (br s, 1H), 7.29-7.33 (m, 5H), 7.52 (t, J=7.9 Hz, 1H), 7.57 (d, J=8.5 Hz, 1H), 7.77 (s, 1H), 7.84 (s, 1H), 8.09 (s, 1H), 9.42 (s, 1H), 9.66 (s, 1H), 9.71 (br s, 1H), 10.1 (br s, 1H). MS (ES+): m/z 577 (M+H)$^+$.

Example 227

(2-Chloro-5-methyl-pyrimidin-4-yl)-(2-methyl-3-trifluoromethyl-phenyl)-amine (Intermediate 80)

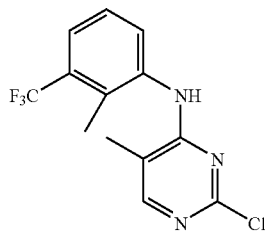

80

A mixture of 2-chloro-5-methyl-pyrimidin-4-ylamine (0.18 g, 5.9 mmol), 1-bromo-2-methyl-3-trifluoromethyl-benzene (0.33 g, 1.4 mmol), Pd$_2$(dba)$_3$ (0.12 g, 0.13 mmol), Xantphos (0.15 g, 0.25 mmol) and cesium carbonate (1.23 g, 3.8 mmol) were suspended in dioxane (8 mL) microwaved at 160° C. for 18 min. Reaction vessel was then centrifuged down and decanted. Solvents then evaporated and resulting residue was purified by flash chromatography on silica gel to afford title compound as white solids (0.095 g, 25%).

Example 228

5-Methyl-N$^4$-(2-methyl-3-trifluoromethyl-phenyl)-N$^2$-[4-(piperidin-4-yloxy)-phenyl]-pyrimidine-2,4-diamine (Compound CL)

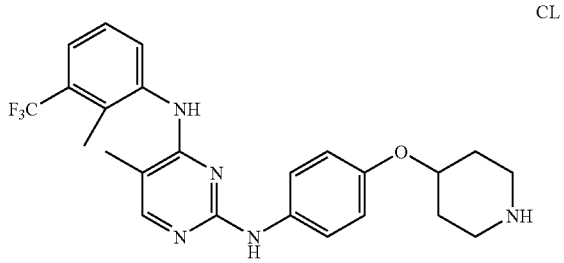

CL

A mixture of intermediate 80 (0.058 g, 0.2 mmol) and 4-(4-amino-phenoxy)-piperidine-1-carboxylic acid tert-butyl ester (0.073 g, 0.25 mmol) were diluted with HOAc (5 mL) and microwaved at 150° C. for 15 min. Solvents then removed and resulting residue purified on HPLC. Title compound isolated as white solids (0.025 g, 30%).

$^1$H NMR (500 MHz, DMSO-$d_6$): δ 1.71-1.78 (m, 2H), 2.00-2.04 (m, 2H), 2.18 (s, 3H), 2.25 (s, 3H), 3.08 (br s, 2H), 3.22 (br s, 2H), 4.50-4.52 (m, 1H), 6.70 (d, J=8.3 Hz, 2H), 7.10 (d, J=8.9 Hz, 2H), 7.54 (t, J=7.8 Hz, 1H), 7.62 (d, J=7.7 Hz, 1H), 7.75 (d, J=7.8 Hz, 1H), 7.91 (s, 1H), 8.54 (br s, 1H), 8.61 (br s, 1H), 9.88 (s, 1H), 10.34 (br s, 1H). MS (ES+): m/z 458 (M+H)$^+$.

Example 229

(3-Bromo-phenyl)-pyrrolidin-1-yl-methanone (Intermediate 81)

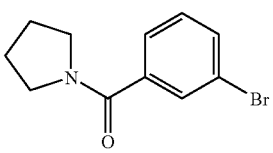

81

A solution of 3-bromo-benzoyl chloride (2.7 g, 12 mmol) in DCM (40 mL) was chilled to zero degrees and treated with pyrrolidine (3 mL, 36.8 mmol). Reaction was allowed to come to room temperature and stir for 4 h. Mixture was then poured onto water and washed once. Organic phase then washed with brine, dried over sodium sulfate, filtered and evaporated to amber oil (3.1 g, 100%).

Example 230

[3-(2-Chloro-5-methyl-pyrimidin-4-ylamino)-phenyl]-pyrrolidin-1-yl-methanone (Intermediate 82)

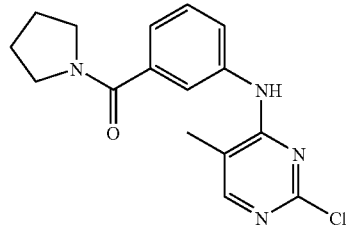

A mixture of 2-chloro-5-methyl-pyrimidin-4-ylamine (0.22 g, 1.5 mmol), intermediate 81 (0.46 g, 1.8 mmol), Pd$_2$(dba)$_3$ (0.14 g, 0.15 mmol), Xantphos (0.17 g, 0.3 mmol) and cesium carbonate (1.5 g, 4.5 mmol) were suspended in dioxane (8 mL) microwaved at 160° C. for 18 min. Reaction vessel was then centrifuged down and decanted. Solvents then evaporated and resulting residue was purified by flash chromatography on silica gel to afford title compound as white solids (0.25 g, 53%).

Example 231

(3-{5-Methyl-2-[4-(piperidin-4-yloxy)-phenylamino]-pyrimidin-4-ylamino}-phenyl)-pyrrolidin-1-yl-methanone (Compound CLI)

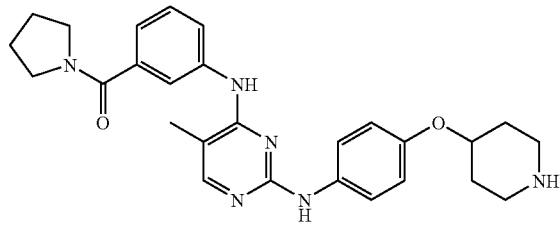

A mixture of intermediate 82 (0.1 g, 0.32 mmol) and 4-(4-amino-phenoxy)-piperidine-1-carboxylic acid tert-butyl ester (0.12 g, 0.41 mmol) were diluted with HOAc (6 mL) and microwaved at 150° C. for 15 min. Solvents then removed and resulting residue purified on HPLC. Title compound isolated as white solids (0.005 g, 3%).

$^1$H NMR (500 MHz, DMSO-d$_6$): δ 1.74-1.81 (m, 4H), 1.83-1.88 (m, 2H), 2.05-2.09 (m, 2H), 2.16 (s, 3H), 2.25 (s, 3H), 3.25 (br s, 2H), 3.34 (t, J=6.5 Hz, 2H), 3.46 (t, J=6.9 Hz, 2H), 4.45-4.59 (m, 1H), 6.91 (d, J=8.8 Hz, 2H), 7.32 (d, J=8.9 Hz, 2H), 7.36 (d, J=7.7 Hz, 1H), 7.43 (t, J=7.8 Hz, 1H), 7.67 (d, J=7.9 Hz, 1H), 7.70 (s, 1H), 7.89 (s, 1H), 8.50 (br s, 1H), 8.56 (br s, 1H), 9.64 (br s, 1H), 10.21 (br s, 1H). MS (ES+): m/z 473 (M+H)$^+$.

Example 232

3-Bromo-N-isopropyl-benzamide (Intermediate 83)

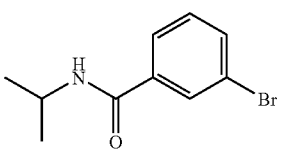

A solution of 3-bromo-benzoyl chloride (0.83 g, 3.8 mmol) in DCM (40 mL) was chilled to zero degrees and treated with isopropylamine (0.96 mL, 11.32 mmol). Reaction was allowed to come to room temperature and stir for 24 h. Mixture was then poured onto water and washed once. Organic phase then washed with brine, dried over sodium sulfate, filtered and evaporated to white solids (0.6 g, 66%).

Example 233

N-Isopropyl-3-{5-methyl-2-[4-(4-methyl-piperazin-1-yl)-phenylamino]-pyrimidin-4-ylamino}-benzamide (Compound CLII)

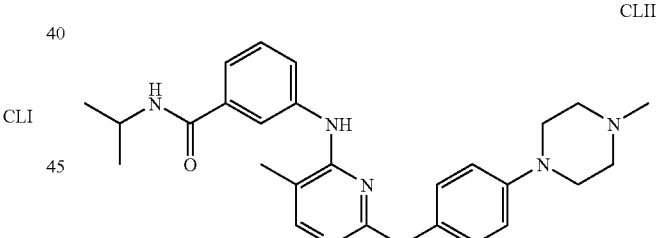

A mixture of intermediate 32 (0.1 g, 0.34 mmol), intermediate 83 (0.13 g, 0.54 mmol), Pd$_2$(dba)$_3$ (0.031 g, 0.034 mmol), Xantphos (0.039 g, 0.067 mmol) and cesium carbonate (0.33 g, 1 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.011 g, 7%).

$^1$H NMR (500 MHz, DMSO-d$_6$): δ 1.14 (d, J=6.7 Hz, 6H), 2.16 (s, 4H), 2.87 (s, 4H), 3.10 (br s, 2H), 3.51 (s, 2H), 4.22 (m, 1H), 6.85 (d, J=8.8 Hz, 2H), 7.30-7.32 (m, 2H), 7.45 (t, J=7.8 Hz, 1H), 7.69-7.70 (m, 2H), 7.90 (s, 1H), 7.99 (s, 1H), 8.24 (d, J=7.7 Hz, 1H), 9.70 (br s, 1H), 9.94 (br s, 1H), 10.2 (br s, 1H). MS (ES+): m/z 460 (M+H)$^+$.

Example 234

3-Bromo-N-tert-butyl-benzamide (Intermediate 84)

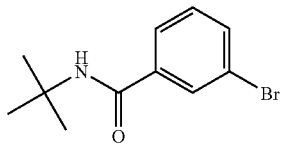

A solution of 3-bromo-benzoyl chloride (0.83 g, 3.8 mmol) in DCM (10 mL) was chilled to zero degrees and treated with tert-butylamine (1.2 mL, 11.3 mmol). Reaction was allowed to come to room temperature and stir for 4 h. Mixture was then poured onto water and washed once. Organic phase then washed with brine, dried over sodium sulfate, filtered and evaporated to amber oil (0.9 g, 94%).

Example 235

N-tert-Butyl-3-{5-methyl-2-[4-(4-methyl-piperazin-1-yl)-phenylamino]-pyrimidin-4-ylamino}-benzamide (Compound CLIII)

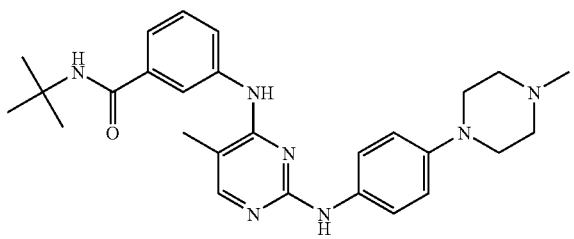

A mixture of intermediate 32 (0.1 g, 0.34 mmol), intermediate 84 (0.1 g, 0.4 mmol), Pd$_2$(dba)$_3$ (0.031 g, 0.034 mmol), Xantphos (0.039 g, 0.067 mmol) and cesium carbonate (0.33 g, 1 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.055 g, 35%).

$^1$H NMR (500 MHz, DMSO-d$_6$): δ 1.36 (s, 9H), 2.09 (s, 3H), 2.21 (s, 3H), 2.43 (t, J=2.8 Hz, 4H), 3.00 (t, J=2.8 Hz, 4H), 6.74 (d, J=9.1 Hz, 2H), 7.35 (t, J=7.9 Hz, 1H), 7.44-7.48 (m, 3H), 7.67 (s, 1H), 7.85 (s, 1H), 7.88-7.92 (m, 2H), 8.36 (s, 1H), 8.74 (s, 1H). MS (ES+): m/z 474 (M+H)$^+$.

Example 236

5-Methyl-N$^2$-[4-(4-methyl-piperazin-1-yl)-phenyl]-N$^4$-(3-piperidin-4-yl-phenyl)-pyrimidine-2,4-diamine (Compound CLIV)

A mixture of intermediate 32 (0.08 g, 0.27 mmol), 4-(3-bromo-phenyl)-piperidine (0.084 g, 0.35 mmol), Pd$_2$(dba)$_3$ (0.025 g, 0.027 mmol), Xantphos (0.031 g, 0.054 mmol) and cesium carbonate (0.26 g, 0.81 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.007 g, 6%).

$^1$H NMR (500 MHz, DMSO-d$_6$): δ 1.74-1.79 (m, 3H), 2.09 (s, 3H), 2.21 (s, 3H), 2.43 (t, J=2.8 Hz, 4H), 3.00 (t, J=2.8 Hz, 4H), 6.76 (d, J=9.1 Hz, 2H), 6.90 (d, J=7.7 Hz, 1H), 7.24 (t, J=7.9 Hz, 1H), 7.47-7.53 (m, 3H), 7.68 (d, J=8.2 Hz, 1H), 7.82 (s, 1H), 8.18 (s, 1H), 8.67 (s, 1H). MS (ES+): m/z 458 (M+H)$^+$.

Example 237

4-(3-{5-Methyl-2-[4-(4-methyl-piperazin-1-yl)-phenylamino]-pyrimidin-4-ylamino}-benzenesulfonyl)-piperidine-1-carboxylic acid benzyl ester (Intermediate 85)

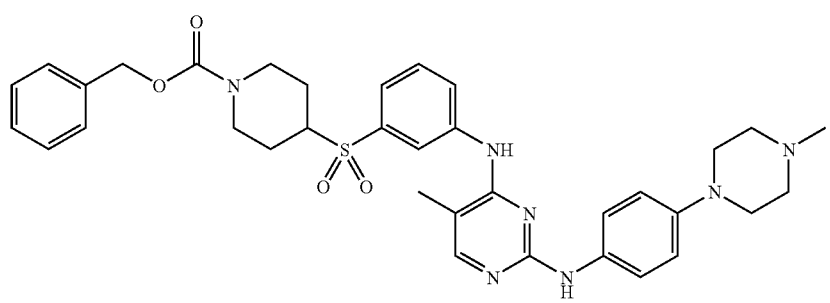

A mixture of intermediate 32 (0.17 g, 0.58 mmol), 4-(3-bromo-benzenesulfonyl)-piperidine-1-carboxylic acid benzyl ester (0.28 g, 0.64 mmol), Pd$_2$(dba)$_3$ (0.053 g, 0.058 mmol), Xantphos (0.067 g, 0.12 mmol) and cesium carbonate (0.57 g, 1.74 mmol) were suspended in dioxane (8 mL) microwaved at 160° C. for 15 min. Reaction vessel was then centrifuged down and decanted onto ice. Yellow solids collected, dried and used without further purification (0.4 g, 100%).

Example 238

5-Methyl-N$^2$-[4-(4-methyl-piperazin-1-yl)-phenyl]-N$^4$-[3-(piperidine-4-sulfonyl)-phenyl]-pyrimidine-2,4-diamine (Compound CLV)

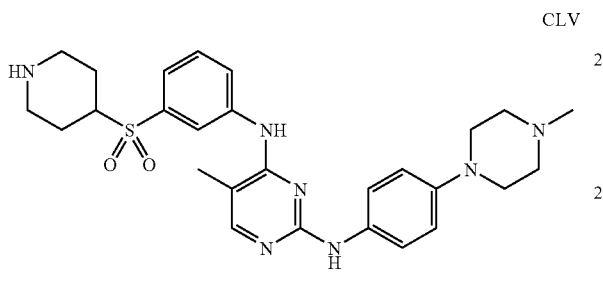

CLV

A stirring solution of intermediate 85 (0.17 g, 0.26 mmol) in DCM (15 mL) was treated with 1M BBr$_3$ in DCM (2 mL, 2 mmol). After 4 h, reaction was quenched by slow addition of MeOH (4 mL) followed by removal of solvents. Residue purified by HPLC to provide title compound as purple powder (0.008 g, 6%).

$^1$H NMR (500 MHz, DMSO-d$_6$): δ 1.31-1.40 (m, 2H), 1.75 (d, J=10.8 Hz, 2H), 2.12 (s, 3H), 2.21 (s, 3H), 2.36-2.41 (m, 2H), 2.44 (t, J=4.9 Hz, 4H), 2.95 (d, J=12.5 Hz, 2H), 3.02 (t, J=4.9 Hz, 4H), 3.24 (tt, J=11.7 Hz, J=3.8 Hz, 1H), 6.81 (d, J=9.0 Hz, 2H), 7.44 (m, 3H), 7.56 (t, J=8.0 Hz, 1H), 7.90-7.91 (m, 2H), 8.49 (d, J=7.6 Hz, 1H), 8.60 (s, 1H), 8.74 (s, 1H). MS (ES+): m/z 522 (M+H)$^+$.

Example 239 tert-Butyl 4-(4-(4-(1H-indol-4-ylamino)-5-methylpyrimidin-2-ylamino)phenoxy)piperidine-1-carboxylate (Intermediate 86)

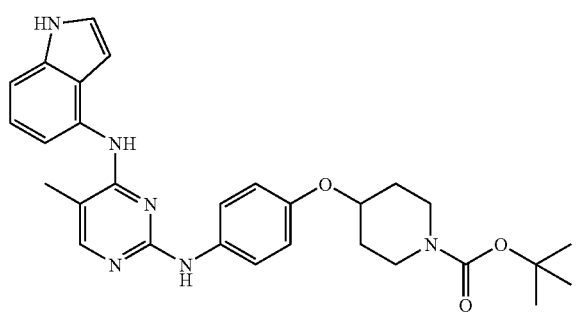

86

A mixture of 4-bromo-1H-indole (41 μL, 0.33 mmol), intermediate 42 (131 mg, 0.33 mmol), Pd$_2$(dba)$_3$ (30 mg, 0.03 mmol), Xantphos (60 mg, 0.10 mmol) and cesium carbonate (428 mg, 1.31 mmol) in dioxane (3 mL) was irradiated in the microwaved at 160° C. for 20 min. The reaction mixture was cooled to room temperature and filtered rinsing with DCM. The filtrate was concentrated and purified by gradient flash chromatography (0-15% MeOH in DCM) to afford the title compound as a white solid (30 mg, 17%).

Example 240

N$^4$-(1H-Indol-4-yl)-5-methyl-N$^2$-(4-(piperidin-4-yloxy)phenyl)pyrimidine-2,4-diamine (Compound CLVI)

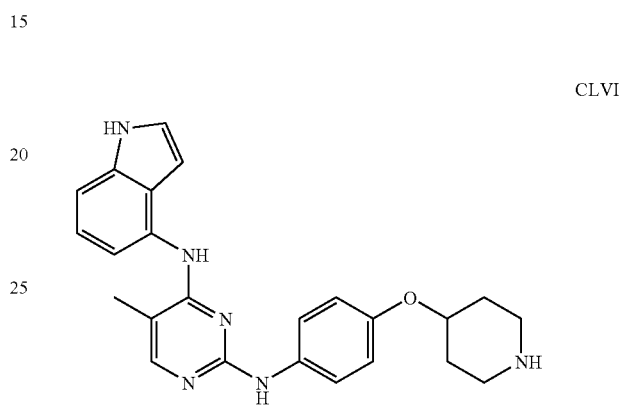

CLVI

A mixture of intermediate 86 (27 mg, 0.05 mmol) in 30% TFA/DCM (1 mL) was stirred for 3 h. The reaction mixture was concentrated in vacuo and purified by preparative HPLC. The resulting fractions were concentrated in vacuo to obtain the TFA salt of the title compound as a tan solid (11 mg, 43%).

$^1$H NMR (500 MHz, DMSO-d$_6$): δ 1.71-1.77 (m, 2H), 1.98-2.06 (m, 2H), 2.22 (s, 3H), 3.03-3.12 (m, 2H), 3.19-3.27 (m, 2H), 4.44-4.53 (m, 1H), 6.34-6.37 (m, 1H), 6.64 (br d, J=8.3 Hz, 2H), 7.08 (t, J=7.2 Hz, 3H), 7.14 (t, J=7.8 Hz, 1H), 7.36 (t, J=2.7 Hz, 1H), 7.39 (d, J=8.1 Hz, 1H), 7.84 (s, 1H), 8.48 (br s, 1H), 8.55 (br s, 1H), 9.85 (br s, 1H), 9.98 (br s, 1H), 11.27 (s, 1H).

Example 241

2-Chloro-N-{2-[4-(2-pyrrolidin-1-yl-ethoxy)-phenylamino]-pyrimidin-5-yl}-5(3-trifluoromethyl-benzoylamino)-benzamide (Compound CLVII)

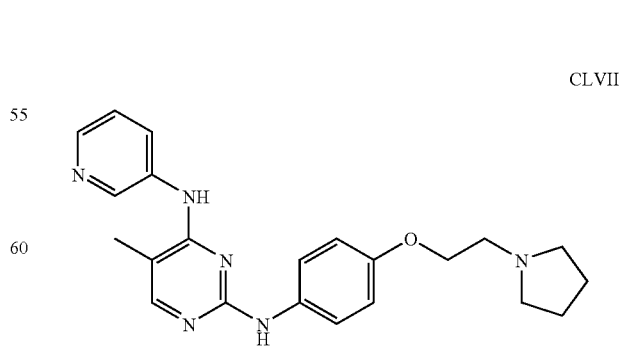

CLVII

A mixture of 3-bromopyridine (379 mg, 2.4 mmol), 4-amino-2-chloro-5-methylpyrimidine (287 mg, 2.0 mmol), Pd$_2$(dba)$_3$ (18 mg, 0.02 mmol), xantphos (23 mg, 0.04 mmol) and cesium carbonate (975 mg, 3.0 mmol) in dioxane (15 mL) was heated under refluxed for 1 h under argon. The solvent was removed and the residue on purification by HPLC gave an intermediate, 2-chloro-5-methyl-N-(pyridin-3-yl)pyrimidin-4-amine as yellow solid (252 mg, 57%). For second Buckwald, a mixture of 2-chloro-5-methyl-N-(pyridin-3-yl)pyrimidin-4-amine (80 mg, 0.36 mmol), 4-(2-(pyrrolidin-1-yl)ethoxy)benzenamine (74 mg, 0.34 mmol), Pd$_2$(dba)$_3$ (3.2 mg, 0.003 mmol), xantphos (4.2 mg, 0.007 mmol) and cesium carbonate (234 mg, 0.72 mmol) in dioxane (5 mL) was heated under refluxed for 1 h under argon. The crude reaction mixture on purification using HPLC gave the title compound as light brown solid (28 mg, 20%).

$^1$H NMR (500 MHz, DMSO-d$_6$): δ 1.85-1.95 (m, 2H), 2.0-2.09 (m, 2H), 2.18 (s, 3H), 3.09-3.18 (m, 2H), 3.55-3.65 (m, 4H), 4.27 (dd, J=5.2, 4.7 Hz, 2H), 6.94 (d, J=8.9 Hz, 2H), 7.35 (d, J=8.9 Hz, 2H), 7.50 (dd, J=8.2, 4.8 Hz, 1H), 7.92-7.96 (m, 1H), 8.08-8.15 (m, 1H), 8.45 (dd, J=4.8, 1.4, 1H), 8.84, 9.75, 9.85, 10.24 (4 br s, 1H each). MS (ES+): m/z 329 (M+H)$^+$.

Example 242

N$^2$-(4-(2-(pyrrolidin-1-yl)ethoxy)phenyl)-5-methyl-N$^4$-(3-(trifluoromethoxy)phenyl)pyrimidine-2,4-diamine (Compound CLVIII)

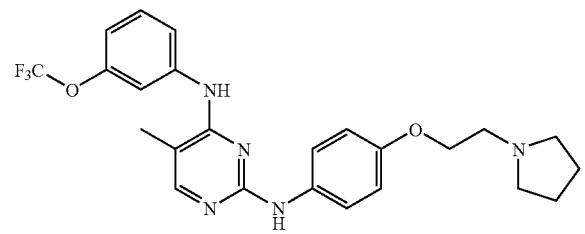

CLVIII

A mixture of 1-bromo-3-(trifluoromethoxy)benzene (241 mg, 1.0 mmol), 4-amino-2-chloro-5-methylpyrimidine (143 mg, 1.0 mmol), Pd$_2$(dba)$_3$ (9 mg, 0.01 mmol), xantphos (14 mg, 0.02 mmol) and cesium carbonate (650 mg, 2.0 mmol) in dioxane (15 mL) was heated under refluxed for 10 h under argon. The solvent was removed and the residue on purification by HPLC gave an intermediate, 2-chloro-5-methyl-N-(pyridin-3-yl)pyrimidin-4-amine as brown solid (260 mg, 85%). A mixture of this intermediate (100 mg, 0.33 mmol) and 4-(2-(pyrrolidin-1-yl)ethoxy)benzenamine (67 mg, 0.33 mmol) in glacial acetic acid (5 mL) was heated under refluxed for 3 h under argon. The crude reaction mixture on purification using HPLC gave the title compound as white solid (11 mg, 7%).

$^1$H NMR (500 MHz, DMSO-d$_6$): δ 1.65-1.72 (m, 4H), 2.11 (s, 3H), 2.51-2.55 (m, 2H, superimposed with solvent peak), 2.75 (t, J=5.9 Hz, 2H), 3.25-3.34 (m, 2H, superimposed with water peak), 3.99 (t, J=5.9 Hz, 2H), 6.79 (d, J=8.9 Hz, 2H), 6.98 (d, J=8.0 Hz, 1H), 7.40 (dd, J=7.6, 7.4 Hz, 1H), 7.50 (d, J=8.9 Hz, 2H), 7.76 (br s, 1H), 7.87 (d, J=8.4 1H), 7.90, 8.31, 8.41, 8.84 (4 s, 1H each). MS (ES+): m/z 474 (M+H)$^+$.

Example 243

N$^2$-(4-(2-(pyrrolidin-1-yl)ethoxy)phenyl)-N$^4$-(4-chloro-3-(trifluoromethyl)phenyl)-5-methylpyrimidine-2,4-diamine (Compound CLIX)

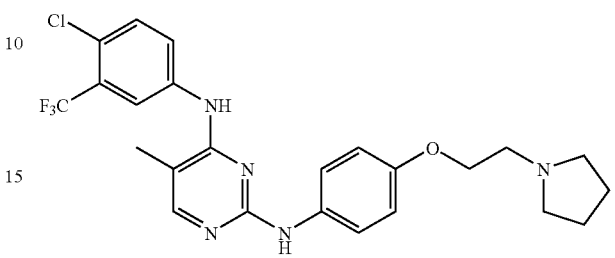

CLIX

A mixture of 4-bromo-1-chloro-2-(trifluoromethyl)benzene (259 mg, 1.0 mmol), 4-amino-2-chloro-5-methylpyrimidine (143 mg, 1.0 mmol), Pd$_2$(dba)$_3$ (9 mg, 0.01 mmol), xantphos (14 mg, 0.02 mmol) and cesium carbonate (650 mg, 2.0 mmol) in dioxane (15 mL) was heated under refluxed for 10 h under argon. The solvent was removed and the residue was purified by HPLC to give an intermediate 2-chloro-N-(4-chloro-3-(trifluoromethyl)phenyl)-5-methylpyrimidin-4-amine as brown solid (200 mg, 62%). A mixture of this intermediate (161 mg, 0.5 mmol) and 4-(2-(pyrrolidin-1-yl)ethoxy)benzenamine (103 mg, 0.5 mmol) in glacial acetic acid (5 mL) was heated under refluxed for 3 h under argon. The crude reaction mixture on purification using HPLC gave the title compound as brown solid (75 mg, 31%).

$^1$H NMR (500 MHz, DMSO-d$_6$): δ 1.65-1.72 (m, 4H), 2.10 (s, 3H), 2.51-2.55 (m, 4H, superimposed with solvent peak), 2.75 (t, J=6.0 Hz, 2H), 4.0 (t, J=5.9 Hz, 2H), 6.79 (d, J=8.5 Hz, 2H), 7.47 (d, J=9.0 Hz, 2H), 7.58 (d, J=9.0 Hz, 2H), 7.93 (s, 1H), 8.01 (d, J=2.5 Hz, 1H), 8.22 (d, J=8.5 Hz, 2H), 8.60, 8.88 (2 s, 1H each). MS (ES+): m/z 492 (M+H)$^+$.

Example 244

IC$_{50}$ Value Determinations for Jak2 Kinase

The IC$_{50}$ values for compounds were determined using a luminescence-based kinase assay with recombinant JAK2 obtained from Upstate Cell Signaling Solutions. In white, flat-bottom, 96-well plates (Nunc) parallel assays were run at room temperature at a final volume of 50 μL. Each well contained 40 μL of buffer consisting of 40 mM Tris buffer, pH 7.4, containing 50 mM MgCl$_2$, 800 μM EGTA, 350 μM Triton X-100, 2 mM β-mercaptoethanol, 100 μM peptide substrate (PDKtide; Upstate Cell Signaling Solutions) and an appropriate amount of JAK2 (75-25 ng/well) such that the assay was linear over 60 min. The final concentrations of TargeGen compounds for IC$_{50}$ value determinations ranged from 1000 to 0.01 μM by adding the appropriate amount of compound in 2.5 μL of DMSO; the DMSO present in each assay was constant at 5%. The reaction was initiated by the addition of 10 μL of ATP to a final assay concentration of 3 μM. After the reaction had proceeded for 60 min, 50 μL of Kinase-Glo reagent (Promega) was added to terminate the reaction. This solution was then allowed to proceed for an additional 10 min to maximize the luminescence reaction.

Values were then measured using an Ultra 384 instrument (Tecan) set for luminosity measurements. Two control reactions were also ran: one reaction containing no compound and the second containing neither inhibitor nor peptide substrate. $IC_{50}$ values were derived from experimental data using the non-linear curve fitting capabilities of Prism (Version 4; GraphPad Software). The results are shown in Table 1.

TABLE 1

Compounds of the Invention And Their IC Values for Jak2 Kinase

| Structure | Name | JAK2 IC50 |
|---|---|---|
| 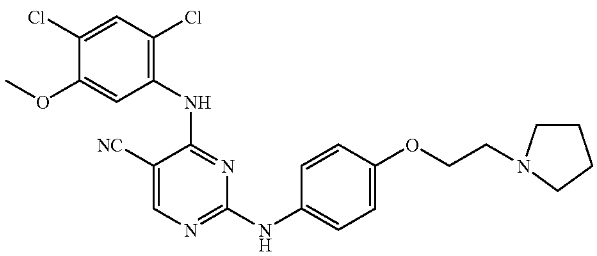 | 4-(2,4-Dichloro-5-methoxy-phenylamino)-2-[4-(2-pyrrolidin-1-yl-ethoxy)-phenylamino]-pyrimidine-5-carbonitrile | 6240 |
| 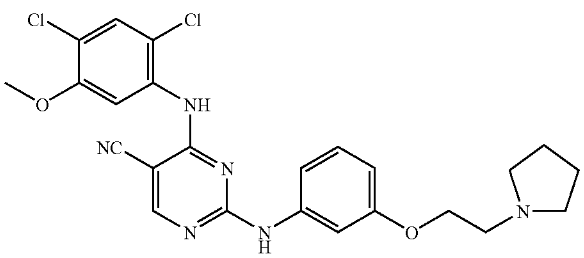 | 4-(2,4-Dichloro-5-methoxy-phenylamino)-2-[3-(2-pyrrolidin-1-yl-ethoxy)-phenylamino]-pyrimidine-5-carbonitrile | 10500 |
| 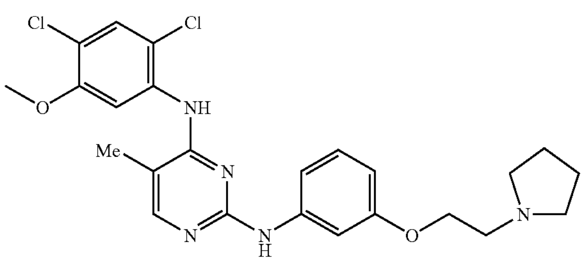 | N4-(2,4-Dichloro-5-methoxy-phenyl)-5-methyl-N2-[3-(2-pyrrolidin-1-yl-ethoxy)-phenyl]-pyrimidine-2,4-diamine | 2040 |
| 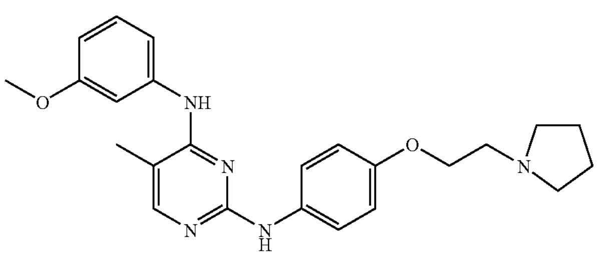 | N2-(4-(2-(pyrrolidin-1-yl)ethoxy)phenyl)-N4-(3-methoxyphenyl)-5-methylpyrimidine-2,4-diamine Hydrochloride | 52.8 |
| 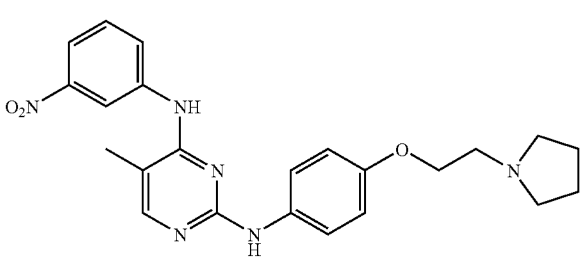 | N2-(4-(2-(pyrrolidin-1-yl)ethoxy)phenyl)-5-methyl-N4-(3-nitrophenyl)pyrimidine-2,4-diamine Hydrochloride | 61.1 |

TABLE 1-continued

Compounds of the Invention And Their IC Values for Jak2 Kinase

| Structure | Name | JAK2 IC50 |
|---|---|---|
| 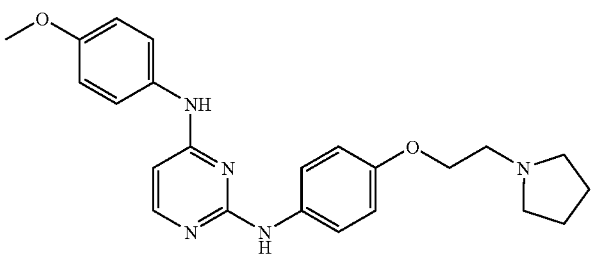 | N4-(4-Methoxy-phenyl)-N2-[4-(2-pyrrolidin-1-yl-ethoxy)-phenyl]-pyrimidine-2,4-diamine trifluoroacetate | 4330 |
| 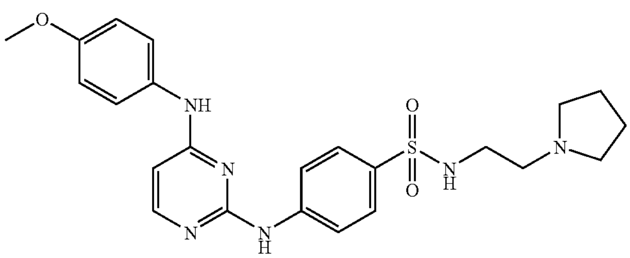 | 4-[4-(4-Methoxy-phenylamino)-pyrimidin-2-ylamino]-N-(2-pyrrolidin-1-yl-ethyl)-benzenesulfonamide trifluoroacetate | 10700 |
| 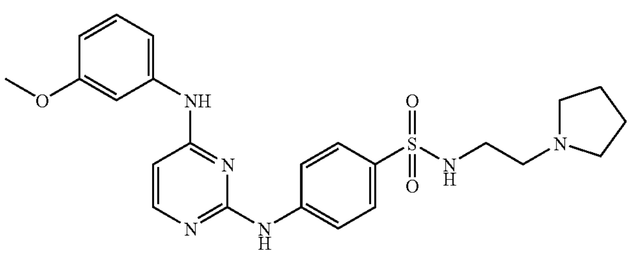 | 4-[4-(3-Methoxy-phenylamino)-pyrimidin-2-ylamino]-N-(2-pyrrolidin-1-yl-ethyl)-benzenesulfonamide trifluoroacetate | 638 |
| 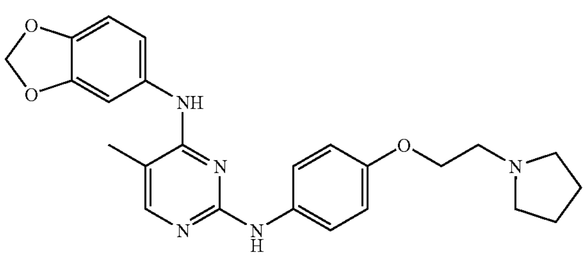 | N4-Benzo[1,3]dioxol-5-yl-5-methyl-N2-[4-(2-pyrrolidin-1-yl-ethoxy)-phenyl]-pyrimidine-2,4-diamine trifluoroacetate | 87.2 |
| 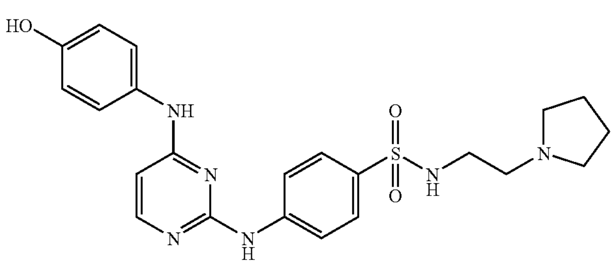 | 4-[4-(4-Hydroxy-phenylamino)-pyrimidin-2-ylamino]-N-(2-pyrrolidin-1-yl-ethyl)-benzenesulfonamide | 9740 |

TABLE 1-continued

Compounds of the Invention And Their IC Values for Jak2 Kinase

| Structure | Name | JAK2 IC50 |
|---|---|---|
| 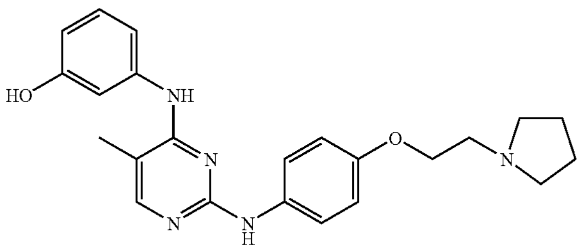 | 3-(2-(4-(2-(pyrrolidin-1-yl)ethoxy)phenylamino)-5-methylpyrimidin-4-ylamino)phenol Hydrochloride | 203 |
| 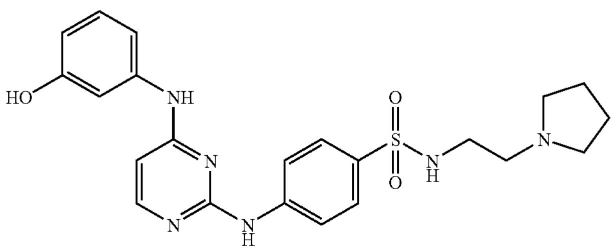 | 4-[4-(3-Hydroxy-phenylamino)-pyrimidin-2-ylamino]-N-(2-pyrrolidin-1-yl-ethyl)-benzenesulfonamide trifluoroacetate | 3620 |
| 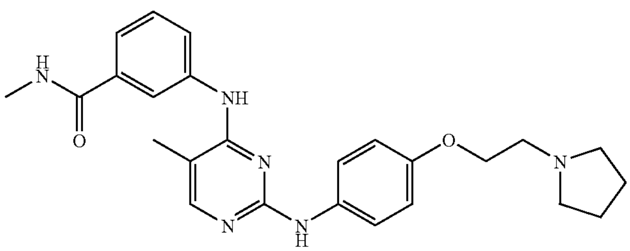 | N-Methyl-3-{5-methyl-2-[4-(2-pyrrolidin-1-yl-ethoxy)-phenylamino]-pyrimidin-4-ylamino}-benzamide | 257 |
| 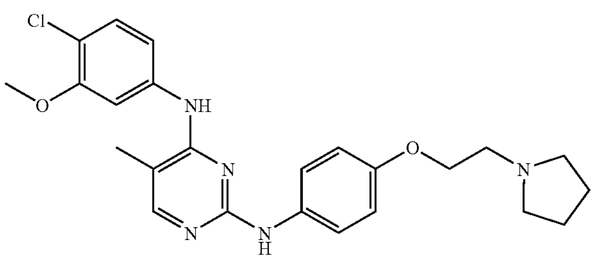 | N4-(4-Chloro-3-methoxy-phenyl)-5-methyl-N2-[4-(2-pyrrolidin-1-yl-ethoxy)-phenyl]-pyrimidine-2,4-diamine | 7.96 |
| 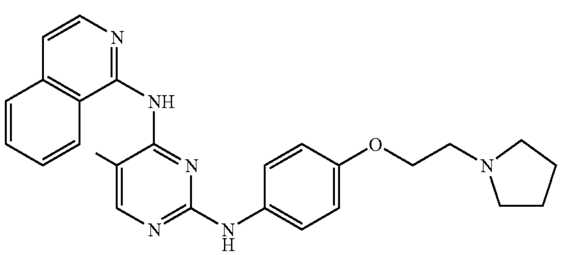 | N2-(4-(2-(pyrrolidin-1-yl)ethoxy)phenyl)-N4-(isoquinolin-1-yl)-5-methylpyrimidine-2,4-diamine | 1050 |
| 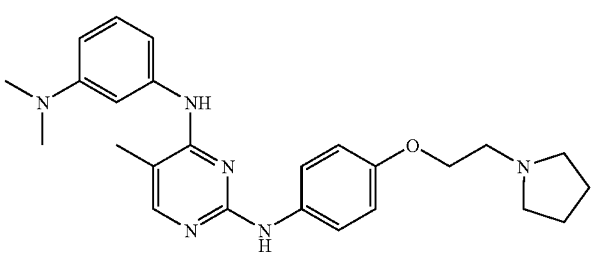 | N4-(3-Dimethylamino-phenyl)-5-methyl-N2-[4-(2-pyrrolidin-1-yl-ethoxy)-phenyl]-pyrimidine-2,4-diamine | 19.7 |

TABLE 1-continued

Compounds of the Invention And Their IC Values for Jak2 Kinase

| Structure | Name | JAK2 IC50 |
|---|---|---|
| 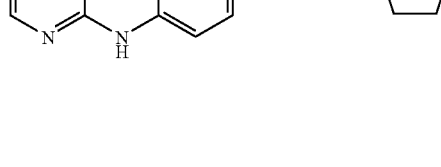 | 4-(2-(4-(2-(pyrrolidin-1-yl)ethoxy)phenylamino)-5-methylpyrimidin-4-ylamino)-2-chlorobenzonitrile Hydrochloride | 67.5 |
| 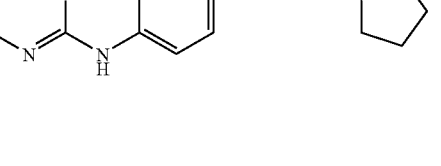 | N2-(4-(2-(pyrrolidin-1-yl)ethoxy)phenyl)-5-methyl-N4-(naphthalen-1-yl)pyrimidine-2,4-diamine Hydrochloride | 20 |
| 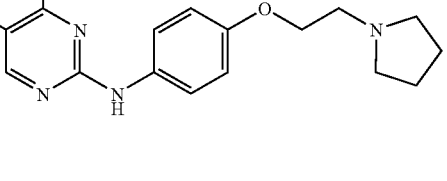 | N4-(3,4-Dichloro-phenyl)-5-methyl-N2-[4-(2-pyrrolidin-1-yl-ethoxy)-phenyl]-pyrimidine-2,4-diamine | 25.7 |
| 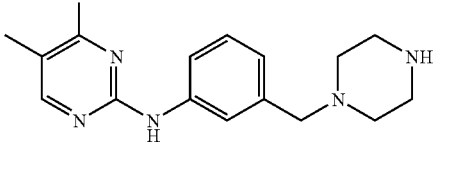 | N4-(4-Chloro-3-methoxy-phenyl)-5-methyl-N2-(3-piperazin-1-ylmethyl-phenyl)-pyrimidine-2,4-diamine | 15.8 |
| 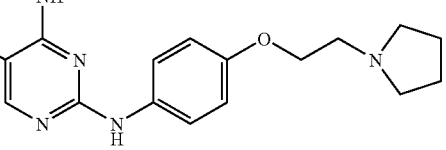 | N2-(4-(2-(pyrrolidin-1-yl)ethoxy)phenyl)-N4-(1H-indol-4-yl)-5-methylpyrimidine-2,4-diamine Hydrochloride | 19.2 |

TABLE 1-continued

Compounds of the Invention And Their IC Values for Jak2 Kinase

| Structure | Name | JAK2 IC50 |
|---|---|---|
| 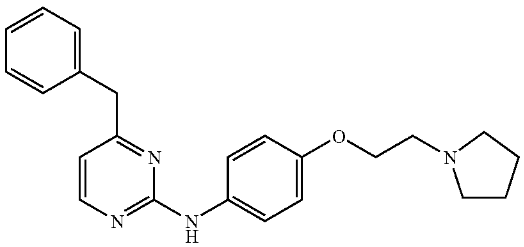 | N-(4-(2-(pyrrolidin-1-yl)ethoxy)phenyl)-4-benzylpyrimidin-2-amine | 702.000000 |
| 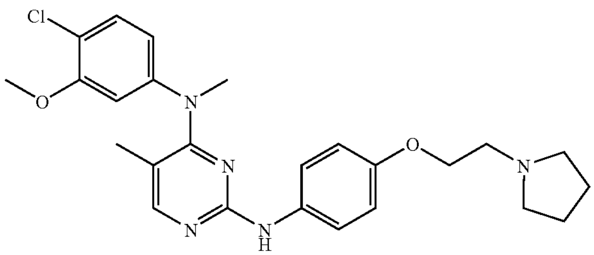 | N2-(4-(2-(pyrrolidin-1-yl)ethoxy)phenyl)-N4-(4-chloro-3-methoxyphenyl)-N4,5-dimethylpyrimidine-2,4-diamine trifluoroacetate | 4900 |
| 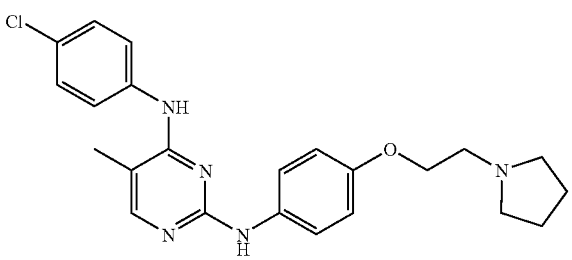 | N4-(4-Chloro-phenyl)-5-methyl-N2-[4-(2-pyrrolidin-1-yl-ethoxy)-phenyl]-pyrimidine-2,4-diamine trifluoroacetate | 18.2 |
| 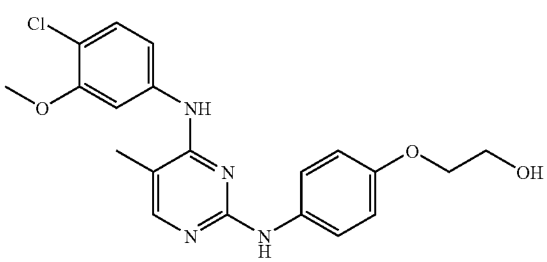 | 2-{4-[4-(4-Chloro-3-methoxy-phenylamino)-5-methyl-pyrimidin-2-ylamino]-phenoxy}-ethanol | 9.14 |
| 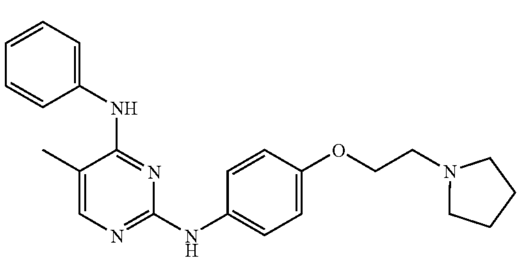 | 5-Methyl-N4-phenyl-N2-[4-(2-pyrrolidin-1-yl-ethoxy)-phenyl]-pyrimidine-2,4-diamine | 16.7 |

TABLE 1-continued

Compounds of the Invention And Their IC Values for Jak2 Kinase

| Structure | Name | JAK2 IC50 |
|---|---|---|
| 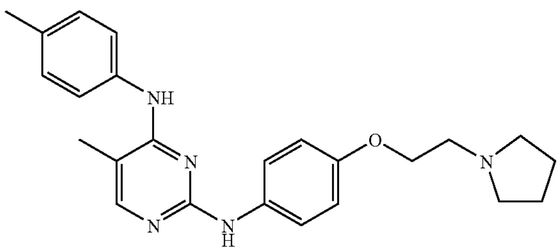 | N2-(4-(2-(pyrrolidin-1-yl)ethoxy)phenyl)-5-methyl-N4-p-tolylpyrimidine-2,4-diamine Hydrochloride | 35.7 |
| 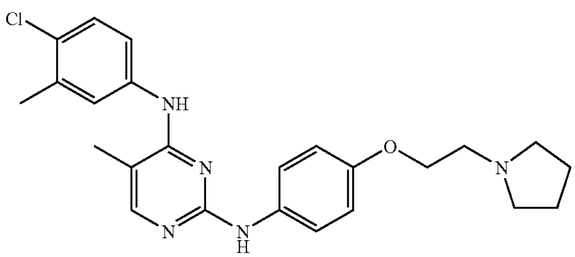 | N2-(4-(2-(pyrrolidin-1-yl)ethoxy)phenyl)-N4-(4-chloro-3-methylphenyl)-5-methylpyrimidine-2,4-diamine Hydrochloride | 12.4 |
| 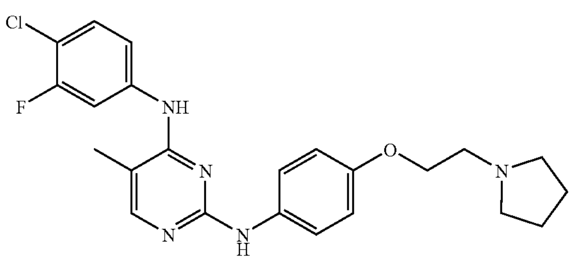 | N4-(4-Chloro-3-fluoro-phenyl)-5-methyl-N2-[4-(2-pyrrolidin-1-yl-ethoxy)-phenyl]-pyrimidine-2,4-diamine | 40.1 |
| 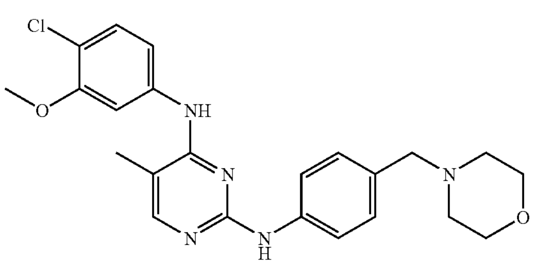 | N4-(4-Chloro-3-methoxy-phenyl)-5-methyl-N2-(4-morpholin-4-ylmethyl-phenyl)-pyrimidine-2,4-diamine trifluoroacetate | 13.3 |
| 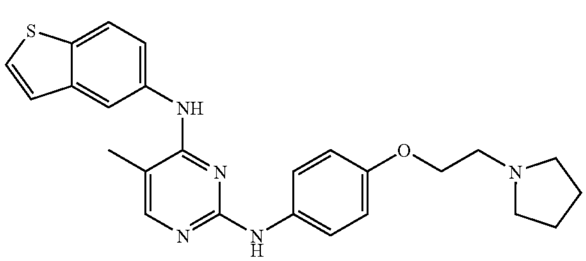 | N4-Benzo[b]thiophen-5-yl-5-methyl-N2-[4-(2-pyrrolidin-1-yl-ethoxy)-phenyl]-pyrimidine-2,4-diamine | 28.5 |

TABLE 1-continued

Compounds of the Invention And Their IC Values for Jak2 Kinase

| Structure | Name | JAK2 IC50 |
|---|---|---|
| 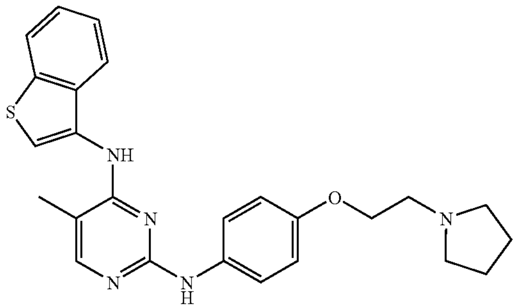 | N4-Benzo[b]thiophen-3-yl-5-methyl-N2-[4-(2-pyrrolidin-1-yl-ethoxy)-phenyl]-pyrimidine-2,4-diamine | 12.4 |
| 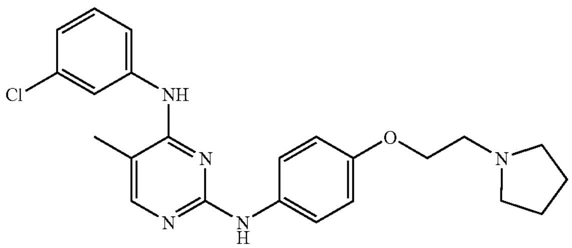 | N4-(3-Chloro-phenyl)-5-methyl-N2-[4-(2-pyrrolidin-1-yl-ethoxy)-phenyl]-pyrimidine-2,4-diamine | 20.8 |
| 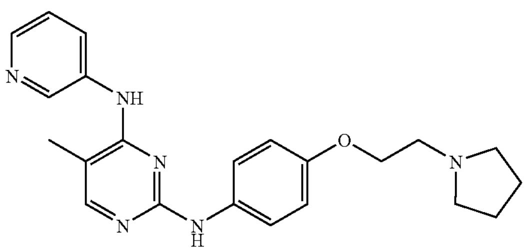 | 2-Chloro-N-{2-[4-(2-pyrrolidin-1-yl-ethoxy)-phenylamino]-pyrimidin-5-yl}-5-(3-trifluoromethyl-benzoylamino)-benzamide | 304 |
| 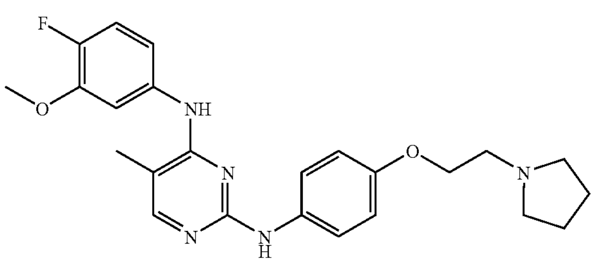 | N4-(4-Fluoro-3-methoxy-phenyl)-5-methyl-N2-[4-(2-pyrrolidin-1-yl-ethoxy)-phenyl]-pyrimidine-2,4-diamine | 14.8 |
| 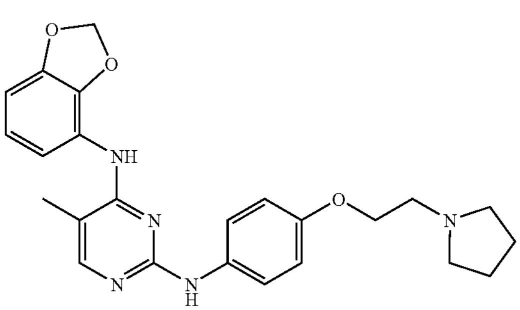 | N4-Benzo[1,3]dioxol-4-yl-5-methyl-N2-[4-(2-pyrrolidin-1-yl-ethoxy)-phenyl]-pyrimidine-2,4-diamine | 16.9 |

TABLE 1-continued

Compounds of the Invention And Their IC Values for Jak2 Kinase

| Structure | Name | JAK2 IC50 |
|---|---|---|
| 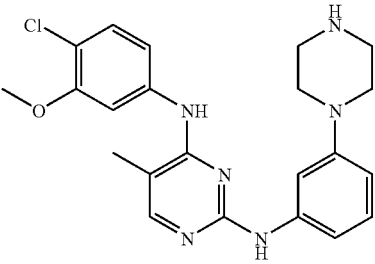 | N4-(4-Chloro-3-methoxy-phenyl)-5-methyl-N2-(3-piperazin-1-yl-phenyl)-pyrimidine-2,4-diamine | 9.52 |
| 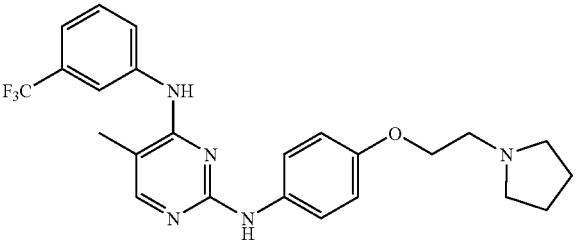 | N2-(4-(2-(pyrrolidin-1-yl)ethoxy)phenyl)-N4-(3-(trifluoromethyl)phenyl)-5-methylpyrimidine-2,4-diamine | 17.6 |
| 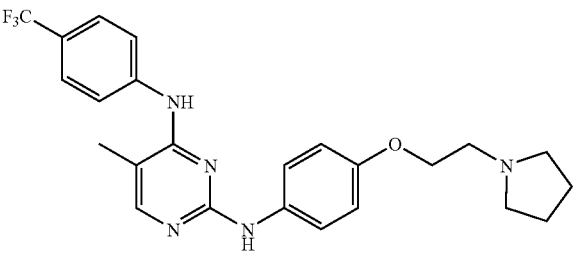 | N2-(4-(2-(pyrrolidin-1-yl)ethoxy)phenyl)-N4-(4-(trifluoromethyl)phenyl)-5-methylpyrimidine-2,4-diamine hydrochloride | 39.8 |
| 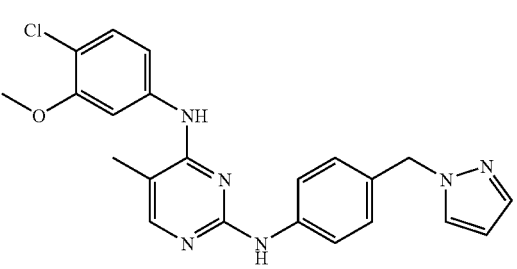 | N4-(4-Chloro-3-methoxy-phenyl)-5-methyl-N2-(4-pyrazol-1-ylmethyl-phenyl)-pyrimidine-2,4-diamine | 18.9 |
| 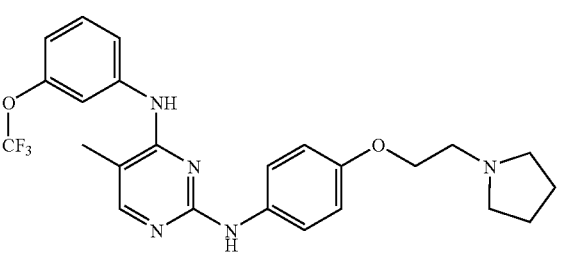 | N2-(4-(2-(pyrrolidin-1-yl)ethoxy)phenyl)-5-methyl-N4-(3-(trifluoromethoxy)phenyl)-pyrimidine-2,4-diamine | 20.7 |

TABLE 1-continued

Compounds of the Invention And Their IC Values for Jak2 Kinase

| Structure | Name | JAK2 IC50 |
|---|---|---|
| 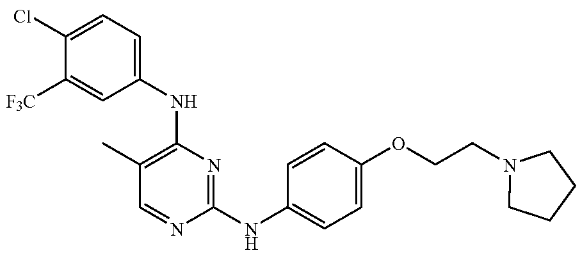 | N2-(4-(2-(pyrrolidin-1-yl)ethoxy)phenyl)-N4-(4-chloro-3-(trifluoromethyl)phenyl)-5-methylpyrimidine-2,4-diamine | 23.4 |
| 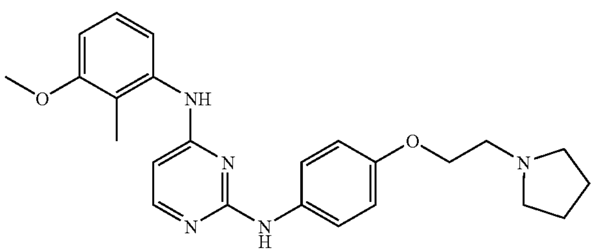 | N4-(3-Methoxy-2-methyl-phenyl)-N2-[4-(2-pyrrolidin-1-yl-ethoxy)-phenyl]-pyrimidine-2,4-diamine | 371 |
| 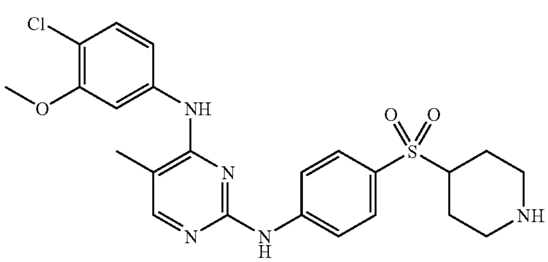 | N4-(4-Chloro-3-methoxy-phenyl)-5-methyl-N2-[4-(piperidine-4-sulfonyl)-phenyl]-pyrimidine-2,4-diamine | 13 |
| 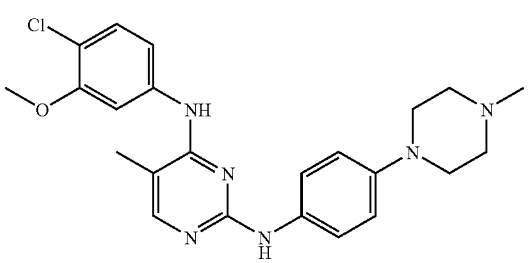 | N4-(4-Chloro-3-methoxy-phenyl)-5-methyl-N2-[4-(4-methyl-piperazin-1-yl)-phenyl]-pyrimidine-2,4-diamine | 5.5 |
| 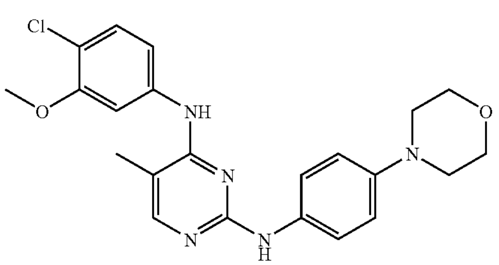 | N4-(4-Chloro-3-methoxy-phenyl)-5-methyl-N2-(4-morpholin-4-yl-phenyl)-pyrimidine-2,4-diamine | 130 |

TABLE 1-continued

Compounds of the Invention And Their IC Values for Jak2 Kinase

| Structure | Name | JAK2 IC50 |
|---|---|---|
| 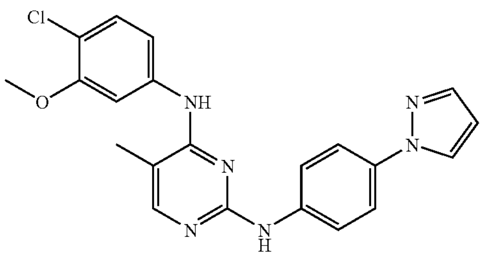 | N4-(4-Chloro-3-methoxy-phenyl)-5-methyl-N2-(4-pyrazol-1-yl-phenyl)-pyrimidine-2,4-diamine trifluoroacetate | 35.3 |
| 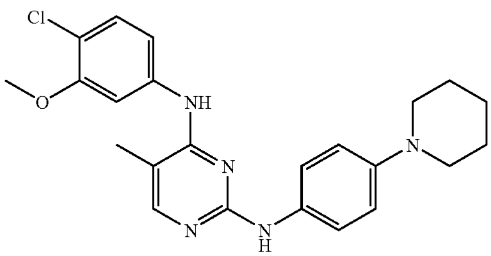 | N4-(4-Chloro-3-methoxy-phenyl)-5-methyl-N2-(4-piperidin-1-yl-phenyl)-pyrimidine-2,4-diamine | 35.3 |
| 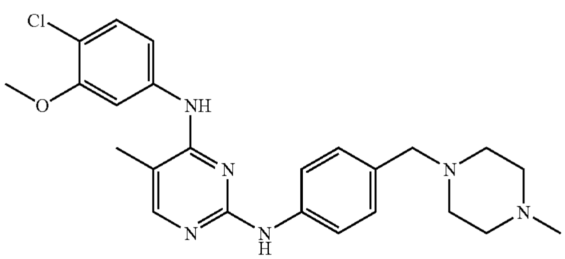 | N4-(4-Chloro-3-methoxy-phenyl)-5-methyl-N2-[4-(4-methyl-piperazin-1-ylmethyl)-phenyl]-pyrimidine-2,4-diamine | 12 |
| 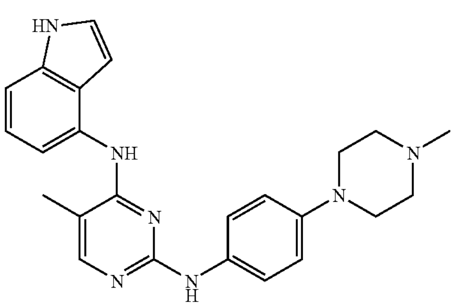 | N4-(1H-indol-4-yl)-5-methyl-N2-(4-(4-methylpiperazin-1-yl)phenyl)pyrimidine-2,4-diamine Hydrochloride | 9.53 |
| 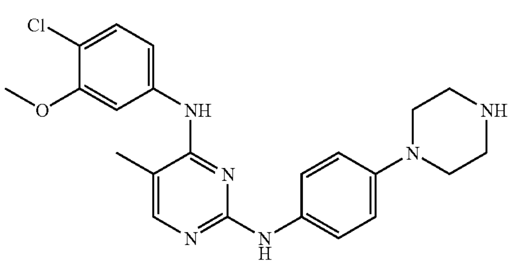 | N4-(4-Chloro-3-methoxy-phenyl)-5-methyl-N2-(4-piperazin-1-yl-phenyl)-pyrimidine-2,4-diamine | 6.15 |

TABLE 1-continued

Compounds of the Invention And Their IC Values for Jak2 Kinase

| Structure | Name | JAK2 IC50 |
|---|---|---|
| 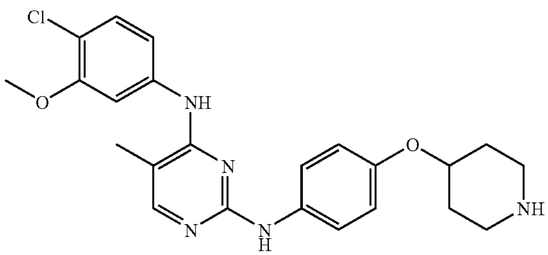 | N4-(4-Chloro-3-methoxy-phenyl)-5-methyl-N2-[4-(piperidin-4-yloxy)-phenyl]-pyrimidine-2,4-diamine | 4.14 |
| 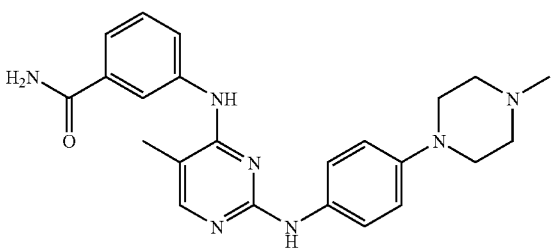 | 3-{5-Methyl-2-[4-(4-methyl-piperazin-1-yl)-phenylamino]-pyrimidin-4-ylamino}-benzamide | 23 |
| 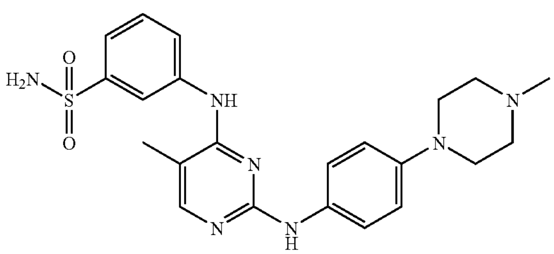 | 3-{5-Methyl-2-[4-(4-methyl-piperazin-1-yl)-phenylamino]-pyrimidin-4-ylamino}-benzenesulfonamide | 13.6 |
| 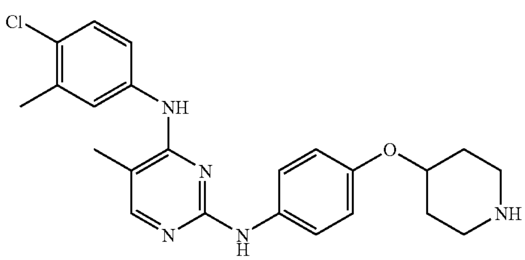 | N4-(4-Chloro-3-methyl-phenyl)-5-methyl-N2-[4-(piperidin-4-yloxy)-phenyl]-pyrimidine-2,4-diamine | 8.41 |
| 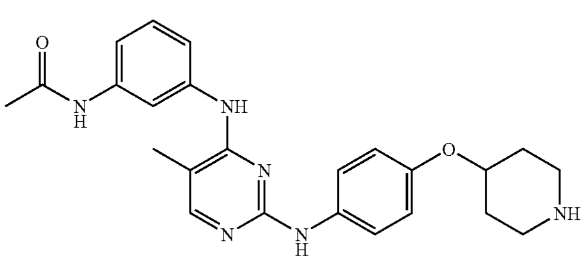 | N-(3-{5-Methyl-2-[4-(piperidin-4-yloxy)-phenylamino]-pyrimidin-4-ylamino}-phenyl)-acetamide | 137 |

TABLE 1-continued

Compounds of the Invention And Their IC Values for Jak2 Kinase

| Structure | Name | JAK2 IC50 |
|---|---|---|
| 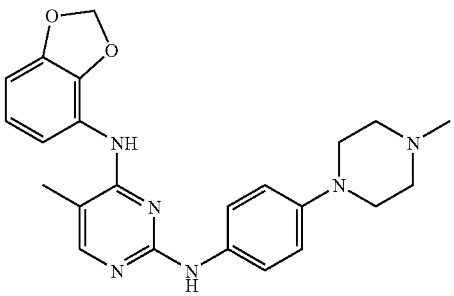 | N4-Benzo[1,3]dioxol-4-yl-5-methyl-N2-[4-(4-methyl-piperazin-1-yl)-phenyl]-pyrimidine-2,4-diamine | 14.2 |
| 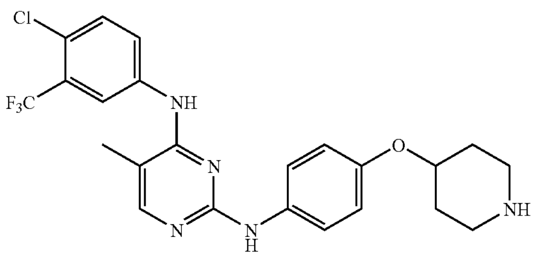 | N4-(4-Chloro-3-trifluoromethyl-phenyl)-5-methyl-N2-[4-(piperidin-4-yloxy)-phenyl]-pyrimidine-2,4-diamine | 11.4 |
| 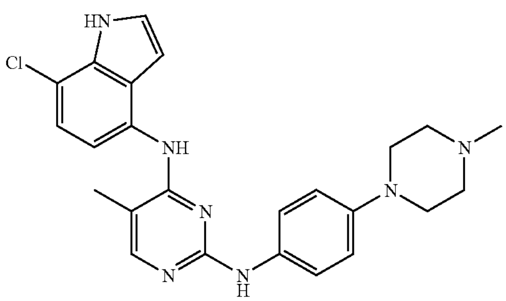 | N4-(7-chloro-1H-indol-4-yl)-5-methyl-N2-(4-(4-methylpiperazin-1-yl)phenyl)pyrimidine-2,4-diamine | 5.36 |
| 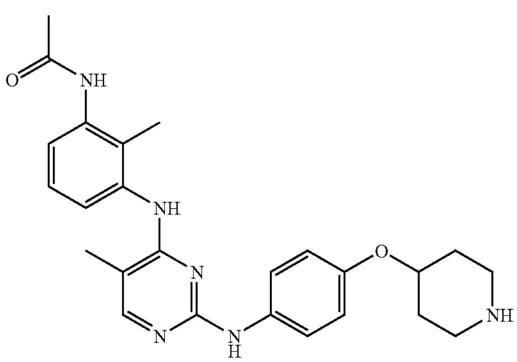 | N-(2-Methyl-3-{5-methyl-2-[4-(piperidin-4-yloxy)-phenylamino]-pyrimidin-4-ylamino}-phenyl)-acetamide | 146 |
| 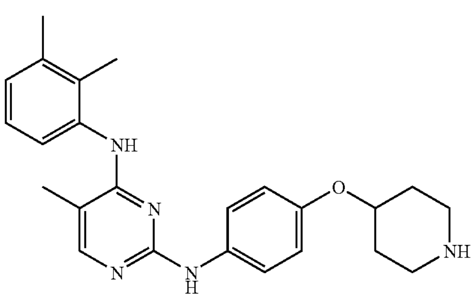 | 5-methyl-N4-(2,3-dimethylphenyl)-N2-(4-(piperidin-4-yloxy)phenyl)pyrimidine-2,4-diamine Hydrochloride | 4.38 |

TABLE 1-continued

Compounds of the Invention And Their IC Values for Jak2 Kinase

| Structure | Name | JAK2 IC50 |
|---|---|---|
| 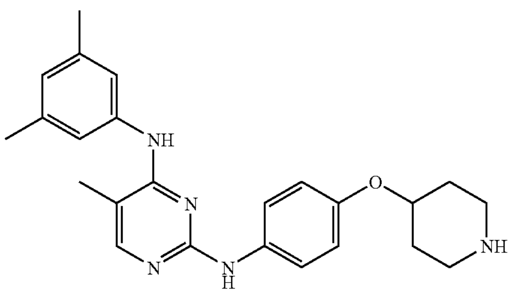 | 5-methyl-N4-(3,5-dimethylphenyl)-N2-(4-(piperidin-4-yloxy)phenyl)pyrimidine-2,4-diamine hydrochloride | 37.2 |
| 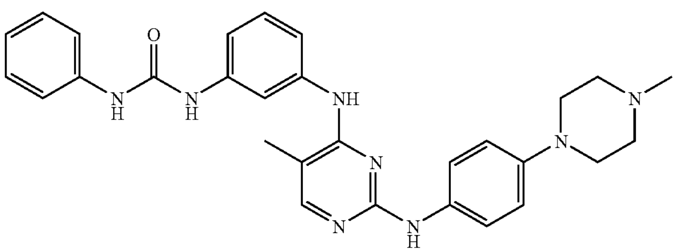 | 1-(3-{5-Methyl-2-[4-(4-methyl-piperazin-1-yl)-phenylamino]-pyrimidin-4-ylamino}-phenyl)-3-phenyl-urea | 63.6 |
| 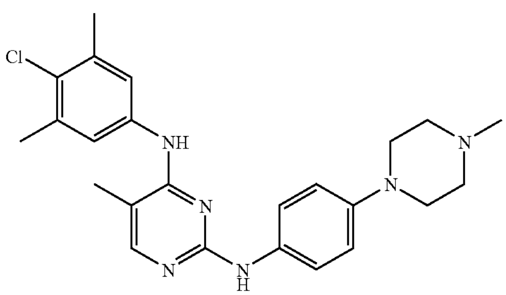 | N4-(4-chloro-3,5-dimethylphenyl)-5-methyl-N2-(4-(4-methylpiperazin-1-yl)phenyl)pyrimidine-2,4-diamine Hydrochloride | 38 |
| 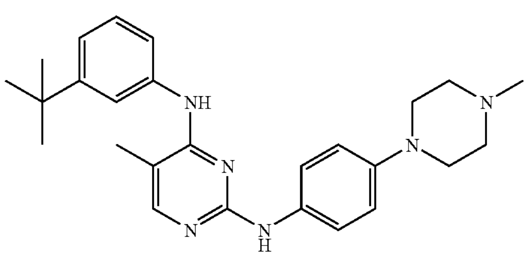 | N4-(3-tert-butylphenyl)-5-methyl-N2-(4-(4-methylpiperazin-1-yl)phenyl)pyrimidine-2,4-diamine Hydrochloride | 4.7 |
| 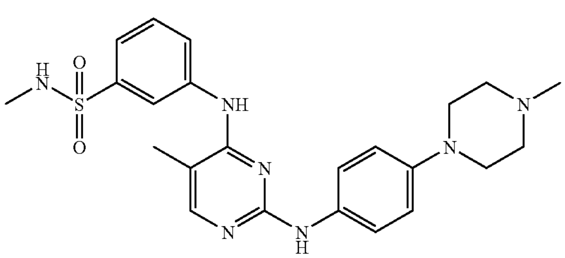 | N-Methyl-3-{5-methyl-2-[4-(4-methyl-piperazin-1-yl)-phenylamino]-pyrimidin-4-ylamino}-benzenesulfonamide | 16.1 |

TABLE 1-continued

Compounds of the Invention And Their IC Values for Jak2 Kinase

| Structure | Name | JAK2 IC50 |
|---|---|---|
| 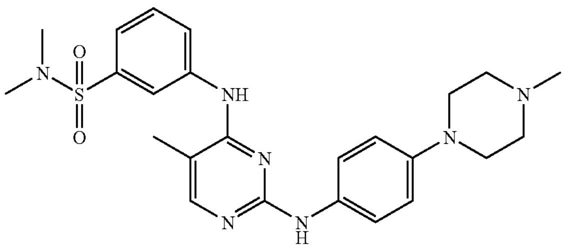 | N,N-Dimethyl-3-{5-methyl-2-[4-(4-methyl-piperazin-1-yl)-phenylamino]-pyrimidin-4-ylamino}-benzenesulfonamide | 9.5 |
| 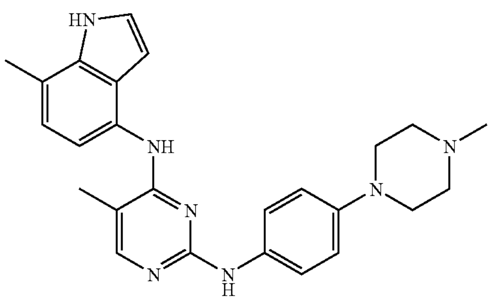 | 5-methyl-N4-(7-methyl-1H-indol-4-yl)-N2-(4-(4-methylpiperazin-1-yl)phenyl)pyrimidine-2,4-diamine Hydrochloride | 3.84 |
| 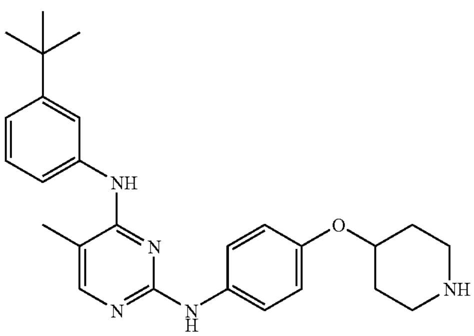 | N4-(3-tert-butylphenyl)-5-methyl-N2-(4-(piperidin-4-yloxy)phenyl)pyrimidine-2,4-diamine Hydrochloride | 2.73 |
| 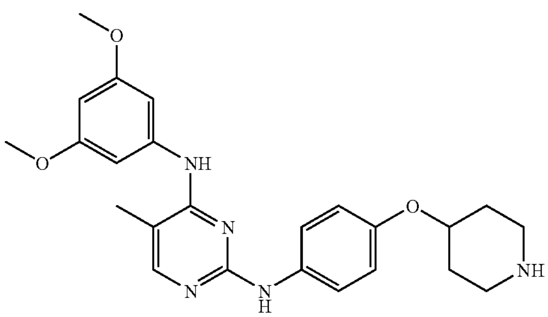 | N4-(3,5-dimethoxyphenyl)-5-methyl-N2-(4-(piperidin-4-yloxy)phenyl)pyrimidine-2,4-diamine trifluoroacetate | 137 |
| 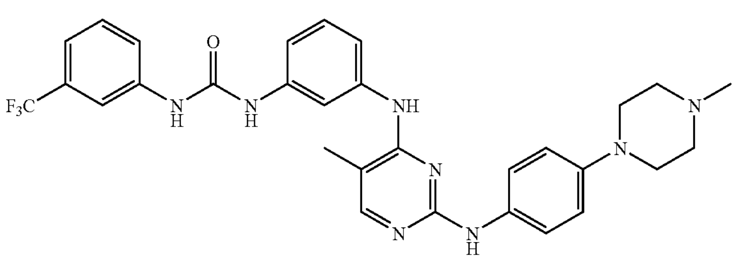 | 1-(3-{5-Methyl-2-[4-(4-methyl-piperazin-1-yl)-phenylamino]-pyrimidin-4-ylamino}-phenyl)-3-(3-trifluoromethyl-phenyl)-urea | 126 |

TABLE 1-continued

Compounds of the Invention And Their IC Values for Jak2 Kinase

| Structure | Name | JAK2 IC50 |
|---|---|---|
| 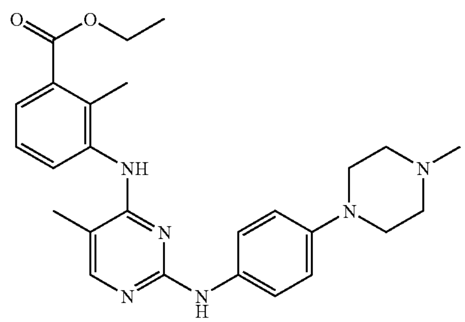 | 2-Methyl-3-{5-methyl-2-[4-(4-methyl-piperazin-1-yl)-phenylamino]-pyrimidin-4-ylamino}-benzoic acid ethyl ester | 27.8 |
| 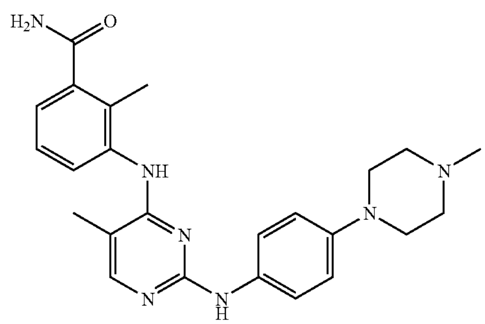 | 2-Methyl-3-{5-methyl-2-[4-(4-methyl-piperazin-1-yl)-phenylamino]-pyrimidin-4-ylamino}-benzamide | 26.2 |
| 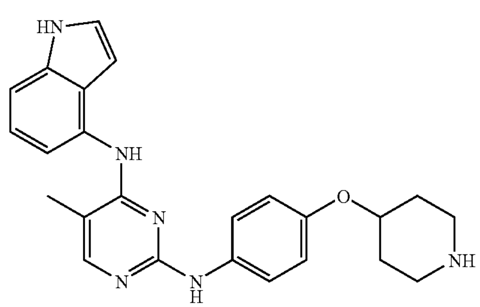 | N4-(1H-indol-4-yl)-5-methyl-N2-(4-(piperidin-4-yloxy)phenyl)pyrimidine-2,4-diamine trifluoroacetic acid salt | 4.27 |
| 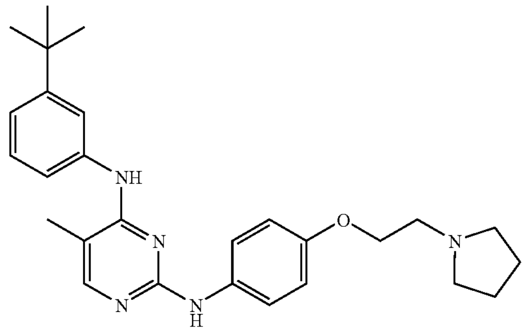 | N2-(4-(2-(pyrrolidin-1-yl)ethoxy)phenyl)-N4-(3-tert-butylphenyl)-5-methylpyrimidine-2,4-diamine Hydrochloride | 6.71 |

TABLE 1-continued

Compounds of the Invention And Their IC Values for Jak2 Kinase

| Structure | Name | JAK2 IC50 |
|---|---|---|
| 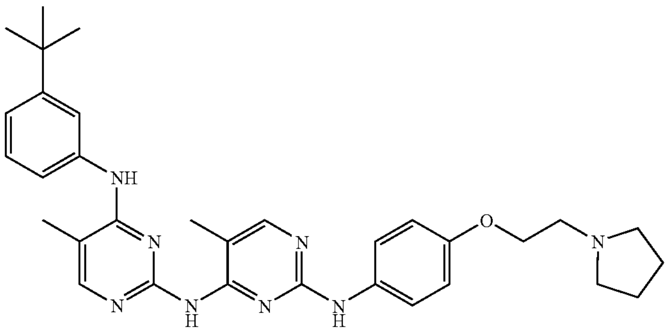 | N2-(4-(2-(pyrrolidin-1-yl)ethoxy)phenyl)-N4-(4-(3-tert-butylphenylamino)-5-methylpyrimidin-2-yl)-5-methylpyrimidine-2,4-diamine Hydrochloride | 153 |
| 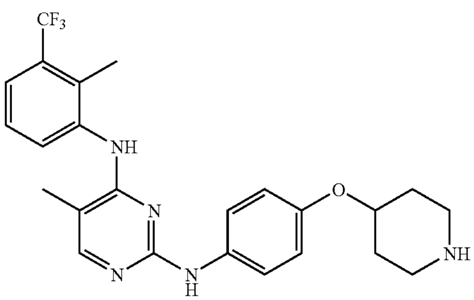 | 5-Methyl-N4-(2-methyl-3-trifluoromethyl-phenyl)-N2-[4-(piperidin-4-yloxy)-phenyl]-pyrimidine-2,4-diamine | 52.9 |
| 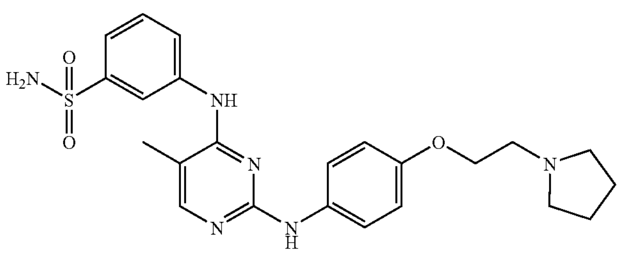 | 3-{5-Methyl-2-[4-(2-pyrrolidin-1-yl-ethoxy)-phenylamino]-pyrimidin-4-ylamino}-benzenesulfonamide | 72.2 |
| 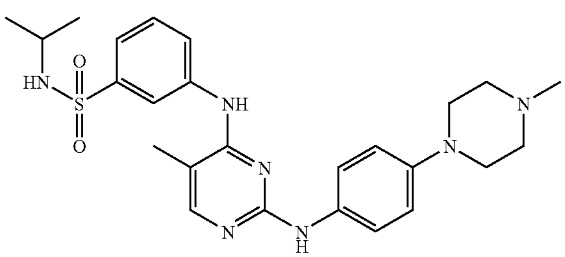 | N-Isopropyl-3-{5-methyl-2-[4-(4-methyl-piperazin-1-yl)-phenylamino]-pyrimidin-4-ylamino}-benzenesulfonamide | 11.8 |
| 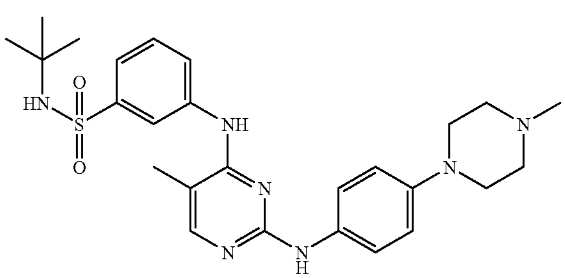 | N-tert-Butyl-3-{5-methyl-2-[4-(4-methyl-piperazin-1-yl)-phenylamino]-pyrimidin-4-ylamino}-benzenesulfonamide | 6.06 |

TABLE 1-continued

Compounds of the Invention And Their IC Values for Jak2 Kinase

| Structure | Name | JAK2 IC50 |
|---|---|---|
| 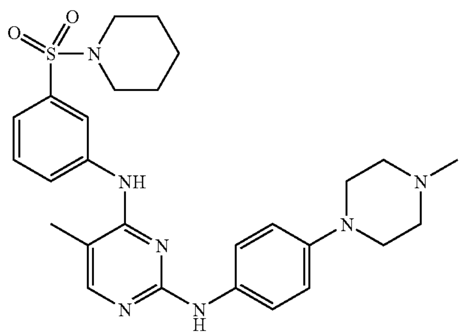 | 5-Methyl-N2-[4-(4-methyl-piperazin-1-yl)-phenyl]-N4-[3-(piperidine-1-sulfony)-phenyl]-pyrimidine-2,4-diamine Hydrochloride | 24.8 |
| 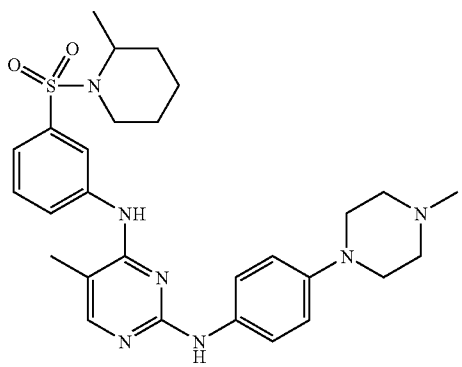 | 5-Methyl-N2-[4-(4-methyl-piperazin-1-yl)-phenyl]-N4-[3-(2-methyl-piperidine-1-sulfony)-phenyl]-pyrimidine-2,4-diamine Hydrochloride | 33.5 |
| 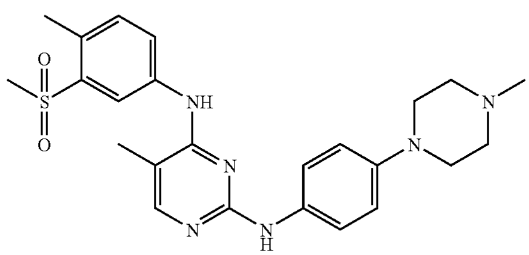 | N4-(3-Methanesulfonyl-4-methyl-phenyl)-5-methyl-N2-[4-(4-methyl-piperazin-1-yl)-phenyl]-pyrimidine-2,4-diamine | 160 |
| 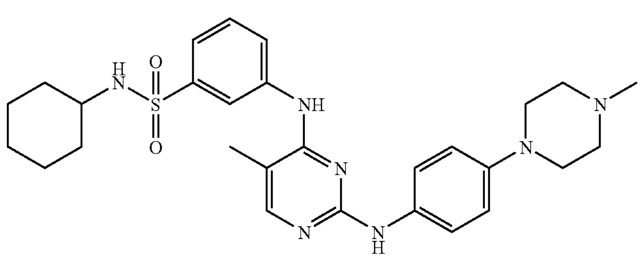 | N-Cyclohexyl-3-{5-methyl-2-[4-(4-methyl-piperazin-1-yl)-phenylamino]-pyrimidin-4-ylamino}-benzenesulfonamide | 39.4 |
| 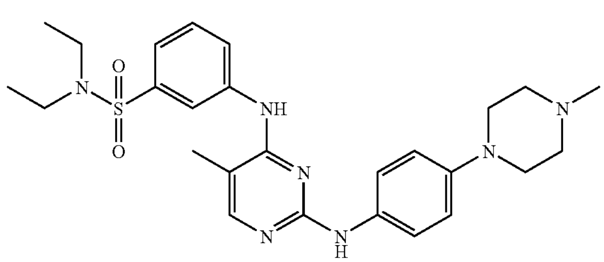 | N,N-Diethyl-3-{5-methyl-2-[4-(4-methyl-piperazin-1-yl)-phenylamino]-pyrimidin-4-ylamino}-benzenesulfonamide | 60.3 |

TABLE 1-continued

Compounds of the Invention And Their IC Values for Jak2 Kinase

| Structure | Name | JAK2 IC50 |
|---|---|---|
| 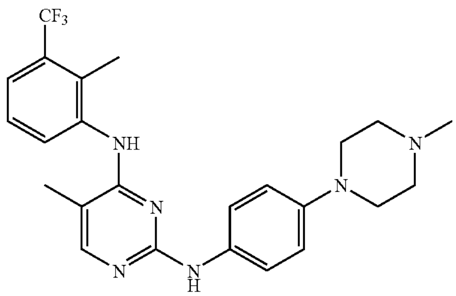 | N4-(3-(trifluoromethyl)-2-methylphenyl)-5-methyl-N2-(4-(4-methylpiperazin-1-yl)phenyl)pyrimidine-2,4-diamine hydrochloride | 87.1 |
| 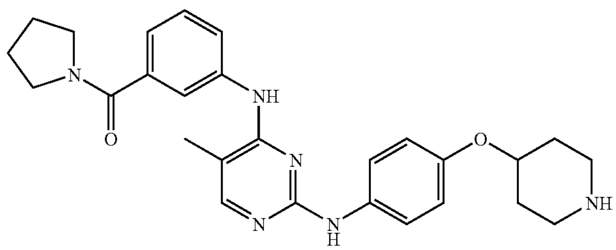 | (3-{5-Methyl-2-[4-(piperidin-4-yloxy)-phenylamino]-pyrimidin-4-ylamino}-phenyl)-pyrrolidin-1-yl-methanone | 113 |
| 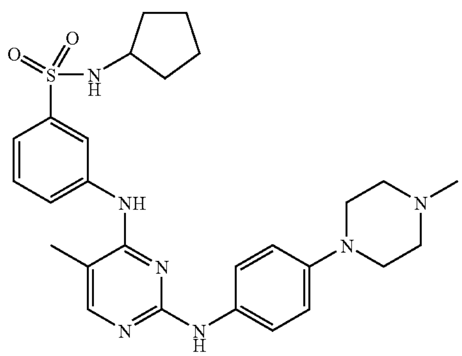 | N-Cyclopentyl3-{5-Methyl-2-[4-(4-methyl-piperazin-1-yl)-phenylamino]-pyrimidine-4-ylamino}-benzenesulfonamide Hydrochloride | 19.8 |
| 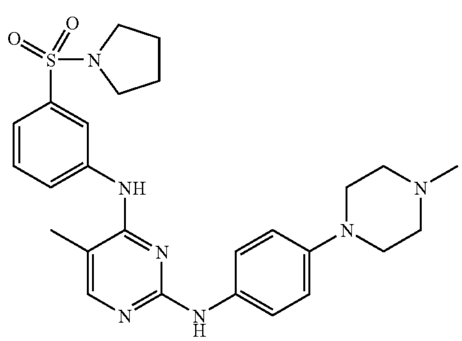 | 5-Methyl-N2-[4-(4-methyl-piperazin-1-yl)-phenyl]-N4-[3-(pyrrolidine-1-sulfony)-phenyl]-pyrimidine-2,4-diamine Hydrochloride | 17.1 |
| 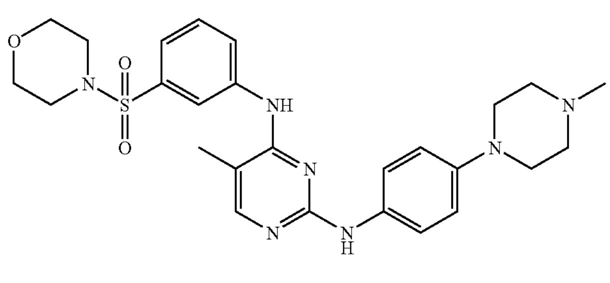 | 5-Methyl-N2-[4-(4-methyl-piperazin-1-yl)-phenyl]-N4-[3-(morpholine-4-sulfonyl)-phenyl]-pyrimidine-2,4-diamine | 20.7 |

TABLE 1-continued

Compounds of the Invention And Their IC Values for Jak2 Kinase

| Structure | Name | JAK2 IC50 |
|---|---|---|
| 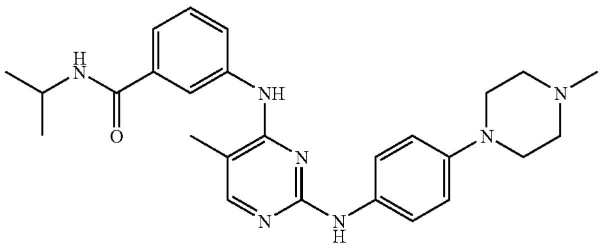 | N-Isopropyl-3-{5-methyl-2-[4-(4-methyl-piperazin-1-yl)-phenylamino]-pyrimidin-4-ylamino}-benzamide | 541 |
| 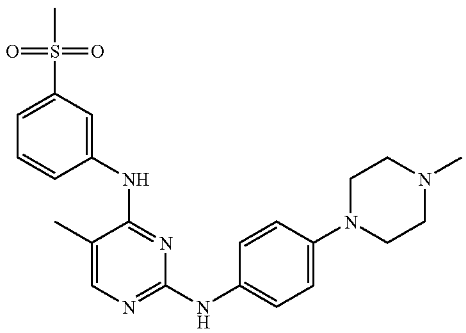 | 5-methyl-N2-(4-(4-methylpiperazin-1-yl)phenyl)-N4-(3-(methylsulfonyl)phenyl)-pyrimidine-2,4-diamine | 215 |
| 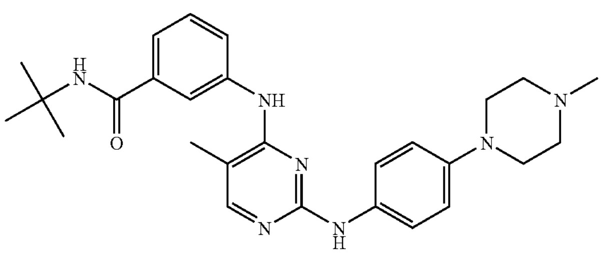 | N-tert-Butyl-3-{5-methyl-2-[4-(4-methyl-piperazin-1-yl)-phenylamino]-pyrimidin-4-ylamino}-benzamide | 890 |
| 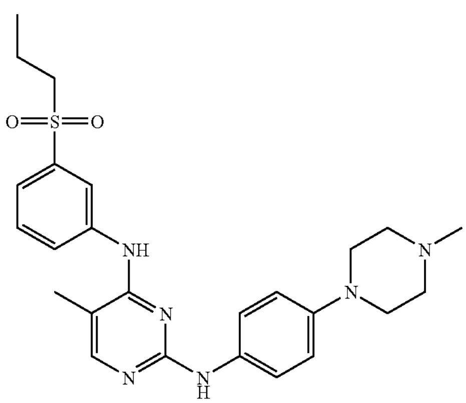 | 5-methyl-N2-(4-(4-methylpiperazin-1-yl)phenyl)-N4-(3-(propylsulfonyl)phenyl)-pyrimidine-2,4-diamine | 8 |
| 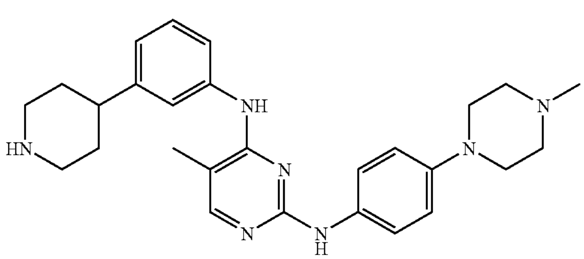 | 5-Methyl-N2-[4-(4-methyl-piperazin-1-yl)-phenyl]-N4-(3-piperidin-4-yl-phenyl)-pyrimidine-2,4-diamine | 42.5 |

TABLE 1-continued

Compounds of the Invention And Their IC Values for Jak2 Kinase

| Structure | Name | JAK2 IC50 |
|---|---|---|
| 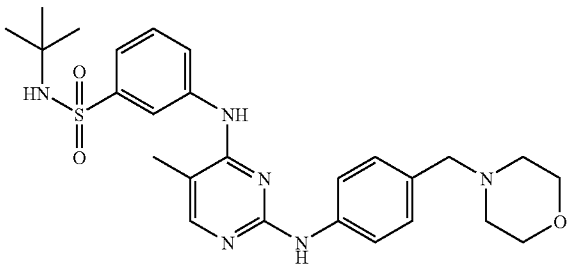 | N-tert-Butyl-3-[5-methyl-2-(4-morpholin-4-ylmethyl-phenylamino)-pyrimidin-4-ylamino]-benzenesulfonamide | 12.5 |
| 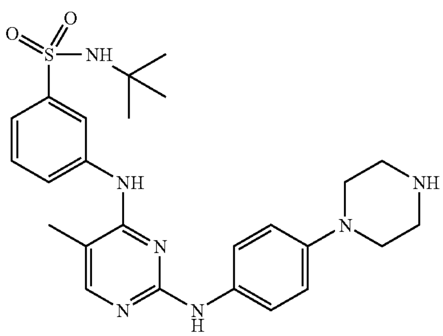 | N-tert-Butyl-3-[5-methyl-2-(4-piperazin-1-yl-phenylamino)-pyrimidin-4-ylamino]-benzenesulfonamide Hydrochloride | 7.59 |
| 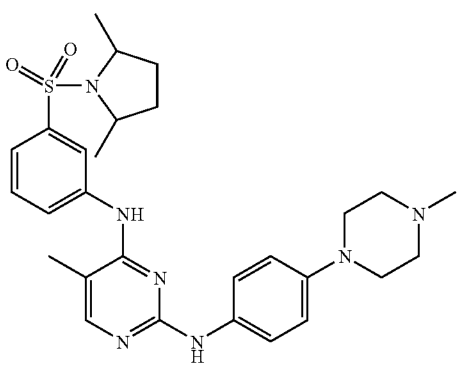 | N4-[3-(2,5-Dimethyl-pyrrolidine-1-sulfonyl)-phenyl]-5-methyl-N2-[4-(4-methyl-piperazin-1-yl)-phenyl]-pyrimidine-2,4-diamine Hydrochloride | 18.8 |
| | N-tert-Butyl-3-(2-{4-[4-(2-hydroxy-ethyl)-piperazin-1-yl]-phenylamino}-5-methyl-pyrimidin-4-ylamino]-benzenesulfonamide Hydrochloride | 7.09 |

TABLE 1-continued

Compounds of the Invention And Their IC Values for Jak2 Kinase

| Structure | Name | JAK2 IC50 |
|---|---|---|
| 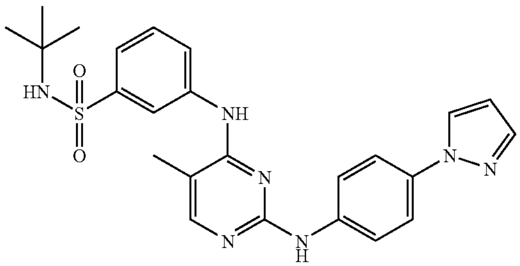 | N-tert-Butyl-3-[5-methyl-2-(4-pyrazol-1-yl-phenylamino)-pyrimidin-4-ylamino]-benzenesulfonamide | 19 |
| 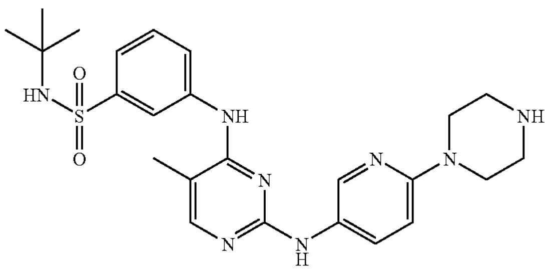 | N-tert-Butyl-3-[5-methyl-2-(6-piperazin-1-yl-pyridin-3-ylamino)-pyrimidin-4-ylamino]-benzenesulfonamide | 10 |
| 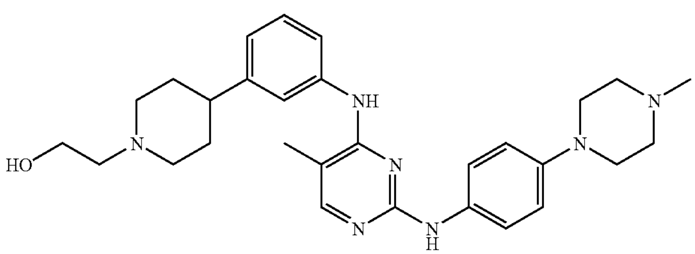 | 2-[4-(3-{5-Methyl-2-[4-(4-methyl-piperazin-1-yl)-phenylamino]-pyrimidin-4-ylamino}-phenyl)-piperidin-1-yl]-ethanol | 8.46 |
| 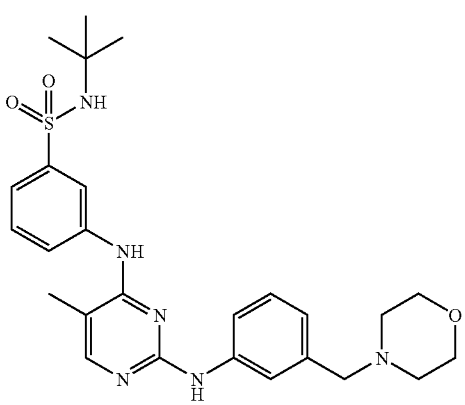 | N-tert-Butyl-3-[5-methyl-2-(3-morpholin-4-ylmethyl-phenylamino)-pyrimidin-4-ylamino]-benzenesulfonamide | 7.06 |
| 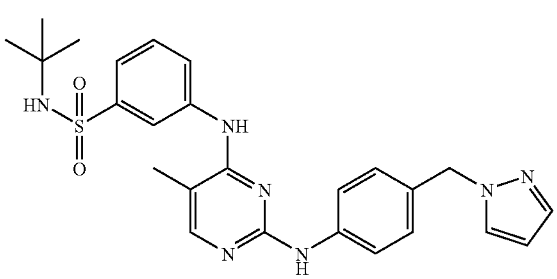 | N-tert-Butyl-3-[5-methyl-2-(4-pyrazol-1-ylmethyl-phenylamino)-pyrimidin-4-ylamino}-benzenesulfonamide | 18.6 |

TABLE 1-continued

Compounds of the Invention And Their IC Values for Jak2 Kinase

| Structure | Name | JAK2 IC50 |
|---|---|---|
| 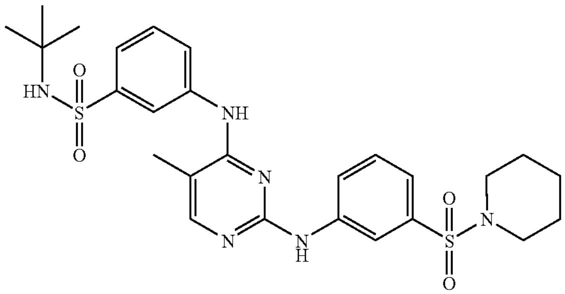 | N-tert-Butyl-3-{5-methyl-2-[3-(piperidine-1-sulfonyl)-phenylamino]-pyrimidin-4-ylamino}-benzenesulfonamide | 316 |
| 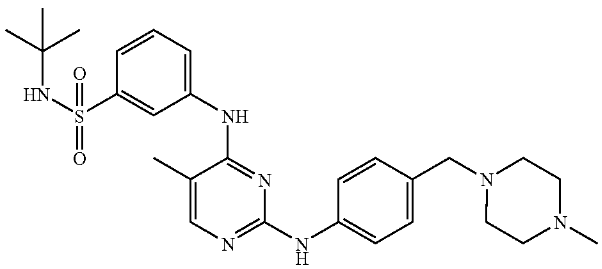 | N-tert-butyl-3-{[5-methyl-2-({4-[(4-methylpiperazin-1-yl)methyl]phenyl}amino)-pyrimidin-4-yl]amino}benzenesulfonamide | 29.8 |
| 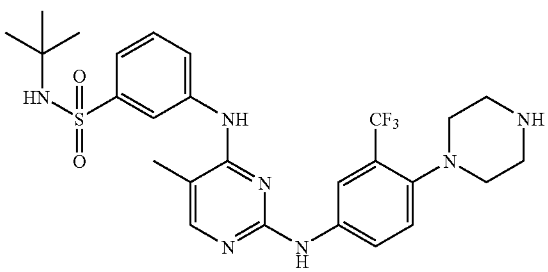 | N-tert-butyl-3-[(5-methyl-2-{[4-piperazin-1-yl-3-(trifluoromethyl)phenyl]amino}-pyrimidin-4-yl)amino]benzenesulfonamide | 22.5 |
| 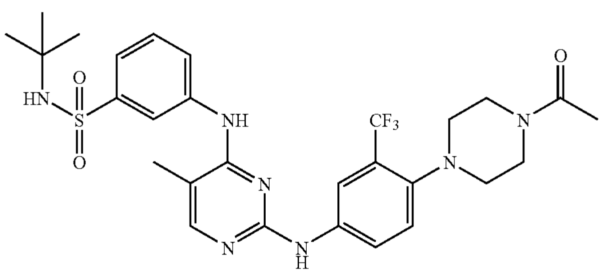 | 3-[(2-{[4-(4-acetylpiperazin-1-yl)-3-(trifluoromethyl)phenyl]amino}-5-methylpyrimidin-4-yl)amino]-N-tert-butylbenzenesulfonamide | 35.7 |
| 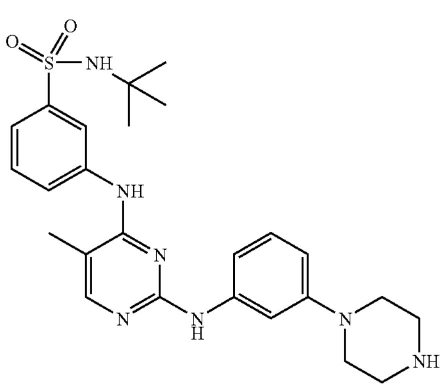 | N-tert-Butyl-3-[5-methyl-2-(3-piperazin-1-yl-phenylamino)-pyrimidin-4-ylamino]-benzenesulfonamide Hydrochloride | 18 |

TABLE 1-continued

Compounds of the Invention And Their IC Values for Jak2 Kinase

| Structure | Name | JAK2 IC50 |
|---|---|---|
| 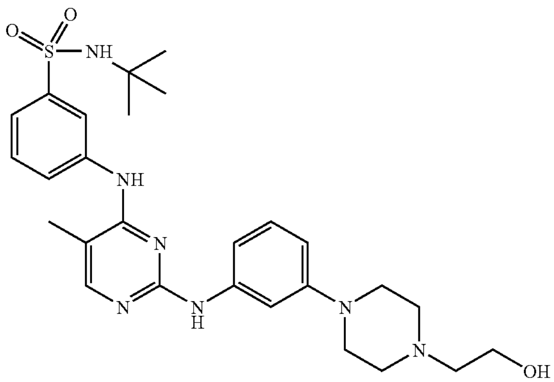 | N-tert-Butyl-3-(2-{3-[4-(2-hydroxy-ethyl)-piperazin-1-yl]-phenylamino}-[5-methyl-pyrimidin-4-ylamino]-benzenesulfonamide Hydrochloride | 40.5 |
| 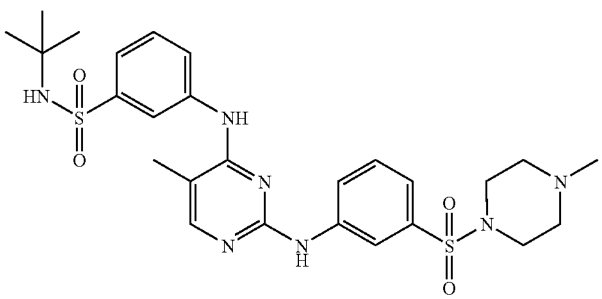 | N-tert-butyl-3-{[5-methyl-2-({3-[(4-methylpiperazin-1-yl)sulfonyl]phenyl}amino)-pyrimidin-4-yl]amino}benzenesulfonamide | 650 |
| 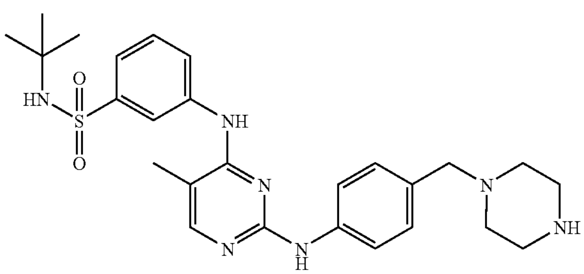 | N-tert-butyl-3-[(5-methyl-2-{[4-(piperazin-1-ylmethyl)phenyl]amino}-pyrimidin-4-yl)amino]benzenesulfonamide | 4.6 |
| 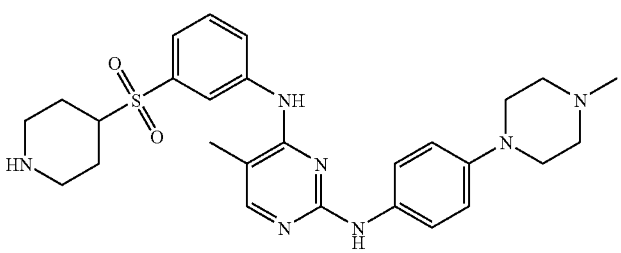 | 5-Methyl-N2-[4-(4-methyl-piperazin-1-yl)-phenyl]-N4-[3-(piperidine-4-sulfonyl)-phenyl]-pyrimidine-2,4-diamine | 198 |
| 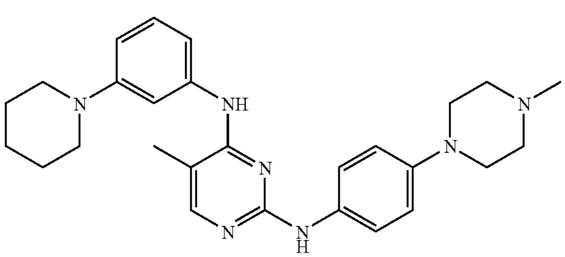 | 5-methyl-N2-(4-(4-methylpiperazin-1-yl)phenyl)-N4-(3-(piperidin-1-yl)phenyl)pyrimidine-2,4-diamine | 46.3 |

TABLE 1-continued

Compounds of the Invention And Their IC Values for Jak2 Kinase

| Structure | Name | JAK2 IC50 |
|---|---|---|
| 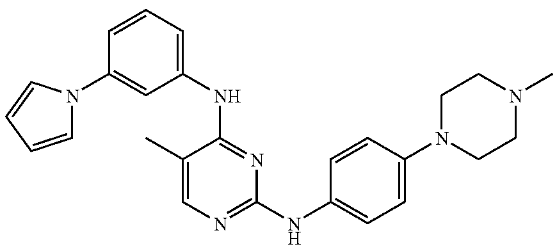 | N4-(3-(1H-pyrrol-1-yl)phenyl)-5-methyl-N2-(4-(4-methylpiperazin-1-yl)phenyl)pyrimidine-2,4-diamine | 33.8 |
| 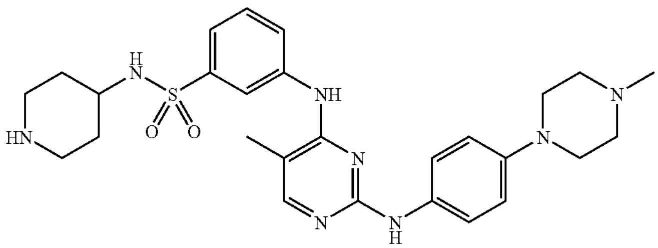 | 3-{5-Methyl-2-[4-(4-methyl-piperazin-1-yl)-phenylamino]-pyrimidin-4-ylamino}-N-piperidin-4-yl-benzenesulfonamide | 543 |
| 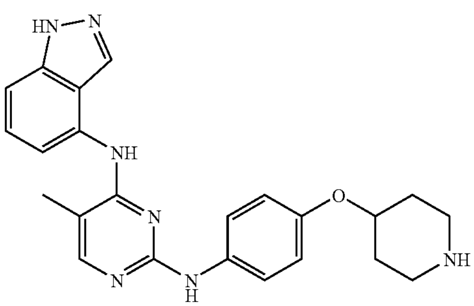 | N4-(1H-indazol-4-yl)-5-methyl-N2-(4-(piperidin-4-yloxy)phenyl)pyrimidine-2,4-diamine Hydrochloride | |
| 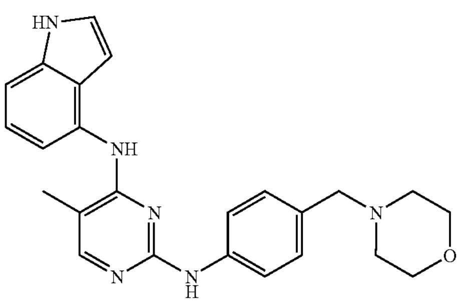 | N4-(1H-Indol-4-yl)-5-methyl-N2-(4-morpholin-4-ylmethyl-phenyl)-pyrimidine-2,4-diamine | 7.42 |
| 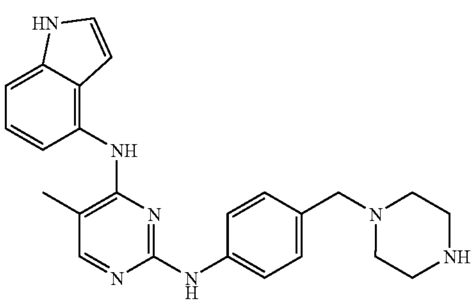 | N4-(1H-Indol-4-yl)-5-methyl-N2-(4-piperazin-1-ylmethyl-phenyl)-pyrimidine-2,4-diamine | 10.1 |

TABLE 1-continued

Compounds of the Invention And Their IC Values for Jak2 Kinase

| Structure | Name | JAK2 IC50 |
|---|---|---|
| 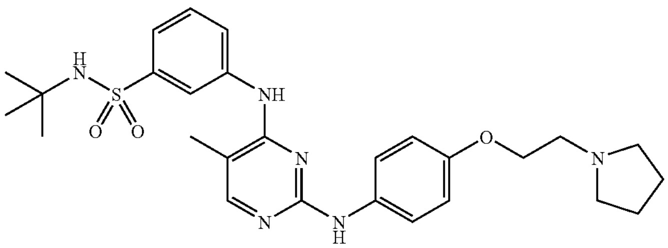 | N-tert-Butyl-3-{5-methyl-2-[4-(2-pyrrolidin-1-yl-ethoxy)-phenylamino]-pyrimidin-4-ylamino}-benzenesulfonamide | 12.5 |
| 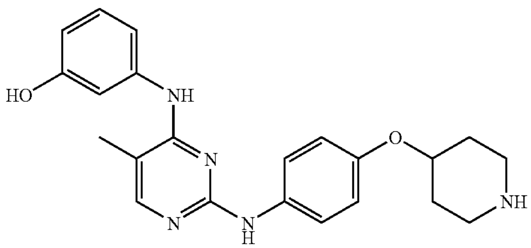 | 3-(2-(4-(piperidin-4-yloxy)phenylamino)-5-methylpyrimidin-4-ylamino)phenol | 51.9 |
| 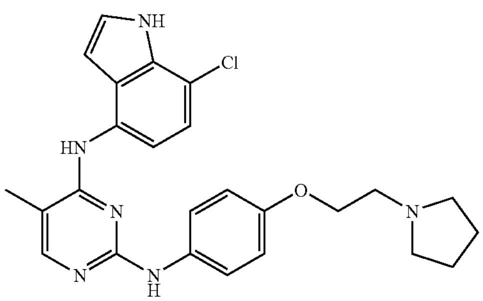 | N2-(4-(2-(pyrrolidin-1-yl)ethoxy)phenyl)-N4-(7-chloro-1H-indol-4-yl)-5-methylpyrimidine-2,4-diamine Hydrochloride | 1.16 |
| 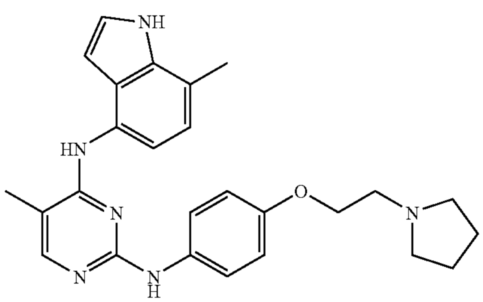 | N2-(4-(2-(pyrrolidin-1-yl)ethoxy)phenyl)-5-methyl-N4-(7-methyl-1H-indol-4-yl)pyrimidine-2,4-diamine Hydrochloride | 6.98 |
| 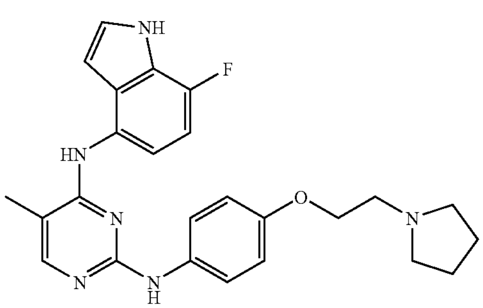 | N2-(4-(2-(pyrrolidin-1-yl)ethoxy)phenyl)-N4-(7-fluoro-1H-indol-4-yl)-5-methylpyrimidine-2,4-diamine Hydrochloride | 9.28 |

TABLE 1-continued

Compounds of the Invention And Their IC Values for Jak2 Kinase

| Structure | Name | JAK2 IC50 |
|---|---|---|
| 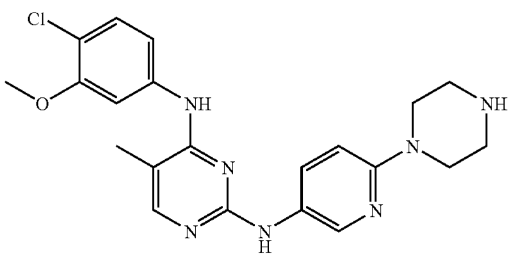 | N4-(4-Chloro-3-methoxy-phenyl)-5-methyl-N2-(6-piperazin-1-yl-pyridin-3-yl)-pyrimidine-2,4-diamine | 12.1 |
| 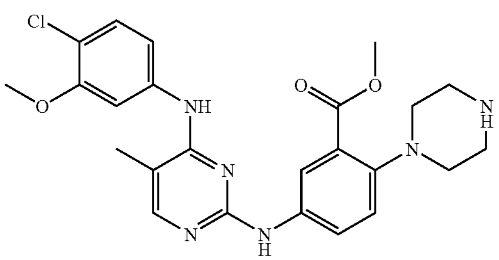 | 5-[4-(4-Chloro-3-methoxy-phenylamino)-5-methyl-pyrimidin-2-ylamino]-2-piperazin-1-yl-benzoic acid methyl ester | 5.12 |
| 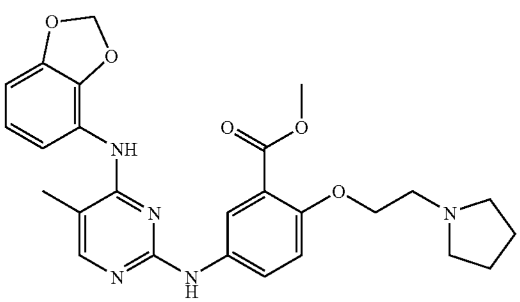 | 5-[4-(Benzo[1,3]dioxol-4-ylamino)-5-methyl-pyrimidin-2-ylamino]-2-(2-pyrrolidin-1-yl-ethoxy)-benzoic acid methyl ester | 16.4 |
| 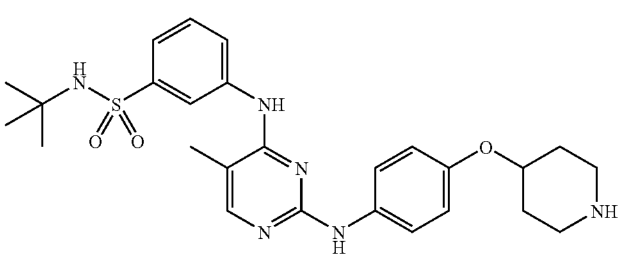 | N-tert-Butyl-3-{5-methyl-2-[4-(piperidin-4-yloxy)-phenylamino]-pyrimidin-4-ylamino}-benzenesulfonamide | 7.3 |
| 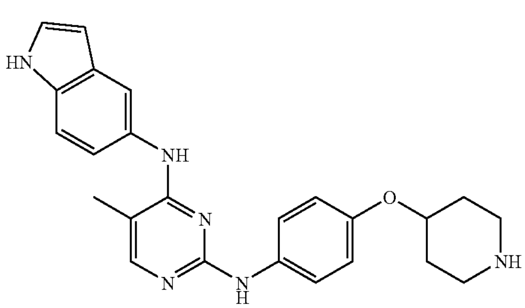 | N4-(1H-Indol-5-yl)-5-methyl-N2-[4-(piperidin-4-yloxy)-phenyl]-pyrimidine-2,4-diamine |  |

TABLE 1-continued

Compounds of the Invention And Their IC Values for Jak2 Kinase

| Structure | Name | JAK2 IC50 |
|---|---|---|
| 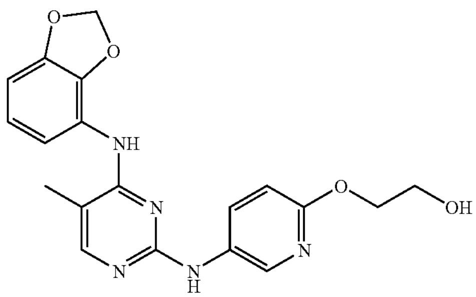 | 2-{5-[4-(Benzo[1,3]dioxol-4-ylamino)-5-methyl-pyrimidin-2-ylamino]-pyridin-2-yloxy}-ethanol | 116 |
| 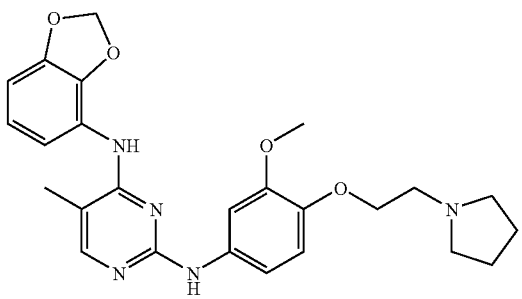 | N4-Benzo[1,3]dioxol-4-yl-N2-[3-methoxy-4-(2-pyrrolidin-1-yl-ethoxy)-phenyl]-5-methyl-pyrimidine-2,4-diamine | 9.34 |
| 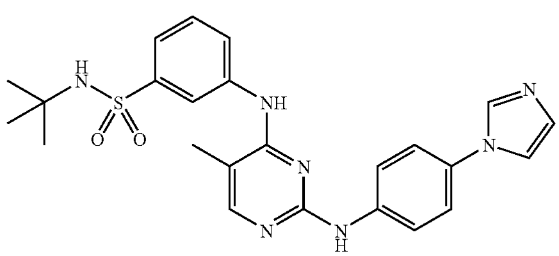 | N-tert-Butyl-3-[2-(4-imidazol-1-yl-phenylamino)-5-methyl-pyrimidin-4-ylamino]-benzenesulfonamide | 12.3 |
| 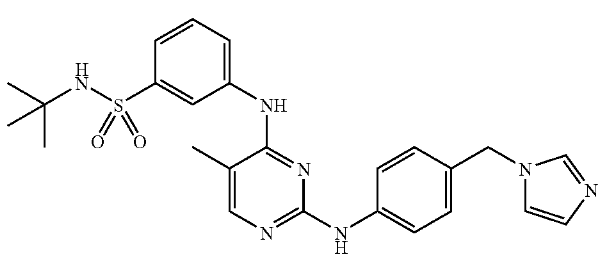 | N-tert-Butyl-3-[2-(4-imidazol-1-ylmethyl-phenylamino)-5-methyl-pyrimidin-4-ylamino]-benzenesulfonamide | 8.42 |
| 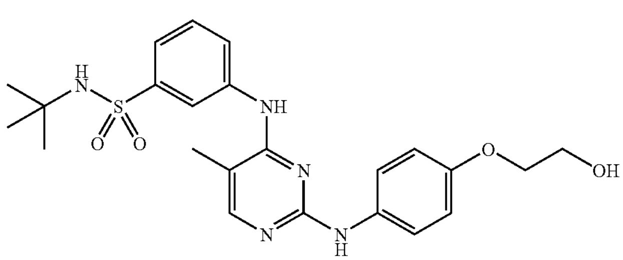 | N-tert-Butyl-3-{2-[4-(2-hydroxy-ethoxy)-phenylamino]-5-methyl-pyrimidin-4-ylamino}-benzenesulfonamide | 20.3 |

TABLE 1-continued

Compounds of the Invention And Their IC Values for Jak2 Kinase

| Structure | Name | JAK2 IC50 |
|---|---|---|
| 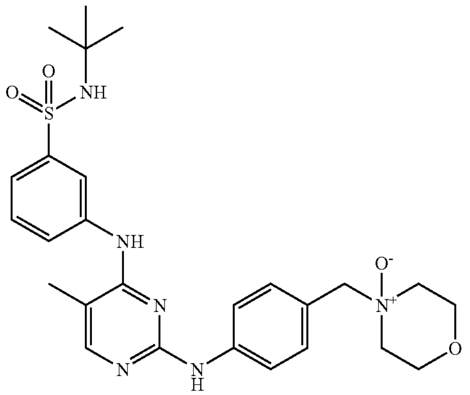 | N-tert-Butyl-3-{5-methyl-2-[4-(4-oxy-morpholin-4-ylmethyl)-phenylamino]-pyrimidin-4-ylamino}-benzenesulfonamide | 48.6 |
| 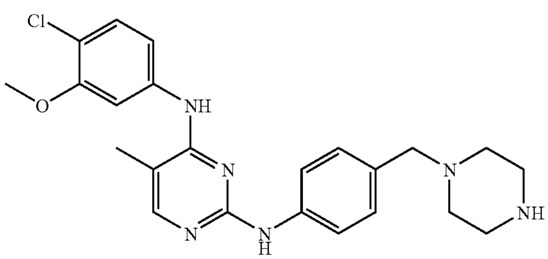 | N4-(4-Chloro-3-methoxy-phenyl)-5-methyl-N2-(4-piperazin-1-ylmethyl-phenyl)-pyrimidine-2,4-diamine | 15.2 |
| 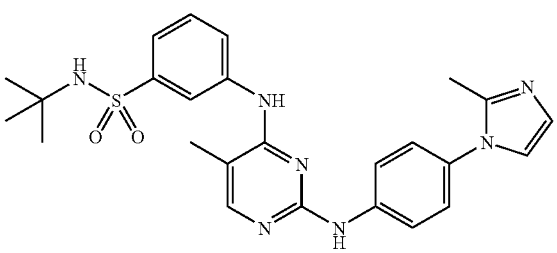 | N-tert-Butyl-3-{5-methyl-2-[4-(2-methyl-imidazol-1-yl)-phenylamino]-pyrimidin-4-ylamino}-benzenesulfonamide | 34.3 |
| 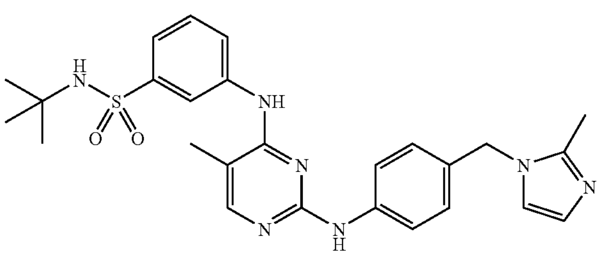 | N-tert-Butyl-3-{5-methyl-2-[4-(2-methyl-imidazol-1-ylmethyl)-phenylamino]-pyrimidin-4-ylamino}-benzenesulfonamide | 21.9 |
| 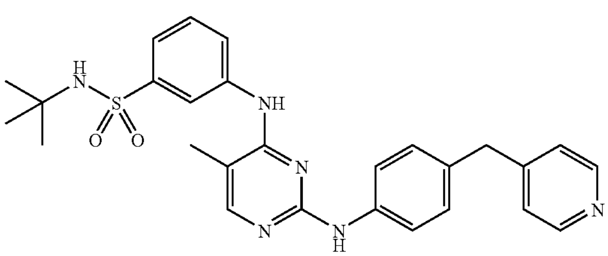 | N-tert-Butyl-3-[5-methyl-2-(4-pyridin-4-ylmethyl-phenylamino)-pyrimidin-4-ylamino]-benzenesulfonamide | 80.7 |

TABLE 1-continued

Compounds of the Invention And Their IC Values for Jak2 Kinase

| Structure | Name | JAK2 IC50 |
|---|---|---|
| 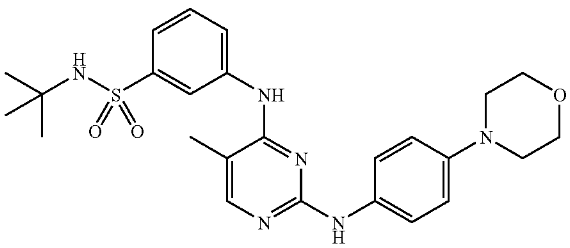 | N-tert-Butyl-3-[5-methyl-2-(4-morpholin-4-yl-phenylamino)-pyrimidin-4-ylamino]-benzenesulfonamide | 12.1 |
| 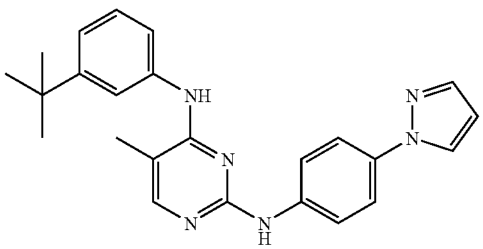 | N2-(4-(1H-pyrazol-1-yl)phenyl)-N4-(3-tert-butylphenyl)-5-methylpyrimidine-2,4-diamine | 151 |
| 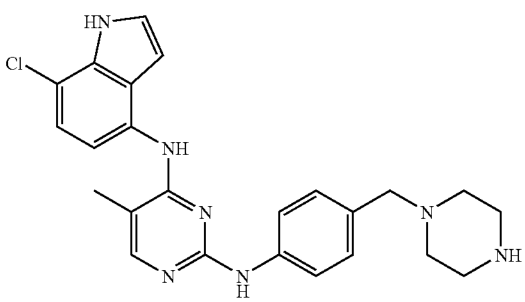 | N4-(7-chloro-1H-indol-4-yl)-5-methyl-N2-(4-((piperazin-1-yl)methyl)phenyl)pyrimidine-2,4-diamine Hydrochloride | 694 |
| | N4-(3-tert-butylphenyl)-5-methyl-N2-(4-(2-methyl-1H-imidazol-1-yl)phenyl)pyrimidine-2,4-diamine Hydrochloride | 38.4 |
| | N4-(3-tert-butylphenyl)-5-methyl-N2-(4-(2-methyl-1H-imidazol-1-yl)phenyl)pyrimidine-2,4-diamine Hydrochloride | 94.1 |

TABLE 1-continued

Compounds of the Invention And Their IC Values for Jak2 Kinase

| Structure | Name | JAK2 IC50 |
|---|---|---|
| 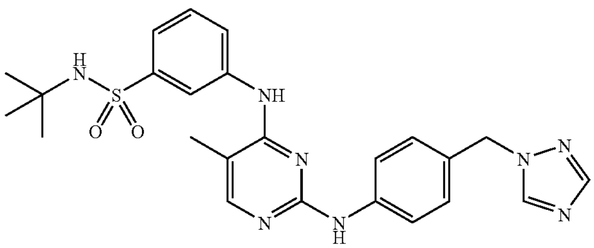 | N-tert-Butyl-3-[5-methyl-2-(4-[1,2,4]triazol-1-ylmethyl-phenylamino)-pyrimidin-4-ylamino]-benzenesulfonamide | 35.4 |
| 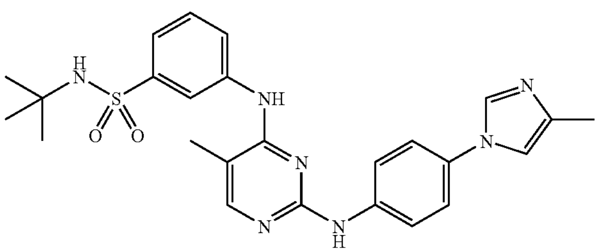 | N-tert-Butyl-3-{5-methyl-2-[4-(4-methyl-imidazol-1-yl)-phenylamino]-pyrimidin-4-ylamino}-benzenesulfonamide | 41.7 |
| 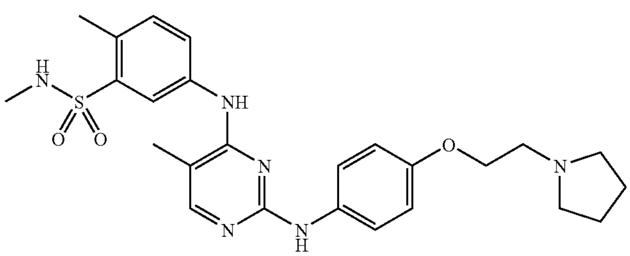 | 2,N-Dimethyl-5-{5-methyl-2-[4-(2-pyrrolidin-1-yl-ethoxy)-phenylamino]-pyrimidin-4-ylamino}-benzenesulfonamide | 127 |
| 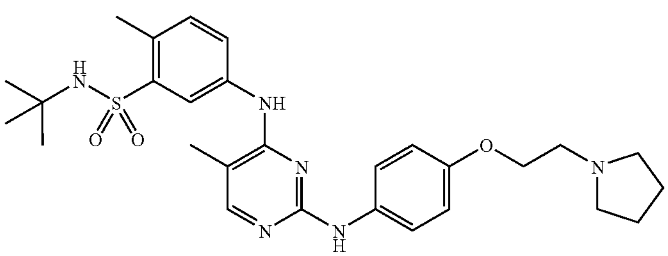 | N-tert-Butyl-2-methyl-5-{5-methyl-2-[4-(2-pyrrolidin-1-yl-ethoxy)-phenylamino]-pyrimidin-4-ylamino}-benzenesulfonamide | 44.4 |
| 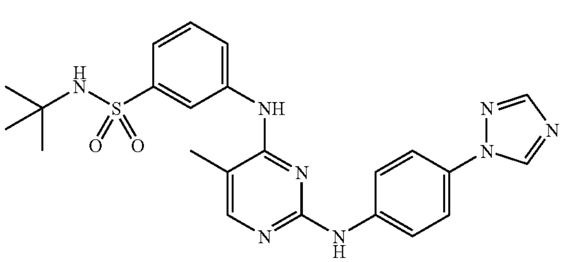 | N-tert-Butyl-3-[5-methyl-2-(4-[1,2,4]triazol-1-yl-phenylamino)-pyrimidin-4-ylamino]-benzenesulfonamide | 41.4 |

TABLE 1-continued

Compounds of the Invention And Their IC Values for Jak2 Kinase

| Structure | Name | JAK2 IC50 |
|---|---|---|
| 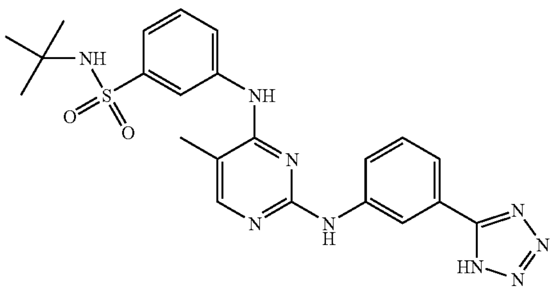 | N-tert-Butyl-3-{5-methyl-2-[3-(1H-tetrazol-5-yl)-phenylamino]-pyrimidin-4-ylamino}-benzenesulfonamide | 55.9 |
| 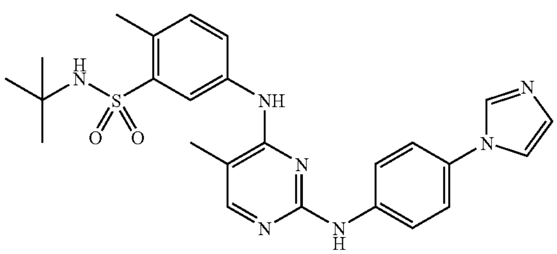 | N-tert-Butyl-5-[2-(4-imidazol-1-yl-phenylamino)-5-methyl-pyrimidin-4-ylamino]-2-methyl-benzenesulfonamide | 88.2 |
| 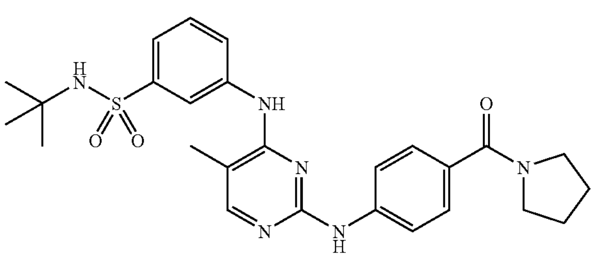 | N-tert-Butyl-3-{5-methyl-2-[4-(pyrrolidine-1-carbonyl)-phenylamino]-pyrimidin-4-ylamino}-benzenesulfonamide | 33.5 |
| 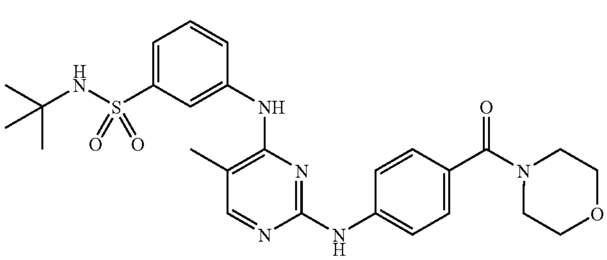 | N-tert-Butyl-3-{5-methyl-2-{4-(morpholine-4-carbonyl)-phenylamino]-pyrimidin-4-ylamino}-benzenesulfonamide | 32.9 |
| 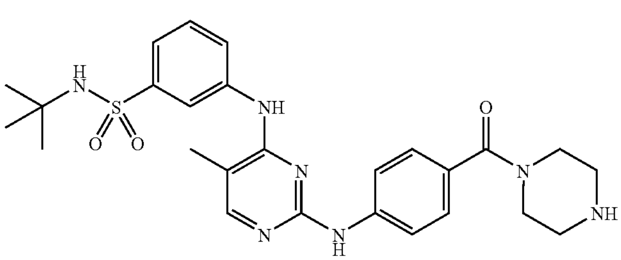 | N-tert-Butyl-3-{5-methyl-2-[4-(piperazine-1-carbonyl)-phenylamino]-pyrimidin-4-ylamino}-benzenesulfonamide | 69 |

TABLE 1-continued

Compounds of the Invention And Their IC Values for Jak2 Kinase

| Structure | Name | JAK2 IC50 |
|---|---|---|
| 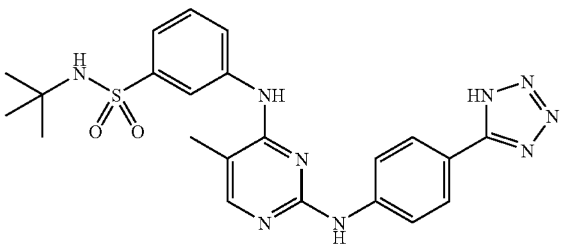 | N-tert-Butyl-3-{5-methyl-2-[4-(1H-tetrazol-5-yl)-phenylamino]-pyrimidin-4-ylamino}-benzenesulfonamide | 96.7 |
| 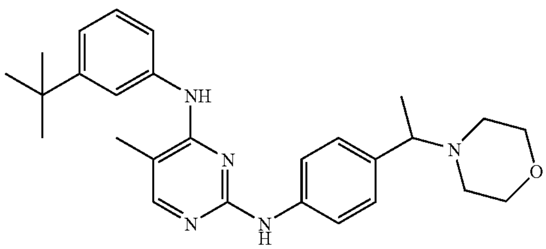 | N4-(3-tert-butylphenyl)-5-methyl-N2-(4-(1-morpholinoethyl)-phenyl)pyrimidine-2,4-diamine Hydrochloride | 19.9 |
| 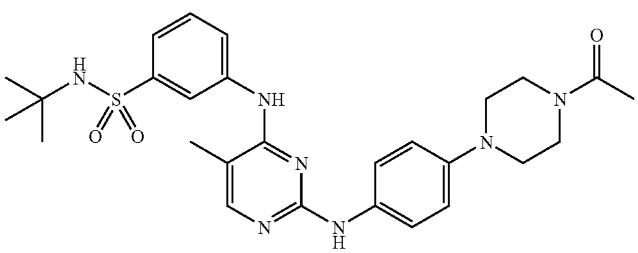 | 3-{2-[4-(4-Acetyl-piperazin-1-yl)-phenylamino]-5-methyl-pyrimidin-4-ylamino}-N-tert-butyl-benzenesulfonamide | 18.6 |
| 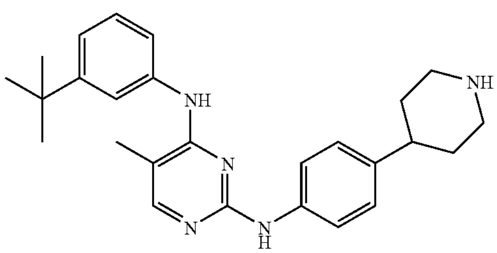 | N4-(3-tert-butylphenyl)-5-methyl-N2-(4-(piperidin-4-yl)phenyl)pyrimidine-2,4-diamine Hydrochloride | 20.9 |
| 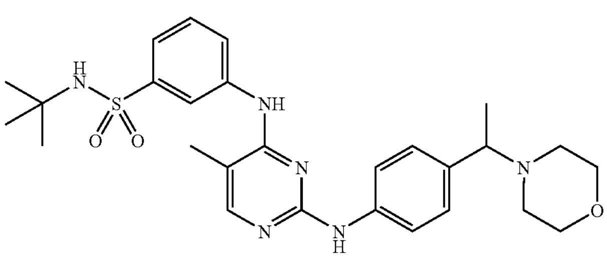 | N-tert-Butyl-3-{5-methyl-2-[4-(1-morpholin-4-yl-ethyl)-phenylamino]-pyrimidin-4-ylamino}-benzenesulfonamide | 29.7 |

TABLE 1-continued

Compounds of the Invention And Their IC Values for Jak2 Kinase

| Structure | Name | JAK2 IC50 |
|---|---|---|
| 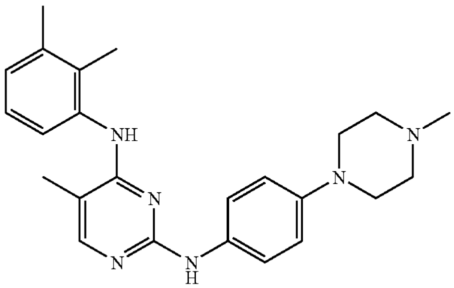 | 5-methyl-N4-(2,3-dimethylphenyl)-N2-(4-(4-methylpiperazin-1-yl)phenyl)pyrimidine-2,4-diamine Hydrochloride | 16 |
| 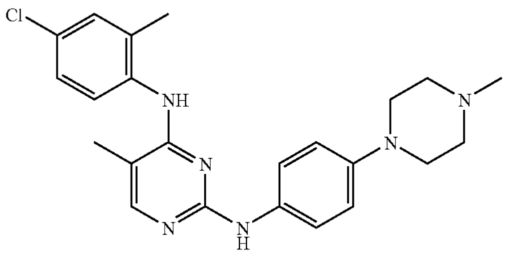 | N4-(4-chloro-2-methylphenyl)-5-methyl-N2-(4-(4-methylpiperazin-1-yl)phenyl)pyrimidine-2,4-diamine Hydrochloride | 15.9 |
| 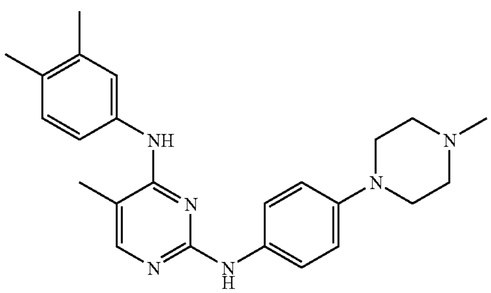 | 5-methyl-N4-(3,4-dimethylphenyl)-N2-(4-(4-methylpiperazin-1-yl)phenyl)pyrimidine-2,4-diamine Hydrochloride | 16.6 |

Example 245

Determination Of Efficacy Of Selected Compounds

HEL, CTLL-2 & normal human dermal fibroblasts (NHDF) were from the American Tissue Culture Collection Rockville, Md.). BaF/3 cells were obtained from DKFZ Cancer Research Center (Heidelberg, Germany).

BaF/3, HEL & NHDF cells were grown in RPMI 1640 medium (Gibco BRL, Gaithersburg, Md.) supplemented with penicillin, streptomycin, L-glutamine, and 10% fetal bovine serum (FBS). CTLL-2 cells were grown in the same media further supplemented with 20 U/mL recombinant IL-2 (Hoffmann-LaRoche, Nutley, N.J.). Plasmid containing the human JAK2 coding sequence was purchased from Invitrogen (Madison, Wis.). JAK2$^{V617F}$ cDNA was generated by using site-directed mutagenesis to introduce the V617F mutation into the human JAK2 coding sequence followed by verification using two-directional sequencing. This cDNA was subsequently subcloned into a retroviral vector and transduced into BaF/3 cells. Permanently transduced BaF/3 cells expressing JAK2$^{V617F}$ were selected and maintained with 1 mg/ml G418. GFP was introduced into this cells by lentiviral transduction using pLenti6-GFP (Invitrogen) followed by selection with blasticidin and confirmation of GFP expression using FACs analysis.

Cell proliferation assay was performed using the XTT cell proliferation kit according to the manufacturer's instructions (Roche, Alameda, Calif.). In brief, approximately 2.5×103 cells were plated in triplicate into microtiter-plate wells in 100 μL RPMI growth media plus various doses of XLV. After 72 hour incubation twenty microliters of XTT was added to the wells and allowed to incubate for 4-6 hours. The colored formazan product that is formed was measured spectrophotometrically using the Vmax spectrophotometer (Molecular Devices, Sunnyvale, Calif.) at 450 nm with correction at 650 nm. IC50 values were determined using the GraphPad Prism 4.0 software (San Diego, Calif.), wherefore OD values were plotted on y-axis (linear scale) and concentration (mM) on the x-axis (log scale). Data was subjected to a non-linear regression fit analysis and IC$_{50}$ values were determined as the concentration which inhibited proliferation 50%.

Proliferation EC50:
HEL—270 nM
Baf3:JAK2V617F—297 nM
Control data: IL-2-induced JAK3-dependent proliferation—3395 nM
Control data: Normal human dermal fibroblast control—6487 nM Apoptosis Assays BaF/3-JAK$^{V617F}$ cells cultured in growth medium (RPMI, 10% FBS, 1 mg/ml G418 and 10 μg/ml blasticidin) were treated with XLV at 1, 3 and 10 μM for 24 h. Following harvesting cells by centrifugation at 890 RCF (relative centrifugation force) for 5 min, genomic DNA was isolated from cell pellets using a DNA isolation kit (Puregen, Chino, Calif.). 5 μg genomic DNA of each sample was subjected to 1.2% agarose gel electrophoresis to detect genomic DNA fragmentation (DNA laddering assay). As a control, adherent normal human dermal fibroblasts (NHDF) cultured in growth medium (Cambrex, Walkersville, Md.) at 60% confluence were treated with XLV as described above. Following 2 washes with ice cold PBS, genomic DNA was isolated from the NHDF cells for agarose gel electrophoresis.

Immunoblotting

BaF/3-JAK$^{V617F}$ cells treated with XLV or vehicle control were centrifuged, washed 2× with ice-cold PBS and lysed using RIPA buffer. Protein concentration was determined using the BCA method (Pierce, Rockford, Ill.) and 100 μg of total cellular protein of each sample in 1× Laemmli buffer were subjected to Western blot analysis. The protein blot was probed with an anti-phospho-STAT5 (Tyr694/699) (Upstate Biotechnology, Charlottesville, Va.), subsequently stripped and re-probed with an anti-STAT5 antibody (Cell Signaling Technology, Danvers, Mass.). The phospho-STAT5 or STAT5 protein was visualized by the enhanced chemoluminescence method (Pierce). In vivo signaling studies were done in a similar fashion. Briefly, on day 11 after cell injection, animals were orally dosed with either vehicle or 100 mg/kg of XLV. Spleens were harvested 7 h after dosing and quickly homogenized in a FastPrep machine (Qbiogen, Irvine, Calif.). 100 μg of each spleen homogenate were subjected to Western blot analysis. The protein blot was probed with an blot was probed with an anti-phospho-STAT5 (Tyr694/699) (Upstate Biotechnology, Charlottesville, Va.), subsequently stripped and re-probed with an anti-STAT5 antibody (Cell Signaling Technology, Danvers, Mass.). The phospho-STAT5 or STAT5 protein was visualized by the enhanced chemoluminescence method (Pierce). In vivo signaling studies were done in a similar fashion. Briefly, on day 11 after cell injection, animals were orally dosed with either vehicle or 100 mg/kg of XLV. Spleens were harvested 7 h after dosing and quickly homogenized in a FastPrep machine (Qbiogen, Irvine, Calif.). 100 μg of each spleen homogenate were subjected to Western blot analysis. The protein blot was probed with an anti-phospho-STAT5 (Tyr694/699) and subsequently with an anti-STAT5 antibody and visualized by the enhanced chemoluminescence method.

FACs Analysis of Circulating Tumor Burden

Figure 38:
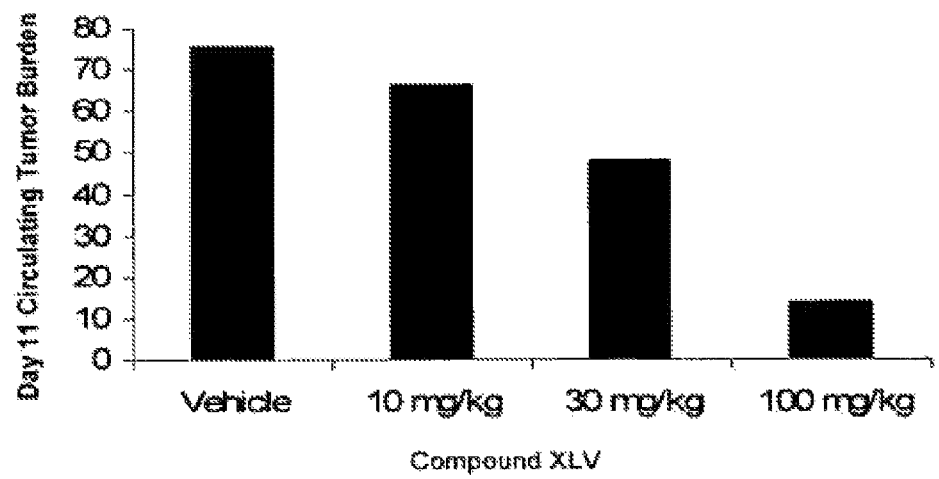
FIG. 38 shows the results of an FACS analysis on isolated $JAK2^{V617F}$ tumor cells.

On day 11 after injection of BaF/3-JAK2$^{V617F}$ cell suspension, 1 mL blood was collected by a terminal cardiac bleeding method from one mouse that received vehicle, moreover, 0.1 mL blood was collected by a non-lethal retro-orbital collection method from 10 mice of each of the three groups dosed with 10, 30 or 100 mg/kg of XLV and pooled together within the dose groups. Blood mono-nucleated cells were isolated by a Ficoll (Sigma-Aldrich, St. Louis, Mo.) cushion centrifugation method (600 RCF and 30 min). The isolated cells were subjected to FACS analysis to determine the percentage of GFP positive BaF/3:JAK2$^{V617F}$ cells. The results are shown in FIG. 38.

Circulating Tumor Model

Figure 39:
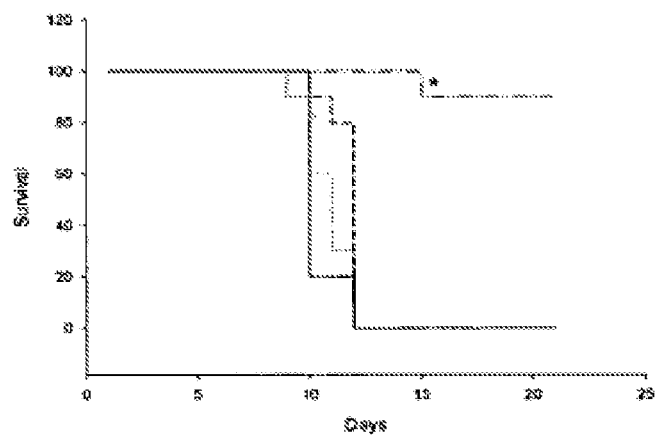
FIG. 39 shows the results of an in-vivo circulating tumor model.

SCID mice were intravenously injected with BaF/3 cells expressing JAK2$^{V617F}$ and GFP. XLV was dosed orally at the indicated doses beginning 3 days after infusion and ending 20 days after infusion. On day 11 blood was taken from animals in each group and subjected to FACs analysis to determine the percentage of circulating cells which were GFP positive. In a parallel study animals were treated as described above with the exception that they were given a single 100 mg/kg dose of drug on day 11 followed by 4 hours later by sacrifice and analysis of STAT5 phosphorylation in the tumor-bearing enlarged spleen. The results are shown in FIG. 39.

Ocular Exposure and Efficacy Data

Exposure data of compounds at 0.1% via eye drop administration:

On topical dosing of compounds formulated as 0.1% doses in 0.2% tyloxapol/1% HPMC/4% Mannitol, exposure levels in found in back of the eye tissues of the mouse are shown at two different time points, namely at 2 h and at 7 h. The efficacy data for selected compounds are shown in Table 2.

TABLE 2

Concentration (nM) in mouse ocular tissues following bilateral topical instillation of 0.1% formulation QDX1

| Formulation concentration for selected compounds | Time (hr) | Concentration (nM) | | |
|---|---|---|---|---|
| | | retina | Sclera/choroid | Cornea |
| 0.1% XVII | 2 | 495 | 6040 | 8840 |
| | 6 | 351 | 2970 | 3780 |
| 0.1% XXXVI | 2 | 816 | 7250 | 7870 |
| | 7 | 11200 | 34800 | 18600 |
| 0.1% XLIV | 2 | 406 | 4840 | 103000 |
| | 7 | 321 | 3180 | 26600 |
| 0.1% LXXXII | 2 | 267 | 2340 | 69900 |
| | 7 | 592 | 2250 | 45400 |
| 0.1% LXXIV | 2 | 2120 | 6090 | 45000 |
| | 7 | 2150 | 7350 | 21000 |

Example 246

Compound XVII in an Ocular Efficacy Study in an Oxygen-induced Retinopathy (OIR) Model Compound XVII was tested using the mouse oxygen-induced retinopathy (OIR) model, in which retinal neovascularization is triggered by cycling mouse pups from normoxia to hyperoxia and then back to normoxia. Litters of C57BL/6 mice were transferred to a hyperoxic environment (70% $O_2$) starting on postnatal day 7 (P7). After 5 days, litters were returned to a normoxic environment (21)% $O_2$), where they were then maintained for an additional 5 days, during which time they received topical applications of either compound XVII or an appropriate vehicle. At the end of this period, retinal whole-mounts were prepared and stained with a fluorescently-labeled lectin (BSL I) that recognizes murine endothelium. Finally, digital images were obtained by fluorescence microscopy and analyzed with an image analysis software program in order to quantify vascular area. In one study, animals dosed with a 0.1% formulation of compound XVII twice daily (bid) showed a 29% reduction in vascular area as compared to vehicle-treated animals (P<0.05, n=11-15); in a second study, a 22% reduction was observed (P<0.02, n=6). The results are summarized in Table 3.

TABLE 3

| Study # | Treatment Group | Vascular Area ($mm^2$, mean ± SD) | % Change vs. Vehicle Control |
|---|---|---|---|
| OIR-004 | Vehicle | 4.9 ± 1.6 | — |
| | 0.1% XVII | 3.5 ± 0.6 | −29% |

TABLE 3-continued

| Study # | Treatment Group | Vascular Area (mm², mean ± SD) | % Change vs. Vehicle Control |
|---|---|---|---|
| OIR-007 | Vehicle | 8.3 ± 0.8 | — |
|  | 0.1% XVII | 6.4 ± 1.6 | −22% |

Example 247

Using Compound LVII for the Treatment of Myeloproliferative Disorders

Figure 2:
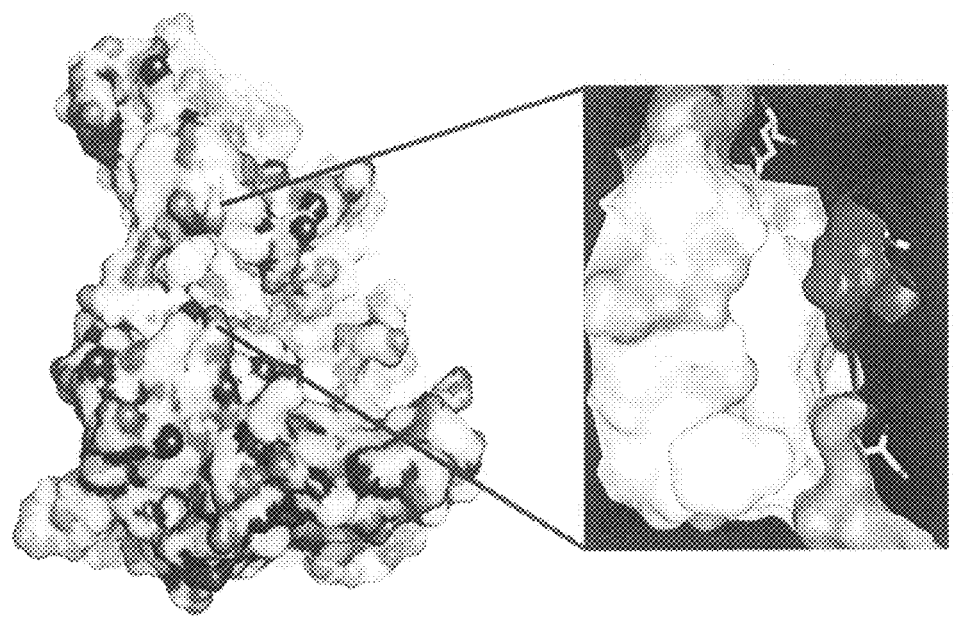
FIG. 2 is an illustration of co-crystallization of a compound of the present invention with JAK2 kinase.
Figure 3:
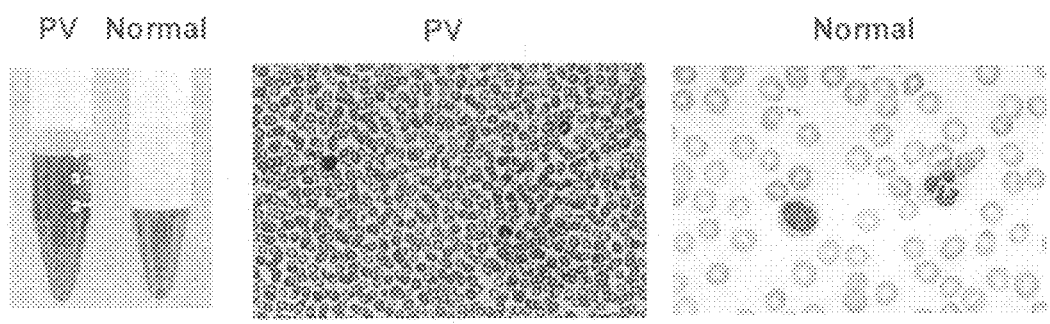
FIG. 3 shows that JAK2$^{V617F}$ mutation is present in a large number of patients with an unmet clinical need.

Compound LVII was tested as a potential kinase inhibitor to be used for the treatment of myeloproliferative disorders. The results are illustrated on FIGS. 1-9. As shown by FIG. 1, JAK2 transmits proliferation and survival signals from cytokine receptors. FIG. 2 demonstrates a co-crystal of compound LVII with JAK2 kinase, thus showing that crystallography and molecular modeling enabled identification of key interaction sites and discovery of potent, selective ATP competitive JAK2 inhibitors. FIG. 3 shows that JAK2$^{V617F}$ mutation is present in a large number of patients with an unmet clinical need. For example, the prevalence of was found in 99% of Polycythemia Vera, 71% of essential thrombocythemia, and 56% of myelofibrosis with myeloid metaplasia. Typically, this type of disease-dependence on a single kinase is rare. Complications typically include splenomegaly, bleeding, thrombosis, risk of leukemic progression, and treatment is unsatisfactory using hydroxyurea, interferon-α, phlebotomy, or anagrelide.

Compound LVII was profiled in 223 kinases. IC$_{50}$ was <50 for the following kinases: JAK2—3 nM; JAK2$^{V617F}$—3 nM; Flt3—15 nM; and Ret—48 nM. The same for primary anti-target (JAK3) was 1030 nM. Table 4 summarizes the potency and selectiveness data of compound LVII as an inhibitor of JAK2 kinase.

TABLE 4

| Compound | Primary Target JAK2 IC$_{50}$ (nM) | JAK Family Selectivity Profile (X-fbld selectivity) | | |
|---|---|---|---|---|
|  |  | JAK2 vs. JAK3 | JAK2 vs. JAK1 | JAK2 vs. TYK2 |
| LVII | 3 | 343 | 35 | 135 |

Figure 4:
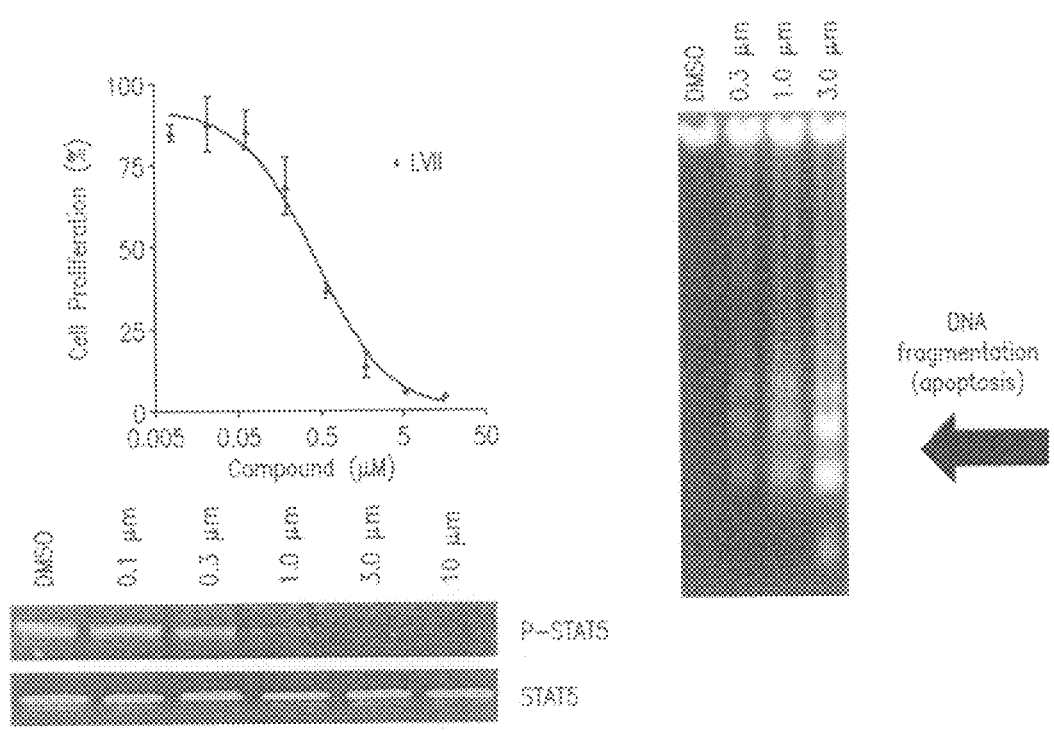
FIG. 4 illustrates schematically inhibition of JAK2$^{V617F}$ kinase by a compound of the present invention.
Figure 5:
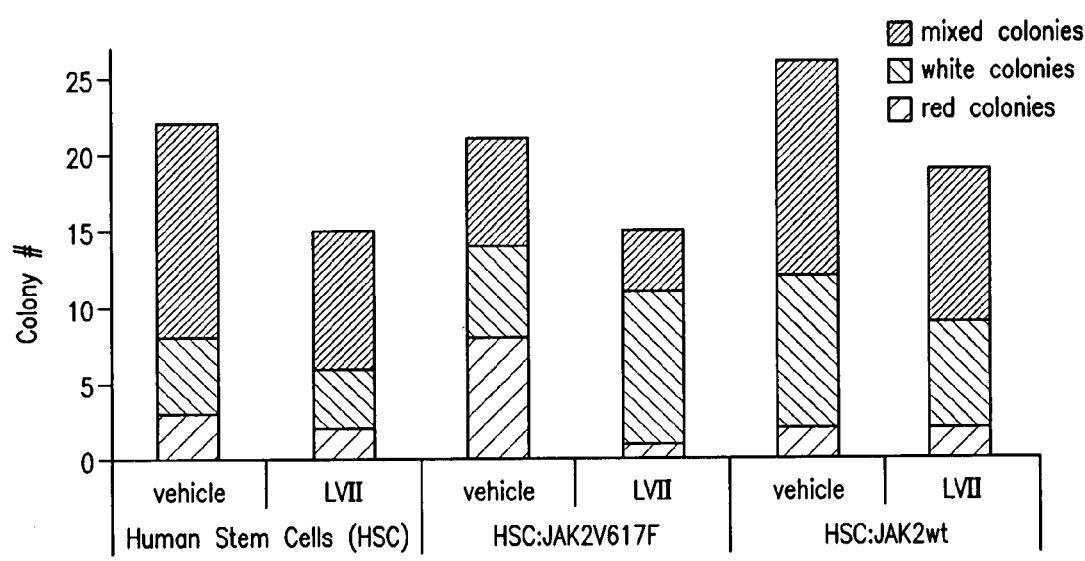
FIG. 5 illustrates schematically selectively reduction of erythrocyte colony formation in human stem cells by a compound of the present invention.

FIG. 4 shows that compound LVII inhibits JAK2 in cells leading to inhibition of proliferation and induction of apoptosis in HEL cells expressing JAK2$^{V617F}$. FIG. 5 shows that compound LVII selectively reduces erythrocyte colony formation in human stem cells. To obtain the data shown on FIG. 5, human stem cells were transduced with a retrovirus containing either the empty vector, JAK2$^{V617F}$ or JAK2 wild type and then evaluated in colony forming assays in the presence of 300 nM compound LVII. Erythrocyte colony formation was only inhibited in cells expressing JAK2$^{V617F}$, suggesting that compound LVII is more active in cells with a mutationally active pathway than control normal cells.

Figure 6:
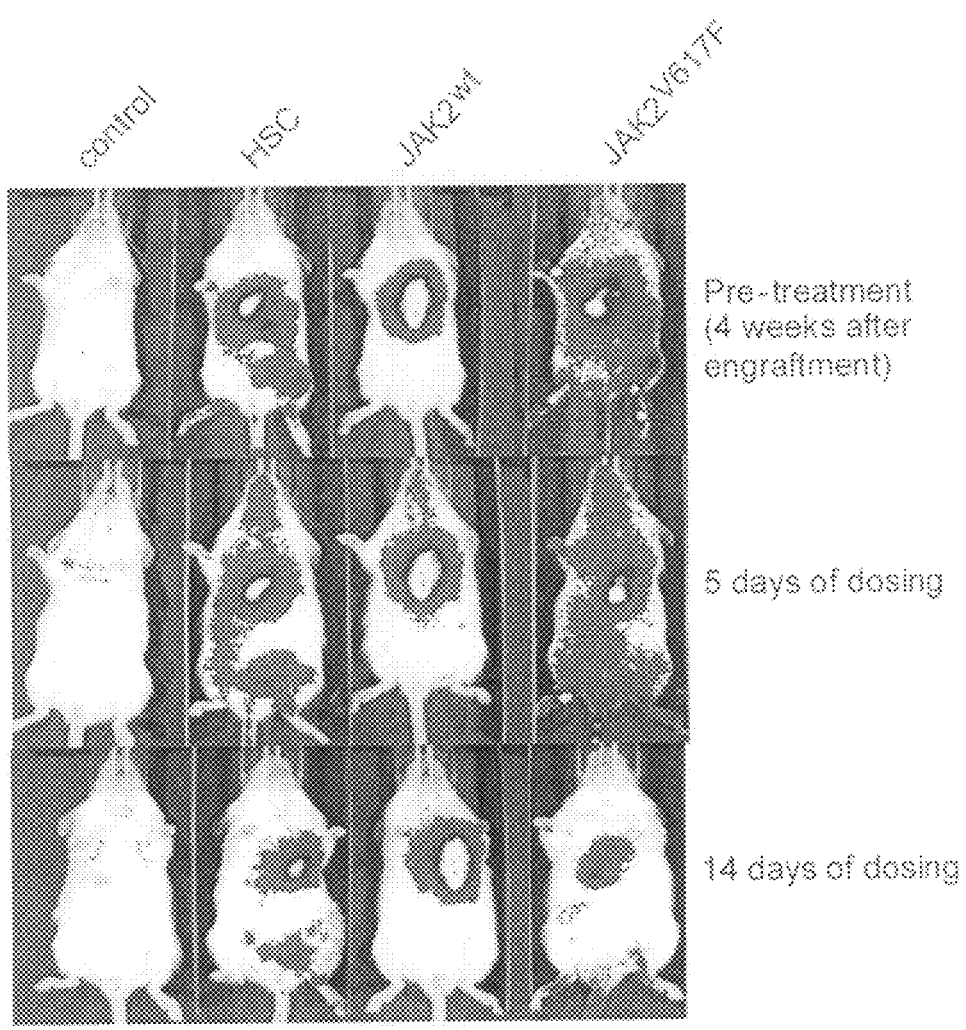
FIG. 6 shows selective reversal of engraftment of human stem cells expressing JAK2$^{V617F}$ using compound of the present invention.

FIG. 6 shows that compound LVII selectively reverses engraftment of human stem cells expressing JAK2$^{V617F}$—human stem cells prepared as described in above were injected into the liver of 1 day old immunocompromised mice and cell engraftment was allowed to progress for 4 weeks. Consistent with the results shown on FIG. 5, stem cells bearing JAK2$^{V617F}$ experienced a reversal of engraftment when that compound LVII was dosed orally, while mice bearing normal stem cells or stem cells bearing JAK2 wild type had no change in engraftment.

Figure 7:
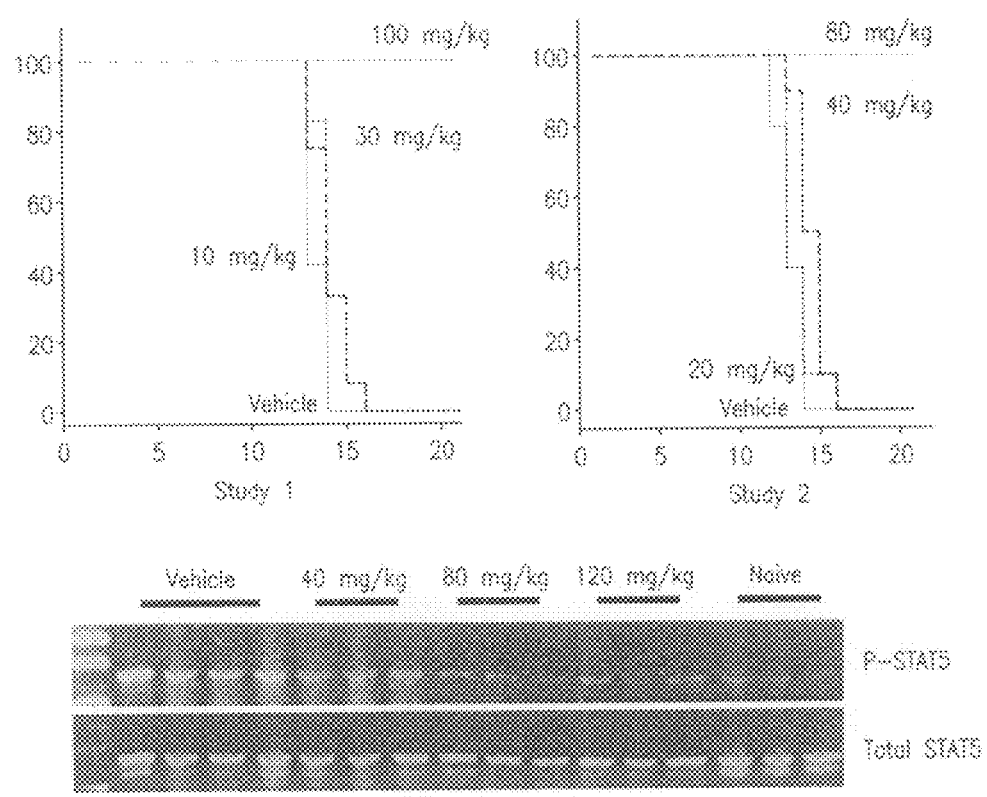
FIG. 7 illustrates schematically that an orally administered compound of the present invention inhibits JAK2$^{V617F}$ signaling in vivo.

FIG. 7 shows that orally administered compound LVII inhibits JAK2$^{V617F}$ signaling in vivo leading to increased survival in a Baf3/JAK2$^{V617F}$ system. Baf3 cells expressing JAK2$^{V617F}$ were injected into SCID mice leading to a splenomegaly and death. Orally administered compound LVII inhibited JAK2 signaling in the enlarged spleens of day 11 animals leading to a significant dose-dependent survival advantage.

Figure 8:
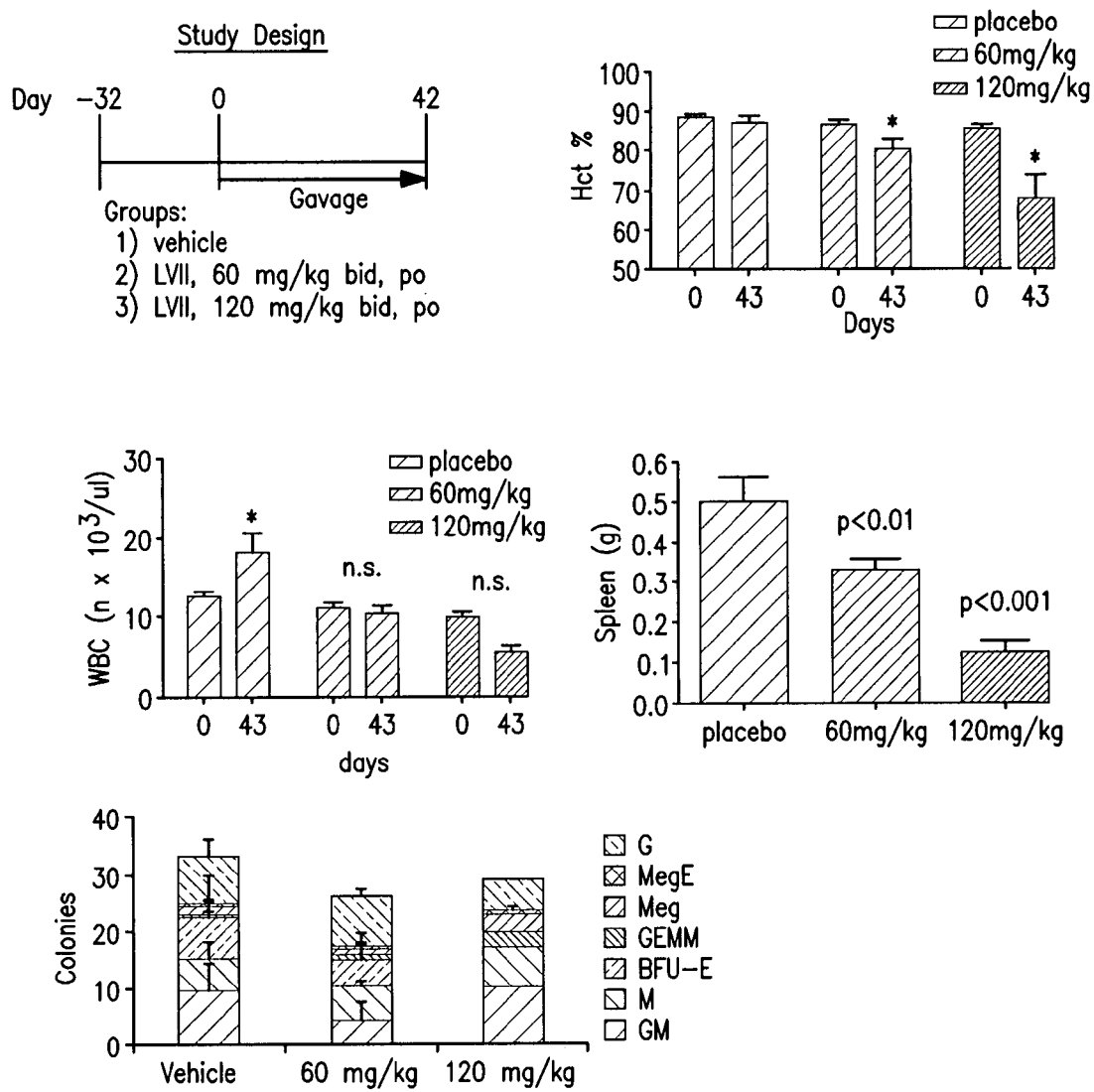
FIG. 8 shows reversal of polycythemia vera-like symptoms in mice by oral administration of a compound of the present invention.
Figure 9:
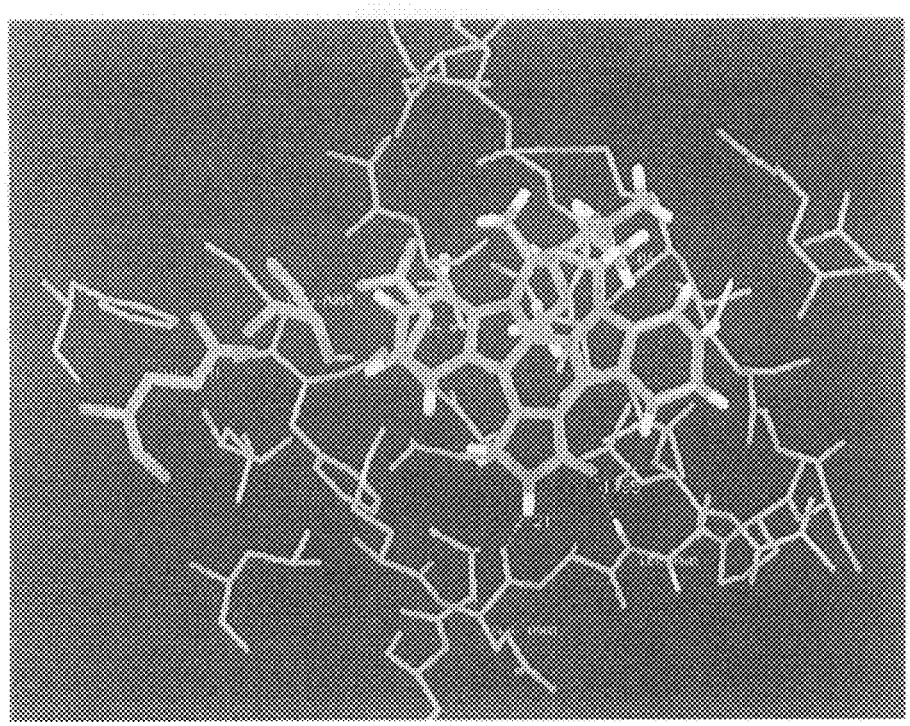
FIG. 9 shows 1YVJ crystal structure of the JAK3 kinase domain in complex with a staurosporine analog.

FIG. 8 shows that orally administered compound LVII reverses polycythemia vera-like symptoms in mice. The disease was induced by replacing the bone marrow of irradiated C57 mice with donor marrow that had been transduced with lentiviral JAK2$^{V617F}$. This results in an aggressive polycythemia vera-like phenotype characterized by elevated hematocrit, leukocytosis and splenomegaly. The disease was allowed to progress for 32 days prior to drug administration at which point the mice had dramatic disease-like symptoms as evidenced by a hematocrit of 90% at treatment start. Oral administration of compound LVII for 42 days, ⅓ of the RBC half-life, resulted in a dose-dependent resolution of these PV-like, JAK2$^{V617F}$-induced clinical symptoms.

In sum, compound LVII is active in vitro against cultured and patient-derived cells bearing the JAK2$^{V617F}$ mutations. In contrast, activity is much less against hematopoietic cells in which the JAK-STAT pathway is not activated by mutations. In vivo, oral administration of compound LVII reverses mutant cell engraftment and polycythemia-like symptoms in multiple animal models of the disease. This includes studies performed using a bone marrow transplant model in which normal mouse marrow is replaced with marrow expressing JAK2$^{V617F}$. After allowing a 1 month engraftment period in this model oral administration of compound LVII reversed the polycythemia, leukocytosis, extramedullary hematopoiesis and splenomegaly in a statistically significant, dose-dependent manner.

Example 248

Design of Inhibitors Targeting JAK2

As discussed above, somatic mutations in JAK2 (JAK2$^{V617F}$) and in the associated receptor kinases (MPLW515L/K) play a role in keeping the JAK2 pathway constitutively active, and are associated with the pathogenesis of the myeloproliferative disorders (MPDs), such as polycythemic vera (PV), essential thrombocythemia (ET) and myelofibrosis with myeloid metaplasia (MMM). JAK2 pathway dysregulation gives proliferative and survival advantages to hematopoietic precursors. Therefore, JAK2 inhibitors may find therapeutic utility in myeloid disease states in which the JAK2 pathway is involved JAK3 does form one co-crystal structure with an inhibitor (1YVJ, FIG. 9) in the PDB. This structure is, however, exceptional, and there were no other known JAK crystal structures. Based on this JAK3 crystal structure, we built a JAK2 homology model has been built to guide compound design by medicinal chemistry.

The JAK2 binding model has been validated via X-ray crystallography and a limited screen of a select set of compounds give the initial hits with JAK2 IC50 of 2-10 μM (Table 5).

TABLE 5

Initial Screening Hits for JAK2

| Compound | Structure | JAK2 (IC$_{50}$, nM) |
|---|---|---|
| 1 | 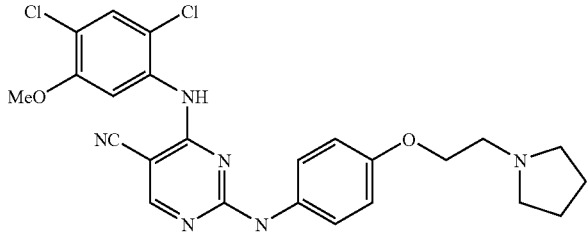 | 6240 |
| 2 | 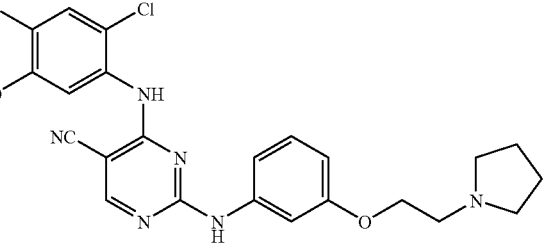 | 10500 |
| 3 | 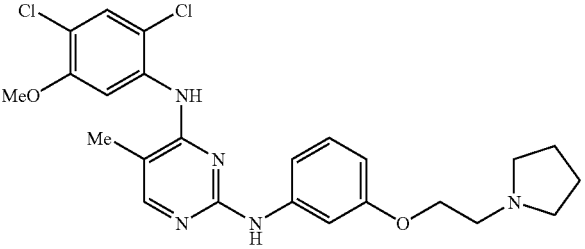 | 2040 |

Figure 10:
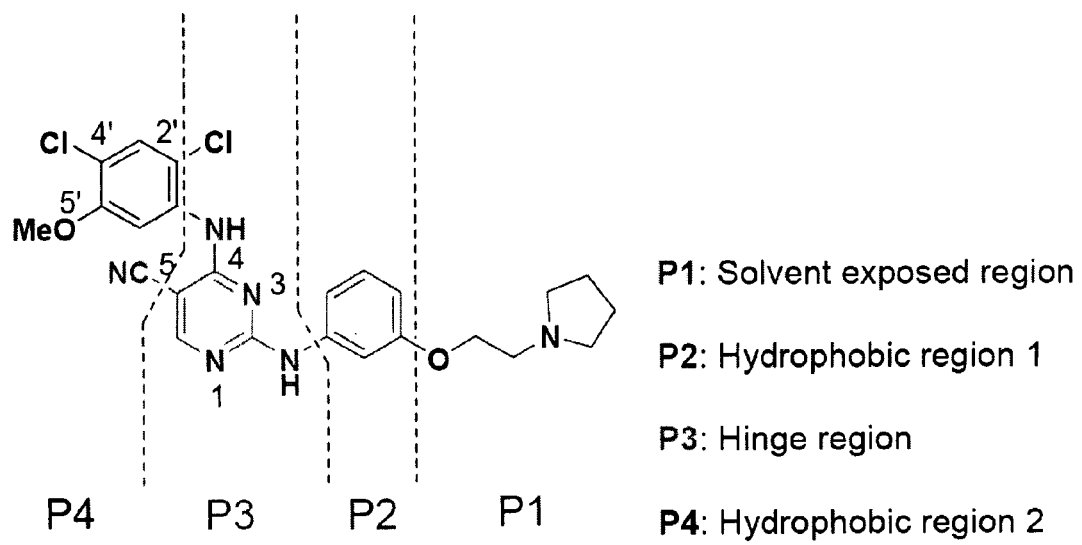
FIG. 10 shows design-template regions analyzed in designing inhibitors targeting JAK2.
Figure 11:
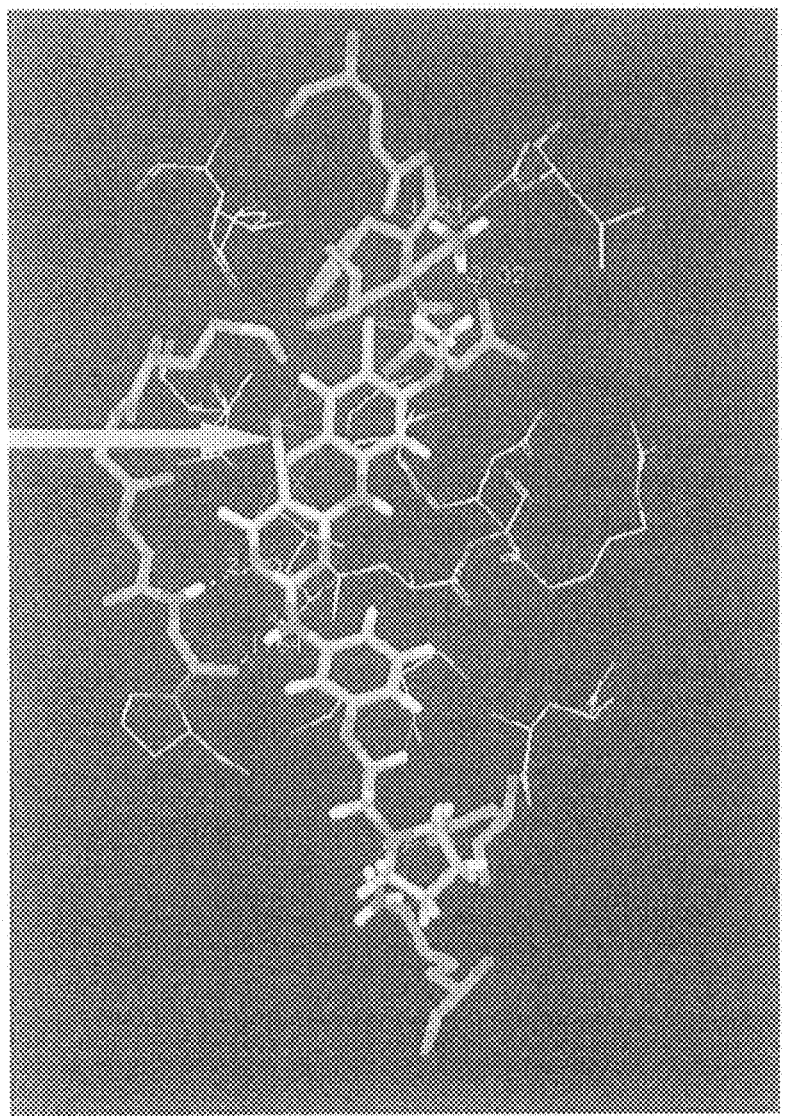
FIG. 11 shows the structure of a compound used in homology model of JAK2.

However, molecular modeling shows that there are significant intra-molecular conflicts due to 2'-Cl and the 5-CN group in compound 2 of Table 5 (see, FIGS. 10 & 11). Therefore, to reduce intra-molecular conflicts, compounds 4-6 were synthesized and showed significant enhancement of potency toward JAK2 (Table 6)

TABLE 6

| Compound | Structure | JAK2 (IC$_{50}$, nM) |
|---|---|---|
| 4 | 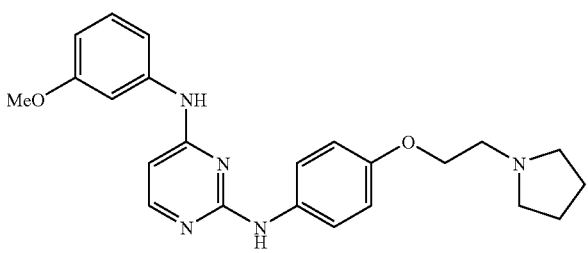 | 105 |
| 5 | 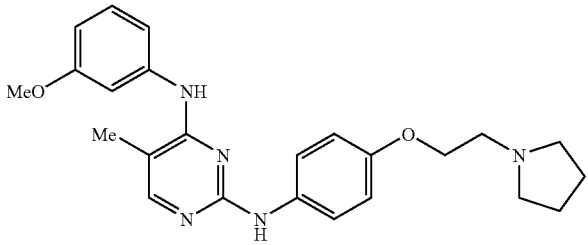 | 53 |

TABLE 6-continued

| Compound | Structure | JAK2 (IC$_{50}$, nM) |
|---|---|---|
| 6 | [Structure: 4-Cl, 3-MeO-phenyl-NH linked to 5-Me-pyrimidine, 2-NH linked to 4-(2-pyrrolidin-1-yl-ethoxy)phenyl] | 8 |

Furthermore, the principles for design, synthesis, and SAR have been developed starting from the 2-10 µM hits to obtain low nM inhibitors of JAK2. The results can be summarized as follows. SAR for the P3 region is shown in Table 7. As can be seen from the results presented in table 7, the 5-position Me in the P3 region enhances JAK2 inhibition while the CN group on same position decreases JAK2 inhibition (2 vs 3 & 4 vs 5). At the same time, the 6-position Me group is not well tolerated (7 vs 8). However, the O-linker on the 4-position of the P3 region is tolerated but there is preference for the NH linker (9 vs 10). Finally, the NMe-linker on the 4-position of the P3 region significantly decreases JAK2 inhibition (6 vs 11).

SAR of the P4 region is shown in Table 8. As can be seen from Table 8, 2,5-di-substituted phenyl ring is not well tolerated in the P4 region (4 vs 12, but ) the 3-position on the phenyl ring is well tolerated. Examples include electron donating groups, Cl (14), OMe (15), electron accepting groups, OCF$_3$ (17), NO$_2$ (18), sterically hindered groups both hydrophobic and hydrophilic, tBu (9), SO$_2$NH$_2$ (19), SO$_2$NHR (20-21), SO$_2$NRR' (22-25), SO$_2$R (26) and piperidine (27-28). 3-OH substituted phenyl is less tolerated compared to 3-OMe (16 vs 15). Also, caboxamide is less tolerated in the 3-position of the P4 region (29-30).

TABLE 7

| Compound | Structure | JAK2 (IC$_{50}$, nM) |
|---|---|---|
| 2 | [Structure: 4,2-diCl, 5-MeO-phenyl-NH linked to 5-CN-pyrimidine, 2-NH linked to 3-(2-pyrrolidin-1-yl-ethoxy)phenyl] | 10500 |
| 3 | [Structure: 4,2-diCl, 5-MeO-phenyl-NH linked to 5-Me-pyrimidine, 2-NH linked to 3-(2-pyrrolidin-1-yl-ethoxy)phenyl] | 2040 |
| 4 | [Structure: 3-MeO-phenyl-NH linked to pyrimidine, 2-NH linked to 4-(2-pyrrolidin-1-yl-ethoxy)phenyl] | 105 |

TABLE 7-continued

| Compound | Structure | JAK2 (IC$_{50}$, nM) |
|---|---|---|
| 5 | 3-methoxyphenyl-NH / 5-Me-pyrimidine / NH-(4-(2-pyrrolidin-1-yl-ethoxy)phenyl) | 53 |
| 7 | benzo[1,3]dioxol-4-yl-NH / 5-Me-pyrimidine / NH-(4-methoxyphenyl) | 46 |
| 8 | benzo[1,3]dioxol-4-yl-NH / 5,6-diMe-pyrimidine / NH-phenyl | >10000 |
| 9 | 3-tert-butylphenyl-NH / 5-Me-pyrimidine / NH-(4-(2-pyrrolidin-1-yl-ethoxy)phenyl) | 7 |
| 10 | 3-tert-butylphenoxy / 5-Me-pyrimidine / NH-(4-(2-pyrrolidin-1-yl-ethoxy)phenyl) | 58 |

TABLE 7-continued
| Compound | Structure | JAK2 (IC$_{50}$, nM) |
|---|---|---|
| 6 | 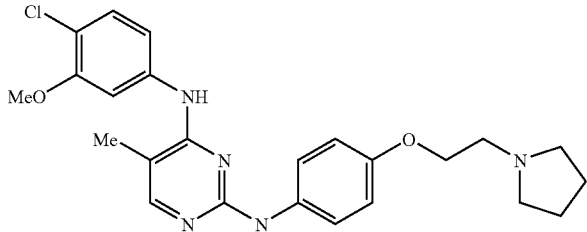 | 8 |
| 11 | 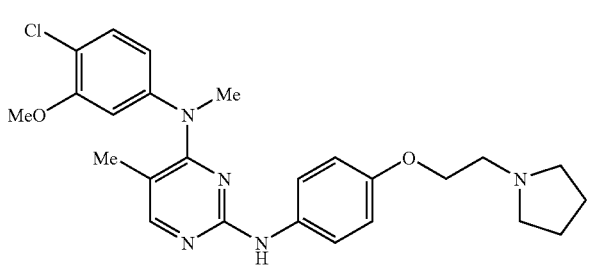 | 4900 |
TABLE 8
Compounds 4 & 12
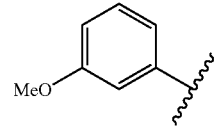
| Compound | P4 | JAK2 (IC50, nM) | Compound | P4 | JAK2 (IC$_{50}$, nM) |
|---|---|---|---|---|---|
| 4 | 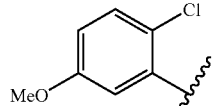 | tC5 | 12 | 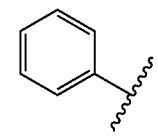 | 1330 |
Compounds 13-18
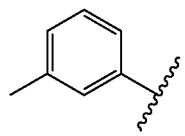
| Compound | P4 | JAK2 (IC50, nM) | Compound | P4 | JAK2 (IC$_{50}$, nM) |
|---|---|---|---|---|---|
| 13 | | 17 | 17 | | 21 |

TABLE 8-continued

| Compound | P4 | JAK2 (IC50, nM) | Compound | P4 | JAK2 (IC50, nM) |
|---|---|---|---|---|---|
| 14 | 3-Cl-phenyl | 21 | 18 | 3-O2N-phenyl | 61 |
| 15 | 3-Me2-phenyl | 53 | 9 | 3-Bu-phenyl | 7 |
| 16 | phenyl (H) | 203 | | | |

Compounds 19-35

| Compound | P4 | JAK2 (IC50, nM) | Compound | P4 | JAK2 (IC50, nM) |
|---|---|---|---|---|---|
| 19 | 3-(H2N-SO2)-phenyl | 14 | 28 | 3-(1-propyl-tetrahydropyran-4-yl)-phenyl | 8 |
| 20 | 3-(propionyl)-phenyl | 5 | 29 | 3-(C(O)NH-)-phenyl | 541 |
| 21 | 3-(MeNH-SO2)-phenyl | 12 | 30 | 3-(C(O)NH-)-phenyl | 830 |
| 22 | 3-(tetrahydropyranyl-O-SO2)-phenyl | 17 | 31 | pyridin-3-yl | 304 |

TABLE 8-continued
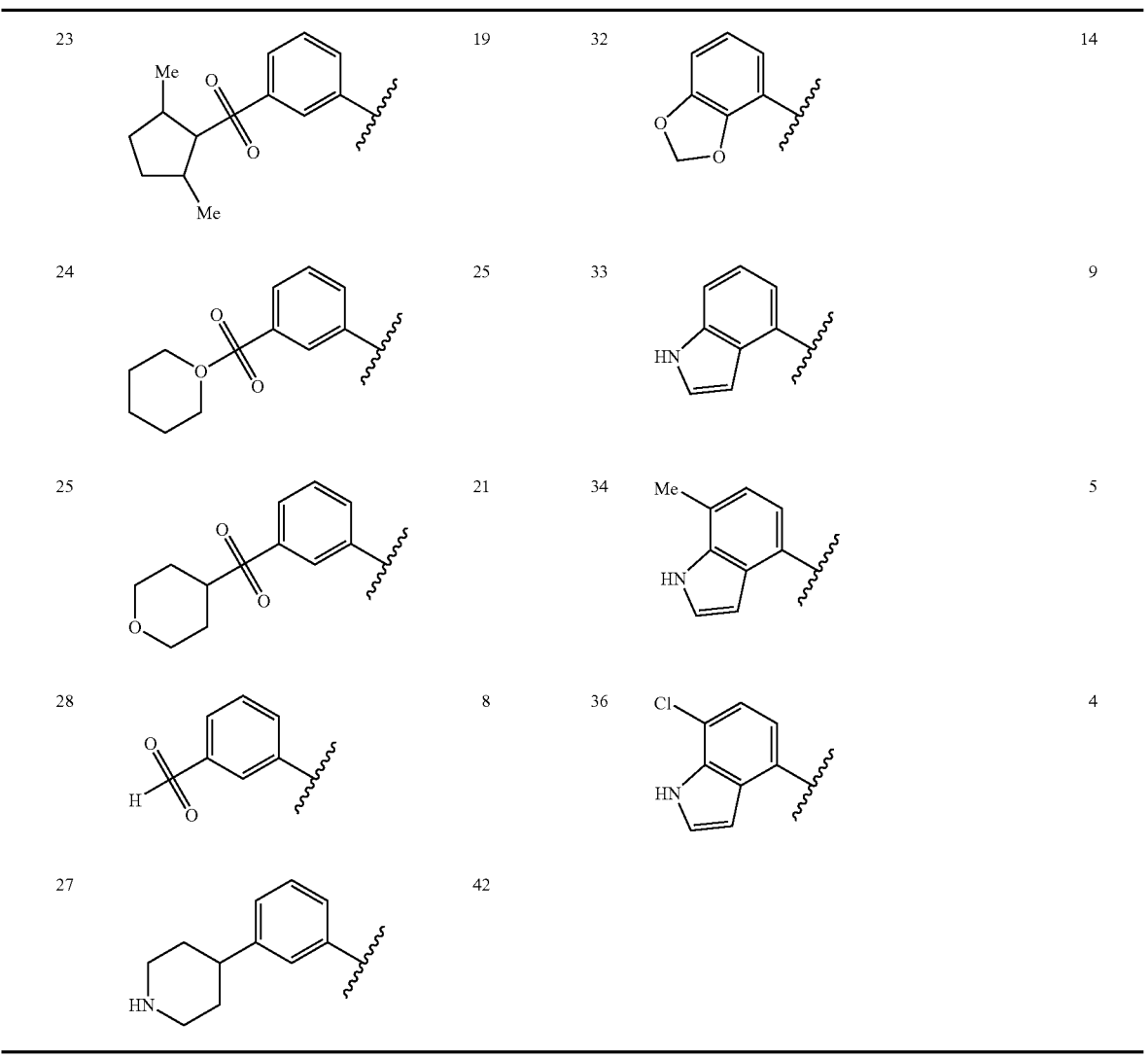
Compounds 36-39
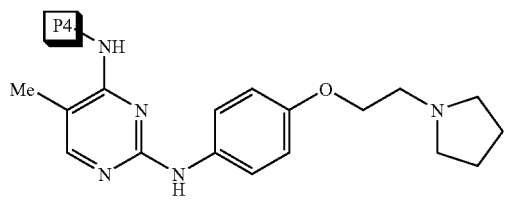
| Compound | P4 | JAK2 (IC50, nM) | Compound | P4 | JAK2 (IC$_{50}$, nM) |
|---|---|---|---|---|---|
| 36 | | 20 | 38 | | 12 |

TABLE 8-continued

| | | | | | |
|---|---|---|---|---|---|
| 37 | (indene) | 28 | 39 | (isoquinoline) | 1050 |

The P4 region tolerates several 2,3-fused bicyclic moieties, such as benzodioxole (32), indole (33-35), naphthalene (36), benzothiophene (37-38). However, the P4 region does not tolerate the pyridine ring (31 vs 13) or the isoquinoline ring (39). SAR of the P2/P1 Region is shown in (Table 9)

TABLE 9

| Compound | P2/P1 | JAK2 (IC50, nM) | Compound | P2/P1 | JAK2 (IC$_{50}$, nM) |
|---|---|---|---|---|---|
| 40 | | 12 | 49 | | 19 |
| 20 | | 6 | 50 | | 18 |
| 41 | | 8 | 51 | | 22 |

TABLE 9-continued

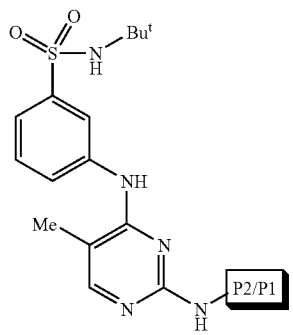

| Compound | P2/P1 | JAK2 (IC50, nM) | Compound | P2/P1 | JAK2 (IC50, nM) |
|---|---|---|---|---|---|
| 42 | 4-(4-(2-hydroxyethyl)piperazin-1-yl)phenyl | 7 | 52 | 4-(piperazin-1-yl)-3-(trifluoromethyl)phenyl | 22 |
| 43 | 3-(piperazin-1-yl)phenyl | 18 | 53 | 4-(4-acetylpiperazin-1-yl)-3-(trifluoromethyl)phenyl | 36 |
| 44 | 4-((4-methylpiperazin-1-yl)methyl)phenyl | 29 | 54 | 4-(2-(3,3-difluoropyrrolidin-1-yl)ethoxy)phenyl | 49 |
| 45 | 4-morpholinophenyl | 12 | 55 | 4-(2-(3,3-difluoroazetidin-1-yl)ethoxy)phenyl | 190 |
| 46 | 4-(morpholinomethyl)phenyl | 13 | 56 | 6-(piperazin-1-yl)pyridin-3-yl | 10 |
| 47 | 3-(morpholinomethyl)phenyl | 7 | 57 | 3-(piperidin-1-ylsulfonyl)phenyl | 316 |

TABLE 9-continued

| Compound | P2/P1 | JAK2 (IC50, nM) | Compound | P2/P1 | JAK2 (IC50, nM) |
|---|---|---|---|---|---|
| 48 | (4-piperidinylmethyl-phenyl) | 7 | 58 | (3-(N-tert-butylsulfamoyl)phenyl) | 707 |

As can be seen from table 9, the P2 region tolerates benzene rings (40-55) and pyridine rings (56). No other heteroaromatic rings are tolerated—data not shown. The P1 region tolerates a variety of solubilizing groups. Examples include 4-ethyoxypyrrolidine (40, 54-55), 4, and 3-piperazine (22, 41-44), 4, and 3-mopholine (45-47), pyrazole (49-50), and imidazole (51). However, the P1 region does not tolerate the 3-sulfonamide group (57-58).

Example 249

Structure-Activity Relationship Studies for Optimization of JAK2 Potency

As discussed above, somatic mutations in JAK2 ($JAK2^{V617F}$) and in the associated receptor kinases (MPLW515L/K), play a role in keeping the JAK2 pathway constitutively active and are associated with the pathogenesis of the myeloproliferative disorders (MPDs). $JAK2(^{V617F})$ is widely distributed in the MPDs including in a majority (>95%) of polycythemia vera (PV) cases, and approximately half of the patients with essential thrombocythemia (ET) or agnogenic myeloid metaplasia (AMM). Using structure based drug design, a series of novel and potent compounds targeting JAK2T were designed and synthesized. Subsets of this series were subsequently optimized for selectivity against the highly homologous JAK3 kinase.

Figure 12:
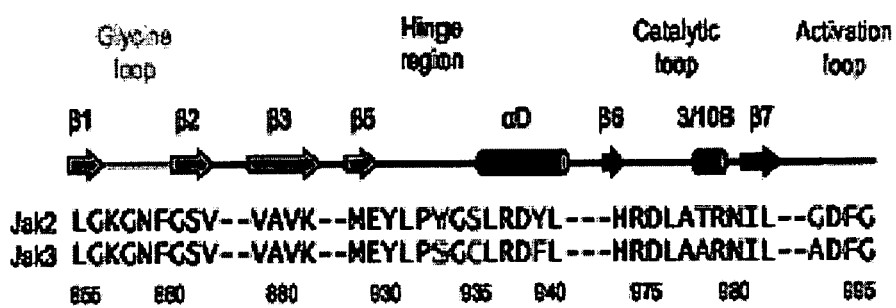
FIG. 12 illustrates homology between JAK2 and JAK3 at the ATP binding site.

As seen from the sequences shown on FIG. 12, there is high homology between JAK2 and JAK3 at the ATP binding site. Using subtle differences in the sequences JAK3 was de-selected because it is an immunosuppressive target. As discussed above, except for one co-crystal structure of JAK3 with an inhibitor (IYVJ), there were no known JAK family crystal structures when we started our discovery work on JAK2. Based on the JAK3 crystal structure (1YVJ), a JAK2 homology model was built to guide compound design.

Compounds were optimized for JAK2 potency. Further SAR studies provided multiple compounds with high JAK2 potency and de-selection of JAK3. These series of compounds occupies the ATP binding pocket of JAK2 as confirmed by X-ray crystallography, and the enzyme pocket walls are pushed significantly closer to the ligand in JAK2 compared to JAK3 resulting in the absence of a back pocket in JAK2.

As indicated by Table 10, substitutions at the 2-, 3-, or 4-positions can enhance JAK2 vs. JAK3 selectivity, but there is no clear trend to explain the JAK2 vs. JAK3 selectivity (for example, 3 vs. 4). P4 region initial selectivity SAR is shown in Table 10. Several other moieties in the P1 region has been also known as potent inhibitors of JAK2. To further explore the JAK2 vs. JAK3 selectivity these other P1 sub-series were examined, one of which is shown in Table 11.

TABLE 10

| Compound | P4 moeity | JAK2 IC50 (nM) | JAK3 IC50 (nM) | JAK3/JAK2 |
|---|---|---|---|---|
| 1 | (4-chloro-3-methoxybenzyl) | 8 | 69 | 9x |

TABLE 10-continued

[Structure: P4-NH attached to 5-methylpyrimidine with NH-phenyl-O-CH2CH2-pyrrolidine]

| Compound | P4 moiety | JAK2 IC$_{50}$ (nM) | JAK3 IC$_{50}$ (nM) | JAK3/JAK2 |
|---|---|---|---|---|
| 2 | 3-tert-butylphenyl | 7 | 71 | 11x |
| 3 | 7-fluoro-indolin-4-yl | 9 | 197 | 21x |
| 4 | 2-chloro-4-methylphenyl | 12 | 350 | 28x |
| 5 | 7-chloro-indolin-4-yl | 1 | 45 | 39x |

TABLE 11

[Structure: P4-NH attached to 5-methylpyrimidine with NH-phenyl-(4-methylpiperazin-1-yl)]

| Compound | P4 moiety | JAK2 IC$_{50}$ (nM) | JAK3 IC$_{50}$ (nM) | JAK3/JAK2 |
|---|---|---|---|---|
| 6 | 7-chloro-indolin-4-yl | 6 | 19 | 4x |
| 7 | 2,3-dimethylphenyl | 7 | 71 | 11x |
| 8 | 3-(N-tert-butylsulfamoyl)phenyl | 8 | 169 | 28x |
| 9 | 3-(2,5-dimethylpyrrolidin-1-ylsulfonyl)phenyl | 19 | 678 | 36x |

TABLE 11-continued

[Structure: P4-NH attached to methyl-pyrimidine, NH-phenyl-piperazine-N-methyl]

| Compound | P4 moiety | JAK2 IC$_{50}$ (nM) | JAK3 IC$_{50}$ (nM) | JAK3/JAK2 |
|---|---|---|---|---|
| 10 | [3-(N,N-dimethylsulfamoyl)phenyl] | 10 | 431 | 47x |

The complex relationship between moieties in the P4 region and the P1 region is clearly shown with 5 (Table 10) vs. 6 (Table 11). Substitutions at the 2- or 3-positions in the P4 region again enhance JAK2 vs. JAK3 selectivity.

Further optimization was achieved by holding the P4 region constant and probing changes in the P1 region. A representative sub-series is shown in Table 12.

The synergistic effect of the t-butyl sulfonamide moiety in the P4 region with the group in the P1 region is exemplified by 8 (Table 11) vs. 16 (Table 12).

The inhibitors make a hinge interaction and occupy the pocket taking advantage of key hydrophobic interactions in the P4 area, along with a solubilizing group in the solvent exposed P1 region.

TABLE 12

[Structure: t-butyl-sulfonamide-phenyl-NH-methylpyrimidine-NH-phenyl-P1]

| Compound | P1 moiety | JAK2 IC$_{50}$ (nM) | JAK3 IC$_{50}$ (nM) | JAK3/JAK2 |
|---|---|---|---|---|
| 11 | morpholinomethyl | 13 | 709 | 57x |
| 12 | 4-piperidinyloxy | 7 | 533 | 73x |
| 13 | 1-(morpholino)ethyl | 30 | 2980 | 100x |

TABLE 12-continued

| Compound | P1 moiety | JAK2 IC$_{50}$ (nM) | JAK3 IC$_{50}$ (nM) | JAK3/JAK2 |
|---|---|---|---|---|
| 14 | 2-methylimidazolyl | 34 | 3600 | 105x |
| 15 | imidazolyl | 12 | 1490 | 121x |
| 16 | imidazolylmethyl | 8 | 1330 | 158x |

Example 250

Inhibitors of JAK Kinase for the Treatment of Myeloproliferative Disorders

A series of structurally novel compounds capable of inhibiting JAK2$^{V617F}$ were designed and synthesized. Compounds were identified which potently inhibited JAK2 enzyme, with potencies as low as 1 nM. Subsets of this group were subsequently identified which were highly selectivity against undesirable off-target kinases, including up to 100× selectivity versus JAK3 and potently inhibiting less than 5% of the kinases evaluated in a commercially available, phylogenetically diverse panel of 75 kinases.

Compounds were then advanced into in vitro assays in JAK2$^{V617F}$ transformed cell lines in which exemplary compounds potently inhibited JAK2-driven cell proliferation and STAT5 phosphorylation. Compounds from this series were subsequently shown to be orally available in multiple species and efficacious in rodent models of JAK2-driven disease. The results are demonstrated on FIGS. 13-21.

Figure 13:
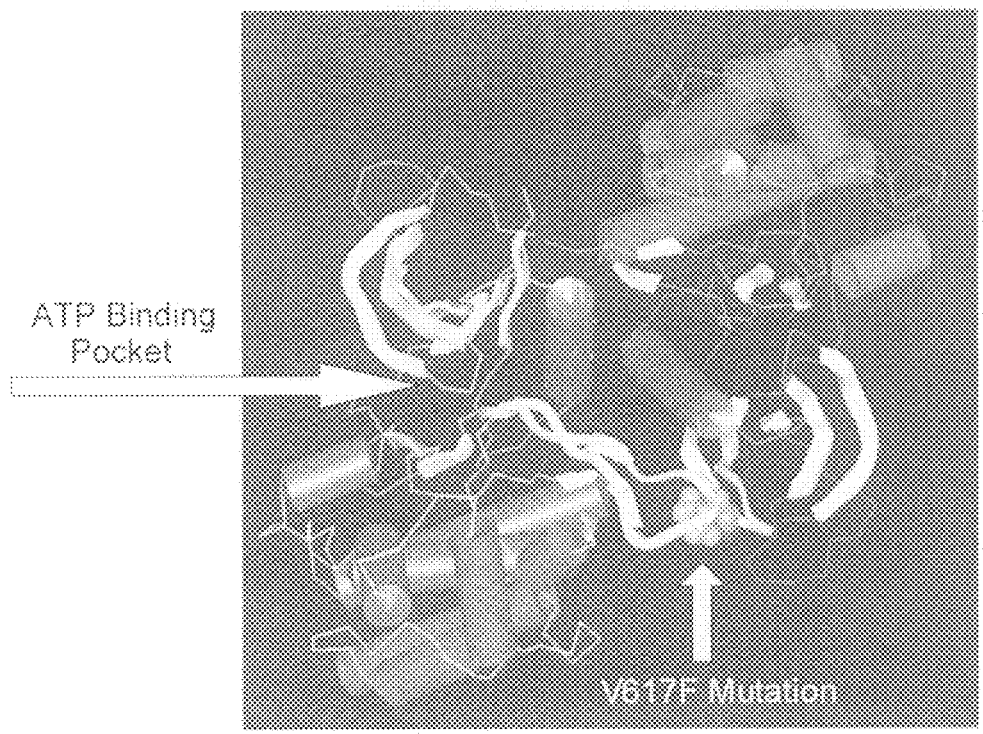
FIG. 13 shows that small molecule JAK2 inhibitor development is enabled by location of V617F mutation distal from ATP binding pocket.
Figure 14:
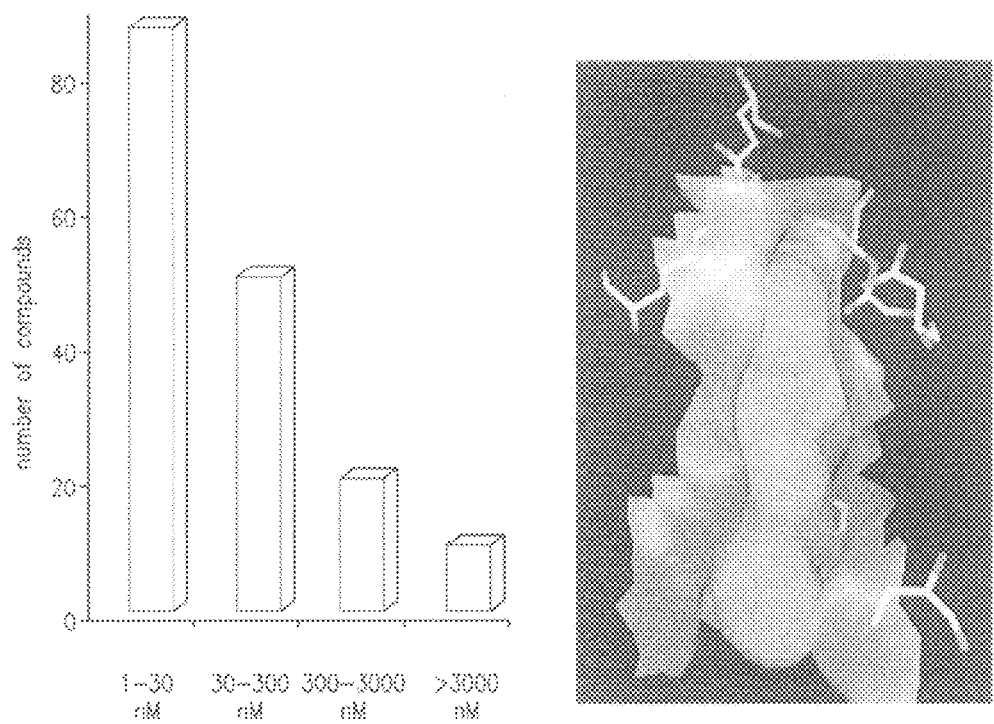
FIG. 14 provides an illustration of the use of molecular modeling to enable rational design of a large number of potent small molecule inhibitors of JAK2.
Figure 15:
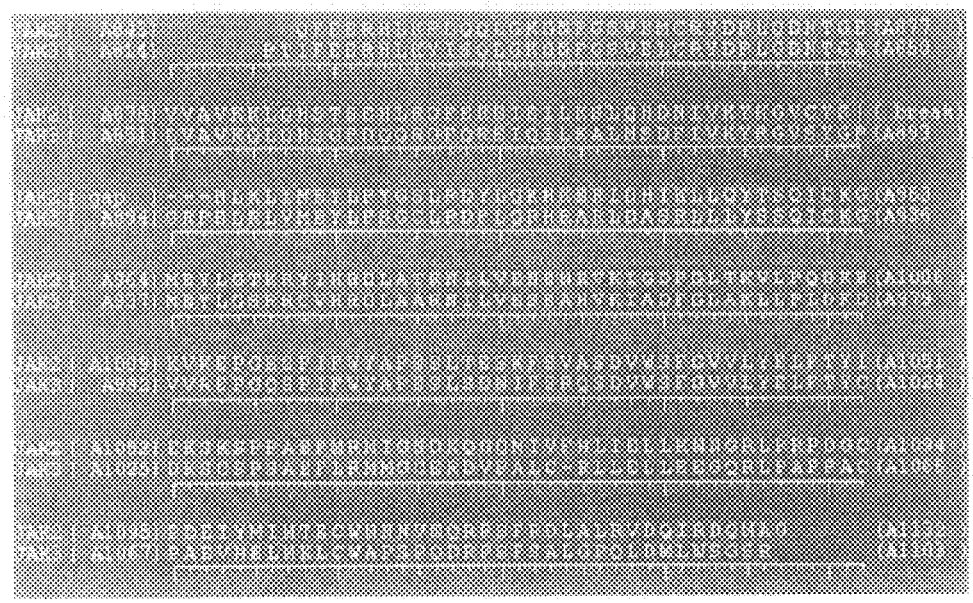
FIG. 15 demonstrates the differences between JAK2 and JAK3 selection—There are few amino acid differences around the ATP binding site that can be exploited for selectivity.
Figure 16:
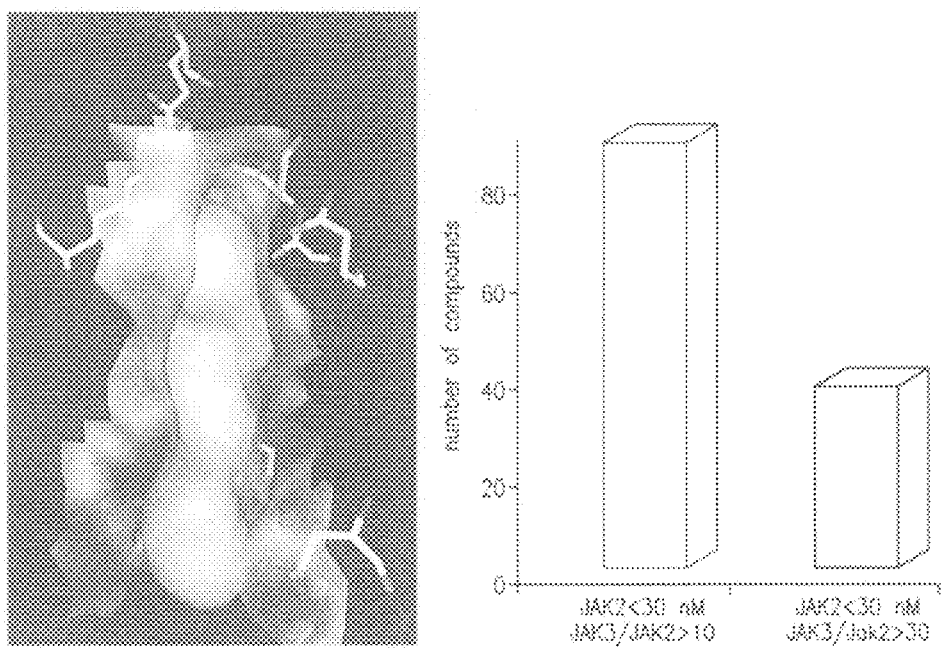
FIG. 16 provides another illustration of the use of molecular modeling to enable rational design of a large number of potent small molecule inhibitors of JAK2.

FIG. 13 shows that small molecule JAK2 inhibitor development is enabled by location of V617F mutation distal from ATP binding pocket. FIGS. 14 and 16 demonstrate the use of molecular modeling to enable rational design of a large number of potent small molecule inhibitors of JAK2. FIG. 15 demonstrates the differences between JAK2 and JAK3 selection. As can be ween from FIG. 15, there are few amino acid differences around the ATP binding site that can be exploited for selectivity.

FIG. 17 demonstrates that compound LVII is highly selective across a breadth of kinases. Compound LVII, an exemplary JAK2 inhibitor, was evaluated internally (upper box) and externally against multiple kinases. Compound LVII is 83 times more potent on JAK2 than JAK3, and 500 nM compound LVII inhibited only 2 kinases in a broad, phylogenetically diverse panel from InVitrogen—Flt3 and Ret.

Figure 18:
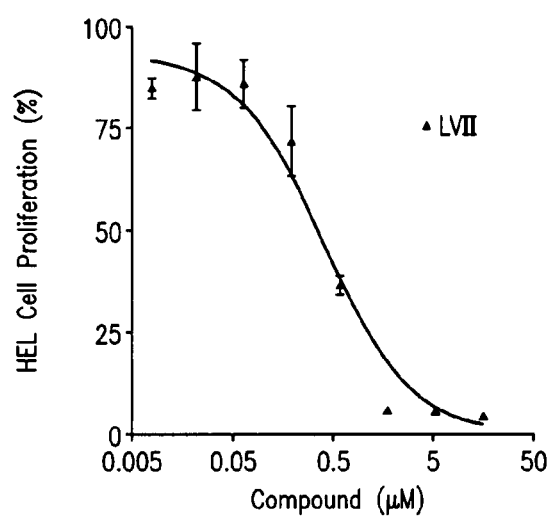
FIG. 18 demonstrates selectively inhibition of JAK2-mediated cell proliferation by a compound of the present invention.
Figure 19:
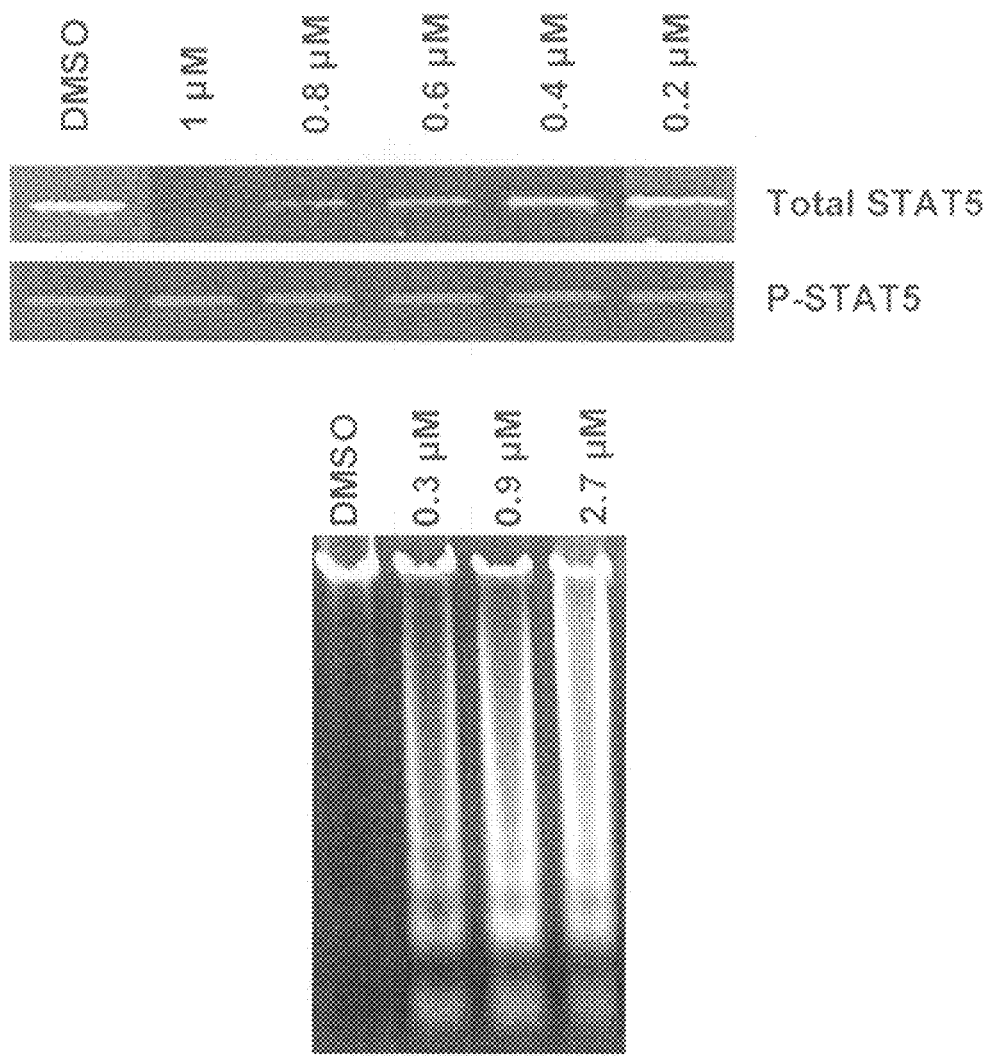
FIG. 19 demonstrates that a compound of the present invention reduces JAK2-induced STAT5 phosphorylation.
Figure 20:
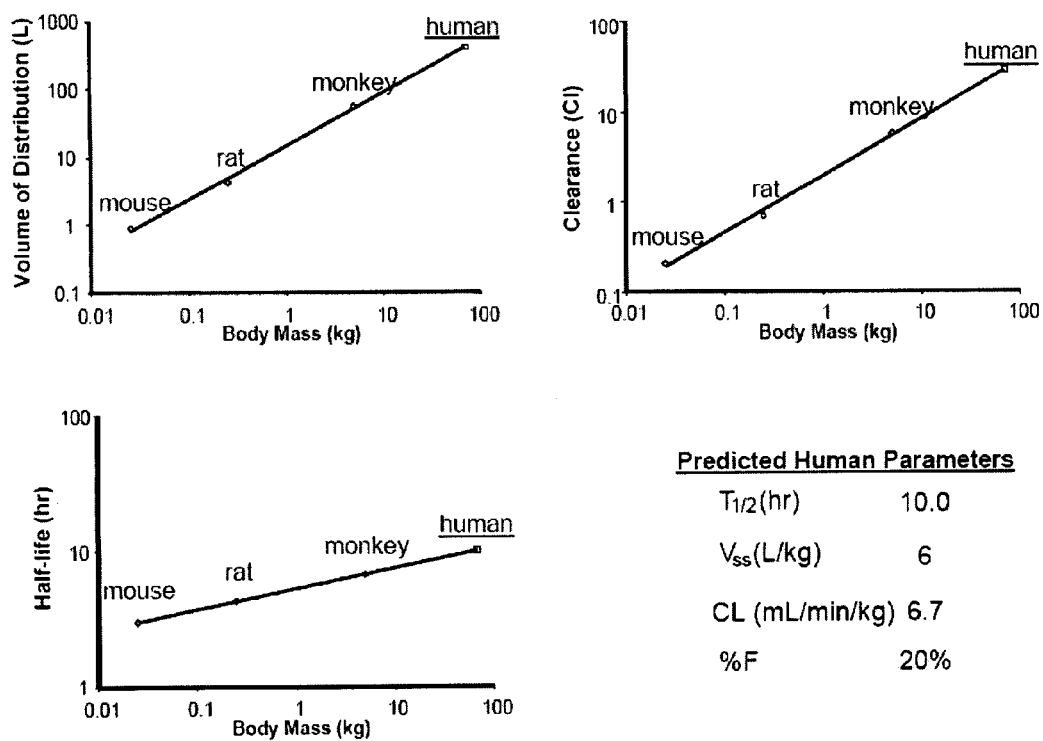
FIG. 20 demonstrates allometric scaling of pharmacokinetic parameters for one compound of the present invention.

FIG. 18 demonstrates that compound LVII selectively inhibits JAK2-mediated cell proliferation. Compound LVII potently inhibits JAK2$^{V617F}$-driven proliferation in HEL cells, but is about 10 times less potent at inhibition of IL-2 driven proliferation of CTLL-2 cells. In a further study, HEL cells were treated with the indicated concentration of compound LVII for 12 hours followed by lysis and analysis of STAT5 phosphorylation and apoptosis (DNA laddering). Then results provided on FIG. 19 demonstrate that compound LVII reduces JAK2-induced STAT5 phosphorylation and induces apoptosis in a dose-dependent manner.

In a further experiment, compound LVII was dosed orally and PK parameters evaluated in mouse, rat and monkey. Based on this data human PK parameters were estimated using allometric scaling, shown on FIG. 20.

Figure 21:
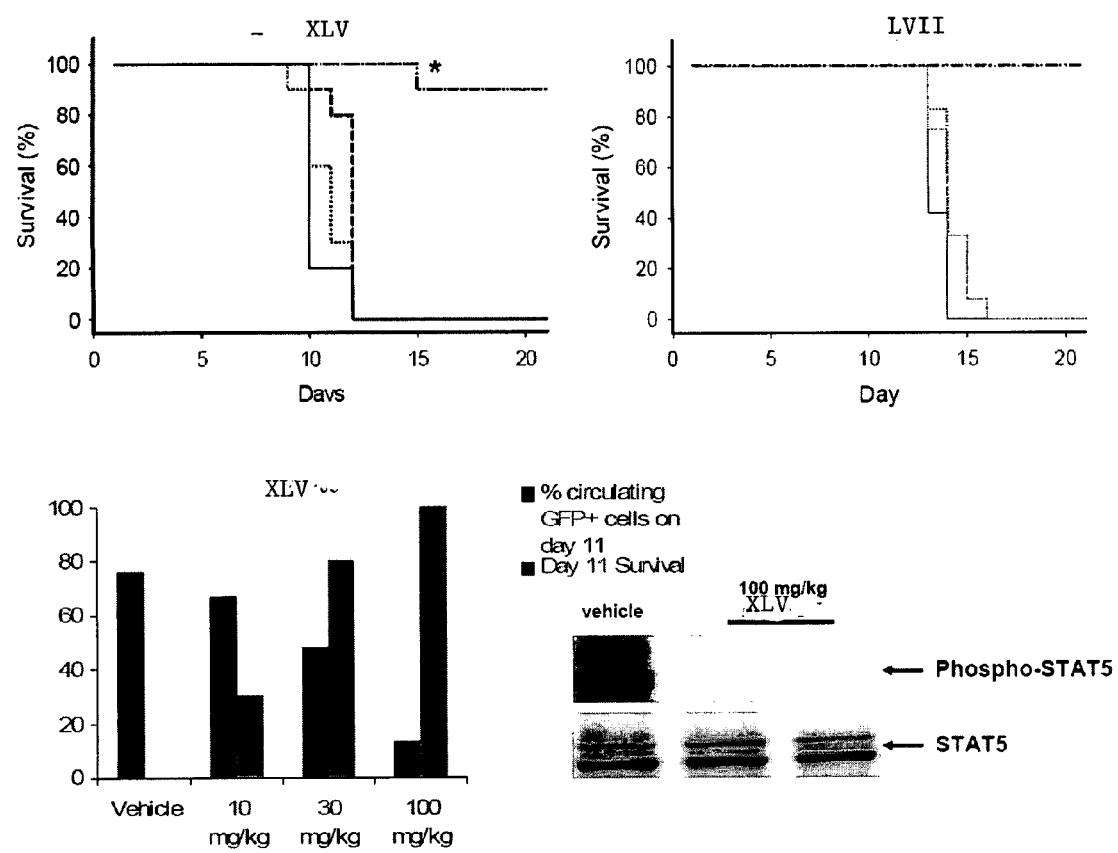
FIG. 21 demonstrates that certain compounds of the present invention increase survival and reduce JAK2$^{V617F}$ cell burden after oral dosing in rodent model.
Figure 22:
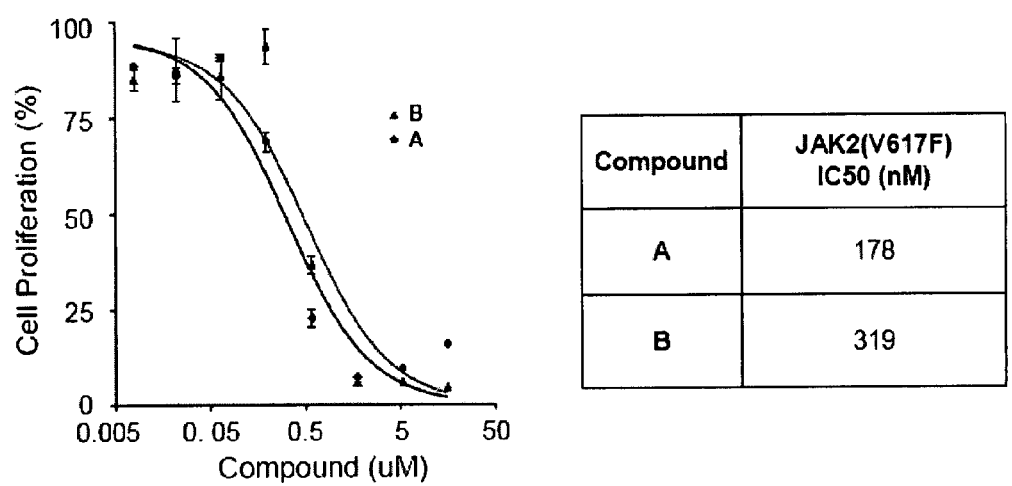
FIG. 22 demonstrates inhibition of JAK2(V617F)-driven cell proliferation by JAK2 inhibitors.

In a further experiment, GFP labeled, Ba/F3: JAK2$^{V617F}$ were injected intravenously and allowed to establish for 3 days prior to dosing. A compound of the invention, as shown by FIG. 21, was administered bid, at the doses indicated on FIG. 21, which demonstrates that certain inhibitors of the present invention increase survival and reduce JAK2$^{V617F}$ cell burden after oral dosing in rodent model. On day 12-13, when vehicle animals were displaying advanced clinical signs, eyebleeds were performed for FACs analysis of GFP-expressing cells. A parallel group of animals were dosed a single time with drug on day 11 followed by extraction of their spleens and analysis of STAT5 phosphorylation.

Example 251

Low nM JAK2 Selective Inhibitors Exhibiting Potent In Vitro Activities with Favorable Preclinical Properties The SAR and optimized compounds to obtain low nM JAK2 inhibitors have been developed. Tables 13-17 describe the SAR for the sulfonamide series. More specifically, Table 13 demonstrates data for mono-substituted sulfonamide inhibitors. Table 14 demonstrates data for di-substituted sulfonamide inhibitors. Tables 15 and 16 demonstrates data for SAR of P2 in para- and meta-positions, respectively. Table 17 demonstrates data for P2-P1 SAR.

TABLE 13

| Compound | R | JAK2 IC$_{50}$ (nM) | JAK3 IC$_{50}$ (nM) | JAK3/ JAK2 | HEL EC$_{50}$ (nM) |
|---|---|---|---|---|---|
| 1 | H | 14 | 402 | 29X | 4,336 |
| 2 | Me | 16 | 266 | 17X | 703 |
| 3 | 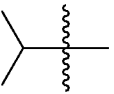 | 12 | 301 | 25X | 490 |
| 4 | 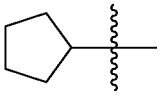 | 6 | 169 | 28X | 178 |
| 5 | 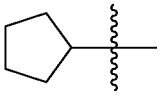 | 20 | 194 | 10X | 688 |

TABLE 13-continued
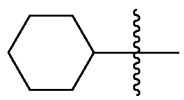
| Compound | R | JAK2 IC$_{50}$ (nM) | JAK3 IC$_{50}$ (nM) | JAK3/ JAK2 | HEL EC$_{50}$ (nM) |
|---|---|---|---|---|---|
| 6 | cyclohexyl-CH- | 39 | 196 | 5X | 1,410 |
HEL: Human erythroid leukemia cells expressing JAK2(V617F)
TABLE 14
| Compound | R | JAK2 IC$_{50}$ (nM) | JAK3 IC$_{50}$ (nM) | JAK3/ JAK2 | HEL EC$_{50}$ (nM) |
|---|---|---|---|---|---|
| 7 | (CH$_3$)$_2$N-CH- | 10 | 451 | 45X | 420 |
| 8 | piperidinyl-CH- | 25 | 337 | 13X | 309 |
| 9 | 3-methylpiperidinyl-CH- | 34 | 363 | 11X | 453 |
| 10 | morpholinyl-CH- | 21 | 299 | 14X | 409 |
| 11 | pyrrolidinyl-CH- | 17 | 189 | 11X | 125 |

TABLE 15

| Compound | P1 moiety | JAK2 IC$_{50}$ (nM) | JAK3 IC$_{50}$ (nM) | JAK3/ JAK2 | HEL EC$_{50}$ (nM) |
|---|---|---|---|---|---|
| 4 | N-methylpiperazine | 6 | 169 | 28X | 178 |
| 12 | piperazine | 8 | 225 | 28X | 2771* |
| 13 | morpholine (N-linked) | 12 | 841 | 70X | 465 |
| 14 | 4-(2-hydroxyethyl)piperazine | 7 | 230 | 33X | 2040* |
| 15 | CH$_2$-morpholine | 13 | 709 | 55X | 297* |
| 16 | CH$_2$-piperazine | 5 | 286 | 57X | 3,445 |
| 17 | O-piperidin-4-yl | 7 | 533 | 76X | 4,547 |
| 18 | CH$_2$-pyrazol-1-yl | 19 | 1,440 | 76X | 2,956 |
| 19 | imidazol-1-yl | 12 | 1,490 | 124X | 1,032 |

TABLE 15-continued

| Compound | P1 moiety | JAK2 IC$_{50}$ (nM) | JAK3 IC$_{50}$ (nM) | JAK3/ JAK2 | HEL EC$_{50}$ (nM) |
| --- | --- | --- | --- | --- | --- |
| 20 | 2-methylimidazol-1-yl | 34 | 3,600 | 106X | 2,076 |
| 21 | 1,2,4-triazol-1-yl | 41 | 2,760 | 67X | 1,154 |

*Ba/F3 cells expressing JAK2(V617F)

TABLE 16

| Compound | P1 moiety | JAK2 IC50 (nM) | JAK3 IC50 (nM) | JAK3/ JAK2 | HEL EC50 (nM) |
| --- | --- | --- | --- | --- | --- |
| 22 | piperazin-1-yl | 18 | 1,070 | 59X | 3,031 |
| 23 | 4-(2-hydroxyethyl)piperazin-1-yl | 41 | 1,540 | 38X | 1,996 |
| 24 | morpholin-4-ylmethyl | 7 | 606 | 87X | 812 |

TABLE 17

P2 = Substituted- or hetero- aryl

| Compound | P2-P1 moiety | JAK2 IC50 (nM) | JAK3 IC50 (nM) | JAK3/ JAK2 | HEL EC50 (nM) |
|---|---|---|---|---|---|
| 25 | (2-CF3, 4- piperazinyl phenyl) | 23 | 461 | 20X | 568 |
| 26 | (2-CF3, 4-(4-Ac-piperazinyl) phenyl) | 36 | 1,410 | 39X | 1778 |
| 27 | (5-(piperazin-1-yl)pyridin-2-yl) | 10 | 629 | 63X | 4700 |

The top left from the P4 region (FIG. 10) is used to illustrate the optimization of the inhibitors in this series. The choice of N-methyl phenyl piperazine as our starting P2-P1 moiety was based on previous SAR studies. As shown in Tables 13 and 14, the phenyl group in the P4 region displays high tolerance to a variety of mono- and di-substituted sulfonamide groups (in vitro JAK2 $IC_{50}$ in the range of 6-40 nM).

Sulfonamide as part of the P4 aryl moiety provides compounds with less potency against JAK3 (up to ~50-fold vs. JAK2, see compound 7 in Table 14).

Substitution on the sulfonamide group increases compound cell activity (1 vs. 2-6 or 1 vs. 7-11). In the mono-substituted sulfonamide compounds, substitution with branched alkyl groups provides better selectivity towards JAK2 compared to that seen with the cyclo alkyls (3 or 4 vs. 5 and 6). In a similar fashion to that seen in the mono-substituted sulfonamide compounds, cycloalkyl di-substitution leads to less selective inhibitors (7 vs. 8-11).

Based on the JAK3 de-selection and favorable cellular potency, the focus was on the tert-butyl sulfonamide series. Further SAR studies on the tert-butyl sulfonamide series are presented in Tables 15-17. As shown in the biochemical data (Tables 15 and 16), the phenyl group in the P2 region displays high tolerance to a variety of P1 moieties, which enhance solubility and optimize de-selection from JAK3.

All compounds maintain potent activity for JAK2 (5-40 nM) and de-selection from JAK3 (ca. 30-120X). Heterocycles in the P1 region with basic nitrogen and hetero-aryl groups are well tolerated, with hetero-aryls provide better selectivity (see compounds 19 and 20 in Table 15). Both meta- and para-substitutions maintain good potency and selectivity (12 vs. 22 or 14 vs. 23 or 15 vs. 24). In the cellular assay, compounds with P1 hetero-aryls are less tolerated than that of hetero-cycles. Meta-substitution, in general, provide compounds with µM cellular potency. Compounds with para-substitution easily achieve ca. 200-500 nM cellular potency.

As shown in Table 17, compounds with the pyridyl group and substituted aryls in the P2 region are well tolerated and maintain high selectivity for JAK2 in the biochemical assay (see compounds 25-27). Both compounds 25 and 26 with substituted aryl in the P2 region exhibited decent cellular activity (ca. 500-2000 nM).

The in vitro cellular data are presented next. Ba/F3 cells were treated with the indicated concentration of A for 24 h followed by lysis and analysis of STAT5 phosphorylation and apoptosis (DNA laddering). GFP labeled, Ba/F3: JAK2 (V617F) cells administered i.v. to SCID mice. On day 3, dose with compound A (10, 30, 100 mg/kg p.o. b.i.d.). Survival as endpoint; FACS analysis of circulation tumor burden.

Figure 23:
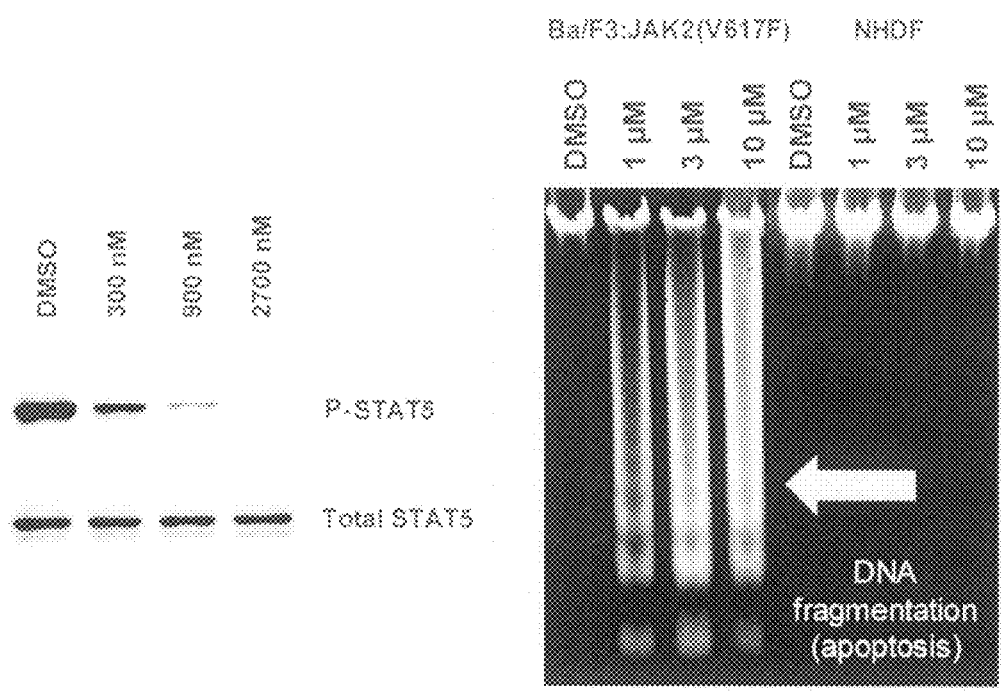
FIG. 23 demonstrates inhibition JAK2(V617F)-mediated protein phosphorylation and inducing apoptosis in JAK (V617F) cells by a compound of the invention.
Figure 24:
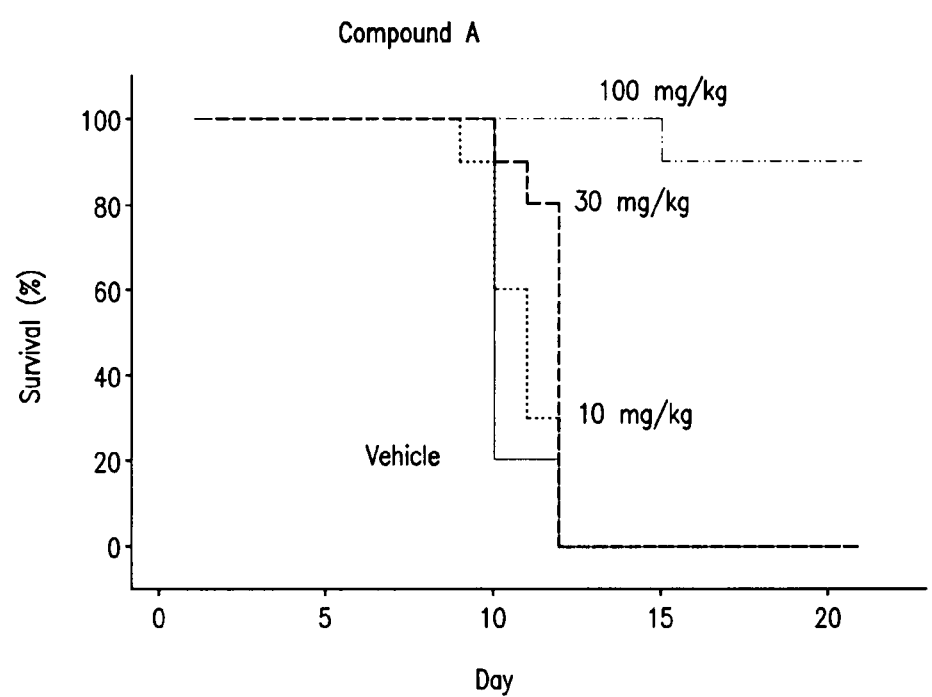
FIG. 24 demonstrates survival benefit of a compound of the invention in JAK2(V617F)-driven circulating tumor model.
Figure 25:
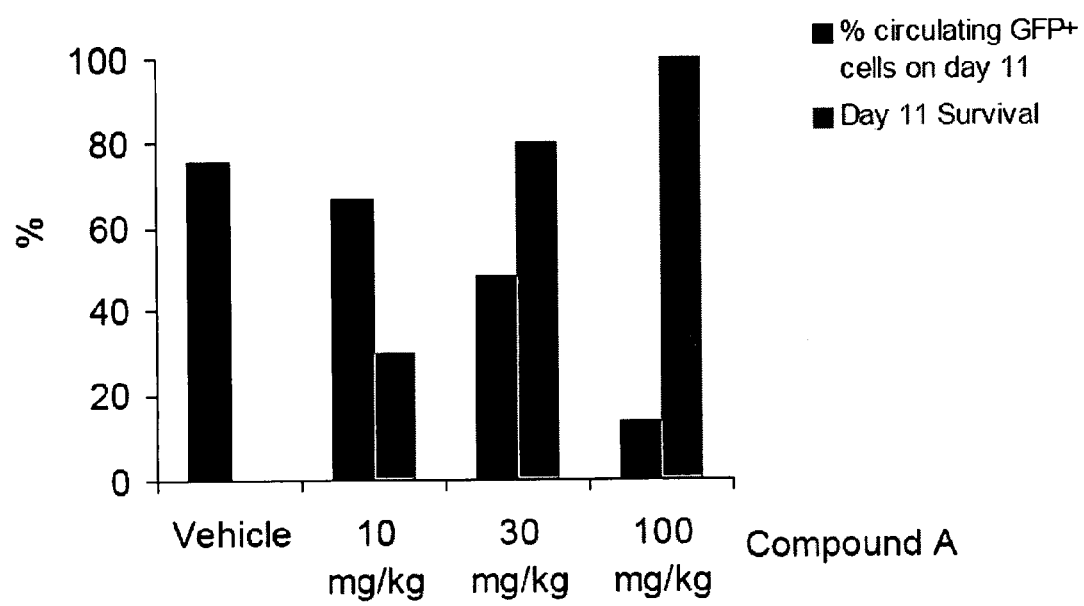
FIG. 25 demonstrates that a compound of the invention reduces JAK2(V617F) cell burden in JAK2(V617F)-driven circulating tumor model.

Group of animals were dosed a single time with A on day 11 followed by extraction of their spleens after 5 h and analysis of STAT5 phosphorylation. Compound A inhibits of JAK2 (V617F)-induced protein phosphorylation in the spleen of mice implanted with Ba/F3: JAK2(V617F) cells As can be seen, compounds A and B (FIG. 23) potently inhibit JAK2(V617F)-mediated proliferation in human ethyroid leukemia (HEL) cells, and compound A increases survival in a dose dependent manner in the rodent model (FIG. 24). Dose-dependent survival benefit correlates with dose-dependent reduction in mutant-bearing circulating tumor cells measured at day 12 (FIG. 25).

Example 252

Inhibition of JAK2 V617F-Induced Erythroid Skewing of Hematopoietic Stem Cell Differentiation with a Selective JAK2 Anatagonist It was investigated whether a selective JAK2 inhibitor decreased Jak2 V617F induced erythroid differentiation. Normal peripheral blood and cord blood (CB) HSC (CD34+/CD38−/CD90+) were clone sorted using FACS Aria and transduced with Lenti viruses expressing wild-type JAK2 (JAK-WT), mutant JAK2 (JAK-MT), Lenti-backbone (BACKBONE) or No-vector in methocult media +/− compound LVII JAK2 inhibitor. Samples from PV patients were sorted as well to media +/−30-600 nM of a selective JAK2 inhibitor, +/− compound LVII or directly to RNA lysis buffer. Colonies were scored at day 14.

Cord Blood Progenitors (CD34+/CD38−) transduced with JAK-WT, JAK-MT or BACKBONE in combination with luciferase-GFP lentivirus or PV Progenitors marked with luciferase-GFP lentivirus, were transplanted intrahepatically 48 hrs after transduction to neonatal Rag2/gama-chain KO mice.

Figure 26:
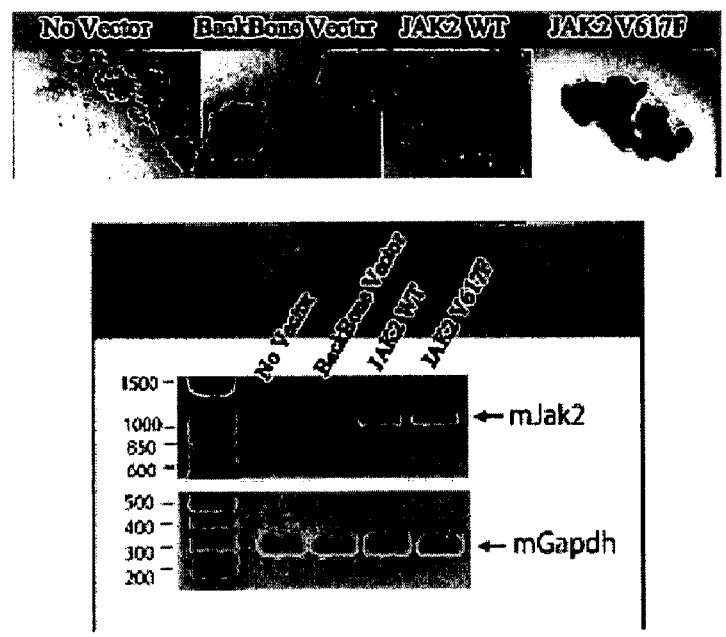
FIG. 26 demonstrates enhanced erythroid differentiation of normal progenitors transduced with lentiviral JAK2 V617F.

FIG. 26 shows: photomicrographs (50×) of normal cord blood HSC day 14 colonies with no vector, backbone vector, JAK2 wild-type (wt) or JAK2 V617F (upper) and Human cord blood HSC derived colonies were collected after 14 days in methylcellulose culture and murine JAK2 PCR verified transduction with the lentiviral vectors (lower).

Transduction of cord blood HSC with the mutant Jak2 vector resulted in skewed erythroid colony formation compared to wild-type Jak2, vector alone and untransduced HSC (FIG. 26: n=3). RT-PCR with murine Jak2 compared to wild-type Jak2, vector alone and untransduced HSC (FIG. 26: n=3). RT=PCR with murine Jak2 specific primers resulted in 900 bp fragments corresponding to murine Jak2 from colonies transduced with the wildtype and mutant Jak2 and confirmed by sequencing, but not those from colonies transduced with the vector alone or the untransduced cells (FIG. 26).

Like the results in cord blood cells, adult peripheral blood CD34+ cells transduced with the mutant Jak2 developed a skewed developmental pattern, with far greater erythroid colony formation compared to wild-type Jak2 or vector alone. In megacult assays, CD34+ cells transduced with the mutant Jak2 had similar megakaryocytic potential as wild-type Jak2 or vector alone.

Figure 27:
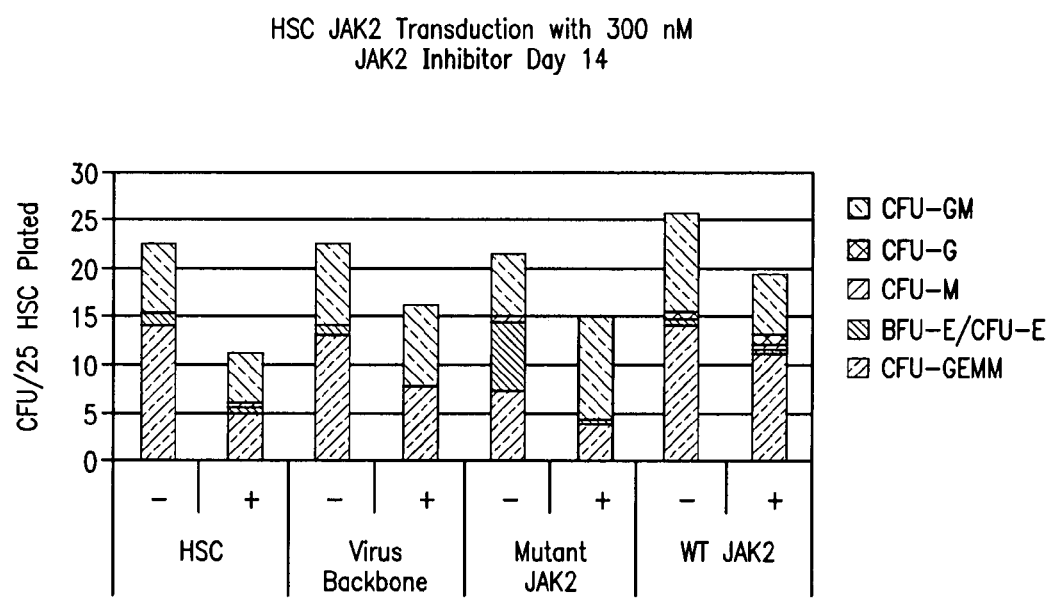
FIG. 27 shows inhibition of Jak2 induced erythroid differentiation by a compound of the present invention.

FIG. 27 shows the results of treatment of human cord blood HSC (CD34+CD38−CD90+Lin−) transduced with lentiviral backbone, JAK2 WT or JAK2 V617F(Mutant) vectors, (25 cells/well in 96 well plate with Methylcellulose), with or without 300 nM of +/− compound LVII, a selective JAK2 inhibitor, and colonies scored on day 14.

Figure 28:
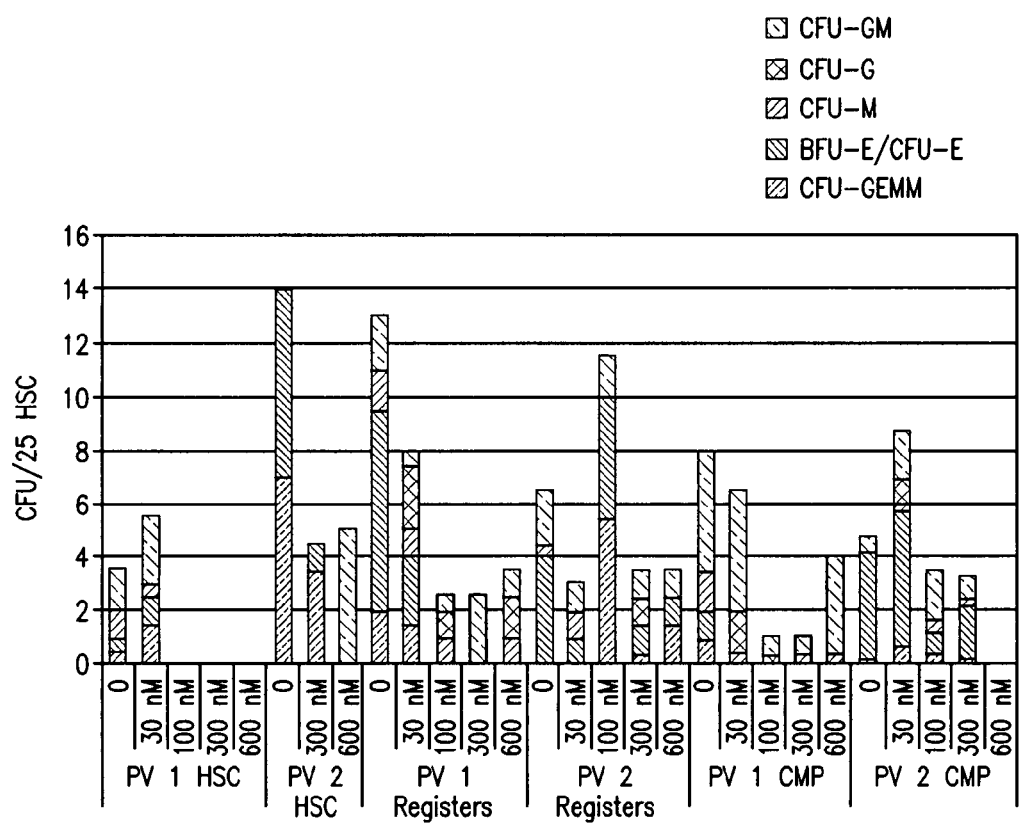
FIG. 28 shows alteration of erythroid skewed differentiation in Polycythemia Vera (PV) with a specific JAK2 inhibitor.

FIG. 28 shows the results of an experiment in which HSC (CD34+CD38−CD90+Lin), progenitors (CD34+CD38+Lin−) or common myeloid progenitors (CMP; CD34+CD38+IL3Ralpha+CD45RA−Lin−) cells from two JAK2 V617F+ PV patients were clone-sorted (25 cells/well) with the aid of a FACS Aria and treated with 0,30,100,300 or 600 nM of compound LVII in methylcellulose. Differential colony counts were performed on day 14. These results mirrored those seen with the JAK2 V617F transduced cord blood HSC (FIG. 27) in that compound LVII selectively inhibited JAK2 V617F-skewed erythroid differentiation Untransduced HSC served as a control. As can be seen, these experiments (n=3) demonstrated inhibition of JAK2 V617F skewed erythroid colony formation. Addition of compound LVII (300 nM), inhibited mutant kinase-induced erythroid colony formation (FIG. 27) in 3 experiments while 100-300 nM was inhibitory to PV (n=2 patients) HSC and progenitors (FIG. 28).

Figure 29:
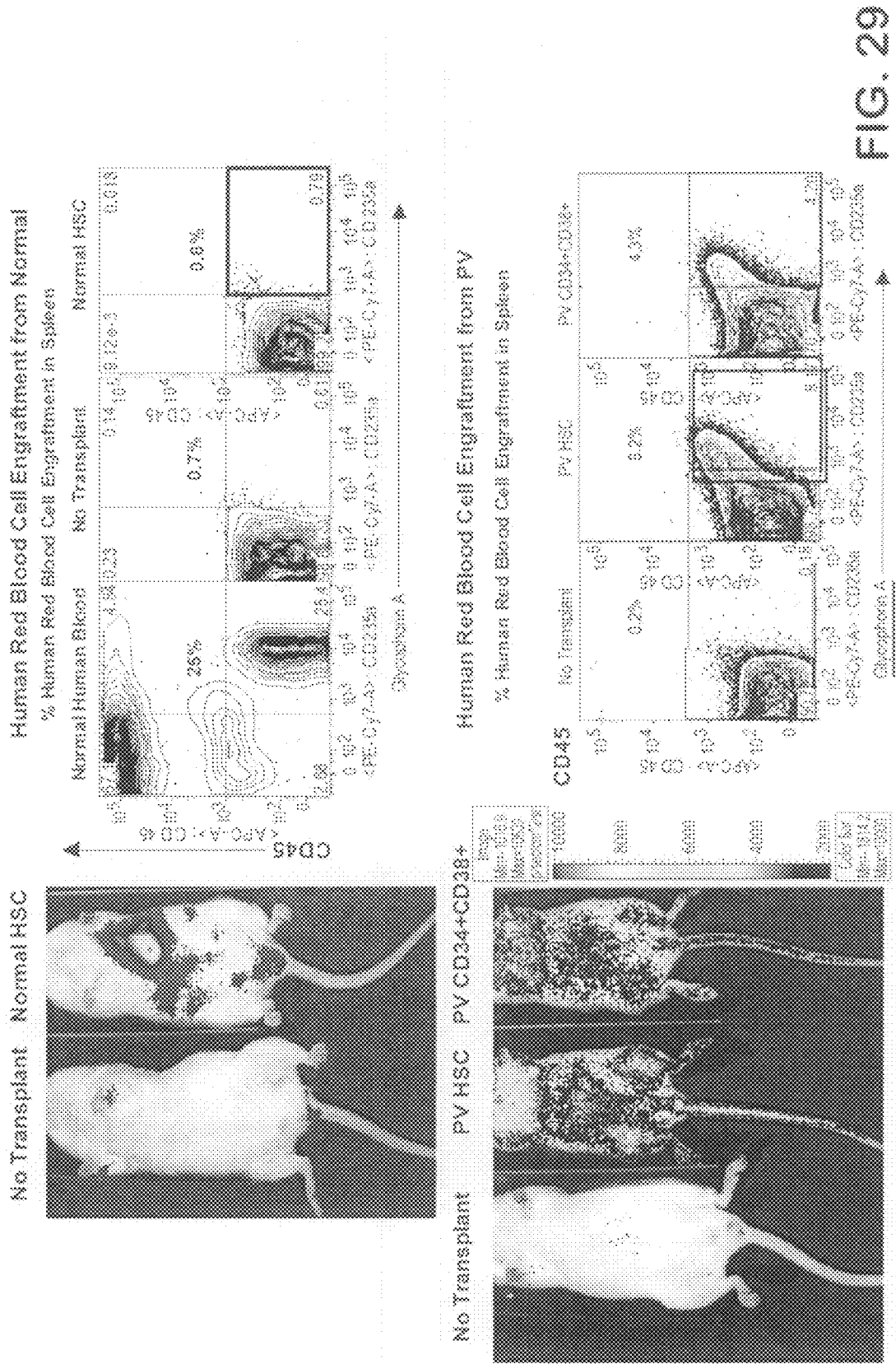
FIG. 29 shows that PV HSC have enhanced erythroid engraftment potential.

FIG. 29 shows the results of an experiment in which FACS cloned HSC and progenitors from a PV patient or normal human cord blood were marked with Luc-GFP lentivirus and 48 hrs later transplanted intrahepatically in new-born immunodeficient mice. Mice were analyzed for bioluminescence with the aid of an IVIS 200 in vivo imaging system (Xenogen Inc). Mice were sacrificed 8 weeks after transplantation. Hematopoietic organs (spleen, liver, bone marrow and thymus) were harvested for FACS analysis which demonstrated enhanced erythroid by PV HSC and progenitors compared with their normal counterparts Transplantation of PV patient HSCs (CD34+,CD38−CD90+Lin−) in neonatal immunodeficient mice (RAG$_2$−/−gamma$_c$−/−) resulted in enhanced erythroid engraftment compared with more committed PV progenitors and normal HSC (FIG. 29).

Figure 30:
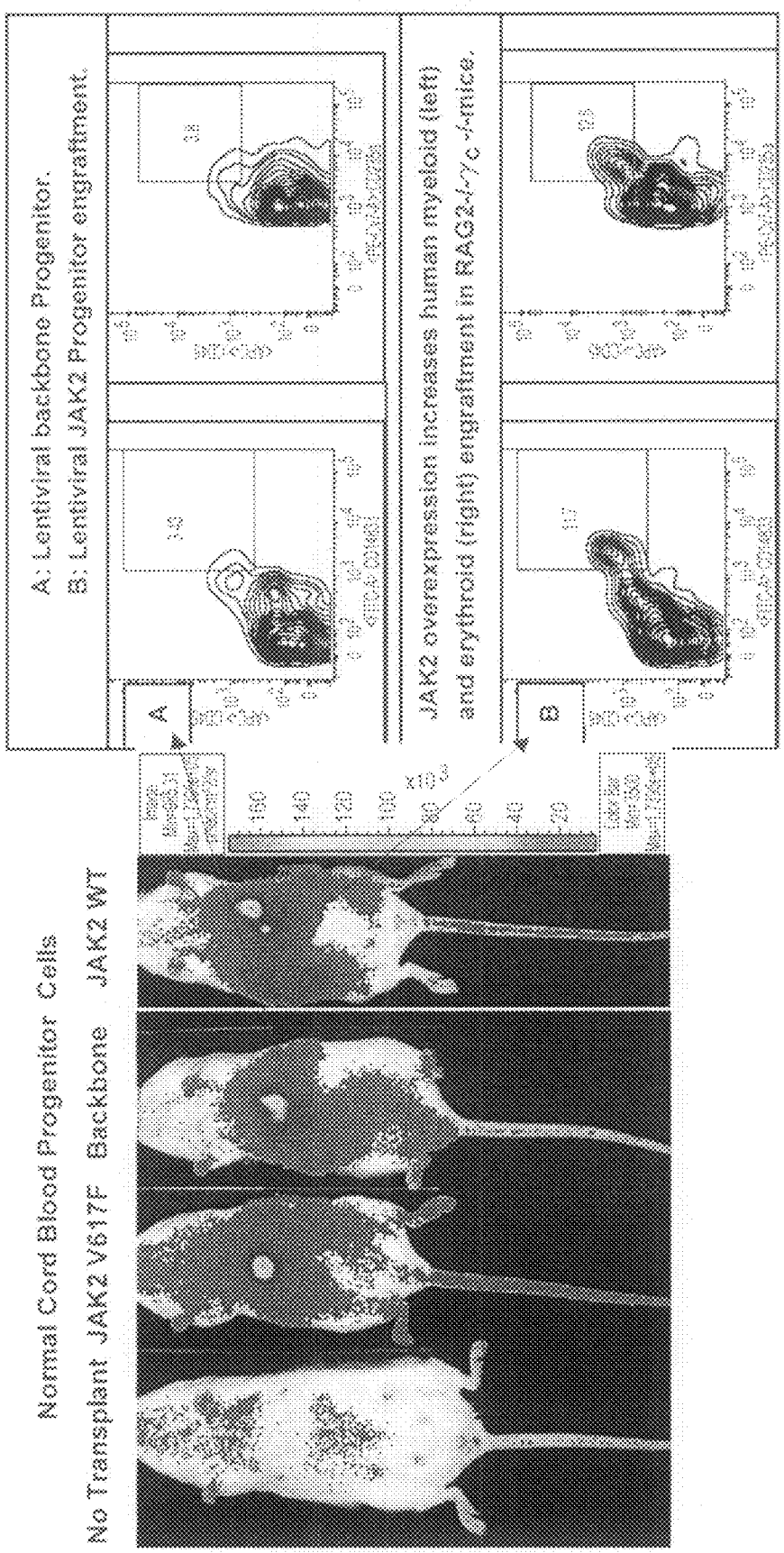
FIG. 30 shows that JAK2 overexpression enhances human engraftment in RAG2−/−γc−/− mice at 8 weeks post-transplant.

FIG. 30 shows the results of an experiment in which FACS purified normal cord blood progenitors were transduced with backbone JAK2WT or JAK2 V617F and marked with Luc-GFP lentivirus for 48 hrs. Subsequently, cells were transplanted intrahepatically into newborn immunodeficient mice. Mice were analyzed for bioluminescence in an IVIS 200 and sacrificed 8 weeks after transplantation. Hematopoietic organs (spleen, liver, bone marrow and thymus) were harvested for FACS analysis. This analysis demonstrated increased human myeloid and erythroid engraftment in the setting of JAK2 overexpression.

Analysis of mice transplanted with cord blood progenitors (CD34+CD38−Lin−) transduced with JAK-WT, JAK-MT or BACKBONE in combination with luciferase-GFP lentivirus revealed enhanced engraftment capacity of JAK2 overexpressing cells (FIG. 30).

Example 253

Selective Inhibition of JAK2 Kinase by Compound XLV for Treatment of Myeloproliferative Disorder-Associated JAK2V617F and MPLW515L/K Mutations The potential of compound XLV to inhibit mutations that constitutively activate JAK-STAT signaling in MPD was studied. The molecular structure of compound XLV, which is one such JAK2 selective inhibitor that was further characterized, is shown on FIG. 31A. A molecular model showing compound XLV docked in the ATP pocket of JAK2 kinase, highlighting the key interactions is shown on FIG. 31B. Compound XLV was most active against JAK2 (IC50=6 nM), and exhibited selectivity for JAK2 relative to JAK3 (28× greater inhibition of JAK2) (FIG. 31C).

Figure 32:
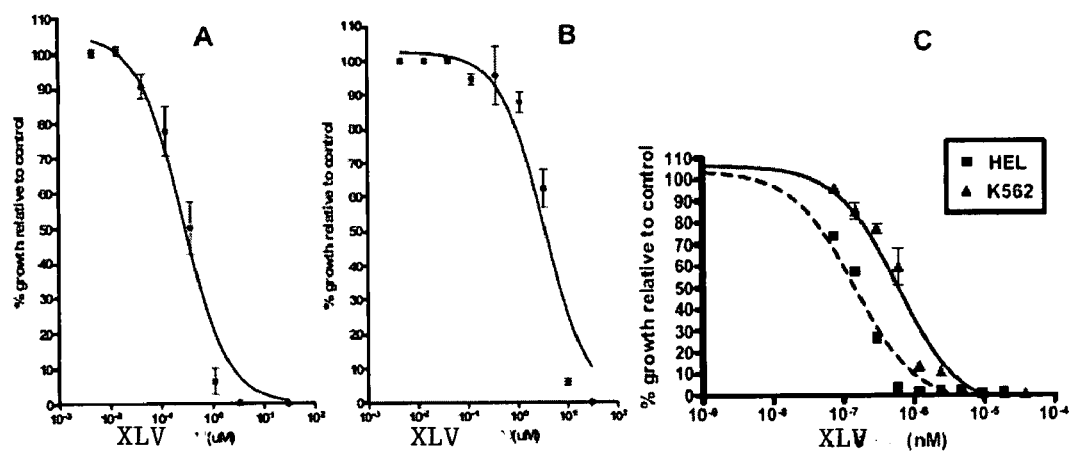
FIG. 32 shows inhibition of JAK2 in vitro by a compound of the present invention.

It was further shown that compound XLV inhibits JAK2V167F in vitro. Compound XLV inhibited the growth of Ba/F3-V617F cells with an IC50 of 300 nM (FIG. 32A). In contrast, compound XLV had minimal effect on the growth of CTLL-2 cells, a clone of IL-2 dependent cytotoxic T-cells (IC50 of 3400 nM) (FIG. 32B). As expected, parental Ba/F3 cells were also inhibited by compound XLV (IC50=470; data not shown), reflecting their dependence on signaling by wild type JAK2. Treatment with compound XLV resulted in a dose-dependent inhibition of HEL cells that are homozygous for the JAK2V617F allele (IC50=300 nM) (FIG. 32C). In control experiments, compound XLV inhibited BCR–ABL+ K562 cells with an IC50=1 μM.

Figure 33:
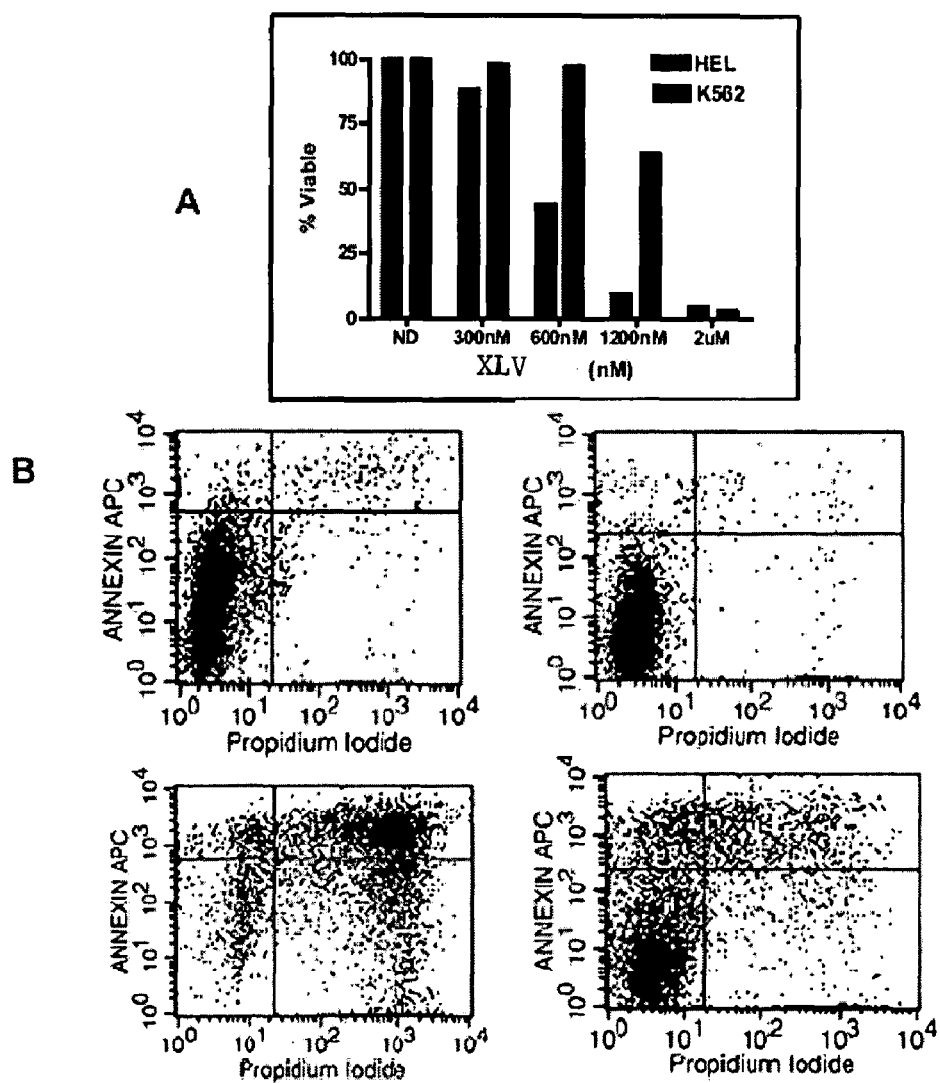
FIG. 33 shows selectively inducement of apoptosis of JAK2V617F-expressing cells by a compound of the present invention.

It was also shown that compound XLV selectively induced apoptosis of JAK2V617F-expressing cells. At 48 hours, HEL cells treated with compound XLV showed a dose-dependent increase in annexin-V+/PI+ apoptotic cells when compared to untreated cells (60% at 600 nM; FIGS. 33A and 33B, left panels). In control experiments, compound XLV was less effective at inducing apoptosis of K562 cells (35% at 1200 nM; FIGS. 33A and 33B, right panels). Compound XLV also effectively induced apoptosis of BalF3-V617F cells (data not shown).

Furthermore, compound XLV selectively induced cell cycle arrest of JAK2V617F-expressing cells. After 24-hours with 600 nM compound XLV (IC50), the proportion of HEL cells in G0/G1 (40%) was greater as compared to untreated cells (15%), indicating G0/G1-arrest (FIGS. 34A and 34B). In control experiments, the G0/G1 fraction of K562 cells increased from 45% to 50% with 1200 nM compound XLV (IC50) (FIGS. 34C and 34D).

Figure 35A:
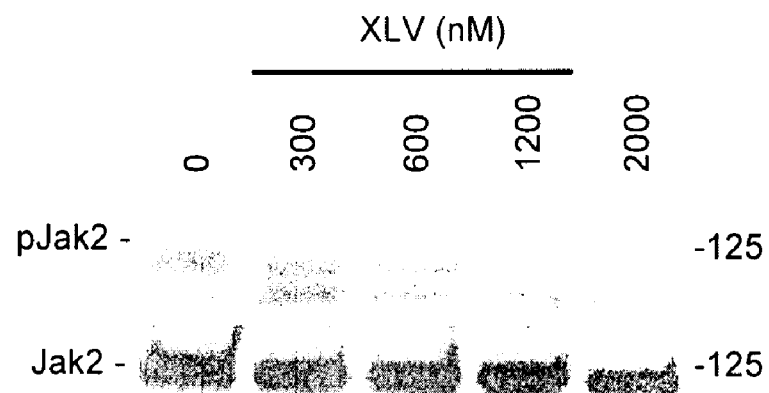
FIG. 35 shows inhibition of phosphorylation of JAK2V617F, STAT5, and STAT3 in JAK2V617F-expressing cells by a compound of the present invention.
Figure 35B:
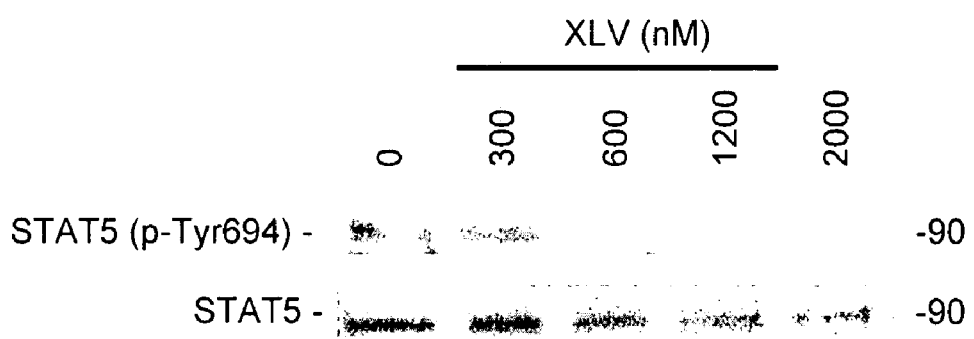
Figure 35C:
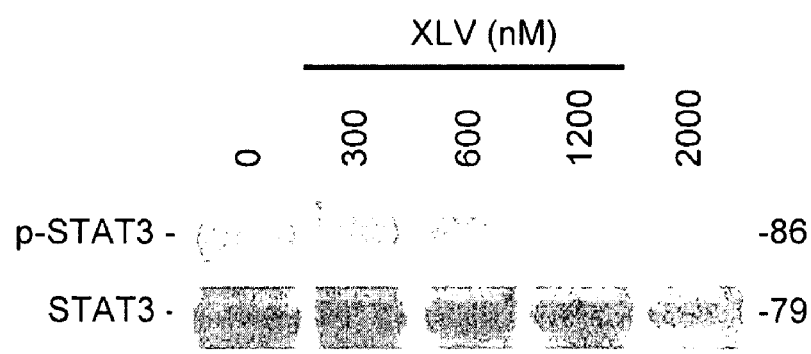

Also, it was demonstrated that compound XLV inhibited phosphorylation of JAK2V617F, STAT5, and STAT3 in JAK2V617F-expressing cells. In HEL cells, a dose dependent decrease in levels of phospho-JAK2V617F, phospho-STAT5, as well as phospho-STAT3 was observed with compound XLV treatment (IC50=300-600 nM) (FIG. 35). Compound XLV also potently inhibited STAT5 phosphorylation in Ba/F3-V617F cells (IC50=300 nM) (data not shown).

In addition, it was shown that compound XLV effectively treated JAK2V617F-induced hematopoietic malignancy in mice. Injection of Ba/F3-V617F-GFP cells into SCID mice produces a rapidly fatal JAK2V617F-induced hematopoietic malignancy, with latency of 11 days and 100% penetrance (FIG. 36A). Recipient mice were treated with compound XLV by gavage at the following doses: 0 mg/day (placebo control), or 20 mg/kg/day, 60 mg/kg/day, or 200 mg/kg/day, each in 2 divided doses, from days +3 to +20 following tumor cell injection. Compound XLV treatment (200 mg/kg/day) was effective at increasing survival of affected animals as compared to placebo (10 days; $P<0.02$) (FIG. 36A). Furthermore, compound XLV induced a significant dose-dependent reduction in circulating tumor cells (75% and 15% GFP+ cells in placebo– vs. 200 mg/day compound XLV-treated animals, respectively; $P<0.02$) (FIG. 36B). Clinical benefit of compound XLV correlated with a marked decrease in STAT-5 phosphorylation in splenic tumors, evident as early as 7 hours after administration of a single dose of compound XLV (100 mg/kg) (FIG. 36C).

Finally, it was demonstrated, by comparison of effects on progenitors from normal controls versus myeloproliferative disorder patients, that compound XLV inhibited hematopoietic colony formation in vitro. Compound XLV effect on hematopoietic colony growth was studied in MPD patients carrying either JAK2V617F (n=5) or MPLW515L/K (n=3) mutations (Table 18 below).

CD34+ cells in methylcellulose (±cytokines) were plated and followed changes in (i) colony number, (ii) colony size/morphology, and (iii) mutant colony burden, after incubation with compound XLV (0 nM, 300 nM, or 600 nM). Compound XLV more potently inhibited colonies derived from CD34+ cells of PV or AMM patients, relative to control CD34+ cells (AMM>PV>normal) (Table 18).

Figure 37A:
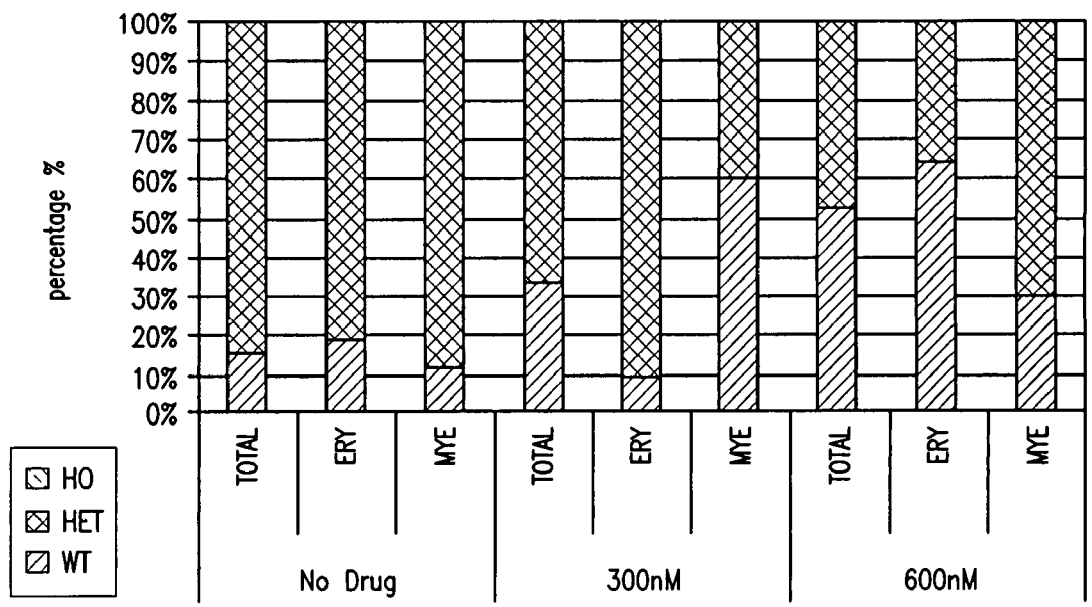
FIG. 37 shows inhibition of hematopoietic colony formation in vitro by a compound of the present invention.
Figure 37B:
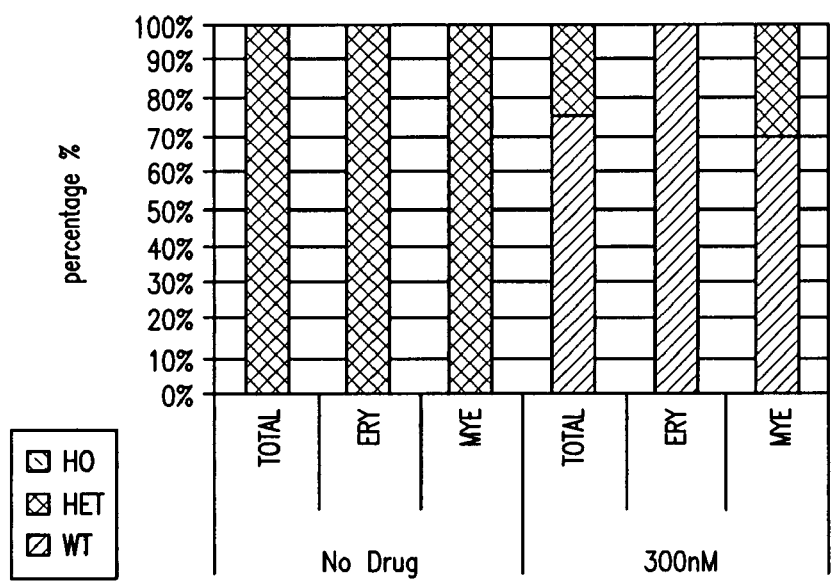

Genotyping of individual colonies for JAK2V617F revealed a selective suppression of mutation-positive colonies in the presence of compound XLV, for 3 of 5 PV patients (Table 18) (FIG. 37A). Similarly, single colony genotyping confirmed a selective suppression of MPLW515-positive colonies with compound XLV, for 2 of the 3 AMM patients (AMM1 and AMM2) (Table 18) (FIG. 37B).

TABLE 18

TG101209 effect on in vitro hematopoietic colony growth from MPD patients carrying JAK2V617F or MPLW515 mutations
Cytokine-supported colonies - mutation pattern as assessed by genotyping of 575 Individual colonies

| Patient | Mutation | $IC_{50}$ (nM) Erythroid | $IC_{50}$ (nM) Myeloid | Total no. colonies genotyped | Mutation pattern without inhibitor (% colonies genotyped) | Mutation pattern with inhibitor (% colonies genotyped) | Lineage-specific mutation burden without inhibitor (% mutation-positive colonies) Erythroid | Lineage-specific mutation burden without inhibitor (% mutation-positive colonies) Myeloid | Lineage-specific mutation burden with inhibitor (% mutation-positive colonies) Erythroid | Lineage-specific mutation burden with inhibitor (% mutation-positive colonies) Myeloid |
|---|---|---|---|---|---|---|---|---|---|---|
| Normal | WT | 1000 | 600 | n/a | n/a | n/a | n/a | | | |
| PV1 | JAK2V617F | ~600 | 300-600 | 62 | HET/WT (85/15) | HET/WT (57/43) | 82 | 90 | 36 | 70 |

TABLE 18-continued

TG101209 effect on in vitro hematopoietic colony growth from MPD patients carrying JAK2V617F or MPLW515 mutations
Cytokine-supported colonies - mutation pattern as assessed by genotyping of 575 Individual colonies

| Patient | Mutation | $IC_{50}$ (nM) Erythroid | $IC_{50}$ (nM) Myeloid | Total no. colonies genotyped | Mutation pattern without inhibitor (% colonies genotyped) | Mutation pattern with inhibitor (% colonies genotyped) | Lineage-specific mutation burden without inhibitor (% mutation-positive colonies) Erythroid | Lineage-specific mutation burden without inhibitor (% mutation-positive colonies) Myeloid | Lineage-specific mutation burden with inhibitor (% mutation-positive colonies) Erythroid | Lineage-specific mutation burden with inhibitor (% mutation-positive colonies) Myeloid |
|---|---|---|---|---|---|---|---|---|---|---|
| PV2 | JAK2V617F | ~600 | ~300 | 111 | HET/WT (65/35) | HET/WT (60/40) | 70 | 55 | 60 | 20 |
| PV3 | JAK2V617F | NA | | 59 | HOM/WT (23/77) | HOM/HET/WT (8/8/84) | 20 | 30 | 30 | 0 |
| PV4 | JAK2V617F | >600 | ~600 | 61 | HOM/HET/WT (4/4/92) | HOM/HET/WT (8/11/81) | 7 | 10 | 17 | 10 |
| PV5 | JAK2V617F | ~300 | 300-600 | 47 | HOM/HET/WT (74/4/22) | HOM/HET/WT (92/4/4) | 64 | 92 | 82 | 100 |
| AMM1 | MPLW515K | <300 | ~300 | 59 | HET/WT (93/7) | HET/WT (17/83) | 100 | 90 | 0 | 20 |
| AMM2 | MPLW515K | 300-600 | ~300 | 86 | HET/WT (90/10) | HET/WT (39/61) | 100 | 90 | 25 | 36 |
| AMM3 | MPLW515L | 300-600 | 300-600 | 90 | HOM/HET (91/9) | HOM/HET/WT (71/22/7) | 100 | 100 | 92 | 90 |
| AMM4 | WT | >600 | 300-600 | n/a | n/a | n/a | n/a | | | |

PV indicates polycythemia vera;
AMM, agnogenic myeloid metaplasia;
WT, wild-type;
HET, heterozygous;
HOM, homozygous;
n/a, not applicable;
nM, nanomolar;
NA, not available;
No., number;
%, percentage; and
$IC_{50}$, inhibitor (TG101209) concentration that suppresses colony number by 50%.

The compounds of the present invention were designed to obtain selectivity for inhibiting JAK2. While not wanting to be bound by a particular theory, it is believed that removal of the methyl group or replacement with hydrophilic or larger groups results in a substantial loss in activity of the compounds of the invention. In another example, it is believed that a CH is important in the pyrimidine ring or for example, in a para position to R7 for activity and selectivity over JAK3 and other JAK family kinases. Larger substitutions at R7, preferably branched are believed to be important to maintain JAK2 activity and selectivity for the JAK2 over the other JAK family members, especially JAK3. An NH connected to a position between two nitrogens in the pyrimidine ring is seemingly important in the position for JAK2 activity. Further, an aromatic ring connected to the above-mentioned NH is seemingly important, such as a phenyl ring. Replacement of this phenyl ring with a pyrimidine for example results in complete loss in activity. The portion on the right side prefers to be a heterocyclic moiety. In the case of using aromatic heterocyclic groups there is a loss in cellular activity Although the invention has been described with reference to the above examples, it will be understood that modifications and variations are encompassed within the spirit and scope of the invention. Accordingly, the invention is limited only by the following claims.

What is claimed is
1. A compound having the structure (B):

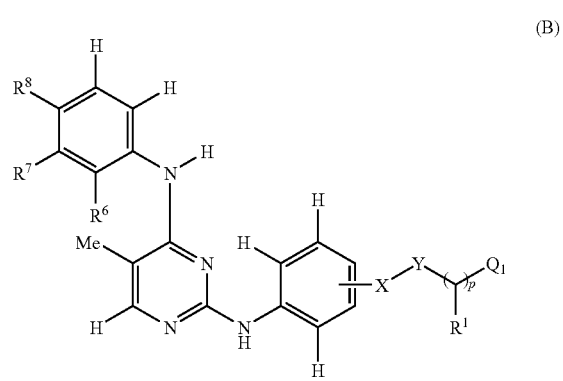

(B)

wherein:
X is selected from a group consisting of a bond, O, C=O, $SO_2$, and $CH_2$; Y is selected from a group consisting of a bond and $NR^9$; or X and Y taken together is a bond;

$R^9$ is selected from a group consisting of H, $C_1$-$C_6$ alkyl, $C_1$-$C_6$ cycloalkyl, $C_1$-$C_6$ branched alkyl, $C_1$-$C_6$ aminoalkyl, and $C_1$-$C_6$ hydroxyalkyl;

each of $R^1$ is independently selected from a group consisting of H, $C_1$-$C_6$ alkyl, cycloalkyl, and heterocycle;

each of n, or p is independently an integer having the value between 0 and 6;

$Q_1$ is a 4-7 membered heterocycle connected through carbon or nitrogen, with one or more heteroatoms in the heterocycle, and each carbon or nitrogen in the heterocycle is optionally substituted independently with $C_1$-$C_6$ alkyl, $C_1$-$C_6$ alkenyl, $C_1$-$C_6$ alkynyl, $C_1$-$C_6$ hydroxyalkyl or aminoalkyl, $C_1$-$C_6$ branched alkyl, $C_1$-$C_6$ cycloalkyl, aryl connected through carbon or a heteroatom, a halogen, $CF_3$, —$OCF_3$, $NO_2$, CN, OH, $CONR^3R^4$, and $COR^3$;

each of $R^6$, $R^7$, $R^8$ is independently selected from a group consisting of H, $C_1$-$C_6$ alkyl, $C_1$-$C_6$ alkenyl, $C_1$-$C_6$ alkynyl, $C_1$-$C_6$ hydroxyalkyl or aminoalkyl, $C_1$-$C_6$ branched alkyl, $C_1$-$C_6$ cycloalkyl, aryl, $C_1$-$C_6$ alkoxy, a halogen, $CF_3$, —$OCF_3$, $CHR^3R^4$, $SR^3$, $SOR^3$, $SO_2R^3$, $SO_2NR^3R^4$, $SO_3R^3$, $POR^3$, $PO_2R^3$, $PO_2NR^3R^4$, $PO_2CR^3R^4$, $PO_3R^3$, $NR^3R^4$, $NO_2$, CN, OH, $CONR^3R^4$, $COR^3$, $COOR^3$, $NR^3COR^4$, $NR^3CONR^3R^4$, $OCONR^3R^4$, $CSNR^3R^4$, $CSR^3$, $NR^3CSNR^3R^4$, $SCONR^3R^4$, and $SCSNR^3R^4$; or any of $R^6$ and $R^7$ taken together, or $R^7$ and $R^8$ taken together, or $R^6$ and $R^8$ taken together form a moiety independently selected from a group consisting of —HN—CH=CH—, —HN—N=CH—, —HN—N=N—, —O($CH_2$)$_n$O—, —S($CH_2$)$_n$S—, —N=CH—S—, —CH=N—O—, —CH=N—S—, —N=CH—O—, —C=N—O—, —CH=CH—CH=CH—, —N=CH—CH=CH—, —CH=N—CH=CH—, —O—CH=CH—, and —S—CH=CH—;

each of $R^3$ and $R^4$ is independently selected from a group consisting of H, $C_1$-$C_6$ alkyl, $C_1$-$C_6$ hydroxyalkyl or aminoalkyl, and $C_1$-$C_6$ branched alkyl, with the further provisos that:

(a) at least one of $R^6$, $R^7$ and $R^8$ is not hydrogen;

(b) $R^6$ and $R^7$, or $R^6$ and $R^8$, or $R^7$ and $R^8$ are substituted with non-hydrogen atoms, or if only one of $R^6$, $R^7$ and $R^8$ is substituted, then the substitution contains at least three non-hydrogen atoms;

(c) any one of $R^6$, $R^7$ or $R^8$ optionally comprises a heteroatom selected from a group consisting of O, N and S; and (d) the moiety $Q_1$ excludes hetero-aromatic cyclic rings, or a pharmaceutically acceptable salt, or an individual diastereomer of the compound (B).

2. The compound of claim 1, having the structure (C):

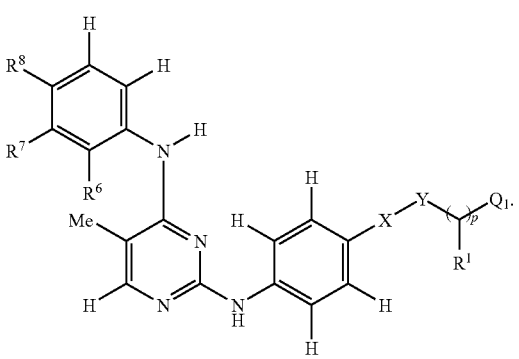

3. The compound of claim 1 having the structure (D):

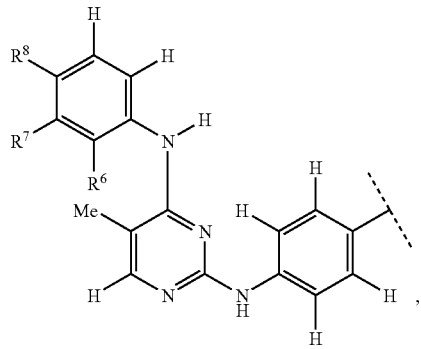

wherein the moiety attached to a connection point shown in structure (D) is selected from a group consisting of:

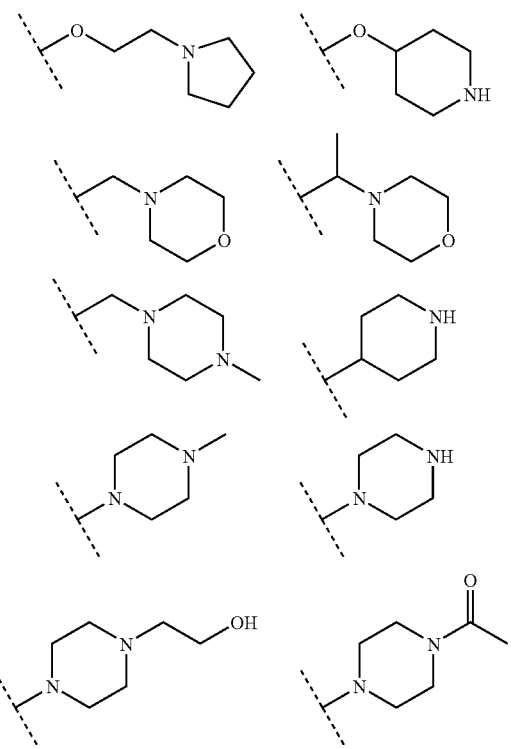

4. The compound of claim 1, having the structure (E):

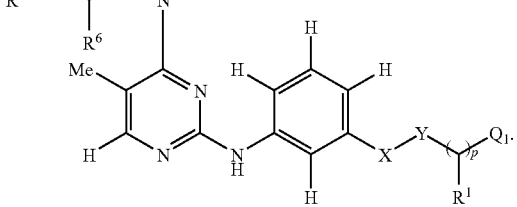

5. The compound of claim 1, having the structure (F):

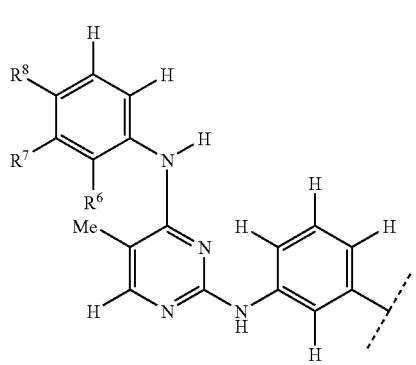

wherein the moiety attached to a connection point shown in structure (F) is selected from a group consisting of:

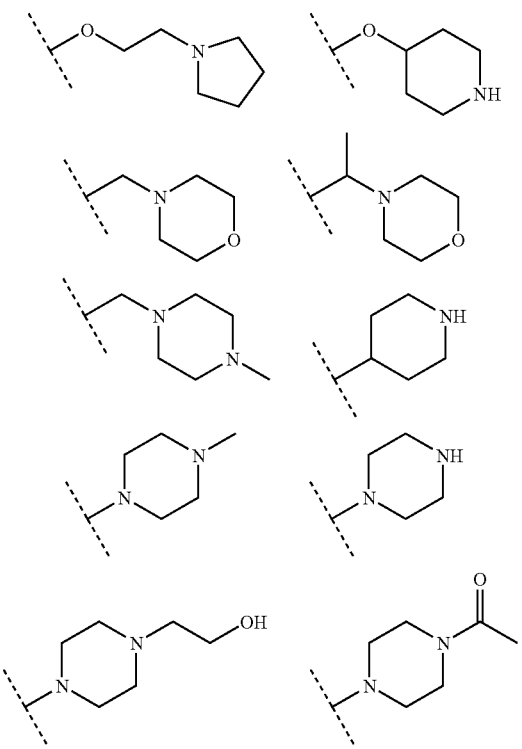

6. The compound of claim 1, having the structure (G):

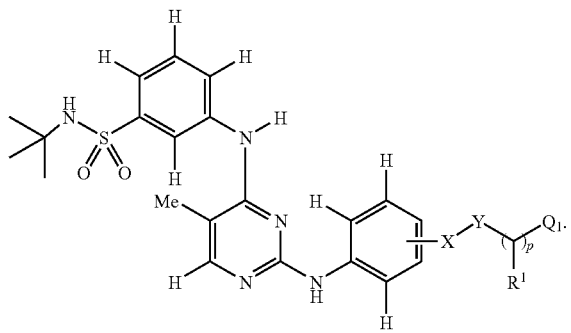

7. The compound of claim 1, having the structure (H):

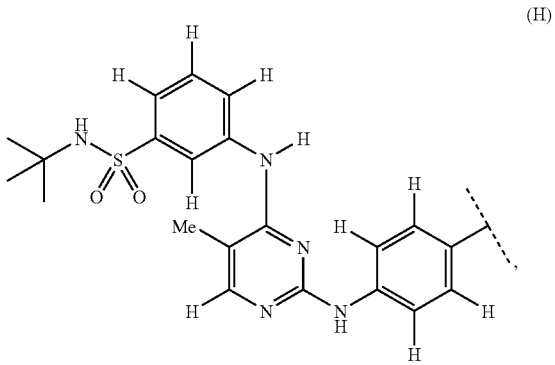

wherein the moiety attached to a connection point shown in structure (H) is selected from a group consisting of:

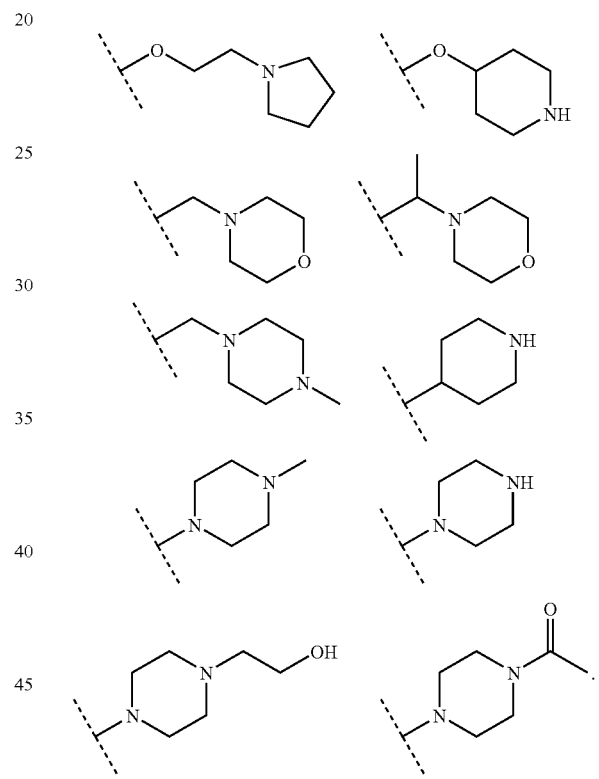

8. The compound of claim 1, having the structure (I):

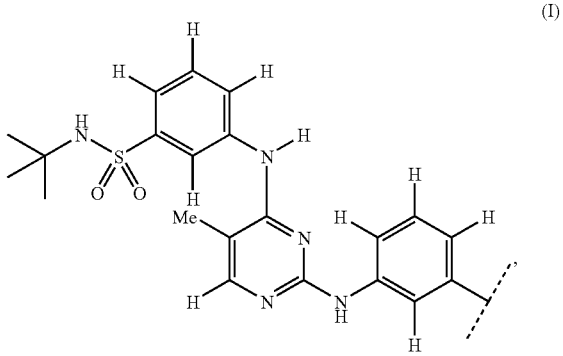

wherein the moiety attached to a connection point shown in structure (H) is selected from a group consisting of:
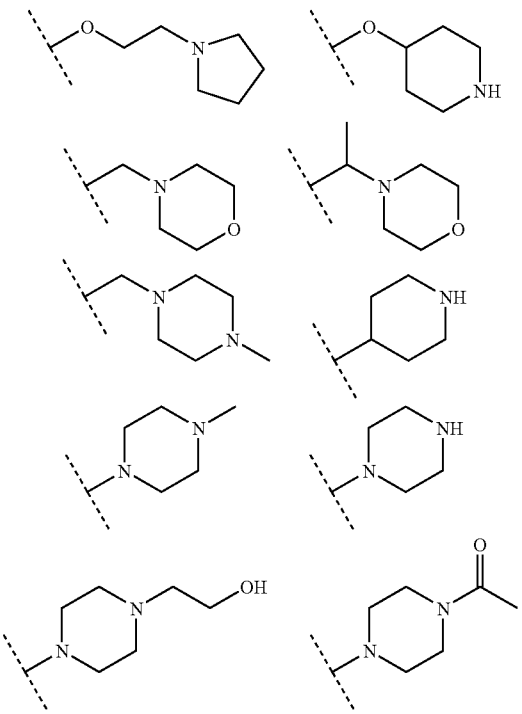
9. The compound of claim 1, having the structure (J):
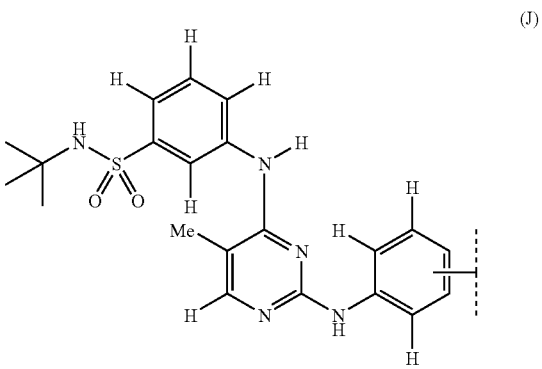
wherein the moiety attached to a connection point shown in structure (J) is
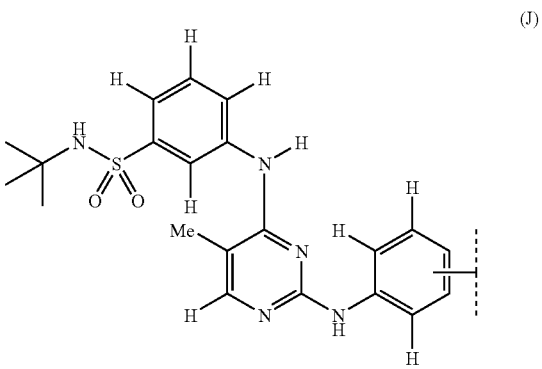
\* \* \* \* \*

UNITED STATES PATENT AND TRADEMARK OFFICE
CERTIFICATE OF CORRECTION

Page 1 of 2

PATENT NO. : 7,825,246 B2
APPLICATION NO. : 11/796717
DATED : November 2, 2010
INVENTOR(S) : Glenn Noronha et al.

It is certified that error appears in the above-identified patent and that said Letters Patent is hereby corrected as shown below:

- In Column 2, line 30, please replace "in cell based experiments, (b) V617F JAK2- indcued" with --in cell based experiments, (b) V617F JAK2-induced--

- In Column 7, lines 60-63, please replace "taken together can form a moiety such as one of the $(CH_2)_m$, $(CH_2)_r$-S-$(CH_2)_m$, $(CH_2)_r$-SO-$(CH_2)_m$, $CH_2)_r$–$SO_2$– $(CH_2)_m$, $(CH_2)_r$-$NR^9$-$(CH_2)_m$, or $(CH_2)_r$ –O- $(CH_2)_m$; or $R^1$ and $R^4$ taken together can form a moiety such" with --taken together can form a moiety such as one of the $(CH_2)_m$, $(CH_2)_r$-S-$(CH_2)_m$, $(CH_2)_r$-SO-$(CH_2)_m$, $(CH_2)_r$–$SO_2$– $(CH_2)_m$, $(CH_2)_r$-$NR^9$-$(CH_2)_m$, or $(CH_2)_r$ –O- $(CH_2)_m$; or $R^1$ and $R^4$ taken together can form a moiety such--

- In Column 36, lines 35-45, please amend the chemical structure (the fourth structure from the top)

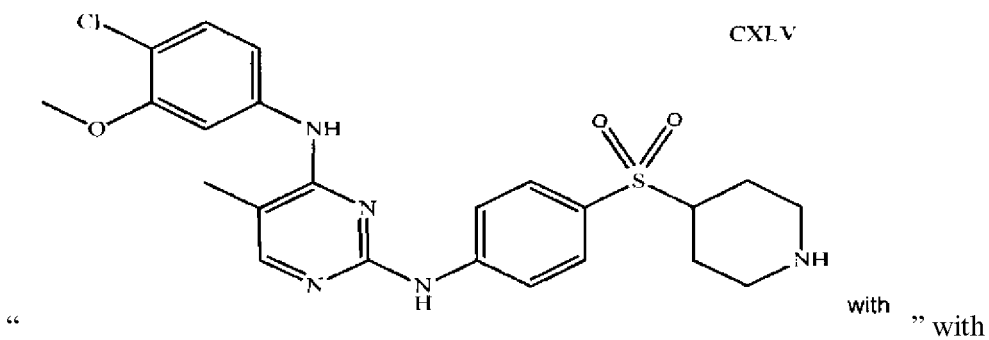

" with

Signed and Sealed this
Twenty-ninth Day of May, 2012

David J. Kappos
*Director of the United States Patent and Trademark Office*

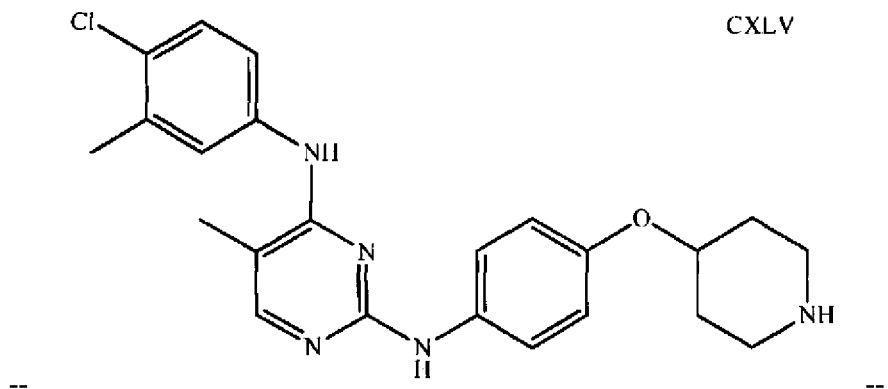
- In column 74, line 4, please replace "the title compound X (10mg, 32%) as alight brown solid." with --the title compound X (10mg, 32%) as a light brown solid.--
- In Column 176, line 2, please replace "chromatography (25%-i 00% EtOAc in Hexanes). Product" with --chromatography 25%-100% EtOAc in Hexanes). Product--